United States Patent
Cogan

(10) Patent No.: US 12,084,420 B2
(45) Date of Patent: Sep. 10, 2024

(54) INDOLINE COMPOUNDS FOR INHIBITING KIF18A

(71) Applicant: Volastra Therapeutics, Inc., New York, NY (US)

(72) Inventor: Derek A. Cogan, New York, NY (US)

(73) Assignee: Volastra Therapeutics, Inc., New York, NY (US)

( * ) Notice: Subject to any disclaimer, the term of this patent is extended or adjusted under 35 U.S.C. 154(b) by 0 days.

(21) Appl. No.: 17/896,037

(22) Filed: Aug. 25, 2022

(65) Prior Publication Data

US 2023/0147507 A1 May 11, 2023

Related U.S. Application Data

(60) Provisional application No. 63/344,435, filed on May 20, 2022, provisional application No. 63/306,452, filed on Feb. 3, 2022, provisional application No. 63/237,275, filed on Aug. 26, 2021.

(51) Int. Cl.

| | | |
|---|---|---|
| *C07D 209/96* | (2006.01) | |
| *A61P 35/00* | (2006.01) | |
| *C07D 401/06* | (2006.01) | |
| *C07D 401/12* | (2006.01) | |
| *C07D 401/14* | (2006.01) | |
| *C07D 403/06* | (2006.01) | |
| *C07D 403/12* | (2006.01) | |
| *C07D 403/14* | (2006.01) | |
| *C07D 405/06* | (2006.01) | |
| *C07D 405/12* | (2006.01) | |
| *C07D 405/14* | (2006.01) | |
| *C07D 409/06* | (2006.01) | |
| *C07D 409/12* | (2006.01) | |
| *C07D 409/14* | (2006.01) | |
| *C07D 413/12* | (2006.01) | |
| *C07D 491/107* | (2006.01) | |
| *C07D 491/113* | (2006.01) | |
| *C07F 9/572* | (2006.01) | |

(52) U.S. Cl.
CPC ............ *C07D 209/96* (2013.01); *A61P 35/00* (2018.01); *C07D 401/06* (2013.01); *C07D 401/12* (2013.01); *C07D 401/14* (2013.01); *C07D 403/06* (2013.01); *C07D 403/12* (2013.01); *C07D 403/14* (2013.01); *C07D 405/06* (2013.01); *C07D 405/12* (2013.01); *C07D 405/14* (2013.01); *C07D 409/06* (2013.01); *C07D 409/12* (2013.01); *C07D 409/14* (2013.01); *C07D 413/12* (2013.01); *C07D 491/107* (2013.01); *C07D 491/113* (2013.01); *C07F 9/5728* (2013.01)

(58) Field of Classification Search
CPC .. C07D 405/12; C07D 405/14; C07D 405/06; C07D 403/12; C07D 403/14; C07D 403/06; C07D 401/06; C07D 401/12; C07D 401/14; C07D 209/96; C07D 413/12; C07D 491/102; C07D 491/113
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 7,423,018 B2 | 9/2008 | Pereira et al. |
| 8,486,950 B2 | 7/2013 | Goodacre et al. |
| 11,236,069 B2 | 2/2022 | Tamayo et al. |
| 2004/0241760 A1 | 12/2004 | Pereira et al. |
| 2006/0287302 A1 | 12/2006 | Coleman et al. |
| 2008/0020461 A1 | 1/2008 | Pereira et al. |
| 2008/0051463 A1 | 2/2008 | Gerlach et al. |
| 2009/0312365 A1 | 12/2009 | Qian et al. |
| 2010/0021420 A1 | 1/2010 | Lyons et al. |
| 2010/0183550 A1 | 7/2010 | Vennemann et al. |
| 2010/0317643 A1 | 12/2010 | Goodacre et al. |
| 2016/0115128 A1 | 4/2016 | Aida et al. |
| 2019/0077752 A1 | 3/2019 | Lerchen et al. |
| 2021/0130903 A1 | 3/2021 | Ehrlich et al. |
| 2021/0226492 A1 | 7/2021 | Chen et al. |
| 2021/0253987 A1 | 8/2021 | Engler et al. |
| 2022/0056015 A1 | 2/2022 | Tamayo et al. |
| 2022/0106293 A1 | 4/2022 | Tamayo et al. |
| 2023/0117405 A1 | 4/2023 | Verma et al. |
| 2023/0151432 A1 | 5/2023 | Payton |
| 2023/0382889 A1 | 11/2023 | Cogan |

FOREIGN PATENT DOCUMENTS

| | | |
|---|---|---|
| CN | 113528509 | 10/2021 |
| CN | 115772159 | 3/2023 |
| CN | 115785068 | 3/2023 |

(Continued)

OTHER PUBLICATIONS

Registry No. 1632322-51-0, file Registry on STN, entered Nov. 11, 2014.*
Registry No. 1582899-72-6, file Registry on STN, entered Apr. 10, 2014.*
Registry No. 1449770-19-7, file Registry on STN, entered Sep. 5, 2013.*
Zeng et al., Advanced Materials Research, vol. 683, pp. 34-37, 2013.*
Kim et al., Chem. Commun., 2014, 50, 14249-1452, and Supplementary Information, pp. S1-S80.*

(Continued)

*Primary Examiner* — Rebecca L Anderson
(74) *Attorney, Agent, or Firm* — MORRISON & FOERSTER LLP

(57) ABSTRACT

The present disclosure relates generally to inhibitors of KIF18A, compositions thereof, and methods of using the compounds and compositions thereof. More specifically, the present disclosure relates to indoline inhibitors of KIF18A and methods of their use for treating disease mediated by KIF18A, such as cancer.

35 Claims, 5 Drawing Sheets

(56) References Cited

FOREIGN PATENT DOCUMENTS

| EP | 2295543 | 3/2011 |
|---|---|---|
| EP | 3823147 | 5/2021 |
| EP | 3964590 | 3/2022 |
| JP | 2011-085261 | 4/2011 |
| JP | 2015-020184 | 2/2015 |
| WO | WO 2002/012268 | 2/2002 |
| WO | WO 2002/047679 | 6/2002 |
| WO | WO 2004/039774 | 5/2004 |
| WO | WO 2004/045543 | 6/2004 |
| WO | WO 2006/002236 | 1/2006 |
| WO | WO 2006/114788 | 11/2006 |
| WO | WO 2007/056078 | 5/2007 |
| WO | WO 2008/015265 | 2/2008 |
| WO | WO 2011/085261 | 7/2011 |
| WO | WO 2012/159565 | 11/2012 |
| WO | WO 2013/188600 | 12/2013 |
| WO | WO 2015/183776 | 12/2015 |
| WO | WO 2016/100882 | 6/2016 |
| WO | WO 2016/168660 | 10/2016 |
| WO | WO 2016/177340 | 11/2016 |
| WO | WO 2016/187508 | 11/2016 |
| WO | WO 2017/162663 | 9/2017 |
| WO | WO 2019/140380 | 7/2019 |
| WO | WO 2020/035195 | 2/2020 |
| WO | WO 2020/132648 | 6/2020 |
| WO | WO 2020/132649 | 6/2020 |
| WO | WO 2020/132651 | 6/2020 |
| WO | WO 2020/132653 | 6/2020 |
| WO | WO 2020/206385 | 10/2020 |
| WO | WO 2020/226333 | 11/2020 |
| WO | WO 2021/011634 | 1/2021 |
| WO | WO 2021/026098 | 2/2021 |
| WO | WO 2021/026099 | 2/2021 |
| WO | WO 2021/026100 | 2/2021 |
| WO | WO 2021/026101 | 2/2021 |
| WO | WO 2021/161323 | 8/2021 |
| WO | WO 2021/211549 | 10/2021 |
| WO | WO 2021/231413 | 11/2021 |
| WO | WO 2022/032073 | 2/2022 |
| WO | WO 2022/214054 | 10/2022 |
| WO | WO 2022/268230 | 12/2022 |
| WO | WO 2023/004075 | 1/2023 |
| WO | WO 2023/041055 | 5/2023 |
| WO | WO 2023/088441 | 5/2023 |
| WO | WO 2023/212240 | 11/2023 |

OTHER PUBLICATIONS

Registry No. 1578401-55-4, file Registry on STN, entered Apr. 1, 2014.*
Registry No. 2184103-96-4, File Registry on STN, entered STN Mar. 4, 2018.*
Berge et al., "Pharmaceutical Salts," J Pharmaceutical Sciences (1977) 66(1):1-19.
Evans et al., "Synthesis of radiolabeled compounds," J Radioanal Xhem (1981) 64(1-2):9-32.
Kabalka et al., "The Synthesis of Radiolabeled Compounds via Organometallic Intermediates," Tetrahedron (1989) 45(21): 6601-21.
STN Registry No. 1387009-88-2 (Aug. 6, 2012), 1 page.
STN Registry No. 1387292-97-8 (Aug. 7, 2012), 1 page.
STN Registry No. 1390315-20-4 (Aug. 13, 2012), 1 page.
STN Registry No. 1390403-65-2 (Aug. 13, 2012), 1 page.
STN Registry No. 1578129-13-1 (Apr. 1, 2014), 1 page.
STN Registry No. 1578401-55-4 (Apr. 1, 2014), 1 page.
STN Registry No. 1603626-11-4 (May 13, 2014), 1 page.
STN Registry No. 1604077-15-7 (May 13, 2014), 1 page.
STN Registry No. 1826462-23-0 (Dec. 10, 2015), 1 page.
STN Registry No. 1826462-24-1 (Dec. 10, 2015), 1 page.
STN Registry No. 1837704-86-5 (Dec. 27, 2015), 1 page.
STN Registry No. 1837704-87-6 (Dec. 27, 2015), 1 page.
STN Registry No. 1946685-40-0 (Jul. 6, 2016), 1 page.
STN Registry No. 1957459-57-2 (Jul. 27, 2016), 1 page.
STN Registry No. 2093557-65-2 (Apr. 28, 2017), 1 page.
STN Registry No. 2094382-97-3 (May 2, 2017), 1 page.
STN Registry No. 2126661-48-9 (Sep. 8, 2017), 1 page.
STN Registry No. 2127863-55-0 (Sep. 15, 2017), 1 page.
STN Registry No. 2128018-41-5 (Sep. 17, 2017), 1 page.
STN Registry No. 2128299-61-4 (Sep. 18, 2017), 1 page.
STN Registry No. 2129139-81-5 (Oct. 12, 2017), 1 page.
STN Registry No. 2129593-05-9 (Sep. 22, 2017), 1 page.
STN Registry No. 2130484-98-7 (Sep. 23, 2017), 1 page.
STN Registry No. 2224059-75-8 (May 20, 2018), 1 page.
STN Registry No. 2263973-22-2 (Jan. 31, 2019), 1 page.
STN Registry No. 2264018-07-5 (Jan. 31, 2019), 1 page.
STN Registry No. 2264193-96-4 (Feb. 1, 2019), 1 page.
STN Registry No. 2264411-35-8 (Feb. 1, 2019), 1 page.
STN Registry No. 2264759-51-3 (Feb. 1, 2019), 1 page.
STN Registry No. 2265034-24-8 (Feb. 1, 2019), 1 page.
STN Registry No. 2265109-53-1 (Feb. 1, 2019), 1 page.
STN Registry No. 2339908-60-8 (Jun. 19, 2019), 1 page.
STN Registry No. 2419484-12-9 (Jun. 5, 2020), 1 page.
STN Registry No. 2426061-91-6 (Jun. 16, 2020), 1 page.
STN Registry No. 2450679-58-8 (Jun. 28, 2020), 1 page.
STN Registry No. 2452014-12-7 (Aug. 2, 2020), 1 page.
STN Registry No. 2453298-96-7 (Aug. 4, 2020), 1 page.
STN Registry No. 2454370-11-5 (Aug. 7, 2020), 1 page.
STN Registry No. 2464222-00-0 (Aug. 27, 2020), 1 page.
STN Registry No. 2464480-02-0 (Aug. 27, 2020), 1 page.
STN Registry No. 2467080-69-7 (Aug. 28, 2020), 1 page.
STN Registry No. 2727996-88-3 (Nov. 10, 2021), 1 page.
STN Registry No. 2728072-36-2 (Nov. 10, 2021), 1 page.
STN Registry No. 2728080-61-1 (Nov. 10, 2021), 1 page.
STN Registry No. 2728133-29-5 (Nov. 10, 2021), 1 page.
STN Registry No. 2728136-26-1 (Nov. 10, 2021), 1 page.
STN Registry No. 2728324-06-7 (Nov. 10, 2021), 1 page.
STN Registry No. 2728378-77-4 (Nov. 10, 2021), 1 page.
STN Registry No. 2728378-81-0 (Nov. 10, 2021), 1 page.
STN Registry No. 2728381-92-6 (Nov. 10, 2021), 1 page.
STN Registry No. 2728416-07-5 (Nov. 10, 2021), 1 page.
STN Registry No. 2728519-35-3 (Nov. 10, 2021), 1 page.
STN Registry No. 2728563-69-5 (Nov. 10, 2021), 1 page.
STN Registry No. 2728631-75-0 (Nov. 10, 2021), 1 page.
Braun et al., "Synthesis and biological evaluation of optimized inhibitors of the mitotic kinesin Kif18A," ACS Chem Biol. (2015) 10(2):554-560.
Girgis et al., "Novel synthesis of nicotinamide derivatives of cytotoxic properties," Bioorganic & Medicinal Chemistry (2006) 14(13):4466-4476.
Hackney et al., "Assays for kinesin microtubule-stimulated ATPase activity," Methods Mol Biol. (2001) 164:65-71.
Zhang et al., "High performance enzyme kinetics of turnover, activation and inhibition for translational drug discovery," Expert Opin Drug Discov. (2017) 12(1): 17-37.
U.S. Appl. No. 18/299,558, filed Apr. 12, 2023, by Cantley et al.
U.S. Appl. No. 18/140,533, filed Apr. 27, 2023, by Cogan.
Kim et al., "Decarboxylative acylation of indolines with α-keto acids under palladium catalysis: a facile strategy for the synthesis of 7-substituted indoles," Chem Commun (2014) 50:14249-14252.
McMahon, "VEGF receptor signaling in tumor angiogenesis," The Oncologist (2000) 5(Suppl 1):3-10.
Pinedo et al., "Translational Research: the role of VEGF in tumor angiogenesis," The Oncologist (2000) 5(suppl 1):1-2.
Sammeta et al., "A New Chemotype of Chemically Tractable Nonsteroidal Estrogens Based on a Thieno[2,3-d]pyrimidine Core," ACS Med Chem Lett (2022) 13(7):1151-1158.
Sammeta et al., "A New Chemotype of Chemically Tractable Nonsteroidal Estrogens Based on a Thieno[2,3-d]pyrimidine Core," ACS Med Chem Lett (2022) 13(7):1151-1158. Supporting Information, compound Z1841446907, p. S3.
U.S. Appl. No. 18/693,483, filed Mar. 19, 2024, by Verma et al.
U.S. Appl. No. 18/580,564, filed Jan. 18, 2024, by Wu et al.

* cited by examiner

INDOLINE COMPOUNDS FOR INHIBITING KIF18A

CROSS-REFERENCE TO RELATED APPLICATIONS

This application claims priority to and benefit of U.S. Provisional Patent Application No. 63/237,275, filed Aug. 26, 2021; U.S. Provisional Patent Application No. 63/306,452, filed Feb. 3, 2022; and U.S. Provisional Patent Application No. 63/344,435, filed May 20, 2022, the disclosures of each of which are hereby incorporated herein by reference in their entirety.

FIELD

The present disclosure relates generally to inhibitors of KIF18A, compositions thereof, and methods of using said compounds and compositions thereof. More specifically, the present disclosure relates to indoline inhibitors of KIF18A and methods of their use for treating disease mediated by KIF18A, such as cancer.

BACKGROUND

KIF18A is a kinesin involved in assisting the kinetochore-microtubule (kt-MT) attachment and chromosomal alignment during cell mitosis. Its cargo domain binds directly to protein phosphatase 1 (PP1) and carries it to the plus end of MT where PP1 dephosphorylates Hec1, a kinetochore complex component, further enhancing kt-MT attachment throughout metaphase and anaphase. Its MT-binding motor domain has ATPase activity that powers the KIF18A translocation along MT lattice, enhanced by its C-terminal MT-binding site, and caps and depolymerizes growing microtubule at the plus end, thus dampening MT dynamics. This modulation of MT dynamics by KIF18A often occurs at the following (or trailing) sister chromatid, thereby providing a counterbalancing tension to the leading sister chromatid movement catalyzed by another kinesin Kif2C/MCAK. Loss of KIF18A function causes defective kt-MT attachments and loss of tension within the spindle in cells of high chromosome instability (CIN), leading to hyper stable, longer and multipolar spindles, mitotic arrest, centrosome fragmentation and spindle assembly checkpoint activation or cell death. KIF18A is identified from DEPMAP RNAi data re-analysis as one of the top candidates essential for CIN-high cells. Reported synthetic lethality screens also singled out KIF18A as a potential anticancer target whose knockdown preferentially renders CIN-high (but not CIN-low), aneuploid and whole-genome doubled cells vulnerable to death. Cellular toxicity assay in isogenic cell lines confirmed the enhanced sensitivity of CIN-high cells to KIF18A inhibitors. Ongoing in vivo mouse models using KIF18A inhibitor or knockdown demonstrated effect of inhibited tumor growth. Thus, there is a need for new compounds for use in treating diseases mediated by KIF18A.

BRIEF SUMMARY

The present disclosure provides compounds of Formula (I), compositions thereof, and methods of using said compounds and compositions thereof for the treatment of diseases or conditions associated with KIF18a. In one aspect, provided is a compound of Formula (I):

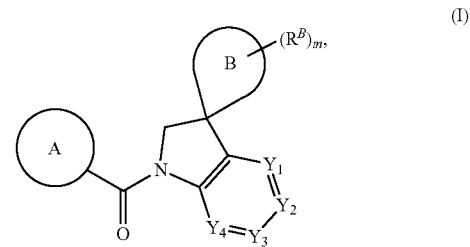

or a pharmaceutically acceptable salt thereof, wherein: ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —$NR^{a1}C(O)NR^{a2}R^{a3}$, —$NR^{a4}C(O)OR^{a5}$, —$NR^{a6}R^{a7}$, —N=S(O)$R^{a8}R^{a9}$, —$OR^{a10}$, —$S(O)R^{a11}$, —$S(O)(NR^{a12})R^{a13}$, —$S(O)_2NR^{a14}R^{a15}$, —$S(O)_2R^{a16}$, —$(CR^{a17}R^{a18})_{0-1}C(O)NR^{a19}R^{a20}$, —$SR^{a1}$, —$C(O)R^{a2}$, and $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo; $R^{a1}$-$R^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =$CR^{1a1}R^{1a2}$, and $C_{1-6}$ alkyl optionally substituted with one or more substituents independently selected from the group consisting of halo, —OH, and —O($C_{1-6}$ alkyl), wherein $R^{1a1}$ and $R^{1a2}$ are each independently hydrogen or $C_{1-6}$ alkyl; ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon; each $R^B$ group is independently halo, $C_{1-6}$ alkyl optionally substituted with one or more halo, or $C_{2-6}$ alkenyl; or two vicinal $R^B$ groups are taken together with the carbon atoms to which they are attached to form $C_{3-10}$ cycloalkyl; or two geminal $R^B$ groups are taken together with the carbon atom to which they are attached to form $C_{3-10}$ cycloalkyl; m is 0, 1, 2, 3, or 4; $Y^1$ is N or $CR^{C1}$; $Y^2$ is N or $CR^{C2}$; $Y^3$ is N or $CR^{C3}$; $Y^4$ is N or $CR^{C4}$; wherein no more than three of $Y^1$, $Y^2$, $Y^3$, and $Y^4$ are N; $R^{C1}$-$R^{C4}$ are each independently hydrogen, halo, cyano, —OH, —$NO_2$, —$C(O)NR^{c1}R^{c2}$, —$NR^{c3}R^{c4}$, —$NR^{c5}S(O)_2R^{c6}$, —$P(O)R^{c7}R^{c8}$, —N=S(O)$R^{c9}R^{c10}$, —$S(O)(NR^{c11})R^{c12}$, —$S(O)_2R^{c13}$—$NR^{c14}C(O)OR^{c15}$, —$NR^{c16}S(O)_2(CH_2)_{1-6}NR^{c17}C(O)R^{c18}$, or $C_{1-6}$ alkyl optionally substituted with one or more substituents independently selected from the group consisting of halo and —OH; $R^{c1}$-$R^{c18}$ are each independently hydrogen, $C_{3-10}$ cycloalkyl, or $C_{1-6}$ alkyl optionally substituted with one or more substituents independently selected from the group consisting of halo and —OH.

In another aspect, provided is a compound of Formula (II):

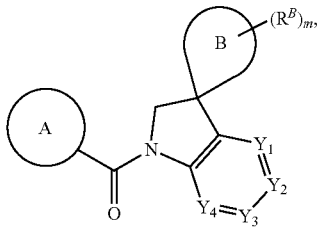

or a pharmaceutically acceptable salt thereof, wherein: ring A is

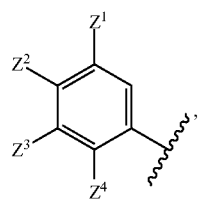

wherein $Z^1$, $Z^2$, $Z^3$, and $Z^4$ are each independently hydrogen or $R^D$, wherein $R^D$ is halo, —OH, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, —P(O)(R$^{a23}$)(R$^{a24}$), —C=NR$^{a25}$, or $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo or $C_{1-3}$ alkyl, provided that (1) when $Z^4$ is hydrogen then at least one of $Z^1$ and $Z^3$ is $R^D$; and (2) when $Z^4$ is $R^D$, then $Z^1$ is $R^D$, or

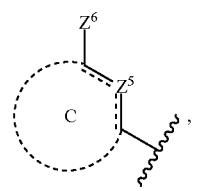

wherein ⟋ is a single bond or a double bond, $Z^5$ is C—H, N, O, S, or N—X, wherein X is H or $C_{1-6}$alkyl, $Z^6$ is —NR$^{a26}$C(O)NR$^{a27}$R$^{a28}$, —NR$^{a29}$C(O)OR$^{a30}$, —N=S(O)R$^{a31}$R$^{a32}$, —S(O)R$^{a33}$, —S(O)(NR$^{a34}$)R$^{a35}$, —S(O)$_2$NR$^{a36}$R$^{a37}$, —S(O)$_2$R$^{a38}$, —SR$^{a39}$, 3- to 10-membered heterocycloalkyl, —C(O)R$^{a40}$ or —CH(Z$^7$)(Z$^8$), wherein $Z^7$ is hydrogen or —OH, and $Z^8$ is $C_{1-6}$ alkyl, $C_{3-10}$ cycloalkyl optionally substituted with one or more halo, or 3- to 10-membered heterocycloalkyl optionally substituted with one or more halo, and ring C is 5- to 6-membered heteroaryl optionally substituted with one or more $R^E$ substituents, wherein each $R^E$ substituent is independently selected from the group consisting of halo, —OH, and $C_{1-6}$ alkyl, or two $R^E$ substituents are taken, together with the atoms to which they are attached, to form $C_{5-6}$ cycloalkyl, $C_{5-6}$ cycloalkenyl, 5- to 6-membered heterocycloalkyl, 5- to 6-membered heterocycloalkenyl, or 5- to 6-membered heteroaryl; $R^{a4}$-$R^{a40}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein $R^{1a1}$ and $R^{1a2}$ are each independently hydrogen or $C_{1-6}$ alkyl; ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon; each $R^B$ group is independently halo or $C_{1-6}$ alkyl optionally substituted with one or more halo; or two vicinal $R^B$ groups are taken together with the carbon atoms to which they are attached to form $C_{3-10}$ cycloalkyl; or two geminal $R^B$ groups are taken together with the carbon atom to which they are attached to form $C_{3-10}$ cycloalkyl; or two geminal $R^B$ groups are taken together to form a =CR$^{1a3}$R$^{1a4}$ group, wherein $R^{1a3}$ and $R^{1a4}$ are each independently hydrogen or $C_{1-6}$ alkyl; m is 0, 1, 2, 3, or 4; $Y^1$ is N or CR$^{C1}$; $Y^2$ is N or CR$^{C2}$; $Y^3$ is N or CR$^{C3}$; $Y^4$ is N or CR$^{C4}$; wherein no more than three of $Y^1$, $Y^2$, $Y^3$, and $Y^4$ are N; $R^{C1}$-$R^{C4}$ are each independently hydrogen or $R^F$, wherein $R^F$ is halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, —O—S(O)$_2$R$^{c19}$, or $C_{1-6}$ alkyl substituted with one or more substituents independently selected from the group consisting of halo and —OH, and $R^{c1}$-$R^{c19}$ are each independently hydrogen, $C_{3-10}$ cycloalkyl, or $C_{1-6}$ alkyl optionally substituted with one or more substituents independently selected from the group consisting of halo, —O($C_{1-6}$ alkyl), —NHC(O)($C_{1-6}$ alkyl), and —OH; provided that (1) when ring B is unsubstituted cyclopentyl, then ring A is

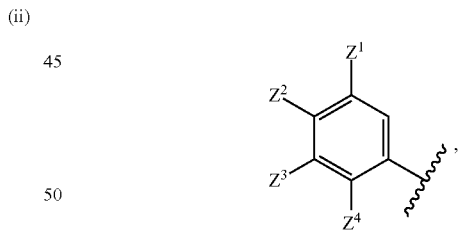

wherein at least one of $Z^1$-$Z^4$ is —S(O)$_2$-(3- to 10-membered heterocycloalkyl) substituted with one or more halo, (2) when ring B is unsubstituted cyclohexyl and ring A is

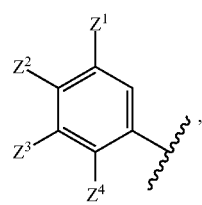

then at least one of $R^{C1}$-$R^{C4}$ is $R^F$, and (3) when ring B is 5- to 7-membered heterocycloalkyl optionally substituted with 1-4 $R^B$, then ring A is

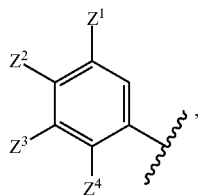

wherein at least one of $Z^1$-$Z^4$ is —$S(O)_2$-(3- to 10-membered heterocycloalkyl) optionally substituted with one or more halo.

In another aspect, provided is pharmaceutical composition comprising a compound of Formula (I), Formula (I-1), Formula (Ia1), Formula (Ia2), Formula (I-3), Formula (Ia1), Formula (Ia2), or Formula (II), or a pharmaceutically acceptable salt thereof, and a pharmaceutically acceptable carrier or excipient.

In another aspect, provided herein is a method of inhibiting KIF18A comprising contacting a cell with an effective amount of a compound or a pharmaceutical composition as described herein.

In another aspect, provided herein are methods of treating or preventing a disease or condition in an individual, comprising administering to the subject a therapeutically effective amount of a compound or a pharmaceutical composition as described herein. In some embodiments, the disease or condition is mediated by KIF18A. In some embodiments, the disease or condition is cancer. In some embodiments, the disease or condition is a cellular proliferation disorder.

DESCRIPTION OF FIGURES

FIG. 1A shows Compound 22 (10 mg/kg BID, 30 mg/kg BID, 60 mg/kg BID) treatment of HCC15 implanted SCID Beige mice.

FIG. 1B shows Compound 22 (10 mg/kg QD, 30 mg/kg QD, 60 mg/kg QD) treatment of OVCAR-3 implanted Balb/C nude mice.

FIG. 1C shows Compound 134 (10 mg/kg BID, 30 mg/kg BID, 60 mg/kg BID) treatment of HCC15 implanted SCID Beige mice.

FIG. 1D shows Compound 134 (10 mg/kg BID, 30 mg/kg BID, 60 mg/kg BID) treatment of OVCAR-3 implanted Balb/C nude mice.

FIG. 1E shows Compound 134 (30 mg/kg BID, 30 mg/kg QD, 60 mg/kg QD) treatment of OVCAR-3 implanted Balb/C nude mice.

DETAILED DESCRIPTION

Figure 1A:
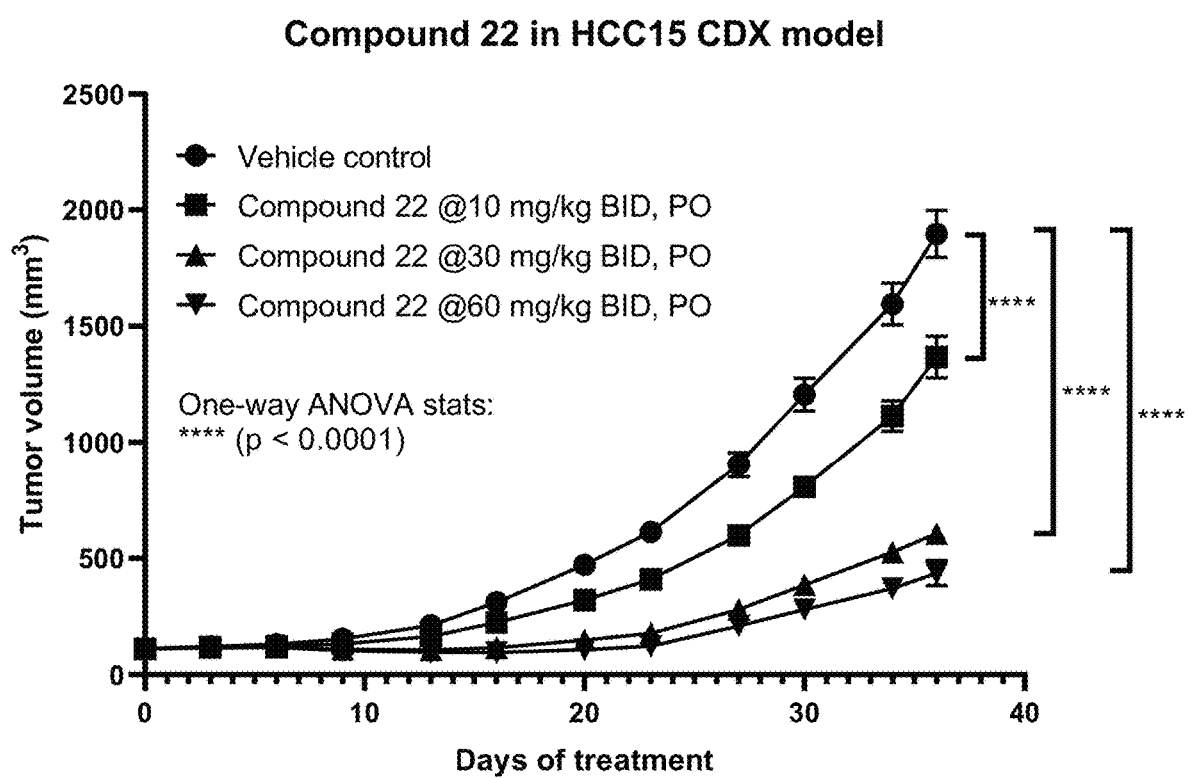
FIGS. 1A-1E show graphs of tumor volume of vehicle- and compound-treated mice plotted as a function of time after start of treatment.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

As used in the present specification, the following words and phrases are generally intended to have the meanings as set forth below, except to the extent that the context in which they are used indicates otherwise.

Throughout this application, unless the context indicates otherwise, references to a compound of Formula (I), Formula (I-1), Formula (Ia1), Formula (Ia2), Formula (I-2), Formula (I-3), Formula (Ia1), Formula (Ia2), or Formula (II) include all subgroups defined herein, such as Formula (I-1), (Ia1), or (Ia2), including all substructures, subgenera, preferences, embodiments, examples and particular compounds defined and/or described herein. In some embodiments, references to a compound of Formula (I), Formula (I-1), Formula (Ia1), Formula (Ia2), Formula (I-2), Formula (I-3), Formula (Ia1), Formula (Ia2), or Formula (II), and subgroups thereof, such as Formula (I-1), (Ia1), or (Ia2), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (I), Formula (I-1), Formula (Ia1), Formula (Ia2), Formula (I-2), Formula (I-3), Formula (Ia1), Formula (Ia2), or Formula (II), and subgroups thereof, such as Formula (I-1), (Ia1), or (Ia2), include polymorphs, solvates, co-crystals, isomers, tautomers and/or oxides thereof. In some embodiments, references to a compound of Formula (I), Formula (I-1), Formula (I-2), Formula (I-3), Formula (Ia1), Formula (Ia2), or Formula (II), and subgroups thereof, such as Formula (I-1), (Ia1), or (Ia2), include polymorphs, solvates, and/or co-crystals thereof. In some embodiments, references to a compound of Formula (I), Formula (I-1), Formula (I-2), Formula (I-3), Formula (Ia1), Formula (Ia2), or Formula (II), and subgroups thereof, such as Formula (I-1), (Ia1), or (Ia2), include isomers, tautomers and/or oxides thereof. In some embodiments, references to a compound of Formula (I), Formula (I-1), Formula (I-2), Formula (I-3), Formula (Ia1), Formula (Ia2), or Formula (II), and subgroups thereof, such as Formula (I-1), (Ia1), or (Ia2), include solvates thereof.

"Alkyl" encompasses straight and branched carbon chains having the indicated number of carbon atoms, for example, from 1 to 20 carbon atoms, or 1 to 8 carbon atoms, or 1 to 6 carbon atoms, or 1 to 3 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7- naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluoro, chloro, bromo or iodo.

"Haloalkyl" refers to alkyl substituted with one or more halogen. A haloalkyl group may have a halogen substituent at any valence-permitted location on the alkyl and may have any number of halogen substituents ranging from one to the maximum valence-permitted number. Particular haloalkyl groups have 1, 2, or 3 halogen substituents. Examples of haloalkyl groups include, but are not limited to, —CH$_2$F, —CHF$_2$, —CF$_3$, —CH$_2$CH$_2$F, —CH$_2$CHF$_2$, —CH$_2$CF$_3$, —CH$_2$Cl, —CHCl$_2$, —CCl$_3$, —CH$_2$CH$_2$C$_1$, —CH$_2$CHCl$_2$, —CH$_2$CCl$_3$.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocycloalkyl, heterocycloalkenyl, aralkyl, aminosulfonyl, sulfonylamino, sulfonyl, oxo and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^2$H, $^3$H, $^{11}$C, $^{13}$C and/or $^{14}$C. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.*, 2000; 6(10); Kabalka, G. et al., The Synthesis of Radiolabeled Compounds via Organometallic Intermediates, *Tetrahedron*, 1989, 45(21), 6601-

21; and Evans, E., Synthesis of radiolabeled compounds, *J. Radioanal. Chem.,* 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient, individual, or subject is a human, for example a human that has been or will be the object of treatment, observation or experiment. The compounds, compositions and methods described herein can be useful in both human therapy and veterinary applications.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation (e.g., inhibition) of KIF18a. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat," "treated," "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

It is understood that embodiments described herein as "comprising" include "consisting of" and "consisting essentially of" embodiments.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

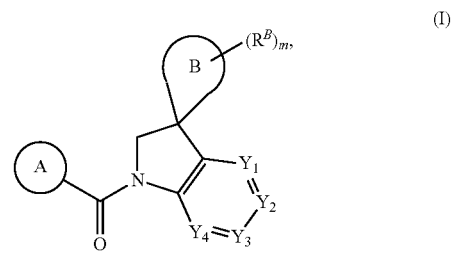

or a pharmaceutically acceptable salt thereof, wherein:

ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo;

R$^{a1}$-R$^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein R$^{1a1}$ and R$^{1a2}$ are each independently hydrogen or $C_{1-6}$ alkyl;

ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;

each R$^B$ group is independently halo, $C_{1-6}$ alkyl optionally substituted with one or more halo, or $C_{2-6}$ alkenyl; or two vicinal R$^B$ groups are taken together with the carbon atoms to which they are attached to form $C_{3-10}$ cycloalkyl; or two geminal R$^B$ groups are taken together with the carbon atom to which they are attached to form $C_{3-10}$ cycloalkyl;

m is 0, 1, 2, 3, or 4;

$Y^1$ is N or CR$^{C1}$;

$Y^2$ is N or CR$^{C2}$;

$Y^3$ is N or CR$^{C3}$;

$Y^4$ is N or CR$^{C4}$;

wherein no more than three of $Y^1$, $Y^2$, $Y^3$, and $Y^4$ are N;

R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or $C_{1-6}$ alkyl optionally substituted with one or more substituents independently selected from the group consisting of halo and —OH;

R$^{c1}$-R$^{c18}$ are each independently hydrogen, $C_{3-10}$ cycloalkyl, or $C_{1-6}$ alkyl optionally substituted with one or more substituents independently selected from the group consisting of halo and —OH.

In one aspect, provided are compounds of Formula (I-1):

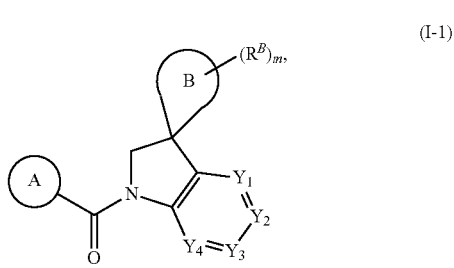

(I-1)

or a pharmaceutically acceptable salt thereof, wherein:
ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, and —(CR$^{a17}$R$^{a18}$)$_{0-1}$C(O)NR$^{a19}$R$^{a20}$.

R$^{a1}$-R$^{a20}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein R$^{1a1}$ and R$^{1a2}$ are each independently hydrogen or $C_{1-6}$ alkyl;

ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;

each R$^B$ group is independently halo, $C_{1-6}$ alkyl, or $C_{2-6}$ alkenyl; or two vicinal R$^B$ groups are taken together with the carbon atoms to which they are attached to form $C_{3-10}$ cycloalkyl; or two geminal R$^B$ groups are taken together with the carbon atom to which they are attached to form $C_{3-10}$ cycloalkyl;

m is 0, 1, 2, 3, or 4;
$Y^1$ is N or CR$^{C1}$;
$Y^2$ is N or CR$^{C2}$;
$Y^3$ is N or CR$^{C3}$;
$Y^4$ is N or CR$^{C4}$;
wherein no more than three of $Y^1$, $Y^2$, $Y^3$, and $Y^4$ are N;
R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, or $C_{1-6}$ alkyl optionally substituted with one or more substituents independently selected from the group consisting of halo and —OH;

R$^{c1}$-R$^{c13}$ are each independently hydrogen, $C_{3-10}$ cycloalkyl, or $C_{1-6}$ alkyl optionally substituted with one or more substituents independently selected from the group consisting of halo and —OH.

In another aspect, provided herein is a compound of Formula (I-2)

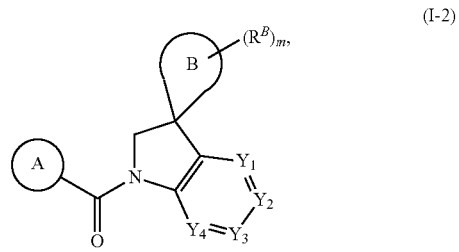

(I-2)

or a pharmaceutically acceptable salt thereof, wherein:
ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo;

R$^{a1}$-R$^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein R$^{1a1}$ and R$^{1a2}$ are each independently hydrogen or $C_{1-6}$ alkyl;

ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;

each R$^B$ group is independently halo, $C_{1-6}$ alkyl optionally substituted with one or more halo, or $C_{2-6}$ alkenyl; or two vicinal R$^B$ groups are taken together with the carbon atoms to which they are attached to form $C_{3-10}$ cycloalkyl; or two geminal R$^B$ groups are taken together with the carbon atom to which they are attached to form $C_{3-10}$ cycloalkyl;

m is 0, 1, 2, 3, or 4;
$Y^1$ is N or CR$^{C1}$;
$Y^2$ is N or CR$^{C2}$;
$Y^3$ is N or CR$^{C3}$;
$Y^4$ is N or CR$^{C4}$;
wherein no more than three of $Y^1$, $Y^2$, $Y^3$, and $Y^4$ are N;
R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, or $C_{1-6}$ alkyl optionally substituted with one or more substituents independently selected from the group consisting of halo and —OH;

R$^{c1}$-R$^{c15}$ are each independently hydrogen, $C_{3-10}$ cycloalkyl, or $C_{1-6}$ alkyl optionally substituted with one or more substituents independently selected from the group consisting of halo and —OH.

In another aspect, provided herein is a compound of Formula (I-3):

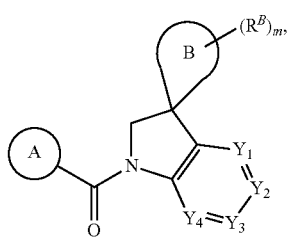

or a pharmaceutically acceptable salt thereof, wherein:
ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo;
R$^{a1}$-R$^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein R$^{1a1}$ and R$^{1a2}$ are each independently hydrogen or $C_{1-6}$ alkyl;
ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;
m is 2;
the two R$^B$ groups are attached to the same carbon atom on ring B and are taken together with the carbon atom to which they are attached to form $C_{3-7}$ cycloalkyl;
Y$^1$ is N or CR$^{C1}$;
Y$^2$ is N or CR$^{C2}$;
Y$^3$ is N or CR$^{C3}$;
Y$^4$ is N or CR$^{C4}$;
wherein no more than three of Y$^1$, Y$^2$, Y$^3$, and Y$^4$ are N;
R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or $C_{1-6}$ alkyl optionally substituted with one or more substituents independently selected from the group consisting of halo and —OH;
R$^{c1}$-R$^{c18}$ are each independently hydrogen, $C_{3-10}$ cycloalkyl, or $C_{1-6}$ alkyl optionally substituted with one or more substituents independently selected from the group consisting of halo and —OH.

In some embodiments of Formula (I), Formula (I-1), Formula (I-2), and Formula (I-3), or a pharmaceutically acceptable salt thereof, ring A is substituted with one, two, three, four, five, or more substituents independently selected from the group consisting of —SR$^{a21}$, —C(O)R$^{a22}$, and $C_{1-6}$ alkyl substituted with one, two, three, four, five, or more substituents independently selected from the group consisting of —OH, cyano, $C_{3-10}$ cycloalkyl, and 3- to 10-membered heterocycloalkyl optionally substituted with one, two, three, four, five, or more halo. In some embodiments, ring A is substituted with —SR$^{a21}$, —C(O)R$^{a22}$, or $C_{1-6}$ alkyl substituted with one, two, three, four, five, or more substituents independently selected from the group consisting of —OH, cyano, $C_{3-10}$ cycloalkyl, and 3- to 10-membered heterocycloalkyl optionally substituted with one, two, three, four, five, or more halo. In some embodiments, R$^{a21}$ and R$^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein R$^{1a1}$ and R$^{1a2}$ are each independently hydrogen or $C_{1-6}$ alkyl.

In some embodiments of Formula (I), Formula (I-1), Formula (I-2), and Formula (I-3), or a pharmaceutically acceptable salt thereof, one or more R$^B$ groups are independently $C_{1-6}$ alkyl substituted with one, two, three, four, five, or more halo. In some embodiments, an R$^B$ group is $C_{1-6}$ alkyl substituted with one, two, three, four, five, or more halo.

In some embodiments of Formula (I), Formula (I-1), Formula (I-2), and Formula (I-3), or a pharmaceutically acceptable salt thereof, R$^{C2}$ is —NR$^{c14}$C(O)OR$^{c15}$ wherein R$^{c14}$ and R$^{c15}$ are each independently hydrogen, $C_{3-10}$ cycloalkyl, or $C_{1-6}$ alkyl optionally substituted with one or more substituents independently selected from the group consisting of halo and —OH.

In some embodiments, cycloalkyl or heterocycloalkyl groups include spiro groups. In some embodiments, cycloalkyl or heterocycloalkyl groups include fused groups.

In some embodiments of Formula (I), Formula (I-1), Formula (I-2), and Formula (I-3), or a pharmaceutically acceptable salt thereof, ring A is $C_{6-14}$ aryl or 5- to 12-membered heteroaryl, each optionally substituted. In some embodiments, ring A is optionally substituted $C_6$-14 aryl. In some embodiments, ring A is optionally substituted phenyl. In some embodiments, ring A is optionally substituted 5- to 12-membered heteroaryl. In some embodiments, ring A is optionally substituted 6-membered heteroaryl. In some embodiments, ring A is optionally substituted 5-membered heteroaryl. In some embodiments, ring A is indolyl, indazolyl, pyridinyl, thiophenyl, furanyl, pyrazolyl, pyrrolyl, oxazolyl, chromanyl, or quinolinyl, each optionally substituted. In some embodiments, ring A is optionally substituted thiophenyl.

In some embodiments Formula (I), Formula (I-1), Formula (I-2), and Formula (I-3) Formula (II), ring A is optionally substituted with one, two, three, four, five, or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and C$_{1-6}$ alkyl substituted with one or more substituents independently selected from the group consisting of —OH, cyano, C$_{3-10}$ cycloalkyl, and 3- to 10-membered heterocycloalkyl optionally substituted with one or more halo. In some embodiments, R$^{a1}$-R$^{a22}$ are each independently hydrogen, C$_{1-6}$ alkyl, C$_{2-6}$ alkenyl, C$_{3-10}$ cycloalkyl, C$_{3-10}$ cycloalkenyl, 3- to 10-membered heterocycloalkyl, 3- to 10-membered heterocycloalkenyl C$_{6-14}$ aryl, or 5- to 12-membered heteroaryl, each optionally substituted with one, two, three, four, five, or more substituents independently selected from the group consisting of halo, cyano, —OH, —O(C$_{1-6}$ alkyl), C$_{2-6}$ alkenyl, C$_{3-10}$ cycloalkyl, —S(C$_{1-6}$ alkyl), =CR$^{1a1}$R$^{1a2}$, and C$_{1-6}$ alkyl optionally substituted with one, two, three, four, five, or more substituents independently selected from the group consisting of halo, —OH, and —O(C$_{1-6}$ alkyl), wherein R$^{1a1}$ and R$^{1a2}$ are each independently hydrogen or C$_{1-6}$ alkyl.

In some embodiments, the 3- to 10-membered heterocycloalkyl is piperidinyl. In some embodiments, the 3- to 10-membered heterocycloalkyl is

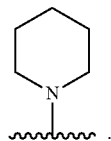

In some embodiments, R$^{a1}$ is hydrogen or C$_{1-6}$ alkyl. In some embodiments, R$^{a1}$ is hydrogen. In some embodiments, R$^{a2}$ and R$^{a3}$ are each independently hydrogen, C$_{1-6}$ alkyl, or C$_{3-10}$ cycloalkyl. In some embodiments, R$^{a2}$ and R$^{a3}$ are each independently hydrogen, cyclopropyl, ethyl, or isopropyl. In some embodiments, R$^{a4}$ is hydrogen or C$_{1-6}$ alkyl. In some embodiments, R$^{a4}$ is hydrogen. In some embodiments, R$^{a5}$ is hydrogen or C$_{1-6}$ alkyl. In some embodiments, R$^{a5}$ is tert-butyl. In some embodiments, R$^{a6}$ and R$^{ay}$ are each independently hydrogen, C$_{1-6}$ alkyl, or 5- to 12-membered heteroaryl optionally substituted with C$_{1-6}$ alkyl. In some embodiments, R$^{a6}$ and R$^{ay}$ are each independently hydrogen, imidazolyl, methylimidazolyl, or pyrimidinyl. In some embodiments, —N=S(O)R$^{a8}$R$^{a9}$ is

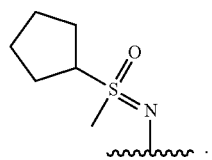 [SMILES: *N=S(C)(=O)C1CCCC1]

In some embodiments, R$^{a8}$ and R$^{a9}$ are each independently hydrogen, C$_{1-6}$ alkyl, or C$_{3-10}$ cycloalkyl. In some embodiments, R$^{a8}$ and R$^{a9}$ are each independently methyl or cyclopentyl. In some embodiments, —OR$^{a10}$ is

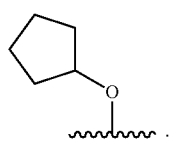

In some embodiments, R$^{a10}$ is C$_{3-10}$ cycloalkyl. In some embodiments, R$^{a10}$ is cyclopentyl. In some embodiments, —S(O)R$^{a11}$ is

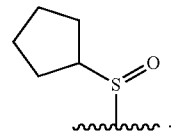 [SMILES: *S(=O)C1CCCC1]

In some embodiments, R$^{a11}$ is C$_{3-10}$ cycloalkyl. In some embodiments, R$^{a11}$ is cyclopentyl. In some embodiments, —S(O)(NR$^{a12}$)R$^{a13}$ is

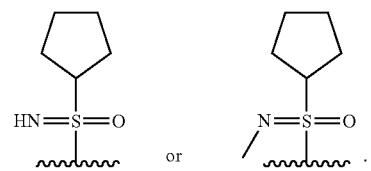

In some embodiments, R$^{a12}$ is hydrogen or C$_{1-6}$ alkyl. In some embodiments, R$^{a12}$ is hydrogen or methyl. In some embodiments, R$^{a13}$ is C$_{3-10}$ cycloalkyl. In some embodiments, R$^{a13}$ is cyclopentyl. In some embodiments, —S(O)$_2$NR$^{a14}$R$^{a15}$ is

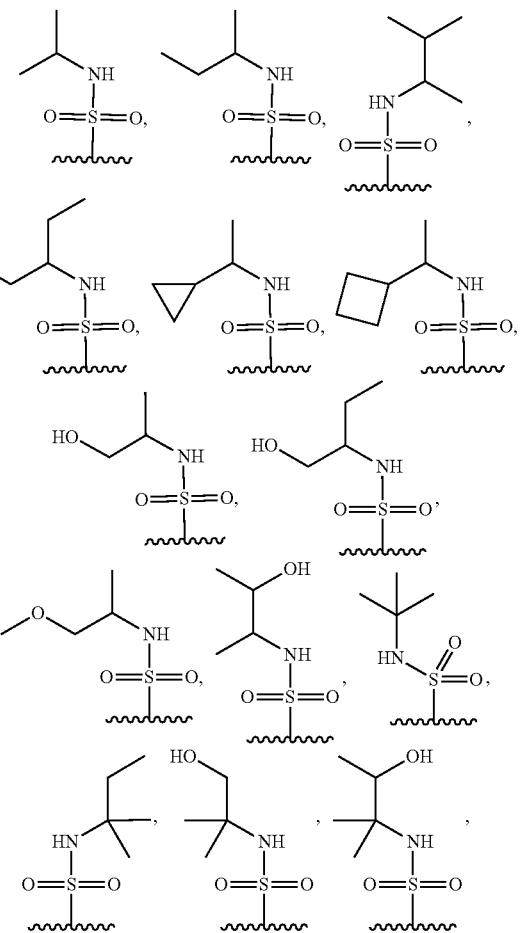

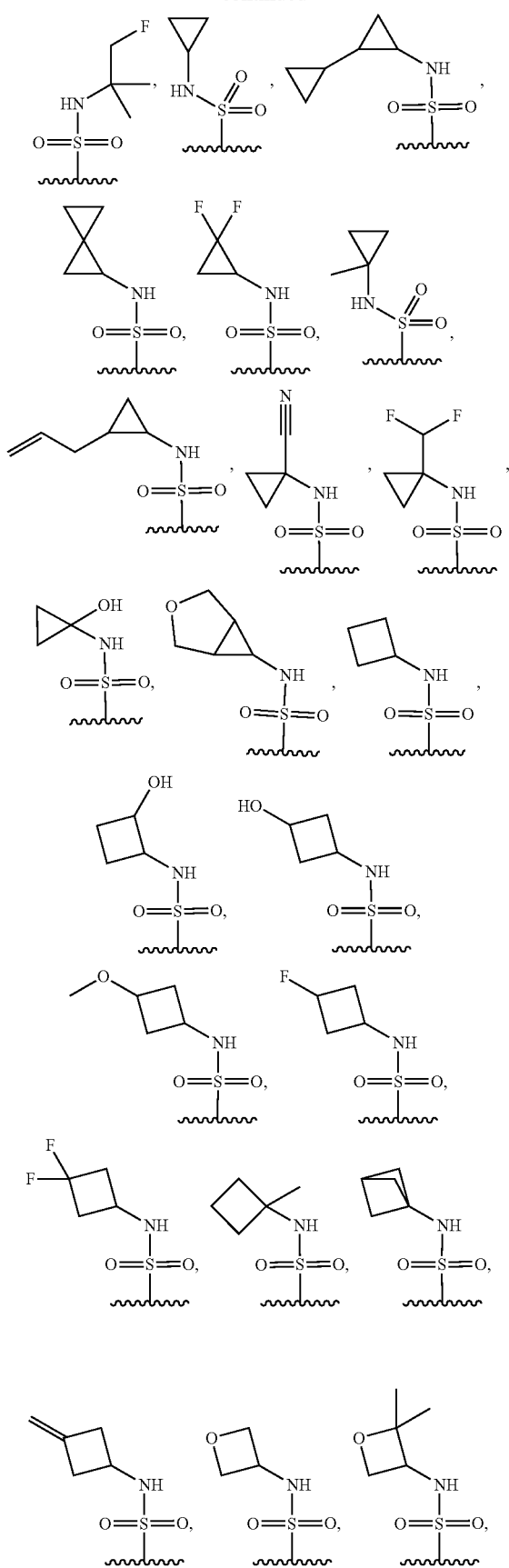
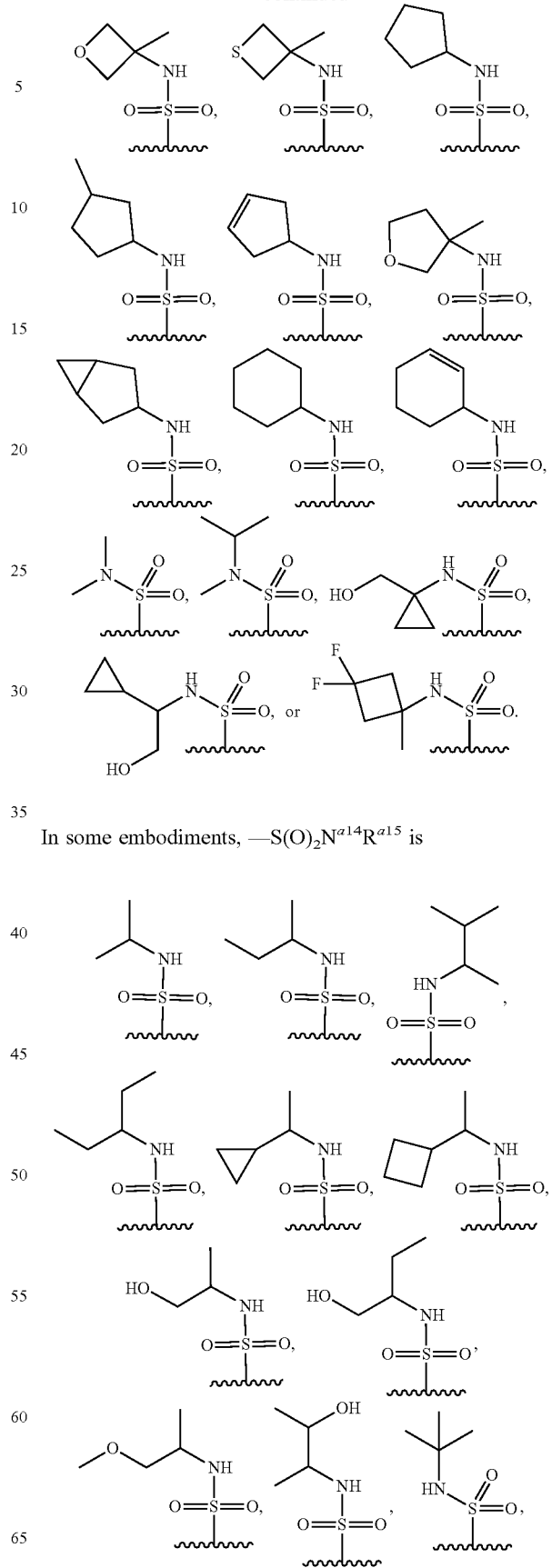
In some embodiments, $-S(O)_2N^{a14}R^{a15}$ is

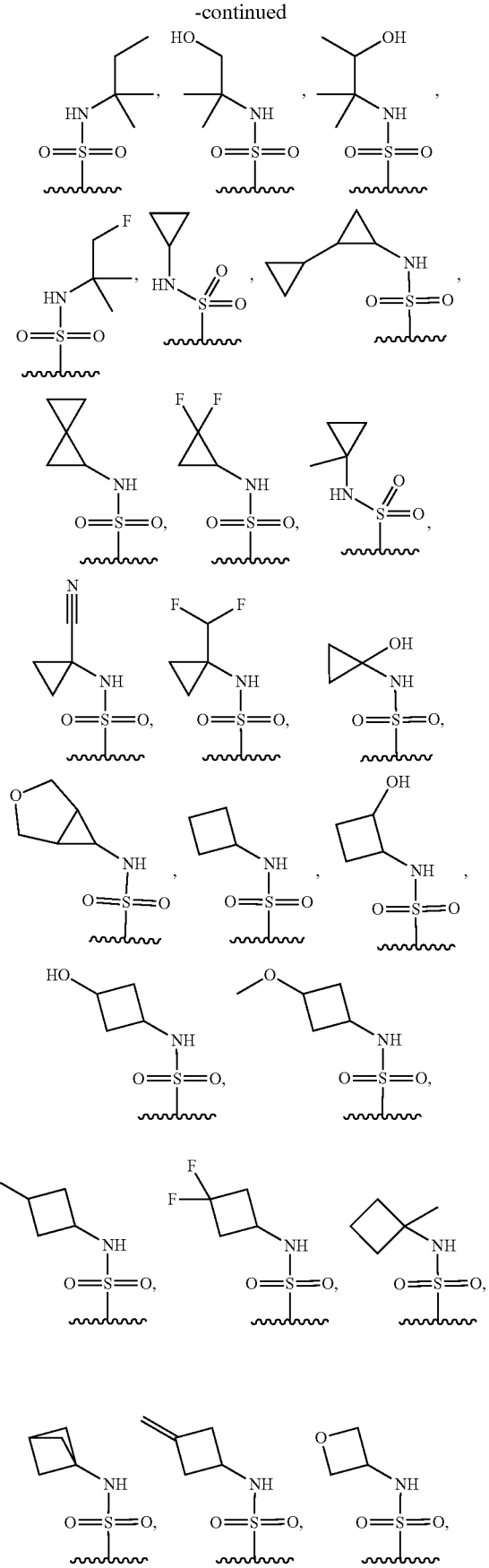
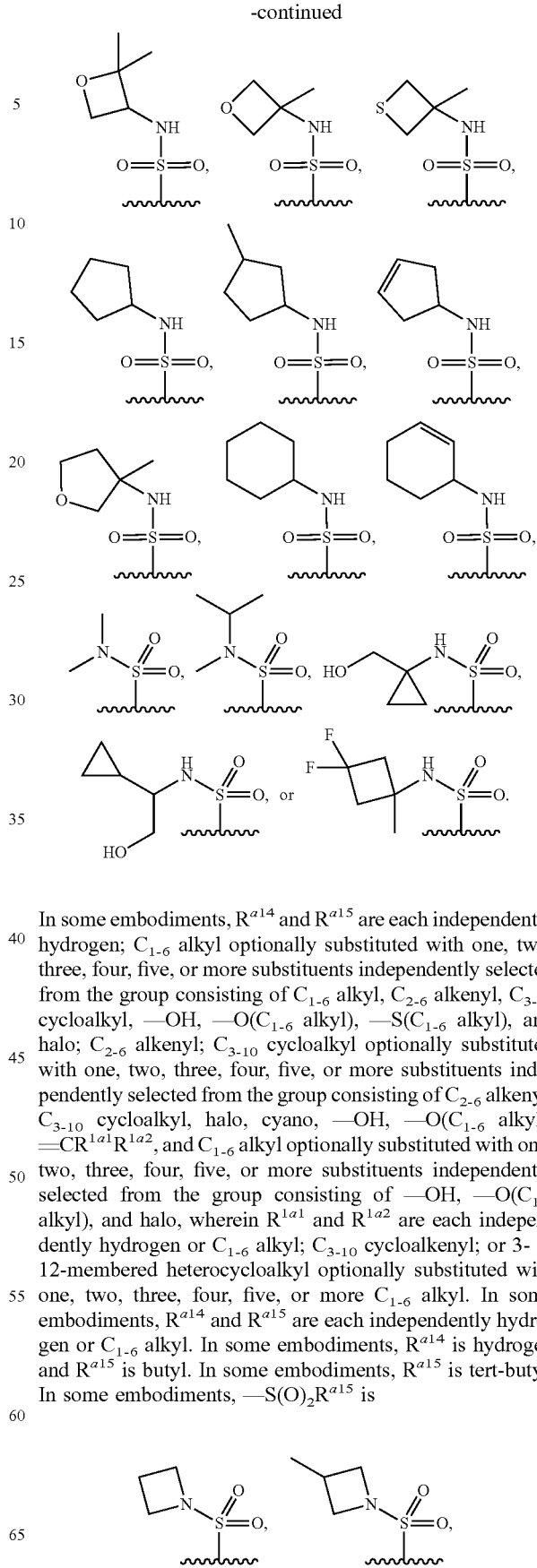

In some embodiments, $R^{a14}$ and $R^{a15}$ are each independently hydrogen; $C_{1-6}$ alkyl optionally substituted with one, two, three, four, five, or more substituents independently selected from the group consisting of $C_{1-6}$ alkyl, $C_{2-6}$ alkenyl, $C_{3-10}$ cycloalkyl, —OH, —O($C_{1-6}$ alkyl), —S($C_{1-6}$ alkyl), and halo; $C_{2-6}$ alkenyl; $C_{3-10}$ cycloalkyl optionally substituted with one, two, three, four, five, or more substituents independently selected from the group consisting of $C_{2-6}$ alkenyl, $C_{3-10}$ cycloalkyl, halo, cyano, —OH, —O($C_{1-6}$ alkyl), =$CR^{1a1}R^{1a2}$, and $C_{1-6}$ alkyl optionally substituted with one, two, three, four, five, or more substituents independently selected from the group consisting of —OH, —O($C_{1-6}$ alkyl), and halo, wherein $R^{1a1}$ and $R^{1a2}$ are each independently hydrogen or $C_{1-6}$ alkyl; $C_{3-10}$ cycloalkenyl; or 3- to 12-membered heterocycloalkyl optionally substituted with one, two, three, four, five, or more $C_{1-6}$ alkyl. In some embodiments, $R^{a14}$ and $R^{a15}$ are each independently hydrogen or $C_{1-6}$ alkyl. In some embodiments, $R^{a14}$ is hydrogen and $R^{a15}$ is butyl. In some embodiments, $R^{a15}$ is tert-butyl. In some embodiments, —S(O)$_2R^{a15}$ is -continued

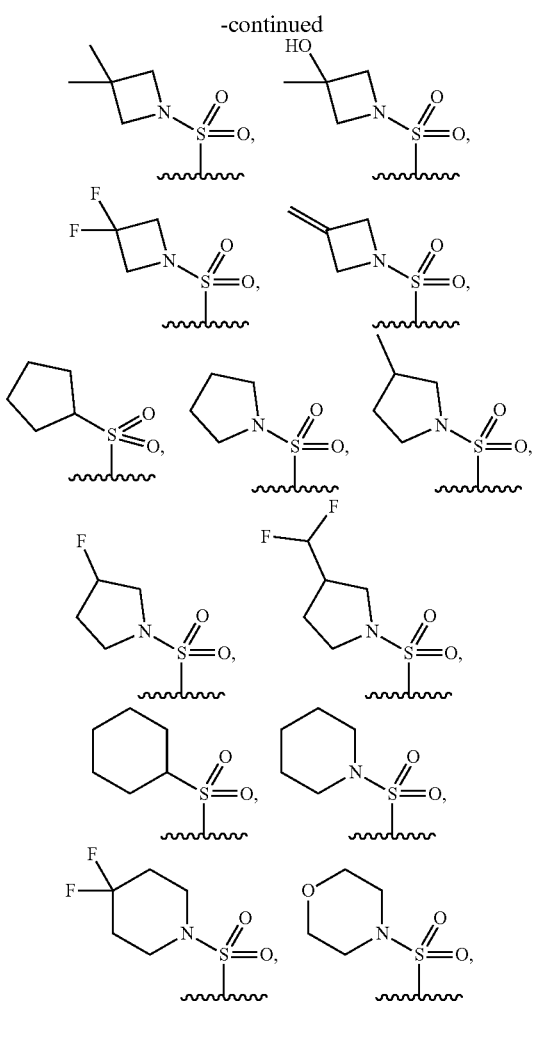

In some embodiments, —S(O)$_2$R$^{a16}$ is

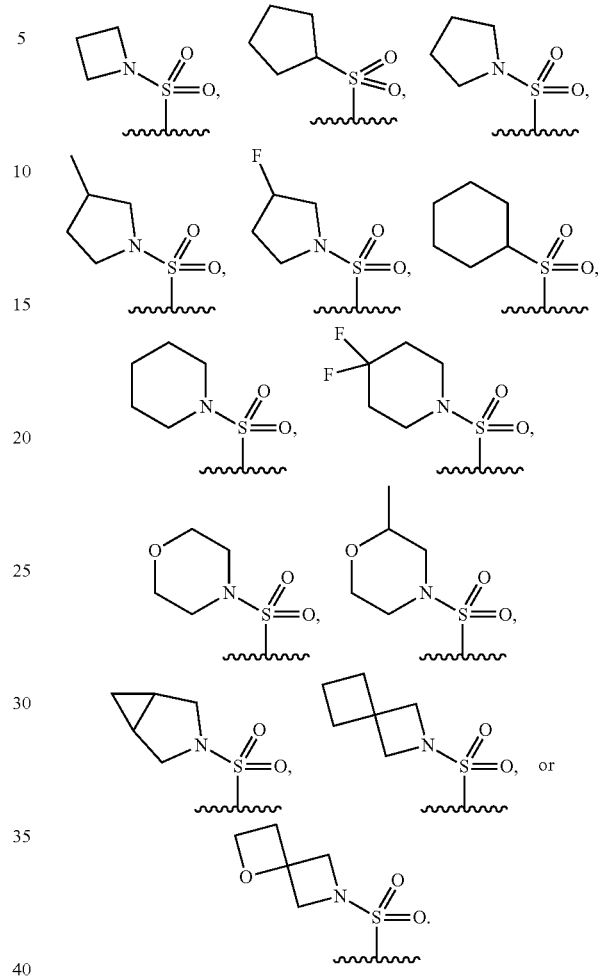

In some embodiments, R$^{a16}$ is C$_{3-10}$ cycloalkyl; or 3- to 12-membered heterocycloalkyl optionally substituted with one, two, three, four, five, or more substituents independently selected from the group consisting of C$_{1-6}$ alkyl or halo. In some embodiments, —(CR$^{a17}$R$^{a18}$)$_{0-1}$C(O) NR$^{a19}$R$^{a20}$ is —C(O)NR$^{a19}$R$^{a20}$ or —(CR$^{a17}$R$^{a18}$)C(O) NR$^{a19}$R$^{a20}$. In some embodiments, —(CR$^{a17}$R$^{a18}$)$_{0-1}$C(O) NR$^{a19}$R$^{a20}$ is —C(O)NR$^{a19}$R$^{a20}$. In some embodiments, —(CR$^{a17}$R$^{a18}$)$_{0-1}$C(O)NR$^{a19}$R$^{a20}$ is —(CR$^{a17}$R$^{a18}$)C(O) NR$^{a19}$R$^{a20}$. In some embodiments, R$^{a17}$ and R$^{a18}$ are each independently hydrogen or C$_{1-6}$ alkyl. In some embodiments, R$^{a17}$ and R$^{a18}$ are each hydrogen. In some embodiments, R$^{a19}$ and R$^{a20}$ are each independently hydrogen, C$_{1-6}$ alkyl, or C$_{3-10}$ cycloalkyl. In some embodiments, R$^{a19}$ and R$^{a20}$ are each independently hydrogen or cyclopropyl. In some embodiments, —SR$^{a21}$ is

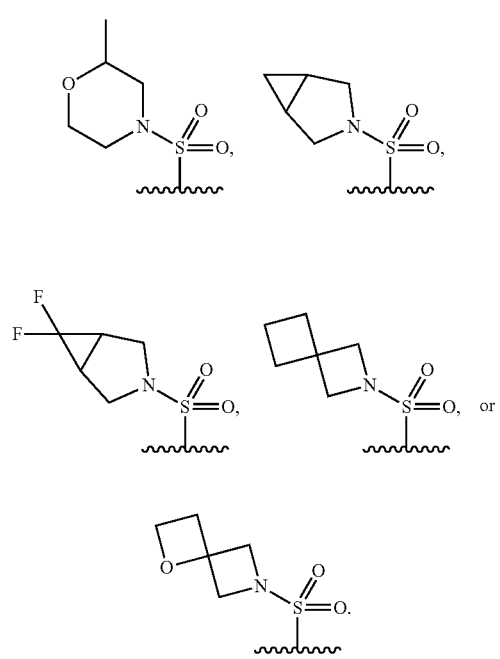

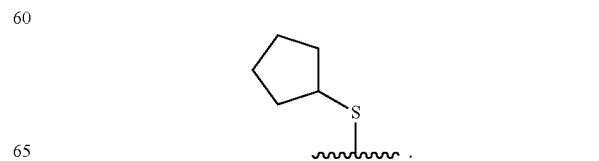

In some embodiments, $R^{a21}$ is $C_{3-10}$ cycloalkyl. In some embodiments, $-C(O)R^{a22}$ is

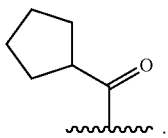 [SMILES: *C(=O)C1CCCC1]

In some embodiments, $R^{a22}$ is $C_{3-10}$ cycloalkyl. In some embodiments, the optionally substituted $C_{1-6}$ alkyl is

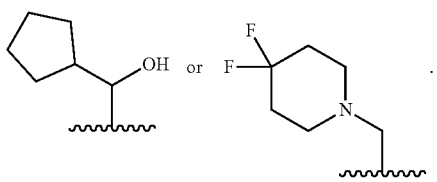 [SMILES: *C(O)C1CCCC1 ; *CN1CCC(F)(F)CC1]

In some embodiments, $C_{1-6}$ alkyl is optionally substituted with one, two, three, four, five, or more substituents independently selected from the group consisting of —OH, cyano, $C_{3-10}$ cycloalkyl, and 3- to 10-membered heterocycloalkyl optionally substituted with one, two, three, four, five, or more halo. In some embodiments, the 3- to 10-membered heterocycloalkyl is piperidinyl optionally substituted with one, two, three, four, five, or more halo. In some embodiments, the 3- to 10-membered heterocycloalkyl is optionally substituted with one, two, three, four, five, or more fluoro. In some embodiments, the 3- to 10-membered heterocycloalkyl is piperidinyl optionally substituted with one, two, three, four, five, or more fluoro.

In some embodiments, ring A is substituted with one or more substituents independently selected from the group consisting of fluoro, chloro, —OH, amino,

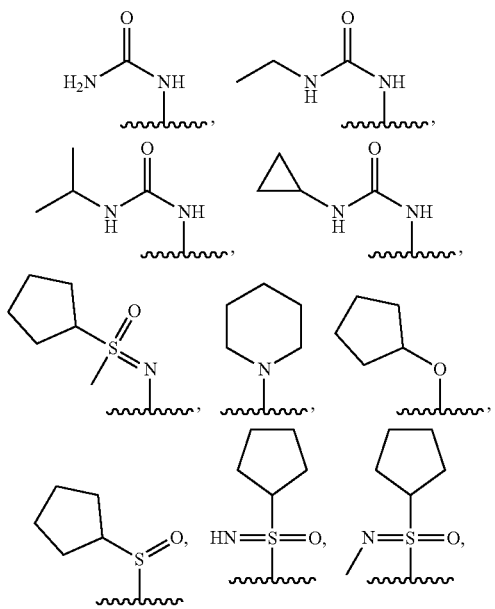

-continued

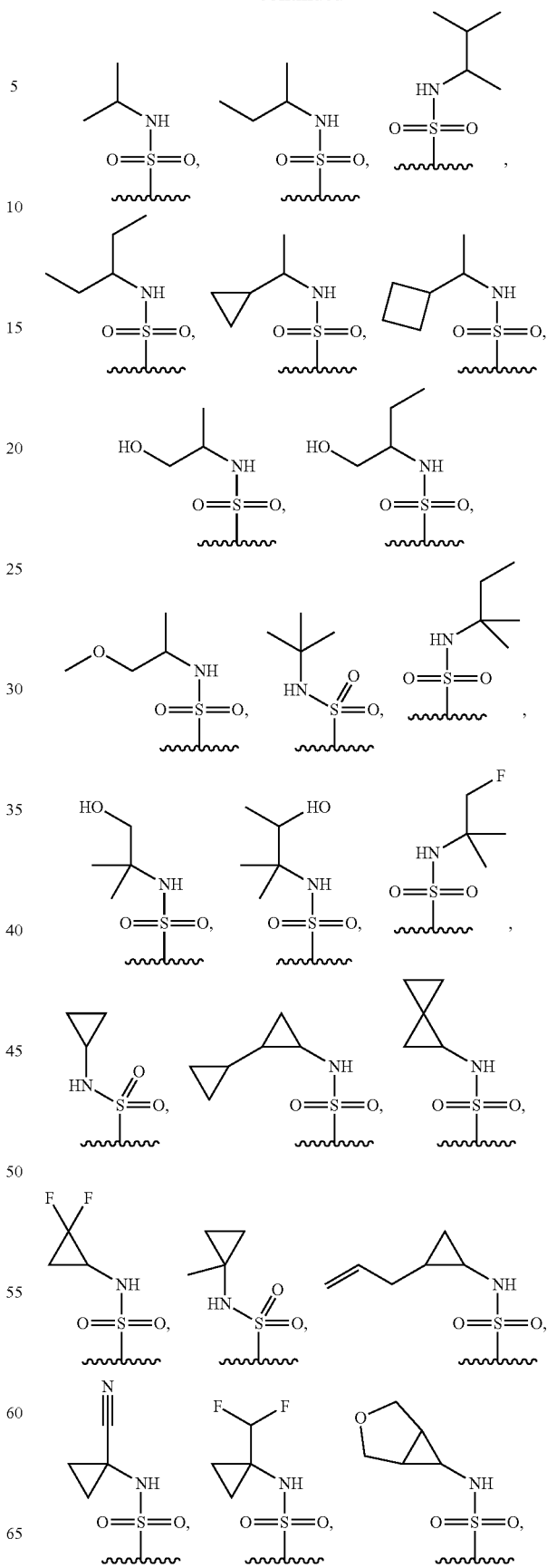

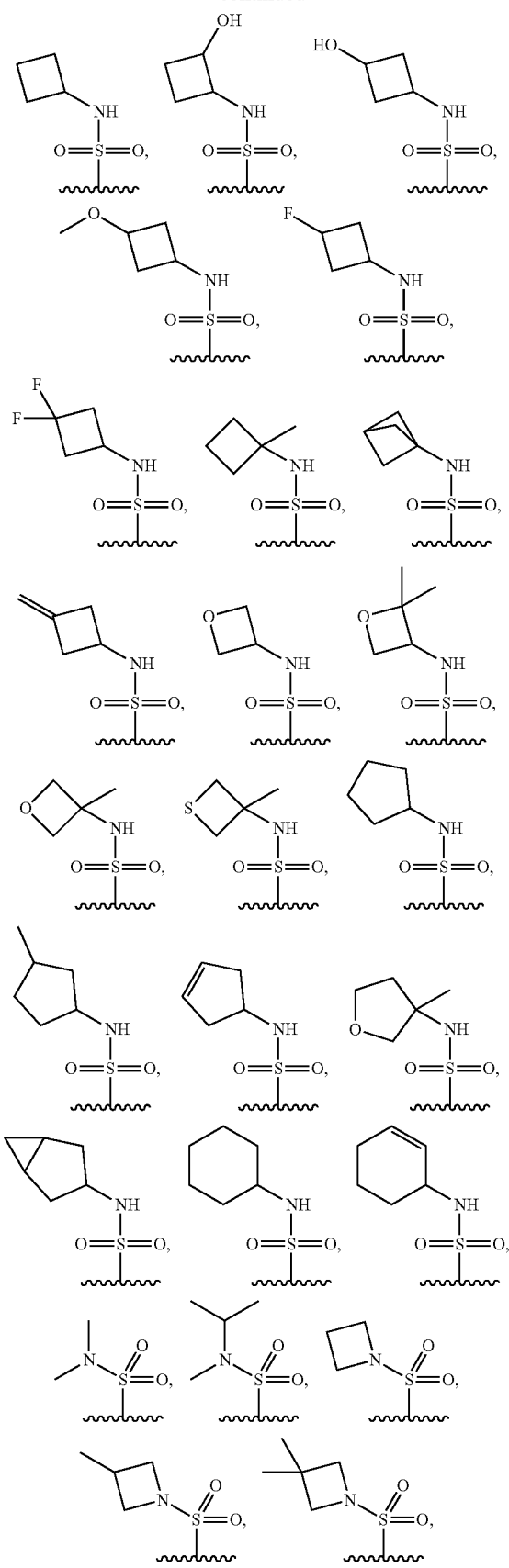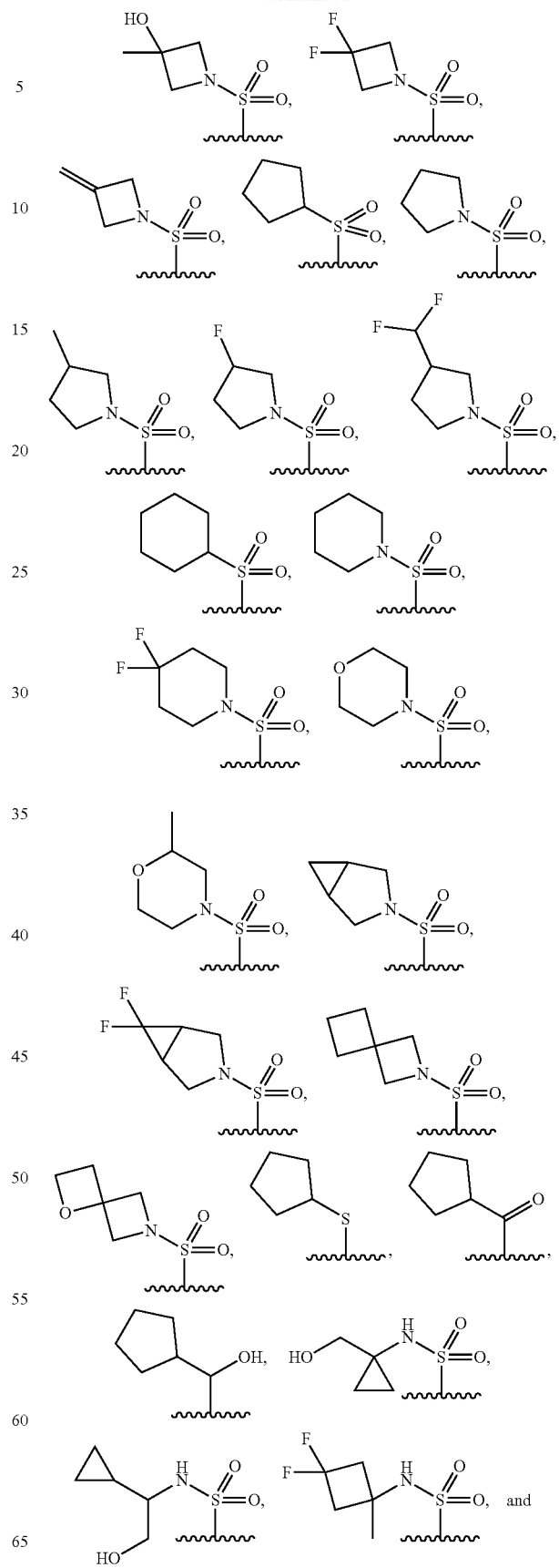

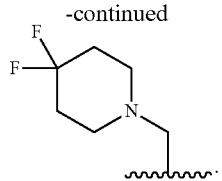
In some embodiments, ring A is optionally substituted with one, two, three, four, five, or more substituents independently selected from the group consisting of fluoro, chloro, —OH amino,
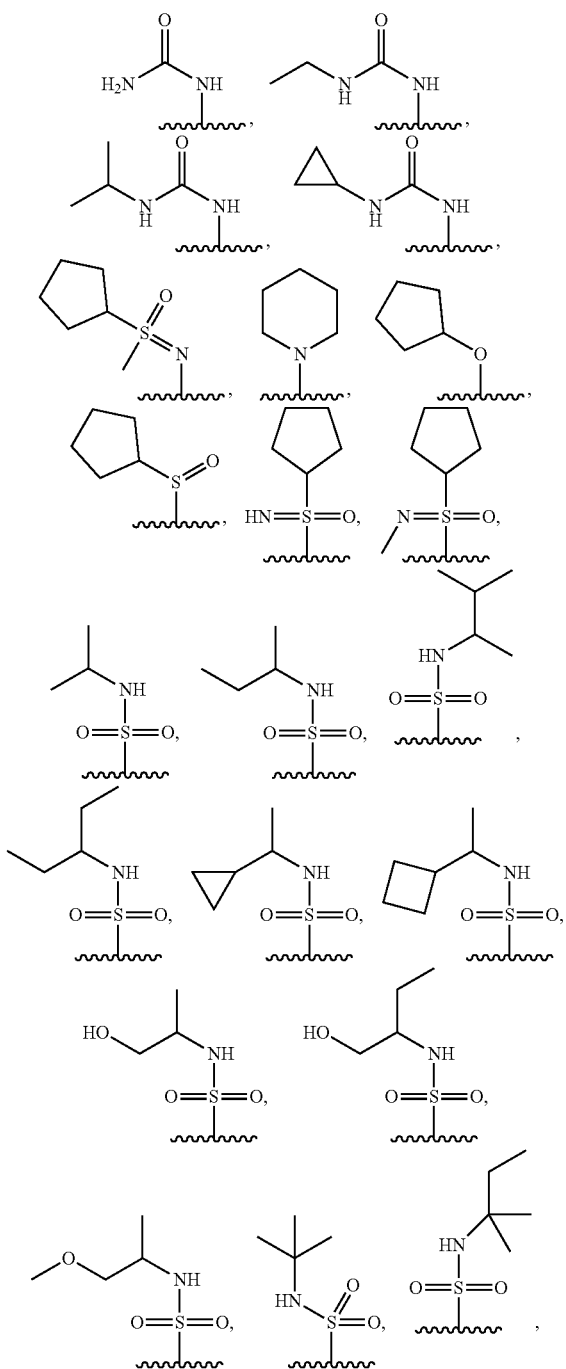
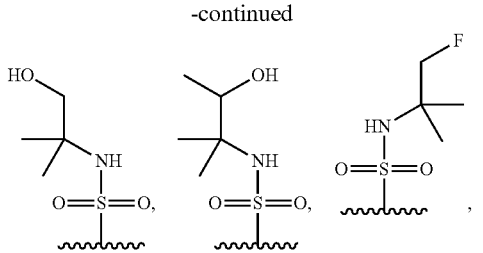
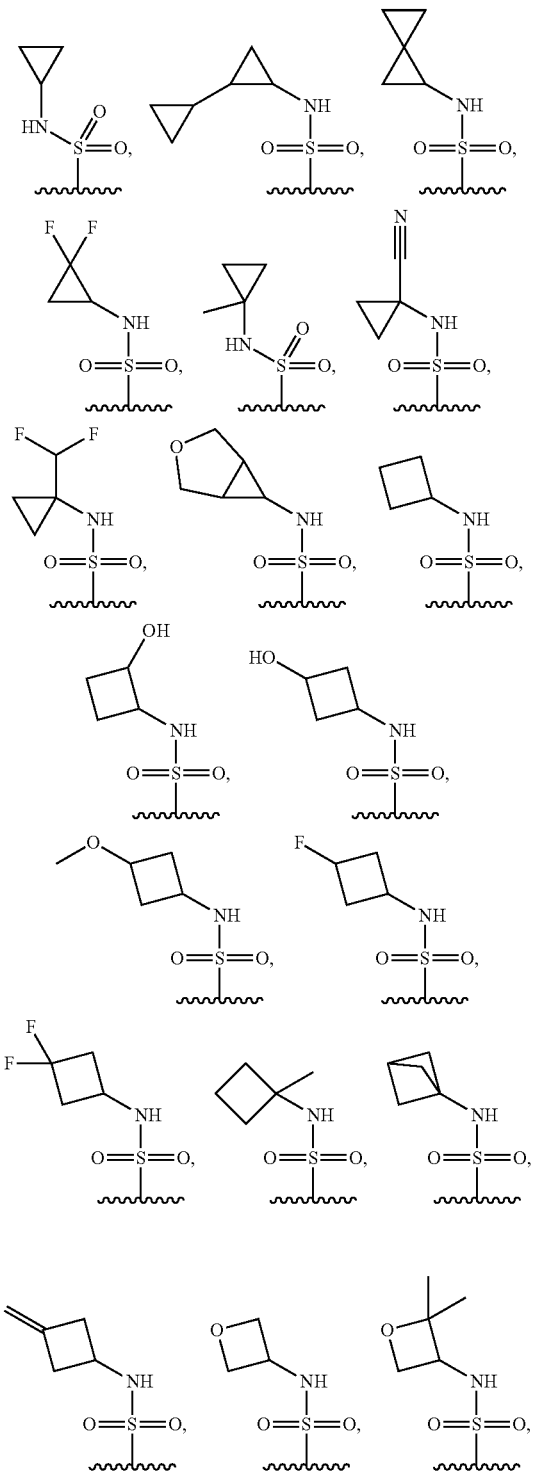

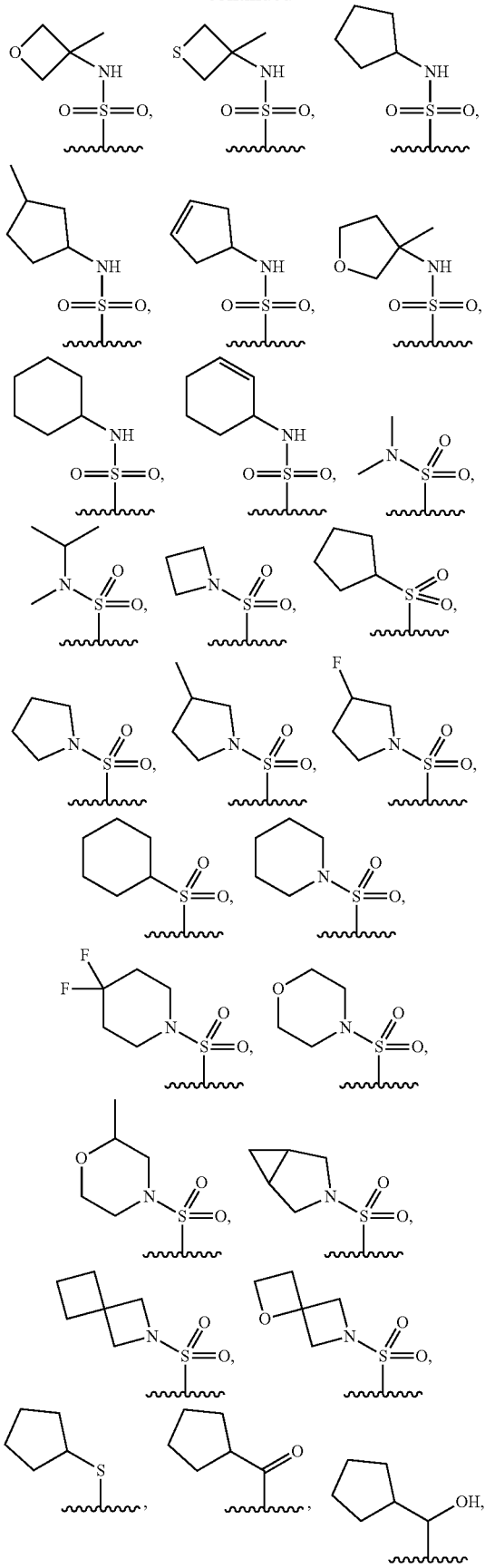

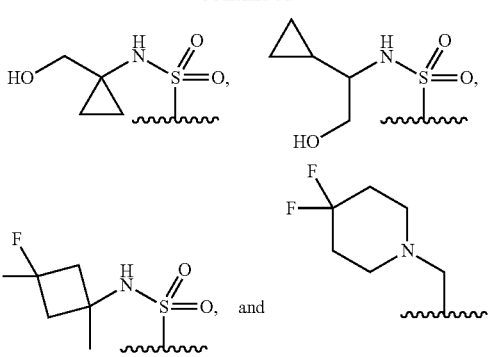

In some embodiments of Formula (I), Formula (I-1), Formula (I-2), and Formula (I-3), or a pharmaceutically acceptable salt thereof, ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon. In some embodiments, ring B is $C_{5-7}$ cycloalkyl. In some embodiments, ring B is cyclopentyl, cyclohexyl, or cycloheptyl. In some embodiments, ring B is

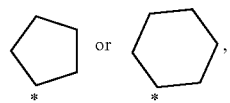

wherein * denotes the point of attachment to the rest of Formula (I), Formula (I-1), Formula (I-2), or Formula (I-3). In some embodiments, ring B is $C_{5-7}$ cycloalkenyl. In some embodiments, ring B is cyclopentenyl, cyclohexenyl, or cycloheptenyl. In some embodiments, ring B is

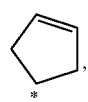

wherein * denotes the point of attachment to the rest of Formula (I), Formula (I-1), Formula (I-2), or Formula (I-3). In some embodiments, ring B is

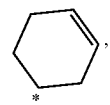

wherein * denotes the point of attachment to the rest of Formula (I), Formula (I-1), Formula (I-2), or Formula (I-3). In some embodiments, ring B is 5- to 7-membered heterocycloalkyl. In some embodiments, ring B is 5- to 7-membered heterocycloalkyl wherein one or two of the ring atoms are each oxygen and the remaining ring atoms are each carbon. In embodiments, ring B is tetrahydrofuranyl or 1,3-dioxanyl. In some embodiments, ring B is

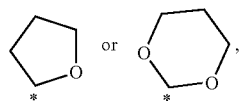

wherein * denotes the point of attachment to the rest of Formula (I), Formula (I-1), Formula (I-2), or Formula (I-3).

In some embodiments, ring B is substituted with m $R^B$ groups, wherein each $R^B$ group is independently halo, $C_{1-6}$ alkyl optionally substituted with one, two, three, four, five, or more halo, or $C_{2-6}$ alkenyl; or two vicinal $R^B$ groups are taken together with the carbon atoms to which they are attached to form $C_{3-10}$ cycloalkyl; or two geminal $R^B$ groups are taken together with the carbon atom to which they are attached to form $C_{3-10}$ cycloalkyl. In some embodiment, an $R^B$ group is methyl or ethyl. In some embodiment, two vicinal $R^B$ groups are taken together with the carbon atoms to which they are attached to form cyclopropyl. In some embodiments, two geminal $R^B$ groups are taken together with the carbon atom to which they are attached to form cyclopropyl.

In some embodiments, m is 0, 1, 2, 3, or 4. In some embodiments, m is 0, 1, 2, or 3. In some embodiments, m is 0, 1, or 2. In some embodiments, m is 0 or 1. In some embodiments, m is 0. In some embodiments, m is 1.

In some embodiments,

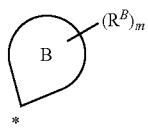

of Formula (I), Formula (I-1), Formula (I-2), or Formula (I-3), is

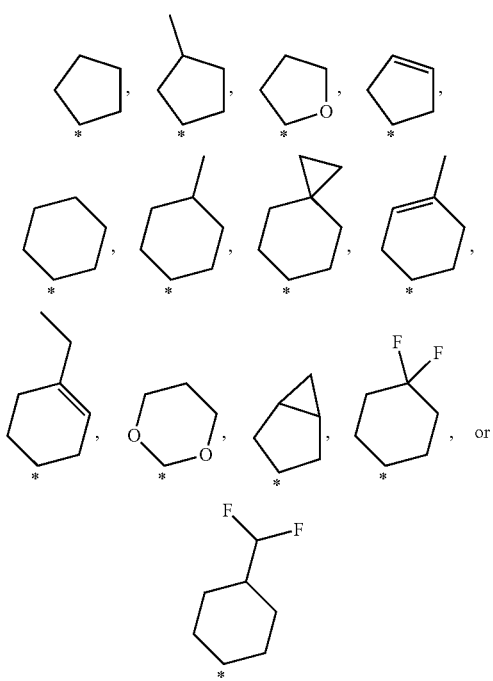

wherein * denotes the point of attachment to the rest of Formula (I), Formula (I-1), Formula (I-2), or Formula (I-3). In some embodiments,

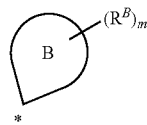

of Formula I is

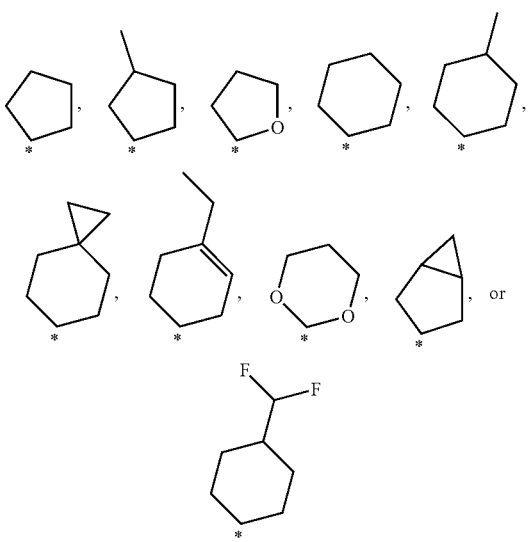

wherein * denotes the point of attachment to the rest of Formula (I), Formula (I-1), Formula (I-2), or Formula (I-3).

In some embodiments of Formula (I), Formula (I-1), Formula (I-2), and Formula (I-3), or a pharmaceutically acceptable salt thereof, $Y^1$ is N or $CR^{C1}$; $Y^2$ is N or $CR^{C2}$; $Y^3$ is N or $CR^{C3}$; and $Y^4$ is N or $CR^{C4}$. In some embodiments, no more than three of $Y^1$, $Y^2$, $Y^3$, and $Y^4$ are N. In some embodiments, no more than two of $Y^1$, $Y^2$, $Y^3$, and $Y^4$ are N. In some embodiments, no more than one of $Y^1$, $Y^2$, $Y^3$, and $Y^4$ is N. In some embodiments, $Y^1$ is $CR^{C1}$; $Y^2$ is $CR^{C2}$; $Y^3$ is $CR^{C3}$; and $Y^4$ is $CR^{C4}$. In some embodiments, $Y^1$ is N; $Y^2$ is $CR^{C2}$; $Y^3$ is $CR^{C3}$; and $Y^4$ is $CR^{C4}$ In some embodiments, $Y^1$ is $CR^{C1}$; $Y^2$ is N; $Y^3$ is $CR^{C3}$; and $Y^4$ is $CR^{C4}$.

In some embodiments, $R^{C1}$-$R^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or $C_{1-6}$ alkyl optionally substituted with one, two, three, four, five, or more substituents independently selected from the group consisting of halo and —OH. In some embodiments, $R^{c1}$-$R^{c18}$ are each independently hydrogen, $C_{3-10}$ cycloalkyl, or $C_{1-6}$ alkyl optionally substituted with one, two, three, four, five, or more substituents independently selected from the group consisting of halo and —OH.

In some embodiments, $R^{C1}$-$R^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)

$OR^{c15}$, or $C_{1-6}$ alkyl optionally substituted with one, two, three, four, five, or more substituents independently selected from the group consisting of halo and —OH. In some embodiments, $R^{c1}$-$R^{c15}$ are each independently hydrogen, $C_{3-10}$ cycloalkyl, or $C_{1-6}$ alkyl optionally substituted with one, two, three, four, five, or more substituents independently selected from the group consisting of halo and —OH.

In some embodiments, $R^{C1}$ is hydrogen or halo. In some embodiments, $R^{C1}$ is hydrogen or fluoro. In some embodiments, $R^{C3}$ is hydrogen. In some embodiments, $R^{C4}$ is hydrogen or —NH$_2$. In some embodiments, $R^{C1}$, $R^{C3}$, and $R^{C4}$ are each independently hydrogen, halo, or —NH$_2$.

In some embodiments, $R^{C2}$ is cyano, —OH, —CH$_2$OH, bromo, —NO$_2$,

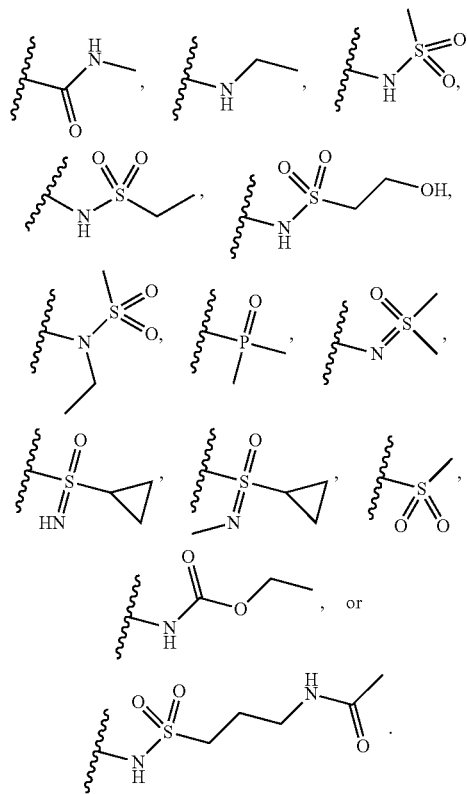

In some embodiments, $R^{C2}$ is cyano, —OH, —CH$_2$OH, bromo, —NO$_2$,

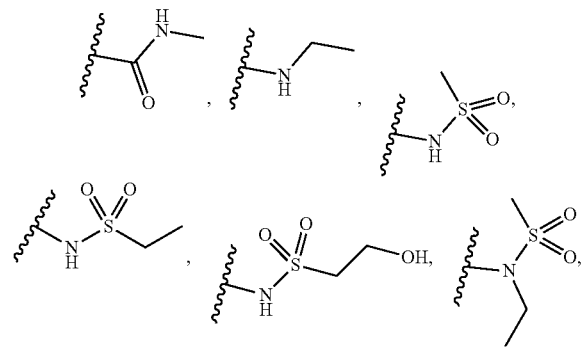

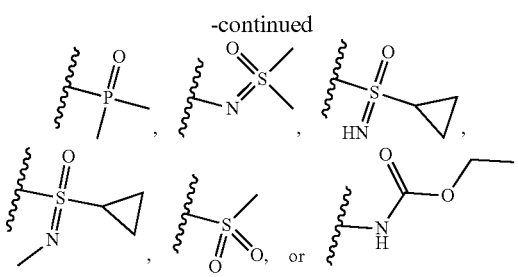

In some embodiments, $R^{C2}$ is cyano, —OH, halo, —NO$_2$, $C(O)NR^{c1}R^{c2}$, —$NR^{c3}R^{c4}$, —$NR^{c5}S(O)_2R^{c6}$, —$P(O)R^{c7}R^{c8}$, —$N=S(O)R^{c9}R^{c10}$, —$S(O)(NR^{c11})R^{c12}$, —$S(O)_2R^{c13}$, —$NR^{c14}C(O)OR^{c15}$, —$NR^{c16}S(O)_2(CH_2)_{1-6}NR^{c17}C(O)R^{c18}$, or $C_{1-6}$ alkyl optionally substituted with one, two, three, four, five, or more substituents independently selected from the group consisting of halo and —OH. In some embodiments, $R^{C2}$ is cyano, —OH, halo, —NO$_2$, $C(O)NR^{c1}R^{c2}$, —$NR^{c3}R^{c4}$, —$NR^{c5}S(O)_2R^{c6}$, —$P(O)R^{c7}R^{c8}$, —$N=S(O)R^{c9}R^{c10}$, —$S(O)(NR^{c11})R^{c12}$, —$S(O)_2R^{c13}$, —$NR^{c14}C(O)OR^{c15}$, or $C_{1-6}$ alkyl optionally substituted with one, two, three, four, five, or more substituents independently selected from the group consisting of halo and —OH.

In some embodiments, —$C(O)NR^{c1}R^{c2}$ is

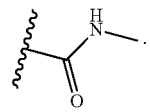 [SMILES: *C(=O)NC]

In some embodiments, $R^{c1}$ and $R^{c2}$ are each independently hydrogen or $C_{1-6}$ alkyl. In some embodiments, $R^{c1}$ and $R^{c2}$ are each independently hydrogen, methyl, or ethyl. In some embodiments, —$NR^{c3}R^{c4}$ is

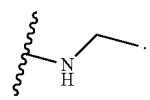

In some embodiments, $R^{c3}$ and $R^{c4}$ are each independently hydrogen or $C_{1-6}$ alkyl. In some embodiments, $R^{c1}$ and $R^{c2}$ are each independently hydrogen, methyl, or ethyl. In some embodiments, —$NR^{c5}S(O)_2R^{c6}$ is

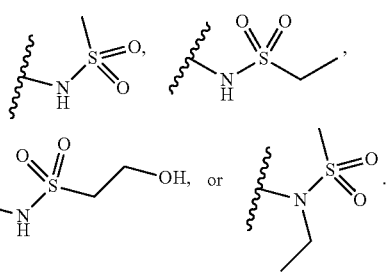

In some embodiments, $R^{c5}$ is hydrogen or $C_{1-6}$ alkyl. In some embodiments, $R^{c5}$ is hydrogen, methyl, or ethyl. In some embodiments, $R^{c6}$ is hydrogen or $C_{1-6}$ alkyl optionally substituted with one, two, three, four, five, or more substituents independently selected from halo and —OH. In some embodiments, $R^{c5}$ is methyl or —CH$_2$CH$_2$OH. In some embodiments, $R^{c5}$ is hydrogen. In some embodiments, $R^{c6}$ is ethyl. In some embodiments, —P(O)$R^{c7}R^{c8}$ is

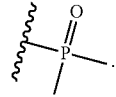

In some embodiments, $R^{c7}$ and $R^{c8}$ are each independently C$_{1-6}$ alkyl. In some embodiments, $R^{c7}$ and $R^{c8}$ are each methyl. In some embodiments, —N=S(O)$R^{c9}R^{c10}$ is

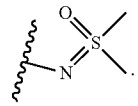

In some embodiments, $R^{c9}$ and $R^{c10}$ are each independently C$_{1-6}$ alkyl. In some embodiments, $R^{c9}$ and $R^{c10}$ are each methyl. In some embodiments, —S(O)(N$R^{c11}$)$R^{c12}$ is

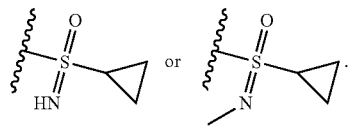

In some embodiments, $R^{c11}$ is hydrogen or C$_{1-6}$ alkyl. In some embodiments, $R^{c11}$ is hydrogen or methyl. In some embodiments, $R^{c12}$ is C$_{1-6}$ alkyl or C$_{3-10}$ cycloalkyl. In some embodiments, $R^{c12}$ is cyclopropyl. In some embodiments, —S(O)$_2R^{c13}$ is

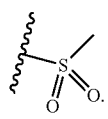

In some embodiments, $R^{c13}$ is C$_{1-6}$ alkyl. In some embodiments, $R^{c13}$ is methyl. In some embodiments, N$R^{c14}$C(O)O$R^{c15}$ is

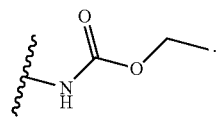

In some embodiments, $R^{c14}$ and $R^{c15}$ are each independently hydrogen or C$_{1-6}$ alkyl. In some embodiments, $R^{c14}$ is hydrogen. In some embodiments, $R^{c15}$ is ethyl. In some embodiments, —N$R^{c16}$S(O)$_2$(CH$_2$)$_{1-6}$N$R^{c17}$C(O)$R^{c18}$ is

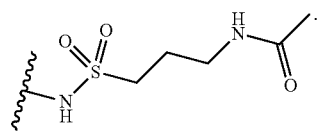 [SMILES: *NS(=O)(=O)CCCNC(C)=O]

In some embodiments, —N$R^{c16}$S(O)$_2$(CH$_2$)$_{1-6}$N$R^{c17}$C(O)$R^{c18}$ is —N$R^{c16}$S(O)$_2$(CH$_2$)$_{1-3}$N$R^{c17}$C(O)$R^{c18}$. In some embodiments, $R^{c16}$, $R^{c17}$ and $R^{c18}$ are each independently hydrogen or C$_{1-6}$ alkyl. In some embodiments, $R^{c16}$ and $R^{c17}$ are hydrogen. In some embodiments, $R^{c18}$ is methyl.

In one aspect, provided are compounds of Formula (Ia1):

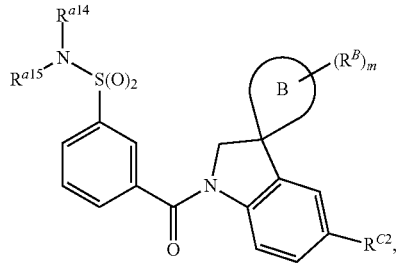

(Ia1)

or a pharmaceutically acceptable salt thereof, wherein $R^{a14}$, $R^{a15}$, ring B, $R^B$, m, and $R^{C2}$ are as defined for Formula (I) or any variation or embodiment thereof. In some embodiments, $R^{C2}$ is halo, cyano, —OH, —NO$_2$, —C(O)N$R^{c1}R^{c2}$, —N$R^{c3}R^{c4}$, —N$R^{c5}$S(O)$_2R^{c6}$, —P(O)$R^{c7}R^{c8}$, —N=S(O)$R^{c9}R^{c10}$, —S(O)(N$R^{c11}$)$R^{c12}$, —S(O)$_2R^{c13}$, —N$R^{c14}$C(O)O$R^{c15}$, —N$R^{c16}$S(O)$_2$(CH$_2$)$_{1-6}$N$R^{c17}$C(O)$R^{c18}$ or C$_{1-6}$ alkyl optionally substituted with one or more substituents independently selected from the group consisting of halo and —OH. In some embodiments, $R^{C2}$ is halo, cyano, —OH, —NO$_2$, —C(O)N$R^{c1}R^{c2}$, —N$R^{c3}R^{c4}$, —N$R^{c5}$S(O)$_2R^{c6}$, —P(O)$R^{c7}R^{c8}$, —N=S(O)$R^{c9}R^{c10}$, —S(O)(N$R^{c11}$)$R^{c12}$, —S(O)$_2R^{c13}$, or C$_{1-6}$ alkyl optionally substituted with one or more substituents independently selected from the group consisting of halo and —OH. In some embodiments, $R^{C2}$ is —N$R^{c5}$S(O)$_2R^{c6}$. In some embodiments, $R^{c5}$ is hydrogen and $R^{C6}$ is C$_{1-6}$ alkyl. In some embodiments, $R^{c5}$ is hydrogen and $R^{c6}$ is ethyl. In some embodiments, $R^{c5}$ is hydrogen. In some embodiments, $R^{c6}$ is ethyl. In some embodiments, $R^{c6}$ is methyl. In some embodiments, $R^{a14}$ is hydrogen and $R^{a15}$ is C$_{1-6}$ alkyl. In some embodiments, $R^{a14}$ is hydrogen and $R^{a15}$ is tert-butyl. In some embodiments, $R^{a14}$ is hydrogen. In some embodiments, $R^{a15}$ is tert-butyl. In some embodiments, ring B is

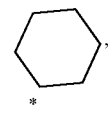

wherein * denotes the point of attachment to the rest of Formula (Ia1). In some embodiments,

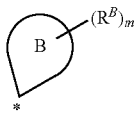

of Formula (Ia1) is

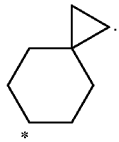

In one aspect, provided are compounds of Formula (Ia2):

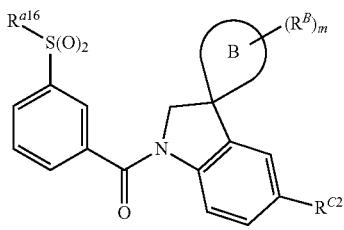

(Ia2)

or a pharmaceutically acceptable salt thereof, wherein $R^{a16}$, ring B, $R^B$, m, and $R^{C2}$ are as defined for Formula (I) or any variation or embodiment thereof. In some embodiments, $R^{C2}$ is halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$—S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or C$_{1-6}$ alkyl optionally substituted with one or more substituents independently selected from the group consisting of halo and —OH. In some embodiments, $R^{C2}$ is halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, or C$_{1-6}$ alkyl optionally substituted with one or more substituents independently selected from the group consisting of halo and —OH.

In some embodiments, ring B is not

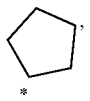

wherein * denotes the point of attachment to the rest of Formula (I). In some embodiments, $R^{C1}$ is not fluoro. In some embodiments, $R^{C2}$ is not hydrogen. In some embodiments, ring B is not

wherein * denotes the point of attachment to the rest of Formula (I); or $R^{C1}$ is not fluoro; or $R^{C2}$ is not hydrogen.

In some embodiments, the compound is not 4'-fluoro-1'-[3-(piperidine-1-sulfonyl)benzoyl]-1',2'-dihydrospiro[cyclopentane-1,3'-indole]; 3-cyclopropyl-1-[3-({4'-fluoro-1',2'-dihydrospiro[cyclopentane-1,3'-indol]-1'-yl}carbonyl)phenyl]urea; 1-[3-({4'-fluoro-1',2'-dihydrospiro[cyclopentane-1,3'-indol]-1'-yl}carbonyl)phenyl]-3-(propan-2-yl)urea; [4-({4'-fluoro-1',2'-dihydrospiro[cyclopentane-1,3'-indol]-1'-yl}carbonyl)phenyl]methanol; 4'-fluoro-1'-(1H-indole-5-carbonyl)-1',2'-dihydrospiro[cyclopentane-1,3'-indole]; N-[3-({4'-fluoro-1',2'-dihydrospiro[cyclopentane-1,3'-indol]-1'-yl}carbonyl)phenyl]pyrimidin-2-amine; 4'-fluoro-1'-[3-(morpholine-4-sulfonyl)benzoyl]-1',2'-dihydrospiro[cyclopentane-1,3'-indole]; or [3-({4'-fluoro-1',2'-dihydrospiro[cyclopentane-1,3'-indol]-1'-yl}carbonyl)phenyl]urea.

In some embodiments, the compound is not a salt of 4'-fluoro-1'-[3-(piperidine-1-sulfonyl)benzoyl]-1',2'-dihydrospiro[cyclopentane-1,3'-indole]; 3-cyclopropyl-1-[3-({4'-fluoro-1',2'-dihydrospiro[cyclopentane-1,3'-indol]-1'-yl}carbonyl)phenyl]urea; 1-[3-({4'-fluoro-1',2'-dihydrospiro[cyclopentane-1,3'-indol]-1'-yl}carbonyl)phenyl]-3-(propan-2-yl)urea; [4-({4'-fluoro-1',2'-dihydrospiro[cyclopentane-1,3'-indol]-1'-yl}carbonyl)phenyl]methanol; 4'-fluoro-1'-(1H-indole-5-carbonyl)-1',2'-dihydrospiro[cyclopentane-1,3'-indole]; N-[3-({4'-fluoro-1',2'-dihydrospiro[cyclopentane-1,3'-indol]-1'-yl}carbonyl)phenyl]pyrimidin-2-amine; 4'-fluoro-1'-[3-(morpholine-4-sulfonyl)benzoyl]-1',2'-dihydrospiro[cyclopentane-1,3'-indole]; or [3-({4'-fluoro-1',2'-dihydrospiro[cyclopentane-1,3'-indol]-1'-yl}carbonyl)phenyl]urea.

In another aspect, provided herein is a compound of Formula (II):

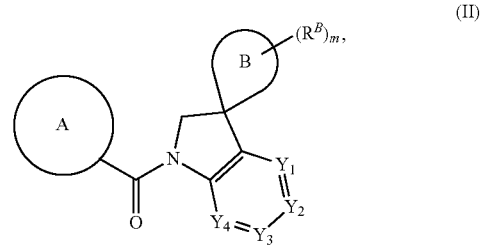

(II)

or a pharmaceutically acceptable salt thereof, wherein:
ring A is

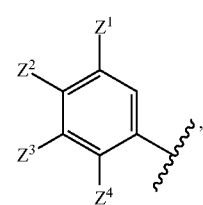

(i)

wherein $Z^1$, $Z^2$, $Z^3$, and $Z^4$ are each independently hydrogen or $R^D$, wherein $R^D$ is halo, —OH, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, —P(O)(R$^{a23}$)(R$^{a24}$), —C=NR$^{a25}$, or C$_{1-6}$ alkyl substituted with one or more substituents independently selected from the group consisting of —OH, cyano, C$_{3-10}$ cycloalkyl, and 3- to 10-membered heterocycloalkyl optionally substituted with one or more halo or C$_{1-3}$ alkyl, provided that (1) when Z$^4$ is hydrogen, then at least one of Z$^1$ and Z$^3$ is R$^D$; and (2) when Z$^4$ is R$^D$, then Z$^1$ is R$^D$, or

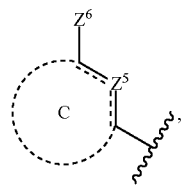

(ii)

wherein

⌿ is a single bond or a double bond,

Z$^5$ is C—H, N, O, S, or N—X, wherein X is H or C$_{1-6}$alkyl.

Z$^6$ is —NR$^{a26}$C(O)NR$^{a27}$R$^{a28}$, —NR$^{a29}$C(O)OR$^{a30}$, —N=S(O)R$^{a31}$R$^{a32}$, —S(O)R$^{a33}$, —S(O)(NR$^{a34}$)R$^{a35}$, —S(O)$_2$NR$^{a36}$R$^{a37}$, —S(O)$_2$R$^{a38}$, —SR$^{a39}$, —C(O)R$^{a40}$, 3- to 10-membered heterocycloalkyl, or —CH(Z$^7$)(Z$^8$), wherein Z$^7$ is hydrogen or —OH, and Z$^8$ is C$_{1-6}$ alkyl, C$_{3-10}$ cycloalkyl optionally substituted with one or more halo, or 3- to 10-membered heterocycloalkyl optionally substituted with one or more halo, and ring C is 5- to 6-membered heteroaryl optionally substituted with one or more R$^E$ substituents, wherein each R$^E$ substituent is independently selected from the group consisting of halo, —OH, and C$_{1-6}$ alkyl, or two R$^E$ substituents are taken, together with the atoms to which they are attached, to form C$_{5-6}$ cycloalkyl, C$_{5-6}$ cycloalkenyl, 5- to 6-membered heterocycloalkyl, 5- to 6-membered heterocycloalkenyl, or 5- to 6-membered heteroaryl;

R$^{a4}$-R$^{a40}$ are each independently hydrogen, C$_{1-6}$ alkyl, C$_{2-6}$ alkenyl, C$_{3-10}$ cycloalkyl, C$_{3-10}$ cycloalkenyl, 3- to 10-membered heterocycloalkyl, 3- to 10-membered heterocycloalkenyl, C$_{6-14}$ aryl, or 5- to 12-membered heteroaryl, each optionally substituted with one or more substituents independently selected from the group consisting of halo, cyano, —OH, —O(C$_{1-6}$ alkyl), C$_{2-6}$ alkenyl, C$_{3-10}$ cycloalkyl, —S(C$_{1-6}$ alkyl), =CR$^{1a1}$R$^{1a2}$, and C$_{1-6}$ alkyl optionally substituted with one or more substituents independently selected from the group consisting of halo, —OH, and —O(C$_{1-6}$ alkyl), wherein R$^{1a1}$ and R$^{1a2}$ are each independently hydrogen or C$_{1-6}$ alkyl;

ring B is C$_{5-7}$ cycloalkyl, C$_{5-7}$ cycloalkenyl, or 5- to 7-membered heterocycloalkyl wherein one or two of the ring atoms are each oxygen and the remaining ring atoms are each carbon;

each R$^B$ group is independently halo or C$_{1-6}$ alkyl optionally substituted with one or more halo; or two vicinal R$^B$ groups are taken together with the carbon atoms to which they are attached to form C$_{3-10}$ cycloalkyl; or two geminal R$^B$ groups are taken together with the carbon atom to which they are attached to form C$_{3-10}$ cycloalkyl; or two geminal R$^B$ groups are taken together to form a =CR$^{1a3}$R$^{1a4}$ group, wherein R$^{1a3}$ and R$^{1a4}$ are each independently hydrogen or C$_{1-6}$ alkyl;

m is 0, 1, 2, 3, or 4;

Y$^1$ is N or CR$^{C1}$;

Y$^2$ is N or CR$^{C2}$;

Y$^3$ is N or CR$^{C3}$;

Y$^4$ is N or CR$^{C4}$;

wherein no more than three of Y$^1$, Y$^2$, Y$^3$, and Y$^4$ are N;

R$^{C1}$-R$^{C4}$ are each independently hydrogen or R$^F$, wherein R$^F$ is halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, —O—S(O)$_2$R$^{c19}$, or C$_{1-6}$ alkyl substituted with one or more substituents independently selected from the group consisting of halo and —OH, and R$^{c1}$-R$^{c19}$ are each independently hydrogen, C$_{3-10}$ cycloalkyl, or C$_{1-6}$ alkyl optionally substituted with one or more substituents independently selected from the group consisting of halo, —O(C$_{1-6}$ alkyl), —NHC(O)(C$_{1-6}$ alkyl), and —OH;

provided that (1) when ring B is unsubstituted cyclopentyl, then ring A is

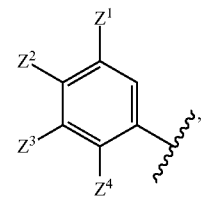

wherein at least one of Z$^1$-Z$^4$ is —S(O)$_2$-(3- to 10-membered heterocycloalkyl) substituted with one or more halo, (2) when ring B is unsubstituted cyclohexyl and ring A is

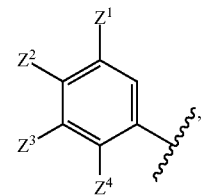

then at least one of R$^{C1}$-R$^{C4}$ is R$^F$, and (3) when ring B is 5- to 7-membered heterocycloalkyl optionally substituted with 1-4 R$^B$, then ring A is

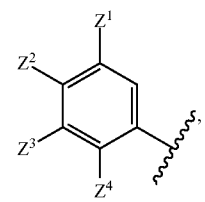

wherein at least one of Z$^1$-Z$^4$ is —S(O)$_2$-(3- to 10-membered heterocycloalkyl) optionally substituted with one or more halo.

In some embodiments of Formula (II), or a pharmaceutically acceptable salt thereof, with one, two, three, or four $Z^1$-$Z^4$ are independently selected from the group consisting of —$SR^{a21}$, —$C(O)R^{a22}$, and $C_{1-6}$ alkyl substituted with one, two, three, four, five, or more substituents independently selected from the group consisting of —OH, cyano, $C_{3-10}$ cycloalkyl, and 3- to 10-membered heterocycloalkyl optionally substituted with one, two, three, four, five, or more halo. In some embodiments, ring A is substituted with —$SR^{a21}$, —$C(O)R^{a22}$, or $C_{1-6}$ alkyl substituted with one, two, three, four, five, or more substituents independently selected from the group consisting of —OH, cyano, $C_{3-10}$ cycloalkyl, and 3- to 10-membered heterocycloalkyl optionally substituted with one, two, three, four, five, or more halo. In some embodiments, $R^{a21}$ and $R^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —$O(C_{1-6}$ alkyl), $C_{2-6}$ alkenyl, $C_{3-10}$ cycloalkyl, —$S(C_{1-6}$ alkyl), =$CR^{1a1}R^{1a2}$, and $C_{1-6}$ alkyl optionally substituted with one or more substituents independently selected from the group consisting of halo, —OH, and —$O(C_{1-6}$ alkyl), wherein $R^{1a1}$ and $R^{1a2}$ are each independently hydrogen or $C_{1-6}$ alkyl.

In some embodiments of Formula (II), or a pharmaceutically acceptable salt thereof, $Z^1$, $Z^2$, $Z^3$, and $Z^4$ are each independently hydrogen or $R^D$, wherein $R^D$ is halo, —OH, —$NR^{a4}C(O)OR^{a5}$, —$NR^{a6}R^{a7}$, —N=$S(O)R^{a8}R^{a9}$, —$OR^{a10}$, —$S(O)R^{a11}$, —$S(O)(NR^{a12})R^{a13}$, —$S(O)_2NR^{a14}R^{a15}$, —$S(O)_2R^{a16}$, —$(CR^{a17}R^{a18})_{0-1}C(O)NR^{a19}R^{a20}$, —$SR^{a21}$, —$C(O)R^{a22}$, —$P(O)(R^{a23})(R^{a24})$, —C=$NR^{a25}$, or $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo or $C_{1-3}$ alkyl, wherein $R^{a4}$-$R^{a25}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —$O(C_{1-6}$ alkyl), $C_{2-6}$ alkenyl, $C_{3-10}$ cycloalkyl, —$S(C_{1-6}$ alkyl), =$CR^{1a1}R^{1a2}$, and $C_{1-6}$ alkyl optionally substituted with one or more substituents independently selected from the group consisting of halo, —OH, and —$O(C_{1-6}$ alkyl), wherein $R^{1a1}$ and $R^{1a2}$ are each independently hydrogen or $C_{1-6}$ alkyl.

In some embodiments of Formula (II), or a pharmaceutically acceptable salt thereof, $Z^4$ is hydrogen and at least one of $Z^1$ and $Z^3$ is $R^D$ wherein $R^D$ is as defined elsewhere herein. In some embodiments of Formula (II), or a pharmaceutically acceptable salt thereof, $Z^4$ is when $Z^4$ is $R^D$ and $Z^1$ is $R^D$ wherein $R^D$ is as defined elsewhere herein.

In some embodiments of Formula (II), or a pharmaceutically acceptable salt thereof, $Z^5$ is C—H, N, O, S, or N—X, wherein X is H or $C_{1-6}$alkyl. In some embodiments, X is H. In some embodiments, X is $C_{1-6}$alkyl. In some embodiments, X is methyl. In some embodiments of Formula (II), or a pharmaceutically acceptable salt thereof, $Z^5$ is C—H, N, O, S, or N—X, wherein X is H or $C_{1-6}$alkyl, $Z^6$ is —$NR^{a26}C(O)NR^{a27}R^{a28}$, —$NR^{a29}C(O)OR^{a30}$, —N=$S(O)R^{a31}R^{a32}$, —$S(O)R^{a33}$, —$S(O)(NR^{a34})R^{a35}$, —$S(O)_2R^{a36}R^{a37}$, —$S(O)_2R^{a38}$, —$SR^{a39}$, 3- to 10-membered heterocycloalkyl, $C(O)R^{a40}$, or —$CH(Z^7)(Z^8)$, wherein $Z^7$ is hydrogen or —OH, and $Z^8$ is $C_{1-6}$ alkyl, $C_{3-10}$ cycloalkyl optionally substituted with one or more halo, or 3- to 10-membered heterocycloalkyl optionally substituted with one or more halo, and ring C is 5- to 6-membered heteroaryl optionally substituted with one or more $R^E$ substituents, wherein each $R^E$ substituent is independently selected from the group consisting of halo, —OH, and $C_{1-6}$ alkyl, or two $R^E$ substituents are taken, together with the atoms to which they are attached, to form $C_{5-6}$ cycloalkyl, $C_{5-6}$ cycloalkenyl, 5- to 6-membered heterocycloalkyl, 5- to 6-membered heterocycloalkenyl, or 5- to 6-membered heteroaryl; and $R^{a26}$-$R^{a40}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —$O(C_{1-6}$ alkyl), $C_{2-6}$ alkenyl, $C_{3-10}$ cycloalkyl, —$S(C_{1-6}$ alkyl), =$CR^{1a1}R^{1a2}$, and $C_{1-6}$ alkyl optionally substituted with one or more substituents independently selected from the group consisting of halo, —OH, and —$O(C_{1-6}$ alkyl), wherein $R^{1a1}$ and $R^{1a2}$ are each independently hydrogen or $C_{1-6}$ alkyl.

In some embodiments of Formula (II), or a pharmaceutically acceptable salt thereof, one or more $R^B$ groups are independently $C_{1-6}$ alkyl substituted with one, two, three, four, five, or more halo. In some embodiments, an $R^B$ group is $C_{1-6}$ alkyl substituted with one, two, three, four, five, or more halo.

In some embodiments of Formula (II), or a pharmaceutically acceptable salt thereof, ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon. In some embodiments of Formula (II), or a pharmaceutically acceptable salt thereof, one or more $R^B$ groups are independently halo or $C_{1-6}$ alkyl optionally substituted with one or more halo. In some embodiments of Formula (II), or a pharmaceutically acceptable salt thereof, two vicinal $R^B$ groups are taken together with the carbon atoms to which they are attached to form $C_{3-10}$ cycloalkyl; or two geminal $R^B$ groups are taken together with the carbon atom to which they are attached to form $C_{3-10}$ cycloalkyl; or two geminal $R^B$ groups are taken together to form a =$CR^{1a3}R^{1a4}$ group, wherein $R^{1a3}$ and $R^{1a4}$ are each independently hydrogen or $C_{1-6}$ alkyl.

In some embodiments of Formula (II), or a pharmaceutically acceptable salt thereof, $R^{c2}$ is —$NR^{c14}C(O)OR^{c15}$ wherein $R^{c14}$ and $R^{c15}$ are each independently hydrogen, $C_{3-10}$ cycloalkyl, or $C_{1-6}$ alkyl optionally substituted with one or more substituents independently selected from the group consisting of halo and —OH.

In some embodiments of Formula (II), or a pharmaceutically acceptable salt thereof, $R^{C1}$-$R^{C4}$ are each independently hydrogen or $R^F$, wherein $R^F$ is halo, cyano, —OH, —$NO_2$, —$C(O)NR^{c1}R^{c2}$, —$NR^{c3}R^{c4}$, —$NR^{c5}S(O)_2R^{c6}$, —$P(O)R^{c7}R^{c8}$, —N=$S(O)R^{c9}R^{c10}$, —$S(O)(NR^{c11})R^{c12}$, —$S(O)_2R^{c13}$, —$NR^{c14}C(O)OR^{c15}$, —$NR^{c16}S(O)_2(CH_2)_{1-6}NR^{c17}C(O)R^{c18}$, —O—$S(O)_2R^{c19}$, or $C_{1-6}$ alkyl substituted with one or more substituents independently selected from the group consisting of halo and —OH; and $R^{c1}$-$R^{c19}$ are each independently hydrogen, $C_{3-10}$ cycloalkyl, or $C_{1-6}$ alkyl optionally substituted with one or more substituents independently selected from the group consisting of halo, —$O(C_{1-6}$ alkyl), —$NHC(O)(C_{1-6}$ alkyl), and —OH. In some embodiments of Formula (II), or a pharmaceutically acceptable salt thereof, $R^{C1}$-$R^{C4}$ are each independently hydrogen or $R^F$, wherein $R^F$ is halo, cyano, —OH, —$NO_2$, —$C(O)NR^{c1}R^{c2}$, —$NR^{c3}R^{c4}$, —$NR^{c5}S(O)_2R^{c6}$, —$P(O)$ $R^{c7}R^{c8}$, —N=S(O)$R^{c9}R^{c10}$, —S(O)(N$R^{c11}$)$R^{c12}$, —S(O)$_2R^{c13}$—N$R^{c14}$C(O)O$R^{c15}$, —N$R^{c16}$S(O)$_2$(CH$_2$)$_{1-6}$N$R^{c17}$C(O)$R^{c18}$, or C$_{1-6}$ alkyl substituted with one or more substituents independently selected from the group consisting of halo and —OH, and $R^{c1}$-$R^{c19}$ are as defined elsewhere herein. In some embodiments of Formula (II), or a pharmaceutically acceptable salt thereof, $R^{C1}$-$R^{C4}$ are each independently —O—S(O)$_2R^{c19}$, wherein $R^{c19}$ is as defined elsewhere herein.

In some embodiments of Formula (II), or a pharmaceutically acceptable salt thereof, ring B is unsubstituted cyclopentyl and at least one of $Z^1$-$Z^4$ is —S(O)$_2$-(3- to 10-membered heterocycloalkyl) is substituted with one or more halo. In some embodiments of Formula (II), or a pharmaceutically acceptable salt thereof, ring B is unsubstituted cyclohexyl, ring A is

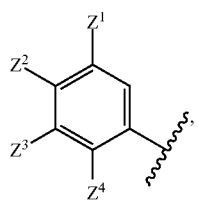

and at least one of $R^{C1}$-$R^{C4}$ is $R^F$, wherein $R^{C1}$-$R^{C4}$ and $R^F$ are as defined elsewhere herein. In some embodiments of Formula (II), or a pharmaceutically acceptable salt thereof, ring B is 5- to 7-membered heterocycloalkyl optionally substituted with 1-4 $R^B$, and at least one of $Z^1$-$Z^4$ is —S(O)$_2$-(3- to 10-membered heterocycloalkyl) is optionally substituted with one or more halo, wherein $R^B$ is as defined elsewhere herein.

In some embodiments, cycloalkyl or heterocycloalkyl groups include spiro groups. In some embodiments, cycloalkyl or heterocycloalkyl groups include fused groups.

In some embodiments of Formula (II), or a pharmaceutically acceptable salt thereof, ring A is C$_{6-14}$ aryl or 5- to 12-membered heteroaryl, each optionally substituted. In some embodiments, ring A is optionally substituted C$_{6-14}$ aryl. In some embodiments, ring A is optionally substituted phenyl. In some embodiments, ring A is optionally substituted 5- to 12-membered heteroaryl. In some embodiments, ring A is optionally substituted 6-membered heteroaryl. In some embodiments, ring A is optionally substituted 5-membered heteroaryl. In some embodiments, ring A is indolyl, indazolyl, pyridinyl, thiophenyl, furanyl, pyrazolyl, pyrrolyl, oxazolyl, chromanyl, or quinolinyl, each optionally substituted. In some embodiments, ring A is optionally substituted thiophenyl.

In some embodiments of Formula (II), or a pharmaceutically acceptable salt thereof, ring A is optionally substituted phenyl. In some embodiments, ring A is optionally substituted 5- to 12-membered heteroaryl. In some embodiments, ring A is optionally substituted 6-membered heteroaryl. In some embodiments, ring A is optionally substituted 5-membered heteroaryl. In some embodiments, ring A is pyridinyl, thiophenyl, furanyl, pyrazolyl, pyrrolyl, or oxazolyl. In some embodiments, ring A is

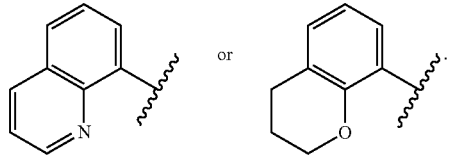 [SMILES: *c1cccc2cccnc12 ; *c1cccc2c1OCCC2]

In some embodiments of Formula (II), $R^{a4}$ is hydrogen or C$_{1-6}$ alkyl. In some embodiments, $R^{a4}$ is hydrogen. In some embodiments, $R^{a5}$ is hydrogen or C$_{1-6}$ alkyl. In some embodiments, $R^{a5}$ is tert-butyl. In some embodiments, $R^{a6}$ and $R^{ay}$ are each independently hydrogen, C$_{1-6}$ alkyl, or 5- to 12-membered heteroaryl optionally substituted with C$_{1-6}$ alkyl. In some embodiments, $R^{a6}$ and $R^{a7}$ are each independently hydrogen, imidazolyl, methylimidazolyl, or pyrimidinyl. In some embodiments, —N=S(O)$R^{a8}R^{a9}$ is

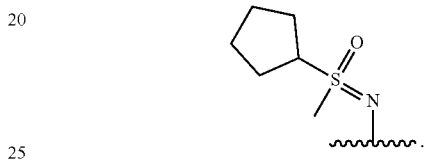

In some embodiments, $R^{a8}$ and $R^{a9}$ are each independently hydrogen, C$_{1-6}$ alkyl, or C$_{3-10}$ cycloalkyl. In some embodiments, $R^{a8}$ and $R^{a9}$ are each independently methyl or cyclopentyl. In some embodiments, —O$R^{a10}$ is

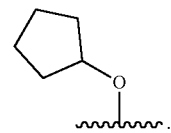

In some embodiments, $R^{a10}$ is C$_{3-10}$ cycloalkyl. In some embodiments, $R^{a10}$ is cyclopentyl. In some embodiments, —S(O)$R^{a11}$ is

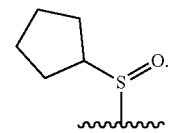 [SMILES: *S(=O)C1CCCC1]

In some embodiments, $R^{a11}$ is C$_{3-10}$ cycloalkyl. In some embodiments, $R^{a11}$ is cyclopentyl. In some embodiments, —S(O)(N$R^{a12}$)$R^{a13}$ is

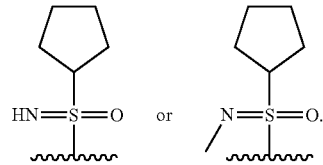

In some embodiments, $R^{a12}$ is hydrogen or C$_{1-6}$ alkyl. In some embodiments, $R^{a12}$ is hydrogen or methyl. In some embodiments, $R^{a13}$ is C$_{3-10}$ cycloalkyl. In some embodiments, $R^{a13}$ is cyclopentyl. In some embodiments, —S(O)$_2$N$R^{a14}R^{a15}$ is

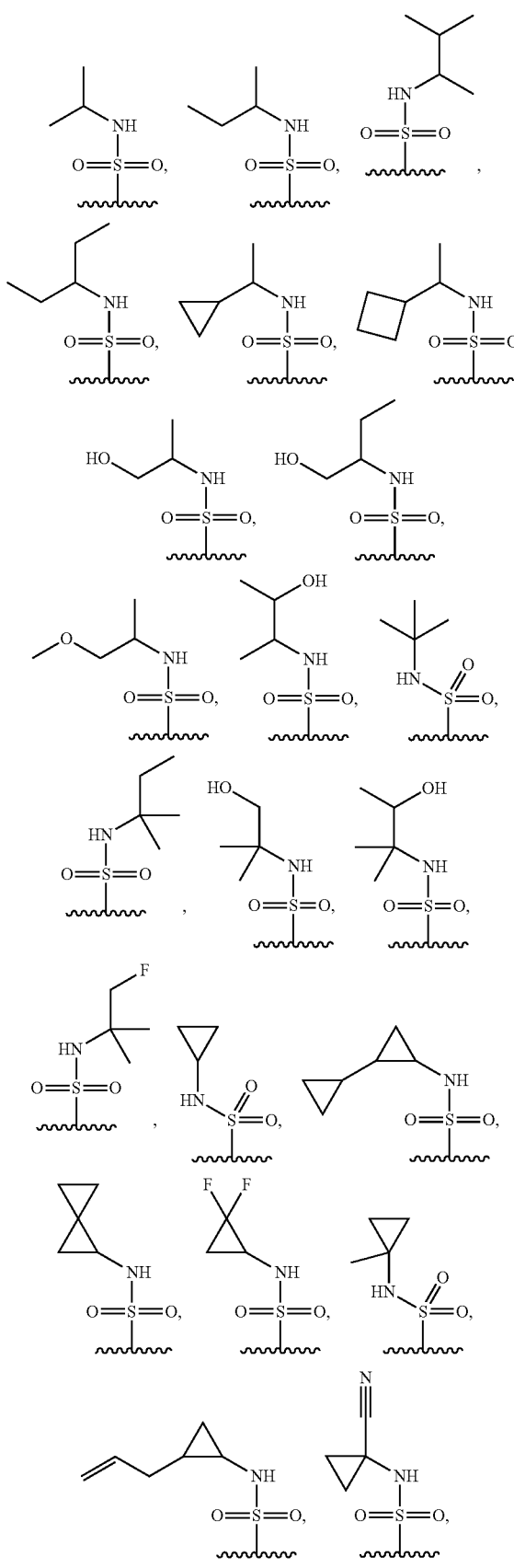
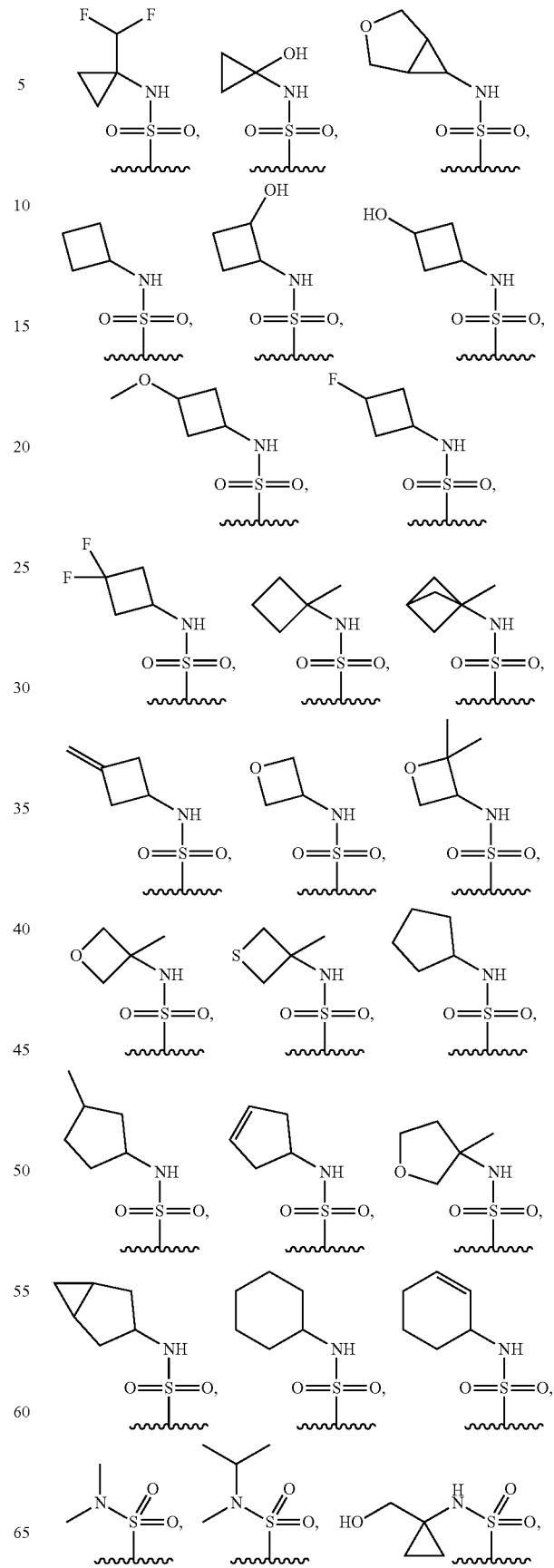

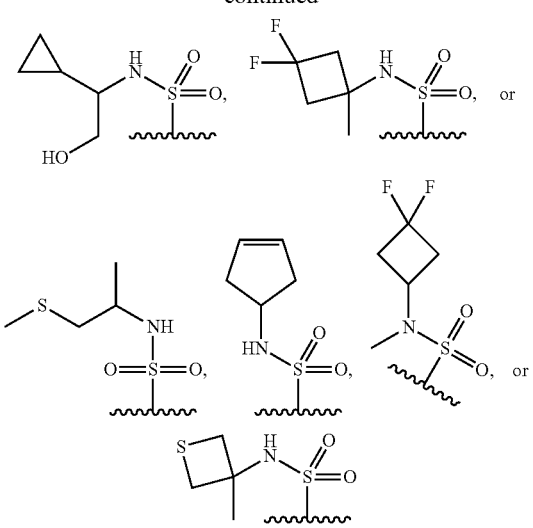
In some embodiments, —S(O)$_2$NR$^{a14}$R$^{a15}$ is
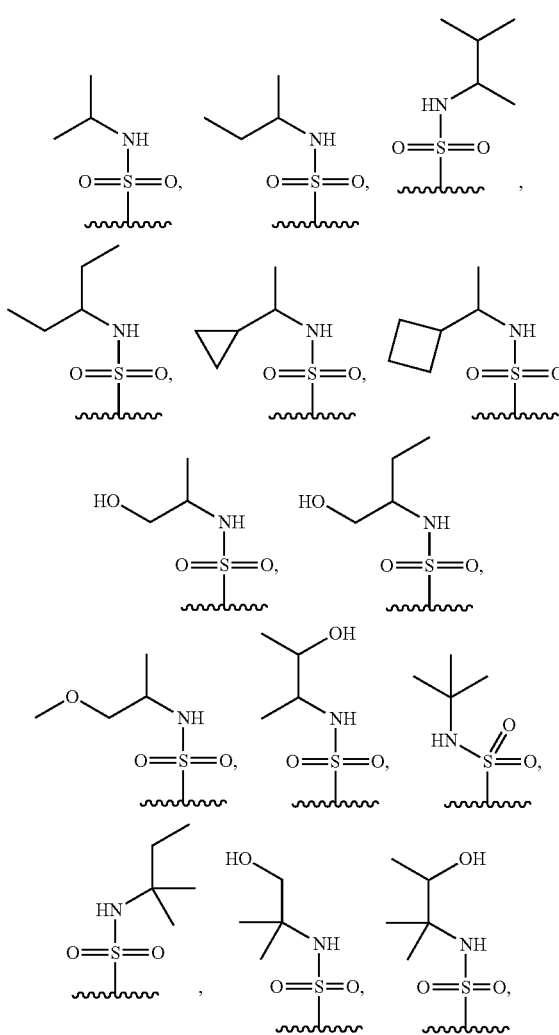
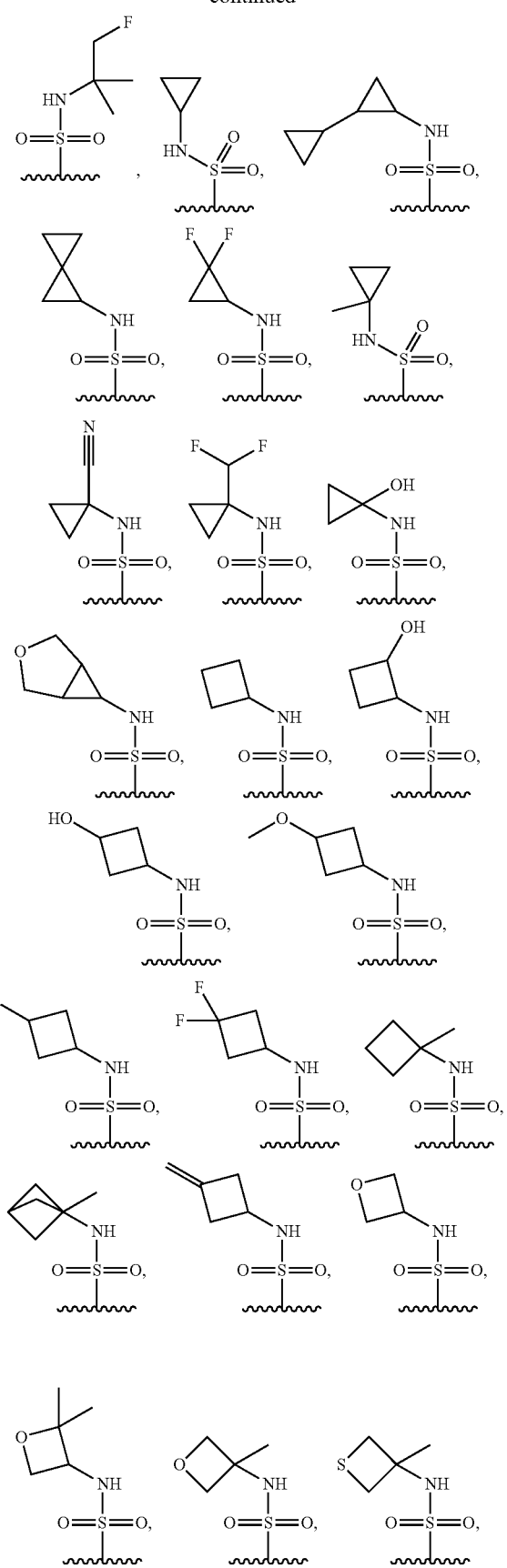

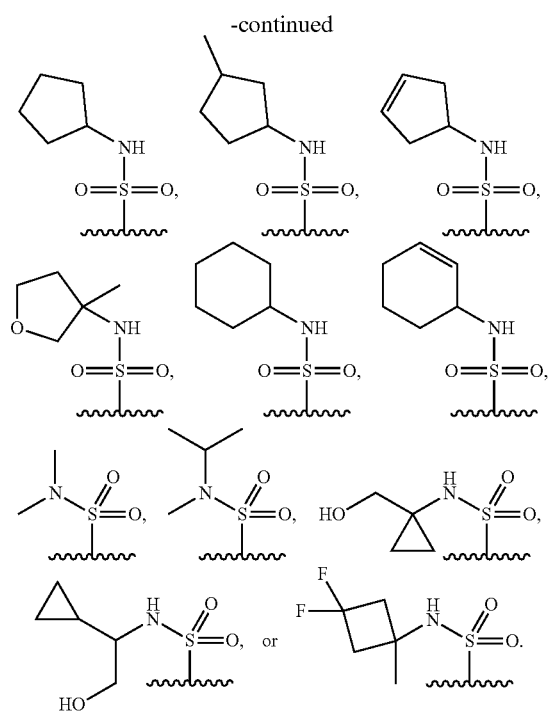

In some embodiments, —S(O)$_2$NR$^{a14}$R$^{a15}$ is

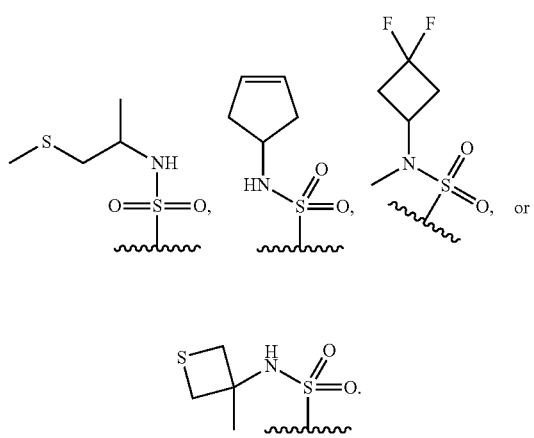

In some embodiments, R$^{a14}$ and R$^{a15}$ are each independently hydrogen; C$_{1-6}$ alkyl optionally substituted with one, two, three, four, five, or more substituents independently selected from the group consisting of C$_{1-6}$ alkyl, C$_{2-6}$ alkenyl, C$_{3-10}$ cycloalkyl, —OH, —O(C$_{1-6}$ alkyl), —S(C$_{1-6}$ alkyl), and halo; C$_{2-6}$ alkenyl; C$_{3-10}$ cycloalkyl optionally substituted with one, two, three, four, five, or more substituents independently selected from the group consisting of C$_{2-6}$ alkenyl, C$_{3-10}$ cycloalkyl, halo, cyano, —OH, —O(C$_{1-6}$ alkyl), =CR$^{1a1}$R$^{1a2}$, and C$_{1-6}$ alkyl optionally substituted with one, two, three, four, five, or more substituents independently selected from the group consisting of —OH, —O(C$_{1-6}$ alkyl), and halo, wherein R$^{1a1}$ and R$^{1a2}$ are each independently hydrogen or C$_{1-6}$ alkyl; C$_{3-10}$ cycloalkenyl; or 3- to 12-membered heterocycloalkyl optionally substituted with one, two, three, four, five, or more C$_{1-6}$ alkyl. In some embodiments, R$^{a14}$ and R$^{a15}$ are each independently hydrogen or C$_{1-6}$ alkyl. In some embodiments, R$^{a14}$ is hydrogen and R$^{a15}$ is butyl. In some embodiments, R$^{a15}$ is tert-butyl. In some embodiments, —S(O)$_2$R$^{a16}$ is

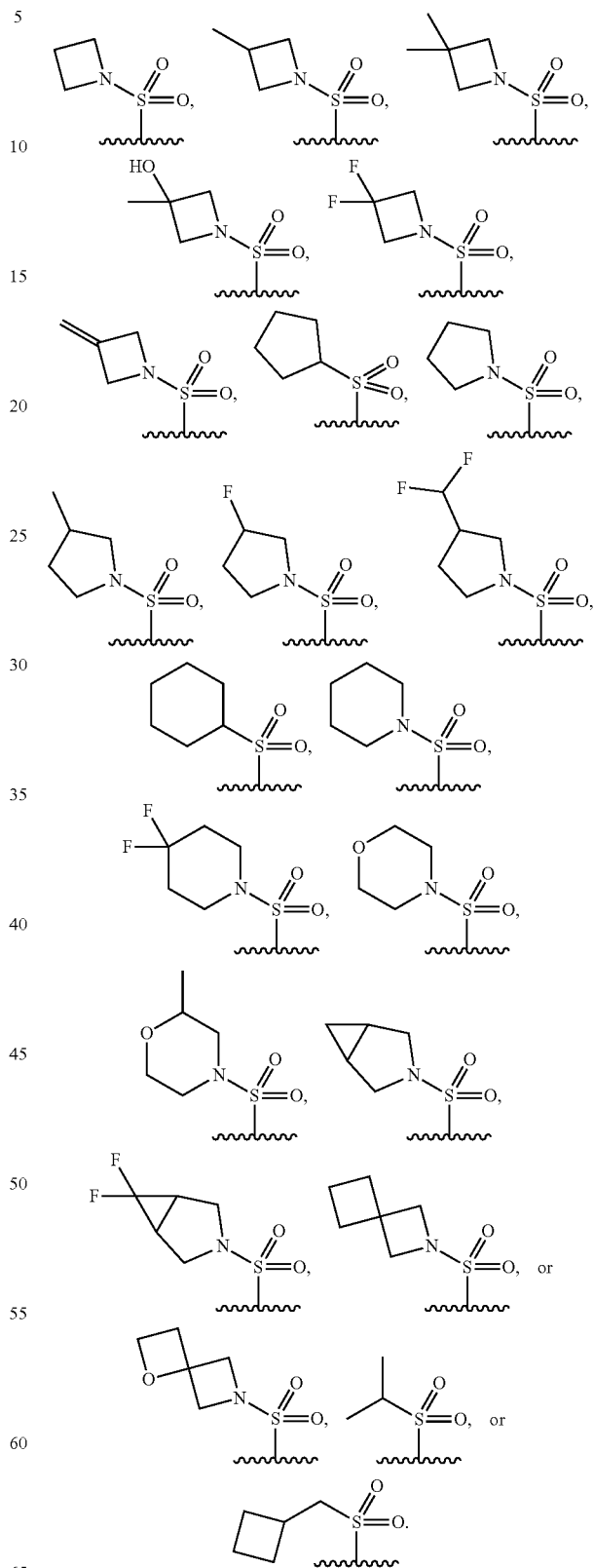

In some embodiments, —S(O)₂R^{a16} is

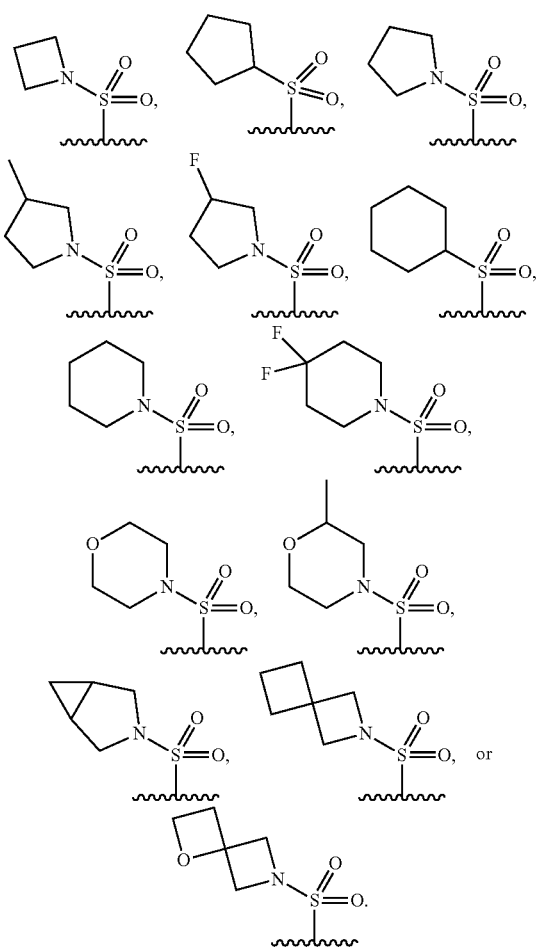

In some embodiments, —S(O)₂R^{a15} is

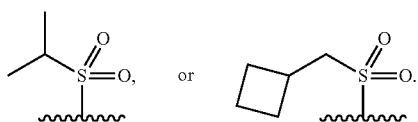

In some embodiments, R^{a16} is $C_{3-10}$ cycloalkyl; or 3- to 12-membered heterocycloalkyl optionally substituted with one, two, three, four, five, or more substituents independently selected from the group consisting of $C_{1-6}$ alkyl or halo. In some embodiments, —(CR^{a17}R^{a18})_{0-1}C(O)NR^{a19}R^{a20} is —C(O)NR^{a19}R^{a20} or —(CR^{a17}R^{a18})C(O)NR^{a19}R^{a20}. In some embodiments, —(CR^{a17}R^{a18})_{0-1}C(O)NR^{a19}R^{a20} is —C(O)NR^{a19}R^{a20}. In some embodiments, —(CR^{a17}R^{a18})_{0-1}C(O)NR^{a19}R^{a20} is —(CR^{a17}R^{a18})C(O)NR^{a19}R^{a20}. In some embodiments, R^{a17} and R^{a18} are each independently hydrogen or $C_{1-6}$ alkyl. In some embodiments, R^{a17} and R^{a18} are each hydrogen. In some embodiments, R^{a19} and R^{a20} are each independently hydrogen, $C_{1-6}$ alkyl, or $C_{3-10}$ cycloalkyl. In some embodiments, R^{a21} is hydrogen, $C_{3-10}$ cycloalkyl, or $C_{1-6}$ alkyl optionally substituted with one or more $C_{3-10}$ cycloalkyl. In some embodiments, —SR^{a21} is

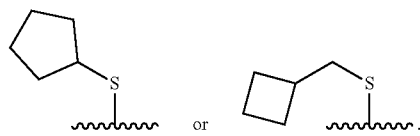 [SMILES: *SC1CCCC1 ; *SCC1CCC1]

In some embodiments, R^{a22} is hydrogen, $C_{3-10}$ cycloalkyl, or $C_{1-6}$ alkyl optionally substituted with one or more $C_{3-10}$ cycloalkyl. In some embodiments, —C(O)R^{a22} is

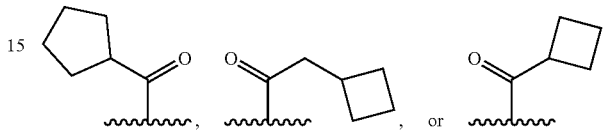

In some embodiments, R^{a23} and R^{a24} are each independently hydrogen, $C_{3-10}$ cycloalkyl, or $C_{1-6}$ alkyl optionally substituted with one or more $C_{3-10}$ cycloalkyl. In some embodiments, —P(O)(R^{a23})(R^{a24}) is

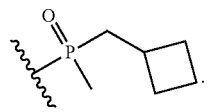 [SMILES: *P(C)(=O)CC1CCC1]

In some embodiments, R^{24} is hydrogen, $C_{3-10}$ cycloalkyl, or $C_{1-6}$ alkyl optionally substituted with one or more $C_{3-10}$ cycloalkyl. In some embodiments, —C=NR^{a25} is

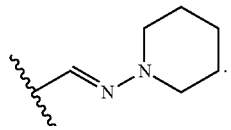 [SMILES: */C=N/N1CCCCC1]

In some embodiments, $Z^1$-$Z^4$ are each independently $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo or $C_{1-3}$ alkyl. In some embodiments, $Z^1$-$Z^4$ are each independently

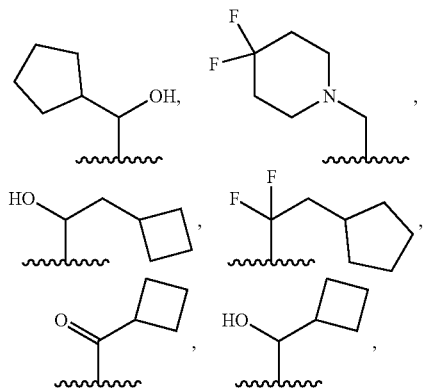

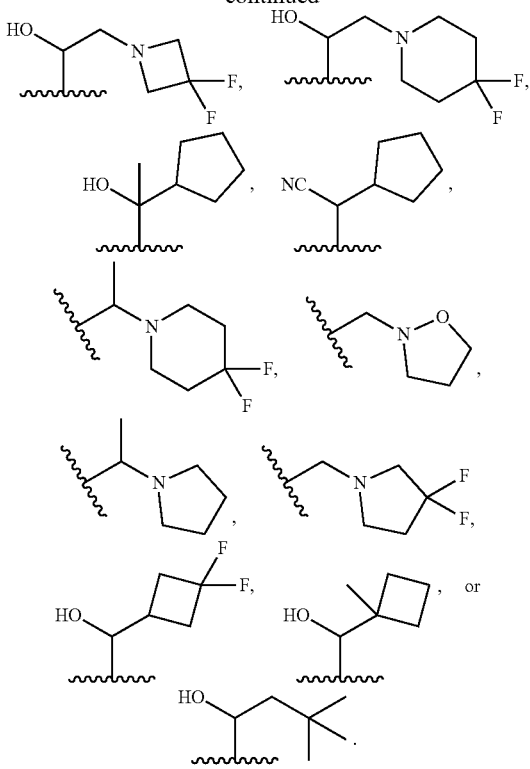

In some embodiments of Formula (II), $Z^6$ is 3- to 10-membered heterocycloalkyl. In some embodiments, $Z^6$ is

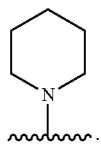

In some embodiments, $R^{a26}$ is hydrogen or $C_{1-6}$ alkyl. In some embodiments, $R^{a27}$ is hydrogen. In some embodiments, $R^{a27}$ and $R^{a28}$ are each independently hydrogen, $C_{1-6}$ alkyl, or $C_{3-10}$ cycloalkyl. In some embodiments, $R^{a27}$ and $R^{a28}$ are each independently hydrogen, cyclopropyl, ethyl, or isopropyl. In some embodiments, $R^{a29}$ is hydrogen or $C_{1-6}$ alkyl. In some embodiments, $R^{a29}$ is hydrogen. In some embodiments, $R^{a30}$ is hydrogen or $C_{1-6}$ alkyl. In some embodiments, $R^{a30}$ is tert-butyl. In some embodiments, —N=S(O)$R^{a31}R^{a32}$ is

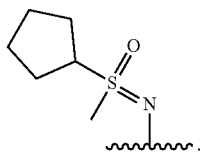 [SMILES: *N=S(C)(=O)C1CCCC1]

In some embodiments, $R^{a31}$ and $R^{a32}$ are each independently hydrogen, $C_{1-6}$ alkyl, or $C_{3-10}$ cycloalkyl. In some embodiments, $R^{a31}$ and $R^{a32}$ are each independently methyl or cyclopentyl. In some embodiments, —S(O)$R^{a33}$ is

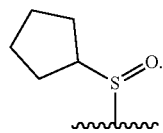 [SMILES: *S(=O)C1CCCC1]

In some embodiments, $R^{a33}$ is $C_{3-10}$ cycloalkyl. In some embodiments, $R^{a33}$ is cyclopentyl. In some embodiments, —S(O)(N$R^{a34}$)$R^{a35}$ is

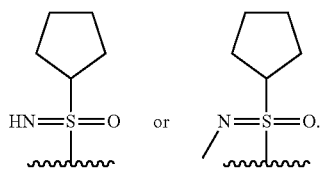

In some embodiments, $R^{a34}$ is hydrogen or $C_{1-6}$ alkyl. In some embodiments, $R^{a34}$ is hydrogen or methyl. In some embodiments, $R^{a35}$ is $C_{3-10}$ cycloalkyl. In some embodiments, $R^{a35}$ is cyclopentyl. In some embodiments, —S(O)$_2$N$R^{a34}R^{a35}$ is

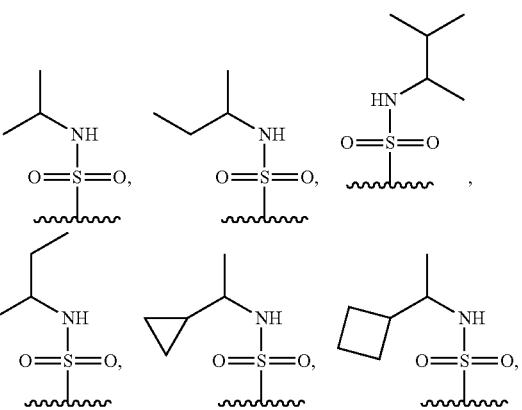

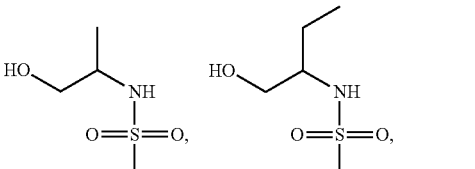

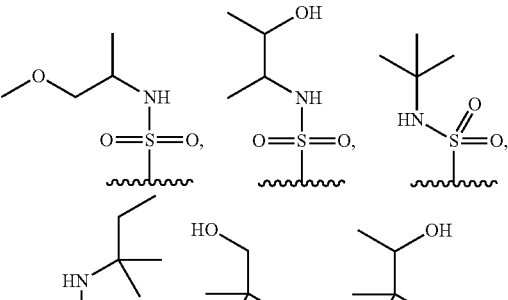

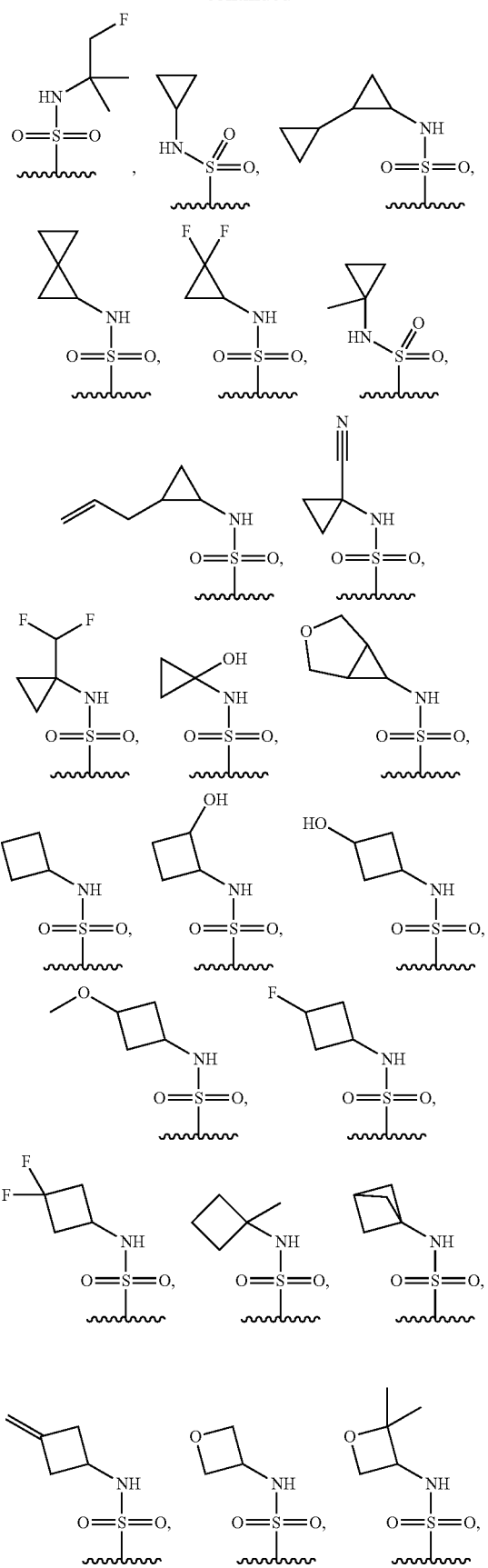
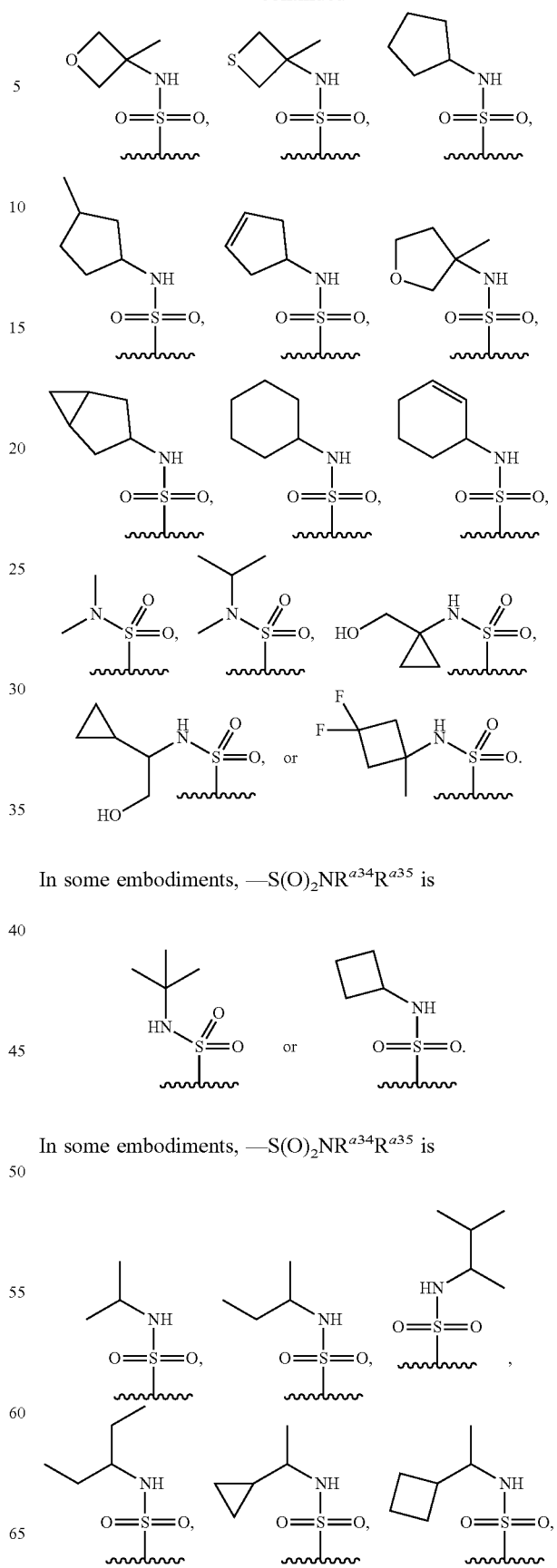
In some embodiments, —S(O)$_2$NR$^{a34}$R$^{a35}$ is
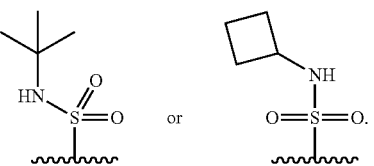
In some embodiments, —S(O)$_2$NR$^{a34}$R$^{a35}$ is
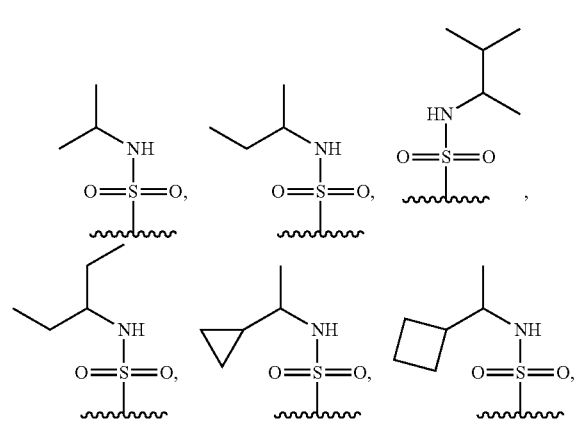

-continued

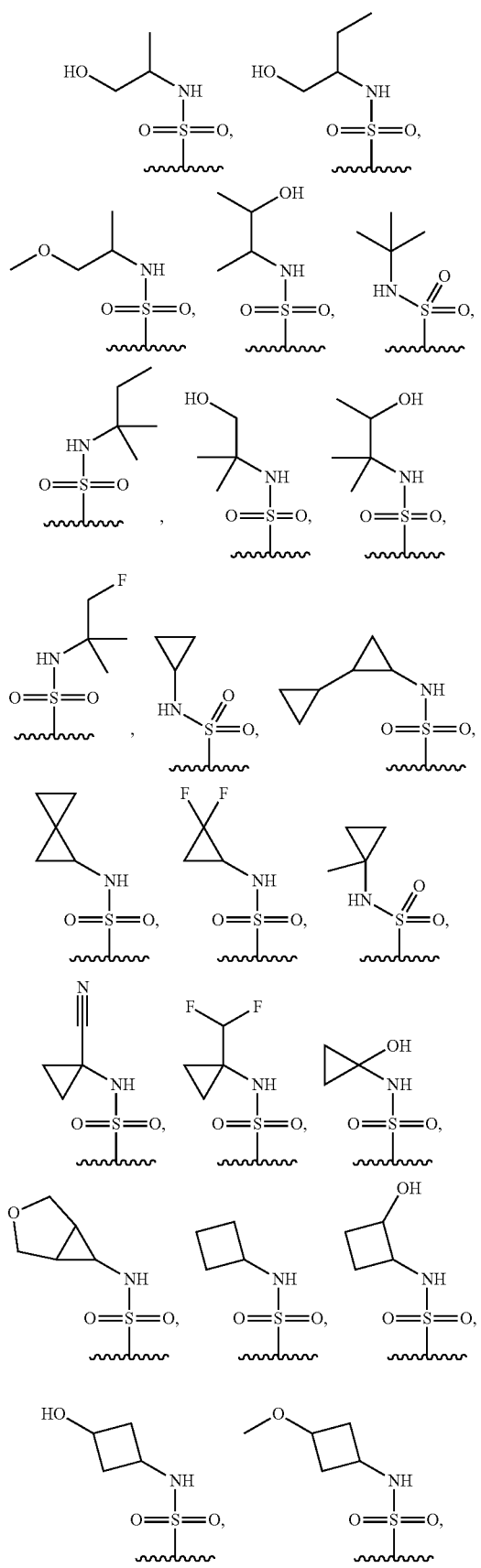

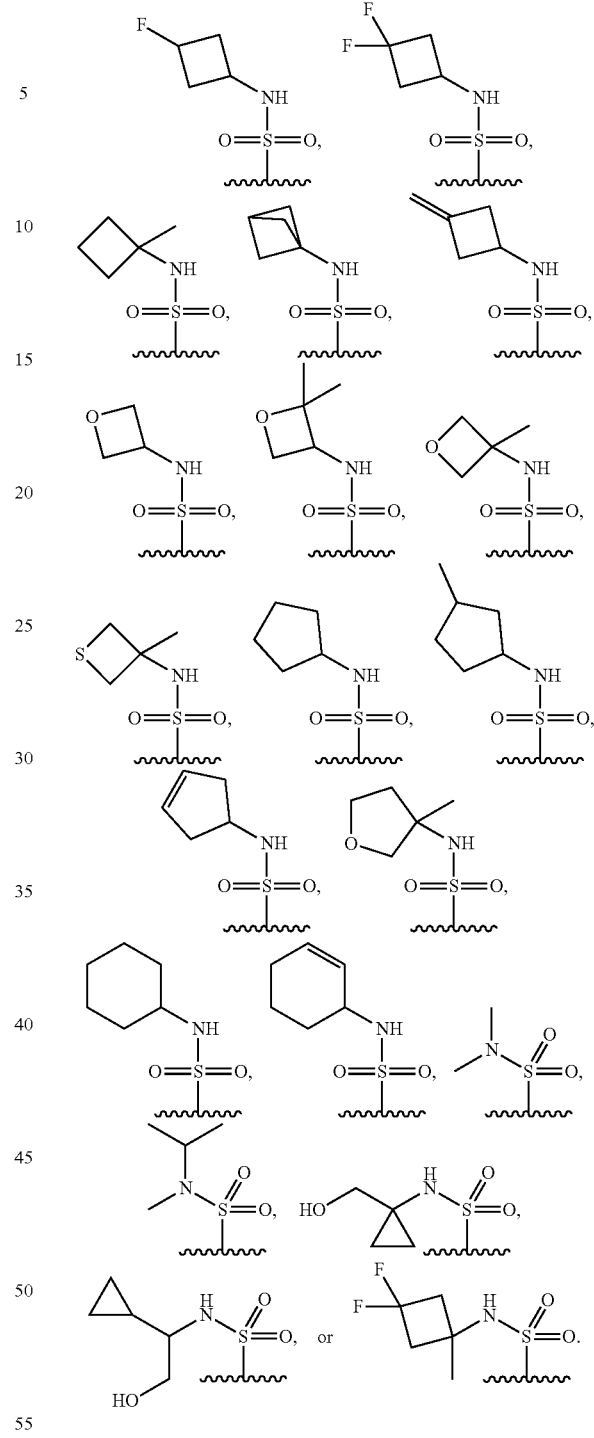

In some embodiments, $R^{a36}$ and $R^{a37}$ are each independently hydrogen; $C_{1-6}$ alkyl optionally substituted with one, two, three, four, five, or more substituents independently selected from the group consisting of $C_{1-6}$ alkyl, $C_{2-6}$ alkenyl, $C_{3-10}$ cycloalkyl, —OH, —O($C_{1-6}$ alkyl), —S($C_{1-6}$ alkyl), and halo; $C_{2-6}$ alkenyl; $C_{3-10}$ cycloalkyl optionally substituted with one, two, three, four, five, or more substituents independently selected from the group consisting of $C_{2-6}$ alkenyl, $C_{3-10}$ cycloalkyl, halo, cyano, —OH, —O($C_{1-6}$ alkyl), =$CR^{1a1}R^{1a2}$, and $C_{1-6}$ alkyl optionally substituted with one, two, three, four, five, or more substituents independently selected from the group consisting of —OH, —O(C$_{1-6}$ alkyl), and halo, wherein R$^{1a1}$ and R$^{1a2}$ are each independently hydrogen or C$_{1-6}$ alkyl; C$_{3-10}$ cycloalkenyl; or 3- to 12-membered heterocycloalkyl optionally substituted with one, two, three, four, five, or more C$_{1-6}$ alkyl. In some embodiments, R$^{a36}$ and R$^{a37}$ are each independently hydrogen or C$_{1-6}$ alkyl. In some embodiments, R$^{a36}$ is hydrogen and R$^{a37}$ is butyl. In some embodiments, R$^{a37}$ is tert-butyl. In some embodiments, —S(O)$_2$R$^{a3}$ is

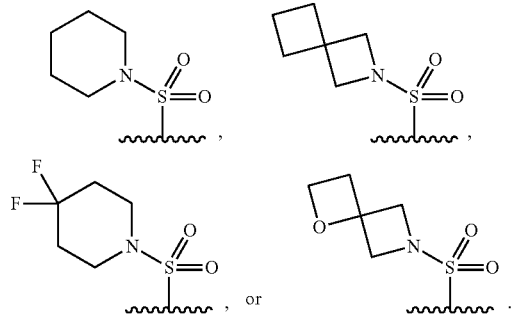

In some embodiments, —S(O)$_2$R$^{a38}$ is

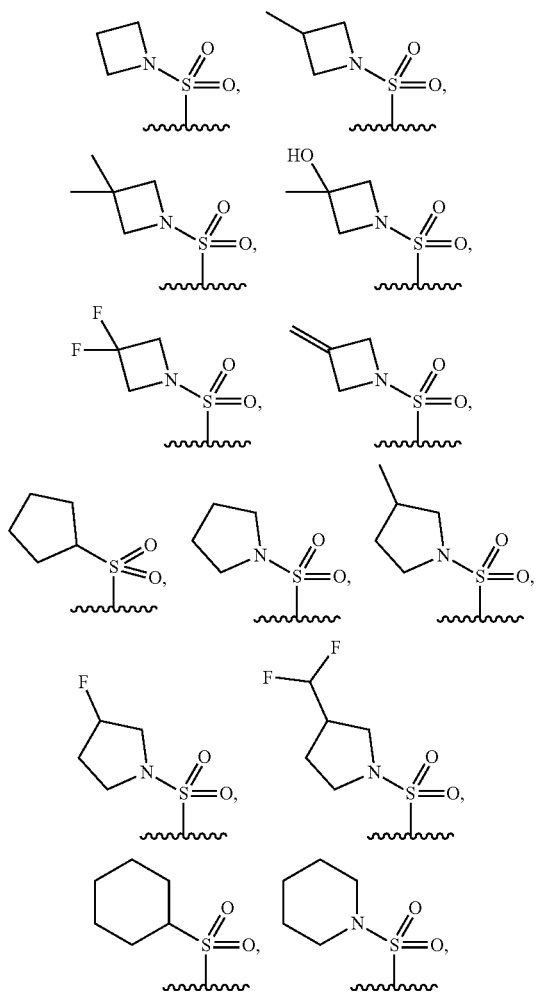

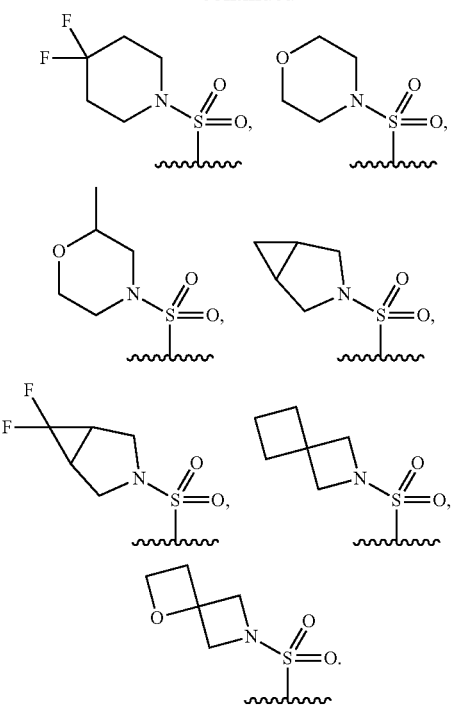

In some embodiments, —S(O)$_2$R$^{a38}$ is

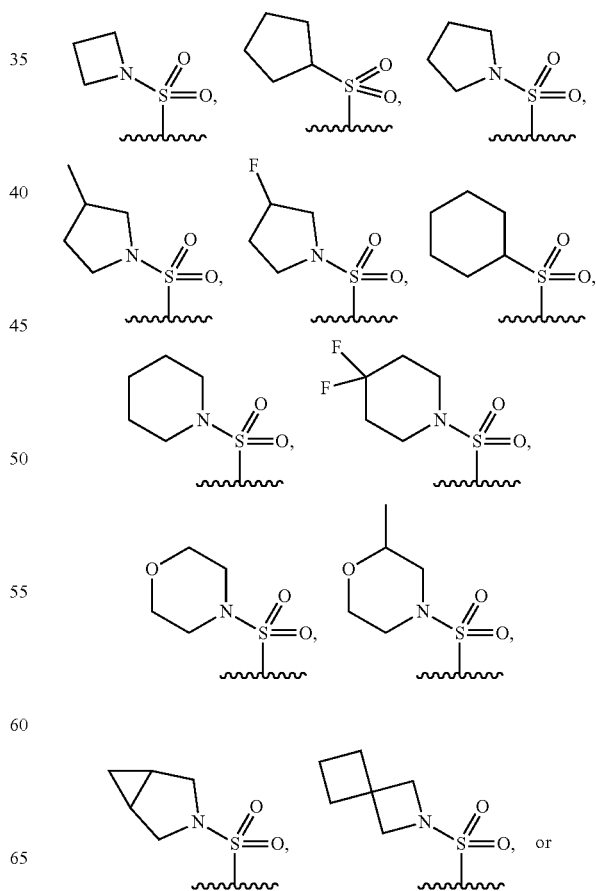

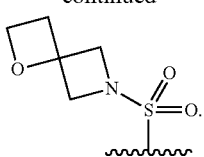

In some embodiments, $R^{a38}$ is $C_{3-10}$ cycloalkyl; or 3- to 12-membered heterocycloalkyl optionally substituted with one, two, three, four, five, or more substituents independently selected from the group consisting of $C_{1-6}$ alkyl or halo. In some embodiments, —$SR^{a39}$ is

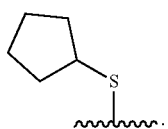

In some embodiments, $R^{a39}$ is $C_{3-10}$ cycloalkyl. In some embodiments, $R^{a40}$ is $C_{3-10}$ cycloalkyl. In some embodiments, —$C(O)R^{a40}$ is

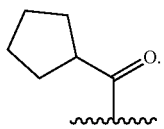

In some embodiments, —$CH(Z^7)(Z^8)$, wherein $Z^7$ is hydrogen or —OH, and $Z^8$ is $C_{1-6}$ alkyl, $C_{3-10}$ cycloalkyl optionally substituted with one or more halo, or 3- to 10-membered heterocycloalkyl optionally substituted with one or more halo. In some embodiments, $Z^7$ is —OH. In some embodiments, $Z^7$ is H. In some embodiments, $Z^8$ is $C_{1-6}$ alkyl. In some embodiments, $Z^8$ is $C_{3-10}$ cycloalkyl optionally substituted with one ore more halo. In some embodiments, $Z^8$ is 3- to 10-membered heterocycloalkyl optionally substituted with one or more halo. In some embodiments, —$CH(Z^7)(Z^8)$ is

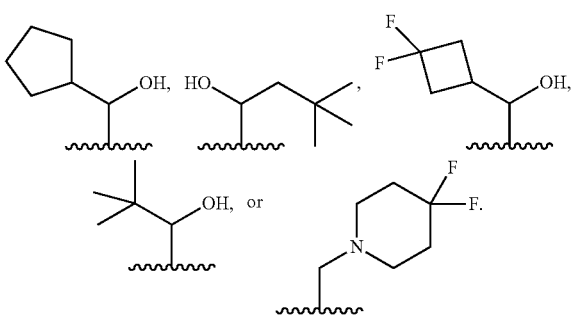

In some embodiments of Formula (II), $Z^1$, $Z^2$, $Z^3$, and $Z^4$ are each independently selected from the group consisting of fluoro, chloro, —OH, amino, —$CH_2OH$,

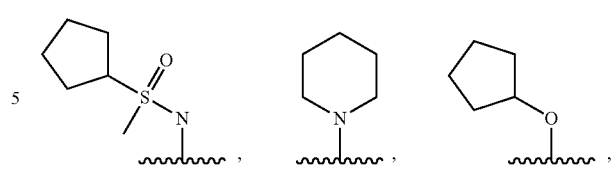

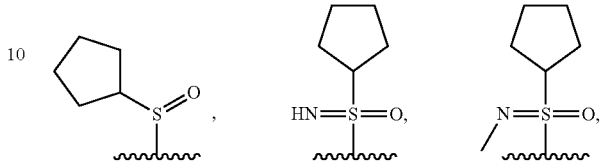

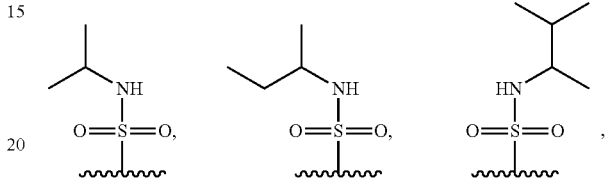

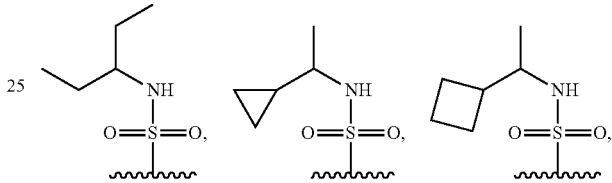

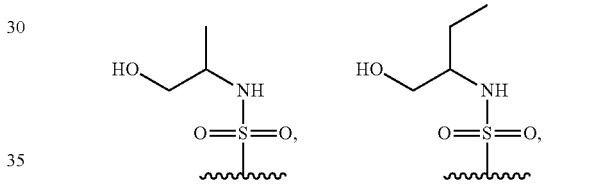


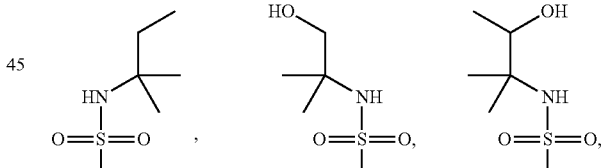

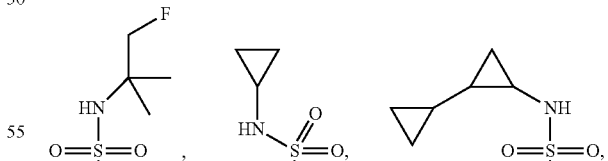

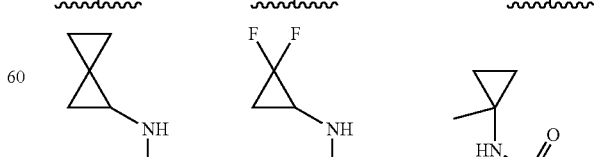

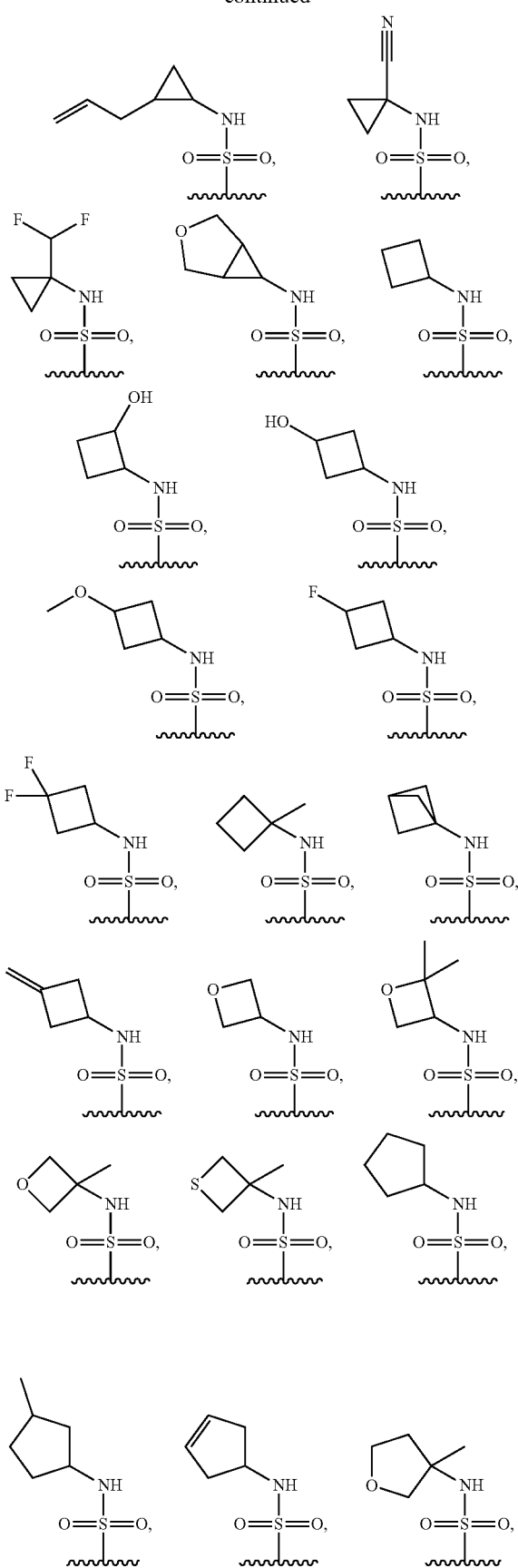
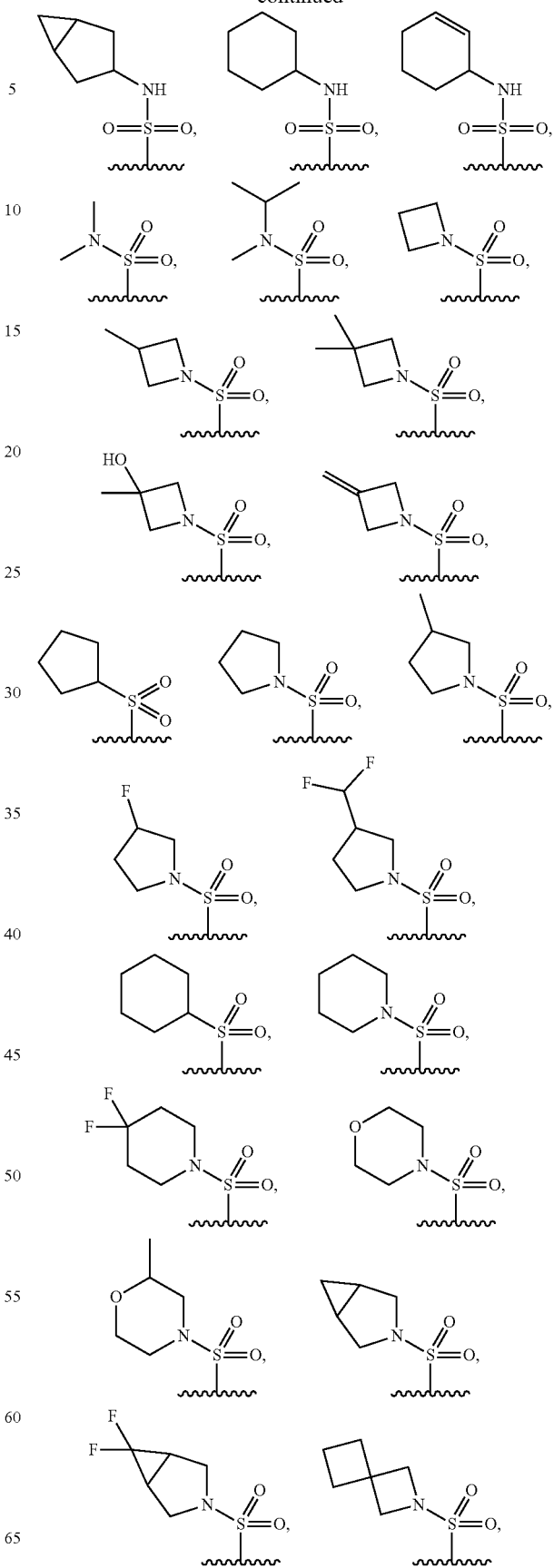

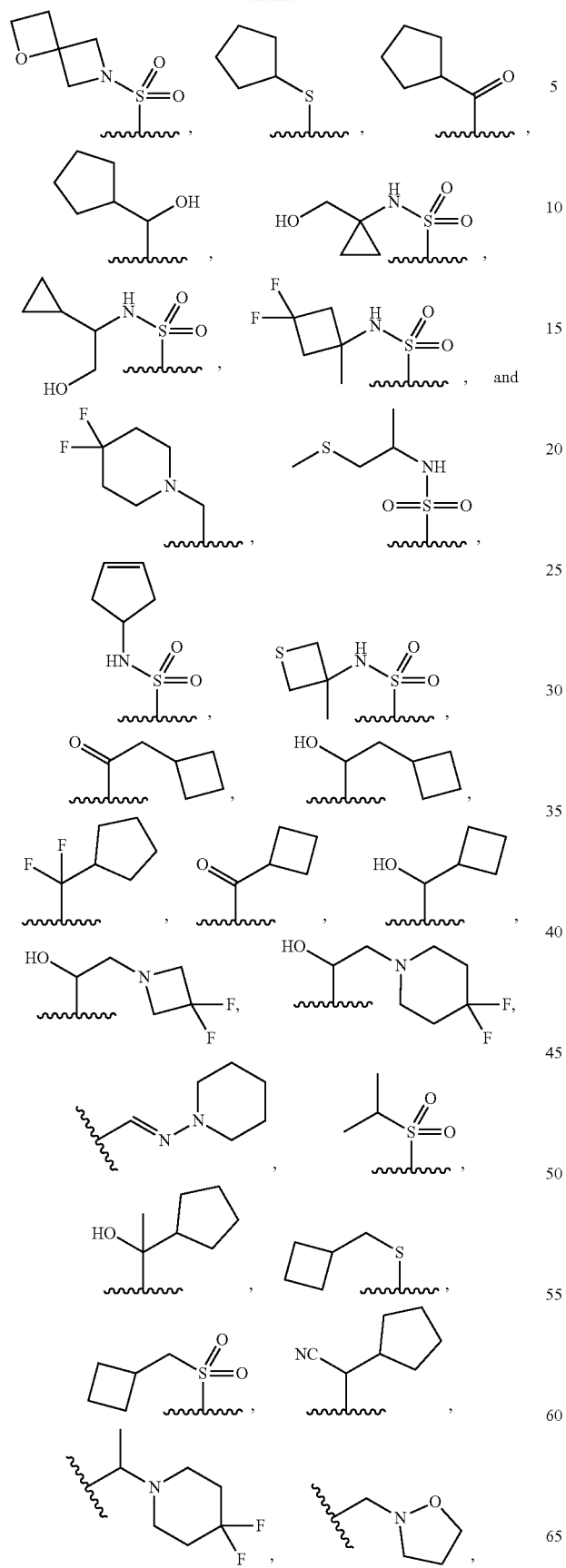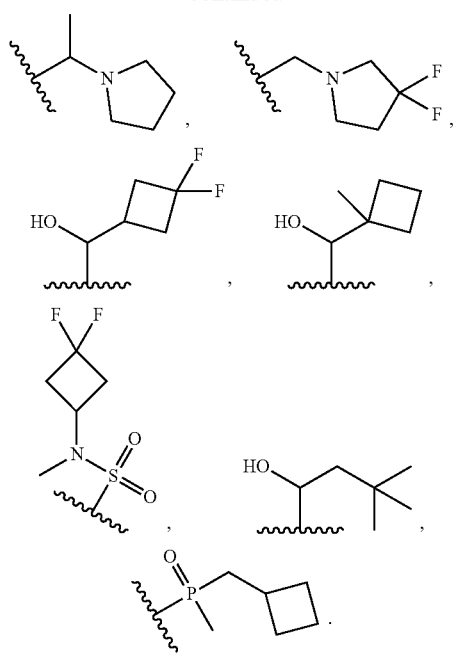
In some embodiments, $Z^1$, $Z^2$, $Z^3$, and $Z^4$ are each independently selected from the group consisting of —CH$_2$OH,

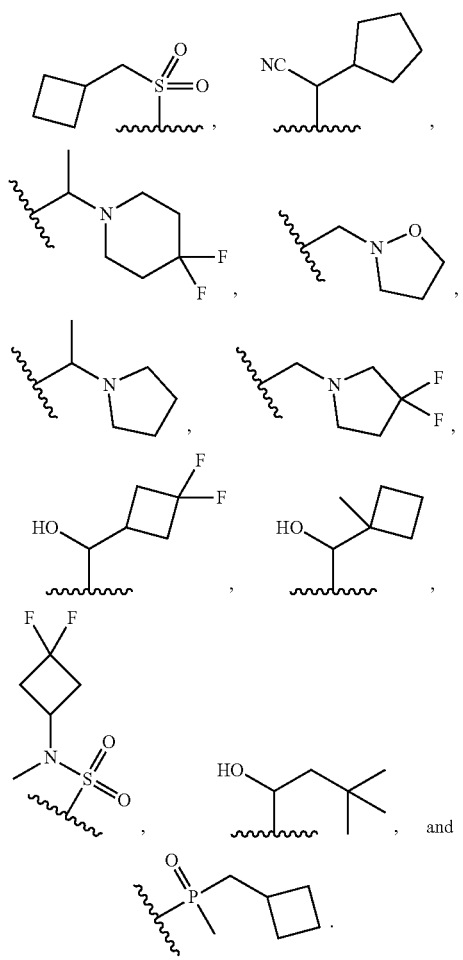
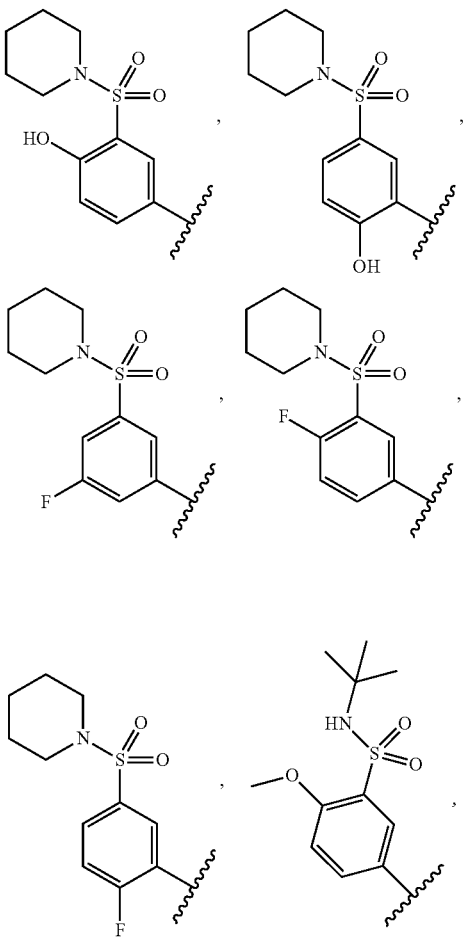
In some embodiments, ring A is bi-substituted phenyl. In some embodiments, ring A is selected from the group consisting of
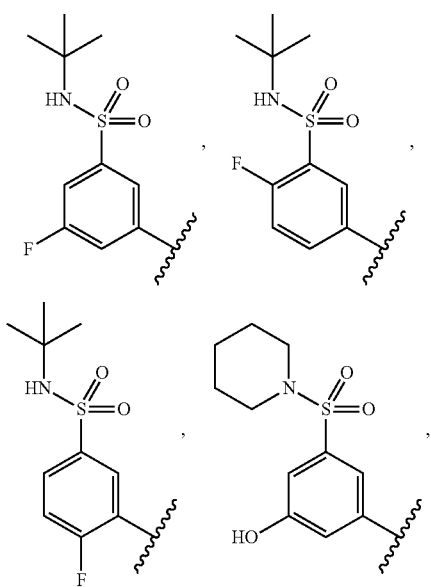
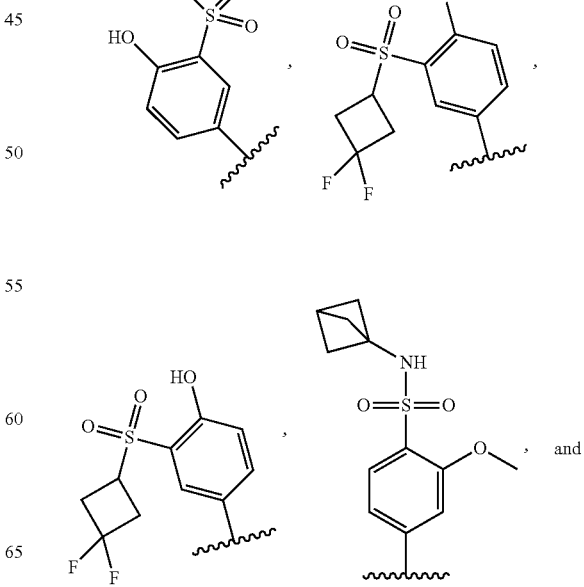

-continued

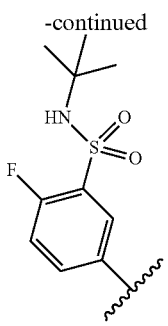

In some embodiments of Formula (II), or a pharmaceutically acceptable salt thereof, ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon. In some embodiments, ring B is $C_{5-7}$ cycloalkyl. In some embodiments, ring B is cyclopentyl, cyclohexyl, or cycloheptyl. In some embodiments, ring B is

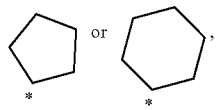

wherein * denotes the point of attachment to the rest of Formula (II). In some embodiments, ring B is $C_{5-7}$ cycloalkenyl. In some embodiments, ring B is cyclopentenyl, cyclohexenyl, or cycloheptenyl. In some embodiments, ring B is

wherein * denotes the point of attachment to the rest of Formula (II). In some embodiments, ring B is

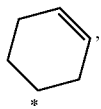

wherein * denotes the point of attachment to the rest of Formula (II). In some embodiments, ring B is 5- to 7-membered heterocycloalkyl. In some embodiments, ring B is 5- to 7-membered heterocycloalkyl wherein one or two of the ring atoms are each oxygen and the remaining ring atoms are each carbon. In some embodiments, ring B is tetrahydrofuranyl or 1,3-dioxanyl. In some embodiments, ring B is

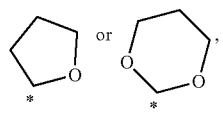

wherein * denotes the point of attachment to the rest of Formula (II).

In some embodiments of Formula (II), ring B is substituted with m $R^B$ groups, wherein each $R^B$ group is independently halo, $C_{1-6}$ alkyl optionally substituted with one, two, three, four, five, or more halo, or $C_{2-6}$ alkenyl; or two vicinal $R^B$ groups are taken together with the carbon atoms to which they are attached to form $C_{3-10}$ cycloalkyl; or two geminal $R^B$ groups are taken together with the carbon atom to which they are attached to form $C_{3-10}$ cycloalkyl. In some embodiment, an $R^B$ group is methyl or ethyl. In some embodiment, two vicinal $R^B$ groups are taken together with the carbon atoms to which they are attached to form cyclopropyl. In some embodiments, two geminal $R^B$ groups are taken together with the carbon atom to which they are attached to form cyclopropyl.

In some embodiments of Formula (II), m is 0, 1, 2, 3, or 4. In some embodiments, m is 0, 1, 2, or 3. In some embodiments, m is 0, 1, or 2. In some embodiments, m is 0 or 1. In some embodiments, m is 0. In some embodiments, m is 1.

In some embodiments,

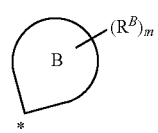

of Formula (II) is

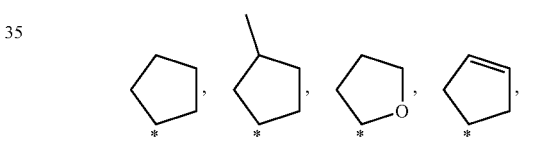

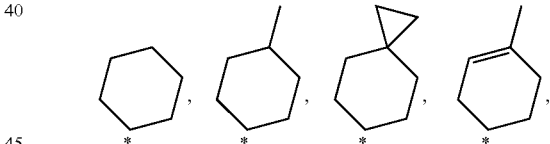

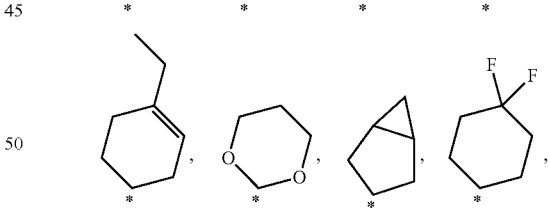

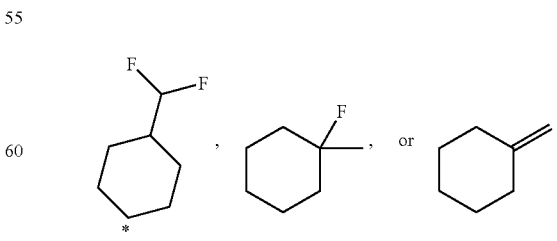

wherein * denotes the point of attachment to the rest of Formula (II). In some embodiments,

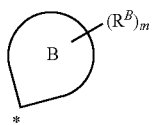

of Formula (II) is

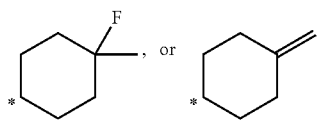

or wherein * denotes the point of attachment to the rest of Formula (II). In some embodiments,

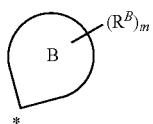

is

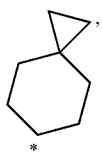

wherein of * denotes the point of attachment to the rest of Formula (II).

In some embodiments of Formula (II), or a pharmaceutically acceptable salt thereof, Y is N or $CR^{C1}$. $Y^2$ is N or $CR^{C2}$; $Y^3$ is N or $CR^{C3}$; and $Y^4$ is N or $CR^{C4}$. In some embodiments, no more than three of $Y^1$, $Y^2$, $Y^3$, and $Y^4$ are N. In some embodiments, no more than two of $Y^1$, $Y^2$, $Y^3$, and $Y^4$ are N. In some embodiments, no more than one of $Y^1$, $Y^2$, $Y^3$, and $Y^4$ is N. In some embodiments, $Y^1$ is $CR^{C1}$. $Y^2$ is $CR^{C2}$; $Y^3$ is $CR^{C3}$; and $Y^4$ is $CR^{C4}$. In some embodiments, $Y^1$ is N; $Y^2$ is $CR^{C2}$; $Y^3$ is $CR^{C3}$; and $Y^4$ is $CR^{C4}$. In some embodiments, $Y^1$ is $CR^{C1}$. $Y^2$ is N; $Y^3$ is $CR^{C3}$; and $Y^4$ is $CR^{C4}$.

In some embodiments of Formula (II), $R^{C1}$-$R^{C4}$ are each independently hydrogen or $R^F$, wherein $R^F$ is halo, cyano, —OH, —$NO_2$, —C(O)$NR^{c1}R^{c2}$, —$NR^{c3}R^{c4}$, —$NR^{c5}$ S(O)$_2R^{c6}$, —P(O)$R^{c7}R^{c8}$, —N=S(O)$R^{c9}R^{c10}$, —S(O)(NR$^{c11}$)$R^{c12}$, —S(O)$_2R^{c13}$, —$NR^{c14}$C(O)OR$^{c15}$, —$NR^{c16}$S(O)$_2$(CH$_2$)$_{1-6}$NR$^{c17}$C(O)R$^{c18}$, —O—S(O)$_2R^{c19}$, or $C_{1-6}$ alkyl substituted with one or more substituents independently selected from the group consisting of halo and —OH.

In some embodiments of Formula (II), $R^{C1}$ is hydrogen or halo. In some embodiments, $R^{C1}$ is hydrogen or fluoro. In some embodiments, $R^{C3}$ is hydrogen. In some embodiments, $R^{C4}$ is hydrogen or —$NH_2$. In some embodiments, $R^{C1}$, $R^{C3}$, and $R^{C4}$ are each independently hydrogen, halo, or —$NH_2$.

In some embodiments of Formula (II), $R^{C2}$ is cyano, —OH, —$CH_2$OH, fluoro, bromo, —$NO_2$,

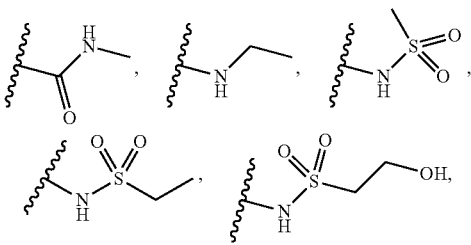

In some embodiments, $R^{C2}$ is cyano, —OH, —$CH_2$OH, bromo, —$NO_2$,

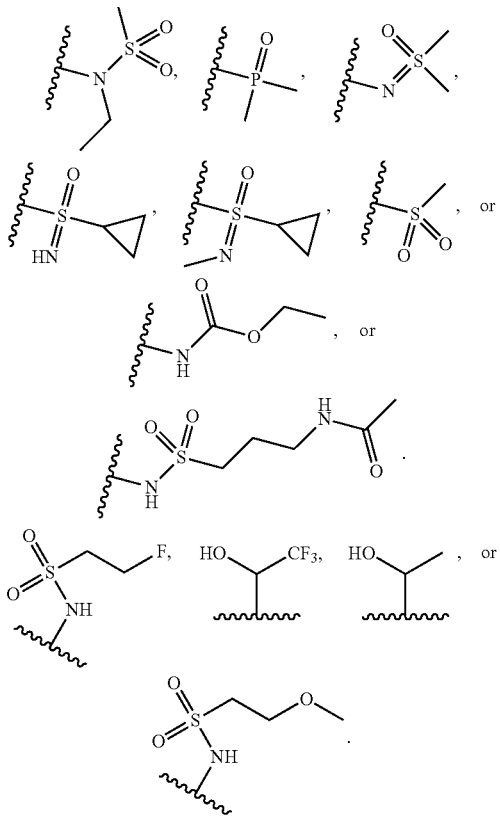

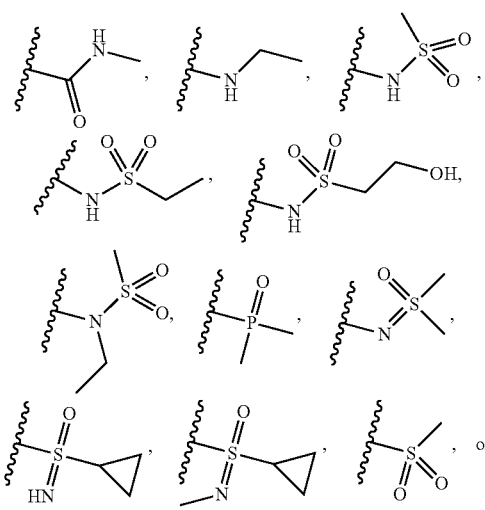

-continued

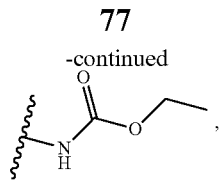

In some embodiments, $R^{C2}$ is

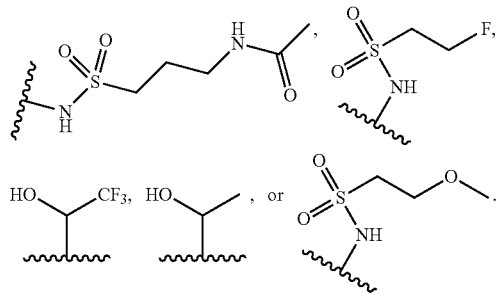

In some embodiments, $R^{C2}$ is cyano, —OH, halo, —NO$_2$, C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$—NR$^{c14}$C(O)OR$^{c15}$, —NR$^{c16}$S(O)$_2$(CH$_2$)$_{1-6}$NR$^{c17}$C(O)R$^{c18}$, or C$_{1-6}$ alkyl optionally substituted with one, two, three, four, five, or more substituents independently selected from the group consisting of halo and —OH. In some embodiments, $R^{C2}$ is cyano, —OH, halo, —NO$_2$, C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$—NR$^{c14}$C(O)OR$^{c15}$, or C$_{1-6}$ alkyl optionally substituted with one, two, three, four, five, or more substituents independently selected from the group consisting of halo and —OH. In some embodiments, $R^{C2}$ is —O—S(O)$_2$R$^{c19}$.

In some embodiments, —C(O)NR$^{c1}$R$^{c2}$ is

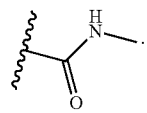 [SMILES: *C(=O)NC]

In some embodiments, $R^{c1}$ and $R^{c2}$ are each independently hydrogen or C$_{1-6}$ alkyl. In some embodiments, $R^{c1}$ and $R^{c2}$ are each independently hydrogen, methyl, or ethyl. In some embodiments, —NR$^{c3}$R$^{c4}$ is

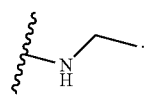

In some embodiments, $R^{c3}$ and $R^{c4}$ are each independently hydrogen or C$_{1-6}$ alkyl. In some embodiments, $R^{c1}$ and $R^{c2}$ are each independently hydrogen, methyl, or ethyl. In some embodiments, —NR$^{c5}$S(O)$_2$R$^{c6}$ is

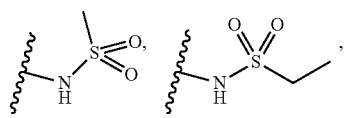

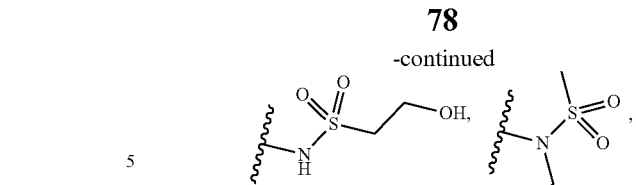

In some embodiments, —NR$^{c5}$S(O)$_2$R$^{c6}$ is

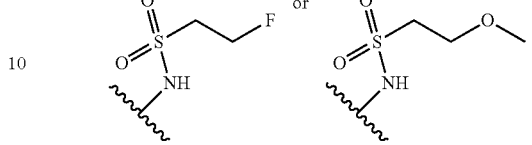

In some embodiments, $R^{c5}$ is hydrogen or C$_{1-6}$ alkyl. In some embodiments, $R^{c5}$ is hydrogen, methyl, or ethyl. In some embodiments, $R^{c6}$ is hydrogen or C$_{1-6}$ alkyl optionally substituted with one, two, three, four, five, or more substituents independently selected from halo, —OH, —O(C$_{1-6}$ alkyl), and —NHC(O)(C$_{1-6}$ alky). In some embodiments, $R^{c5}$ is methyl or —CH$_2$CH$_2$OH. In some embodiments, $R^{c5}$ is hydrogen. In some embodiments, $R^{c6}$ is ethyl. In some embodiments, $R^{c6}$ is —CH$_2$CH$_2$F. In some embodiments, $R^{c6}$ is —OCH$_3$. In some embodiments, —P(O)R$^{c7}$R$^{c8}$ is

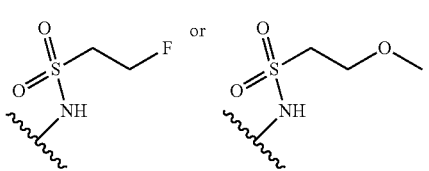

In some embodiments, $R^{c7}$ and $R^{c8}$ are each independently C$_{1-6}$ alkyl. In some embodiments, $R^{c7}$ and $R^{c8}$ are each methyl. In some embodiments, —N=S(O)R$^{c9}$R$^{c10}$ is

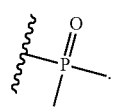

In some embodiments, $R^{c9}$ and $R^{c10}$ are each independently C$_{1-6}$ alkyl. In some embodiments, $R^{c9}$ and $R^{c10}$ are each methyl. In some embodiments, —S(O)(NR$^{c11}$)R$^{c12}$ is

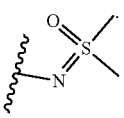

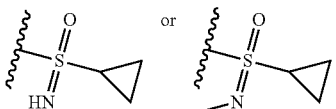

In some embodiments, $R^{c11}$ is hydrogen or C$_{1-6}$ alkyl. In some embodiments, $R^{c11}$ is hydrogen or methyl. In some embodiments, $R^{c12}$ is $C_{1-6}$ alkyl or $C_{3-10}$ cycloalkyl. In some embodiments, $R^{c12}$ is cyclopropyl. In some embodiments, —S(O)$_2$R$^{c13}$ is

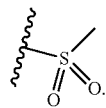

In some embodiments, $R^{c13}$ is $C_{1-6}$ alkyl. In some embodiments, $R^{c13}$ is methyl. In some embodiments, NR$^{c14}$C(O)OR$^{c15}$ is

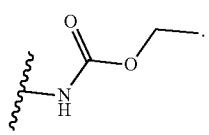 [SMILES: *NC(=O)OCC]

In some embodiments, $R^{c14}$ and $R^{c15}$ are each independently hydrogen or $C_{1-6}$ alkyl. In some embodiments, $R^{c14}$ is hydrogen. In some embodiments, $R^{c15}$ is ethyl. In some embodiments, —NR$^{c16}$S(O)$_2$(CH$_2$)$_{1-6}$NR$^{c17}$C(O)R$^{c18}$ is

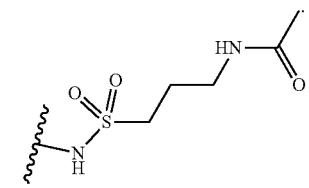 [SMILES: *NS(=O)(=O)CCCNC(C)=O]

In some embodiments, —NR$^{c16}$S(O)$_2$(CH$_2$)$_{1-6}$NR$^{c17}$C(O)R$^{c18}$ is —NR$^{c16}$S(O)$_2$(CH$_2$)$_{1-3}$NR$^{c17}$C(O)R$^{c18}$. In some embodiments, $R^{c16}$, $R^{c17}$ and $R^{c18}$ are each independently hydrogen or $C_{1-6}$ alkyl. In some embodiments, $R^{c16}$ and $R^{c17}$ are hydrogen. In some embodiments, $R^{c18}$ is methyl.

In some embodiments, provided herein are compounds and pharmaceutically acceptable salts thereof described in Table 1.

TABLE 1

| Compound No. | Structure | Name |
|---|---|---|
| Compound 1 | 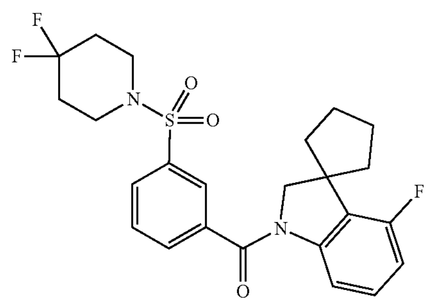 [SMILES: O=C(c1cccc(S(=O)(=O)N2CCC(F)(F)CC2)c1)N1CC2(CCCC2)c2c(F)cccc21] | (3-((4,4-difluoropiperidin-1-yl)sulfonyl)phenyl)(4'-fluorospiro[cyclopentane-1,3'-indolin]-1'-yl)methanone |
| Compound 2 | 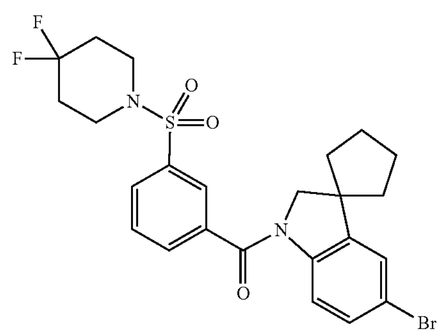 [SMILES: O=C(c1cccc(S(=O)(=O)N2CCC(F)(F)CC2)c1)N1CC2(CCCC2)c2cc(Br)ccc21] | (5'-bromospiro[cyclopentane-1,3'-indolin]-1'-yl)(3-((4,4-difluoropiperidin-1-yl)sulfonyl)phenyl)methanone |
| Compound 3 | 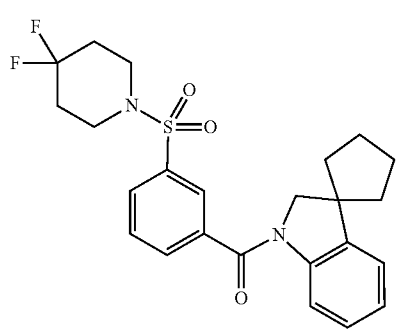 [SMILES: O=C(c1cccc(S(=O)(=O)N2CCC(F)(F)CC2)c1)N1CC2(CCCC2)c2ccccc21] | (3-((4,4-difluoropiperidin-1-yl)sulfonyl)phenyl)(spiro[cyclopentane-1,3'-indolin]-1'-yl)methanone |

TABLE 1-continued

| Compound No. | Structure | Name |
|---|---|---|
| Compound 4 | 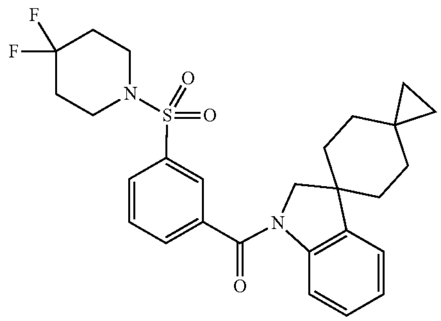 [SMILES: O=C(c1cccc(S(=O)(=O)N2CCC(F)(F)CC2)c1)N1CC2(CCC3(CC3)CC2)c2ccccc21] | (3-((4,4-difluoropiperidin-1-yl)sulfonyl)phenyl)(dispiro[cyclopropane-1,1'-cyclohexane-4',3''-indolin]-1''-yl)methanone |
| Compound 5 | 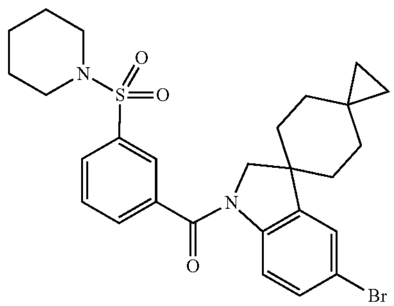 [SMILES: O=C(c1cccc(S(=O)(=O)N2CCCCC2)c1)N1CC2(CCC3(CC3)CC2)c2cc(Br)ccc21] | (5''-bromodispiro[cyclopropane-1,1'-cyclohexane-4',3''-indolin]-1''-yl)(3-(piperidin-1-yl)sulfonyl)phenyl)methanone |
| Compound 6 | 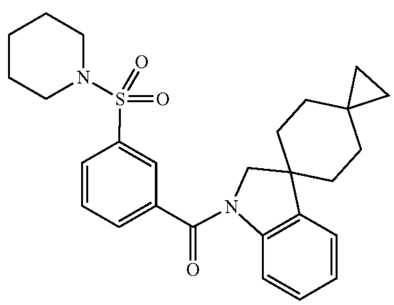 [SMILES: O=C(c1cccc(S(=O)(=O)N2CCCCC2)c1)N1CC2(CCC3(CC3)CC2)c2ccccc21] | dispiro[cyclopropane-1,1'-cyclohexane-4',3''-indolin]-1''-yl(3-(piperidin-1-ylsulfonyl)phenyl)methanone |
| Compound 7 | 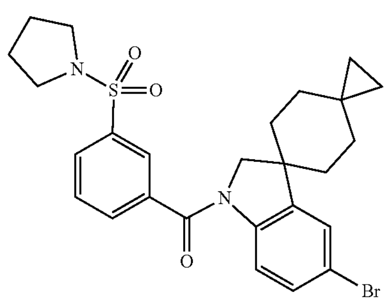 [SMILES: O=C(c1cccc(S(=O)(=O)N2CCCC2)c1)N1CC2(CCC3(CC3)CC2)c2cc(Br)ccc21] | (5''-bromodispiro[cyclopropane-1,1'-cyclohexane-4',3''-indolin]-1''-yl)(3-(pyrrolidin-1-ylsulfonyl)phenyl)methanone |
| Compound 8 | 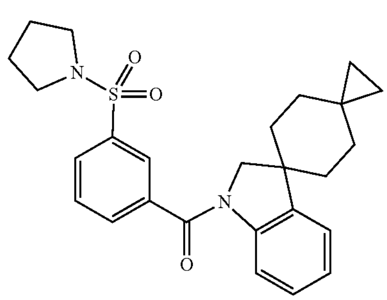 [SMILES: O=C(c1cccc(S(=O)(=O)N2CCCC2)c1)N1CC2(CCC3(CC3)CC2)c2ccccc21] | dispiro[cyclopropane-1,1'-cyclohexane-4',3''-indolin]-1''-yl(3-(pyrrolidin-1-ylsulfonyl)phenyl)methanone |

TABLE 1-continued

| Compound No. | Structure | Name |
|---|---|---|
| Compound 9 | 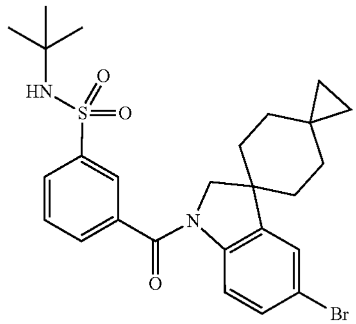 [SMILES: CC(C)(C)NS(=O)(=O)c1cccc(C(=O)N2CC3(CCC4(CC4)CC3)c3cc(Br)ccc32)c1] | 3-(5''-bromodispiro[cyclopropane-1,1'-cyclohexane-4',3''-indoline]-1''-carbonyl)-N-(tert-butyl)benzenesulfonamide |
| Compound 10 | 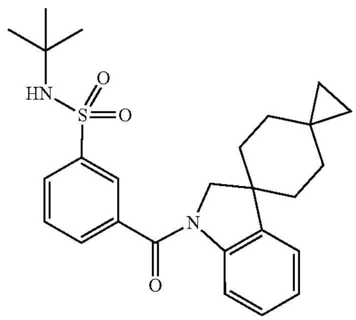 [SMILES: CC(C)(C)NS(=O)(=O)c1cccc(C(=O)N2CC3(CCC4(CC4)CC3)c3ccccc32)c1] | N-(tert-butyl)-3-(dispiro[cyclopropane-1,1'-cyclohexane-4',3''-indoline]-1''-carbonyl)benzenesulfonamide |
| Compound 11 | 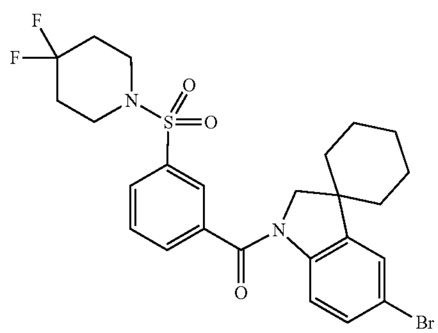 [SMILES: O=C(c1cccc(S(=O)(=O)N2CCC(F)(F)CC2)c1)N1CC2(CCCCC2)c2cc(Br)ccc21] | (5'-bromospiro[cyclohexane-1,3'-indolin]-1'-yl)(3-((4,4-difluoropiperidin-1-yl)sulfonyl)phenyl)methanone |
| Compound 12 | 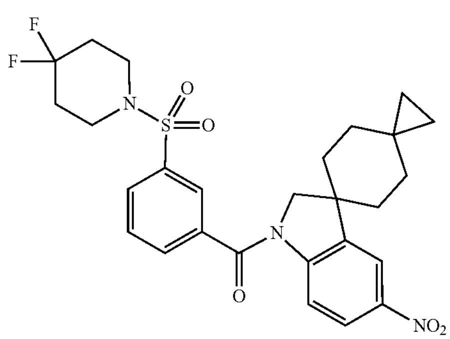 [SMILES: O=C(c1cccc(S(=O)(=O)N2CCC(F)(F)CC2)c1)N1CC2(CCC3(CC3)CC2)c2cc([N+](=O)[O-])ccc21] | (3-((4,4-difluoropiperidin-1-yl)sulfonyl)phenyl)(5''-nitrodispiro[cyclopropane-1,1'-cyclohexane-4',3''-indolin]-1''-yl)methanone |

TABLE 1-continued

| Compound No. | Structure | Name |
|---|---|---|
| Compound 13 | 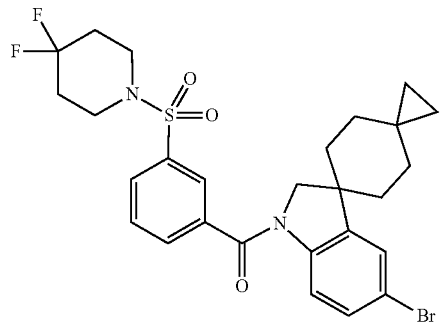 [SMILES: O=C(c1cccc(S(=O)(=O)N2CCC(F)(F)CC2)c1)N1CC2(CCC3(CC3)CC2)c2cc(Br)ccc21] | (5''-bromodispiro[cyclopropane-1,1'-cyclohexane-4',3''-indolin]-1''-yl)(3-((4,4-difluoropiperidin-1-yl)sulfonyl)phenyl)methanone |
| Compound 14 | 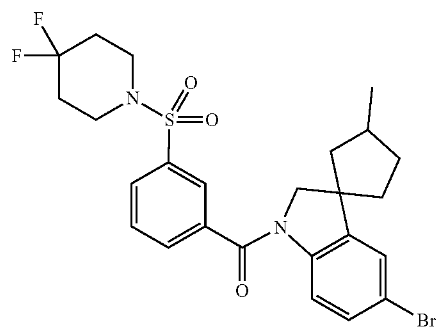 [SMILES: CC1CCC2(C1)CN(C(=O)c1cccc(S(=O)(=O)N3CCC(F)(F)CC3)c1)c1ccc(Br)cc12] | (5'-bromo-3-methylspiro[cyclopentane-1,3'-indolin]-1'-yl)(3-((4,4-difluoropiperidin-1-yl)sulfonyl)phenyl)methanone |
| Compound 15 | 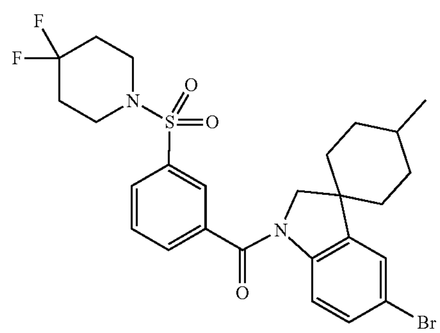 [SMILES: CC1CCC2(CC1)CN(C(=O)c1cccc(S(=O)(=O)N3CCC(F)(F)CC3)c1)c1ccc(Br)cc12] | (5'-bromo-4-methylspiro[cyclohexane-1,3'-indolin]-1'-yl)(3-((4,4-difluoropiperidin-1-yl)sulfonyl)phenyl)methanone |
| Compound 16 | 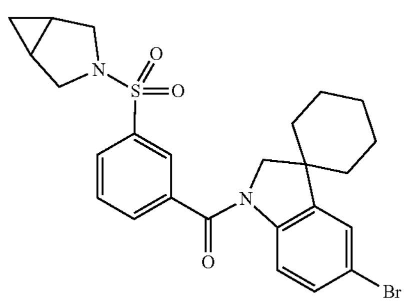 [SMILES: O=C(c1cccc(S(=O)(=O)N2CC3CC3C2)c1)N1CC2(CCCCC2)c2cc(Br)ccc21] | (3-((3-azabicyclo[3.1.0]hexan-3-yl)sulfonyl)phenyl)(5'-bromospiro[cyclohexane-1,3'-indolin]-1'-yl)methanone |

TABLE 1-continued

| Compound No. | Structure | Name |
|---|---|---|
| Compound 17 | 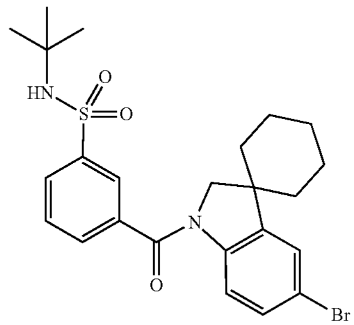 [SMILES: CC(C)(C)NS(=O)(=O)c1cccc(C(=O)N2CC3(CCCCC3)c3cc(Br)ccc32)c1] | 3-(5'-bromospiro[cyclohexane-1,3'-indoline]-1'-carbonyl)-N-(tert-butyl)benzenesulfonamide |
| Compound 18 | 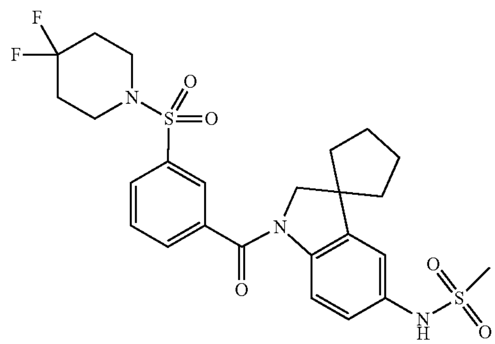 [SMILES: CS(=O)(=O)Nc1ccc2c(c1)C1(CCCC1)CN2C(=O)c1cccc(S(=O)(=O)N2CCC(F)(F)CC2)c1] | N-(1'-(3-((4,4-difluoropiperidin-1-yl)sulfonyl)benzoyl)spiro[cyclopentane-1,3'-indolin]-5'-yl)methanesulfonamide |
| Compound 19 | 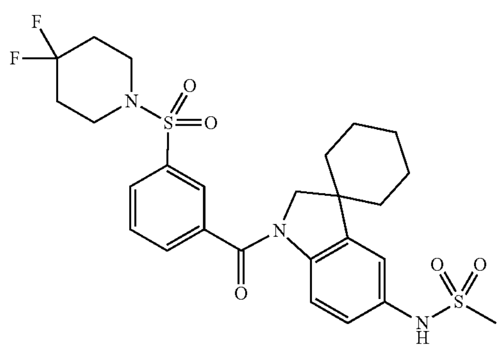 [SMILES: CS(=O)(=O)Nc1ccc2c(c1)C1(CCCCC1)CN2C(=O)c1cccc(S(=O)(=O)N2CCC(F)(F)CC2)c1] | N-(1'-(3-((4,4-difluoropiperidin-1-yl)sulfonyl)benzoyl)spiro[cyclohexane-1,3'-indolin]-5'-yl)methanesulfonamide |
| Compound 20 | 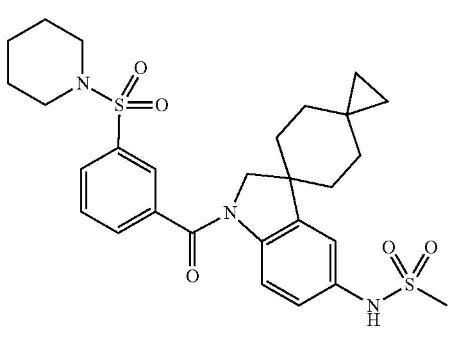 [SMILES: CS(=O)(=O)Nc1ccc2c(c1)C1(CCC3(CC3)CC1)CN2C(=O)c1cccc(S(=O)(=O)N2CCCCC2)c1] | N-(1''-(3-(piperidin-1-ylsulfonyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 21 | 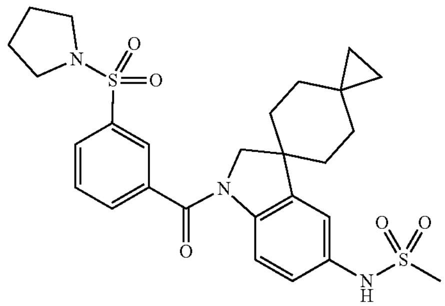 [SMILES: CS(=O)(=O)Nc1ccc2c(c1)C1(CCC3(CC3)CC1)CN2C(=O)c1cccc(S(=O)(=O)N2CCCC2)c1] | N-(1"-(3-(pyrrolidin-1-ylsulfonyl)benzoyl)dispiro[cyclopropane-1,1'-cyclohexane-4',3"-indolin]-5"-yl)methanesulfonamide |
| Compound 22 | 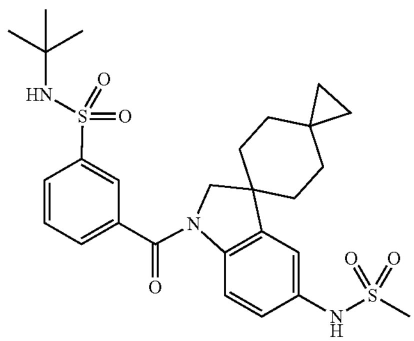 [SMILES: CC(C)(C)NS(=O)(=O)c1cccc(C(=O)N2CC3(CCC4(CC4)CC3)c3cc(NS(C)(=O)=O)ccc32)c1] | N-(tert-butyl)-3-(5"-(methylsulfonamido)dispiro[cyclopropane-1,1'-cyclohexane-4',3"-indoline]-1"-carbonyl)benzenesulfonamide |
| Compound 23 | 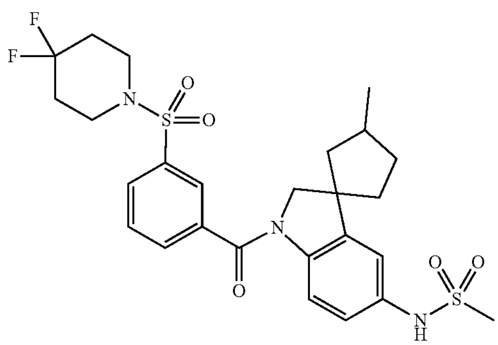 [SMILES: CC1CCC2(C1)CN(C(=O)c1cccc(S(=O)(=O)N3CCC(F)(F)CC3)c1)c1ccc(NS(C)(=O)=O)cc12] | N-(1'-(3-((4,4-difluoropiperidin-1-yl)sulfonyl)benzoyl)-3-methylspiro[cyclopentane-1,3'-indolin]-5'-yl)methanesulfonamide |
| Compound 24 | 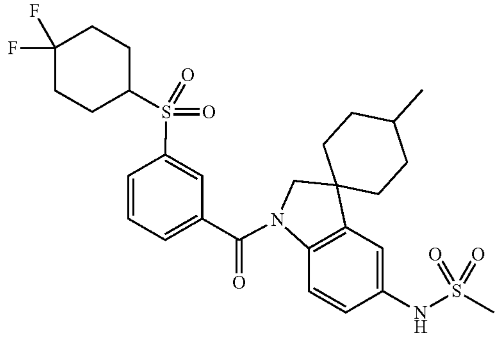 [SMILES: CC1CCC2(CC1)CN(C(=O)c1cccc(S(=O)(=O)C3CCC(F)(F)CC3)c1)c1ccc(NS(C)(=O)=O)cc12] | N-(1'-(3-((4,4-difluoropiperidin-1-yl)sulfonyl)benzoyl)-4-methylspiro[cyclohexane-1,3'-indolin]-5'-yl)methanesulfonamide |

TABLE 1-continued

| Compound No. | Structure | Name |
|---|---|---|
| (1s,4s)-Compound 24 | 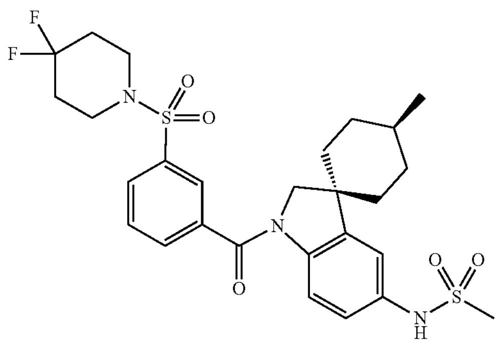 [SMILES: CS(=O)(=O)Nc1ccc2c(c1)[C@]1(CC[C@H](C)CC1)CN2C(=O)c1cccc(S(=O)(=O)N2CCC(F)(F)CC2)c1] | N-((1s,4s)-1'-(3-((4,4-difluoropiperidin-1-yl)sulfonyl)benzoyl)-4-methylspiro[cyclohexane-1,3'-indolin]-5'-yl)methanesulfonamide |
| (1r,4r)-Compound 24 | 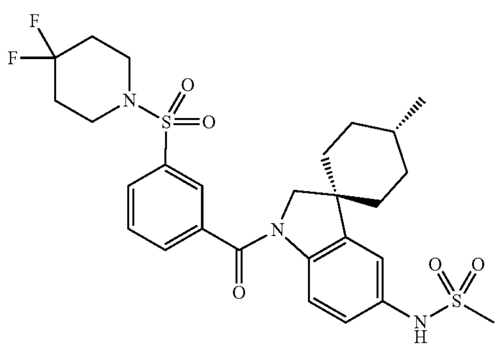 [SMILES: CS(=O)(=O)Nc1ccc2c(c1)[C@]1(CC[C@@H](C)CC1)CN2C(=O)c1cccc(S(=O)(=O)N2CCC(F)(F)CC2)c1] | N-((1r,4r)-1'-(3-((4,4-difluoropiperidin-1-yl)sulfonyl)benzoyl)-4-methylspiro[cyclohexane-1,3'-indolin]-5'-yl)methanesulfonamide |
| Compound 25 | 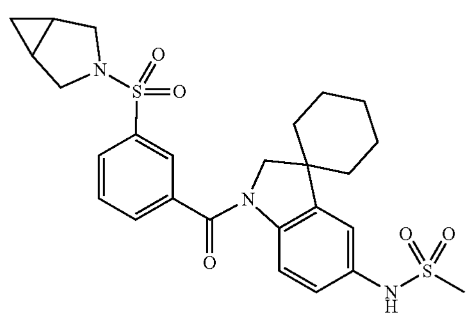 [SMILES: CS(=O)(=O)Nc1ccc2c(c1)C1(CCCCC1)CN2C(=O)c1cccc(S(=O)(=O)N2CC3CC3C2)c1] | N-(1'-(3-((3-azabicyclo[3.1.0]hexan-3-yl)sulfonyl)benzoyl)spiro[cyclohexane-1,3'-indolin]-5'-yl)methanesulfonamide |
| Compound 26 | 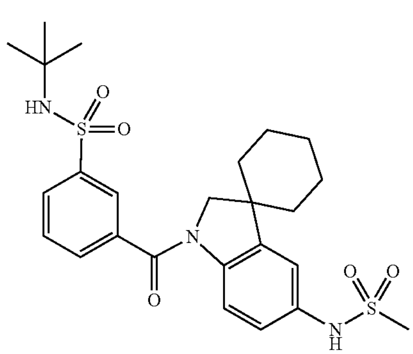 [SMILES: CC(C)(C)NS(=O)(=O)c1cccc(C(=O)N2CC3(CCCCC3)c3cc(NS(C)(=O)=O)ccc32)c1] | N-(tert-butyl)-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 27 | 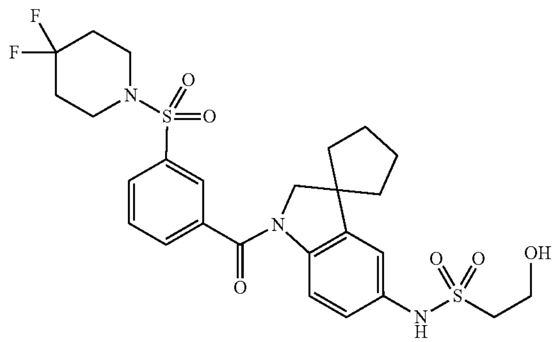 [SMILES: O=C(c1cccc(S(=O)(=O)N2CCC(F)(F)CC2)c1)N1CC2(CCCC2)c2cc(NS(=O)(=O)CCO)ccc21] | N-(1'-(3-((4,4-difluoropiperidin-1-yl)sulfonyl)benzoyl)spiro[cyclopentane-1,3'-indolin]-5'-yl)-2-hydroxyethane-1-sulfonamide |
| Compound 28 | 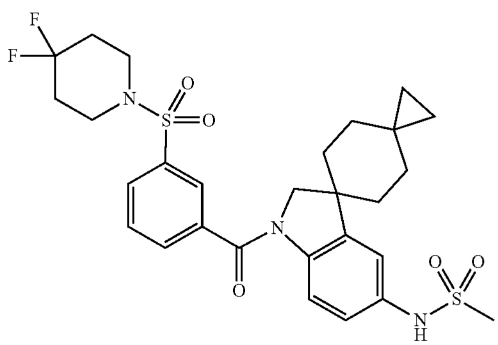 [SMILES: CS(=O)(=O)Nc1ccc2c(c1)C1(CCC3(CC3)CC1)CN2C(=O)c1cccc(S(=O)(=O)N2CCC(F)(F)CC2)c1] | N-(1''-(3-((4,4-difluoropiperidin-1-yl)sulfonyl)benzoyl)dispiro[cyclopropane-1,1'-cyclohexane-4',3''-indolin]-5''-yl)methanesulfonamide |
| Compound 29 | 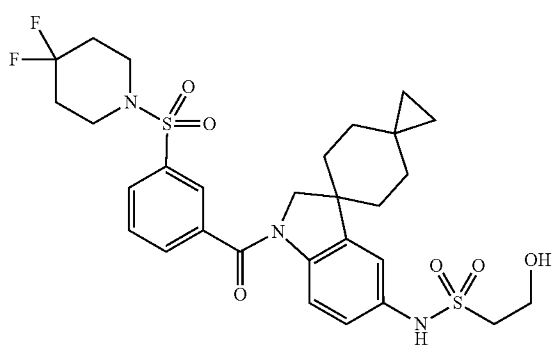 [SMILES: O=C(c1cccc(S(=O)(=O)N2CCC(F)(F)CC2)c1)N1CC2(CCC3(CC3)CC2)c2cc(NS(=O)(=O)CCO)ccc21] | N-(1''-(3-((4,4-difluoropiperidin-1-yl)sulfonyl)benzoyl)dispiro[cyclopropane-1,1'-cyclohexane-4',3''-indolin]-5''-yl)-2-hydroxyethane-1-sulfonamide |
| Compound 30 | 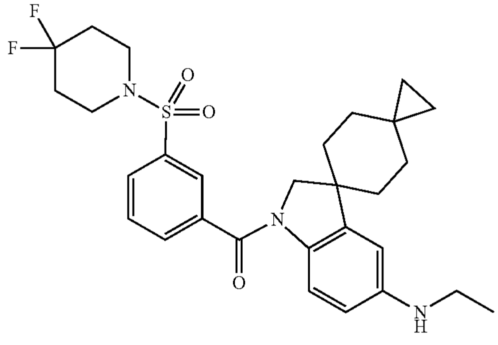 [SMILES: CCNc1ccc2c(c1)C1(CCC3(CC3)CC1)CN2C(=O)c1cccc(S(=O)(=O)N2CCC(F)(F)CC2)c1] | (3-((4,4-difluoropiperidin-1-yl)sulfonyl)phenyl)(5''-(ethylamino)dispiro[cyclopropane-1,1'-cyclohexane-4',3''-indolin]-1''-yl)methanone |

TABLE 1-continued

| Compound No. | Structure | Name |
|---|---|---|
| Compound 31 | 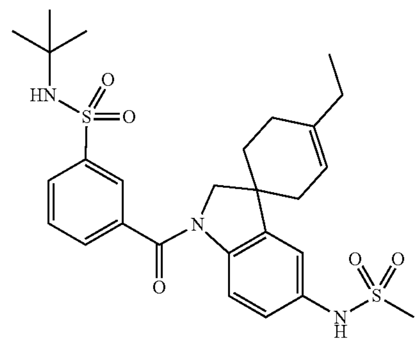 [SMILES: CCC1=CCC2(CC1)CN(C(=O)c1cccc(S(=O)(=O)NC(C)(C)C)c1)c1ccc(NS(C)(=O)=O)cc12] | N-(tert-butyl)-3-(4-ethyl-5'-(methylsulfonamido)spiro[cyclohexane-1,3'-indolin]-3-en-1'-carbonyl)benzenesulfonamide |
| Compound 32 | 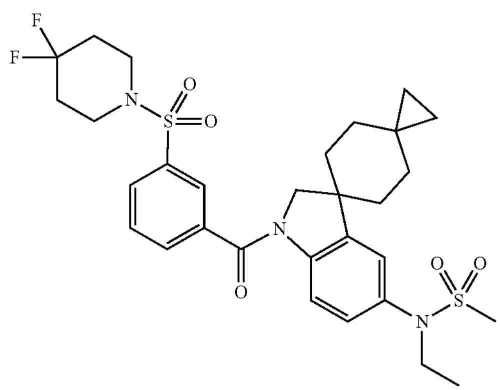 [SMILES: CCN(c1ccc2c(c1)C1(CCC3(CC3)CC1)CN2C(=O)c1cccc(S(=O)(=O)N2CCC(F)(F)CC2)c1)S(C)(=O)=O] | N-(1''-(3-((4,4-difluoropiperidin-1-yl)sulfonyl)benzoyl)dispiro[cyclopropane-1,1'-cyclohexane-4',3''-indolin]-5''-yl)-N-ethylmethanesulfonamide |
| Compound 33 | 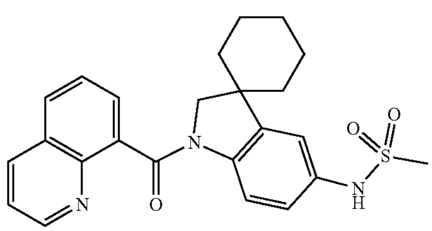 [SMILES: CS(=O)(=O)Nc1ccc2c(c1)C1(CCCCC1)CN2C(=O)c1cccc2cccnc12] | N-(1'-(quinoline-8-carbonyl)spiro[cyclohexane-1,3'-indolin]-5'-yl)methanesulfonamide |
| Compound 34 | 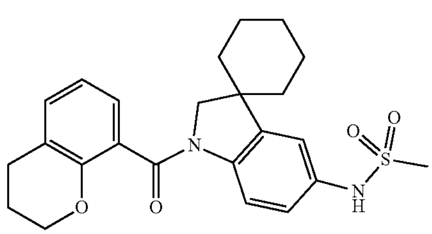 [SMILES: CS(=O)(=O)Nc1ccc2c(c1)C1(CCCCC1)CN2C(=O)c1cccc2c1OCCC2] | N-(1'-(chromane-8-carbonyl)spiro[cyclohexane-1,3'-indolin]-5''-yl)methanesulfonamide |
| Compound 35 | 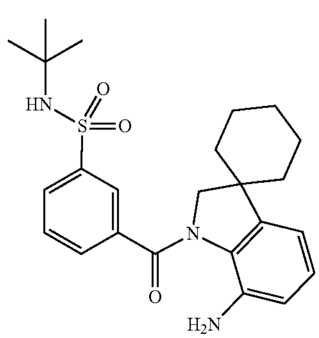 [SMILES: CC(C)(C)NS(=O)(=O)c1cccc(C(=O)N2CC3(CCCCC3)c3cccc(N)c32)c1] | 3-(7'-aminospiro[cyclohexane-1,3'-indoline]-1'-carbonyl)-N-(tert-butyl)benzenesulfonamide |

TABLE 1-continued

| Compound No. | Structure | Name |
|---|---|---|
| Compound 36 | 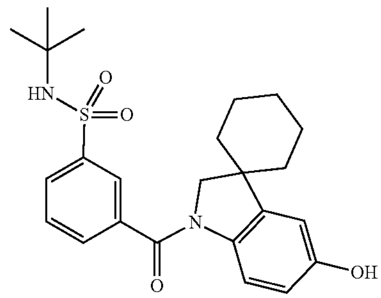 [SMILES: CC(C)(C)NS(=O)(=O)c1cccc(C(=O)N2CC3(CCCCC3)c3cc(O)ccc32)c1] | N-(tert-butyl)-3-(5'-hydroxyspiro[cyclohexane-1,3'-indoline]-1'-carbonyl)benzenesulfonamide |
| Compound 37 | 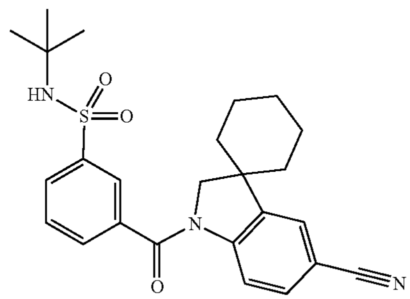 [SMILES: CC(C)(C)NS(=O)(=O)c1cccc(C(=O)N2CC3(CCCCC3)c3cc(C#N)ccc32)c1] | N-(tert-butyl)-3-(5'-cyanospiro[cyclohexane-1,3'-indoline]-1'-carbonyl)benzenesulfonamide |
| Compound 38 | 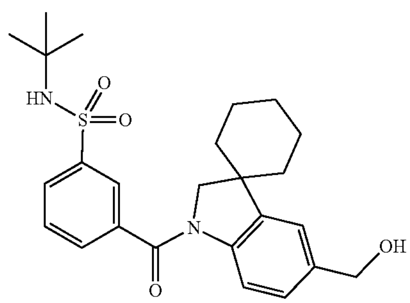 [SMILES: CC(C)(C)NS(=O)(=O)c1cccc(C(=O)N2CC3(CCCCC3)c3cc(CO)ccc32)c1] | N-(tert-butyl)-3-(5'-(hydroxymethyl)spiro[cyclohexane-1,3'-indoline]-1'-carbonyl)benzenesulfonamide |
| Compound 39 | 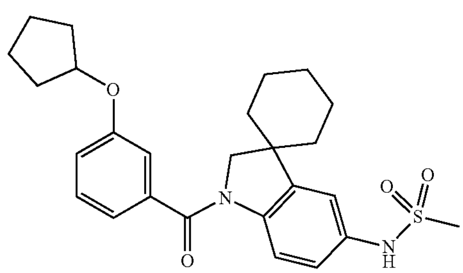 [SMILES: CS(=O)(=O)Nc1ccc2c(c1)C1(CCCCC1)CN2C(=O)c1cccc(OC2CCCC2)c1] | N-(1'-(3-(cyclopentyloxy)benzoyl)spiro[cyclohexane-1,3'-indolin]-5'-yl)methanesulfonamide |
| Compound 40 | 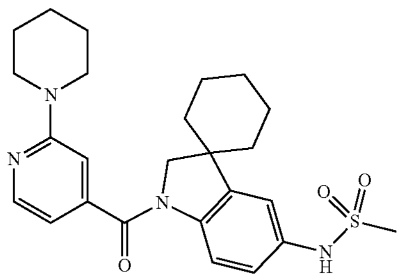 [SMILES: CS(=O)(=O)Nc1ccc2c(c1)C1(CCCCC1)CN2C(=O)c1ccnc(N2CCCCC2)c1] | N-(1'-(2-(piperidin-1-yl)nicotinoyl)spiro[cyclohexane-1,3'-indolin]-5'-yl)methanesulfonamide |

TABLE 1-continued

| Compound No. | Structure | Name |
|---|---|---|
| Compound 41 | 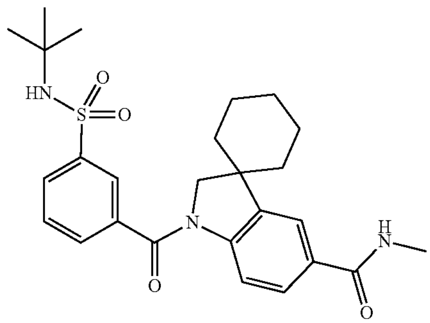 [SMILES: CNC(=O)c1ccc2c(c1)C1(CCCCC1)CN2C(=O)c1cccc(S(=O)(=O)NC(C)(C)C)c1] | 1'-(3-(N-(tert-butyl)sulfamoyl)benzoyl)-N-methylspiro[cyclohexane-1,3'-indoline]-5'-carboxamide |
| Compound 42 | 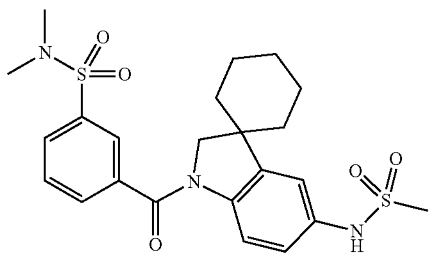 | N,N-dimethyl-3-(5'-(methylsulfonamido)spiro[cyclohexane-1,3-indoline]-1'-carbonyl)benzenesulfonamide |
| Compound 43 | 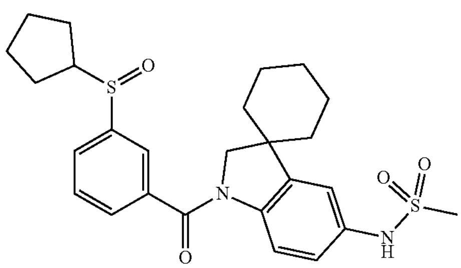 [SMILES: CS(=O)(=O)Nc1ccc2c(c1)C1(CCCCC1)CN2C(=O)c1cccc(S(=O)C2CCCC2)c1] | N-(1'-(3-(cyclopentylsulfinyl)benzoyl)spiro[cyclohexane-1,3'-indolin]-5'-yl)methanesulfonamide |
| Compound 44 | 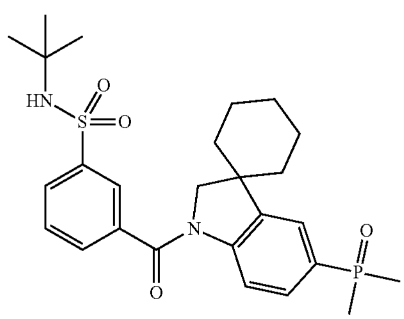 [SMILES: CC(C)(C)NS(=O)(=O)c1cccc(C(=O)N2CC3(CCCCC3)c3cc(P(C)(C)=O)ccc32)c1] | N-(tert-butyl)-3-(5'-(dimethylphosphoryl)spiro[cyclohexane-1,3'-indoline]-1'-carbonyl)benzenesulfonamide |
| Compound 45 | 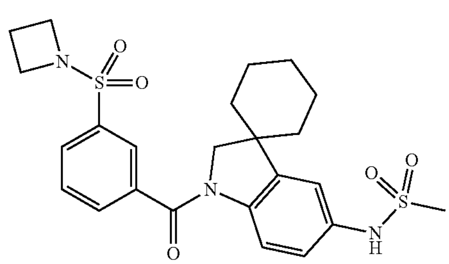 [SMILES: CS(=O)(=O)Nc1ccc2c(c1)C1(CCCCC1)CN2C(=O)c1cccc(S(=O)(=O)N2CCC2)c1] | N-(1'-(3-(azetidin-1-ylsulfonyl)benzoyl)spiro[cyclohexane-1,3'-indolin]-5'-yl)methanesulfonamide |

TABLE 1-continued

| Compound No. | Structure | Name |
|---|---|---|
| Compound 46 | 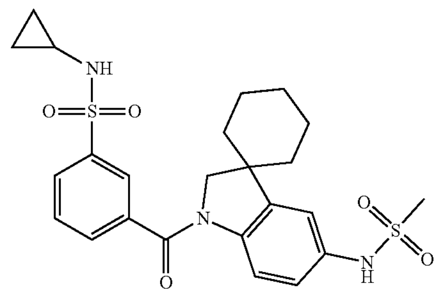 [SMILES: CS(=O)(=O)Nc1ccc2c(c1)C1(CCCCC1)CN2C(=O)c1cccc(S(=O)(=O)NC2CC2)c1] | N-cyclopropyl-3-(5'-(methylsulfonamido)spiro[cyclohexane-1,3'-indoline]-1'-carbonyl)benzenesulfonamide |
| Compound 47 | 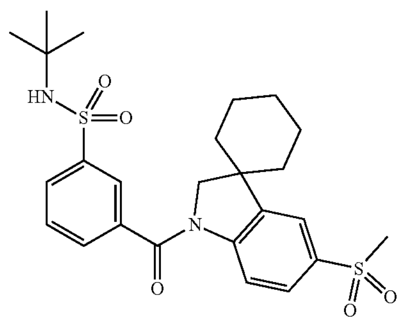 [SMILES: CC(C)(C)NS(=O)(=O)c1cccc(C(=O)N2CC3(CCCCC3)c3cc(S(C)(=O)=O)ccc32)c1] | N-(tert-butyl)-3-(5'-(methylsulfonyl)spiro[cyclohexane-1,3'-indoline]-1'-carbonyl)benzenesulfonamide |
| Compound 48 | 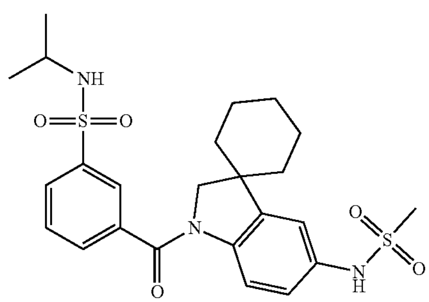 [SMILES: CC(C)NS(=O)(=O)c1cccc(C(=O)N2CC3(CCCCC3)c3cc(NS(C)(=O)=O)ccc32)c1] | N-isopropyl-3-(5'-(methylsulfonamido)spiro[cyclohexane-1,3'-indoline]-1'-carbonyl)benzenesulfonamide |
| Compound 49 | 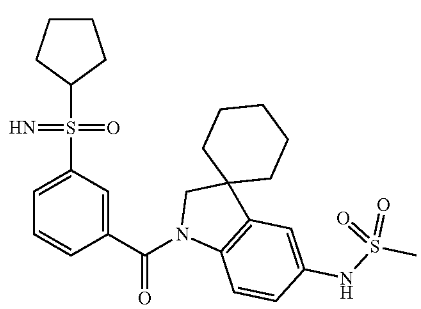 [SMILES: CS(=O)(=O)Nc1ccc2c(c1)C1(CCCCC1)CN2C(=O)c1cccc(S(=N)(=O)C2CCCC2)c1] | N-(1'-(3-(cyclopentanesulfonamidoyl)benzoyl)spiro[cyclohexane-1,3'-indolin]-5'-yl)methanesulfonamide |
| Compound 50 | 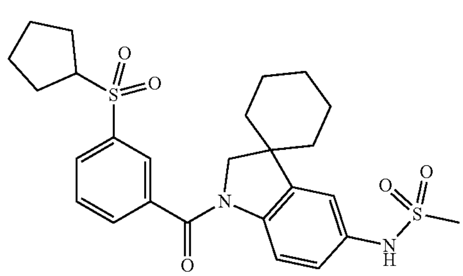 [SMILES: CS(=O)(=O)Nc1ccc2c(c1)C1(CCCCC1)CN2C(=O)c1cccc(S(=O)(=O)C2CCCC2)c1] | N-(1'-(3-(cyclopentylsulfonyl)benzoyl)spiro[cyclohexane-1,3'-indolin]-5'-yl)methanesulfonamide |

TABLE 1-continued

| Compound No. | Structure | Name |
|---|---|---|
| Compound 51 | 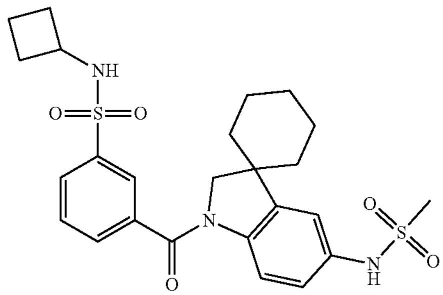 [SMILES: CS(=O)(=O)Nc1ccc2c(c1)C1(CCCCC1)CN2C(=O)c1cccc(S(=O)(=O)NC2CCC2)c1] | N-cyclobutyl-3-(5'-(methylsulfonamido)spiro[cyclohexane-1,3'-indoline]-1'-carbonyl)benzenesulfonamide |
| Compound 52 | 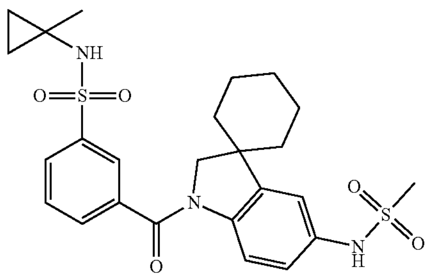 [SMILES: CC1(NS(=O)(=O)c2cccc(C(=O)N3CC4(CCCCC4)c4cc(NS(C)(=O)=O)ccc43)c2)CC1] | 3-({5'-methanesulfonamido-1',2'-dihydrospiro[cyclohexane-1,3'-indol]-1'-yl}carbonyl)-N-(1-methylcyclopropyl)benzene-1-sulfonamide |
| Compound 53 | 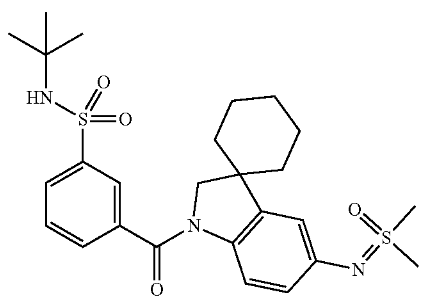 [SMILES: CC(C)(C)NS(=O)(=O)c1cccc(C(=O)N2CC3(CCCCC3)c3cc(N=S(C)(C)=O)ccc32)c1] | N-(tert-butyl)-3-(5'-((dimethyl(oxo)-$\lambda^6$-sulfanylidene)amino)amino)spiro[cyclohexane-1,3'-indoline]-1'-carbonyl)benzenesulfonamide |
| Compound 54 | 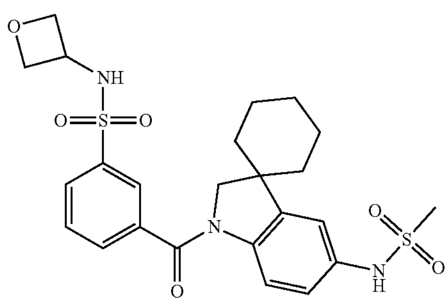 [SMILES: CS(=O)(=O)Nc1ccc2c(c1)C1(CCCCC1)CN2C(=O)c1cccc(S(=O)(=O)NC2COC2)c1] | 3-(5'-(methylsulfonamido)spiro[cyclohexane-1,3'-indoline]-1'-carbonyl)-N-(oxetan-3-yl)benzenesulfonamide |
| Compound 55 | 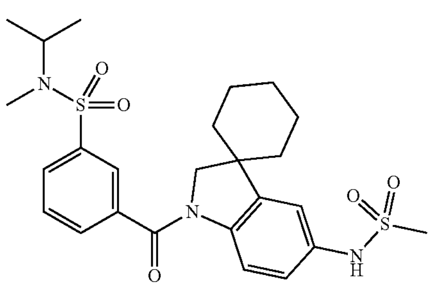 [SMILES: CC(C)N(C)S(=O)(=O)c1cccc(C(=O)N2CC3(CCCCC3)c3cc(NS(C)(=O)=O)ccc32)c1] | N-isopropyl-N-methyl-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 56 | 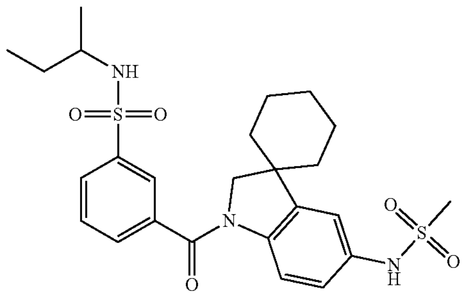 [SMILES: CCC(C)NS(=O)(=O)c1cccc(C(=O)N2CC3(CCCCC3)c3cc(NS(C)(=O)=O)ccc32)c1] | N-(sec-butyl)-3-(5'-(methylsulfonamido)spiro[cyclohexane-1,3'-indoline]-1'-carbonyl)benzenesulfonamide |
| Compound 57 | 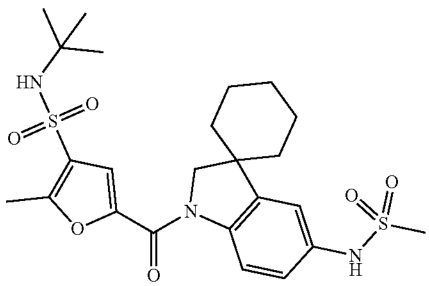 | N-(tert-butyl)-2-methyl-5-(5'-(methylsulfonamido)spiro[cyclohexane-1,3'-indoline]-1'-carbonyl)furan-3-sulfonamide |
| Compound 58 | 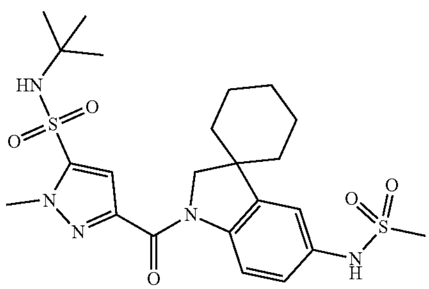 | N-(tert-butyl)-1-methyl-3-(5'-(methylsulfonamido)spiro[cyclohexane-1,3'-indoline]-1'-carbonyl)-1H-pyrazole-5-sulfonamide |
| Compound 59 | 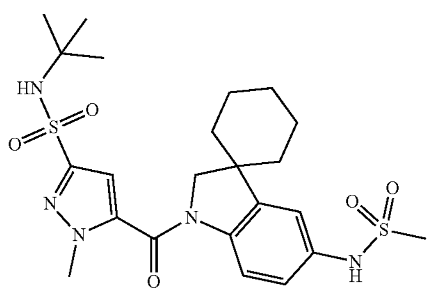 [SMILES: Cn1nc(S(=O)(=O)NC(C)(C)C)cc1C(=O)N1CC2(CCCCC2)c2cc(NS(C)(=O)=O)ccc21] | N-(tert-butyl)-1-methyl-5-(5'-(methylsulfonamido)spiro[cyclohexane-1,3'-indoline]-1'-carbonyl)-1H-pyrazole-3-sulfonamide |
| Compound 60 | 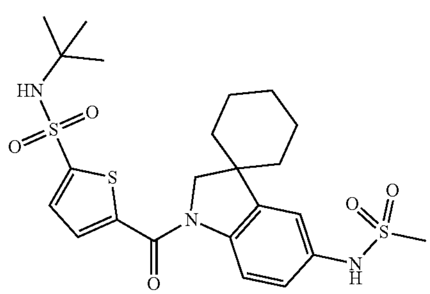 [SMILES: CC(C)(C)NS(=O)(=O)c1ccc(C(=O)N2CC3(CCCCC3)c3cc(NS(C)(=O)=O)ccc32)s1] | N-(tert-butyl)-5-(5'-(methylsulfonamido)spiro[cyclohexane-1,3'-indoline]-1'-carbonyl)thiophene-2-sulfonamide |

TABLE 1-continued

| Compound No. | Structure | Name |
|---|---|---|
| Compound 61 | 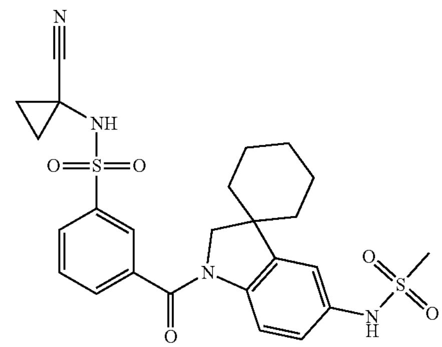 [SMILES: CS(=O)(=O)Nc1ccc2c(c1)C1(CCCCC1)CN2C(=O)c1cccc(S(=O)(=O)NC2(C#N)CC2)c1] | N-(1-cyanocyclopropyl)-3-(5'-(methylsulfonamido)spiro[cyclohexane-1,3'-indoline]-1'-carbonyl)benzenesulfonamide |
| Compound 62 | 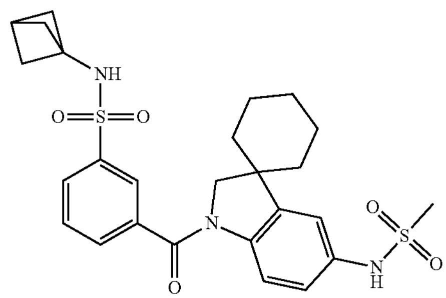 [SMILES: CS(=O)(=O)Nc1ccc2c(c1)C1(CCCCC1)CN2C(=O)c1cccc(S(=O)(=O)NC23CC(C2)C3)c1] | N-(bicyclo[1.1.1]pentan-1-yl)-3-(5'-(methylsulfonamido)spiro[cyclohexane-1,3'-indoline]-1'-carbonyl)benzenesulfonamide |
| Compound 63 | 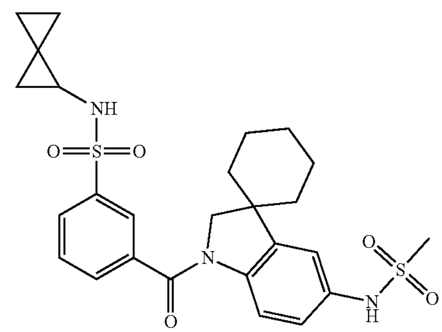 [SMILES: CS(=O)(=O)Nc1ccc2c(c1)C1(CCCCC1)CN2C(=O)c1cccc(S(=O)(=O)NC2CC23CC3)c1] | 3-(5'-(methylsulfonamido)spiro[cyclohexane-1,3'-indoline]-1'-carbonyl)-N-(spiro[2.2]pentan-1-yl)benzensulfonamide |
| Compound 64 | 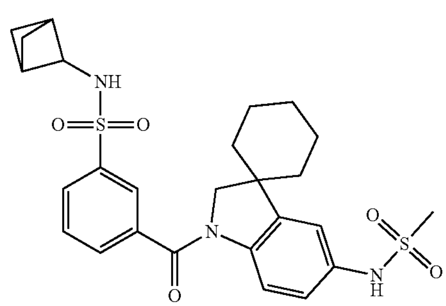 [SMILES: CS(=O)(=O)Nc1ccc2c(c1)C1(CCCCC1)CN2C(=O)c1cccc(S(=O)(=O)NC2C3CC2C3)c1] | N-(bicyclo[1.1.1]pentan-2-yl)-3-(5'-(methylsulfonamido)spiro[cyclohexane-1,3'-indoline]-1'-carbonyl)benzenesulfonamide |
| Compound 65 | 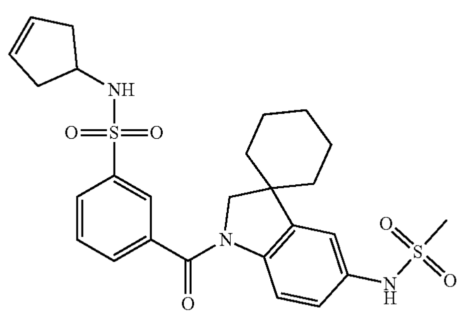 [SMILES: CS(=O)(=O)Nc1ccc2c(c1)C1(CCCCC1)CN2C(=O)c1cccc(S(=O)(=O)NC2CC=CC2)c1] | N-(cyclopent-3-en-1-yl)-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 66 | 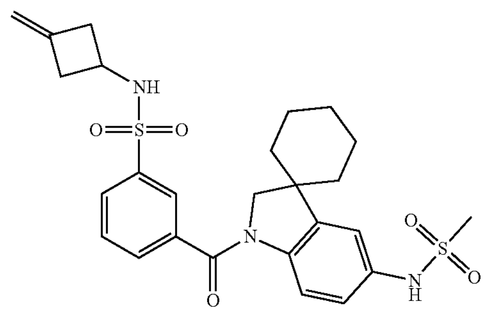 [SMILES: C=C1CC(NS(=O)(=O)c2cccc(C(=O)N3CC4(CCCCC4)c4cc(NS(C)(=O)=O)ccc43)c2)C1] | N-(3-methylenecyclobutyl)-3-(5'-(methylsulfonamido)spiro[cyclohexane-1,3'-indoline]-1'-carbonyl)benzenesulfonamide |
| Compound 67 | 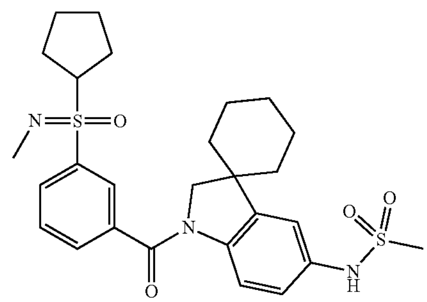 | N-(1'-(3-(N-methylcyclopentanesulfonimidoyl)benzoyl)spiro[cyclohexane-1,3'-indolin]-5'-yl)methanesulfonamide |
| Compound 68 | 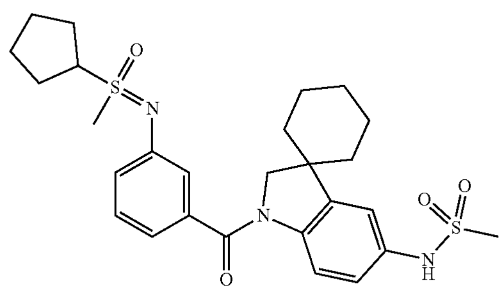 [SMILES: CS(=O)(=O)Nc1ccc2c(c1)C1(CCCCC1)CN2C(=O)c1cccc(N=S(C)(=O)C2CCCC2)c1] | N-(1'-(3-((cyclopentyl(methyl)(oxo)-$\lambda^6$-sulfaneylidene)amino)benzoyl)spiro[cyclohexane-1,3'-indolin]-5'-yl)methanesulfonamide |
| Compound 69 | 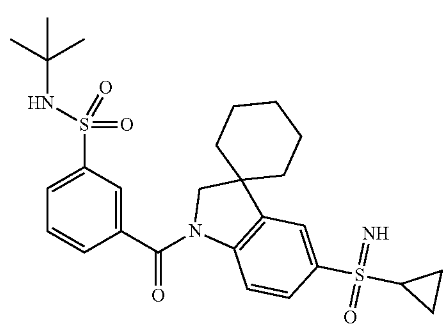 [SMILES: CC(C)(C)NS(=O)(=O)c1cccc(C(=O)N2CC3(CCCCC3)c3cc(S(=N)(=O)C4CC4)ccc32)c1] | N-(tert-butyl)-3-(5'-(cyclopropanesulfonimidoyl)spiro[cyclohexane-1,3'-indoline]-1'-carbonyl)benzenesulfonamide |
| Compound 70 | 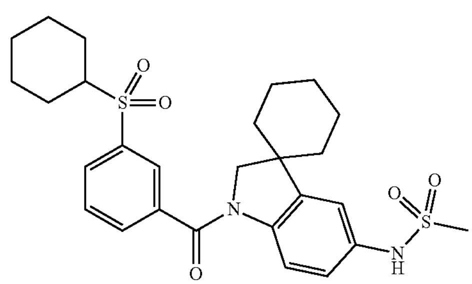 [SMILES: CS(=O)(=O)Nc1ccc2c(c1)C1(CCCCC1)CN2C(=O)c1cccc(S(=O)(=O)C2CCCCC2)c1] | N-(1'-(3-(cyclohexylsulfonyl)benzoyl)spiro[cyclohexane-1,3'-indolin]-5'-yl)methanesulfonamide |

TABLE 1-continued

| Compound No. | Structure | Name |
|---|---|---|
| Compound 71 | 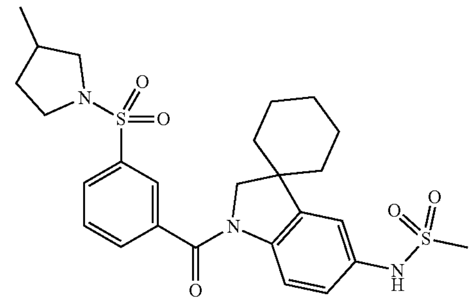 [SMILES: CC1CCN(S(=O)(=O)c2cccc(C(=O)N3CC4(CCCCC4)c4cc(NS(C)(=O)=O)ccc43)c2)C1] | N-(1'-(3-((3-methylpyrrolidin-1-yl)sulfonyl)benzoyl)spiro[cyclohexane-1,3'-indolin]-5'-yl)methanesulfonamide |
| Compound 72 | 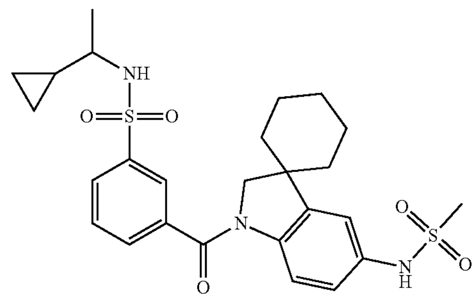 [SMILES: CC(NS(=O)(=O)c1cccc(C(=O)N2CC3(CCCCC3)c3cc(NS(C)(=O)=O)ccc32)c1)C1CC1] | N-(1-cyclopropylethyl)-3-(5'-(methylsulfonamido)spiro[cyclohexane-1,3'-indoline]-1'-carbonyl)benzenesulfonamide |
| Compound 73 | 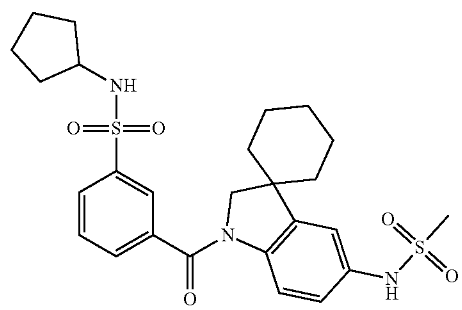 [SMILES: CS(=O)(=O)Nc1ccc2c(c1)C1(CCCCC1)CN2C(=O)c1cccc(S(=O)(=O)NC2CCCC2)c1] | N-cyclopentyl-3-(5'-(methylsulfonamido)spiro[cyclohexane-1,3'-indoline]-1'-carbonyl)benzenesulfonamide |
| Compound 74 | 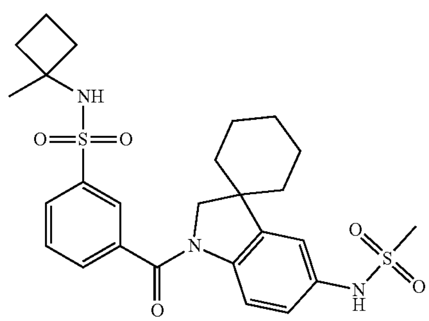 [SMILES: CC1(NS(=O)(=O)c2cccc(C(=O)N3CC4(CCCCC4)c4cc(NS(C)(=O)=O)ccc43)c2)CCC1] | N-(1-methylcyclobutyl)-3-(5'-(methylsulfonamido)spiro[cyclohexane-1,3'-indoline]-1'-carbonyl)benzenesulfonamide |
| Compound 75 | 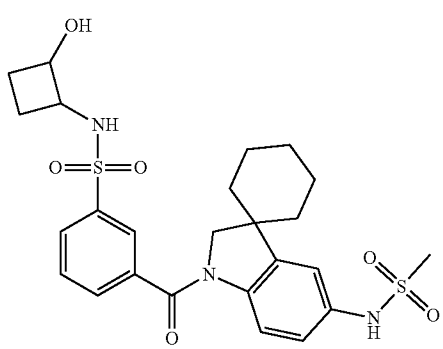 [SMILES: CS(=O)(=O)Nc1ccc2c(c1)C1(CCCCC1)CN2C(=O)c1cccc(S(=O)(=O)NC2CCC2O)c1] | N-(2-hydroxycyclobutyl)-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 76 | 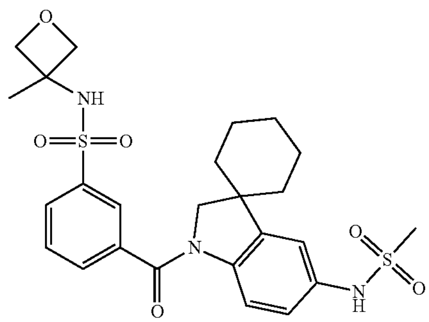 [SMILES: CC1(NS(=O)(=O)c2cccc(C(=O)N3CC4(CCCCC4)c4cc(NS(C)(=O)=O)ccc43)c2)COC1] | N-(3-methyloxetan-3-yl)-3-(5'-(methylsulfonamido)spiro[cyclohexane-1,3'-indoline]-1'-carbonyl)benzenesulfonamide |
| Compound 77 | 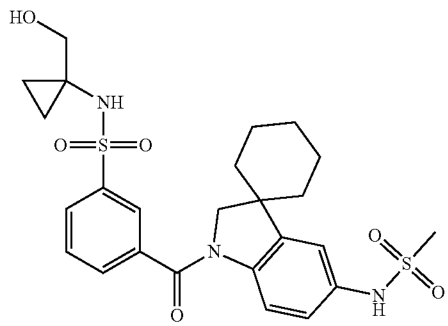 [SMILES: CS(=O)(=O)Nc1ccc2c(c1)C1(CCCCC1)CN2C(=O)c1cccc(S(=O)(=O)NC2(CO)CC2)c1] | N-(1-(hydroxymethyl)cyclopropyl)-3-(5'-(methylsulfonamido)spiro[cyclohexane-1,3'-indoline]-1'-carbonyl)benzenesulfonamide |
| Compound 78 | 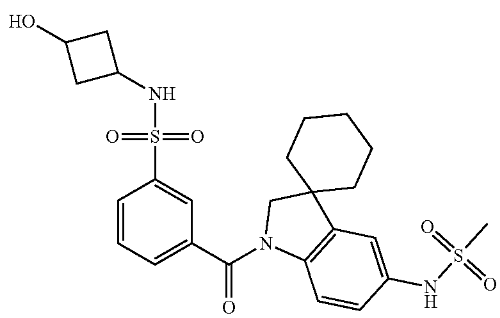 [SMILES: CS(=O)(=O)Nc1ccc2c(c1)C1(CCCCC1)CN2C(=O)c1cccc(S(=O)(=O)NC2CC(O)C2)c1] | N-(3-hydroxycyclobutyl)-3-(5'-(methylsulfonamido)spiro[cyclohexane-1,3'-indoline]-1'-carbonyl)benzenesulfonamide |
| Compound 79 | 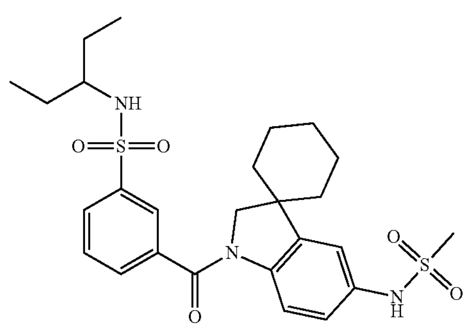 [SMILES: CCC(CC)NS(=O)(=O)c1cccc(C(=O)N2CC3(CCCCC3)c3cc(NS(C)(=O)=O)ccc32)c1] | 3-(5'-(methylsulfonamido)spiro[cyclohexane-1,3'-indoline]-1'-carbonyl)-N-(pentan-3-yl)benzenesulfonamide |

TABLE 1-continued

| Compound No. | Structure | Name |
|---|---|---|
| Compound 80 | 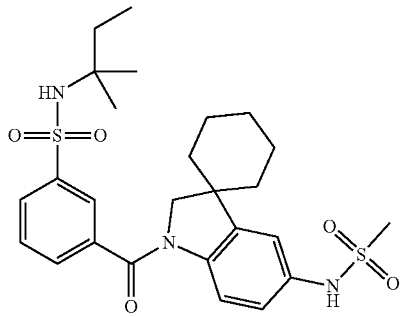 [SMILES: CCC(C)(C)NS(=O)(=O)c1cccc(C(=O)N2CC3(CCCCC3)c3cc(NS(C)(=O)=O)ccc32)c1] | 3-(5'-(methylsulfonamido)spiro[cyclohexane-1,3'-indoline]-1'-carbonyl)-N-(tert-pentyl)benzenesulfonamide |
| Compound 81 | 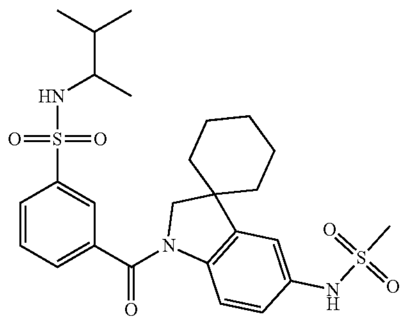 [SMILES: CC(C)C(C)NS(=O)(=O)c1cccc(C(=O)N2CC3(CCCCC3)c3cc(NS(C)(=O)=O)ccc32)c1] | N-(3-methylbutan-2-yl)-3-(5'-(methylsulfonamido)spiro[cyclohexane-1,3'-indoline]-1'-carbonyl)benzenesulfonamide |
| Compound 82 | 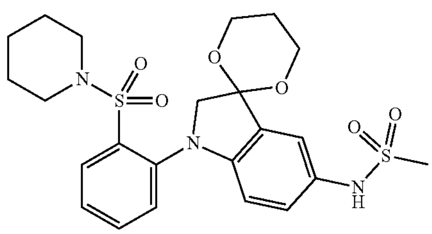 [SMILES: CS(=O)(=O)Nc1ccc2c(c1)C1(CN2c2ccccc2S(=O)(=O)N2CCCCC2)OCCCO1] | N-(1-(3-(piperidin-1-ylsulfonyl)benzoyl)spiro[indoline-3,2'-[1,3]dioxan]-5-yl)methanesulfonamide |
| Compound 83 | 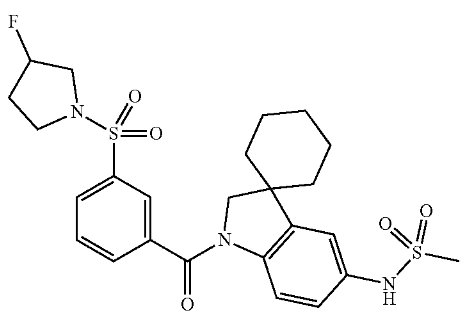 [SMILES: CS(=O)(=O)Nc1ccc2c(c1)C1(CCCCC1)CN2C(=O)c1cccc(S(=O)(=O)N2CCC(F)C2)c1] | N-(1'-(3-((3-fluoropyrrolidin-1-yl)sulfonyl)benzoyl)spiro[cyclohexane-1,3'-indoline]-5'-yl)methanesulfonamide |
| Compound 84 | 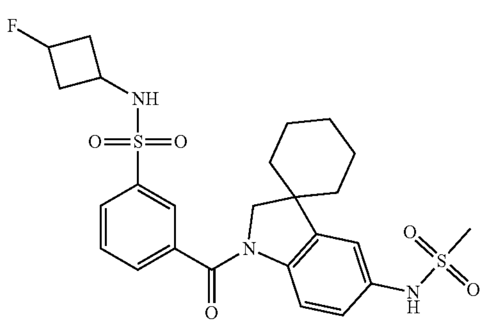 [SMILES: CS(=O)(=O)Nc1ccc2c(c1)C1(CCCCC1)CN2C(=O)c1cccc(S(=O)(=O)NC2CC(F)C2)c1] | N-(3-fluorocyclobutyl)-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 85 | 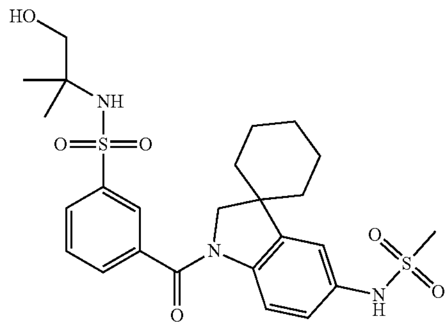 [SMILES: CC(C)(CO)NS(=O)(=O)c1cccc(C(=O)N2CC3(CCCCC3)c3cc(NS(C)(=O)=O)ccc32)c1] | N-(1-hydroxy-2-methylpropan-2-yl)-3-(5'-(methylsulfonamido)spiro[cyclohexane-1,3'-indoline]-1'-carbonyl)benzenesulfonamide |
| Compound 86 | 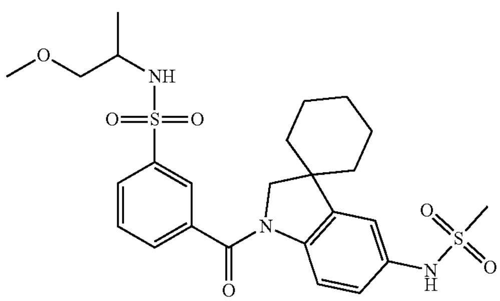 [SMILES: COCC(C)NS(=O)(=O)c1cccc(C(=O)N2CC3(CCCCC3)c3cc(NS(C)(=O)=O)ccc32)c1] | N-(1-methoxypropan-2-yl)-3-(5'-(methylsulfonamido)spiro[cyclohexane-1,3'-indoline]-1'-carbonyl)benzenesulfonamide |
| Compound 87 | 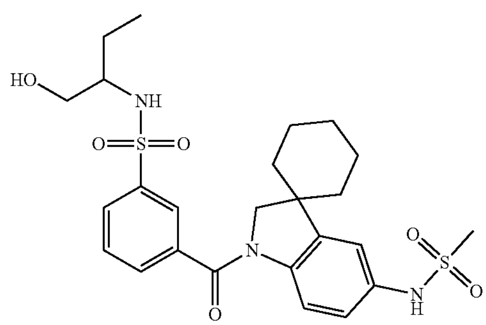 [SMILES: CCC(CO)NS(=O)(=O)c1cccc(C(=O)N2CC3(CCCCC3)c3cc(NS(C)(=O)=O)ccc32)c1] | N-(1-hydroxybutan-2-yl)-3-(5'-(methylsulfonamido)spiro[cyclohexane-1,3'-indoline]-1'-carbonyl)benzenesulfonamide |
| Compound 88 | 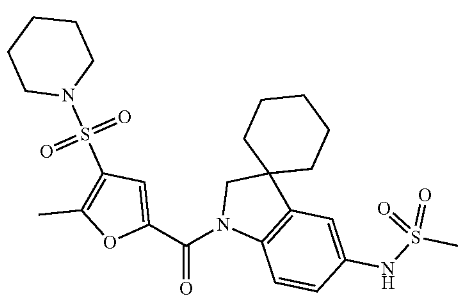 [SMILES: Cc1oc(C(=O)N2CC3(CCCCC3)c3cc(NS(C)(=O)=O)ccc32)cc1S(=O)(=O)N1CCCCC1] | N-(1'-(5-methyl-4-(piperidin-1-ylsulfonyl)furan-2-carbonyl)spiro[cyclohexane-1,3'-indolin]-5'-yl)methanesulfonamide |
| Compound 89 | 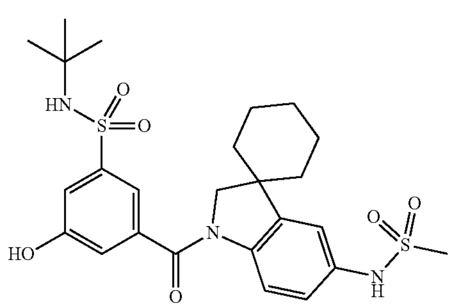 [SMILES: CC(C)(C)NS(=O)(=O)c1cc(O)cc(C(=O)N2CC3(CCCCC3)c3cc(NS(C)(=O)=O)ccc32)c1] | N-(tert-butyl)-3-hydroxy-5-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 90 | 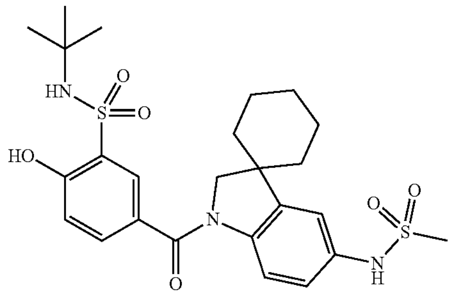 [SMILES: CC(C)(C)NS(=O)(=O)c1cc(C(=O)N2CC3(CCCCC3)c3cc(NS(C)(=O)=O)ccc32)ccc1O] | N-(tert-butyl)-2-hydroxy-5-(5'-(methylsulfonamido)spiro[cyclohexane-1,3'-indoline]-1'-carbonyl)benzenesulfonamide |
| Compound 91 | 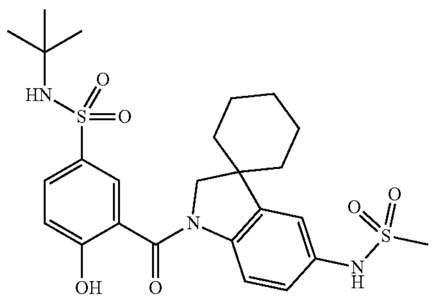 [SMILES: CC(C)(C)NS(=O)(=O)c1ccc(O)c(C(=O)N2CC3(CCCCC3)c3cc(NS(C)(=O)=O)ccc32)c1] | N-(tert-butyl)-4-hydroxy-3-(5'-(methylsulfonamido)spiro[cyclohexane-1,3'-indoline]-1'-carbonyl)benzenesulfonamide |
| Compound 92 | 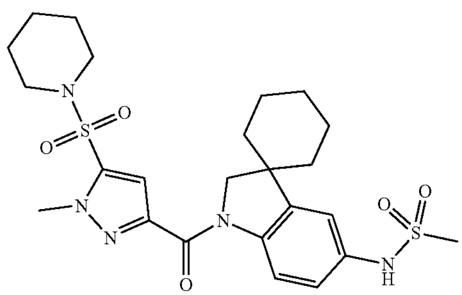 [SMILES: Cn1nc(C(=O)N2CC3(CCCCC3)c3cc(NS(C)(=O)=O)ccc32)cc1S(=O)(=O)N1CCCCC1] | N-(1'-(1-methyl-5-(piperidin-1-ylsulfonyl)-1H-pyrazole-3-carbonyl)spiro[cyclohexane-1,3'-indolin]-5'-yl)methanesulfonamide |
| Compound 93 | 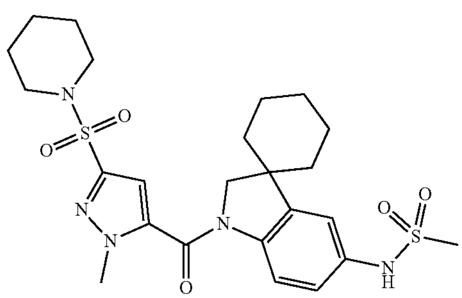 [SMILES: Cn1nc(S(=O)(=O)N2CCCCC2)cc1C(=O)N1CC2(CCCCC2)c2cc(NS(C)(=O)=O)ccc21] | N-(1'-(1-methyl-3-(piperidin-1-ylsulfonyl)-1H-pyrazole-5-carbonyl)spiro[cyclohexane-1,3'-indolin]-5'-yl)methanesulfonamide |
| Compound 94 | 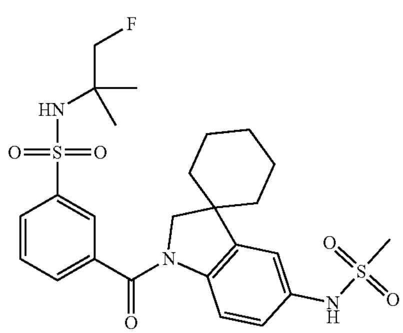 [SMILES: CC(C)(CF)NS(=O)(=O)c1cccc(C(=O)N2CC3(CCCCC3)c3cc(NS(C)(=O)=O)ccc32)c1] | N-(1-fluoro-2-methylpropan-2-yl)-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 95 | 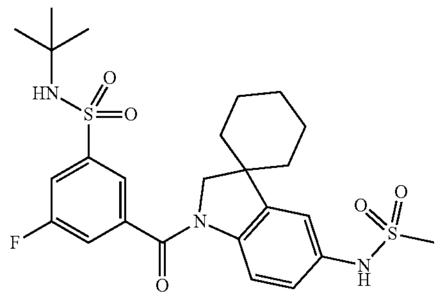 [SMILES: CC(C)(C)NS(=O)(=O)c1cc(F)cc(C(=O)N2CC3(CCCCC3)c3cc(NS(C)(=O)=O)ccc32)c1] | N-(tert-butyl)-3-fluoro-5-(5'-(methylsulfonamido)spiro[cyclohexane-1,3'-indoline]-1'-carbonyl)benzenesulfonamide |
| Compound 96 | 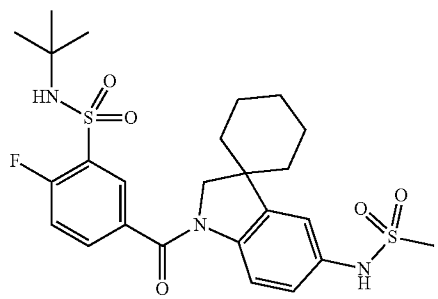 [SMILES: CC(C)(C)NS(=O)(=O)c1cc(C(=O)N2CC3(CCCCC3)c3cc(NS(C)(=O)=O)ccc32)ccc1F] | N-(tert-butyl)-2-fluoro-5-(5'-(methylsulfonamido)spiro[cyclohexane-1,3'-indoline]-1'-carbonyl)benzenesulfonamide |
| Compound 97 | 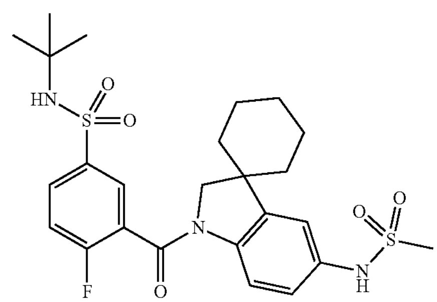 [SMILES: CC(C)(C)NS(=O)(=O)c1ccc(F)c(C(=O)N2CC3(CCCCC3)c3cc(NS(C)(=O)=O)ccc32)c1] | N-(tert-butyl)-4-fluoro-3-(5'-(methylsulfonamido)spiro[cyclohexane-1,3'-indoline]-1'-carbonyl)benzenesulfonamide |
| Compound 98 | 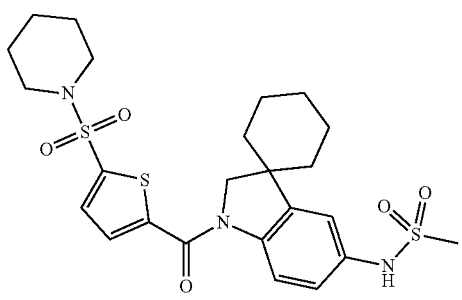 [SMILES: CS(=O)(=O)Nc1ccc2c(c1)C1(CCCCC1)CN2C(=O)c1ccc(S(=O)(=O)N2CCCCC2)s1] | N-(1'-(5-(piperidin-1-ylsulfonyl)thiophene-2-carbonyl)spiro[cyclohexane-1,3'-indolin]-5'-yl)methanesulfonamide |
| Compound 99 | 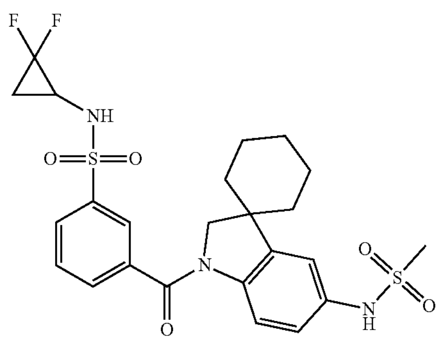 [SMILES: CS(=O)(=O)Nc1ccc2c(c1)C1(CCCCC1)CN2C(=O)c1cccc(S(=O)(=O)NC2CC2(F)F)c1] | N-(2,2-difluorocyclopropyl)-3-(5'-(methylsulfonamido)spiro[cyclohexane]-1,3'-indoline]-1'-carbonyl)benzenesulfonamide |

TABLE 1-continued

| Compound No. | Structure | Name |
|---|---|---|
| Compound 100 | 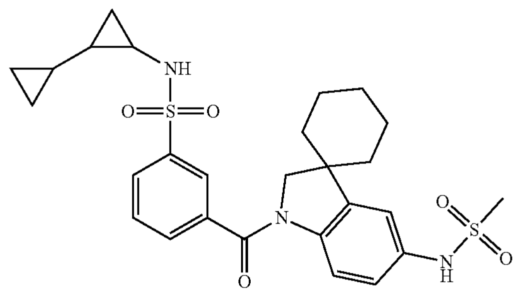 [SMILES: CS(=O)(=O)Nc1ccc2c(c1)C1(CCCCC1)CN2C(=O)c1cccc(S(=O)(=O)NC2CC2C2CC2)c1] | N-([(1,1'-bi(cyclopropan)]-2-yl)-3-(5'-(methylsulfonamido)spiro[cyclohexane-1,3'-indoline]-1'-carbonyl)benzenesulfonamide |
| Compound 101 | 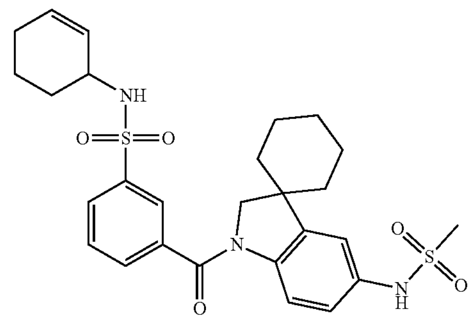 [SMILES: CS(=O)(=O)Nc1ccc2c(c1)C1(CCCCC1)CN2C(=O)c1cccc(S(=O)(=O)NC2C=CCCC2)c1] | N-(cyclohex-2-en-1-yl)-3-(5'-(methylsulfonamido)spiro[cyclohexane-1,3'-indoline]-1'-carbonyl)benzenesulfonamide |
| Compound 102 | 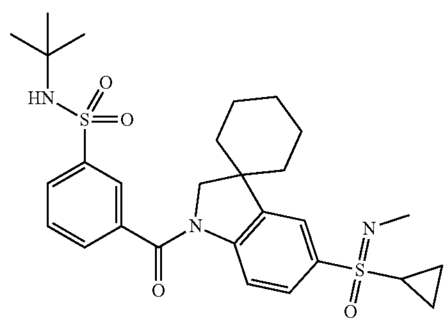 [SMILES: CN=S(=O)(c1ccc2c(c1)C1(CCCCC1)CN2C(=O)c1cccc(S(=O)(=O)NC(C)(C)C)c1)C1CC1] | N-(tert-butyl)-3-(5'-(N-methylcyclopropanesulfonimidoyl)spiro[cyclohexane-1,3'indoline]-1'-carbonyl)benzenesulfonamide |
| Compound 103 | 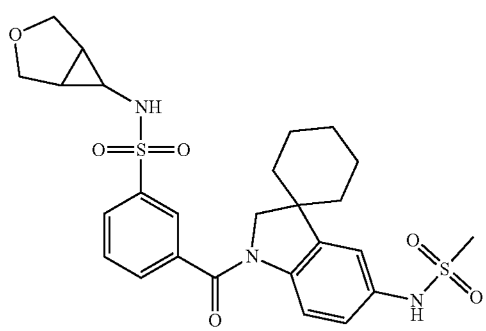 [SMILES: CS(=O)(=O)Nc1ccc2c(c1)C1(CCCCC1)CN2C(=O)c1cccc(S(=O)(=O)NC2C3COCC32)c1] | N-(3-oxabicyclo[3.1.0]hexan-6-yl)-3-(5'-(methylsulfonamido)spiro[cyclohexane-1,3'-indoline]-1'-carbonyl)benzenesulfonamide |
| Compound 104 | 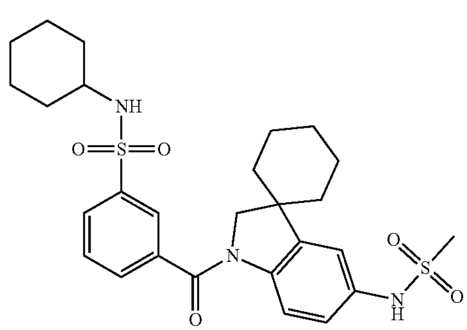 [SMILES: CS(=O)(=O)Nc1ccc2c(c1)C1(CCCCC1)CN2C(=O)c1cccc(S(=O)(=O)NC2CCCCC2)c1] | N-cyclohexyl-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 105 | 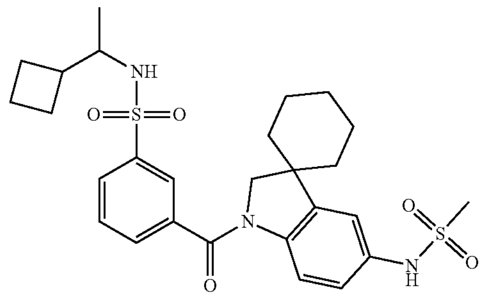 [SMILES: CC(NS(=O)(=O)c1cccc(C(=O)N2CC3(CCCCC3)c3cc(NS(C)(=O)=O)ccc32)c1)C1CCC1] | N-(1-cyclobutylethyl)-3-(5'-(methylsulfonamido)spiro[cyclohexane-1,3'-indoline]-1'-carbonyl)benzenesulfonamide |
| Compound 106 | 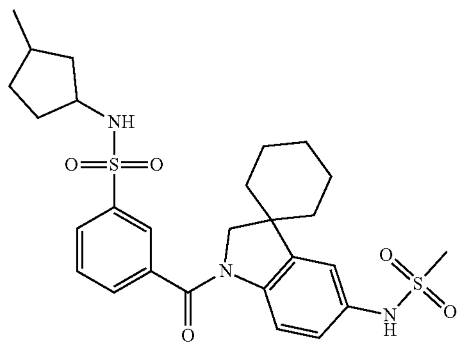 [SMILES: CC1CCC(NS(=O)(=O)c2cccc(C(=O)N3CC4(CCCCC4)c4cc(NS(C)(=O)=O)ccc43)c2)C1] | N-(3-methylcyclopentyl)-3-(5'-(methylsulfonamido)spiro[cyclohexane-1,3'-indoline]-1'-carbonyl)benzenesulfonamide |
| Compound 107 | 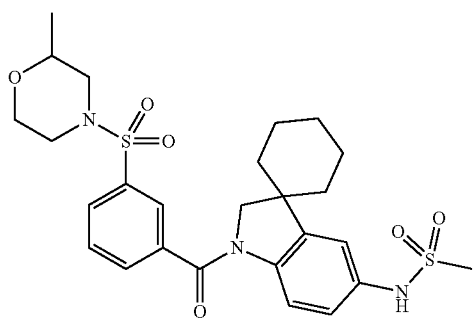 [SMILES: CC1CN(S(=O)(=O)c2cccc(C(=O)N3CC4(CCCCC4)c4cc(NS(C)(=O)=O)ccc43)c2)CCO1] | N-(1'-(3-((2-methylmorpholino)sulfonyl)benzoyl)spiro[cyclohexane-1,3'-indolin]-5'-yl)methanesulfonamide |
| Compound 108 | 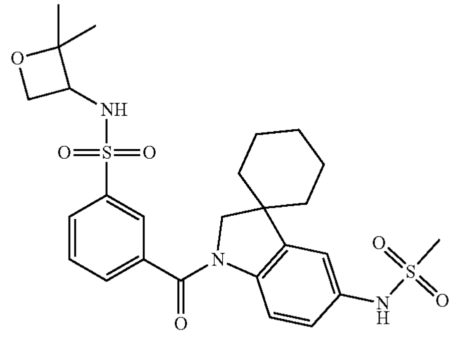 [SMILES: CC1(C)OCC1NS(=O)(=O)c1cccc(C(=O)N2CC3(CCCCC3)c3cc(NS(C)(=O)=O)ccc32)c1] | N-(2,2-dimethyloxetan-3-yl)-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 109 | 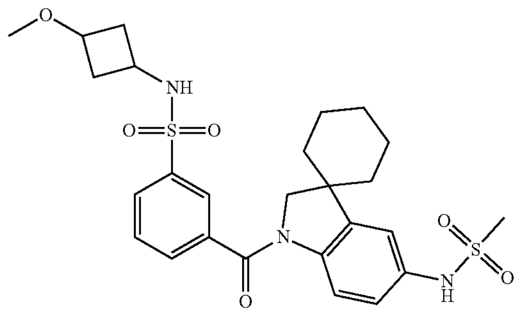 [SMILES: COC1CC(NS(=O)(=O)c2cccc(C(=O)N3CC4(CCCCC4)c4cc(NS(C)(=O)=O)ccc43)c2)C1] | N-(3-methoxycyclobutyl)-3-(5'-(methylsulfonamido)spiro[cyclohexane-1,3'-indoline]-1'-carbonyl)benzenesulfonamide |
| Compound 110 | 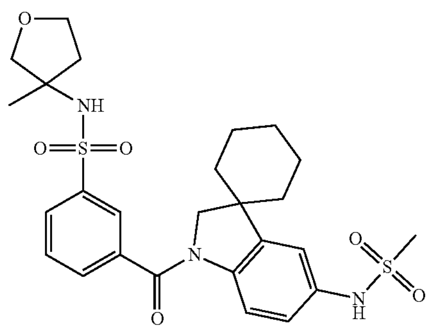 [SMILES: CC1(NS(=O)(=O)c2cccc(C(=O)N3CC4(CCCCC4)c4cc(NS(C)(=O)=O)ccc43)c2)CCOC1] | 3-(5'-(methylsulfonamido)spiro[cyclohexane-1,3'-indoline]-1'-carbonyl)-N-(3-methyltetrahydrofuran-3-yl)benzenesulfonamide |
| Compound 111 | 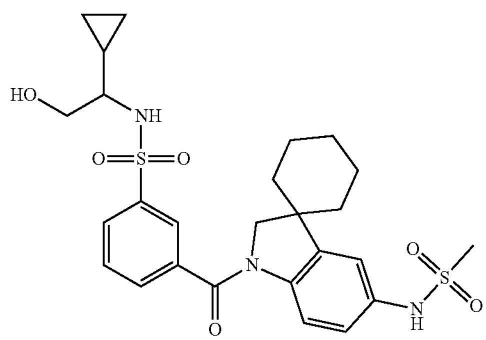 [SMILES: CS(=O)(=O)Nc1ccc2c(c1)C1(CCCCC1)CN2C(=O)c1cccc(S(=O)(=O)NC(CO)C2CC2)c1] | N-(1-cyclopropyl-2-hydroxyethyl)-3-(5'-(methylsulfonamido)spiro[cyclohexane-1,3'-indoline]-1'-carbonyl)benzenesulfonamide |
| Compound 112 | 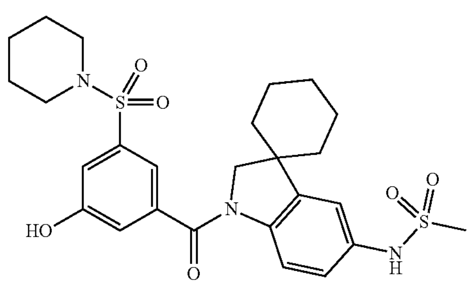 [SMILES: CS(=O)(=O)Nc1ccc2c(c1)C1(CCCCC1)CN2C(=O)c1cc(O)cc(S(=O)(=O)N2CCCCC2)c1] | N-(1'-(3-hydroxy-5-(piperidin-1-ylsulfonyl)benzoyl)spiro[cyclohexane-1,3'-indolin]-5'-yl)methanesulfonamide |
| Compound 113 | 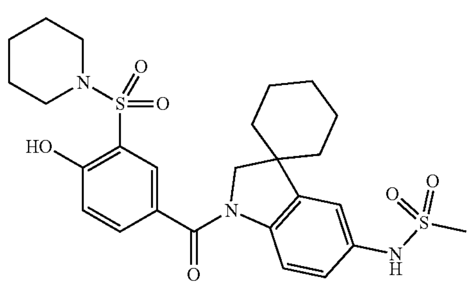 [SMILES: CS(=O)(=O)Nc1ccc2c(c1)C1(CCCCC1)CN2C(=O)c1ccc(O)c(S(=O)(=O)N2CCCCC2)c1] | N-(1'-(4-hydroxy-3-(piperidin-1-ylsulfonyl)benzoyl)spiro[cyclohexane-1,3'indolin]-5'-yl)methanesulfonamide |

TABLE 1-continued

| Compound No. | Structure | Name |
|---|---|---|
| Compound 114 | 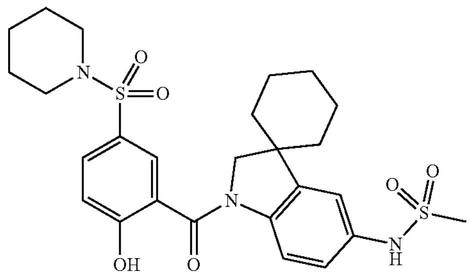 [SMILES: CS(=O)(=O)Nc1ccc2c(c1)C1(CCCCC1)CN2C(=O)c1cc(S(=O)(=O)N2CCCCC2)ccc1O] | N-(1'-(2-hydroxy-5-(piperidin-1-ylsulfonyl)benzoyl)spiro[cyclohexane-1,3'-indolin]-5'-yl)methanesulfonamide |
| Compound 115 | 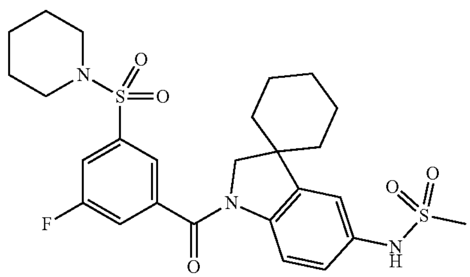 [SMILES: CS(=O)(=O)Nc1ccc2c(c1)C1(CCCCC1)CN2C(=O)c1cc(F)cc(S(=O)(=O)N2CCCCC2)c1] | N-(1'-(3-fluoro-5-(piperidin-1-ylsulfonyl)benzoyl)spiro[cyclohexane-1,3'-indolin]-5'-yl)methanesulfonamide |
| Compound 116 | 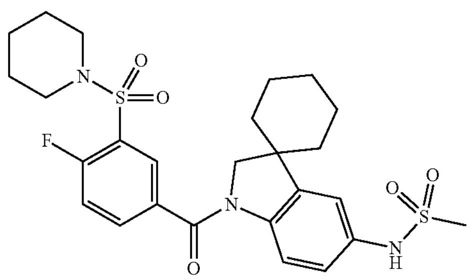 [SMILES: CS(=O)(=O)Nc1ccc2c(c1)C1(CCCCC1)CN2C(=O)c1ccc(F)c(S(=O)(=O)N2CCCCC2)c1] | N-(1'-(4-fluoro-3-(piperidin-1-ylsulfonyl)benzoyl)spiro[cyclohexane-1,3'-indolin]-5'-yl)methanesulfonamide |
| Compound 117 | 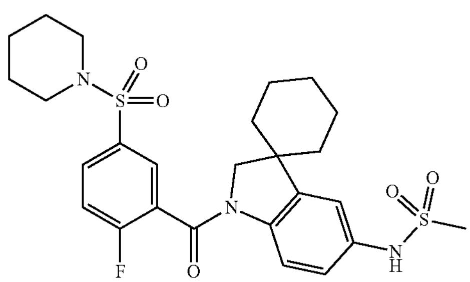 [SMILES: CS(=O)(=O)Nc1ccc2c(c1)C1(CCCCC1)CN2C(=O)c1cc(S(=O)(=O)N2CCCCC2)ccc1F] | N-(1'-(2-fluoro-5-(piperidin-1-ylsulfonyl)benzoyl)spiro[cyclohexane-1,3'-indolin]-5'-yl)methanesulfonamide |
| Compound 118 | 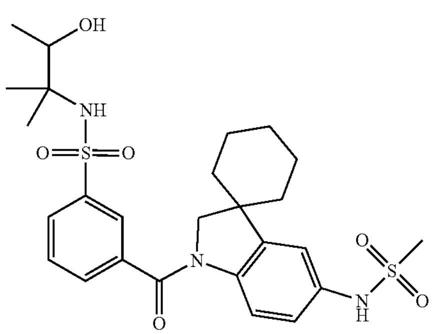 [SMILES: CC(O)C(C)(C)NS(=O)(=O)c1cccc(C(=O)N2CC3(CCCCC3)c3cc(NS(C)(=O)=O)ccc32)c1] | N-(3-hydroxy-2-methylbutan-2-yl)-3-(5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 119 | 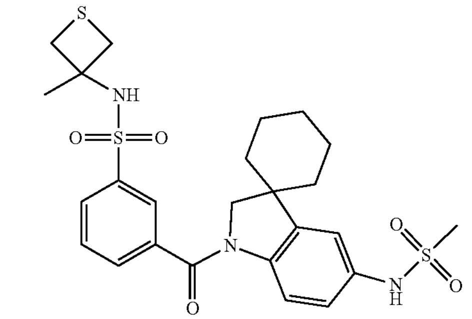 | 3-(5'-(methylsulfonamido) spiro[cyclohexane-1,3'-indoline]-1'-carbonyl)-N-(3-methylthietan-3-yl)benzenesulfonamide |
| Compound 120 | 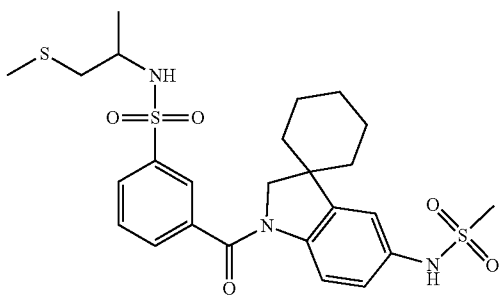 | 3-(5'-(methylsulfonamido) spiro[cyclohexane-1,3'-indoline]-1'-carbonyl)-N-(1-(methylthio)propan-2-yl)benzenesulfonamide |
| Compound 121 | 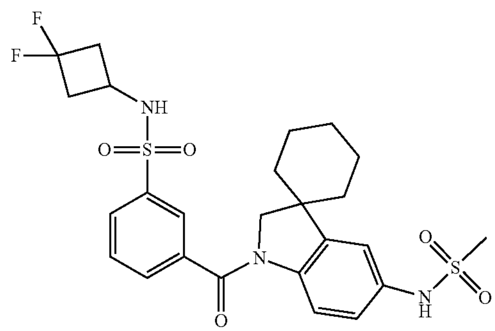 [SMILES: CS(=O)(=O)Nc1ccc2c(c1)C1(CCCCC1)CN2C(=O)c1cccc(S(=O)(=O)NC2CC(F)(F)C2)c1] | N-(3,3-difluorocyclobutyl)-3-(5'-(methylsulfonamido)spiro[cyclohexane-1,3'-indoline]-1'-carbonyl)benzenesulfonamide |
| Compound 122 | 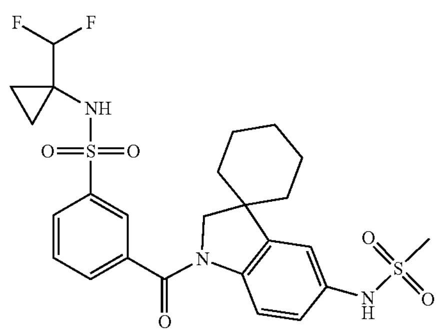 [SMILES: CS(=O)(=O)Nc1ccc2c(c1)C1(CCCCC1)CN2C(=O)c1cccc(S(=O)(=O)NC2(C(F)F)CC2)c1] | N-(1-(difluoromethyl)cyclopropyl)-3-(5'-(methylsulfonamido)spiro[cyclohexane-1,3'-indoline]-1'-carbonyl)benzenesulfonamide |
| Compound 123 | 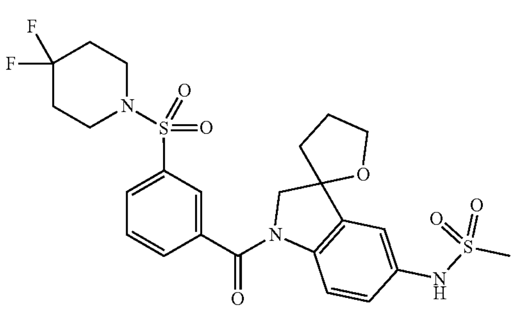 [SMILES: CS(=O)(=O)Nc1ccc2c(c1)C1(CCCO1)CN2C(=O)c1cccc(S(=O)(=O)N2CCC(F)(F)CC2)c1] | N-(1'-(3-((4,4-difluoropiperidin-1-yl)sulfonyl)benzoyl)-4,5-dihydro-3H-spiro[furan-2,3'-indolin]-5'-yl)methanesulfonamide |

TABLE 1-continued

| Compound No. | Structure | Name |
|---|---|---|
| Compound 124 | 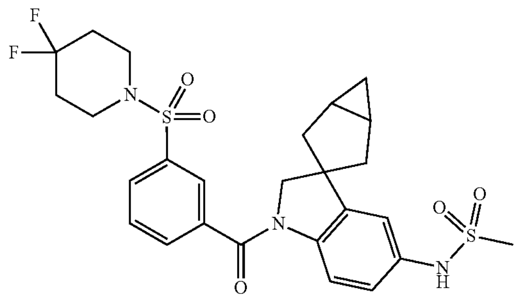 [SMILES: CS(=O)(=O)Nc1ccc2c(c1)C1(CC3CC3C1)CN2C(=O)c1cccc(S(=O)(=O)N2CCC(F)(F)CC2)c1] | N-(1'-(3-((4,4-difluoropiperidin-1-yl)sulfonyl)benzoyl)spiro[bicyclo[3.1.0]hexane-3,3-indolin]-5'-yl)methanesulfonamide |
| Compound 125 | 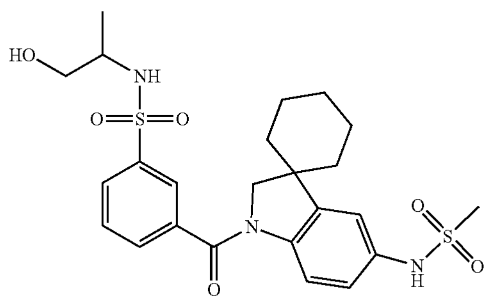 [SMILES: CC(CO)NS(=O)(=O)c1cccc(C(=O)N2CC3(CCCCC3)c3cc(NS(C)(=O)=O)ccc32)c1] | N-(1-hydroxypropan-2-yl)-3-(5'-(methylsulfonamido)spiro[cyclohexane-1,3'-indoline]-1'-carbonyl)benzenesulfonamide |
| Compound 126 | 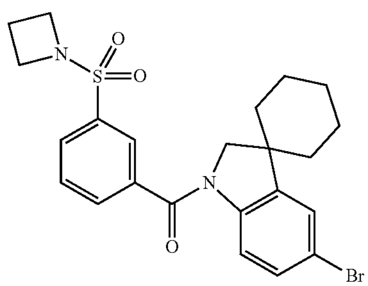 [SMILES: O=C(c1cccc(S(=O)(=O)N2CCC2)c1)N1CC2(CCCCC2)c2cc(Br)ccc21] | (3-(azetidin-1-ylsulfonyl)phenyl)(5'-bromospiro[cyclohexane-1,3'-indolin]-1'-yl)methanone |
| Compound 128 | 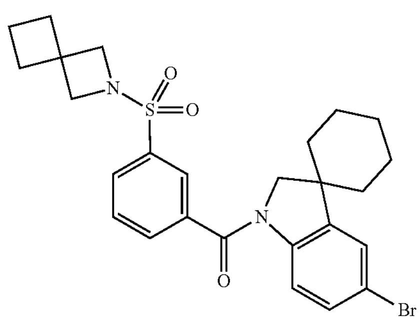 [SMILES: O=C(c1cccc(S(=O)(=O)N2CC3(CCC3)C2)c1)N1CC2(CCCCC2)c2cc(Br)ccc21] | (3-((2-azaspiro[3.3]heptan-2-yl)sulfonyl)phenyl)(5'-bromospiro[cyclohexane-1,3'-indolin]-1'-yl)methanone |
| Compound 129 | 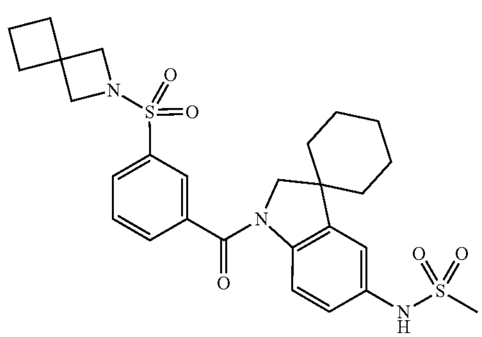 [SMILES: CS(=O)(=O)Nc1ccc2c(c1)C1(CCCCC1)CN2C(=O)c1cccc(S(=O)(=O)N2CC3(CCC3)C2)c1] | N-(1'-(3-((2-azaspiro[3.3]heptan-2-yl)sulfonyl)benzoyl)spiro[cyclohexane-1,3'-indolin]-5'-yL)methanesulfonamide |

TABLE 1-continued

| Compound No. | Structure | Name |
|---|---|---|
| Compound 130 | 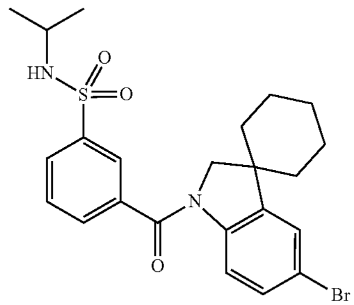 [SMILES: CC(C)NS(=O)(=O)c1cccc(C(=O)N2CC3(CCCCC3)c3cc(Br)ccc32)c1] | 3-(5'-bromospiro[cyclohexane-1,3'-indoline]-1'-carbonyl)-N-isopropylbenzenesulfonamide |
| Compound 132 | 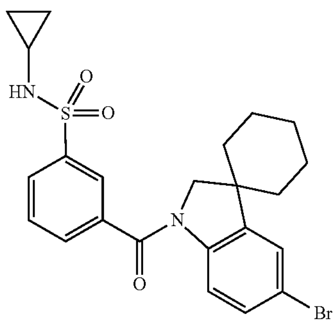 [SMILES: O=C(c1cccc(S(=O)(=O)NC2CC2)c1)N1CC2(CCCCC2)c2cc(Br)ccc21] | 3-(5'-bromospiro[cyclohexane-1,3'-indoline]-1'-carbonyl)-N-cyclopropylbenzenesulfonamide |
| Compound 134 | 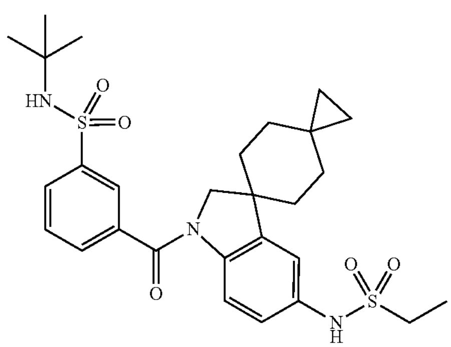 [SMILES: CCS(=O)(=O)Nc1ccc2c(c1)C1(CCC3(CC3)CC1)CN2C(=O)c1cccc(S(=O)(=O)NC(C)(C)C)c1] | N-(tert-butyl)-3-(5''-(ethylsulfonamido)dispiro[cyclopropane-1,1'-cyclohexane-4',3''-indoline]-1''-carbonyl)benzenesulfonamide |
| Compound 135 | 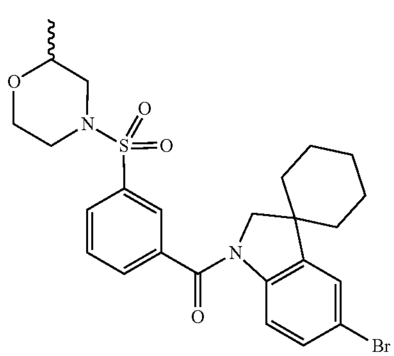 [SMILES: CC1CN(S(=O)(=O)c2cccc(C(=O)N3CC4(CCCCC4)c4cc(Br)ccc43)c2)CCO1] | (5'-bromospiro[cyclohexane-1,3'-indolin]-1'-yl)(3-((2-methylmorpholino)sulfonyl)phenyl)methanone |

TABLE 1-continued

| Compound No. | Structure | Name |
|---|---|---|
| Compound 136 | 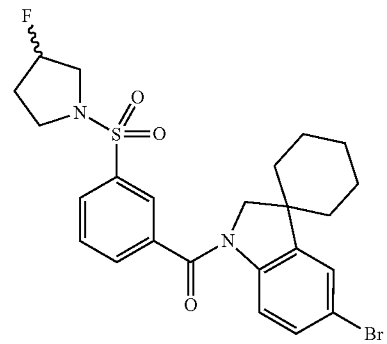 [SMILES: O=C(c1cccc(S(=O)(=O)N2CCC(F)C2)c1)N1CC2(CCCCC2)c2cc(Br)ccc21] | (5'-bromospiro[cyclohexane-1,3'-indolin]-1'-yl)(3-((3-fluoropyrrolidin-1-yl)sulfonyl)phenyl)methanone |
| Compound 137 | 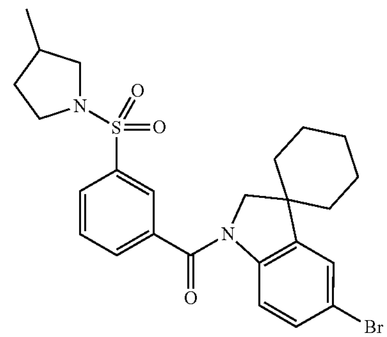 [SMILES: CC1CCN(S(=O)(=O)c2cccc(C(=O)N3CC4(CCCCC4)c4cc(Br)ccc43)c2)C1] | (5'-bromospiro[cyclohexane-1,3'-indolin]-1'-yl)(3-((3-methylpyrrolidin-1-yl)sulfonyl)phenyl)methanone |
| Compound 138 | 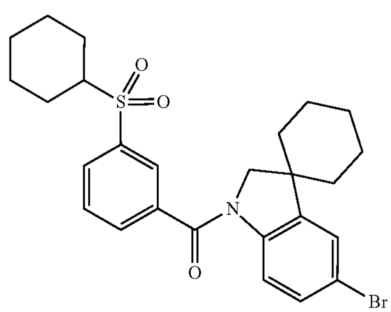 [SMILES: O=C(c1cccc(S(=O)(=O)C2CCCCC2)c1)N1CC2(CCCCC2)c2cc(Br)ccc21] | (5'-bromospiro[cyclohexane-1,3'-indolin]-1'-yl)(3-(cyclohexylsulfonyl)phenyl)methanone |
| Compound 139 | 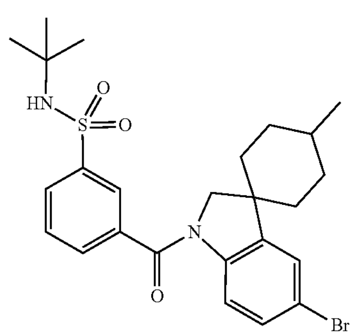 [SMILES: CC1CCC2(CC1)CN(C(=O)c1cccc(S(=O)(=O)NC(C)(C)C)c1)c1ccc(Br)cc12] | 3-(5'-bromo-4-methylspiro[cyclohexane-1,3'-indoline]-1'-carbonyl)-N-(tert-butyl)benzenesulfonamide |

TABLE 1-continued

| Compound No. | Structure | Name |
|---|---|---|
| Compound 140 | 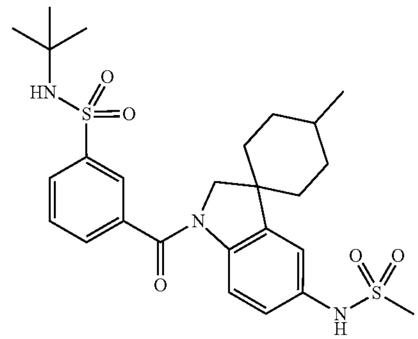 [SMILES: CC1CCC2(CC1)CN(C(=O)c1cccc(S(=O)(=O)NC(C)(C)C)c1)c1ccc(NS(C)(=O)=O)cc12] | N-(tert-butyl)-3-(4-methyl-5'-(methylsulfonamido)spiro[cyclohexane-1,3'-indoline]-1'-carbonyl)benzenesulfonamide |
| Compound 140-(1r,4r) | 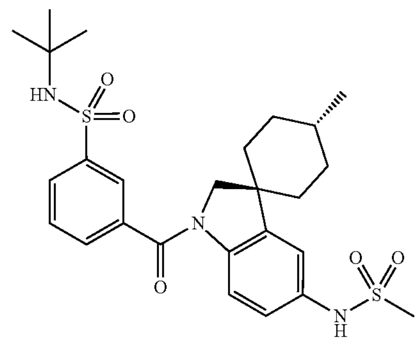 [SMILES: CC(C)(C)NS(=O)(=O)c1cccc(C(=O)N2C[C@]3(CC[C@H](C)CC3)c3cc(NS(C)(=O)=O)ccc32)c1] | N-(tert-butyl)-3-((1r,4r)-4-methyl-5'-(methylsulfonamido)spiro[cyclohexane-1,3'-indoline]-1'-carbonyl)benzenesulfonamide |
| Compound 140-(1s,4s) | 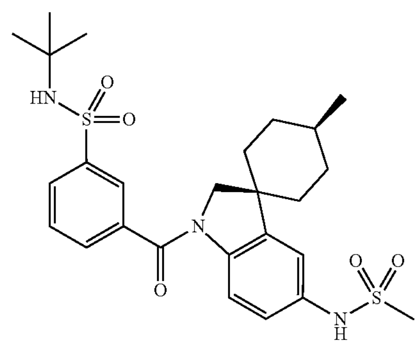 [SMILES: CC(C)(C)NS(=O)(=O)c1cccc(C(=O)N2C[C@]3(CC[C@@H](C)CC3)c3cc(NS(C)(=O)=O)ccc32)c1] | N-(tert-butyl)-3-((1s,4s)-4-methyl-5'-(methylsulfonamido)spiro[cyclohexane-1,3'-indoline]-1'-carbonyl)benzenesulfonamide |
| Compound 141 | 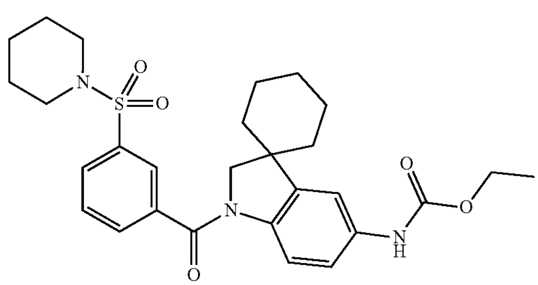 [SMILES: CCOC(=O)Nc1ccc2c(c1)C1(CCCCC1)CN2C(=O)c1cccc(S(=O)(=O)N2CCCCC2)c1] | ethyl (1'-(3-(piperidin-1-ylsulfonyl)benzoyl)spiro[cyclohexane-1,3'-indolin]-5'-yl)carbamate |
| Compound 142 | 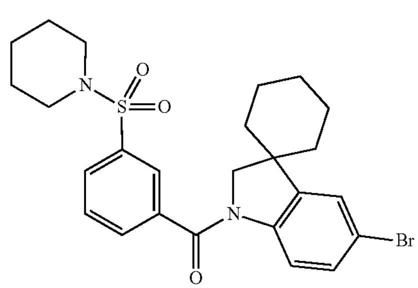 [SMILES: O=C(c1cccc(S(=O)(=O)N2CCCCC2)c1)N1CC2(CCCCC2)c2cc(Br)ccc21] | (5'-bromospiro[cyclohexane-1,3'-indolin]-1'-yl)(3-(piperidin-1-ylsulfonyl)phenyl)methanone |

TABLE 1-continued

| Compound No. | Structure | Name |
|---|---|---|
| Compound 143 | 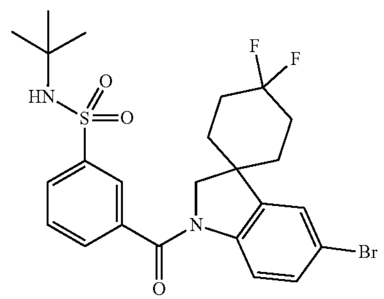 [SMILES: CC(C)(C)NS(=O)(=O)c1cccc(C(=O)N2CC3(CCC(F)(F)CC3)c3cc(Br)ccc32)c1] | 3-(5'-bromo-4,4-difluorospiro[cyclohexane-1,3'-indoline]-1'-carbonyl)-N-(tert-butyl)benzenesulfonamide |
| Compound 144 | 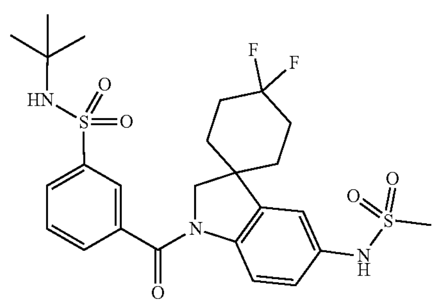 [SMILES: CC(C)(C)NS(=O)(=O)c1cccc(C(=O)N2CC3(CCC(F)(F)CC3)c3cc(NS(C)(=O)=O)ccc32)c1] | N-(tert-butyl)-3-(4,4-difluoro-5'-(methylsulfonamido)spiro[cyclohexane-1,3'-indoline]-1'-carbonyl)benzenesulfonamide |
| Compound 145 | 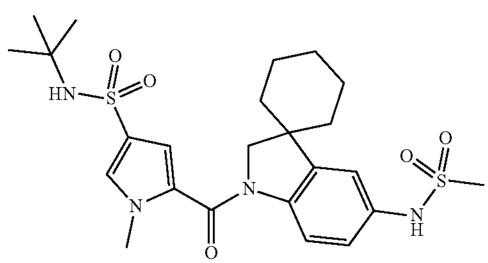 [SMILES: Cn1cc(S(=O)(=O)NC(C)(C)C)cc1C(=O)N1CC2(CCCCC2)c2cc(NS(C)(=O)=O)ccc21] | N-(tert-butyl)-1-methyl-5-(5'-(methylsulfonamido)spiro[cyclohexane-1,3'-indoline]-1'-carbonyl)-1H-pyrrole-3-sulfonamide |
| Compound 146 | 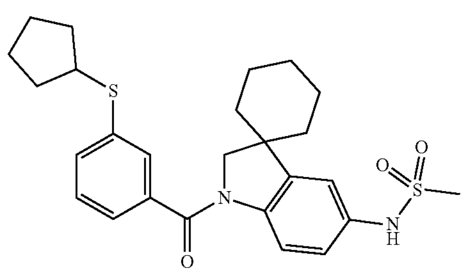 [SMILES: CS(=O)(=O)Nc1ccc2c(c1)C1(CCCCC1)CN2C(=O)c1cccc(SC2CCCC2)c1] | N-(1'-(3-(cyclopentylthio)benzoyl)spiro[cyclohexane-1,3'-indolin]-5'-yl)methanesulfonamide |
| Compound 147 | 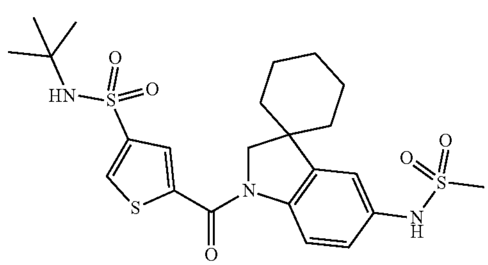 [SMILES: CC(C)(C)NS(=O)(=O)c1csc(C(=O)N2CC3(CCCCC3)c3cc(NS(C)(=O)=O)ccc32)c1] | N-(tert-butyl)-5-(5'-(methylsulfonamido)spiro[cyclohexane-1,3'-indoline]-1'-carbonyl)thiophene-3-sulfonamide |

TABLE 1-continued

| Compound No. | Structure | Name |
|---|---|---|
| Compound 148 | 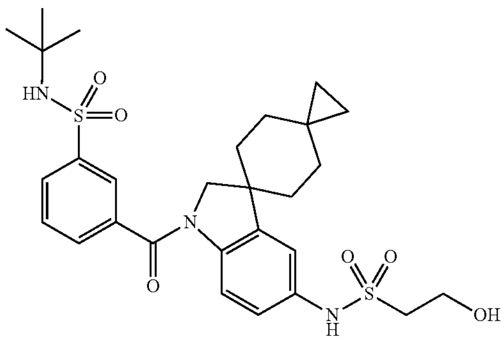 [SMILES: CC(C)(C)NS(=O)(=O)c1cccc(C(=O)N2CC3(CCC4(CC4)CC3)c3cc(NS(=O)(=O)CCO)ccc32)c1] | N-(tert-butyl)-3-(5''-((2-hydroxyethyl)sulfonamido)dispiro[cyclopropane-1,1'-cyclohexane-4',3''-indoline]-1''-carbonyl)benzenesulfonamide |
| Compound 149 | 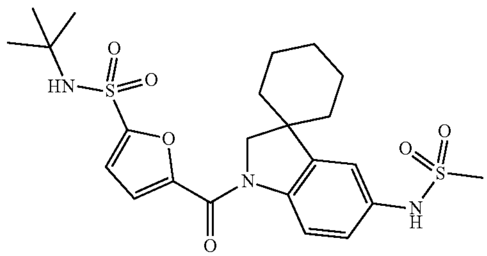 [SMILES: CC(C)(C)NS(=O)(=O)c1ccc(C(=O)N2CC3(CCCCC3)c3cc(NS(C)(=O)=O)ccc32)o1] | N-(tert-butyl)-5-(5'-(methylsulfonamido)spiro[cyclohexane-1,3'-indoline]-1'-carbonyl)furan-2-sulfonamide |
| Compound 150 | 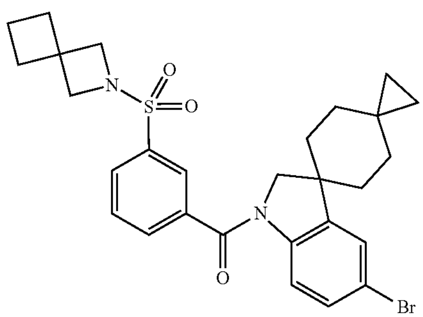 [SMILES: O=C(c1cccc(S(=O)(=O)N2CC3(CCC3)C2)c1)N1CC2(CCC3(CC3)CC2)c2cc(Br)ccc21] | (3-((2-azaspiro[3.3]heptan-2-yl)sulfonyl)phenyl)(5''-bromodispiro[cyclopropane-1,1'-cyclohexane-4',3''-indolin]-1''-yl)methanone |
| Compound 151 | 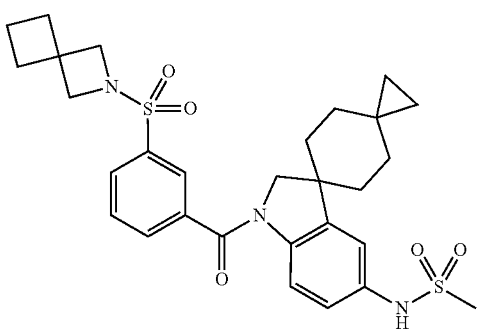 [SMILES: CS(=O)(=O)Nc1ccc2c(c1)C1(CCC3(CC3)CC1)CN2C(=O)c1cccc(S(=O)(=O)N2CC3(CCC3)C2)c1] | N-(1''-(3-((2-azaspiro[3.3]heptan-2-yl)sulfonyl)benzoyl)dispiro[cyclopropane-1,1'-cyclohexane-4',3''-indolin]-5''-yl)methanesulfonamide |
| Compound 152 | 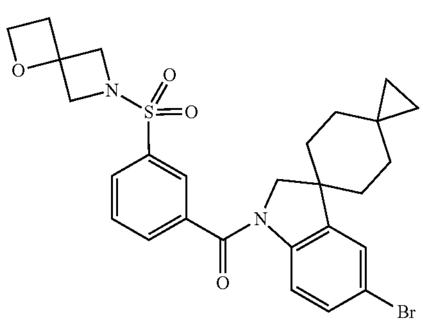 [SMILES: O=C(c1cccc(S(=O)(=O)N2CC3(CCO3)C2)c1)N1CC2(CCC3(CC3)CC2)c2cc(Br)ccc21] | (3-((1-oxa-6-azaspiro[3.3]heptan-6-yl)sulfonyl)phenyl)(5''-bromodispiro[cyclopropane-1,1'-cyclohexane-4',3''-indolin]-1''-yl)methanone |

TABLE 1-continued

| Compound No. | Structure | Name |
|---|---|---|
| Compound 153 | 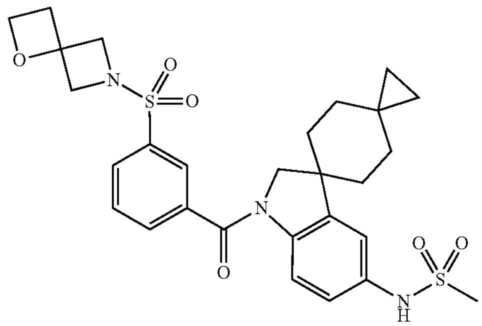 [SMILES: CS(=O)(=O)Nc1ccc2c(c1)C1(CCC3(CC3)CC1)CN2C(=O)c1cccc(S(=O)(=O)N2CC3(CCO3)C2)c1] | N-(1"-(3-((1-oxa-6-azaspiro[3.3]heptan-6-yl)sulfonyl)benzoyl)dispiro[cyclopropane-1,1'-cyclohexane-4',3"-indolin]-5"-yl)methanesulfonamide |
| Compound 154 | 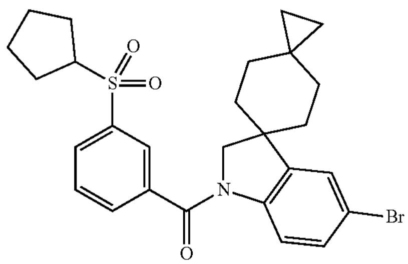 [SMILES: O=C(c1cccc(S(=O)(=O)C2CCCC2)c1)N1CC2(CCC3(CC3)CC2)c2cc(Br)ccc21] | (5"-bromodispiro[cyclopropane-1,1'-cyclohexane-4',3"-indolin]-1"-yl)(3-(cyclopentylsulfonyl)phenyl)methanone |
| Compound 155 | 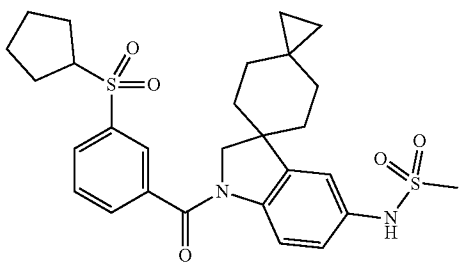 [SMILES: CS(=O)(=O)Nc1ccc2c(c1)C1(CCC3(CC3)CC1)CN2C(=O)c1cccc(S(=O)(=O)C2CCCC2)c1] | N-(1"-(3-(cyclopentylsulfonyl)benzoyl)dispiro[cyclopropane-1,1'-cyclohexane-4',3"-indolin]-5"-yl)methanesulfonamide |
| Compound 156 | 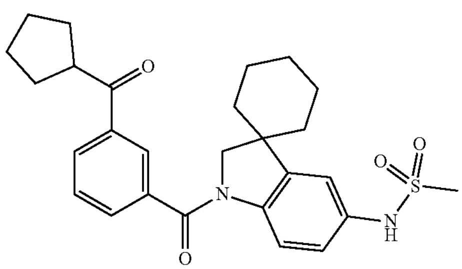 [SMILES: CS(=O)(=O)Nc1ccc2c(c1)C1(CCCCC1)CN2C(=O)c1cccc(C(=O)C2CCCC2)c1] | N-(1'-(3-(cyclopentanecarbonyl)benzoyl)spiro[cyclohexane-1,3'-indolin]-5'-yl)methanesulfonamide |
| Compound 157 | 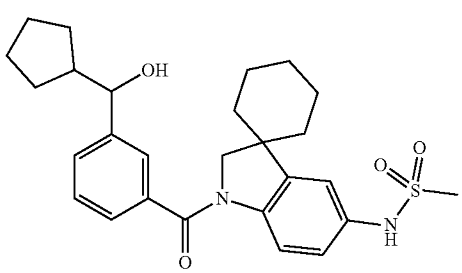 [SMILES: CS(=O)(=O)Nc1ccc2c(c1)C1(CCCCC1)CN2C(=O)c1cccc(C(O)C2CCCC2)c1] | N-(1'-(3-(cyclopentyl(hydroxy)methyl)benzoyl)spiro[cyclohexane-1,3'-indolin]-5'-yl)methanesulfonamide |

TABLE 1-continued

| Compound No. | Structure | Name |
|---|---|---|
| Compound 158 | 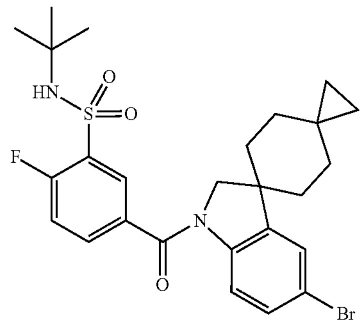 [SMILES: CC(C)(C)NS(=O)(=O)c1cc(C(=O)N2CC3(CCC4(CC4)CC3)c3cc(Br)ccc32)ccc1F] | 5-(5''-bromodispiro[cyclopropane-1,1'-cyclohexane-4',3''-indoline]-1''-carbonyl)-N-(tert-butyl)-2-fluorobenzenesulfonamide |
| Compound 159 | 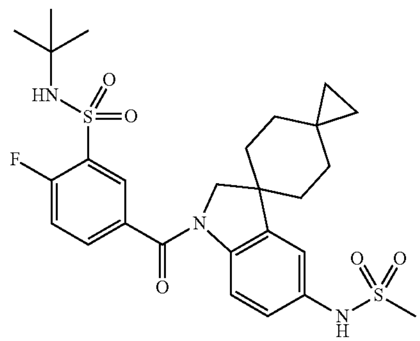 [SMILES: CC(C)(C)NS(=O)(=O)c1cc(C(=O)N2CC3(CCC4(CC4)CC3)c3cc(NS(C)(=O)=O)ccc32)ccc1F] | N-(tert-butyl)-2-fluoro-5-(5''-(methylsulfonamido)dispiro[cyclopropane-1,1'-cyclohexane-4',3''-indoline]-1''-carbonyl)benzenesulfonamide |
| Compound 160 | 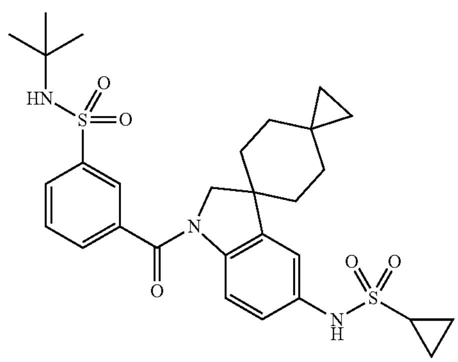 [SMILES: CC(C)(C)NS(=O)(=O)c1cccc(C(=O)N2CC3(CCC4(CC4)CC3)c3cc(NS(=O)(=O)C4CC4)ccc32)c1] | N-(tert-butyl)-3-(5''-(cyclopropanesulfonamido)dispiro[cyclopropane-1,1'-cyclohexane-4',3''-indoline]-1''-carbonyl)benzenesulfonamide |
| Compound 161 | 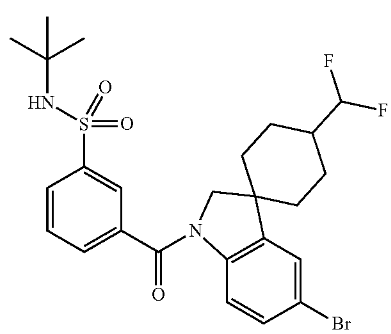 [SMILES: CC(C)(C)NS(=O)(=O)c1cccc(C(=O)N2CC3(CCC(C(F)F)CC3)c3cc(Br)ccc32)c1] | 3-(5'-bromo-4-(difluoromethyl)spiro[cyclohexane-1,3'-indoline]-1'-carbonyl)-N-(tert-butyl)benzenesulfonamide |

TABLE 1-continued

| Compound No. | Structure | Name |
|---|---|---|
| Compound 162 | 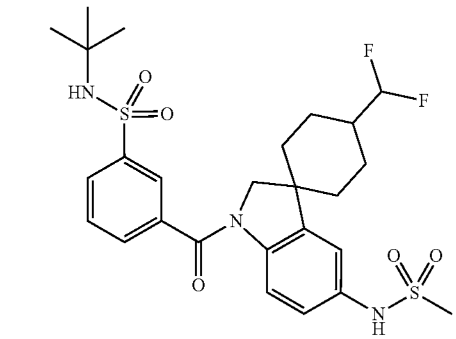 [SMILES: CC(C)(C)NS(=O)(=O)c1cccc(C(=O)N2CC3(CCC(C(F)F)CC3)c3cc(NS(C)(=O)=O)ccc32)c1] | N-(tert-butyl)-3-(4-(difluoromethyl)-5'-(methylsulfonamido)spiro[cyclohexane-1,3'-indoline]-1'-carbonyl)benzenesulfonamide |
| (1s,4s)-Compound 162 | 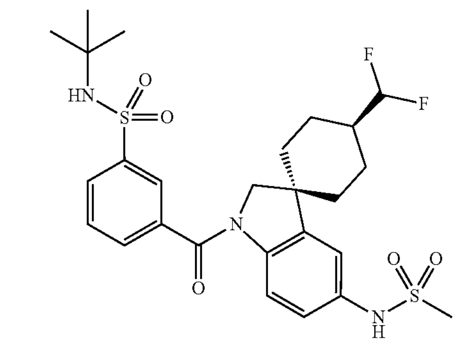 [SMILES: CC(C)(C)NS(=O)(=O)c1cccc(C(=O)N2C[C@]3(CC[C@@H](C(F)F)CC3)c3cc(NS(C)(=O)=O)ccc32)c1] | N-(tert-butyl)-3-((1s,4s)-4-(difluoromethyl)-5'-(methylsulfonamido)spiro[cyclohexane-1,3'-indoline]-1'-carbonyl)benzenesulfonamide |
| (1r,4r)-Compound 162 | 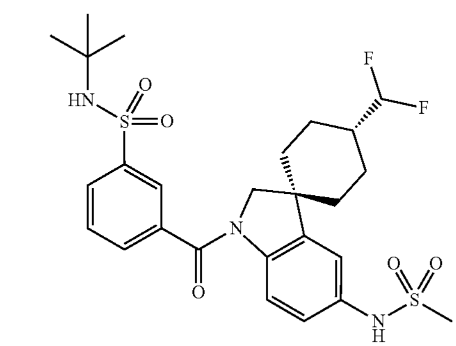 [SMILES: CC(C)(C)NS(=O)(=O)c1cccc(C(=O)N2C[C@]3(CC[C@H](C(F)F)CC3)c3cc(NS(C)(=O)=O)ccc32)c1] | N-(tert-butyl)-3-((1r,4r)-4-(difluoromethyl)-5'-(methylsulfonamido)spiro[cyclohexane-1,3'-indoline]-1'-carbonyl)benzenesulfonamide |
| Compound 163 | 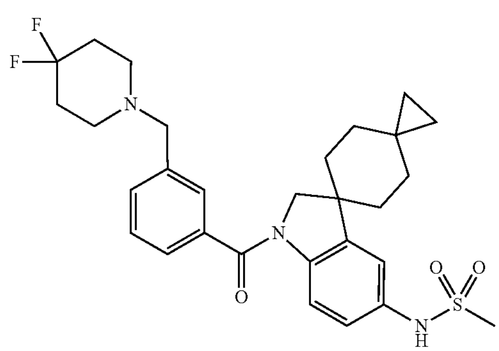 [SMILES: CS(=O)(=O)Nc1ccc2c(c1)C1(CCC3(CC3)CC1)CN2C(=O)c1cccc(CN2CCC(F)(F)CC2)c1] | N-(1''-(3-((4,4-difluoropiperidin-1-yl)methyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 164 | 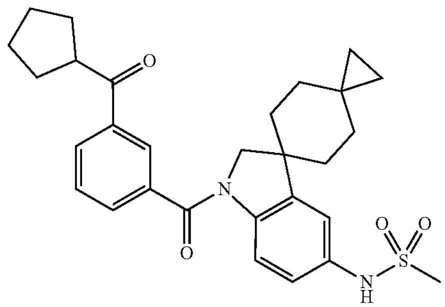 [SMILES: CS(=O)(=O)Nc1ccc2c(c1)C1(CCC3(CC3)CC1)CN2C(=O)c1cccc(C(=O)C2CCCC2)c1] | N-(1''-(3-(cyclopentanecarbonyl)benzoyl)dispiro[cyclopropane-1,1'-cyclohexane-4',3''-indolin]-5''-yl)methanesulfonamide |
| Compound 165 | 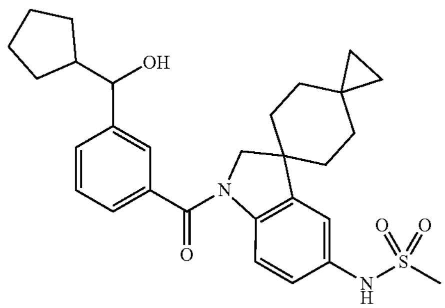 [SMILES: CS(=O)(=O)Nc1ccc2c(c1)C1(CCC3(CC3)CC1)CN2C(=O)c1cccc(C(O)C2CCCC2)c1] | N-(1''-(3-(cyclopentyl(hydroxy)methyl)benzoyl)dispiro[cyclopropane-1,1'-cyclohexane-4',3''indolin]-5''-yl)methanesulfonamide |
| (R)-Compound 165 | 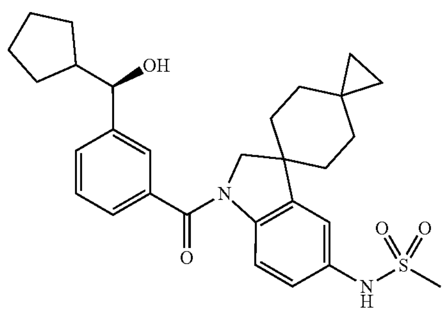 [SMILES: CS(=O)(=O)Nc1ccc2c(c1)C1(CCC3(CC3)CC1)CN2C(=O)c1cccc([C@H](O)C2CCCC2)c1] | (R)-N-(1''-(3-(cyclopentyl(hydroxy)methyl)benzoyl)dispiro[cyclopropane-1,1'-cyclohexane-4',3''-indolin]-5''-yl)methanesulfonamide |
| (S)-Compound 165 | 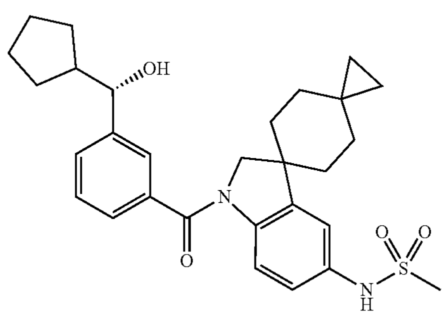 [SMILES: CS(=O)(=O)Nc1ccc2c(c1)C1(CCC3(CC3)CC1)CN2C(=O)c1cccc([C@@H](O)C2CCCC2)c1] | (S)-N-(1''-(3-(cyclopentyl(hydroxy)methyl)benzoyl)dispiro[cyclopropane-1,1'-cyclohexane-4',3''-indolin]-5''-yl)methanesulfonamide |
| Compound 166 | 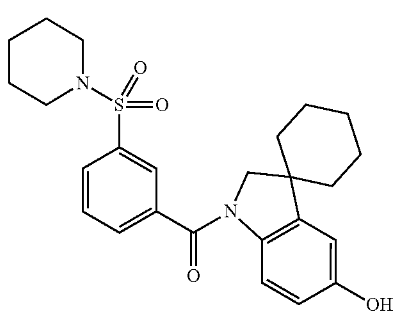 [SMILES: O=C(c1cccc(S(=O)(=O)N2CCCCC2)c1)N1CC2(CCCCC2)c2cc(O)ccc21] | (5'-hydroxyspiro[cyclohexane-1,3'-indolin]-1'-yl)(3-(piperidin-1-ylsulfonyl)phenyl)methanone |

TABLE 1-continued

| Compound No. | Structure | Name |
|---|---|---|
| Compound 167 | 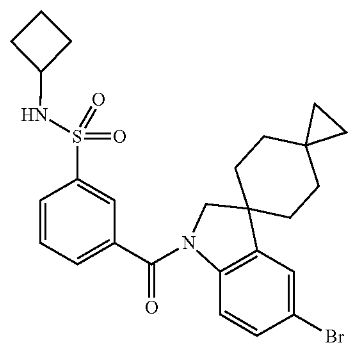 [SMILES: O=C(c1cccc(S(=O)(=O)NC2CCC2)c1)N1CC2(CCC3(CC3)CC2)c2cc(Br)ccc21] | (3-(5''-bromodispiro[cyclopropane-1,1'-cyclohexane-4',3''-indoline]-1''-carbonyl)-N-cyclobutylbenzenesulfonamide |
| Compound 168 | 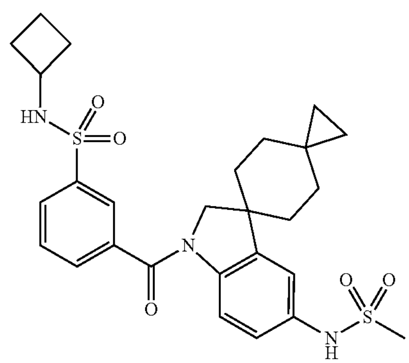 [SMILES: CS(=O)(=O)Nc1ccc2c(c1)C1(CCC3(CC3)CC1)CN2C(=O)c1cccc(S(=O)(=O)NC2CCC2)c1] | N-cyclobutyl-3-(5''-(methylsulfonamido)dispiro[cyclopropane-1,1'-cyclohexane-4',3''-indoline]-1''-carbonyl)benzenesulfonamide |
| Compound 169 | 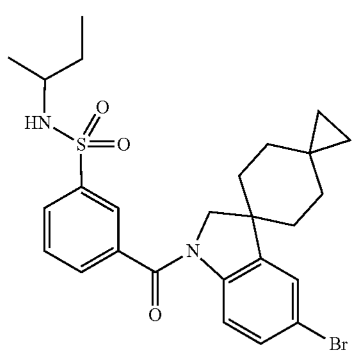 [SMILES: CCC(C)NS(=O)(=O)c1cccc(C(=O)N2CC3(CCC4(CC4)CC3)c3cc(Br)ccc32)c1] | 3-(5''-bromodispiro[cyclopropane-1,1'-cyclohexane-4',3''-indoline]-1''-carbonyl)-N-(sec-butyl)benzenesulfonamide |
| Compound 170 | 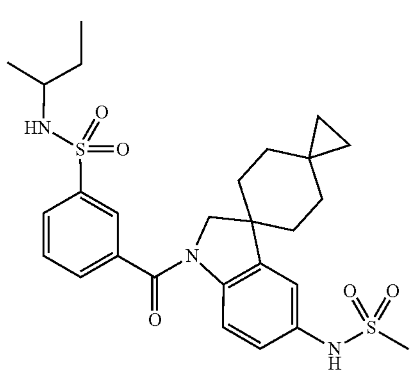 [SMILES: CCC(C)NS(=O)(=O)c1cccc(C(=O)N2CC3(CCC4(CC4)CC3)c3cc(NS(C)(=O)=O)ccc32)c1] | N-(sec-butyl)-3-(5''-(methylsulfonamido)dispiro[cyclopropane-1,1'-cyclohexane-4',3''-indoline]-1''-carbonyl)benzenesulfonamide |

TABLE 1-continued

| Compound No. | Structure | Name |
|---|---|---|
| Compound 171 | 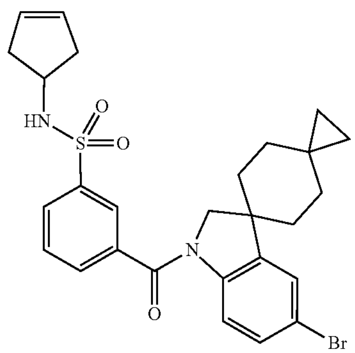 [SMILES: O=C(c1cccc(S(=O)(=O)NC2CC=CC2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-(cyclopent-3-en-1-yl)benzenesulfonamide |
| Compound 172 | 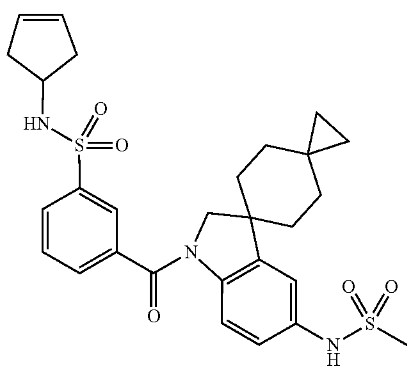 [SMILES: CS(=O)(=O)Nc1ccc2c(c1)C1(CCC3(CC3)CC1)CN2C(=O)c1cccc(S(=O)(=O)NC2CC=CC2)c1] | N-(cyclopent-3-en-1-yl)-3-(5''-(methylsulfonamido)dispiro[cyclopropane-1,1'-cyclohexane-4',3''-indoline]-1''-carbonyl)benzenesulfonamide |
| Compound 173 | 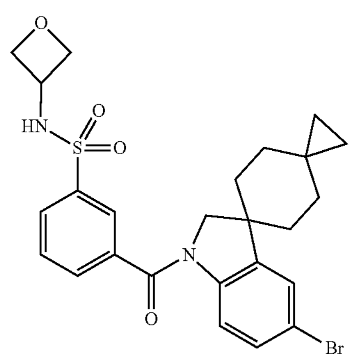 [SMILES: O=C(c1cccc(S(=O)(=O)NC2COC2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-(oxetan-3-yl)benzenesulfonamide |
| Compound 174 | 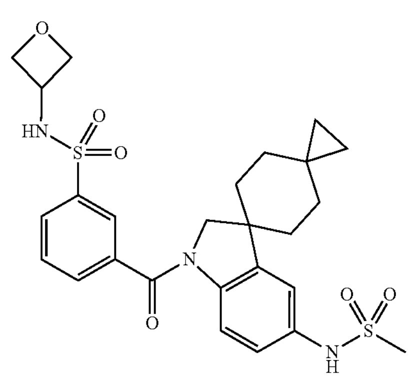 [SMILES: CS(=O)(=O)Nc1ccc2c(c1)C1(CCC3(CC3)CC1)CN2C(=O)c1cccc(S(=O)(=O)NC2COC2)c1] | 3-(5''-(methylsulfonamido)dispiro[cyclopropane-1,1'-cyclohexane-4',3''-indoline]-1''-carbonyl)-N-(oxetan-3-yl)benzenesulfonamide |

TABLE 1-continued

| Compound No. | Structure | Name |
|---|---|---|
| Compound 175 | 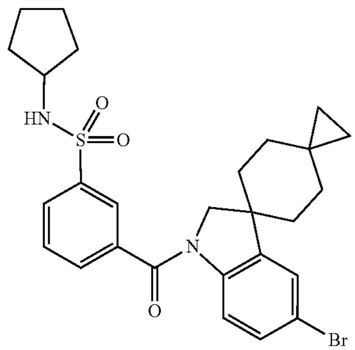 [SMILES: O=C(c1cccc(S(=O)(=O)NC2CCCC2)c1)N1CC2(CCC3(CC3)CC2)c2cc(Br)ccc21] | 3-(5"-bromodispiro[cyclopropane-1,1'-cyclohexane-4',3"-indoline]-1"-carbonyl)-N-cyclopentylbenzenesulfonamide |
| Compound 176 | 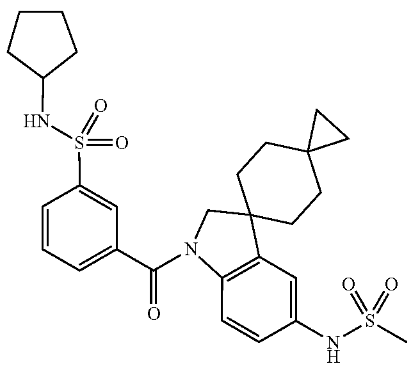 [SMILES: CS(=O)(=O)Nc1ccc2c(c1)C1(CCC3(CC3)CC1)CN2C(=O)c1cccc(S(=O)(=O)NC2CCCC2)c1] | N-cyclopentyl-3-(5"-(methylsulfonamido)dispiro[cyclopropane-1,1"-cyclohexane-4',3"-indoline]-1"-carbonyl)benzenesulfonamide |
| Compound 177 | 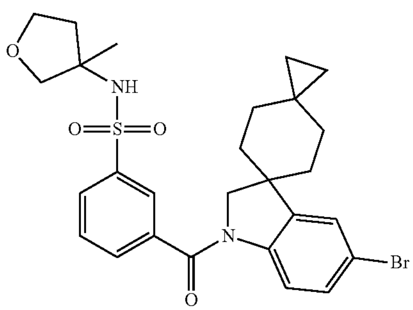 [SMILES: CC1(NS(=O)(=O)c2cccc(C(=O)N3CC4(CCC5(CC5)CC4)c4cc(Br)ccc43)c2)CCOC1] | 3-(5"-bromodispiro[cyclopropane-1,1'-cyclohexane-4',3"-indoline]-1"-carbonyl)-N-(3-methyltetrahydrofuran-3-yl)benzenesulfonamide |
| Compound 178 | 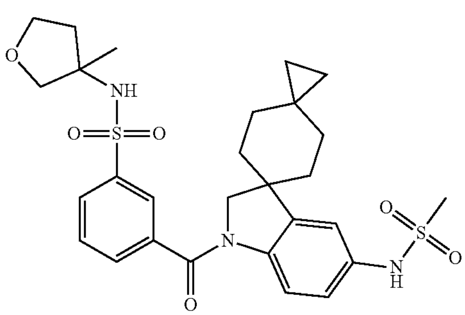 [SMILES: CC1(NS(=O)(=O)c2cccc(C(=O)N3CC4(CCC5(CC5)CC4)c4cc(NS(C)(=O)=O)ccc43)c2)CCOC1] | 3-(5"-(methylsulfonamido)dispiro[cyclopropane-1,1'-cyclohexane-4',3"-indoline]-1"-carbonyl)-N-(3-methyltetrahydrofuran-3-yl)benzenesulfonamide |

TABLE 1-continued

| Compound No. | Structure | Name |
|---|---|---|
| Compound 179 | 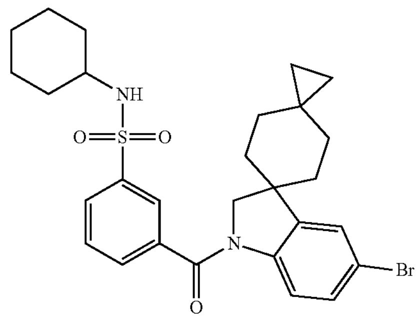 [SMILES: O=C(c1cccc(S(=O)(=O)NC2CCCCC2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-cyclohexylbenzenesulfonamide |
| Compound 180 | 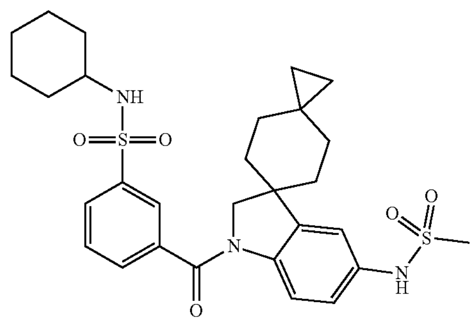 [SMILES: CS(=O)(=O)Nc1ccc2c(c1)C1(CCC3(CC3)CC1)CN2C(=O)c1cccc(S(=O)(=O)NC2CCCCC2)c1] | N-cyclohexyl-3-(5''-(methylsulfonamido)dispiro[cyclopropane-1,1'-cyclohexane-4',3''-indoline]-1''-carbonyl)benzenesulfonamide |
| Compound 181 | 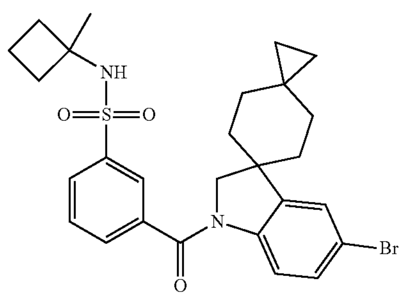 [SMILES: CC1(NS(=O)(=O)c2cccc(C(=O)N3CC4(CCC5(CC5)CC4)c4cc(Br)ccc43)c2)CCC1] | 3-(5''-bromodispiro[cyclopropane-1,1'-cyclohexane-4',3''indoline]-1''-carbonyl)-N-(1-methylcyclobutyl)benzenesulfonamide |
| Compound 182 | 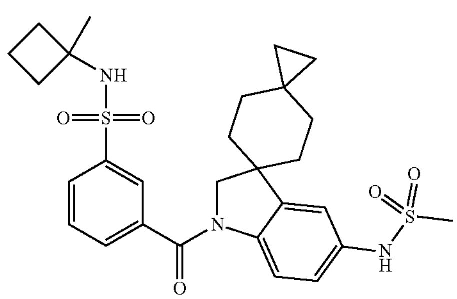 [SMILES: CC1(NS(=O)(=O)c2cccc(C(=O)N3CC4(CCC5(CC5)CC4)c4cc(NS(C)(=O)=O)ccc43)c2)CCC1] | N-(1-methylcyclobutyl)-3-(5''-(methylsulfonamido)dispiro[cyclopropane-1,1'-cyclohexane-4',3''-indoline]-1''-carbonyl)benzenesulfonamide |
| Compound 183 | 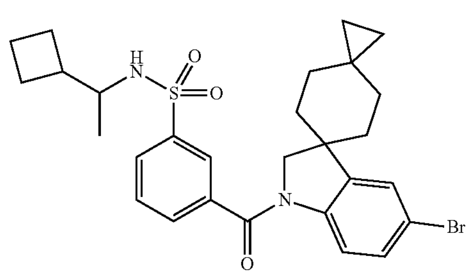 [SMILES: CC(NS(=O)(=O)c1cccc(C(=O)N2CC3(CCC4(CC4)CC3)c3cc(Br)ccc32)c1)C1CCC1] | 3-(5''-bromodispiro[cyclopropane-1,1'-cyclohexane-4',3''-indoline]-1''-carbonyl)-N-(1-cyclobutylethyl)benzenesulfonamide |

TABLE 1-continued

| Compound No. | Structure | Name |
|---|---|---|
| Compound 184 | 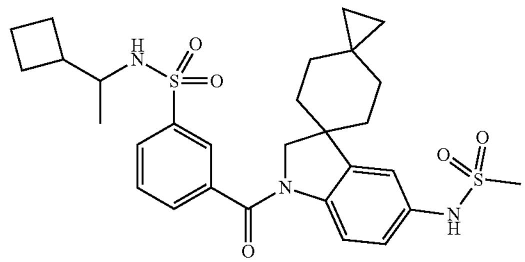 [SMILES: CC(NS(=O)(=O)c1cccc(C(=O)N2CC3(CCC4(CC4)CC3)c3cc(NS(C)(=O)=O)ccc32)c1)C1CCC1] | N-(1-cyclobutylethyl)-3-(5''-(methylsulfonamido)dispiro[cyclopropane-1,1'-cyclohexane-4',3''-indoline]-1''-carbonyl)benzenesulfonamide |
| Compound 185 | 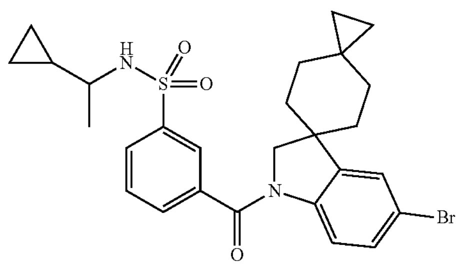 [SMILES: CC(NS(=O)(=O)c1cccc(C(=O)N2CC3(CCC4(CC4)CC3)c3cc(Br)ccc32)c1)C1CC1] | 3-(5''-bromodispiro[cyclopropane-1,1'-cyclohexane-4',3''-indoline]-1''-carbonyl)-N-(1-cyclopropylethyl)benzenesulfonamide |
| Compound 186 | 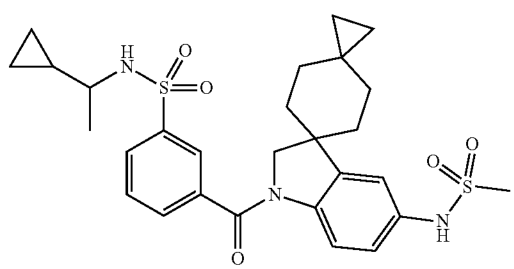 [SMILES: CC(NS(=O)(=O)c1cccc(C(=O)N2CC3(CCC4(CC4)CC3)c3cc(NS(C)(=O)=O)ccc32)c1)C1CC1] | N-(1-cyclopropylethyl)-3-(5''-(methylsulfonamido)dispiro[cyclopropane-1,1'-cyclohexane-4',3''-indoline]-1''-carbonyl)benzenesulfonamide |
| Compound 187 | 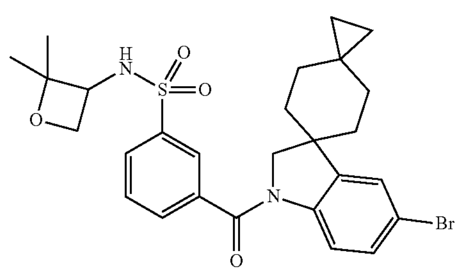 [SMILES: CC1(C)OCC1NS(=O)(=O)c1cccc(C(=O)N2CC3(CCC4(CC4)CC3)c3cc(Br)ccc32)c1] | 3-(5''-bromodispiro[cyclopropane-1,1'-cyclohexane-4',3''-indoline]-1''-carbonyl)-N-(2,2-dimethyloxetan-3-yl)benzenesulfonamide |
| Compound 188 | 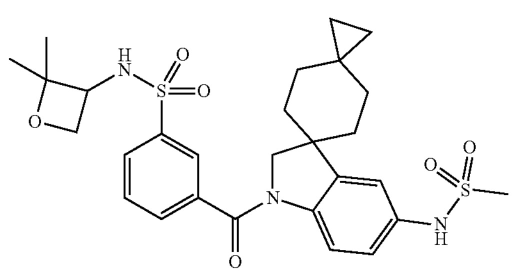 | N-(2,2-dimethyloxetan-3-yl)-3-(5''-(methylsulfonamido)dispiro[cyclopropane-1,1'-cyclohexane-4',3''-indoline]-1''-carbonyl)benzenesulfonamide |

TABLE 1-continued

| Compound No. | Structure | Name |
|---|---|---|
| Compound 189 | 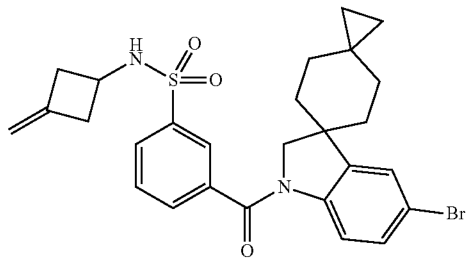 [SMILES: C=C1CC(NS(=O)(=O)c2cccc(C(=O)N3CC4(CCC5(CC5)CC4)c4cc(Br)ccc43)c2)C1] | 3-(5''-bromodispiro[cyclopropane-1,1'-cyclohexane-4',3''-indoline]-1''-carbonyl)-N-(3-methylenecyclobutyl)benzenesulfonamide |
| Compound 190 | 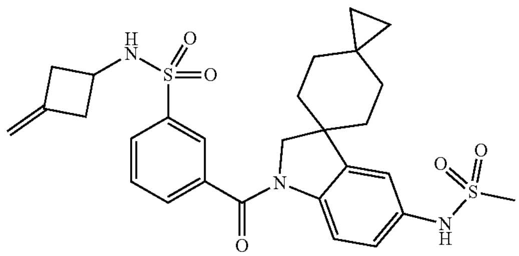 | N-(3-methylenecyclobutyl)-3-(5''-(methylsulfonamido)dispiro[cyclopropane-1,1'-cyclohexane-4',3''-indoline]-1''-carbonyl)benzenesulfonamide |
| Compound 191 | 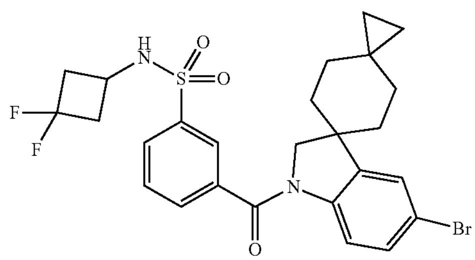 [SMILES: O=C(c1cccc(S(=O)(=O)NC2CC(F)(F)C2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-(3,3-difluorocyclobutyl)benzenesulfonamide |
| Compound 192 | 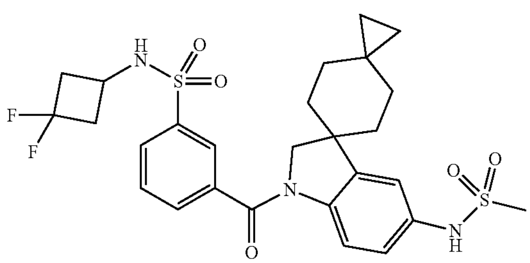 [SMILES: CS(=O)(=O)Nc1ccc2c(c1)C1(CCC3(CC3)CC1)CN2C(=O)c1cccc(S(=O)(=O)NC2CC(F)(F)C2)c1] | N-(3,3-difluorocyclobutyl)-3-(5''-(methylsulfonamido)dispiro[cyclopropane-1,1'-cyclohexane-4',3''-indoline]-1''-carbonyl)benzenesulfonamide |
| Compound 193 | 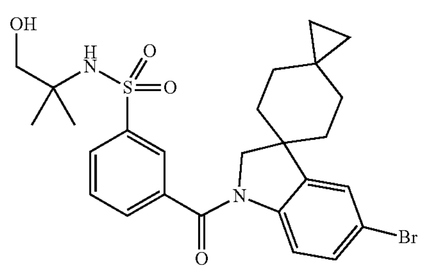 [SMILES: CC(C)(CO)NS(=O)(=O)c1cccc(C(=O)N2CC3(CCC4(CC4)CC3)c3cc(Br)ccc32)c1] | 3-(5''-bromodispiro[cycloprpoane-1,1'-cyclohexane-4',3''-indoline]-1''-carbonyl)-N-(1-hydroxy-2-methylpropan-2-yl)benzenesulfonamide |
| Compound 194 | 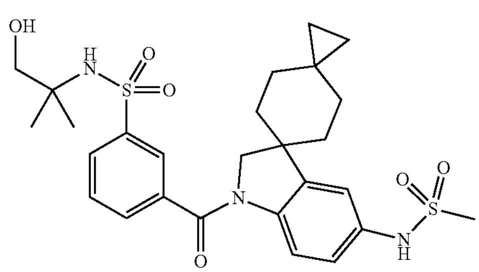 [SMILES: CC(C)(CO)NS(=O)(=O)c1cccc(C(=O)N2CC3(CCC4(CC4)CC3)c3cc(NS(C)(=O)=O)ccc32)c1] | N-(1-hydroxy-2-methylpropan-2-yl)-3-(5''-(methylsulfonamido)dispiro[cyclopropane-1,1'-cyclohexane-4',3''-indoline]-1''-carbonyl)benzenesulfonamide |

TABLE 1-continued

| Compound No. | Structure | Name |
|---|---|---|
| Compound 195 | 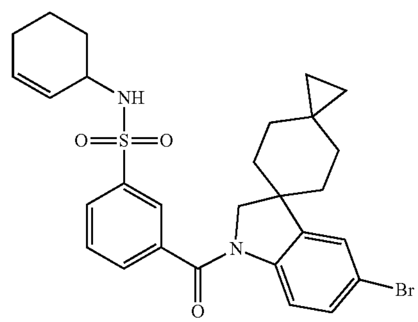 [SMILES: O=C(c1cccc(S(=O)(=O)NC2C=CCCC2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-(cyclohex-2-en-1-yl)benzenesulfonamide |
| Compound 196 | 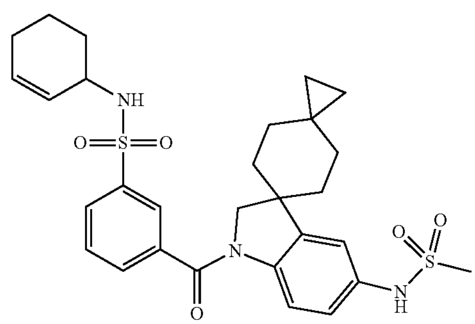 [SMILES: CS(=O)(=O)Nc1ccc2c(c1)C1(CCC3(CC3)CC1)CN2C(=O)c1cccc(S(=O)(=O)NC2C=CCCC2)c1] | N-(cyclohex-2-en-1-yl)-3-(5''-(methylsulfonamido)dispiro[cyclopropane-1,1'-cyclohexane-4',3''-indoline]-1''-carbonyl)benzenesulfonamide |
| Compound 197 | 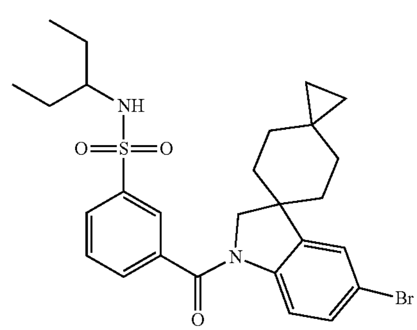 [SMILES: CCC(CC)NS(=O)(=O)c1cccc(C(=O)N2CC3(CCC4(CC4)CC3)c3cc(Br)ccc32)c1] | 3-(5''-bromodispiro[cyclopropane-1,1'-cyclohexane-4',3''-indoline]-1''-carbonyl)-N-(pentan-3-yl)benzenesulfonamide |
| Compound 198 | 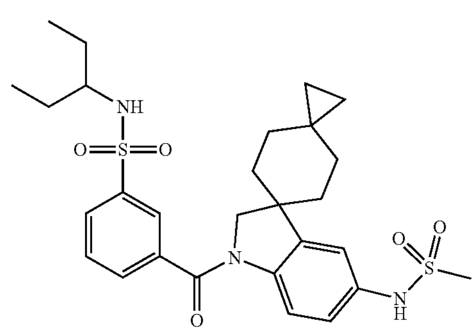 [SMILES: CCC(CC)NS(=O)(=O)c1cccc(C(=O)N2CC3(CCC4(CC4)CC3)c3cc(NS(C)(=O)=O)ccc32)c1] | 3-(5''-(methylsulfonamido)dispiro[cyclopropane-1,1'-cyclohexane-4',3''-indoline]-1''-carbonyl)-N-(pentan-3-yl)benzenesulfonamide |

TABLE 1-continued

| Compound No. | Structure | Name |
|---|---|---|
| Compound 199 | 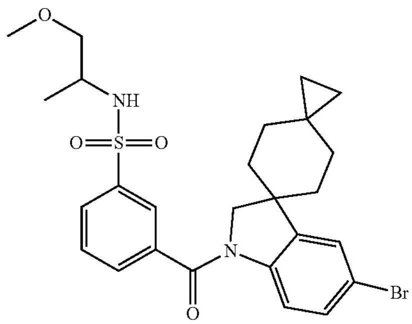 [SMILES: COCC(C)NS(=O)(=O)c1cccc(C(=O)N2CC3(CCC4(CC4)CC3)c3cc(Br)ccc32)c1] | 3-(5''-bromodispiro[cyclopropane-1,1'-cyclohexane-4',3''-indoline]-1''-carbonyl)-N-(1-methoxypropan-2-yl)benzenesulfonamide |
| Compound 200 | 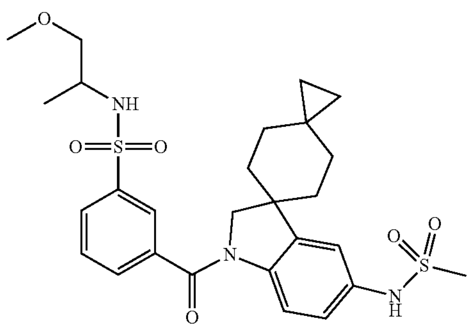 | N-(1-methoxypropan-2-yl)-3-(5''-(methylsulfonamido)dispiro[cyclopropane-1,1'-cyclohexane-4',3''-indoline]-1''-carbonyl)benzenesulfonamide |
| Compound 201 | 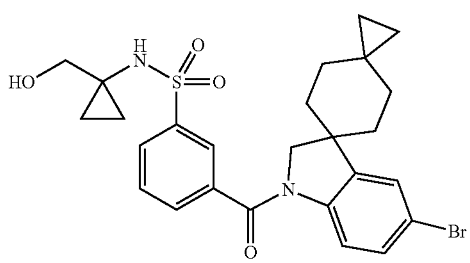 [SMILES: O=C(c1cccc(S(=O)(=O)NC2(CO)CC2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-(1-(hydroxymethyl)cyclopropyl)benzenesulfonamide |
| Compound 202 | 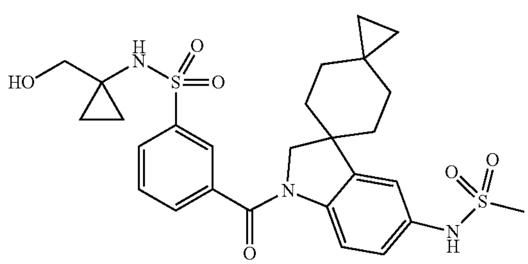 [SMILES: CS(=O)(=O)Nc1ccc2c(c1)C1(CCC3(CC3)CC1)CN2C(=O)c1cccc(S(=O)(=O)NC2(CO)CC2)c1] | N-(1-(hydroxymethyl)cyclopropyl)-3-(5''-(methylsulfonamido)dispiro[cyclopropane-1,1'-cyclohexane-4',3''-indoline]-1''-carbonyl)benzenesulfonamide |
| Compound 203 | 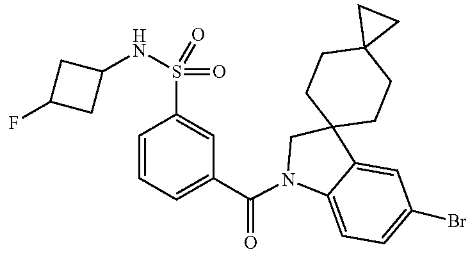 [SMILES: O=C(c1cccc(S(=O)(=O)NC2CC(F)C2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-(3-fluorocyclobutyl)benzenesulfonamide |

TABLE 1-continued

| Compound No. | Structure | Name |
|---|---|---|
| Compound 204 | 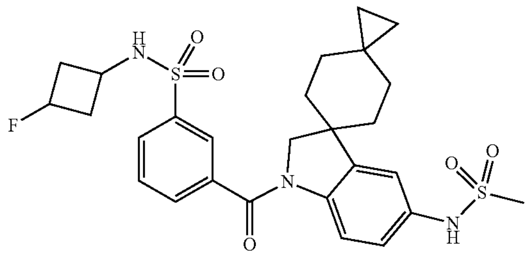 [SMILES: CS(=O)(=O)Nc1ccc2c(c1)C1(CCC3(CC3)CC1)CN2C(=O)c1cccc(S(=O)(=O)NC2CC(F)C2)c1] | N-(3-fluorocyclobutyl)-3-(5''-(methylsulfonamido)dispiro[cyclopropane-1,1'-cyclohexane-4',3''-indoline]-1''-carbonyl)benzenesulfonamide |
| Compound 205 | 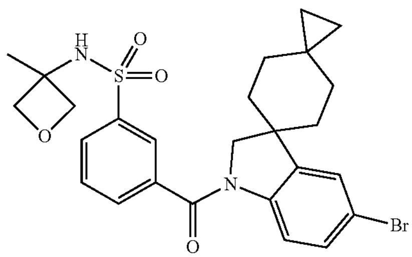 [SMILES: CC1(NS(=O)(=O)c2cccc(C(=O)N3CC4(CCC5(CC5)CC4)c4cc(Br)ccc43)c2)COC1] | 3-(5''-bromodispiro[cyclopropane-1,1'-cyclohexane-4',3''-indoline]-1''-carbonyl)-N-(3-methyloxetan-3-yl)benzenesulfonamide |
| Compound 206 | 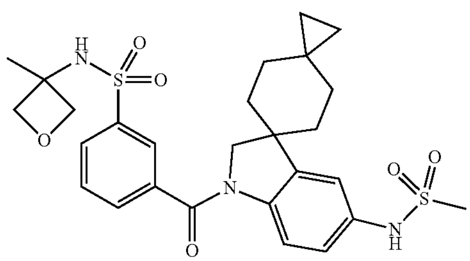 | N-(3-methyloxetan-3-yl)-3-(5''-(methylsulfonamido)dispiro[cyclopropane-1,1'-cyclohexane-4',3''-indoline]-1''-carbonyl)benzenesulfonamide |
| Compound 207 | 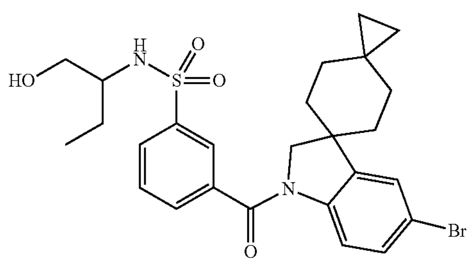 [SMILES: CCC(CO)NS(=O)(=O)c1cccc(C(=O)N2CC3(CCC4(CC4)CC3)c3cc(Br)ccc32)c1] | 3-(5''-bromodispiro[cyclopropane-1,1'-cyclohexane-4',3''-indoline]-1''-carbonyl)-N-(1-hydroxybutan-2-yl)benzenesulfonamide |
| Compound 208 | 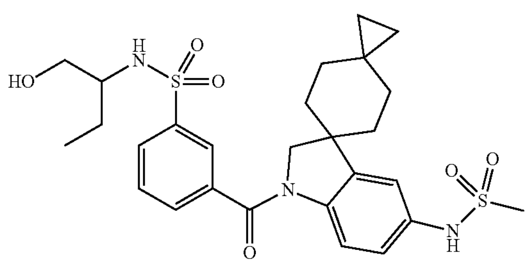 [SMILES: CCC(CO)NS(=O)(=O)c1cccc(C(=O)N2CC3(CCC4(CC4)CC3)c3cc(NS(C)(=O)=O)ccc32)c1] | N-(1-hydroxybutan-2-yl)-3-(5''-(methylsulfonamido)dispiro[cyclopropane-1,1'-cyclohexane-4',3''-indoline]-1''-carbonyl)benzenesulfonamide |
| Compound 209 | 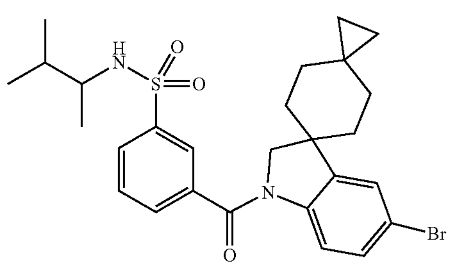 [SMILES: CC(C)C(C)NS(=O)(=O)c1cccc(C(=O)N2CC3(CCC4(CC4)CC3)c3cc(Br)ccc32)c1] | 3-(5''-bromodispiro[cyclopropane-1,1'-cyclohexane-4',3''-indoline]-1''-carbonyl)-N-(3-methylbutan-2-yl)benzenesulfonamide |

TABLE 1-continued

| Compound No. | Structure | Name |
|---|---|---|
| Compound 210 | 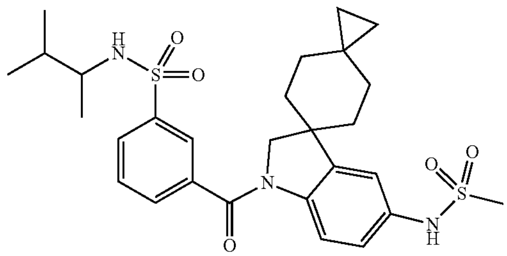 [SMILES: CC(C)C(C)NS(=O)(=O)c1cccc(C(=O)N2CC3(CCC4(CC4)CC3)c3cc(NS(C)(=O)=O)ccc32)c1] | N-(3-methylbutan-2-yl)-3-(5''-(methylsulfonamido)dispiro[cyclopropane-1,1'-cyclohexane-4',3''-indoline]-1''-carbonyl)benzenesulfonamide |
| Compound 211 | 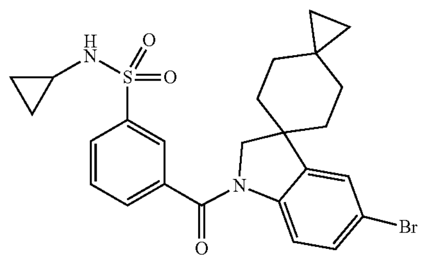 [SMILES: O=C(c1cccc(S(=O)(=O)NC2CC2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-cyclopropylbenzenesulfonamide |
| Compound 212 | 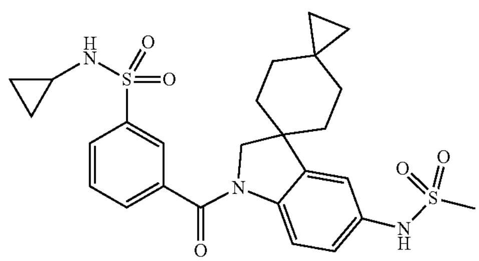 [SMILES: CS(=O)(=O)Nc1ccc2c(c1)C1(CCC3(CC3)CC1)CN2C(=O)c1cccc(S(=O)(=O)NC2CC2)c1] | N-cyclopropyl-3-(5''-(methylsulfonamido)dispiro[cyclopropane-1,1'-cyclohexane-4',3''-indoline]-1''-carbonyl)benzenesulfonamide |
| Compound 213 | 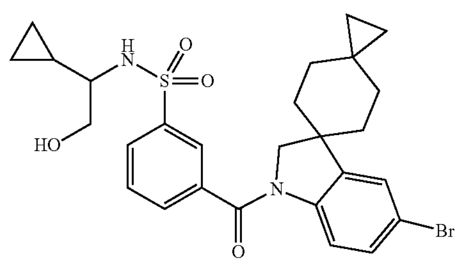 [SMILES: O=C(c1cccc(S(=O)(=O)NC(CO)C2CC2)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-(1-cyclopropyl-2-hydroxyethyl)benzenesulfonamide |
| Compound 214 | 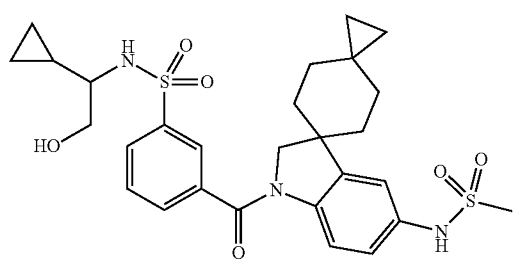 [SMILES: CS(=O)(=O)Nc1ccc2c(c1)C1(CCC3(CC3)CC1)CN2C(=O)c1cccc(S(=O)(=O)NC(CO)C2CC2)c1] | N-(1-cyclopropyl-2-hydroxyethyl)-3-(5''-(methylsulfonamido)dispiro[cyclopropane-1,1'-cyclohexane-4',3''-indoline]-1''-carbonyl)benzenesulfonamide |
| Compound 215 | 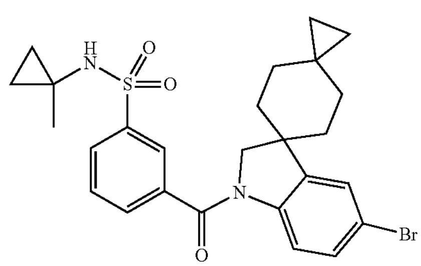 [SMILES: CC1(NS(=O)(=O)c2cccc(C(=O)N3CC4(CCC5(CC5)CC4)c4cc(Br)ccc43)c2)CC1] | 3-(5''-bromodispiro[cyclopropane-1,1'-cyclohexane-4',3''-indoline]-1''-carbonyl)-N-(1-methylcyclopropyl)benzenesulfonamide |

TABLE 1-continued

| Compound No. | Structure | Name |
|---|---|---|
| Compound 216 | 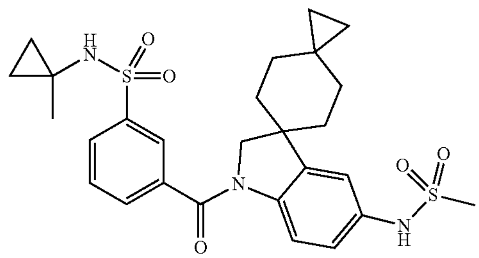 [SMILES: CC1(NS(=O)(=O)c2cccc(C(=O)N3CC4(CCC5(CC5)CC4)c4cc(NS(C)(=O)=O)ccc43)c2)CC1] | N-(1-methylcyclopropyl)-3-(5"-(methylsulfonamido)dispiro[cyclopropane-1,1'-cyclohexane-4',3"-indoline]-1"-carbonyl)benzenesulfonamide |
| Compound 217 | 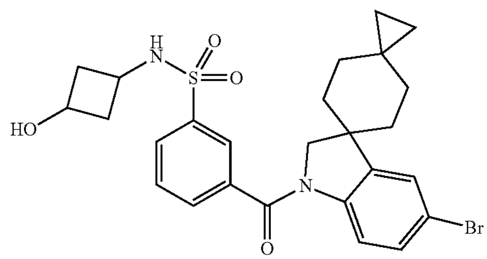 [SMILES: O=C(c1cccc(S(=O)(=O)NC2CC(O)C2)c1)N1CC2(CCC3(CC3)CC2)c2cc(Br)ccc21] | 3-(5"-bromodispiro[cyclopropane-1,1'-cyclohexane-4',3"-indoline]-1"-carbonyl)-N-(3-hydroxycyclobutyl)benzenesulfonamide |
| Compound 218 | 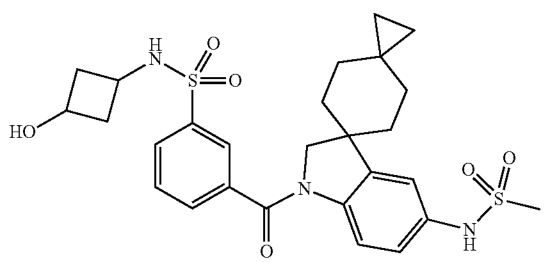 [SMILES: CS(=O)(=O)Nc1ccc2c(c1)C1(CCC3(CC3)CC1)CN2C(=O)c1cccc(S(=O)(=O)NC2CC(O)C2)c1] | N-(3-hydroxycyclobutyl)-3-(5"-(methylsulfonamido)dispiro[cyclopropane-1,1'-cyclohexane-4',3"-indoline]-1"-carbonyl)benzenesulfonamide |
| Compound 219 | 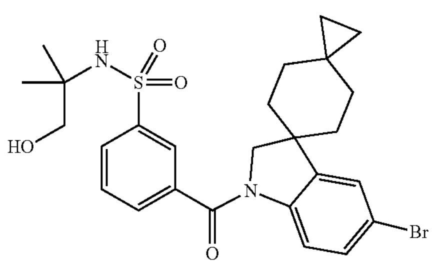 [SMILES: CC(C)(CO)NS(=O)(=O)c1cccc(C(=O)N2CC3(CCC4(CC4)CC3)c3cc(Br)ccc32)c1] | 3-(5"-bromodispiro[cyclopropane-1,1'-cyclohexane-4',3"-indoline]-1"-carbonyl)-N-(1-hydroxy-2-methylpropan-2-yl)benzenesulfonamide |
| Compound 220 | 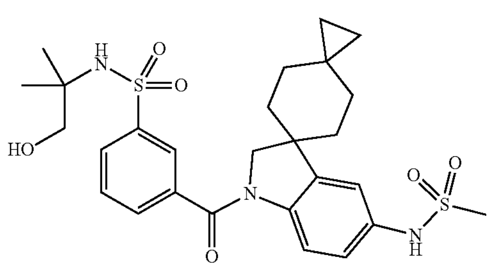 [SMILES: CC(C)(CO)NS(=O)(=O)c1cccc(C(=O)N2CC3(CCC4(CC4)CC3)c3cc(NS(C)(=O)=O)ccc32)c1] | N-(1-hydroxy-2-methylpropan-2-yl)-3-(5"-(methylsulfonamido)dispiro[cyclopropane-1,1'-cyclohexane-4',3"-indoline]-1"-carbonyl)benzenesulfonamide |
| Compound 221 | 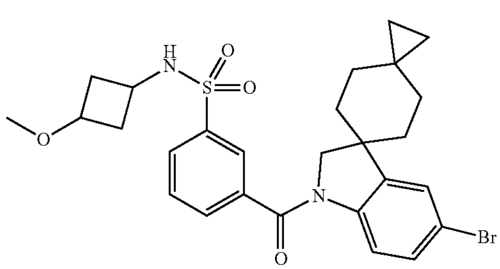 [SMILES: COC1CC(NS(=O)(=O)c2cccc(C(=O)N3CC4(CCC5(CC5)CC4)c4cc(Br)ccc43)c2)C1] | 3-(5"-bromodispiro[cyclopropane-1,1'-cyclohexane-4',3"-indoline]-1"-carbonyl)-N-(3-methoxycyclobutyl)benzenesulfonamide |

TABLE 1-continued

| Compound No. | Structure | Name |
|---|---|---|
| Compound 222 | 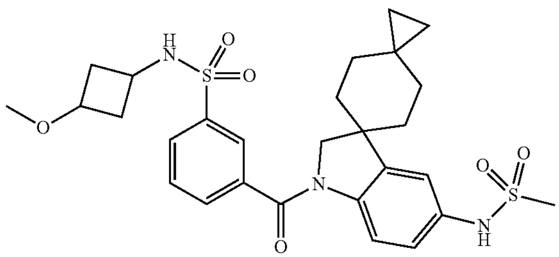 | N-(3-methoxycyclobutyl)-3-(5″-(methylsulfonamido)dispiro[cyclopropane-1,1′-cyclohexane-4′,3″-indoline]-1″-carbonyl)benzenesulfonamide |
| Compound 223 | 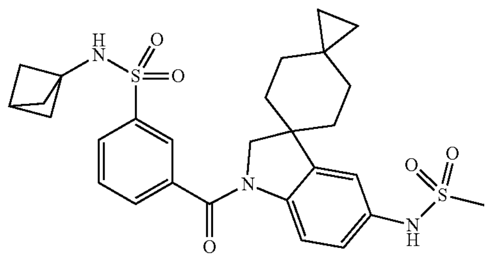 [SMILES: CS(=O)(=O)Nc1ccc2c(c1)C1(CCC3(CC3)CC1)CN2C(=O)c1cccc(S(=O)(=O)NC23CC(C2)C3)c1] | N-(bicyclo[1.1.1]pentan-1-yl)-3-(5″-(methylsulfonamido)dispiro[cyclopropane-1,1′-cyclohexane-4′,3″-indoline]-1″-carbonyl)benzenesulfonamide |
| Compound 224 | 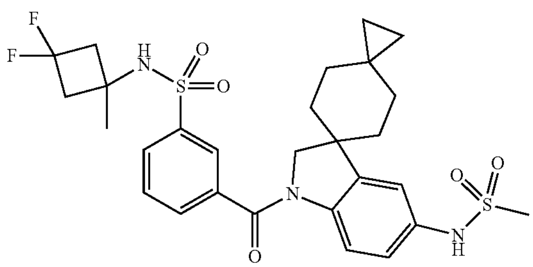 [SMILES: CC1(NS(=O)(=O)c2cccc(C(=O)N3CC4(CCC5(CC5)CC4)c4cc(NS(C)(=O)=O)ccc43)c2)CC(F)(F)C1] | N-(3,3-difluoro-1-methylcyclobutyl)-3-(5″-(methylsulfonamido)dispiro[cyclopropane-1,1′-cyclohexane-4′,3″-indoline]-1″-carbonyl)benzenesulfonamide |
| Compound 225 | 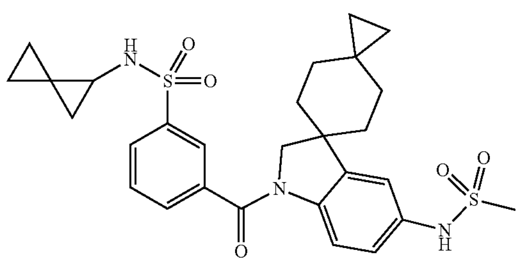 [SMILES: CS(=O)(=O)Nc1ccc2c(c1)C1(CCC3(CC3)CC1)CN2C(=O)c1cccc(S(=O)(=O)NC2CC23CC3)c1] | 3-(5″-(methylsulfonamido)dispiro[cyclopropane-1,1′-cyclohexane-4′,3″-indoline]-1″-carbonyl)-N-(spiro[2.2]pentan-1-yl)benzenesulfonamide |
| Compound 226 | 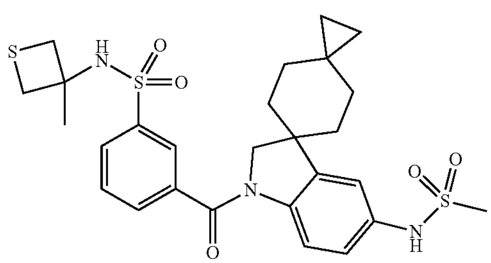 [SMILES: CC1(NS(=O)(=O)c2cccc(C(=O)N3CC4(CCC5(CC5)CC4)c4cc(NS(C)(=O)=O)ccc43)c2)CSC1] | 3-(5″-(methylsulfonamido)dispiro[cyclopropane-1,1′-cyclohexane-4′,3″-indoline]-1″-carbonyl)-N-(3-methylthietan-3-yl)benzenesulfonamide |
| Compound 227 | 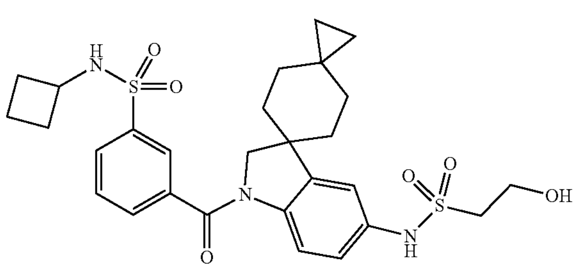 [SMILES: O=C(c1cccc(S(=O)(=O)NC2CCC2)c1)N1CC2(CCC3(CC3)CC2)c2cc(NS(=O)(=O)CCO)ccc21] | N-cyclobutyl-3-(5″-((2-hydroxyethyl)sulfonamido)dispiro[cyclopropane-1,1′-cyclohexane-4′,3″-indoline]-1″-carbonyl)benzenesulfonamide |

TABLE 1-continued

| Compound No. | Structure | Name |
|---|---|---|
| Compound 228 | 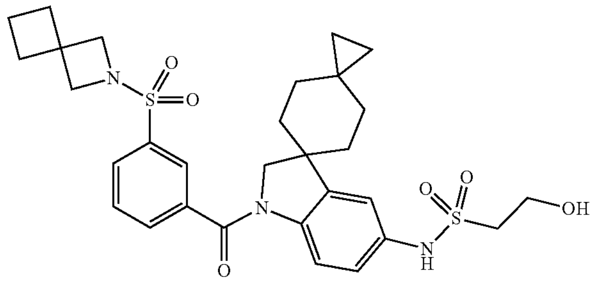 [SMILES: O=C(c1cccc(S(=O)(=O)N2CC3(CCC3)C2)c1)N1CC2(CCC3(CC3)CC2)c2cc(NS(=O)(=O)CCO)ccc21] | N-(1''-(3-((2-azaspiro[3.3]heptan-2-yl)sulfonyl)benzoyl)dispiro[cyclopropane-1,1'-cyclohexane-4',3''-indolin]-5''-yl)-2-hydroxyethane-1-sulfonamide |
| Compound 229 | 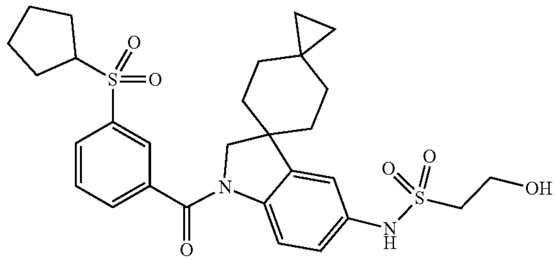 [SMILES: O=C(c1cccc(S(=O)(=O)C2CCCC2)c1)N1CC2(CCC3(CC3)CC2)c2cc(NS(=O)(=O)CCO)ccc21] | N-(1''-(3-(cyclopentylsulfonyl)benzoyl)dispiro[cyclopropane-1,1'-cyclohexane-4',3''-indolin]-5''-yl)-2-hydroxyethane-1-sulfonamide |
| Compound 230 | 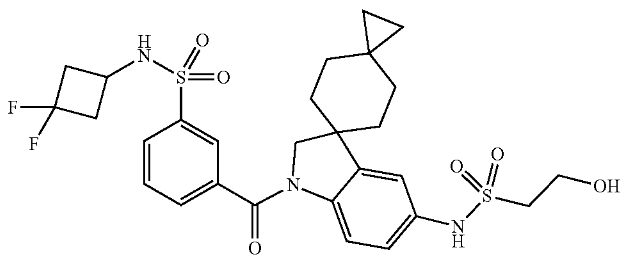 [SMILES: O=C(c1cccc(S(=O)(=O)NC2CC(F)(F)C2)c1)N1CC2(CCC3(CC3)CC2)c2cc(NS(=O)(=O)CCO)ccc21] | N-(3,3-difluorocyclobutyl)-3-(5''-((2-hydroxyethyl)sulfonamido)dispiro[cyclopropane-1,1'-cyclohexane-4',3''-indoline]-1''-carbonyl)benzenesulfonamide |
| Compound 231 | 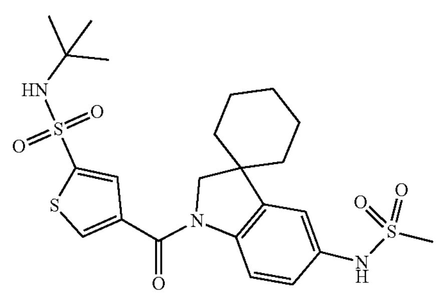 [SMILES: CC(C)(C)NS(=O)(=O)c1cc(C(=O)N2CC3(CCCCC3)c3cc(NS(C)(=O)=O)ccc32)cs1] | N-(tert-butyl)-4-(5'-(methylsulfonamido)spiro[cyclohexane-1,3'-indoline]-1'-carbonyl)thiophene-2-sulfonamide |
| Compound 232 | 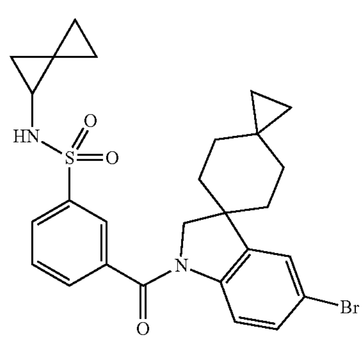 [SMILES: O=C(c1cccc(S(=O)(=O)NC2CC23CC3)c1)N1CC2(CCC3(CC3)CC2)c2cc(Br)ccc21] | 3-(5''-bromodispiro[cyclopropane-1,1'-cyclohexane-4',3''-indoline]-1''-carbonyl)-N-(spiro[2.2]pentan-1-yl)benzenesulfonamide |

TABLE 1-continued

| Compound No. | Structure | Name |
|---|---|---|
| Compound 233 | 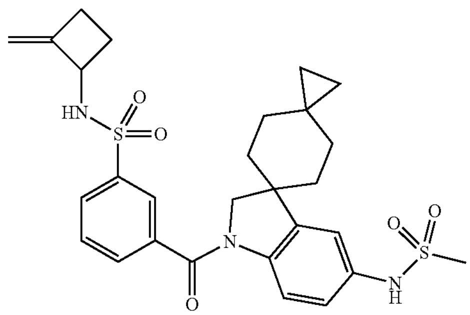 | N-(2-methylenecyclobutyl)-3-(5''-(methylsulfonamido)dispiro[cyclopropane-1,1'-cyclohexane-4',3''-indoline]-1''-carbonyl)benzenesulfonamide |
| Compound 234 | 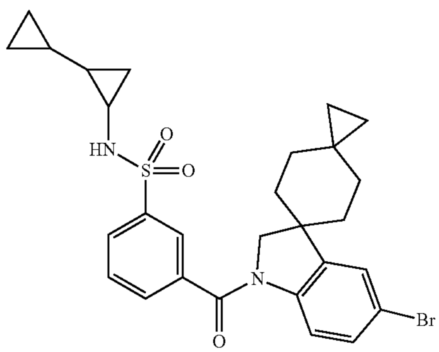 [SMILES: O=C(c1cccc(S(=O)(=O)NC2CC2C2CC2)c1)N1CC2(CCC3(CC3)CC2)c2cc(Br)ccc21] | N([1,1'-bi(cyclopropan)]-2-yl)-3-(5''-bromodispiro[cyclopropane-1,1'-cyclohexane-4',3''-indoline]-1''-carbonyl)benzenesulfonamide |
| Compound 235 | 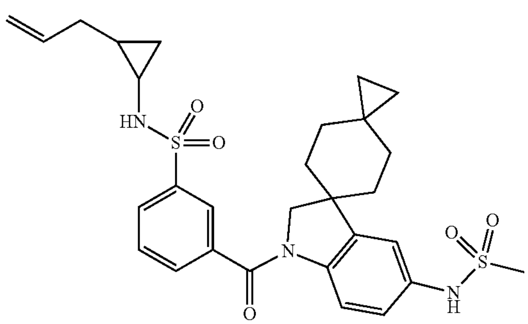 [SMILES: C=CCC1CC1NS(=O)(=O)c1cccc(C(=O)N2CC3(CCC4(CC4)CC3)c3cc(NS(C)(=O)=O)ccc32)c1] | N-(2-allylcyclopropyl)-3-(5''-(methylsulfonamido)dispiro[cyclopropane-1,1'-cyclohexane-4',3''-indoline]-1''-carbonyl)benzenesulfonamide |
| Compound 236 | 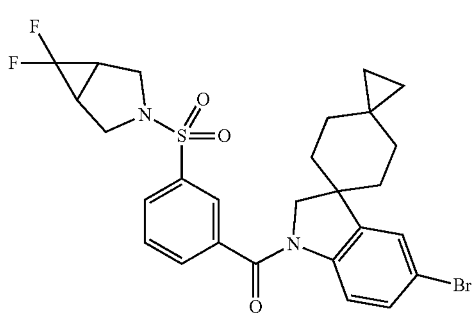 [SMILES: O=C(c1cccc(S(=O)(=O)N2CC3C(C2)C3(F)F)c1)N1CC2(CCC3(CC3)CC2)c2cc(Br)ccc21] | (5''-bromodispiro[cyclopropane-1,1'-cyclohexane-4',3''-indolin]-1''-yl)(3-((6,6-difluoro-3-azabicyclo[3.1.0]hexan-3-yl)sulfonyl)phenyl)methanone |

TABLE 1-continued

| Compound No. | Structure | Name |
|---|---|---|
| Compound 237 | 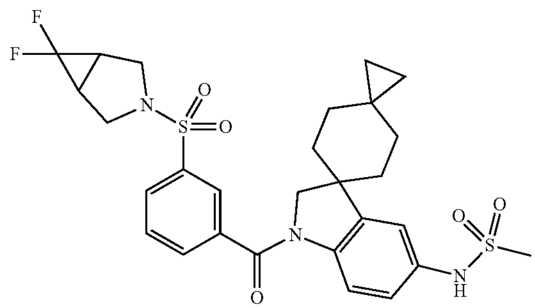 [SMILES: CS(=O)(=O)Nc1ccc2c(c1)C1(CCC3(CC3)CC1)CN2C(=O)c1cccc(S(=O)(=O)N2CC3C(C2)C3(F)F)c1] | N-(1''-(3-((6,6-difluoro-3-azabicyclo[3.1.0]hexan-3-yl)sulfonyl)benzoyl)dispiro[cyclopropane-1,1'-cyclohexane-4',3''-indolin]-5''-yl)methanesulfonamide |
| Compound 238 | 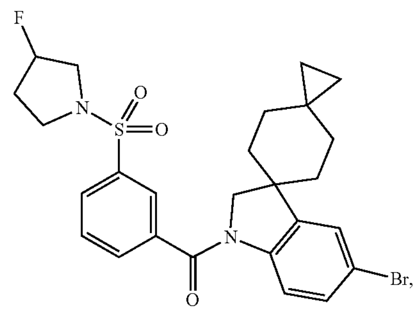 [SMILES: O=C(c1cccc(S(=O)(=O)N2CCC(F)C2)c1)N1CC2(CCC3(CC3)CC2)c2cc(Br)ccc21] | (5''-bromodispiro[cyclopropane-1,1'-cyclohexane-4',3''-indolin]-1''-yl)(3-((3-fluoropyrrolidin-1-yl)sulfonyl)phenyl)methanone |
| (R)-Compound 238 | 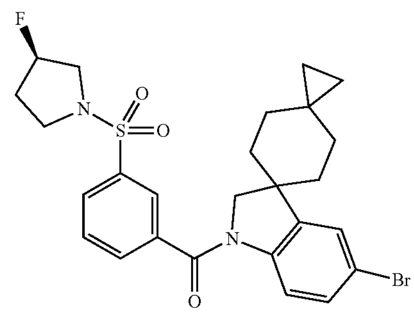 [SMILES: O=C(c1cccc(S(=O)(=O)N2CC[C@@H](F)C2)c1)N1CC2(CCC3(CC3)CC2)c2cc(Br)ccc21] | (R)-(5''-bromodispiro[cyclopropane-1,1'-cyclohexane-4',3''-indolin]-1''-yl)(3-((3-fluoropyrrolidin-1-yl)sulfonyl)phenyl)methanone |
| (S)-Compound 238 | 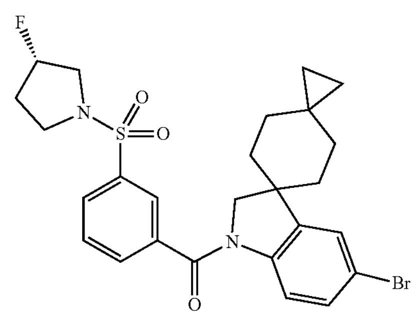 [SMILES: O=C(c1cccc(S(=O)(=O)N2CC[C@H](F)C2)c1)N1CC2(CCC3(CC3)CC2)c2cc(Br)ccc21] | (S)-(5''-bromodispiro[cyclopropane-1,1'-cyclohexane-4',3''-indolin]-1''-yl)(3-((3-fluoropyrrolidin-1-yl)sulfonyl)phenyl)methanone |
| Compound 239 | 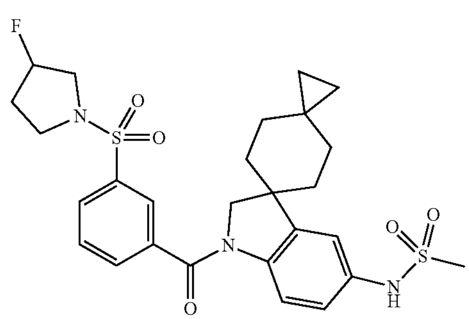 [SMILES: CS(=O)(=O)Nc1ccc2c(c1)C1(CCC3(CC3)CC1)CN2C(=O)c1cccc(S(=O)(=O)N2CCC(F)C2)c1] | N-(1''-(3-((3-fluoropyrrolidin-1-yl)sulfonyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| (R)-Compound 239 | 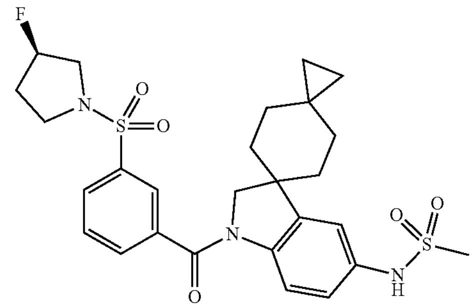 [SMILES: CS(=O)(=O)Nc1ccc2c(c1)C1(CCC3(CC3)CC1)CN2C(=O)c1cccc(S(=O)(=O)N2CC[C@@H](F)C2)c1] | (R)-N-(1"-(3-((3-fluoropyrrolidin-1-yl)sulfonyl)benzoyl)dispiro[cyclopropane-1,1'-cyclohexane-4',3"-indolin]-5"-yl)methanesulfonamide |
| (S)-Compound 240 | 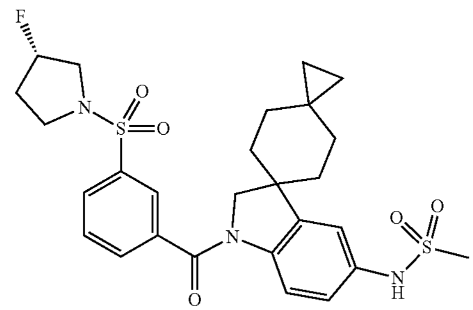 [SMILES: CS(=O)(=O)Nc1ccc2c(c1)C1(CCC3(CC3)CC1)CN2C(=O)c1cccc(S(=O)(=O)N2CC[C@H](F)C2)c1] | (S)-N-(1"-(3-((3-fluoropyrrolidin-1-yl)sulfonyl)benzoyl)dispiro[cyclopropane-1,1'-cyclohexane-4',3"-indolin]-5"-yl)methanesulfonamide |
| Compound 240 | 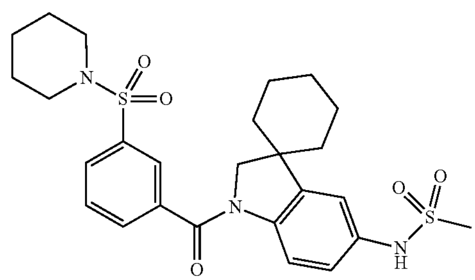 [SMILES: CS(=O)(=O)Nc1ccc2c(c1)C1(CCCCC1)CN2C(=O)c1cccc(S(=O)(=O)N2CCCCC2)c1] | N-(1'-(3-(piperidin-1-ylsulfonyl)benzoyl)spiro[cyclohexane-1,3'-indolin]-5'-yl)methanesulfonamide |
| Compound 241 | 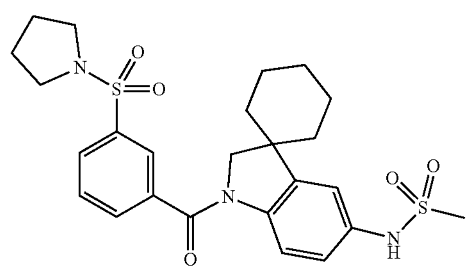 [SMILES: CS(=O)(=O)Nc1ccc2c(c1)C1(CCCCC1)CN2C(=O)c1cccc(S(=O)(=O)N2CCCC2)c1] | N-(1'-(3-(pyrrolidin-1-ylsulfonyl)benzoyl)spiro[cyclohexane-1,3'-indolin]-5'-yl)methanesulfonamide |
| Compound 242 | 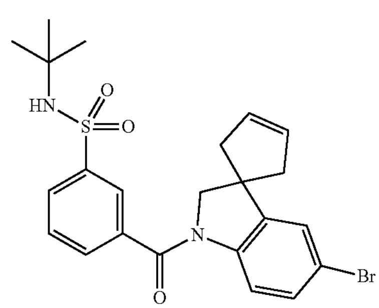 [SMILES: CC(C)(C)NS(=O)(=O)c1cccc(C(=O)N2CC3(CC=CC3)c3cc(Br)ccc32)c1] | 3-(5'-bromospiro[cyclopentane-1,3'-indolin]-3-en-1'-carbonyl)-N-(tert-butyl)benzenesulfonamide |

TABLE 1-continued

| Compound No. | Structure | Name |
|---|---|---|
| Compound 243 | 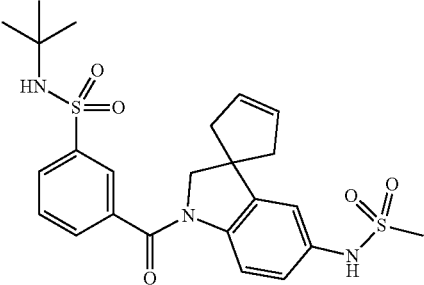 [SMILES: CC(C)(C)NS(=O)(=O)c1cccc(C(=O)N2CC3(CC=CC3)c3cc(NS(C)(=O)=O)ccc32)c1] | N-(tert-butyl)-3-(5'-(methylsulfonamido)spiro[cyclopentane-1,3'-indolin]-3-en-1'-carbonyl)benzenesulfonamide |
| Compound 244 | 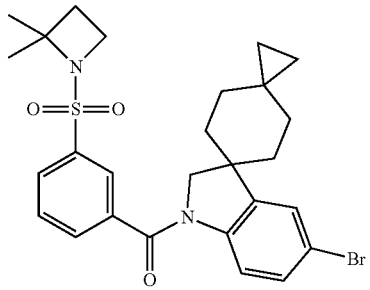 [SMILES: CC1(C)CCN1S(=O)(=O)c1cccc(C(=O)N2CC3(CCC4(CC4)CC3)c3cc(Br)ccc32)c1] | (5''-bromodispiro[cyclopropane-1,1'-cyclohexane-4',3''-indolin]-1''-yl)(3-((2,2-dimethylazetidin-1-yl)sulfonyl)phenyl)methanone |
| Compound 245 | 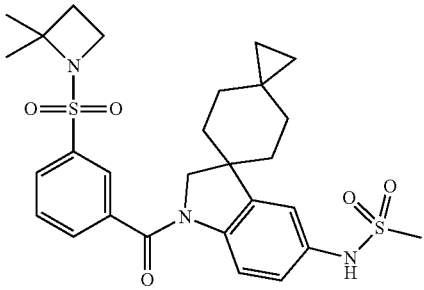 | N-(1''-(3-((2,2-dimethylazetidin-1-yl)sulfonyl)benzoyl)dispiro[cyclopropane-1,1'-cyclohexane-4',3''-indolin]-5''-yl)methanesulfonamide |
| Compound 246 | 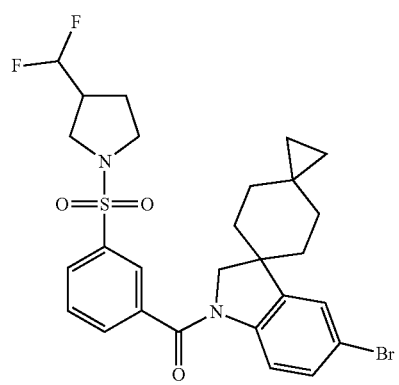 [SMILES: O=C(c1cccc(S(=O)(=O)N2CCC(C(F)F)C2)c1)N1CC2(CCC3(CC3)CC2)c2cc(Br)ccc21] | (5''-bromodispiro[cyclopropane-1,1'-cyclohexane-4',3''-indolin]-1''-yl)(3-((3-(difluoromethyl)pyrrolidin-1-yl)sulfonyl)phenyl)methanone |

TABLE 1-continued

| Compound No. | Structure | Name |
|---|---|---|
| Compound 247 | 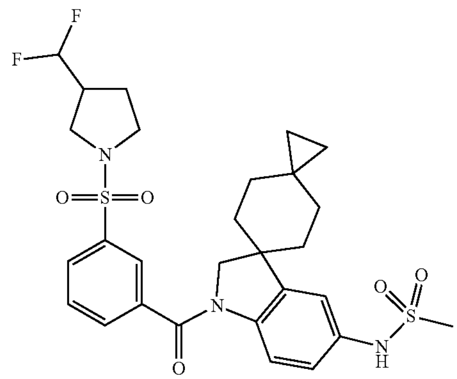 [SMILES: CS(=O)(=O)Nc1ccc2c(c1)C1(CCC3(CC3)CC1)CN2C(=O)c1cccc(S(=O)(=O)N2CCC(C(F)F)C2)c1] | N-(1''-(3-((3-(difluoromethyl)pyrrolidin-1-yl)sulfonyl)benzoyl)dispiro[cyclopropane-1,1'-cyclohexane-4',3''-indolin]-5''-yl)methanesulfonamide |
| Compound 248 | 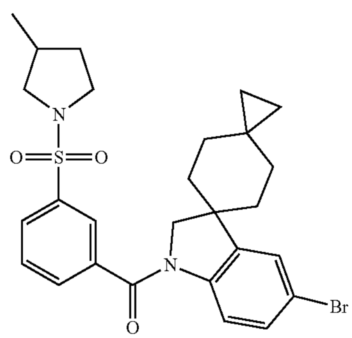 [SMILES: CC1CCN(S(=O)(=O)c2cccc(C(=O)N3CC4(CCC5(CC5)CC4)c4cc(Br)ccc43)c2)C1] | (5''-bromodispiro[cyclopropane-1,1'-cyclohexane-4',3''-indolin]-1''-yl)(3-((3-methylpyrrolidin-1-yl)sulfonyl)phenyl)methanone |
| (S)-Compound 248 | 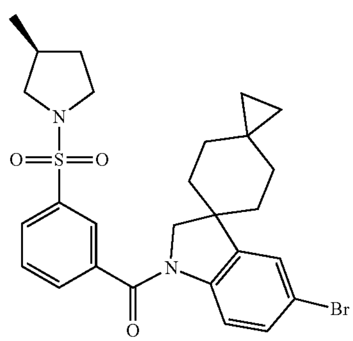 [SMILES: C[C@H]1CCN(S(=O)(=O)c2cccc(C(=O)N3CC4(CCC5(CC5)CC4)c4cc(Br)ccc43)c2)C1] | (S)-(5''-bromodispiro[cyclopropane-1,1'-cyclohexane-4',3''-indolin]-1''-yl)(3-((3-methylpyrrolidin-1-yl)sulfonyl)phenyl)methanone |
| Compound 249 | 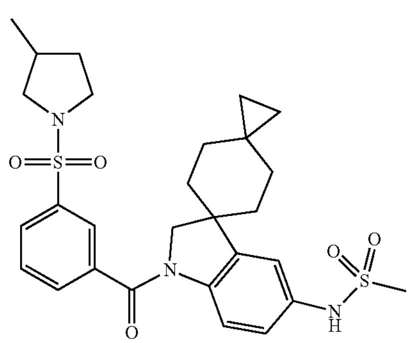 | N-(1''-(3-((3-methylpyrrolidin-1-yl)sulfonyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| (S)-Compound 249 | 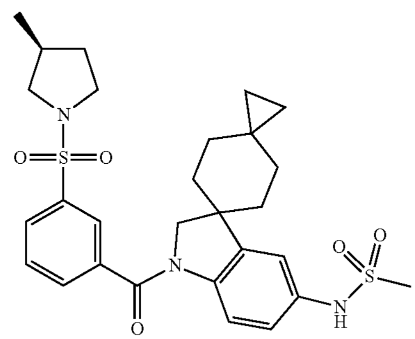 | (S)-N-(1''-(3-((3-methylpyrrolidin-1-yl)sulfonyl)benzoyl)dispiro[cyclopropane-1,1'-cyclohexane-4',3''-indolin]-5''-yl)methanesulfonamide |
| (R)-Compound 249 | 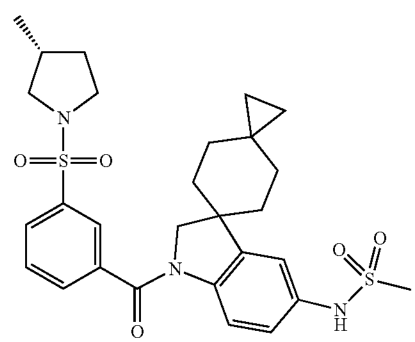 | (R)-N-(1''-(3-((3-methylpyrrolidin-1-yl)sulfonyl)benzoyl)dispiro[cyclopropane-1,1'-cyclohexane-4',3''-indolin]-5''-yl)methanesulfonamide |
| Compound 250 | 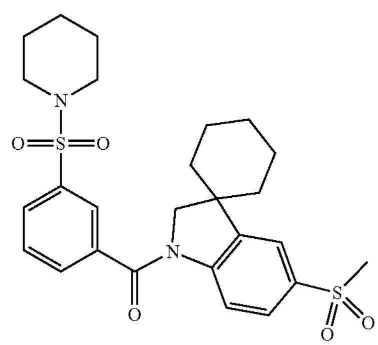 [SMILES: CS(=O)(=O)c1ccc2c(c1)C1(CCCCC1)CN2C(=O)c1cccc(S(=O)(=O)N2CCCCC2)c1] | (5'-(methylsulfonyl)spiro[cyclohexane-1,3'-indolin]-1'-yl)(3-(piperidin-1-ylsulfonyl)phenyl)methanone |
| Compound 251 | 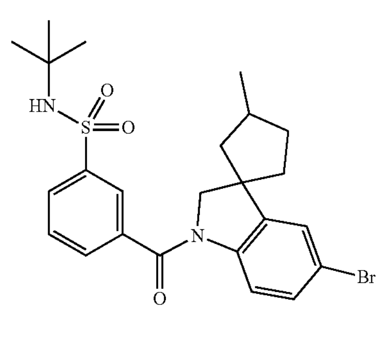 [SMILES: CC1CCC2(C1)CN(C(=O)c1cccc(S(=O)(=O)NC(C)(C)C)c1)c1ccc(Br)cc12] | 3-(5'-bromo-3-methylspiro[cyclopentane-1,3'-indoline]-1'-carbonyl)-N-(tert-butyl)benzenesulfonamide |

TABLE 1-continued

| Compound No. | Structure | Name |
|---|---|---|
| Compound 252 | 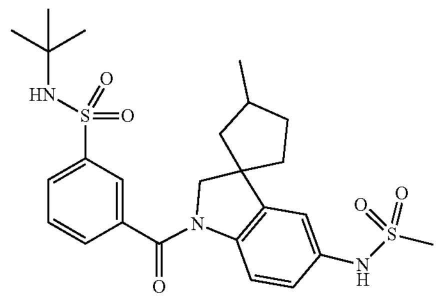 [SMILES: CC1CCC2(C1)CN(C(=O)c1cccc(S(=O)(=O)NC(C)(C)C)c1)c1ccc(NS(C)(=O)=O)cc12] | N-(tert-butyl)-3-(3-methyl-5'-(methylsulfonamido)spiro[cyclopentane-1,3'-indoline]-1'-carbonyl)benzenesulfonamide |
| Compound 253 | 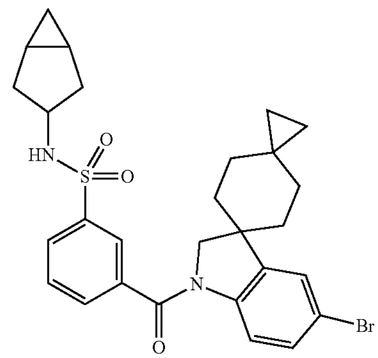 [SMILES: O=C(c1cccc(S(=O)(=O)NC2CC3CC3C2)c1)N1CC2(CCC3(CC3)CC2)c2cc(Br)ccc21] | N-(bicyclo[3.1.0]hexan-3-yl)-3-(5''-bromodispiro[cyclopropane-1,1'-cyclohexane-4',3''-indoline]-1''-carbonyl)benzenesulfonamide |
| Compound 254 | 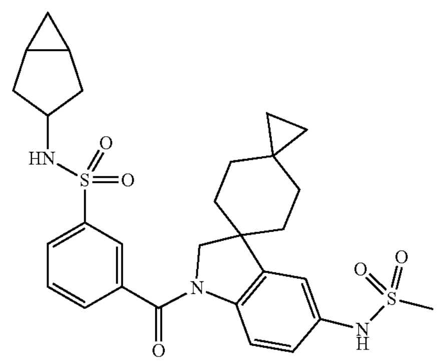 [SMILES: CS(=O)(=O)Nc1ccc2c(c1)C1(CCC3(CC3)CC1)CN2C(=O)c1cccc(S(=O)(=O)NC2CC3CC3C2)c1] | N-(bicyclo[3.1.0]hexan-3-yl)-3-(5''-(methylsulfonamido)dispiro[cyclopropane-1,1'-cyclohexane-4',3''-indoline]-1''-carbonyl)benzenesulfonamide |
| Compound 255 | 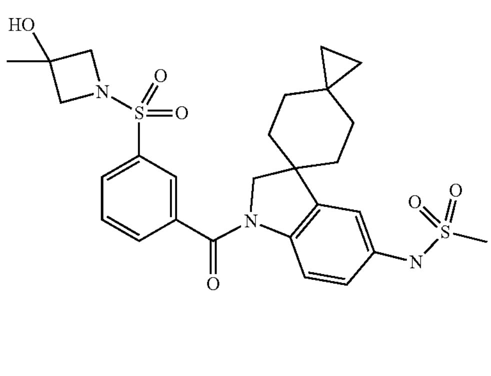 | N-(1''-(3-((3-hydroxy-3-methylazetidin-1-yl)sulfonyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 256 | 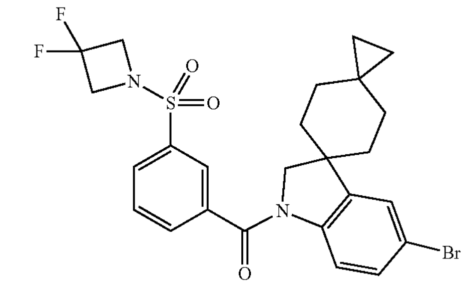 [SMILES: O=C(c1cccc(S(=O)(=O)N2CC(F)(F)C2)c1)N1CC2(CCC3(CC3)CC2)c2cc(Br)ccc21] | (5''-bromodispiro[cyclopropane-1,1'-cyclohexane-4',3''-indolin]-1''-yl)(3-((3,3-difluoroazetidin-1-yl)sulfonyl)phenyl)methanone |
| Compound 257 | 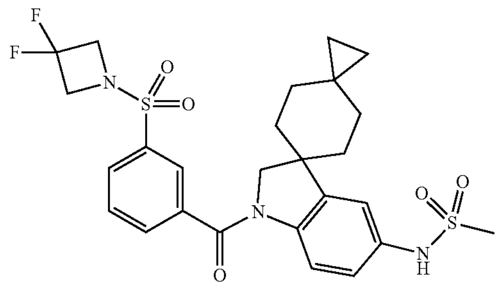 [SMILES: CS(=O)(=O)Nc1ccc2c(c1)C1(CCC3(CC3)CC1)CN2C(=O)c1cccc(S(=O)(=O)N2CC(F)(F)C2)c1] | N-(1''-(3-((3,3-difluoroazetidin-1-yl)sulfonyl)benzoyl)dispiro[cyclopropane-1,1'-cyclohexane-4',3''-indolin]-5''-yl)methanesulfonamide |
| Compound 258 | 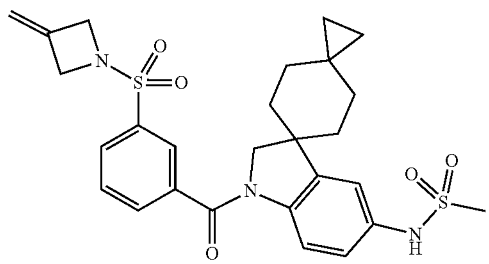 | N-(1''-(3-((3-methylazetidin-1-yl)sulfonyl)benzoyl)dispiro[cyclopropane-1,1'-cyclohexane-4',3''-indolin]-5''-yl)methanesulfonamide |
| Compound 259 | 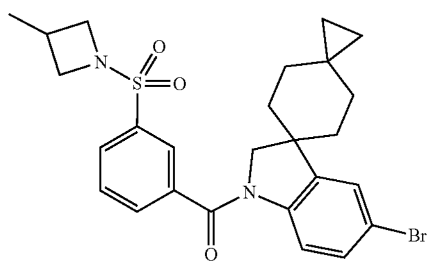 [SMILES: CC1CN(S(=O)(=O)c2cccc(C(=O)N3CC4(CCC5(CC5)CC4)c4cc(Br)ccc43)c2)C1] | (5''-bromospiro[cyclopropane-1,1'-cyclohexane-4',3''-indolin]-1''-yl)(3-((3-methylazetidin-1-yl)sulfonyl)phenyl)methanone |
| Compound 260 | 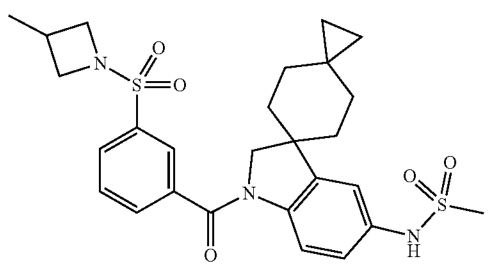 | N-(1''-(3-((3-methylazetidin-1-yl)sulfonyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 261 | 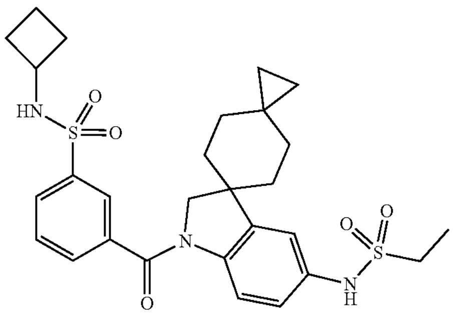 [SMILES: CCS(=O)(=O)Nc1ccc2c(c1)C1(CCC3(CC3)CC1)CN2C(=O)c1cccc(S(=O)(=O)NC2CCC2)c1] | N-cyclobutyl-3-(5''-(ethylsulfonamido)dispiro[cyclopropane-1,1'-cyclohexane-4',3''-indoline]-1''-carbonyl)benzenesulfonamide |
| Compound 262 | 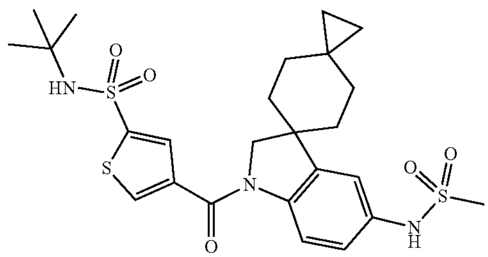 [SMILES: CC(C)(C)NS(=O)(=O)c1cc(C(=O)N2CC3(CCC4(CC4)CC3)c3cc(NS(C)(=O)=O)ccc32)cs1] | N-(tert-butyl)-4-(5''-(methylsulfonamido)dispiro[cyclopropane-1,1'-cyclohexane-4',3''-indoline]-1''-carbonyl)thiophene-2-sulfonamide |
| Compound 263 | 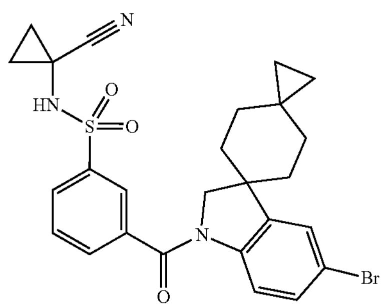 [SMILES: N#CC1(NS(=O)(=O)c2cccc(C(=O)N3CC4(CCC5(CC5)CC4)c4cc(Br)ccc43)c2)CC1] | 3-(5''-bromodispiro[cyclopropane-1,1'-cyclohexane-4',3''-indoline]-1''-carbonyl)-N-(1-cyanocyclopropyl)benzenesulfonamide |
| Compound 264 | 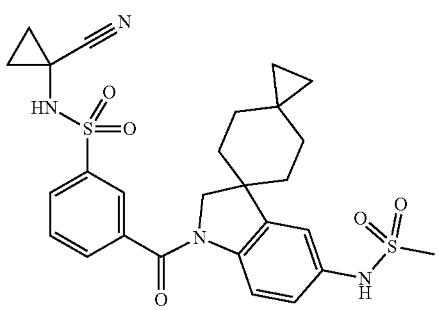 [SMILES: CS(=O)(=O)Nc1ccc2c(c1)C1(CCC3(CC3)CC1)CN2C(=O)c1cccc(S(=O)(=O)NC2(C#N)CC2)c1] | N-(1-cyanocyclopropyl)-3-(5''-(methylsulfonamido)dispiro[cyclopropane-1,1'-cyclohexane-4',3''-indoline]-1''-carbonyl)benzenesulfonamide |
| Compound 265 | 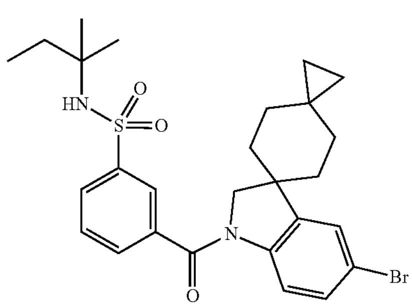 [SMILES: CCC(C)(C)NS(=O)(=O)c1cccc(C(=O)N2CC3(CCC4(CC4)CC3)c3cc(Br)ccc32)c1] | 3-(5''-bromodispiro[cyclopropane-1,1'-cyclohexane-4',3''-indoline]-1''-carbonyl)-N-(tert-pentyl)benzenesulfonamide |

TABLE 1-continued

| Compound No. | Structure | Name |
|---|---|---|
| Compound 266 | 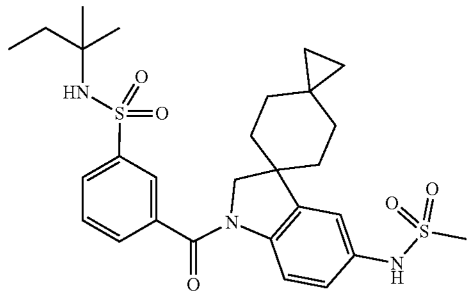 [SMILES: CCC(C)(C)NS(=O)(=O)c1cccc(C(=O)N2CC3(CCC4(CC4)CC3)c3cc(NS(C)(=O)=O)ccc32)c1] | 3-(5''-methylsulfonamido)dispiro[cyclopropane-1,1'-cyclohexane-4',3''-indoline]-1''-carbonyl)-N-(tert-pentyl)benzenesulfonamide |
| Compound 267 | 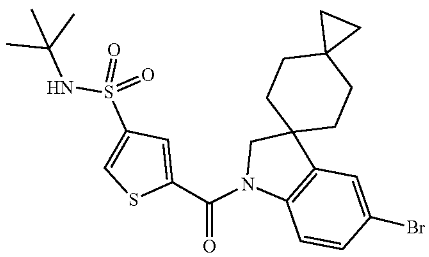 [SMILES: CC(C)(C)NS(=O)(=O)c1csc(C(=O)N2CC3(CCC4(CC4)CC3)c3cc(Br)ccc32)c1] | 5-(5''-bromodispiro[cyclopropane-1,1'-cyclohexane-4',3''-indoline]-1''-carbonyl)-N-(tert-butyl)thiophene-2-sulfonamide |
| Compound 268 | 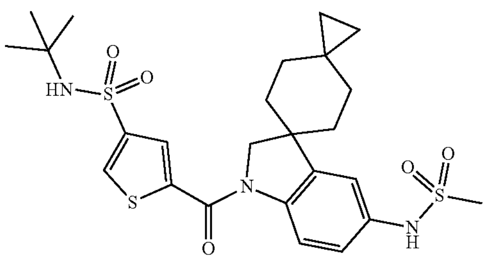 [SMILES: CC(C)(C)NS(=O)(=O)c1csc(C(=O)N2CC3(CCC4(CC4)CC3)c3cc(NS(C)(=O)=O)ccc32)c1] | N-(tert-butyl)-5-(5''-(methylsulfonamido)dispiro[cyclopropane-1,1'-cyclohexane-4',3''-indoline]-1''-carbonyl)thiophene-3-sulfonamide |
| Compound 269 | 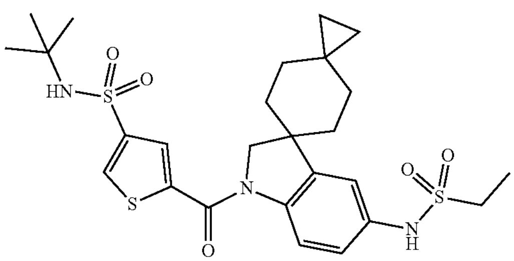 [SMILES: CCS(=O)(=O)Nc1ccc2c(c1)C1(CCC3(CC3)CC1)CN2C(=O)c1cc(S(=O)(=O)NC(C)(C)C)cs1] | N-(tert-butyl)-5-(5''-(ethylsulfonamido)dispiro[cyclopropane-1,1'-cyclohexane-4',3''-indoline]-1''-carbonyl)thiophene-3-sulfonamide |
| Compound 270 | 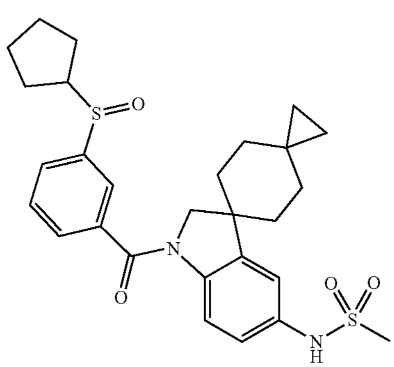 [SMILES: CS(=O)(=O)Nc1ccc2c(c1)C1(CCC3(CC3)CC1)CN2C(=O)c1cccc(S(=O)C2CCCC2)c1] | N-(1''-(3-(cyclopentylsulfinyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 271 | 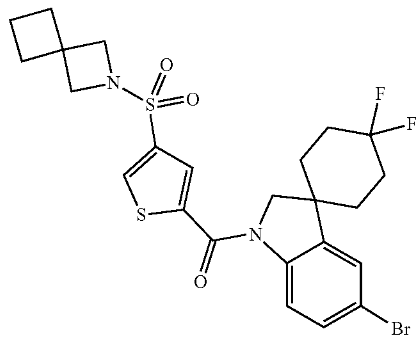 [SMILES: O=C(c1cc(S(=O)(=O)N2CC3(CCC3)C2)cs1)N1CC2(CCC(F)(F)CC2)c2cc(Br)ccc21] | (4-((2-azaspiro[3.3]heptan-2-yl)sulfonyl)thiophen-2-yl)(5'-bromo-4,4-difluorospiro[cyclohexane-1,3'-indolin]-1'-yl)methanone |
| Compound 272 | 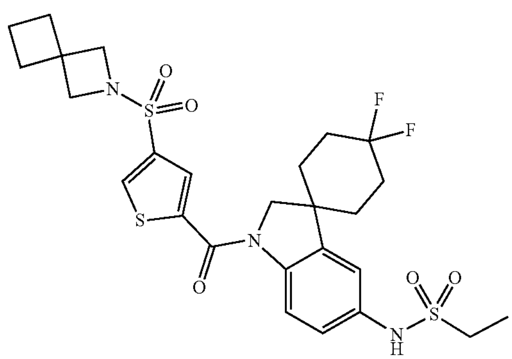 [SMILES: CCS(=O)(=O)Nc1ccc2c(c1)C1(CCC(F)(F)CC1)CN2C(=O)c1cc(S(=O)(=O)N2CC3(CCC3)C2)cs1] | N-(1'-(4-((2-azaspiro[3.3]heptan-2-yl)sulfonyl)thiophene-2-carbonyl)-4,4-difluorospiro[cyclohexane-1,3'-indolin]-5'-yl)ethanesulfonamide |
| Compound 273 | 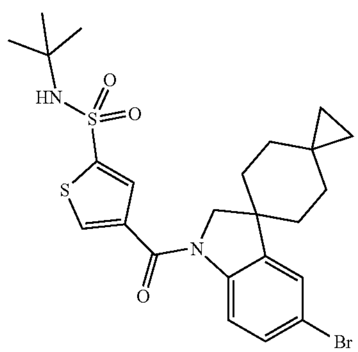 [SMILES: CC(C)(C)NS(=O)(=O)c1cc(C(=O)N2CC3(CCC4(CC4)CC3)c3cc(Br)ccc32)cs1] | 4-(5''-bromodispiro[cyclopropane-1,1'-cyclohexane-4',3''-indoline]-1''-carbonyl)-N-(tert-butyl)thiophene-2-sulfonamide |
| Compound 274 | 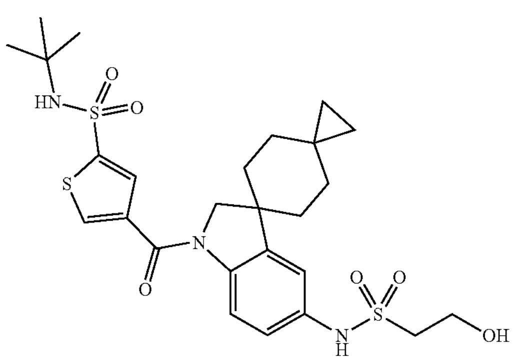 [SMILES: CC(C)(C)NS(=O)(=O)c1cc(C(=O)N2CC3(CCC4(CC4)CC3)c3cc(NS(=O)(=O)CCO)ccc32)cs1] | N-(tert-butyl)-4-(5''-((2-hydroxyethyl)sulfonamido)dispiro[cyclopropane-1,1'-cyclohexane-4',3''-indoline]-1''-carbonyl)thiophene-2-sulfonamide |

TABLE 1-continued

| Compound No. | Structure | Name |
|---|---|---|
| Compound 275 | 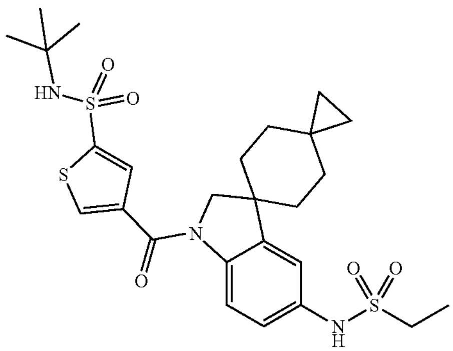 [SMILES: CCS(=O)(=O)Nc1ccc2c(c1)C1(CCC3(CC3)CC1)CN2C(=O)c1csc(S(=O)(=O)NC(C)(C)C)c1] | N-(tert-butyl)-4-(5''-(ethylsulfonamido)dispiro[cyclopropane-1,1'-cyclohexane-4',3''-indoline]-1''-carbonyl)thiophene-2-sulfonamide |
| Compound 276 | 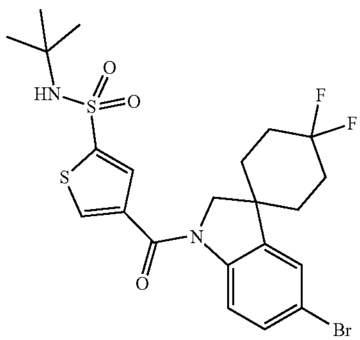 [SMILES: CC(C)(C)NS(=O)(=O)c1cc(C(=O)N2CC3(CCC(F)(F)CC3)c3cc(Br)ccc32)cs1] | 4-(5'-bromo-4,4-difluorospiro[cyclohexane-1,3'-indoline]-1'-carbonyl)-N-(tert-butyl)thiophene-2-sulfonamide |
| Compound 277 | 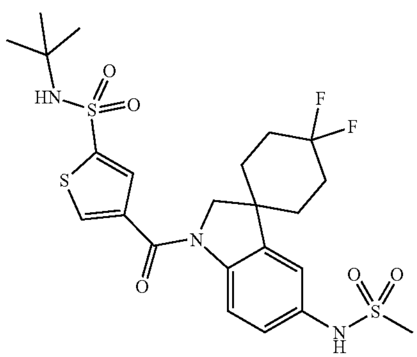 [SMILES: CC(C)(C)NS(=O)(=O)c1cc(C(=O)N2CC3(CCC(F)(F)CC3)c3cc(NS(C)(=O)=O)ccc32)cs1] | N-(tert-butyl)-4-(4,4-difluoro-5'-(methylsulfonamido)spiro[cyclohexane-1,3'-indoline]-1'-carbonyl)thiophene-2-sulfonamide |
| Compound 278 | 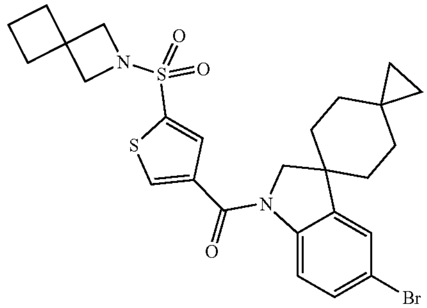 [SMILES: O=C(c1csc(S(=O)(=O)N2CC3(CCC3)C2)c1)N1CC2(CCC3(CC3)CC2)c2cc(Br)ccc21] | (5-((2-azaspiro[3.3]heptan-2-yl)sulfonyl)thiophen-3-yl)(5''-bromodispiro[cyclopropane-1,1'-cyclohexane-4',3''-indolin]-1''-yl)methanone |

TABLE 1-continued

| Compound No. | Structure | Name |
|---|---|---|
| Compound 279 | 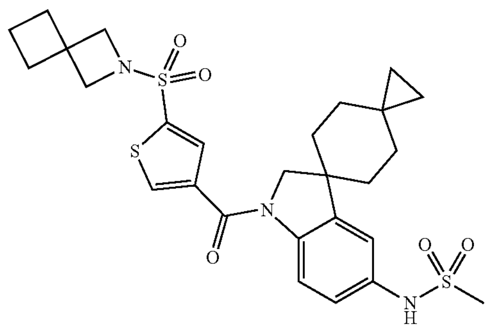 [SMILES: CS(=O)(=O)Nc1ccc2c(c1)C1(CCC3(CC3)CC1)CN2C(=O)c1csc(S(=O)(=O)N2CC3(CCC3)C2)c1] | N-(1''-(5-((2-azaspiro[3.3]heptan-2-yl)sulfonyl)thiophene-3-carbonyl)dispiro[cyclopropane-1,1'-cyclohexane-4',3''-indolin]-5''-yl)methanesulfonamide |
| Compound 280 | 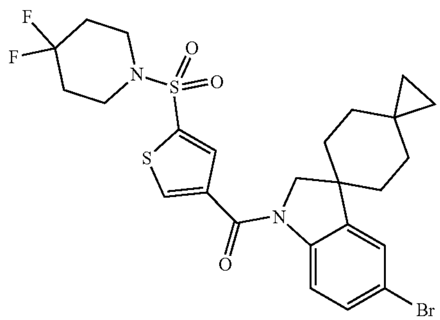 [SMILES: O=C(c1csc(S(=O)(=O)N2CCC(F)(F)CC2)c1)N1CC2(CCC3(CC3)CC2)c2cc(Br)ccc21] | (5''-bromodispiro[cyclopropane-1,1'-cyclohexane-4',3''-indolin]-1''-yl)(5-((4,4-difluoropiperidin-1-yl)sulfonyl)thiophen-3-yl)methanone |
| Compound 281 | 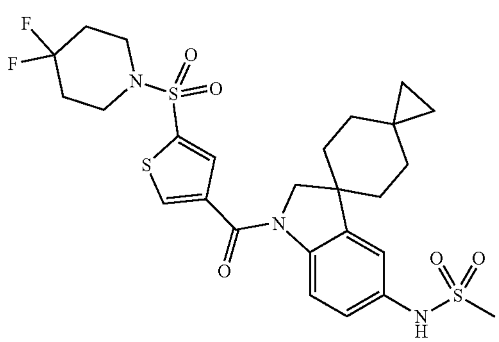 [SMILES: CS(=O)(=O)Nc1ccc2c(c1)C1(CCC3(CC3)CC1)CN2C(=O)c1csc(S(=O)(=O)N2CCC(F)(F)CC2)c1] | N-(1''-(5-((4,4-difluoropiperidin-1-yl)sulfonyl)thiophene-3-carbonyl)dispiro[cyclopropane-1,1'-cyclohexane-4',3''-indolin]-5''-yl)methanesulfonamide |
| Compound 282 | 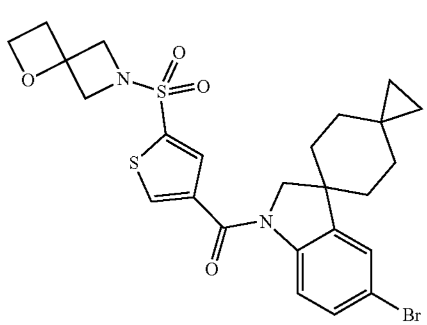 [SMILES: O=C(c1csc(S(=O)(=O)N2CC3(CCO3)C2)c1)N1CC2(CCC3(CC3)CC2)c2cc(Br)ccc21] | (5-((1-oxa-6-azaspiro[3.3]heptan-6-yl)sulfonyl)thiophen-3-yl)(5''-bromodispiro[cyclopropane-1,1'-cyclohexane-4',3''-indolin]-1''-yl)methanone |

| Compound No. | Structure | Name |
|---|---|---|
| Compound 283 | 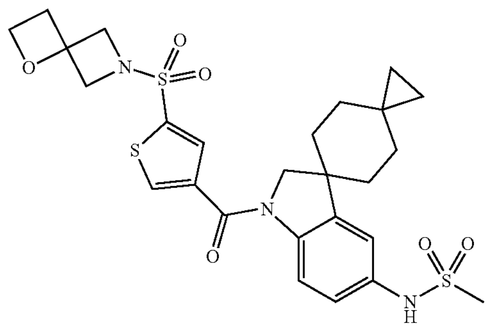 | N-(1''-(5-(((1-oxa-6-azaspiro[3.3]heptan-6-yl)sulfonyl)thiophene-3-carbonyl)dispiro[cyclopropane-1,1'-cyclohexane-4',3''-indolin]-5''-yl)methanesulfonamide |
| Compound 284 | 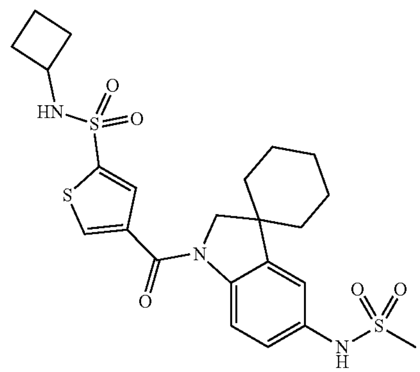 [SMILES: CS(=O)(=O)Nc1ccc2c(c1)C1(CCCCC1)CN2C(=O)c1csc(S(=O)(=O)NC2CCC2)c1] | N-cyclobutyl-4-(5'-(methylsulfonamido)spiro[cyclohexane-1,3'-indoline]-1'-carbonyl)thiophene-2-sulfonamide |
| Compound 285 | 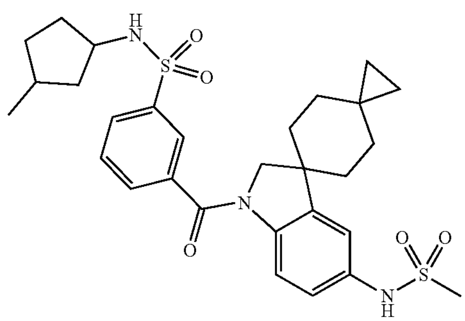 | N-(3-methylcyclopentyl)-3-(5''-(methylsulfonamido)dispiro[cyclopropane-1,1'-cyclohexane-4',3''-indole]-1''-carbonyl)benzenesulfonamide |
| Compound 286 | 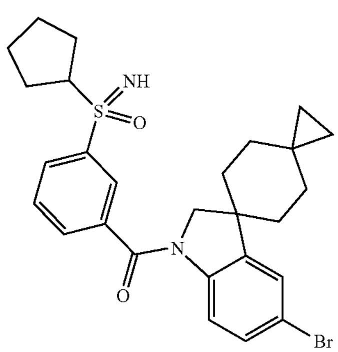 [SMILES: N=S(=O)(c1cccc(C(=O)N2CC3(CCC4(CC4)CC3)c3cc(Br)ccc32)c1)C1CCCC1] | (3-(5''-bromodispiro[cyclopropane-1,1'-cyclohexane-4',3''-indoline]-1''-carbonyl)phenyl)(cyclopentyl)(imino)-l6-sulfanone |

TABLE 1-continued

| Compound No. | Structure | Name |
|---|---|---|
| Compound 287 | 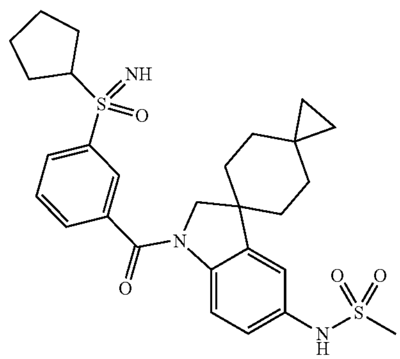 [SMILES: CS(=O)(=O)Nc1ccc2c(c1)C1(CCC3(CC3)CC1)CN2C(=O)c1cccc(S(=N)(=O)C2CCCC2)c1] | N-(1''-(3-(cyclopentanesulfonimidoyl)benzoyl)dispiro[cyclopropane-1,1'-cyclohexane-4',3''-indolin]-5''-yl)methanesulfonamide |
| (R)-Compound 287 | 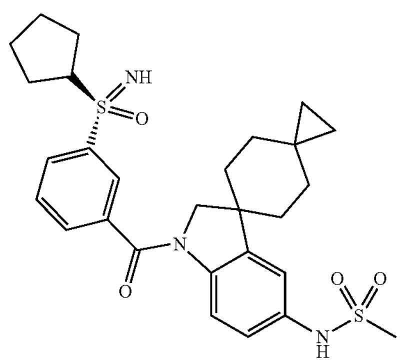 [SMILES: CS(=O)(=O)Nc1ccc2c(c1)C1(CCC3(CC3)CC1)CN2C(=O)c1cccc([S@](=N)(=O)C2CCCC2)c1] | (R)-N-(1''-(3-(cyclopentanesulfonimidoyl)benzoyl)dispiro[cyclopropane-1,1'-cyclohexane-4',3''-indolin]-5''-yl)methanesulfonamide |
| (S)-Compound 287 | 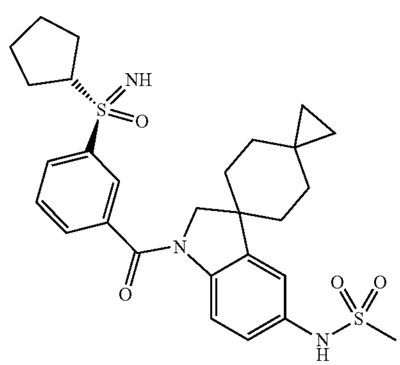 [SMILES: CS(=O)(=O)Nc1ccc2c(c1)C1(CCC3(CC3)CC1)CN2C(=O)c1cccc([S@@](=N)(=O)C2CCCC2)c1] | (S)-N-(1''-(3-(cyclopentanesulfonimidoyl)benzoyl)dispiro[cyclopropane-1,1'-cyclohexane-4',3''-indolin]-5''-yl)methanesulfonamide |
| Compound 288 | 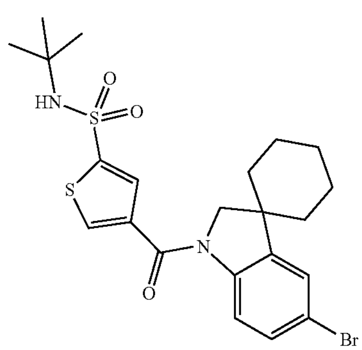 [SMILES: CC(C)(C)NS(=O)(=O)c1cc(C(=O)N2CC3(CCCCC3)c3cc(Br)ccc32)cs1] | 4-(5'-bromospiro[cyclohexane-1,3'-indoline]-1'-carbonyl)-N-(tert-butyl)thiophene-2-sulfonamide |

TABLE 1-continued

| Compound No. | Structure | Name |
|---|---|---|
| Compound 289 | 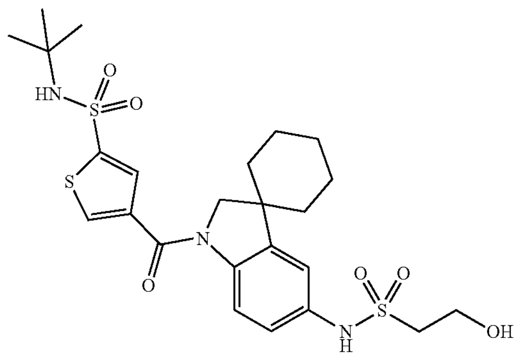 [SMILES: CC(C)(C)NS(=O)(=O)c1cc(C(=O)N2CC3(CCCCC3)c3cc(NS(=O)(=O)CCO)ccc32)cs1] | N-(tert-butyl)-4-(5'-((2-hydroxyethyl)sulfonamido)spiro[cyclohexane-1,3'-indoline]-1'-carbonyl)thiophene-2-sulfonamide |
| Compound 290 | 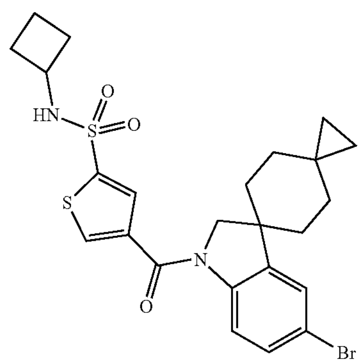 [SMILES: O=C(c1csc(S(=O)(=O)NC2CCC2)c1)N1CC2(CCC3(CC3)CC2)c2cc(Br)ccc21] | 4-(5''-bromodispiro[cyclopropane-1,1'-cyclohexane-4',3''-indoline]-1''-carbonyl)-N-cyclobutylthiophene-2-sulfonamide |
| Compound 291 | 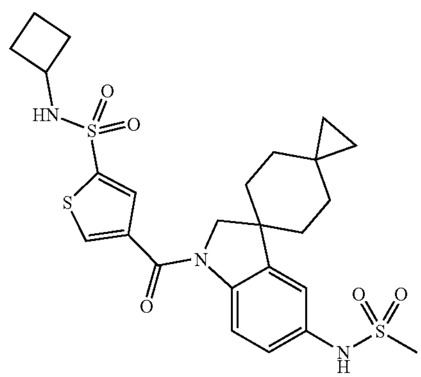 [SMILES: CS(=O)(=O)Nc1ccc2c(c1)C1(CCC3(CC3)CC1)CN2C(=O)c1csc(S(=O)(=O)NC2CCC2)c1] | N-cyclobutyl-4-(5''-(methylsulfonamido)dispiro[cyclopropane-1,1'-cyclohexane-4',3''-indoline]-1''-carbonyl)thiophene-2-sulfonamide |
| Compound 292 | 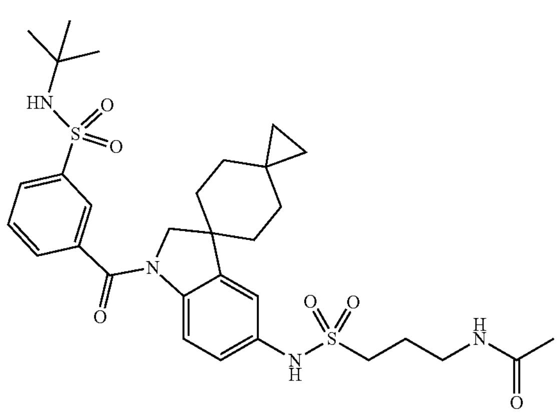 [SMILES: CC(=O)NCCCS(=O)(=O)Nc1ccc2c(c1)C1(CCC3(CC3)CC1)CN2C(=O)c1cccc(S(=O)(=O)NC(C)(C)C)c1] | N-(3-(N-(1''-(3-(N-(tert-butyl)sulfamoyl)benzoyl)dispiro[cyclopropane-1,1'-cyclohexane-4',3''-indolin]-5''-yl)sulfamoyl)propyl)acetamide |

TABLE 1-continued

| Compound No. | Structure | Name |
|---|---|---|
| Compound 293 | 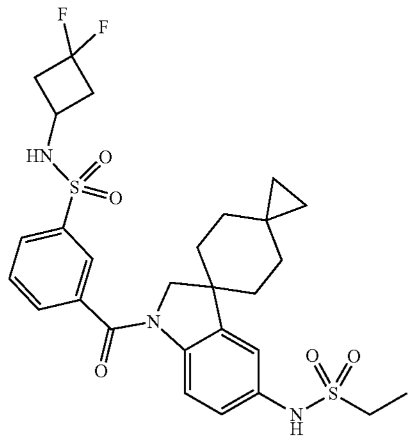 [SMILES: CCS(=O)(=O)Nc1ccc2c(c1)C1(CCC3(CC3)CC1)CN2C(=O)c1cccc(S(=O)(=O)NC2CC(F)(F)C2)c1] | N-(3,3-difluorocyclobutyl)-3-(5''-(ethylsulfonamido)dispiro[cyclopropane-1,1'-cyclohexane-4',3''-indoline]-1''-carbonyl)benzenesulfonamide |
| Compound 294 | 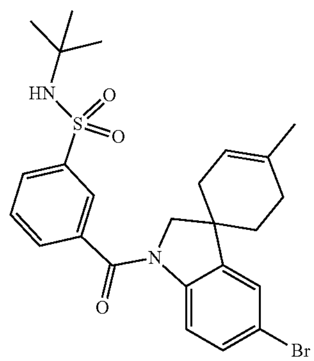 [SMILES: CC1=CCC2(CC1)CN(C(=O)c1cccc(S(=O)(=O)NC(C)(C)C)c1)c1ccc(Br)cc12] | 3-(5'-bromo-4-methylspiro[cyclohexane-1,3'-indolin]-3-en-1'-carbonyl)-N-(tert-butyl)benzenesulfonamide |
| Compound 295 | 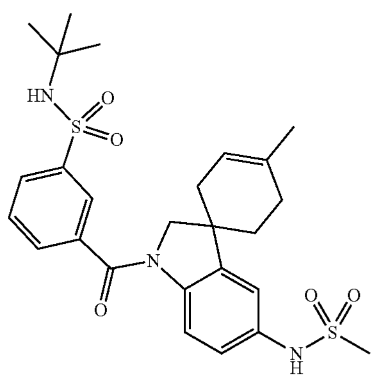 [SMILES: CC1=CCC2(CC1)CN(C(=O)c1cccc(S(=O)(=O)NC(C)(C)C)c1)c1ccc(NS(C)(=O)=O)cc12] | N-(tert-butyl)-3-(4-methyl-5'-(methylsulfonamido)spiro[cyclohexane-1,3'-indolin]-3-en-1'-carbonyl)benzenesulfonamide |
| Compound 296 | 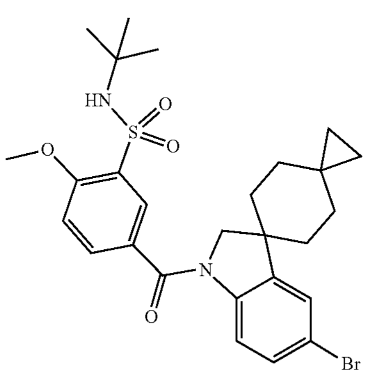 [SMILES: COc1ccc(C(=O)N2CC3(CCC4(CC4)CC3)c3cc(Br)ccc32)cc1S(=O)(=O)NC(C)(C)C] | 5-(5''-bromodispiro[cyclopropane-1,1'-cyclohexane-4',3''-indoline]-1''-carbonyl)-N-(tert-butyl)-2-methoxybenzenesulfonamide |

TABLE 1-continued

| Compound No. | Structure | Name |
|---|---|---|
| Compound 297 | 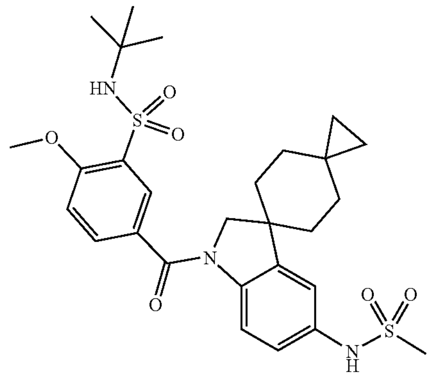 | N-(tert-butyl)-2-methoxy-5-(5"-(methylsulfonamido)dispiro[cyclopropane-1,1'-cyclohexane-4',3"-indoline]-1"-carbonyl)benzenesulfonamide |
| Compound 298 | 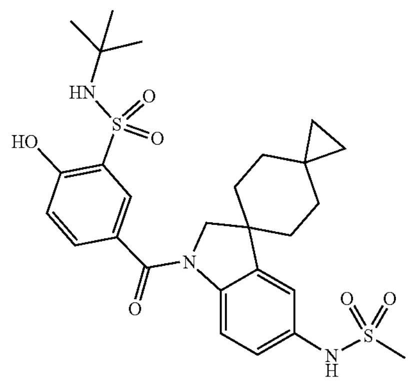 [SMILES: CC(C)(C)NS(=O)(=O)c1cc(C(=O)N2CC3(CCC4(CC4)CC3)c3cc(NS(C)(=O)=O)ccc32)ccc1O] | N-(tert-butyl)-2-hydroxy-5-(5"-(methylsulfonamido)dispiro[cyclopropane-1,1'-cyclohexane-4',3"-indoline]-1"-carbonyl)benzenesulfonamide |
| Compound 299 | 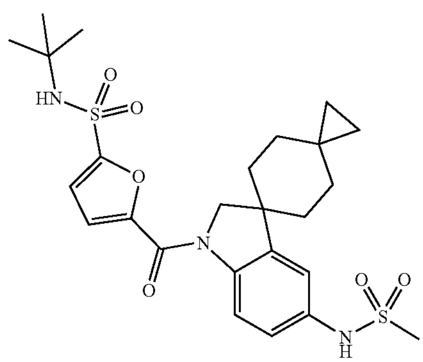 [SMILES: CC(C)(C)NS(=O)(=O)c1ccc(C(=O)N2CC3(CCC4(CC4)CC3)c3cc(NS(C)(=O)=O)ccc32)o1] | N-(tert-butyl)-5-(5"-(methylsulfonamido)dispiro[cyclopropane-1,1'-cyclohexane-4',3"-indoline]-1"-carbonyl)furan-2-sulfonamide |
| Compound 300 | 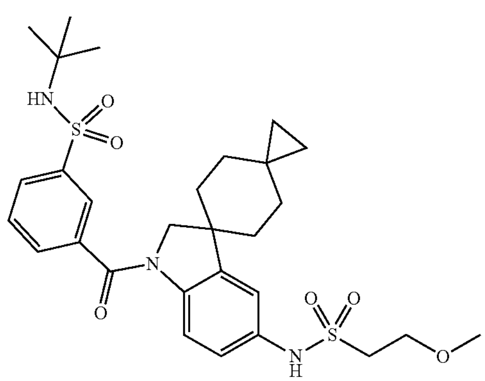 [SMILES: COCCS(=O)(=O)Nc1ccc2c(c1)C1(CCC3(CC3)CC1)CN2C(=O)c1cccc(S(=O)(=O)NC(C)(C)C)c1] | N-(tert-butyl)-3-(5"-((2-methoxyethyl)sulfonamido)dispiro[cyclopropane-1,1'-cyclohexane-4',3"-indoline]-1"-carbonyl)benzenesulfonamide |

TABLE 1-continued

| Compound No. | Structure | Name |
|---|---|---|
| Compound 301 | 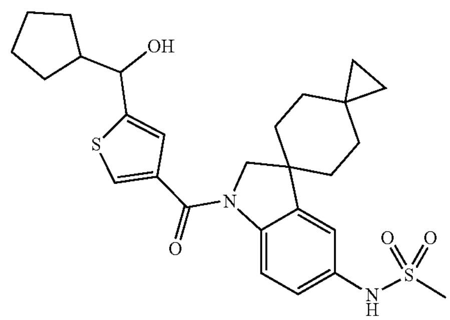 [SMILES: CS(=O)(=O)Nc1ccc2c(c1)C1(CCC3(CC3)CC1)CN2C(=O)c1csc(C(O)C2CCCC2)c1] | N-(1''-(5-(cyclopentyl(hydroxy)methyl)thiophene-3-carbonyl)dispiro[cyclopropane-1,1'-cyclohexane-4',3''-indolin]-5''-yl)methanesulfonamide |
| Compound 302 | 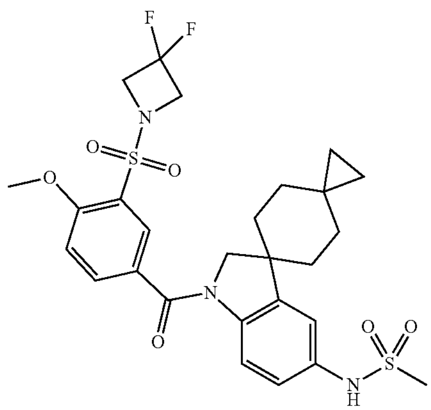 | N-(1''-(3-((3,3-difluoroazetidin-1-yl)sulfonyl)-4-methoxybenzoyl)dispiro[cyclopropane-1,1'-cyclohexane-4',3''-indolin]-5''-yl)methanesulfonamide |
| Compound 303 | 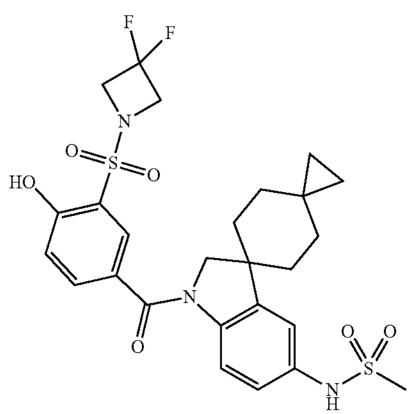 [SMILES: CS(=O)(=O)Nc1ccc2c(c1)C1(CCC3(CC3)CC1)CN2C(=O)c1ccc(O)c(S(=O)(=O)N2CC(F)(F)C2)c1] | N-(1''-(3-((3,3-difluoroazetidin-1-yl)sulfonyl)-4-hydroxybenzoyl)dispiro[cyclopropane-1,1'-cyclohexane-4'',3''-indolin]-5''-yl)methanesulfonamide |
| Compound 304 | 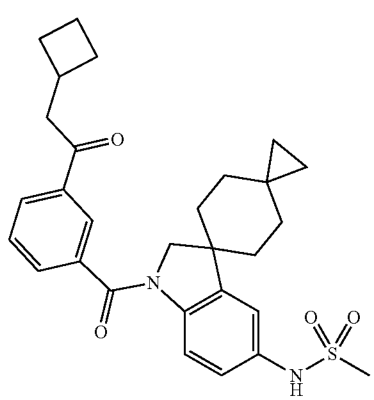 [SMILES: CS(=O)(=O)Nc1ccc2c(c1)C1(CCC3(CC3)CC1)CN2C(=O)c1cccc(C(=O)CC2CCC2)c1] | N-(1''-(3-(2-cyclobutylacetyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 305 | 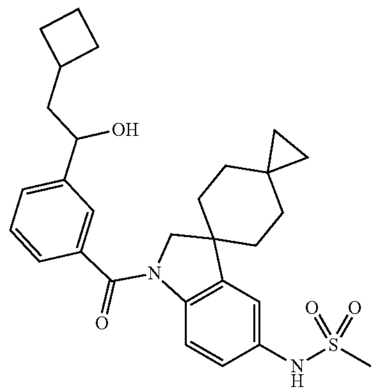 [SMILES: CS(=O)(=O)Nc1ccc2c(c1)C1(CCC3(CC3)CC1)CN2C(=O)c1cccc(C(O)CC2CCC2)c1] | N-(1''-(3-(2-cyclobutyl-1-hydroxyethyl)benzoyl)dispiro[cyclopropane-1,1'-cyclohexane-4',3''-indolin]-5''-yl)methanesulfonamide |
| (R)-Compound 305 | 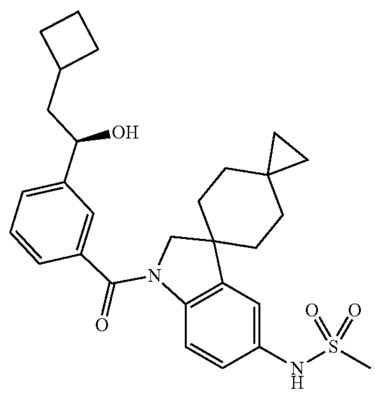 [SMILES: CS(=O)(=O)Nc1ccc2c(c1)C1(CCC3(CC3)CC1)CN2C(=O)c1cccc([C@H](O)CC2CCC2)c1] | (R)-N-(1''-(3-(2-cyclobutyl-1-hydroxyethyl)benzoyl)dispiro[cyclopropane-1,1'-cyclohexane-4',3''-indolin]-5''-yl)methanesulfonamide |
| (S)-Compound 305 | 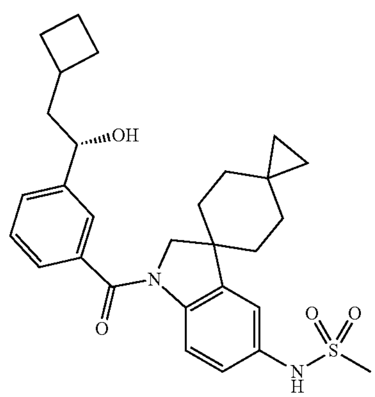 [SMILES: CS(=O)(=O)Nc1ccc2c(c1)C1(CCC3(CC3)CC1)CN2C(=O)c1cccc([C@@H](O)CC2CCC2)c1] | (S)-N-(1''-(3-(2-cyclobutyl-1-hydroxyethyl)benzoyl)dispiro[cyclopropane-1,1'-cyclohexane-4',3''-indolin]-5''-yl)methanesulfonamide |
| Compound 306 | 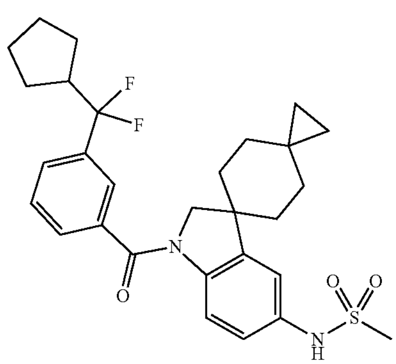 [SMILES: CS(=O)(=O)Nc1ccc2c(c1)C1(CCC3(CC3)CC1)CN2C(=O)c1cccc(C(F)(F)C2CCCC2)c1] | N-(1''-(3-(cyclopentyldifluoromethyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 307 | 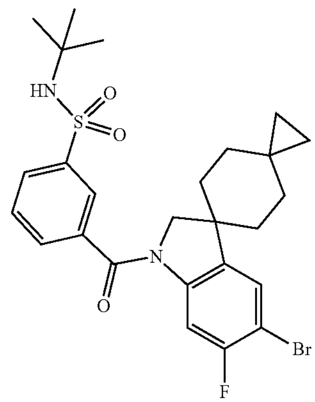 [SMILES: CC(C)(C)NS(=O)(=O)c1cccc(C(=O)N2CC3(CCC4(CC4)CC3)c3cc(Br)c(F)cc32)c1] | 3-(5''-bromo-6''-fluorodispiro[cyclopropane-1,1'-cyclohexane-4',3''-indoline]-1''-carbonyl)-N-(tert-butyl)benzenesulfonamide |
| Compound 308 | 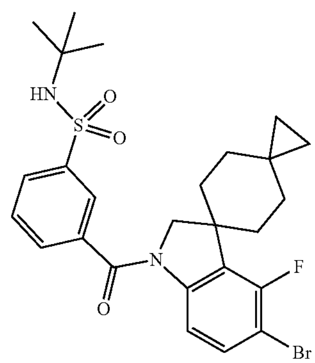 [SMILES: CC(C)(C)NS(=O)(=O)c1cccc(C(=O)N2CC3(CCC4(CC4)CC3)c3c2ccc(Br)c3F)c1] | 3-(5''-bromo-4''-fluorodispiro[cyclopropane-1,1'-cyclohexane-4',3''-indoline]-1''-carbonyl)-N-(tert-butyl)benzenesulfonamide |
| Compound 309 | 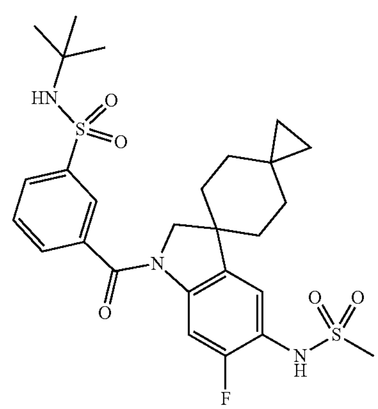 [SMILES: CC(C)(C)NS(=O)(=O)c1cccc(C(=O)N2CC3(CCC4(CC4)CC3)c3cc(NS(C)(=O)=O)c(F)cc32)c1] | N-(tert-butyl)-3-(6''-fluoro-5''-(methylsulfonamido)dispiro[cyclopropane-1,1'-cyclohexane-4',3''-indoline]-1''-carbonyl)benzenesulfonamide |
| Compound 310 | 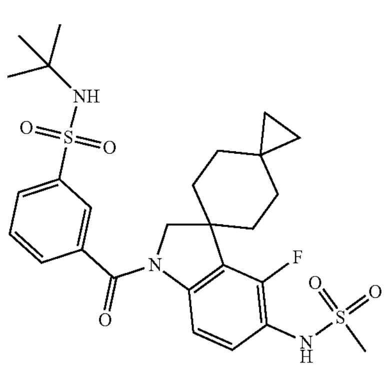 [SMILES: CC(C)(C)NS(=O)(=O)c1cccc(C(=O)N2CC3(CCC4(CC4)CC3)c3c2ccc(NS(C)(=O)=O)c3F)c1] | N-(tert-butyl)-3-(4''-fluoro-5''-(methylsulfonamido)dispiro[cyclopropane-1,1'-cyclohexane-4',3''-indoline]-1''-carbonyl)benzenesulfonamide |

TABLE 1-continued

| Compound No. | Structure | Name |
|---|---|---|
| Compound 311 | 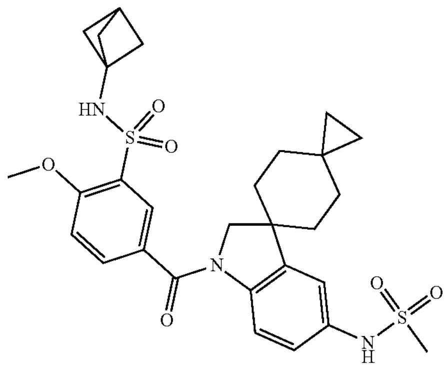 [SMILES: COc1ccc(C(=O)N2CC3(CCC4(CC4)CC3)c3cc(NS(C)(=O)=O)ccc32)cc1S(=O)(=O)NC12CC(C1)C2] | N-(bicyclo[1.1.1]pentan-1-yl)-2-methoxy-5-(5''-(methylsulfonamido)dispiro[cyclopropane-1,1'-cyclohexane-4',3''-indoline]-1''-carbonyl)benzenesulfonamide |
| Compound 312 | 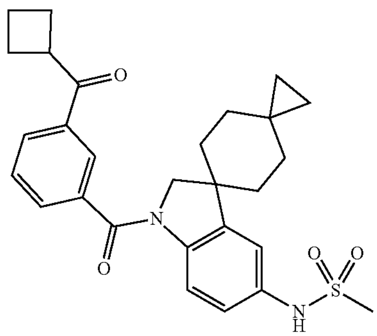 [SMILES: CS(=O)(=O)Nc1ccc2c(c1)C1(CCC3(CC3)CC1)CN2C(=O)c1cccc(C(=O)C2CCC2)c1] | N-(1''-(3-(cyclobutanecarbonyl)benzoyl)dispiro[cyclopropane-1,1'-cyclohexane-4',3''-indolin]-5''-yl)methanesulfonamide |
| Compound 313 | 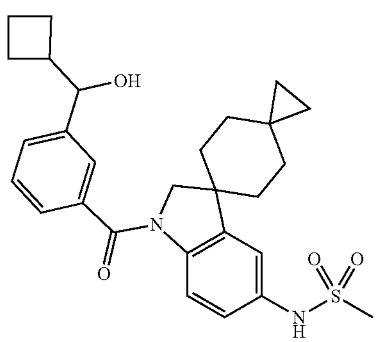 [SMILES: CS(=O)(=O)Nc1ccc2c(c1)C1(CCC3(CC3)CC1)CN2C(=O)c1cccc(C(O)C2CCC2)c1] | N-(1''-(3-(cyclobutyl(hydroxy)methyl)benzoyl)dispiro[cyclopropane-1,1'-cyclohexane-4',3''-indolin]-5''-yl)methanesulfonamide |
| (R)-Compound 313 | 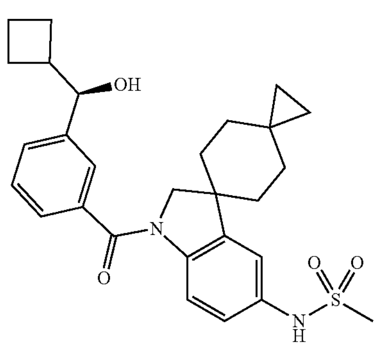 [SMILES: CS(=O)(=O)Nc1ccc2c(c1)C1(CCC3(CC3)CC1)CN2C(=O)c1cccc([C@H](O)C2CCC2)c1] | (R)-N-(1''-(3-(cyclobutyl(hydroxy)methyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| (S)-Compound 313 | 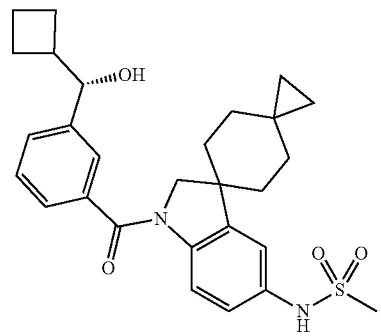 [SMILES: CS(=O)(=O)Nc1ccc2c(c1)C1(CCC3(CC3)CC1)CN2C(=O)c1cccc([C@@H](O)C2CCC2)c1] | (S)-N-(1''-(3-(cyclobutyl(hydroxy)methyl)benzoyl)dispiro[cyclopropane-1,1'-cyclohexane-4',3''-indolin]-5''-yl)methanesulfonamide |
| Compound 314 | 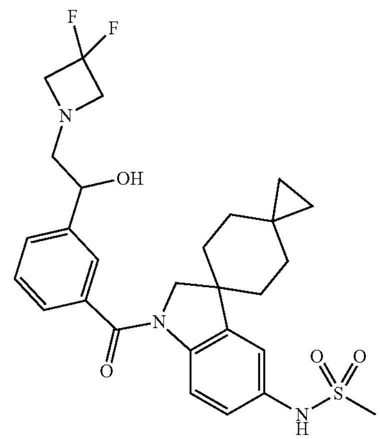 [SMILES: CS(=O)(=O)Nc1ccc2c(c1)C1(CCC3(CC3)CC1)CN2C(=O)c1cccc(C(O)CN2CC(F)(F)C2)c1] | N-(1''-(3-(2-(3,3-difluoroazetidin-1-yl)-1-hydroxyethyl)benzoyl)dispiro[cyclopropane-1,1'-cyclohexane-4',3''-indolin]-5''-yl)methanesulfonamide |
| Compound 315 | 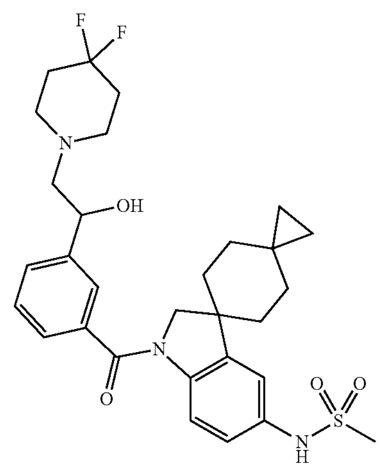 [SMILES: CS(=O)(=O)Nc1ccc2c(c1)C1(CCC3(CC3)CC1)CN2C(=O)c1cccc(C(O)CN2CCC(F)(F)CC2)c1] | N-(1''-(3-(2-(4,4-difluoropiperidin-1-yl)-1-hydroxyethyl)benzoyl)dispiro[cyclopropane-1,1'-cyclohexane-4',3''-indolin]-5''-yl)methanesulfonamide |
| Compound 316 | 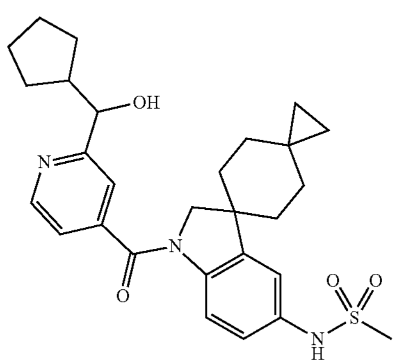 [SMILES: CS(=O)(=O)Nc1ccc2c(c1)C1(CCC3(CC3)CC1)CN2C(=O)c1ccnc(C(O)C2CCCC2)c1] | N-(1''-(2-(cyclopentyl(hydroxy)methyl)isonicotinoyl)dispiro[cyclopropane-1,1'-cyclohexane-4',3''-indolin]-5''-yl)methanesulfonamide |

TABLE 1-continued

| Compound No. | Structure | Name |
| --- | --- | --- |
| (R)-Compound 316 | 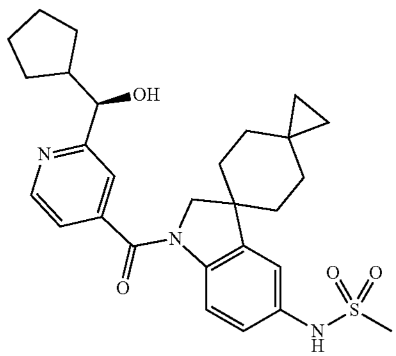 [SMILES: CS(=O)(=O)Nc1ccc2c(c1)C1(CCC3(CC3)CC1)CN2C(=O)c1ccnc([C@H](O)C2CCCC2)c1] | (R)-N-(1''-(2-(cyclopentyl(hydroxy)methyl)isonicotinoyl)dispiro[cyclopropane-1,1'-cyclohexane-4',3''-indolin]-5''-yl)methanesulfonamide |
| (S)-Compound 316 | 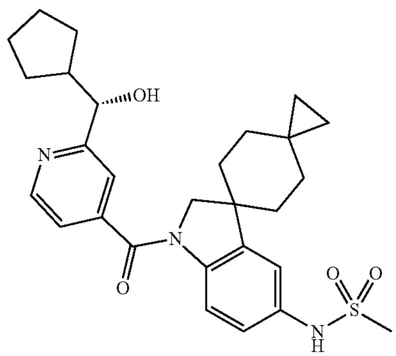 [SMILES: CS(=O)(=O)Nc1ccc2c(c1)C1(CCC3(CC3)CC1)CN2C(=O)c1ccnc([C@@H](O)C2CCCC2)c1] | (S)-N-(1''-(2-(cyclopentyl(hydroxy)methyl)isonicotinoyl)dispiro[cyclopropane-1,1'-cyclohexane-4',3''-indolin]-5''-yl)methanesulfonamide |
| Compound 317 | 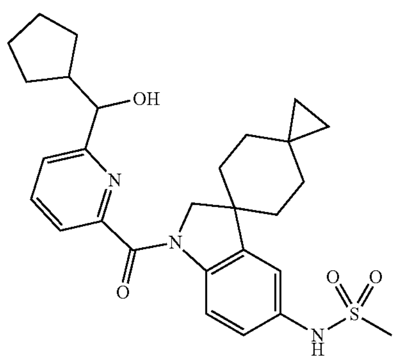 [SMILES: CS(=O)(=O)Nc1ccc2c(c1)C1(CCC3(CC3)CC1)CN2C(=O)c1cccc(C(O)C2CCCC2)n1] | N-(1''-(6-(cyclopentyl(hydroxy)methyl)picolinoyl)dispiro[cyclopropane-1,1'-cyclohexane-4',3''-indolin]-5''-yl)methanesulfonamide |
| (R)-Compound 317 | 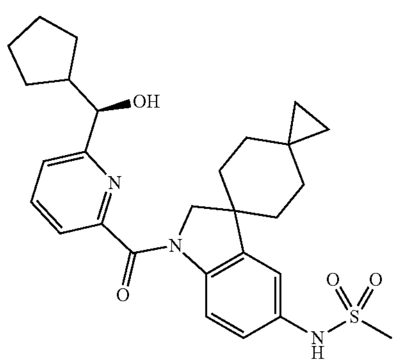 [SMILES: CS(=O)(=O)Nc1ccc2c(c1)C1(CCC3(CC3)CC1)CN2C(=O)c1cccc([C@H](O)C2CCCC2)n1] | (R)-N-(1''-(6-(cyclopentyl(hydroxy)methyl)picolinoyl)dispiro[cyclopropane-1,1'-cyclohexane-4',3''-indolin]-5''-yl)methanesulfonamide |

TABLE 1-continued

| Compound No. | Structure | Name |
|---|---|---|
| (S)-Compound 317 | 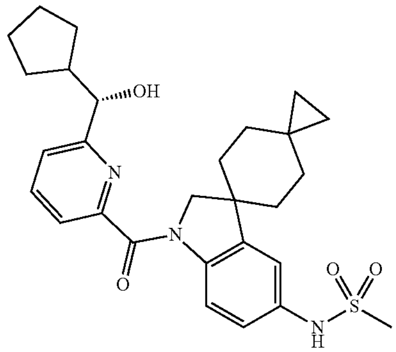 [SMILES: CS(=O)(=O)Nc1ccc2c(c1)C1(CCC3(CC3)CC1)CN2C(=O)c1cccc([C@@H](O)C2CCCC2)n1] | (S)-N-(1"-(6-(cyclopentyl(hydroxy)methyl)picolinoyl)dispiro[cyclopropane-1,1'-cyclohexane-4',3"-indolin]-5"-yl)methanesulfonamide |
| Compound 318 | 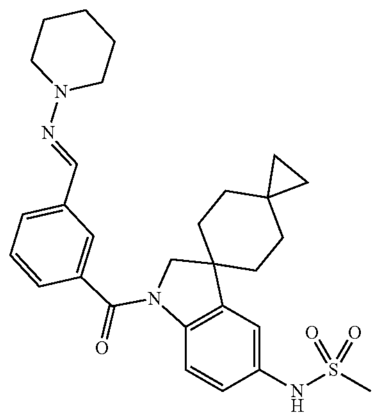 [SMILES: CS(=O)(=O)Nc1ccc2c(c1)C1(CCC3(CC3)CC1)CN2C(=O)c1cccc(/C=N/N2CCCCC2)c1] | N-(1"-(3-((piperidin-1-ylimino)methyl)benzoyl)dispiro[cyclopropane-1,1'-cyclohexane-4',3"-indolin]-5"-yl)methanesulfonamide |
| Compound 319 | 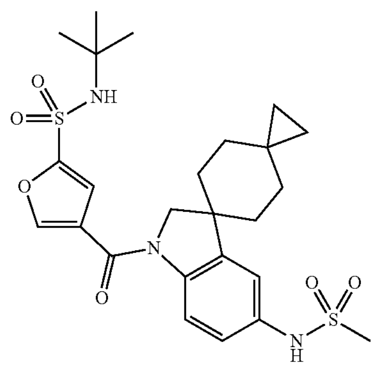 [SMILES: CC(C)(C)NS(=O)(=O)c1cc(C(=O)N2CC3(CCC4(CC4)CC3)c3cc(NS(C)(=O)=O)ccc32)co1] | N-(tert-butyl)-4-(5"-(methylsulfonamido)dispiro[cyclopropane-1,1'-cyclohexane-4',3"-indoline]-1"-carbonyl)furan-2-sulfonamide |
| Compound 320 | 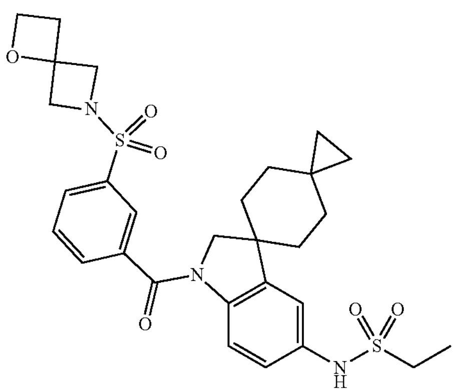 [SMILES: CCS(=O)(=O)Nc1ccc2c(c1)C1(CCC3(CC3)CC1)CN2C(=O)c1cccc(S(=O)(=O)N2CC3(CCO3)C2)c1] | N-(1"-(3-((1-oxa-6-azaspiro[3.3]heptan-6-yl)sulfonyl)benzoyl)dispiro[cyclopropane-1,1'-cyclohexane-4',3"-indolin]-5"-yl)ethanesulfonamide |

TABLE 1-continued

| Compound No. | Structure | Name |
|---|---|---|
| Compound 321 | 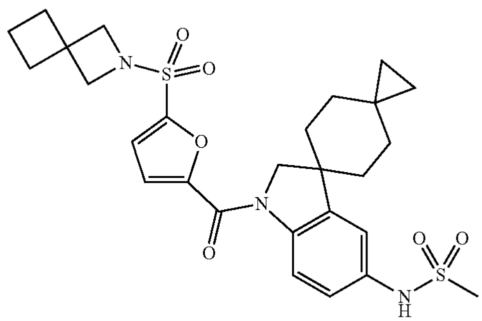 [SMILES: CS(=O)(=O)Nc1ccc2c(c1)C1(CCC3(CC3)CC1)CN2C(=O)c1ccc(S(=O)(=O)N2CC3(CCC3)C2)o1] | N-(1''-(5-((2-azaspiro[3.3]heptan-2-yl)sulfonyl)furan-2-carbonyl)dispiro[cyclopropane-1,1'-cyclohexane-4',3''-indolin]-5''-yl)methanesulfonamide |
| Compound 322 | 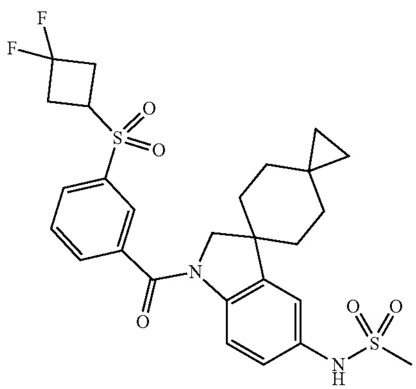 [SMILES: CS(=O)(=O)Nc1ccc2c(c1)C1(CCC3(CC3)CC1)CN2C(=O)c1cccc(S(=O)(=O)C2CC(F)(F)C2)c1] | N-(1''-(3-((3,3-difluorocyclobutyl)sulfonyl)benzoyl)dispiro[cyclopropane-1,1'-cyclohexane-4',3''-indolin]-5''-yl)methanesulfonamide |
| Compound 323 | 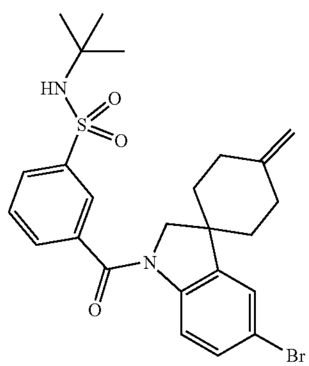 [SMILES: C=C1CCC2(CC1)CN(C(=O)c1cccc(S(=O)(=O)NC(C)(C)C)c1)c1ccc(Br)cc12] | 3-(5'-bromo-4-methylenespiro[cyclohexane-1,3'-indoline]-1'-carbonyl)-N-(tert-butyl)benzenesulfonamide |
| Compound 324 | 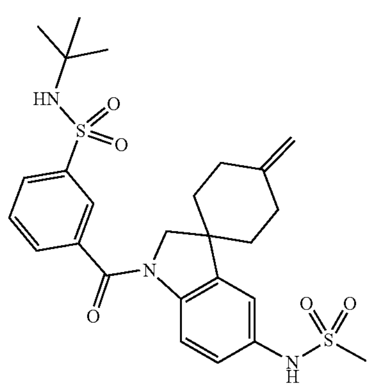 [SMILES: C=C1CCC2(CC1)CN(C(=O)c1cccc(S(=O)(=O)NC(C)(C)C)c1)c1ccc(NS(C)(=O)=O)cc12] | N-(tert-butyl)-3-(4-methylene-5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 325 | 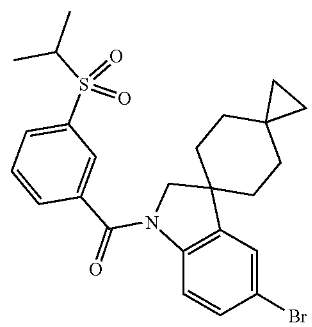 [SMILES: CC(C)S(=O)(=O)c1cccc(C(=O)N2CC3(CCC4(CC4)CC3)c3cc(Br)ccc32)c1] | (5''-bromodispiro[cyclopropane-1,1'-cyclohexane-4',3''-indolin]-1''-yl)(3-(isopropylsulfonyl)phenyl)methanone |
| Compound 326 | 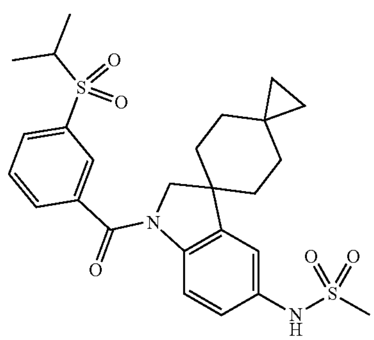 [SMILES: CC(C)S(=O)(=O)c1cccc(C(=O)N2CC3(CCC4(CC4)CC3)c3cc(NS(C)(=O)=O)ccc32)c1] | N-(1''-(3-(isopropylsulfonyl)benzoyl)dispiro[cyclopropane-1,1'-cyclohexane-4',3''-indolin]-5''-yl)methanesulfonamide |
| Compound 327 | 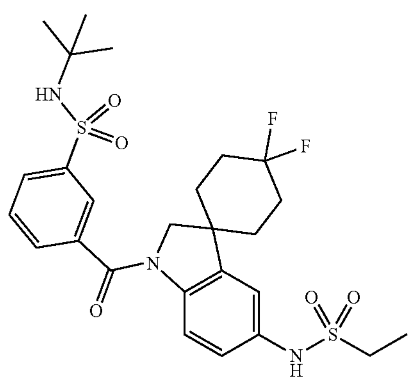 [SMILES: CCS(=O)(=O)Nc1ccc2c(c1)C1(CCC(F)(F)CC1)CN2C(=O)c1cccc(S(=O)(=O)NC(C)(C)C)c1] | N-(tert-butyl)-3-(5'-(ethylsulfonamido)-4,4-difluorospiro[cyclohexane-1,3'-indoline]-1'-carbonyl)benzenesulfonamide |
| Compound 328 | 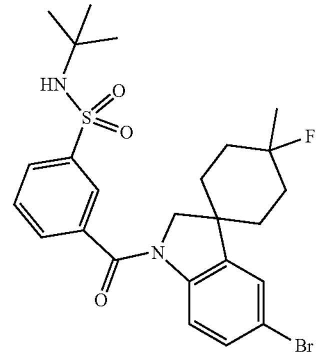 [SMILES: CC1(F)CCC2(CC1)CN(C(=O)c1cccc(S(=O)(=O)NC(C)(C)C)c1)c1ccc(Br)cc12] | 3-(5'-bromo-4-fluoro-4-methylspiro[cyclohexane-1,3'-indoline]-1'-carbonyl)-N-(tert-butyl)benzenesulfonamide |

TABLE 1-continued

| Compound No. | Structure | Name |
|---|---|---|
| Compound 329 | 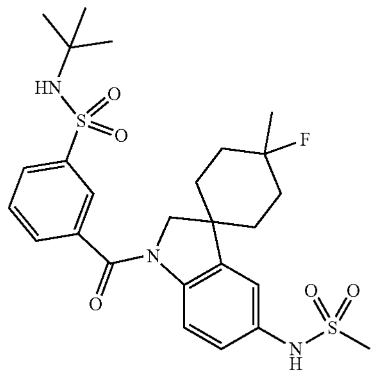 [SMILES: CC1(F)CCC2(CC1)CN(C(=O)c1cccc(S(=O)(=O)NC(C)(C)C)c1)c1ccc(NS(C)(=O)=O)cc12] | N-(tert-butyl)-3-(4-fluoro-4-methyl-5'-(methylsulfonamido)spiro[cyclohexane-1,3'-indoline]-1'-carbonyl)benzenesulfonamide |
| Compound 330 | 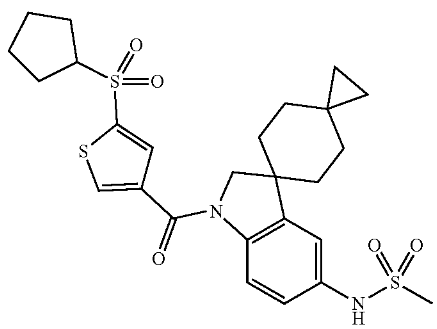 [SMILES: CS(=O)(=O)Nc1ccc2c(c1)C1(CCC3(CC3)CC1)CN2C(=O)c1csc(S(=O)(=O)C2CCCC2)c1] | N-(1''-(5-(cyclopentylsulfonyl)thiophene-3-carbonyl)dispiro[cyclopropane-1,1'-cyclohexane-4',3''-indolin]-5''-yl)methanesulfonamide |
| Compound 331 | 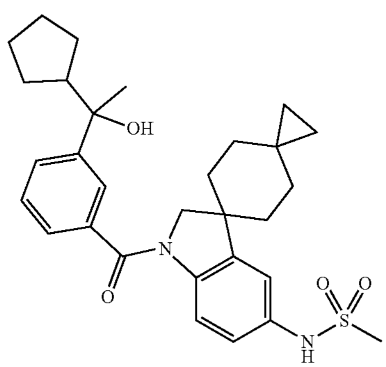 [SMILES: CC(O)(c1cccc(C(=O)N2CC3(CCC4(CC4)CC3)c3cc(NS(C)(=O)=O)ccc32)c1)C1CCCC1] | N-(1''-(3-(1-cyclopentyl-1-hydroxyethyl)benzoyl)dispiro[cyclopropane-1,1'-cyclohexane-4',3''-indolin]-5''-yl)methanesulfonamide |
| Compound 332 | 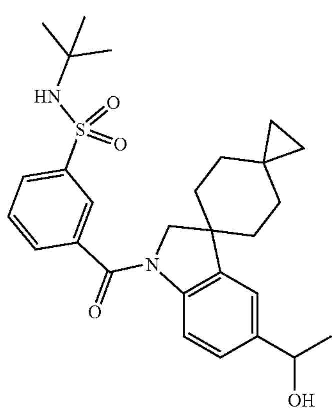 [SMILES: CC(O)c1ccc2c(c1)C1(CCC3(CC3)CC1)CN2C(=O)c1cccc(S(=O)(=O)NC(C)(C)C)c1] | N-(tert-butyl)-3-(5''-(1-hydroxyethyl)dispiro[cyclopropane-1,1'-cyclohexane-4',3''-indoline]-1''-carbonyl)benzenesulfonamide |

TABLE 1-continued

| Compound No. | Structure | Name |
|---|---|---|
| Compound 333 | 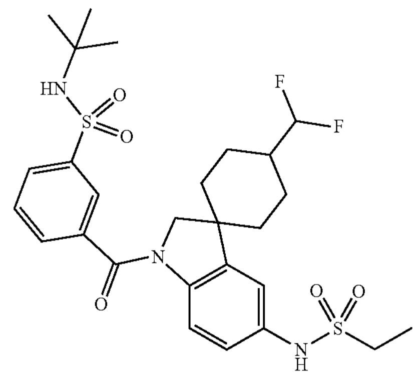 [SMILES: CCS(=O)(=O)Nc1ccc2c(c1)C1(CCC(C(F)F)CC1)CN2C(=O)c1cccc(S(=O)(=O)NC(C)(C)C)c1] | N-(tert-butyl)-3-(4-(difluoromethyl)-5'-(ethylsulfonamido)spiro[cyclohexane-1,3'-indoline]-1'-carbonyl)benzenesulfonamide |
| (1r,4r)-Compound 333 | | N-(tert-butyl)-3-((1r,4r)-4-(difluoromethyl)-5'-(ethylsulfonamido)spiro[cyclohexane-1,3'-indoline]-1'-carbonyl)benzenesulfonamide |
| (1r,4r)-Compound 333 | | N-(tert-butyl)-3-((1s,4s)-4-(difluoromethyl)-5'-(ethylsulfonamido)spiro[cyclohexane-1,3'-indoline]-1'-carbonyl)benzenesulfonamide |
| Compound 334 | 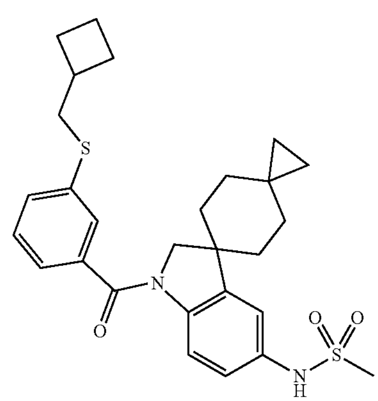 [SMILES: CS(=O)(=O)Nc1ccc2c(c1)C1(CCC3(CC3)CC1)CN2C(=O)c1cccc(SCC2CCC2)c1] | N-(1''-(3-((cyclobutylmethyl)thio)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 335 | 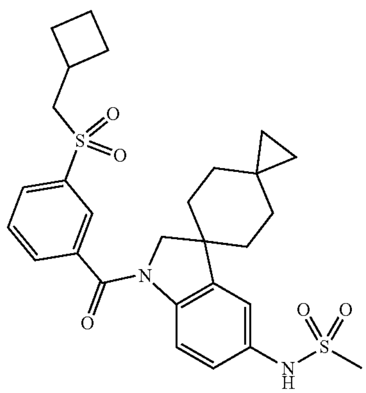 [SMILES: CS(=O)(=O)Nc1ccc2c(c1)C1(CCC3(CC3)CC1)CN2C(=O)c1cccc(S(=O)(=O)CC2CCC2)c1] | N-(1''-(3-((cyclobutylmethyl)sulfonyl)benzoyl)dispiro[cyclopropane-1,1'-cyclohexane-4',3''-indolin]-5''-yl)methanesulfonamide |
| Compound 336 | 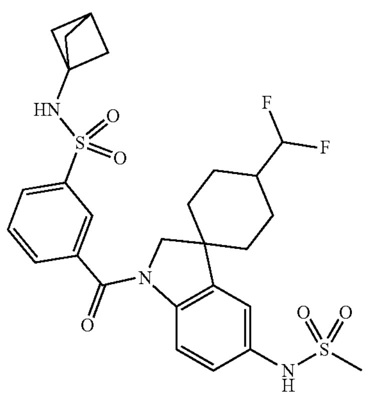 [SMILES: CS(=O)(=O)Nc1ccc2c(c1)C1(CCC(C(F)F)CC1)CN2C(=O)c1cccc(S(=O)(=O)NC23CC(C2)C3)c1] | N-(bicyclo[1.1.1]pentan-1-yl)-3-(4-(difluoromethyl)-5'-(methylsulfonamido)spiro[cyclohexane-1,3'-indoline]-1'-carbonyl)benzenesulfonamide |
| (1r,4r)-Compound 336 | 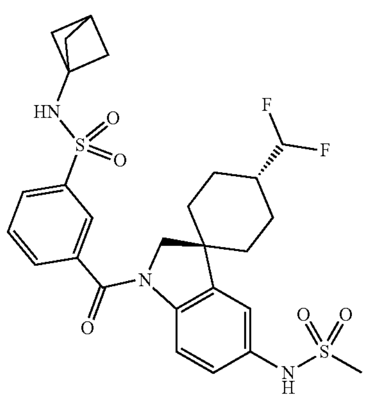 [SMILES: CS(=O)(=O)Nc1ccc2c(c1)[C@]1(CC[C@@H](C(F)F)CC1)CN2C(=O)c1cccc(S(=O)(=O)NC23CC(C2)C3)c1] | N-(bicyclo[1.1.1]pentan-1-yl)-3-((1r,4r)-4-(difluoromethyl)-5'-(methylsulfonamido)spiro[cyclohexane-1,3'-indoline]-1'-carbonyl)benzenesulfonamide |
| (1s,4s)-Compound 336 | 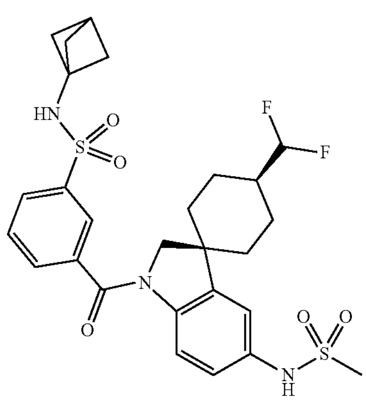 [SMILES: CS(=O)(=O)Nc1ccc2c(c1)[C@]1(CC[C@H](C(F)F)CC1)CN2C(=O)c1cccc(S(=O)(=O)NC23CC(C2)C3)c1] | N-(bicyclo[1.1.1]pentan-1-yl)-3-((1s,4s)-4-(difluoromethyl)-5'-(methylsulfonamido)spiro[cyclohexane-1,3'-indoline]-1'-carbonyl)benzenesulfonamide |

TABLE 1-continued

| Compound No. | Structure | Name |
|---|---|---|
| Compound 337 | 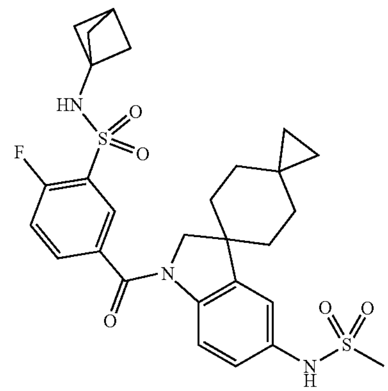 [SMILES: CS(=O)(=O)Nc1ccc2c(c1)C1(CCC3(CC3)CC1)CN2C(=O)c1ccc(F)c(S(=O)(=O)NC23CC(C2)C3)c1] | N-(bicyclo[1.1.1]pentan-1-yl)-2-fluoro-5-(5''-(methylsulfonamido)dispiro[cyclopropane-1,1'-cyclohexane-4',3''-indoline]-1''-carbonyl)benzenesulfonamide |
| Compound 338 | 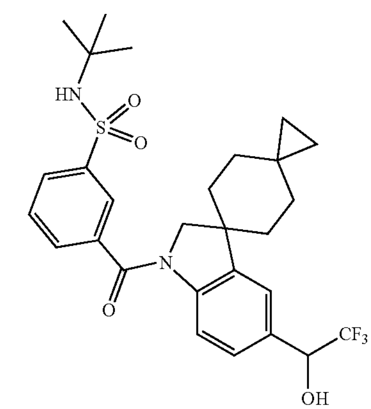 | N-(tert-butyl)-3-(5''-(2,2,2-trifluoro-1-hydroxyethyl)dispiro[cyclopropane-1,1'-cyclohexane-4',3''-indoline]-1''-carbonyl)benzenesulfonamide |
| (R)-Compound 338 | 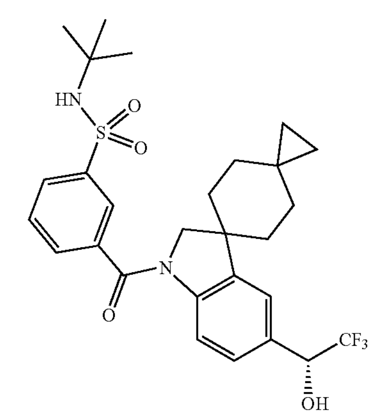 [SMILES: CC(C)(C)NS(=O)(=O)c1cccc(C(=O)N2CC3(CCC4(CC4)CC3)c3cc([C@@H](O)C(F)(F)F)ccc32)c1] | (R)-N-(tert-butyl)-3-(5''-(2,2,2-trifluoro-1-hydroxyethyl)dispiro[cyclopropane-1,1'-cyclohexane-4',3''-indoline]-1''-carbonyl)benzenesulfonamide |

TABLE 1-continued

| Compound No. | Structure | Name |
|---|---|---|
| (S)-Compound 338 | 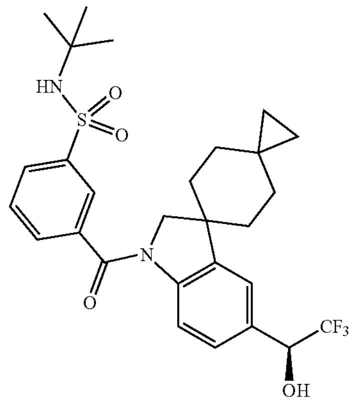 [SMILES: CC(C)(C)NS(=O)(=O)c1cccc(C(=O)N2CC3(CCC4(CC4)CC3)c3cc([C@H](O)C(F)(F)F)ccc32)c1] | (S)-N-(tert-butyl)-3-(5''-(2,2,2-trifluoro-1-hydroxyethyl)dispiro[cyclopropane-1,1'-cyclohexane-4',3''-indoline]-1''-carbonyl)benzenesulfonamide |
| Compound 339 | 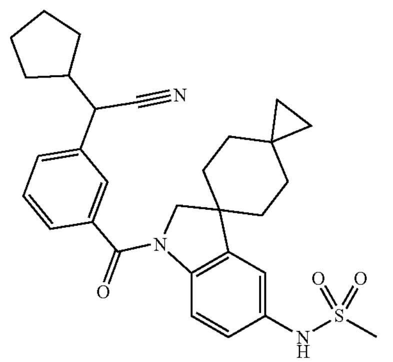 [SMILES: CS(=O)(=O)Nc1ccc2c(c1)C1(CCC3(CC3)CC1)CN2C(=O)c1cccc(C(C#N)C2CCCC2)c1] | N-(1''-(3-(cyano(cyclopentyl)methyl)benzoyl)dispiro[cyclopropane-1,1'-cyclohexane-4',3''-indolin]-5''-yl)methanesulfonamide |
| Compound 340 | 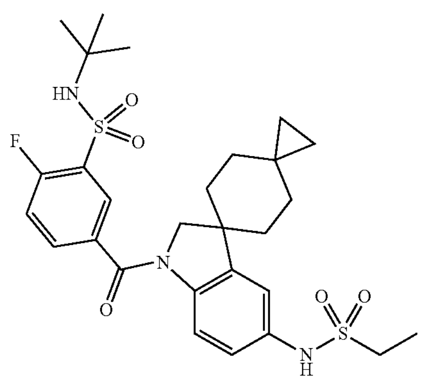 [SMILES: CCS(=O)(=O)Nc1ccc2c(c1)C1(CCC3(CC3)CC1)CN2C(=O)c1ccc(F)c(S(=O)(=O)NC(C)(C)C)c1] | N-(tert-butyl)-5-(5''-(ethylsulfonamido)dispiro[cyclopropane-1,1'-cyclohexane-4',3''-indoline]-1''-carbonyl)-2-fluorobenzenesulfonamide |
| Compound 341 | 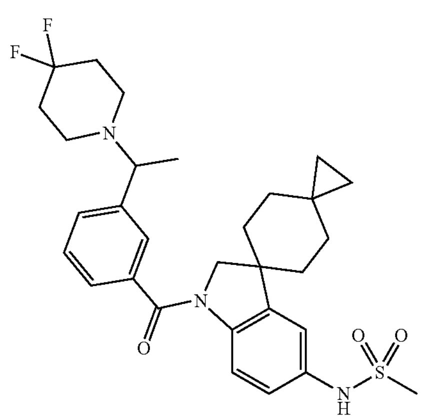 [SMILES: CC(c1cccc(C(=O)N2CC3(CCC4(CC4)CC3)c3cc(NS(C)(=O)=O)ccc32)c1)N1CCC(F)(F)CC1] | N-(1''-(3-(1-(4,4-difluoropiperidin-1-yl)ethyl)benzoyl)dispiro[cyclopropane-1,1'-cyclohexane-4'-3''-indolin]-5''-yl)methanesulfonamide |

TABLE 1-continued

| Compound No. | Structure | Name |
|---|---|---|
| (R)-Compound 341 | 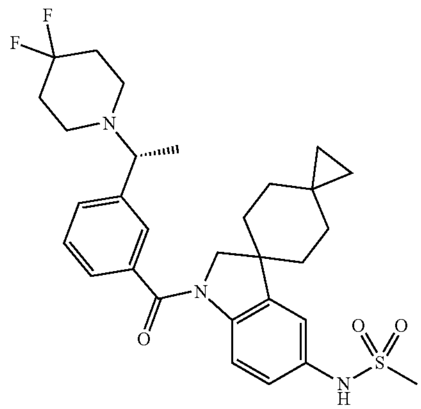 [SMILES: C[C@H](c1cccc(C(=O)N2CC3(CCC4(CC4)CC3)c3cc(NS(C)(=O)=O)ccc32)c1)N1CCC(F)(F)CC1] | (R)-N-(1"-(3-(1-(4,4-difluoropiperidin-1-yl)ethyl)benzoyl)dispiro[cyclopropane-1,1'-cyclohexane-4',3"-indolin]-5"-yl)methanesulfonamide |
| (S)-Compound 341 | 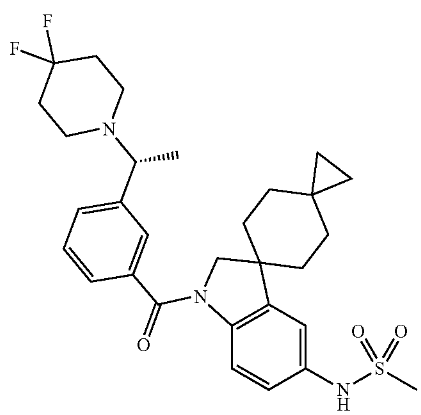 [SMILES: C[C@H](c1cccc(C(=O)N2CC3(CCC4(CC4)CC3)c3cc(NS(C)(=O)=O)ccc32)c1)N1CCC(F)(F)CC1] | (S)-N-(1"-(3-(1-(4,4-difluoropiperidin-1-yl)ethyl)benzoyl)dispiro[cyclopropane-1,1'-cyclohexane-4',3"-indolin]-5"-yl)methanesulfonamide |
| Compound 342 | 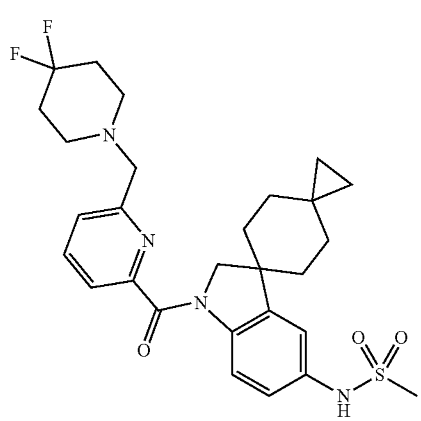 [SMILES: CS(=O)(=O)Nc1ccc2c(c1)C1(CCC3(CC3)CC1)CN2C(=O)c1cccc(CN2CCC(F)(F)CC2)n1] | N-(1"-(6-((4,4-difluoropiperidin-1-yl)methyl)picolinoyl)dispiro[cyclopropane-1,1'-cyclohexane-4',3"-indolin]-5"-yl)methanesulfonamide |

TABLE 1-continued

| Compound No. | Structure | Name |
|---|---|---|
| Compound 343 | 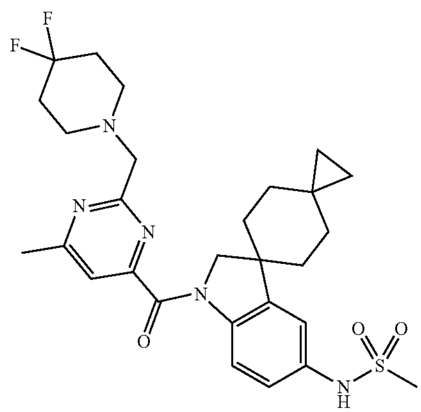 [SMILES: Cc1cc(C(=O)N2CC3(CCC4(CC4)CC3)c3cc(NS(C)(=O)=O)ccc32)nc(CN2CCC(F)(F)CC2)n1] | N-(1''-(2-((4,4-difluoropiperidin-1-yl)methyl)-6-methylpyrimidine-4-carbonyl)dispiro[cyclopropane-1,1'-cyclohexane-4',3''-indolin]-5''-yl)methanesulfonamide |
| Compound 344 | 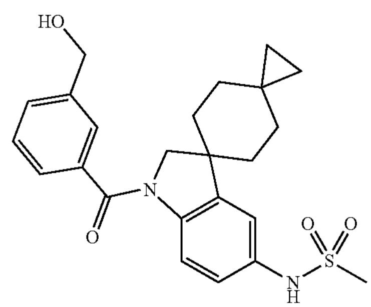 [SMILES: CS(=O)(=O)Nc1ccc2c(c1)C1(CCC3(CC3)CC1)CN2C(=O)c1cccc(CO)c1] | N-(1''-(3-(hydroxymethyl)benzoyl)dispiro[cyclopropane-1,1'-cyclohexane-4',3''-indolin]-5''-yl)methanesulfonamide |
| Compound 345 | 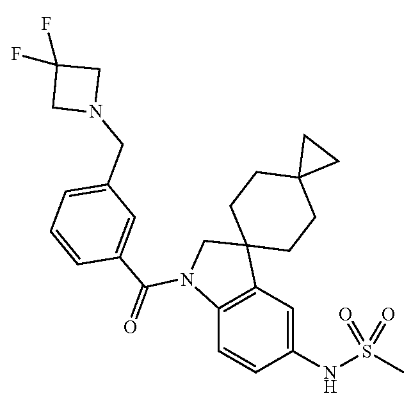 [SMILES: CS(=O)(=O)Nc1ccc2c(c1)C1(CCC3(CC3)CC1)CN2C(=O)c1cccc(CN2CC(F)(F)C2)c1] | N-(1''-(3-((3-difluoroazetidin-1-yl)methyl)benzoyl)dispiro[cyclopropane-1,1'-cyclohexane-4',3''-indolin]-5''-yl)methanesulfonamide |
| Compound 346 | 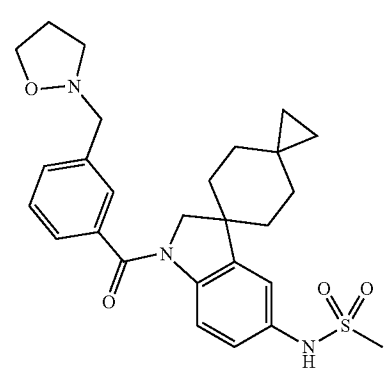 [SMILES: CS(=O)(=O)Nc1ccc2c(c1)C1(CCC3(CC3)CC1)CN2C(=O)c1cccc(CN2CCCO2)c1] | N-(1''-(3-(isoxazolidin-2-ylmethyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 347 | 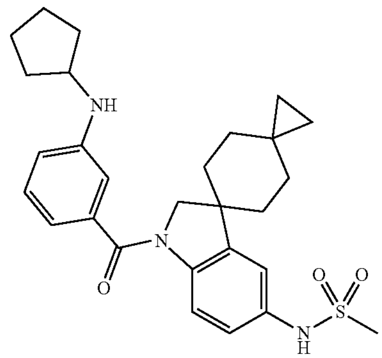 [SMILES: CS(=O)(=O)Nc1ccc2c(c1)C1(CCC3(CC3)CC1)CN2C(=O)c1cccc(NC2CCCC2)c1] | N-(1"-(3-(cyclopentylamino)benzoyl)dispiro[cyclopropane-1,1'-cyclohexane-4',3"-indolin]-5"-yl)methanesulfonamide |
| Compound 348 | 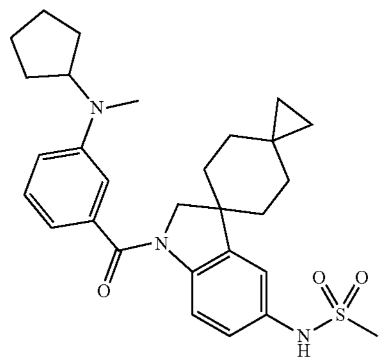 [SMILES: CN(c1cccc(C(=O)N2CC3(CCC4(CC4)CC3)c3cc(NS(C)(=O)=O)ccc32)c1)C1CCCC1] | N-(1"-(3-(cyclopentyl(methyl)amino)benzoyl)dispiro[cyclopropane-1,1'-cyclohexane-4',3"-indolin]-5"-yl)methanesulfonamide |
| Compound 349 | 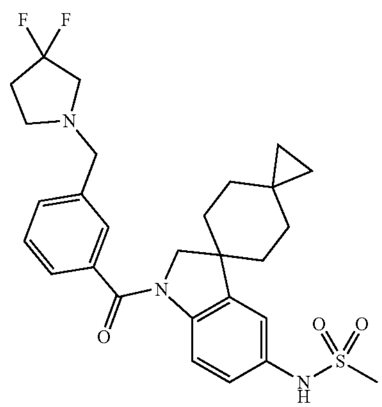 [SMILES: CS(=O)(=O)Nc1ccc2c(c1)C1(CCC3(CC3)CC1)CN2C(=O)c1cccc(CN2CCC(F)(F)C2)c1] | N-(1"-(3-((3,3-difluoropyrrolidin-1-yl)methyl)benzoyl)dispiro[cyclopropane-1,1'-cyclohexane-4',3"-indolin]-5"-yl)methanesulfonamide |
| Compound 350 | 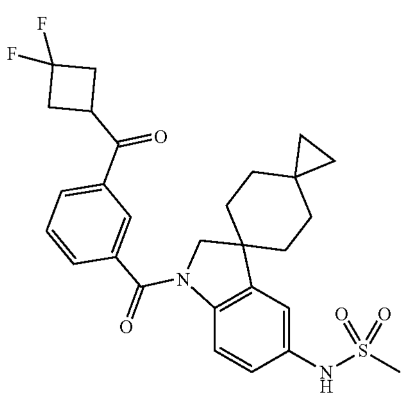 [SMILES: CS(=O)(=O)Nc1ccc2c(c1)C1(CCC3(CC3)CC1)CN2C(=O)c1cccc(C(=O)C2CC(F)(F)C2)c1] | N-(1"-(3-(3,3-difluorocyclobutane-1-carbonyl)benzoyl)dispiro[cyclopropane-1,1'-cyclohexane-4',3"-indolin]-5"-yl)methanesuflonamide |

TABLE 1-continued

| Compound No. | Structure | Name |
|---|---|---|
| Compound 351 | 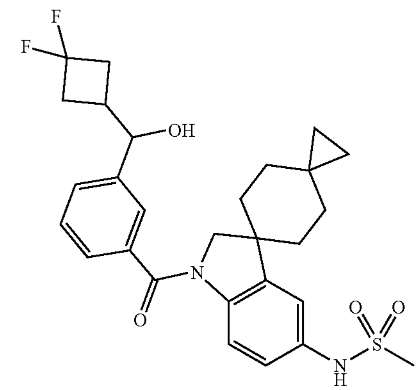 [SMILES: CS(=O)(=O)Nc1ccc2c(c1)C1(CCC3(CC3)CC1)CN2C(=O)c1cccc(C(O)C2CC(F)(F)C2)c1] | N-(1''-(3-((3,3-difluorocyclobutyl)(hydroxyj)methyl)benzoyl)dispiro[cyclopropane-1,1'-cyclohexane-4',3''-indolin]-5''-yl)methanesulfonamide |
| (R)-Compound 351 | 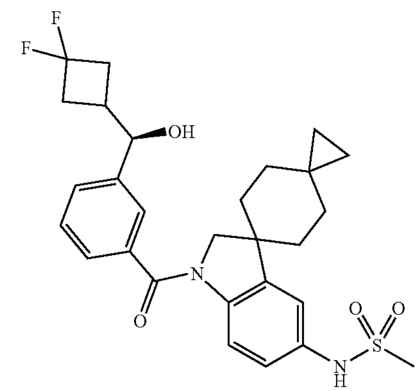 [SMILES: CS(=O)(=O)Nc1ccc2c(c1)C1(CCC3(CC3)CC1)CN2C(=O)c1cccc([C@H](O)C2CC(F)(F)C2)c1] | (R)-N-(1''-(3-((3,3-difluorocyclobutyl)(hydroxy)methyl)benzoyl)dispiro[cyclopropane-1,1'-cyclohexane-4',3''-indolin]-5''-yl)methanesulfonamide |
| (S)-Compound 351 | 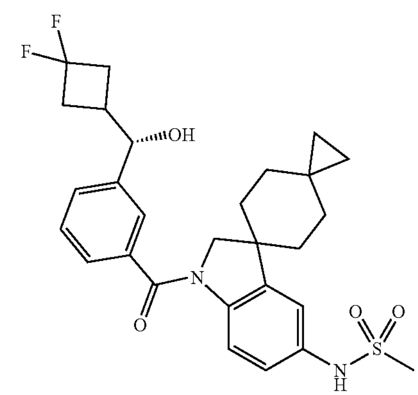 [SMILES: CS(=O)(=O)Nc1ccc2c(c1)C1(CCC3(CC3)CC1)CN2C(=O)c1cccc([C@@H](O)C2CC(F)(F)C2)c1] | (S)-N-(1''-(3-((3,3-difluorocyclobutyl)(hydroxy)methyl)benzoyl)dispiro[cyclopropane-1,1'-cyclohexane-4',3''-indolin]-5''-yl)methanesulfonamide |
| Compound 352 | 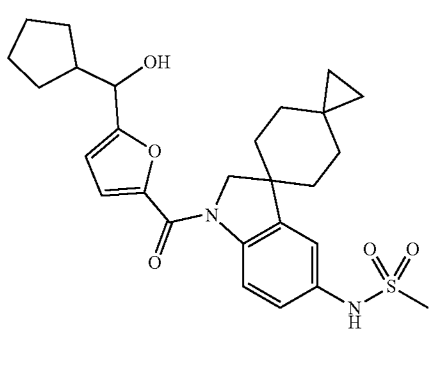 [SMILES: CS(=O)(=O)Nc1ccc2c(c1)C1(CCC3(CC3)CC1)CN2C(=O)c1ccc(C(O)C2CCCC2)o1] | N-(1''-(5-(cyclopentyl(hydroxy)methyl)furan-2-carbonyl)dispiro[cyclopropane-1,1'-cyclohexane-4',3''-indolin]-5''-yl)methanesulfonamide |

TABLE 1-continued

| Compound No. | Structure | Name |
|---|---|---|
| (R)-Compound 352 | 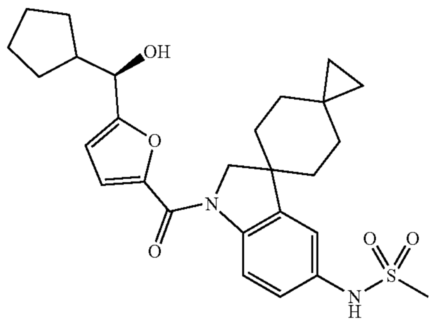 [SMILES: CS(=O)(=O)Nc1ccc2c(c1)C1(CCC3(CC3)CC1)CN2C(=O)c1ccc([C@H](O)C2CCCC2)o1] | (R)-N-(1''-(5-(cyclopentyl(hydroxy)methyl)furan-2-carbonyl)dispiro[cyclopropane-1,1'-cyclohexane-4',3''-indolin]-5''-yl)methanesulfonamide |
| (S)-Compound 352 | 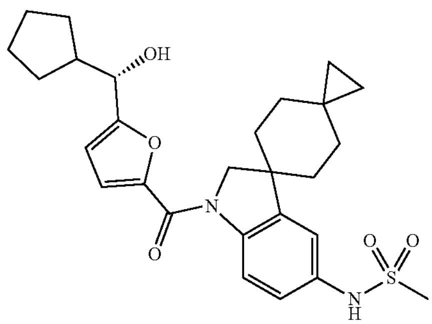 [SMILES: CS(=O)(=O)Nc1ccc2c(c1)C1(CCC3(CC3)CC1)CN2C(=O)c1ccc([C@@H](O)C2CCCC2)o1] | (S)-N-(1''-(5-(cyclopentyl(hydroxy)methyl)furan-2-carbonyl)dispiro[cyclopropane-1,1'-cyclohexane-4',3''-indolin]-5''-yl)methanesulfonamide |
| Compound 353 | 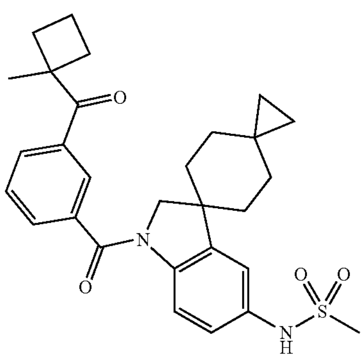 [SMILES: CC1(C(=O)c2cccc(C(=O)N3CC4(CCC5(CC5)CC4)c4cc(NS(C)(=O)=O)ccc43)c2)CCC1] | N-(1''-(3-(1-methylcyclobutane-1-carbonyl)benzoyl)dispiro[cyclopropane-1,1'-cyclohexane-4',3''-indolin]-5''-yl)methanesulfonamide |
| Compound 354 | 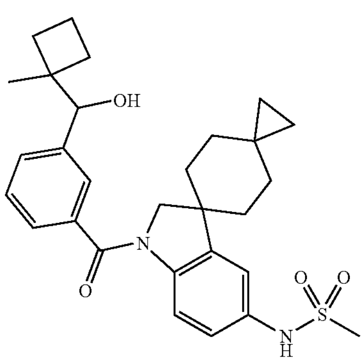 [SMILES: CC1(C(O)c2cccc(C(=O)N3CC4(CCC5(CC5)CC4)c4cc(NS(C)(=O)=O)ccc43)c2)CCC1] | N-(1''-(3-(hydroxy(1-methylcyclobutyl)methyl)benzoyl)dispiro[cyclopropane-1,1'-cyclohexane-4',3''-indolin]-5''-yl)methanesulfonamide |

TABLE 1-continued

| Compound No. | Structure | Name |
| --- | --- | --- |
| Compound 355 | 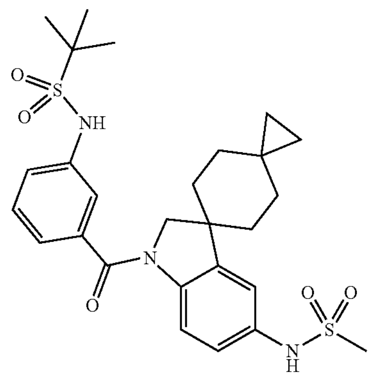 [SMILES: CC(C)(C)S(=O)(=O)Nc1cccc(C(=O)N2CC3(CCC4(CC4)CC3)c3cc(NS(C)(=O)=O)ccc32)c1] | 2-methyl-N-(3-(5''-(methylsulfonamido)dispiro[cyclopropane-1,1'-cyclohexane-4',3''-indoline]-1''-carbonyl)phenyl)propane-2-sulfonamide |
| Compound 356 | 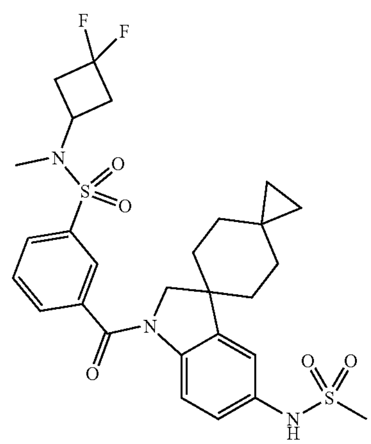 [SMILES: CN(C1CC(F)(F)C1)S(=O)(=O)c1cccc(C(=O)N2CC3(CCC4(CC4)CC3)c3cc(NS(C)(=O)=O)ccc32)c1] | N-(3,3-difluorocyclobutyl)-N-methyl-3-(5''-(methylsulfonamido)dispiro[cyclopropane-1,1'-cyclohexane-4',3''-indoline]-1''-carbonyl)benzenesulfonamide |
| Compound 357 | 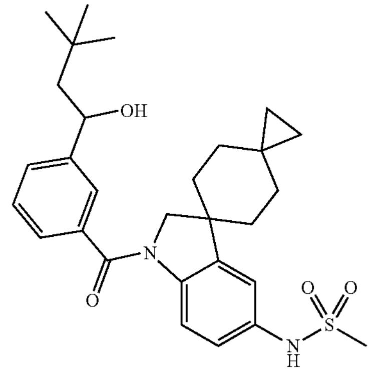 [SMILES: CC(C)(C)CC(O)c1cccc(C(=O)N2CC3(CCC4(CC4)CC3)c3cc(NS(C)(=O)=O)ccc32)c1] | N-(1''-(3-(1-hydroxy-3,3-dimethylbutyl)benzoyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 358 | 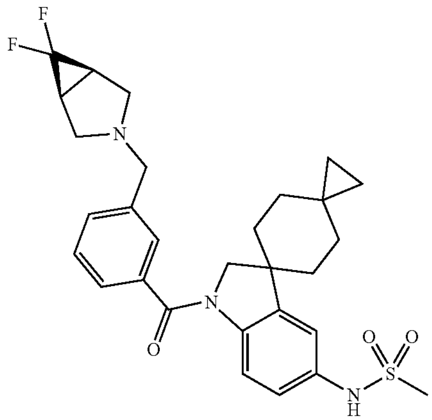 [SMILES: CS(=O)(=O)Nc1ccc2c(c1)C1(CCC3(CC3)CC1)CN2C(=O)c1cccc(CN2C[C@@H]3[C@H](C2)C3(F)F)c1] | N-(1''-(3-((6,6-difluoro-3-azabicyclo[3.1.0]hexan-3-yl)methyl)benzoyl)dispiro[cyclopropane-1,1'-cyclohexane-4',3''-indolin]-5''-yl)methanesulfonamide |
| Compound 359 | 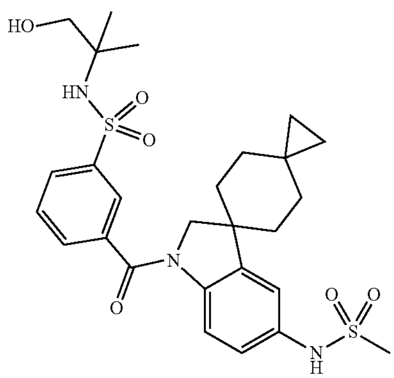 [SMILES: CC(C)(CO)NS(=O)(=O)c1cccc(C(=O)N2CC3(CCC4(CC4)CC3)c3cc(NS(C)(=O)=O)ccc32)c1] | N-(1-hydroxy-2-methylpropan-2-yl)-3-(5''-(methylsulfonamido)dispiro[cyclopropane-1,1'-cyclohexane-4',3''-indoline]-1''-carbonyl)benzenesulfonamide |
| (1s,4s)-Compound 360 | 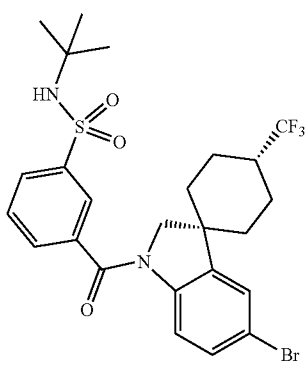 [SMILES: CC(C)(C)NS(=O)(=O)c1cccc(C(=O)N2C[C@]3(CC[C@@H](C(F)(F)F)CC3)c3cc(Br)ccc32)c1] | 3-((1s,4s)-5'-bromo-4-(trifluoromethyl)spiro[cyclohexane-1,3'-indoline]-1'-carbonyl)-N-(tert-butyl)benzenesulfonamide |
| (1r,4r)-Compound 360 | 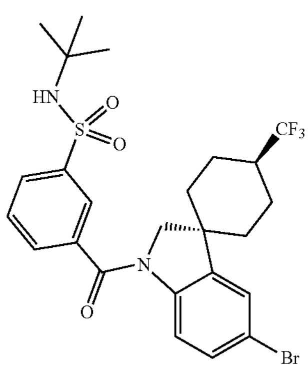 [SMILES: CC(C)(C)NS(=O)(=O)c1cccc(C(=O)N2C[C@]3(CC[C@H](C(F)(F)F)CC3)c3cc(Br)ccc32)c1] | 3-((1r,4r)-5'-bromo-4-(trifluoromethyl)spiro[cyclohexane-1,3'-indoline]-1'-carbonyl)-N-(tert-butyl)benzenesulfonamide |

TABLE 1-continued

| Compound No. | Structure | Name |
|---|---|---|
| (1s,4s)-Compound 361 | 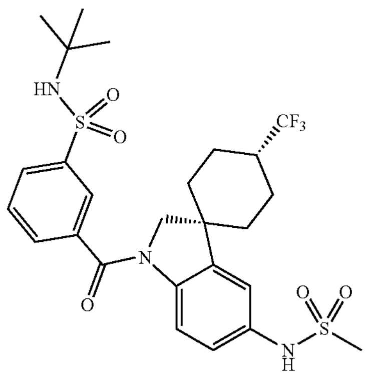 [SMILES: CC(C)(C)NS(=O)(=O)c1cccc(C(=O)N2C[C@]3(CC[C@@H](C(F)(F)F)CC3)c3cc(NS(C)(=O)=O)ccc32)c1] | N-(tert-butyl)-3-((1s,4s)-5'-(methylsulfonamido)-4-(trifluoromethyl)spiro[cyclohexane-1,3'-indoline]-1'-carbonyl)benzenesulfonamide |
| (1r,4r)-Compound 361 | 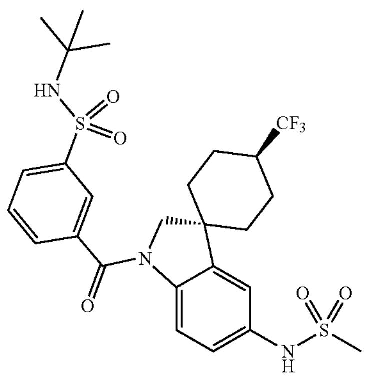 [SMILES: CC(C)(C)NS(=O)(=O)c1cccc(C(=O)N2C[C@]3(CC[C@H](C(F)(F)F)CC3)c3cc(NS(C)(=O)=O)ccc32)c1] | N-(tert-butyl)-3-((1r,4r)-5'-(methylsulfonamido)-4-(trifluoromethyl)spiro[cyclohexane-1,3'-indoline]-1'-carbonyl)benzenesulfonamide |
| Compound 362 | 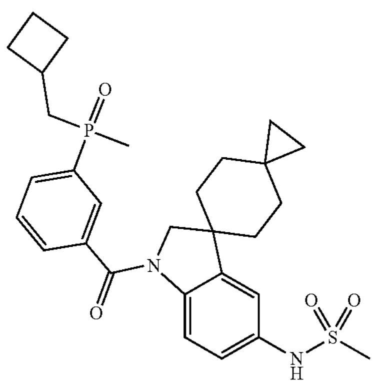 [SMILES: CP(=O)(CC1CCC1)c1cccc(C(=O)N2CC3(CCC4(CC4)CC3)c3cc(NS(C)(=O)=O)ccc32)c1] | N-(1''-(3-(cyclobutylmethyl)(methyl)phosphoryl)benzoyl)dispiro[cyclopropane-1,1'-cyclohexane-4',3''-indolin]-5''-yl)methanesulfonamide |
| Compound 363 | 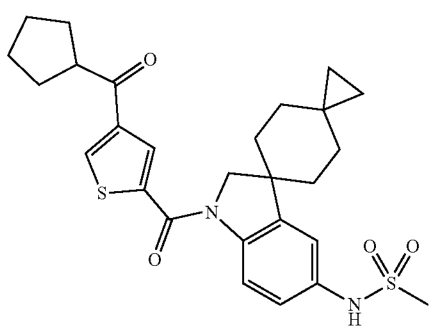 [SMILES: CS(=O)(=O)Nc1ccc2c(c1)C1(CCC3(CC3)CC1)CN2C(=O)c1cc(C(=O)C2CCCC2)cs1] | N-(1''-(4-(cyclopentanecarbonyl)thiophene-2-carbonyl)dispiro[cyclopropane-1,1'-cyclohexane-4',3''-indolin]-5''-yl)methanesulfonamide |

TABLE 1-continued

| Compound No. | Structure | Name |
|---|---|---|
| Compound 364 | 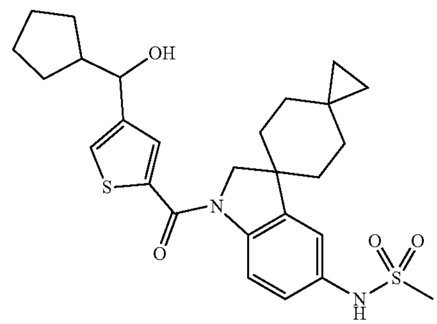 [SMILES: CS(=O)(=O)Nc1ccc2c(c1)C1(CCC3(CC3)CC1)CN2C(=O)c1cc(C(O)C2CCCC2)cs1] | N-(1''-(4-(cyclopentyl(hydroxy)methyl)thiophene-2-carbonyl)dispiro[cyclopropane-1,1'-cyclohexane-4',3''-indolin]-5''-yl)methanesulfonamide |
| Compound 365 | 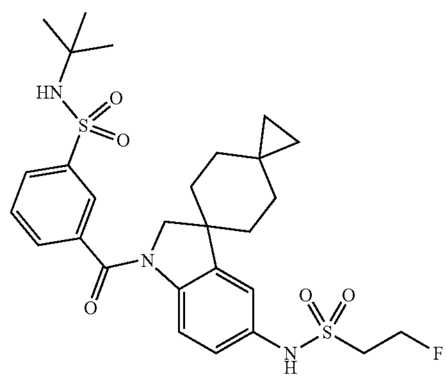 [SMILES: CC(C)(C)NS(=O)(=O)c1cccc(C(=O)N2CC3(CCC4(CC4)CC3)c3cc(NS(=O)(=O)CCF)ccc32)c1] | N-(tert-butyl)-3-(5''-((2-fluoroethyl)sulfonamido)dispiro[cyclopropane-1,1'-cyclohexane-4',3''-indoline]-1''-carbonyl)benzenesulfonamide |
| Compound 366 | 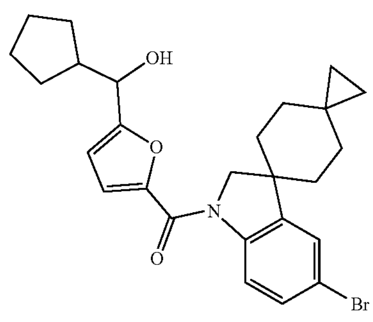 [SMILES: O=C(c1ccc(C(O)C2CCCC2)o1)N1CC2(CCC3(CC3)CC2)c2cc(Br)ccc21] | (5''-bromodispiro[cyclopropane-1,1'-cyclohexane-4',3''-indolin]-1''-yl)(5-(cyclopentyl(hydroxy)methyl)furan-2-yl)methanone |
| Compound 367 | 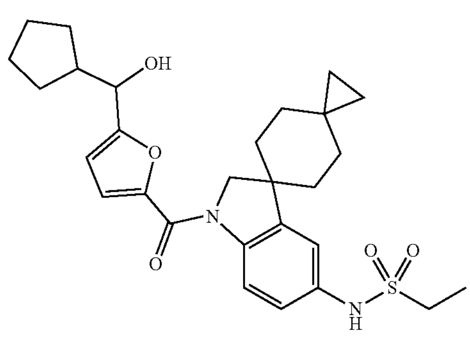 [SMILES: CCS(=O)(=O)Nc1ccc2c(c1)C1(CCC3(CC3)CC1)CN2C(=O)c1ccc(C(O)C2CCCC2)o1] | N-(1''-(5-(cyclopentyl(hydroxy)methyl)furan-2-carbonyl)dispiro[cyclopropane-1,1'-cyclohexane-4',3''-indolin]-5''-yl)ethanesulfonamide |

TABLE 1-continued

| Compound No. | Structure | Name |
|---|---|---|
| (R)-Compound 367 | 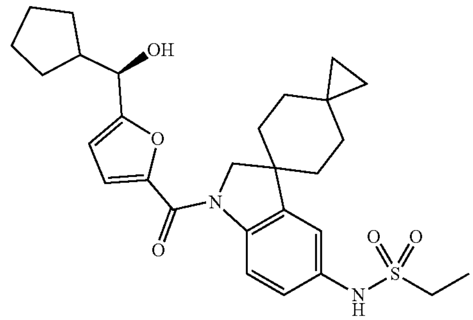 [SMILES: CCS(=O)(=O)Nc1ccc2c(c1)C1(CCC3(CC3)CC1)CN2C(=O)c1ccc([C@H](O)C2CCCC2)o1] | (R)-N-(1''-(5-(cyclopentyl(hydroxy)methyl)furan-2-carbonyl)dispiro[cyclopropane-1,1'-cyclohexane-4',3''-indolin]-5''-yl)ethanesulfonamide |
| (S)-Compound 367 | 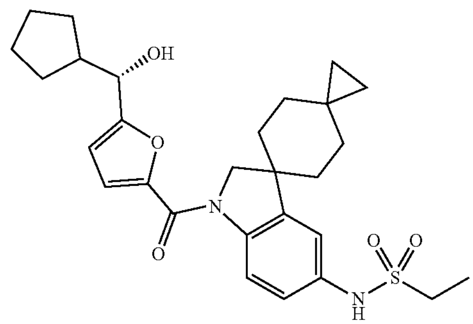 [SMILES: CCS(=O)(=O)Nc1ccc2c(c1)C1(CCC3(CC3)CC1)CN2C(=O)c1ccc([C@@H](O)C2CCCC2)o1] | (S)-N-(1''-(5-(cyclopentyl(hydroxy)methyl)furan-2-carbonyl)dispiro[cyclopropane-1,1'-cyclohexane-4',3''-indolin]-5''-yl)ethanesulfonamide |
| Compound 368 | 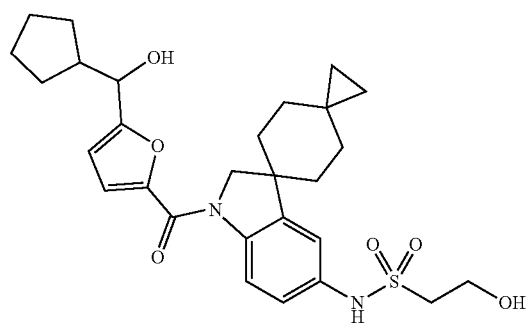 [SMILES: O=C(c1ccc(C(O)C2CCCC2)o1)N1CC2(CCC3(CC3)CC2)c2cc(NS(=O)(=O)CCO)ccc21] | N-(1''-(5-(cyclopentyl(hydroxy)methyl)furan-2-carbonyl)dispiro[cyclopropane-1,1'-cyclohexane-4',3''-indolin]-5''-yl)-2-hydroxyethane-1-sulfonamide |
| (R)-Compound 368 | 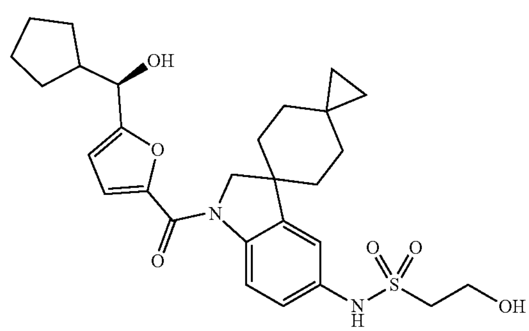 [SMILES: O=C(c1ccc([C@H](O)C2CCCC2)o1)N1CC2(CCC3(CC3)CC2)c2cc(NS(=O)(=O)CCO)ccc21] | (R)-N-(1''-(5-(cyclopentyl(hydroxy)methyl)furan-2-carbonyl)dispiro[cyclopropane-1,1'-cyclohexane-4',3''-indolin]-5''-yl)-2-hydroxyethane-1-sulfonamide |

TABLE 1-continued

| Compound No. | Structure | Name |
| --- | --- | --- |
| (S)-Compound 368 | 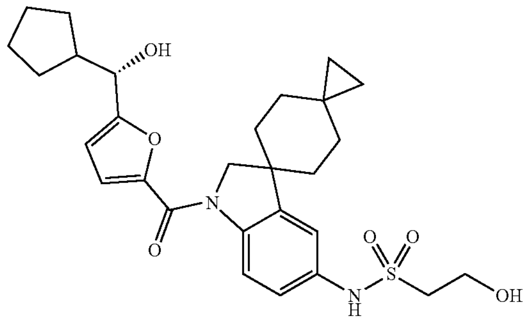 [SMILES: O=C(c1ccc([C@@H](O)C2CCCC2)o1)N1CC2(CCC3(CC3)CC2)c2cc(NS(=O)(=O)CCO)ccc21] | (S)-N-(1"-(5-(cyclopentyl(hydroxy)methyl)furan-2-carbonyl)dispiro[cyclopropane-1,1'-cyclohexane-4',3"-indolin]-5"-yl)-2-hydroxyethane-1-sulfonamide |
| Compound 369 | 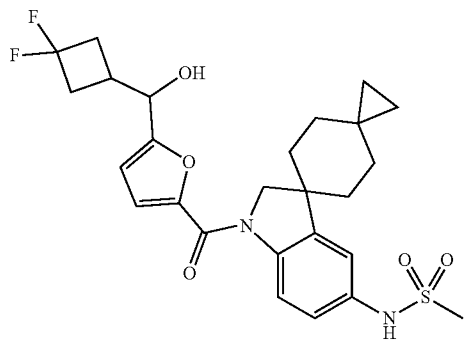 [SMILES: CS(=O)(=O)Nc1ccc2c(c1)C1(CCC3(CC3)CC1)CN2C(=O)c1ccc(C(O)C2CC(F)(F)C2)o1] | N-(1"-(5-((3,3-difluorocyclobutyl)(hydroxy)methyl)furan-2-carbonyl)dispiro[cyclopropane-1,1'-cyclohexane-4',3"-indolin]-5"-yl)methanesulfonamide |
| Compound 370 | 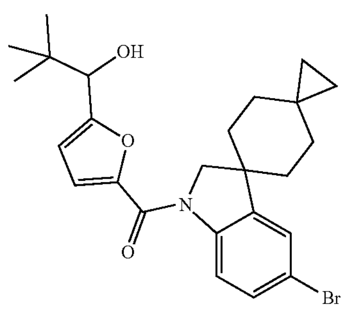 [SMILES: CC(C)(C)C(O)c1ccc(C(=O)N2CC3(CCC4(CC4)CC3)c3cc(Br)ccc32)o1] | (5"-bromodispiro[cyclopropane-1,1'-cyclohexane-4',3"-indolin]-1"-yl)(5-(1-hydroxy-2,2-dimethylpropyl)furan-2-yl)methanone |
| Compound 371 | 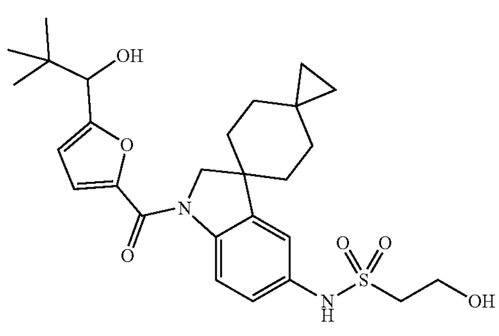 [SMILES: CC(C)(C)C(O)c1ccc(C(=O)N2CC3(CCC4(CC4)CC3)c3cc(NS(=O)(=O)CCO)ccc32)o1] | 2-hydroxy-N-(1"-(5-(1-hydroxy-2,2-dimethylpropyl)furan-2-carbonyl)dispiro[cyclopropane-1,1'-cyclohexane-4',3"-indolin]-5"-yl)ethane-1-sulfonamide |

TABLE 1-continued

| Compound No. | Structure | Name |
|---|---|---|
| (R)-Compound 371 | 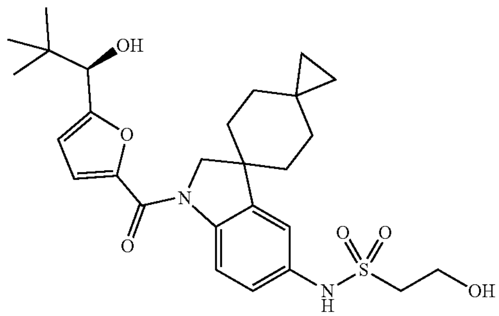 [SMILES: CC(C)(C)[C@@H](O)c1ccc(C(=O)N2CC3(CCC4(CC4)CC3)c3cc(NS(=O)(=O)CCO)ccc32)o1] | (R)-2-hydroxy-N-(1''-(5-(1-hydroxy-2,2-dimethylpropyl)furan-2-carbonyl)dispiro[cyclopropane-1,1'-cyclohexane-4',3''-indolin]-5''-yl)ethane-1-sulfonamide |
| (S)-Compound 371 | 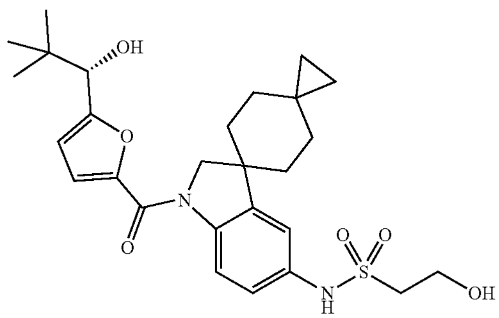 [SMILES: CC(C)(C)[C@H](O)c1ccc(C(=O)N2CC3(CCC4(CC4)CC3)c3cc(NS(=O)(=O)CCO)ccc32)o1] | (S)-2-hydroxy-N-(1''-(5-(1-hydroxy-2,2-dimethylpropyl)furan-2-carbonyl)dispiro[cyclopropane-1,1'-cyclohexane-4',3''-indolin]-5''-yl)ethane-1-sulfonamide |
| Compound 372 | 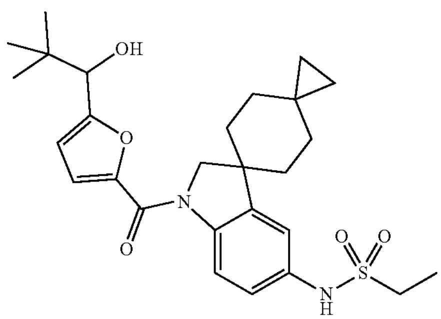 [SMILES: CCS(=O)(=O)Nc1ccc2c(c1)C1(CCC3(CC3)CC1)CN2C(=O)c1ccc(C(O)C(C)(C)C)o1] | N-(1''-(5-(1-hydroxy-2,2-dimethylpropyl)furan-2-carbonyl)dispiro[cyclopropane-1,1'-cyclohexane-4',3''-indolin]-5''-yl)ethanesulfonamide |
| (R)-Compound 372 | 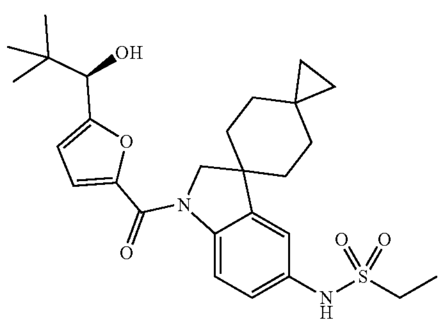 [SMILES: CCS(=O)(=O)Nc1ccc2c(c1)C1(CCC3(CC3)CC1)CN2C(=O)c1ccc([C@H](O)C(C)(C)C)o1] | (R)-N-(1''-(5-(1-hydroxy-2,2-dimethylpropyl)furan-2-carbonyl)dispiro[cyclopropane-1,1'-cyclohexane-4',3''-indolin]-5''-yl)ethanesulfonamide |
| (S)-Compound 372 | 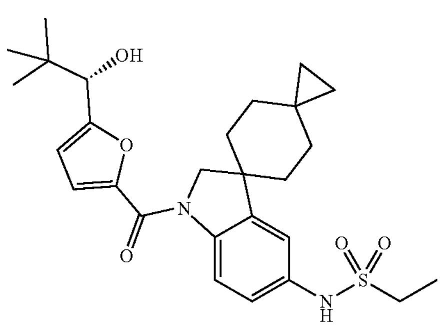 [SMILES: CCS(=O)(=O)Nc1ccc2c(c1)C1(CCC3(CC3)CC1)CN2C(=O)c1ccc([C@@H](O)C(C)(C)C)o1] | (S)-N-(1''-(5-(1-hydroxy-2,2-dimethylpropyl)furan-2-carbonyl)dispiro[cyclopropane-1,1'-cyclohexane-4',3''-indolin]-5''-yl)ethanesulfonamide |

TABLE 1-continued

| Compound No. | Structure | Name |
|---|---|---|
| Compound 373 | 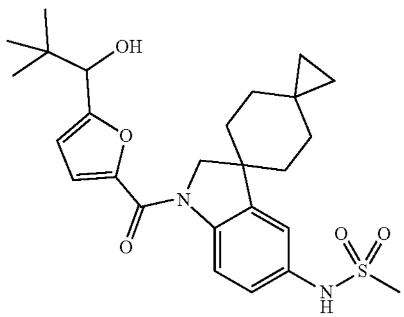 [SMILES: CC(C)(C)C(O)c1ccc(C(=O)N2CC3(CCC4(CC4)CC3)c3cc(NS(C)(=O)=O)ccc32)o1] | N-(1''-(5-(1-hydroxy-2,2-dimethylpropyl)furan-2-carbonyl)dispiro[cyclopropane-1,1'-cyclohexane-4',3''-indolin]-5''-yl)methanesulfonamide |
| (R)-Compound 373 | 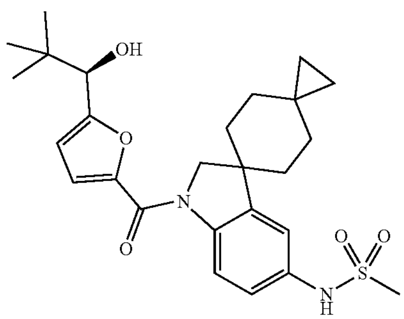 [SMILES: CC(C)(C)[C@@H](O)c1ccc(C(=O)N2CC3(CCC4(CC4)CC3)c3cc(NS(C)(=O)=O)ccc32)o1] | (R)-N-(1''-(5-(1-hydroxy-2,2-dimethylpropyl)furan-2-carbonyl)dispiro[cyclopropane-1,1'-cyclohexane-4',3''-indolin]-5''-yl)methanesulfonamide |
| (S)-Compound 373 | 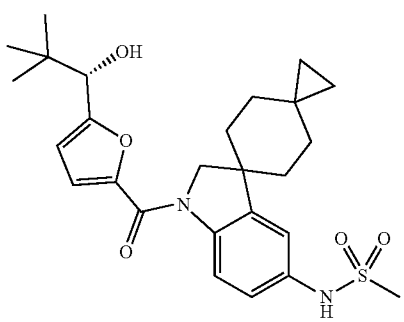 [SMILES: CC(C)(C)[C@H](O)c1ccc(C(=O)N2CC3(CCC4(CC4)CC3)c3cc(NS(C)(=O)=O)ccc32)o1] | (S)-N-(1''-(5-(1-hydroxy-2,2-dimethylpropyl)furan-2-carbonyl)dispiro[cyclopropane-1,1'-cyclohexane-4',3''-indolin]-5''-yl)methanesulfonamide |

In some embodiments, provided herein are compounds and salts thereof described in Table 2. In some embodiments, compounds described herein are not compounds of Table 2.

TABLE 2

| Compound No. | Structure | Name |
|---|---|---|
| Compound 1' | 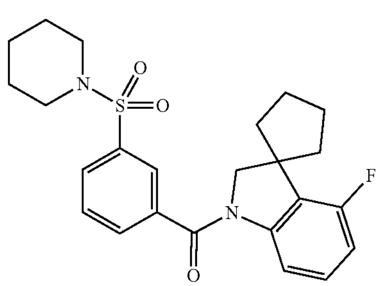 [SMILES: O=C(c1cccc(S(=O)(=O)N2CCCCC2)c1)N1CC2(CCCC2)c2c(F)cccc21] | (4'-fluorospiro[cyclopentane-1,3'-indolin]-1'-yl)(3-(piperidin-1-ylsulfonyl)phenyl)methanone |

TABLE 2-continued

| Compound No. | Structure | Name |
|---|---|---|
| Compound 2' | 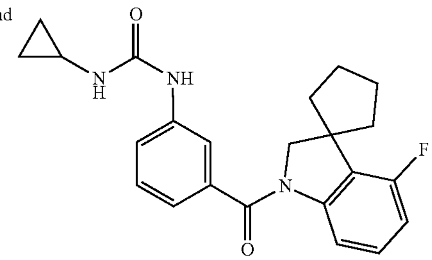 | 1-cyclopropyl-3-(3-(4'-fluorospiro[cyclopentane-1,3'-indolin]-1'-carbonyl)phenyl)urea |
| Compound 3' | 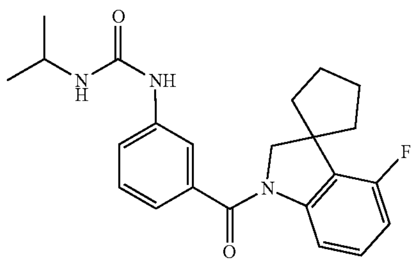 [SMILES: CC(C)NC(=O)Nc1cccc(C(=O)N2CC3(CCCC3)c3c(F)cccc32)c1] | 1-(3-(4'-fluorospiro[cyclopentane-1,3'-indolin]-1'-carbonyl)phenyl)-3-isopropylurea |
| Compound 4' | 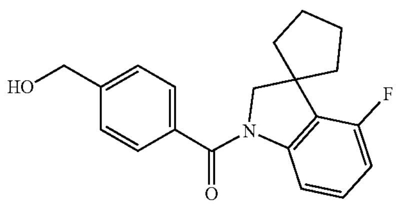 [SMILES: O=C(c1ccc(CO)cc1)N1CC2(CCCC2)c2c(F)cccc21] | (4'-fluorospiro[cyclopentane-1,3'-indolin]-1'-yl)(4-(hydroxymethyl)phenyl)methanone |
| Compound 5' | 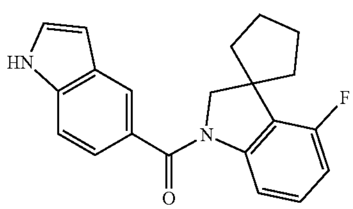 [SMILES: O=C(c1ccc2[nH]ccc2c1)N1CC2(CCCC2)c2c(F)cccc21] | (4'-fluorospiro[cyclopentane-1,3'-indolin]-1'-yl)(1H-indol-5-yl)methanone |
| Compound 6' | 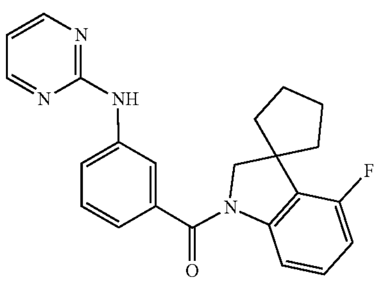 [SMILES: O=C(c1cccc(Nc2ncccn2)c1)N1CC2(CCCC2)c2c(F)cccc21] | (4'-fluorospiro[cyclopentane-1,3'-indolin]-1'-yl)(3-(pyrimidin-2-ylamino)phenyl)methanone |
| Compound 7' | 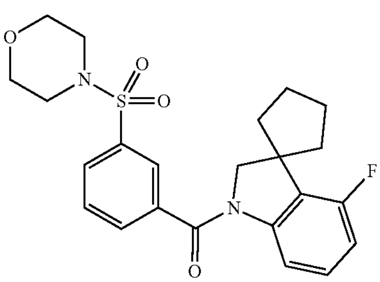 [SMILES: O=C(c1cccc(S(=O)(=O)N2CCOCC2)c1)N1CC2(CCCC2)c2c(F)cccc21] | (4'-fluorospiro[cyclopentane-1,3'-indolin]-1'-yl)(3-(morpholinosulfonyl)phenyl)methanone |

TABLE 2-continued

| Compound No. | Structure | Name |
|---|---|---|
| Compound 8' | [structure: 3-ureidophenyl group connected via carbonyl to N of 4-fluorospiro[cyclopentane-1,3'-indoline]] | 1-(3-(4'-fluorospiro[cyclopentane-1,3'-indolin]-1'-carbonyl)phenyl)urea |

In some variations, any of the compounds described herein, such as a compound of Formula (I), (I-1), (I-2), (I-3), (Ia1), (Ia2), or (II), or any variation thereof, or a compound of Table 1 or 2 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (I), (I-1), (I-2), (I-3), (Ia1), (Ia2), or (II), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of ring A, ring B, ring C, $R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$, $R^{a12}$, $R^{a13}$, $R^{a14}$, $R^{a15}$, $R^{a16}$, $R^{a17}$, $R^{a18}$, $R^{a19}$, $R^{a20}$, $R^{a21}$, $R^{a22}$, $R^{a23}$, $R^{a24}$, $R^{a25}$, $R^{a26}$, $R^{a27}$, $R^{a28}$, $R^{a29}$, $R^{a30}$, $R^{a31}$, $R^{a32}$, $R^{a33}$, $R^{a34}$, $R^{a35}$, $R^{a36}$, $R^{a37}$, $R^{a38}$, $R^{a39}$, $R^{a40}$, $R^{1a1}$, $R^{1a2}$, $R^{1a3}$, $R^{1a4}$, $R^B$, m, X, $Y^1$, $Y^2$, $Y^3$, $Y^4$, $Z^1$, $Z^2$, $Z^3$, $Z^4$, $Z^5$, $Z^6$, $Z^7$, $Z^8$, $R^{C1}$, $R^{C2}$, $R^{C3}$, $R^{C4}$, $R^{c1}$, $R^{c2}$, $R^{c3}$, $R^{c4}$, $R^{c5}$, $R^{c6}$, $R^{c7}$, $R^{c8}$, $R^{c9}$, $R^{c10}$, $R^{c11}$, $R^{c12}$, $R^{c13}$, $R^{c14}$, $R^{c15}$, $R^{c16}$, $R^{c17}$, $R^{c18}$, $R^{c19}$, $R^D$, $R^E$, or $R^F$ provided herein can be combined with every other variation or embodiment of ring A, ring B, ring C, $R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$, $R^{a12}$, $R^{a13}$, $R^{a14}$, $R^{a15}$, $R^{a16}$, $R^{a17}$, $R^{a18}$, $R^{a19}$, $R^{a20}$, $R^{a21}$, $R^{a22}$, $R^{a23}$, $R^{a24}$, $R^{a25}$, $R^{a26}$, $R^{a27}$, $R^{a28}$, $R^{a29}$, $R^{a30}$, $R^{a31}$, $R^{a32}$, $R^{a33}$, $R^{a34}$, $R^{a35}$, $R^{a36}$, $R^{a37}$, $R^{a38}$, $R^{a39}$, $R^{a40}$, $R^{1a1}$, $R^{1a2}$, $R^{1a3}$, $R^{1a4}$, $R^B$, m, X, Y, $Y^2$, $Y^3$, $Y^4$, $Z^1$, $Z^2$, $Z^3$, $Z^4$, $Z^5$, $Z^6$, $Z^7$, $Z^8$, $R^{C1}$, $R^{C2}$, $R^{C3}$, $R^{C4}$, $R^{c1}$, $R^{c2}$, $R^{c3}$, $R^{c4}$, $R^{c5}$, $R^{c6}$, $R^{c7}$, $R^{c8}$, $R^{c9}$, $R^{c10}$, $R^{c11}$, $R^{c12}$, $R^{c13}$, $R^{c14}$, $R^{c15}$, $R^{c16}$, $R^{c17}$, $R^{c18}$, $R^{c19}$, $R^D$, $R^E$, or $R^F$, the same as if each and every combination had been individually and specifically described.

As used herein, when any variable occurs more than one time in a chemical formula, its definition on each occurrence is independent of its definition at every other occurrence.

Compound names provided herein, including in Table 1 and Table 2, are provided by Chemaxon Marvin Structure to Name 20 or ChemDraw Professional 20. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (I), (I-1), (I-2), (I-3), (Ia1), (Ia2), or (II), or a compound of Table 1 or 2, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds that are substantially pure.

Also provided are packaged pharmaceutical compositions, comprising a pharmaceutical composition as described herein and instructions for using the composition to treat a patient suffering from a disease or condition described herein.

Methods of Use

As described herein, the compounds of the present disclosure are inhibitors of KIF18A. In one aspect, the compounds and pharmaceutical compositions herein may be used to inhibit KIF18A. In another aspect, the compounds and pharmaceutical compositions herein may be used to treat or prevent a disease or condition in an individual.

The inhibitory activity of the compounds described herein against KIF18A may be determined and measured by methods known in the art including, but not limited to, inhibition of ATP hydrolysis in the presence of microtubules (Hackney D. D., Jiang W. (2001) Assays for Kinesin Microtubule-Stimulated ATPase Activity. In: Vernos I. (eds) Kinesin Protocols. Methods in Molecular Biology™, vol 164. Humana Press. https://doi.org/10.1385/1-59259-069-1:65).

In one aspect, provided herein is a method of inhibiting KIF18A comprising contacting a cell with an effective amount of a compound or a pharmaceutical composition as described herein. In some embodiments, provided herein are methods of inhibiting KIF18A comprising contacting a cell with an effective amount of a compound of Formula (I), (I-1), (I-2), (I-3), (Ia1), (Ia2) or (II), or a compound of Table 1 or 2, or a pharmaceutically acceptable salt thereof. In some embodiments, provided herein are methods of inhibiting KIF18A comprising contacting a cell with an effective amount of a pharmaceutical composition comprising a compound of Formula (I), (I-1), (I-2), (I-3), (Ia1), (Ia2) or (II) or a compound of Table 1 or 2, or a pharmaceutically acceptable salt thereof. In one variations of the aforementioned embodiments, the cell is contacted in vitro. In other variations of the aforementioned embodiments, the cell is contacted in vivo.

In another aspect, the compounds and pharmaceutical compositions herein may be used to treat or prevent a disease or condition in an individual, comprising administering an effective amount of a compound or a pharmaceutical composition as described herein. When used in a prophylactic manner, the compounds disclosed and/or described herein may prevent a disease or disorder from developing in an individual at risk of developing the disease or disorder, or lessen the extent of a disease or disorder that may develop.

In some embodiments, provided herein are methods of treating or preventing a disease or condition in an individual, comprising administering to the subject a therapeutically effective amount of a compound or a pharmaceutical composition as described herein. In some embodiments, provided herein are methods of treating or preventing a disease or condition in an individual, comprising administering to the subject a therapeutically effective amount of a compound Formula (I), (I-1), (I-2), (I-3), (Ia1), (Ia2) or (II), or a compound of Table 1 or 2, or a pharmaceutically acceptable salt thereof. In some embodiments, provided herein are methods of treating or preventing a disease or condition in an individual, comprising administering to the subject a therapeutically effective amount of a pharmaceutical composition comprising a compound a compound Formula (I), (I-1), (I-2), (I-3), (Ia1), (Ia2) or (II), or a compound of Table 1 or 2, or a pharmaceutically acceptable salt thereof.

In some embodiments, the disease or condition is mediated by KIF18A. In some embodiments, the disease or condition is cancer. In some embodiments, the disease or condition is a cellular proliferation disorder, including uncontrolled cell growth, aberrant cell cycle regulation, centrosome abnormalities (structural and or numeric, fragmentation), a solid tumor, hematopoietic cancer and hyperproliferative disorder, such as thyroid hyperplasia (especially Grave's disease), and cyst (such as hypervascularity of ovarian stroma, characteristic of polycystic ovarian syndrome (Stein-Leventhal syndrome). Solid and hematologically derived tumors, such as carcinomas, may include but are not limited to cancer of the anus, bladder, breast, colon, small intestine, appendix, kidney, renal pelvis, ureter, urothelium, liver, lung (including squamous cell and small cell lung cancer), pleura, esophagus, head and neck, nasopharynx, oropharynx, hypopharynx, oral cavity, larynx, biliary tract, gall-bladder, ovary, testicle, germ cell, uterus, pancreas, stomach, cervix, thyroid, prostate, salivary gland, and skin (including squamous cell carcinoma), hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma), hematopoietic tumors of myeloid lineage (including acute and chronic myelogenous leukemias, myelodysplastic syndrome and promyelocytic leukemia), hematopoietic tumors of any lineage, myeloma, tumors of mesenchymal origin (including fibrosarcoma and rhabdomyosarcoma, and other sarcomas, e.g., soft tissue and bone), tumors of the central and peripheral nervous system (including astrocytoma, neuroblastoma, glioma and schwannomas), tumor of neuroendocrine origin, tumor of endocrine origin, small cell tumors, tumors of unknown primary, other tumors (including retinoblastoma, melanoma, seminoma, teratocarcinoma, osteosarcoma, xenoderoma pigmentosum, keratoctanthoma, thyroid follicular cancer, Ewing's sarcoma, Kaposi's sarcoma), and other cancer-related disorders that are a consequence of cancer presence or progression such as tumor-induced pleural or pericardial effusions, and malignant ascites.

In some embodiments, provided are methods of treating or preventing cancer in an individual, comprising administering to the individual in need thereof a compound of Formula Formula (I), (I-1), (I-2), (I-3), (Ia1), (Ia2) or (II), or a compound of Table 1 or 2, or a pharmaceutically acceptable salt thereof. In some embodiments, provided are methods of treating or preventing cancer in a subject in need thereof comprising administering to the subject a therapeutically effective amount of at least one chemical entity as described herein. Also provided herein is the use of a compound of Formula (I), (I-1), (I-2), (I-3), (Ia1), (Ia2) or (II), or a compound of Table 1 or 2, or a pharmaceutically acceptable salt thereof in the manufacture of a medicament for treatment of a disease in a subject.

In some embodiments, provided herein are methods of treating cancer, comprising administering to an individual in need thereof a compound of Formula (I), (I-1), (I-2), (I-3), (Ia1), (Ia2) or (II), or a compound of Table 1 or 2, or a pharmaceutically acceptable salt thereof. Also provided herein is the use of a compound of Formula (I), (I-1), (I-2), (I-3), (Ia1), (Ia2) or (II), or a compound of Table 1 or 2, or a pharmaceutically acceptable salt thereof in the manufacture of a medicament for treatment of a cancer.

In some embodiments, provided herein are methods of treating a disease or condition mediated by KIF18A in a subject in need thereof, comprising administering to the subject a therapeutically effective amount of a compound or a pharmaceutical composition as described herein.

In some embodiments, provided herein are methods of treating cancer in a subject in need thereof, comprising administering to the subject a therapeutically effective amount of a compound or a pharmaceutical composition as described herein. In some embodiments, the cancer is selected from the group consisting of carcinomas, cancer of the anus, bladder, breast, colon, small intestine, appendix, kidney, renal pelvis, ureter, urothelium, liver, lung, pleura, esophagus, head and neck, nasopharynx, oropharynx, hypopharynx, oral cavity, larynx, biliary tract, gall-bladder, ovary, testicle, germ cell, uterus, pancreas, stomach, cervix, thyroid, prostate, salivary gland, or skin, hematopoietic tumors of lymphoid lineage, hematopoietic tumors of myeloid lineage, hematopoietic tumors of any lineage, myeloma, tumors of mesenchymal origin including sarcomas, tumors of the central and peripheral nervous system, tumor of neuroendocrine origin, tumor of endocrine origin, small cell tumors, tumors of unknown primary, other tumors comprising retinoblastoma, melanoma, seminoma, teratocarcinoma, osteosarcoma, and other cancer-related disorders that are a consequence of cancer presence or progression.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of any disease or condition described herein in an individual in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders.

The compounds and compositions described and/or disclosed herein may be combined with one or more other therapies to treat the diseases or conditions described herein. In some embodiments, the disease or condition is cancer. In some embodiments, the disease or condition is a cellular proliferation disorder, including uncontrolled cell growth, aberrant cell cycle regulation, centrosome abnormalities (structural and or numeric, fragmentation), a solid tumor, hematopoietic cancer and hyperproliferative disorder, such as thyroid hyperplasia (especially Grave's disease), and cyst (such as hypervascularity of ovarian stroma, characteristic of polycystic ovarian syndrome (Stein-Leventhal syndrome). Solid and hematologically derived tumors, such as carcinomas, may include but are not limited to cancer of the anus, bladder, breast, colon, small intestine, appendix, kidney, renal pelvis, ureter, urothelium, liver, lung (including squamous cell and small cell lung cancer), pleura, esophagus, head and neck, nasopharynx, oropharynx, hypopharynx, oral cavity, larynx, biliary tract, gall-bladder, ovary, testicle, germ cell, uterus, pancreas, stomach, cervix, thyroid, prostate, salivary gland, and skin (including squamous cell carcinoma), hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma), hematopoietic tumors of myeloid lineage (including acute and chronic myelogenous leukemias, myelodysplastic syndrome and promyelocytic leukemia), hematopoietic tumors of any lineage, myeloma, tumors of mesenchymal origin (including fibrosarcoma and rhabdomyosarcoma, and other sarcomas, e.g., soft tissue and bone), tumors of the central and peripheral nervous system (including astrocytoma, neuroblastoma, glioma and schwannomas), tumor of neuroendocrine origin, tumor of endocrine origin, small cell tumors, tumors of unknown primary, other tumors (including retinoblastoma, melanoma, seminoma, teratocarcinoma, osteosarcoma, xenoderoma pigmentosum, keratoctanthoma, thyroid follicular cancer, Ewing's sarcoma, Kaposi's sarcoma), and other cancer-related disorders that are a consequence of cancer presence or progression such as tumor-induced pleural or pericardial effusions, and malignant ascites.

General Synthetic Methods

Compounds of Formula (I), (I-1), (I-2), (I-3), (Ia1), (Ia2), or (II) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I), (I-1), (I-2), (I-3), (Ia1), (Ia2), or (II).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (I-1), (I-2), (I-3), (Ia1), (Ia2), or (II), or any variation thereof. Other compounds described herein may be prepared by similar methods.

In some embodiments, compounds provided herein may be synthesized according to Scheme 1, Scheme 2, Scheme 3, and/or Scheme 4. Ring A, Ring B, $Y^1$, $Y^2$, $Y^3$, $Y^4$, m, $R^B$ and $R^C$, as shown in Schemes 1-4 below, are as defined for the compounds of Formula I.

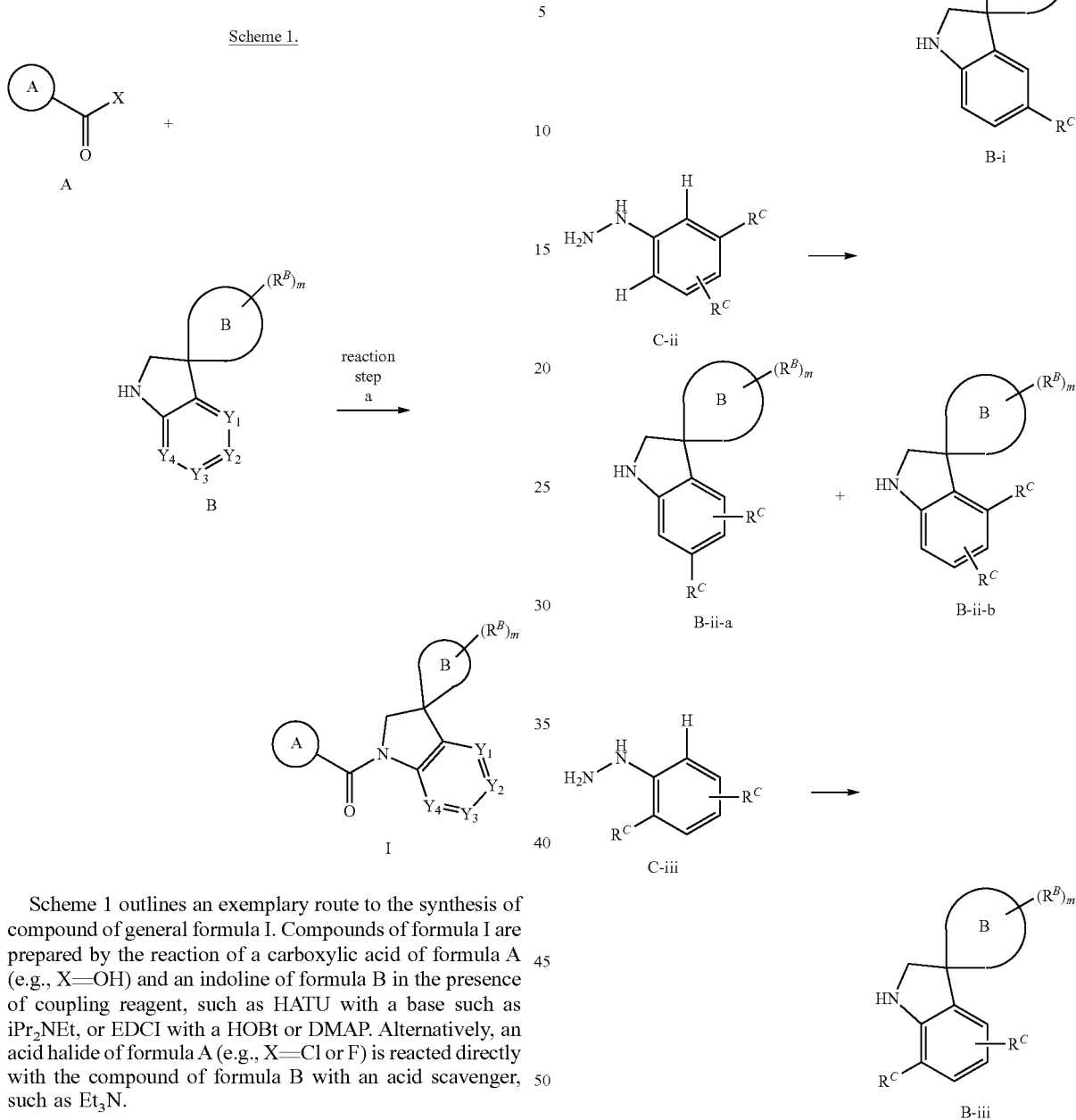

Scheme 1 outlines an exemplary route to the synthesis of compound of general formula I. Compounds of formula I are prepared by the reaction of a carboxylic acid of formula A (e.g., X=OH) and an indoline of formula B in the presence of coupling reagent, such as HATU with a base such as iPr$_2$NEt, or EDCI with a HOBt or DMAP. Alternatively, an acid halide of formula A (e.g., X=Cl or F) is reacted directly with the compound of formula B with an acid scavenger, such as Et$_3$N.

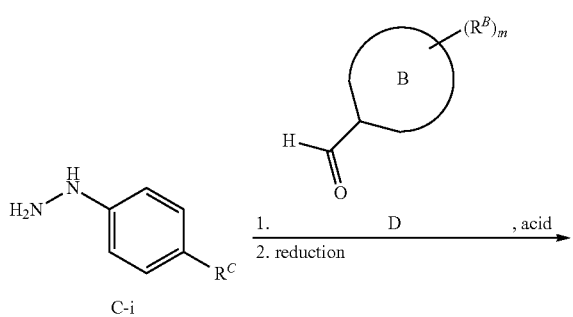

Indoline intermediates of formula B may be prepared via the Fisher Indole Synthesis as described in Scheme 2. Arylhydrazines of formula C (e.g., formula C-i, formula C-ii, and formula C-iii) are reacted with a Ring B-substituted carbaldehyde of formula D in the presence of acid, followed by reaction with a reducing agent such as NaBH$_4$, Pd/C and H$_2$ gas, or Et$_3$SiH. Arylhydrazines of formula C-i, which are para-mono-substituted, provide indolines of formula B-i, while hydrazines of formula C-ii, which contain at least one meta substituent and are not substituted in the ortho positions, provide a mixture of indolines of formulae B-ii-a and B-ii-b. Arylhydrazines of formula C-iii, that are substituted at one ortho position, provide indolines of formula B-iii.

Scheme 3.

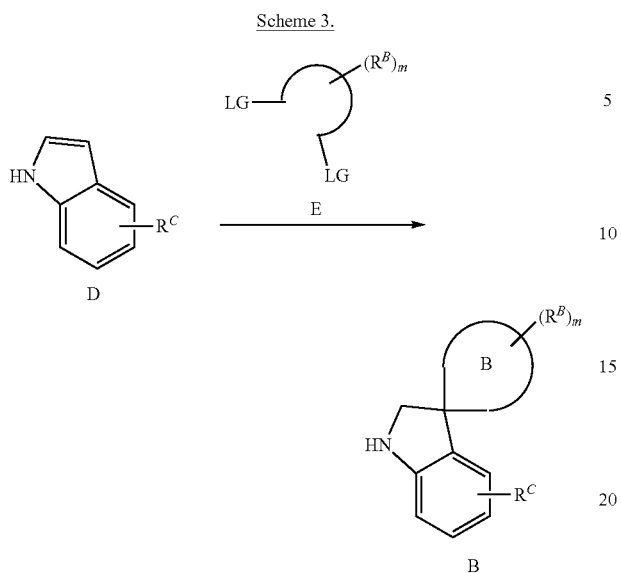

Indolines of formula B may also be prepared via an 3,3-dialkylation method described in Scheme 3. An indole of formula D is reacted with an optionally substituted 3-6 atom aliphatic and heteroaliphatic linear chain with two terminal leaving groups "LG" (formula E). LG may be Cl, Br, I, or sulfonate ester, or another suitable group displaceable by a nucleophile. The transformation may be mediated by a trialkylboron, such as $Et_3B$, and base, such as potassium t-butoxide. The spiroannulation reaction is followed by a reaction with a reducing agent such as $NaBH_4$, Pd/C and $H_2$ gas, or $Et_3SiH$.

Scheme 4.

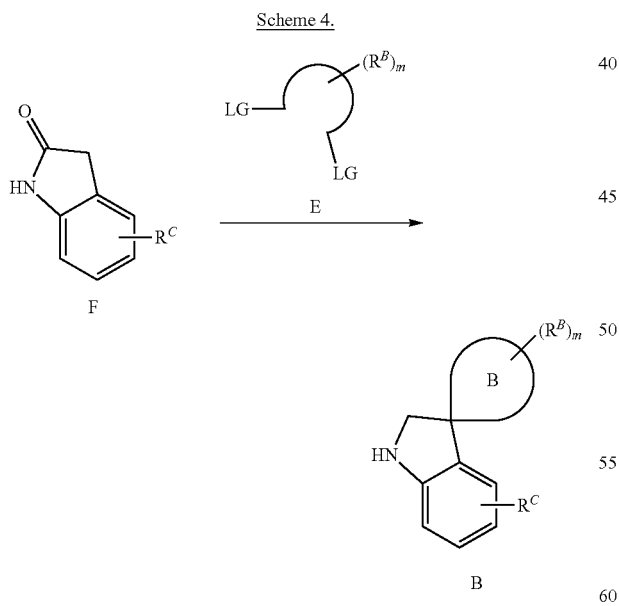

Indolines of formula B may also be prepared via the enolate alkylation of an indolin-2-one of formula F. The indolin-2-one of formula F is deprotonated with a strong base, such as butyllithium, sodium hexamethylsilazide, or potassium t-butoxide, and reacted with an optionally substituted 3-6 atom aliphatic and heteroaliphatic linear chain with two terminal leaving groups "LG" (formula E). LG may be Cl, Br, I, or sulfonate ester, or another suitable group displaceable by a nucleophile. This reaction may be mediated by an additive such as tetramethyldiaminoethane or hexamethylphosphorous triamide. The spiroannulation reaction is followed by a reaction with a reducing agent such as $LiAlH_4$ or borane.

ENUMERATED EMBODIMENTS

The following enumerated embodiments are representative of some aspects of the invention.

1. A compound of Formula (I)

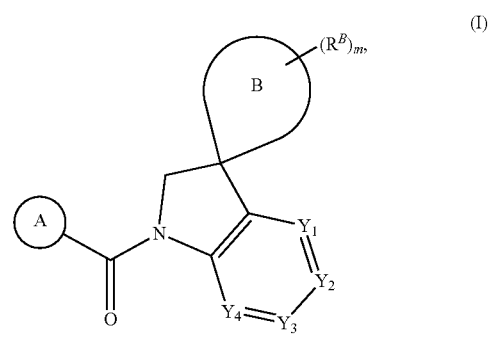

(I)

or a pharmaceutically acceptable salt thereof, wherein:
  ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —$NR^{a1}C(O)NR^{a2}R^{a3}$, —$NR^{a4}C(O)OR^{a5}$, —$NR^{a6}R^{a7}$, —$N=S(O)R^{a8}R^{a9}$, —$OR^{a10}$, —$S(O)R^{a11}$, —$S(O)(NR^{a12})R^{a13}$, —$S(O)_2NR^{a14}R^{a15}$, —$S(O)_2R^{a15}$, and —$(CR^{a17}R^{a18})_{0-1}C(O)NR^{a19}R^{a20}$;
  $R^{a1}$-$R^{a20}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl $C_{6-14}$ aryl, or 5- to 12-membered heteroaryl, each optionally substituted with one or more substituents independently selected from the group consisting of halo, cyano, —OH, —$O(C_{1-6}$ alkyl), $C_{2-6}$ alkenyl, $C_{3-10}$ cycloalkyl, —$S(C_{1-6}$ alkyl), =$CR^{1a1}R^{1a2}$, and $C_{1-6}$ alkyl optionally substituted with one or more substituents independently selected from the group consisting of halo, —OH, and —$O(C_{1-6}$ alkyl), wherein $R^{1a1}$ and $R^{1a2}$ are each independently hydrogen or $C_{1-6}$ alkyl;
  ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;
  each $R^B$ group is independently halo, $C_{1-6}$ alkyl, or $C_{2-6}$ alkenyl; or two vicinal $R^B$ groups are taken together with the carbon atoms to which they are attached to form $C_{3-10}$ cycloalkyl; or two geminal $R^B$ groups are taken together with the carbon atom to which they are attached to form $C_{3-10}$ cycloalkyl;
  m is 0, 1, 2, 3, or 4;
  $Y^1$ is N or $CR^{C1}$;
  $Y^2$ is N or $CR^{C2}$;
  $Y^3$ is N or $CR^{C3}$;
  $Y^4$ is N or $CR^{C4}$;
  wherein no more than three of $Y^1$, $Y^2$, $Y^3$, and $Y^4$ are N;

$R^{C1}$-$R^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$—S(O)$_2$R$^{c13}$, or C$_{1-6}$ alkyl optionally substituted with one or more substituents independently selected from the group consisting of halo and —OH;

R$^{c1}$-R$^{c13}$ are each independently hydrogen, C$_{3-10}$ cycloalkyl, or C$_{1-6}$ alkyl optionally substituted with one or more substituents independently selected from the group consisting of halo and —OH.

2. The compound of embodiment 1, or a pharmaceutically acceptable salt thereof, wherein the compound is not 4'-fluoro-1'-[3-(piperidine-1-sulfonyl)benzoyl]-1',2'-dihydrospiro[cyclopentane-1,3'-indole]; 3-cyclopropyl-1-[3-({4'-fluoro-1',2'-dihydrospiro[cyclopentane-1,3'-indol]-1'-yl}carbonyl)phenyl]urea; 1-[3-({4'-fluoro-1',2'-dihydrospiro[cyclopentane-1,3'-indol]-1'-yl}carbonyl)phenyl]-3-(propan-2-yl)urea; [4-({4'-fluoro-1',2'-dihydrospiro[cyclopentane-1,3'-indol]-1'-yl}carbonyl)phenyl]methanol; 4'-fluoro-1'-(1H-indole-5-carbonyl)-1',2'-dihydrospiro[cyclopentane-1,3'-indole]; N-[3-({4'-fluoro-1',2'-dihydrospiro[cyclopentane-1,3'-indol]-1'-yl}carbonyl)phenyl]pyrimidin-2-amine; 4'-fluoro-1'-[3-(morpholine-4-sulfonyl)benzoyl]-1',2'-dihydrospiro[cyclopentane-1,3'-indole]; [3-({4'-fluoro-1',2'-dihydrospiro[cyclopentane-1,3'-indol]-1'-yl}carbonyl)phenyl]urea; or salt of any of the foregoing.

3. The compound of embodiment 1 or 2, or a pharmaceutically acceptable salt thereof, wherein ring A is optionally substituted C$_{6-14}$ aryl.

4. The compound of embodiment 3, or a pharmaceutically acceptable salt thereof, wherein ring A is optionally substituted phenyl.

5. The compound of embodiment 1 or 2, or a pharmaceutically acceptable salt thereof, wherein ring A is optionally substituted 5- to 10-membered heteroaryl.

6. The compound of embodiment 5, or a pharmaceutically acceptable salt thereof, wherein ring A is indolyl, indazolyl, pyridinyl, thiophenyl, furanyl, pyrazolyl, pyrrolyl, oxazolyl, chromanyl, or quinolinyl, each optionally substituted.

7. The compound of any one of embodiments 1-6, or a pharmaceutically acceptable salt thereof, wherein R$^{a1}$ is hydrogen or C$_{1-6}$ alkyl; R$^{a2}$ and R$^{a3}$ are each independently hydrogen, C$_{1-6}$ alkyl, or C$_{3-10}$ cycloalkyl; R$^{a4}$ is hydrogen or C$_{1-6}$ alkyl; R$^{a5}$ is hydrogen or C$_{1-6}$ alkyl; R$^{a6}$ and R$^{a7}$ are each independently hydrogen, C$_{1-6}$ alkyl, or 5- to 12-membered heteroaryl optionally substituted with C$_{1-6}$ alkyl; R$^{a8}$ and R$^{a9}$ are each independently hydrogen, C$_{1-6}$ alkyl, or C$_{3-10}$ cycloalkyl; R$^{a10}$ is C$_{3-10}$ cycloalkyl; R$^{a11}$ is C$_{3-10}$ cycloalkyl; R$^{a12}$ is hydrogen or C$_{1-6}$ alkyl; R$^{a13}$ is C$_{3-10}$ cycloalkyl; R$^{a16}$ is C$_{3-10}$ cycloalkyl or 3- to 12-membered heterocycloalkyl optionally substituted with one or more substituents independently selected from the group consisting of C$_{1-6}$ alkyl or halo; R$^{a17}$ and R$^{a18}$ are each independently hydrogen or C$_{1-6}$ alkyl; and R$^{a19}$ and R$^{a20}$ are each independently hydrogen, C$_{1-6}$ alkyl, or C$_{3-10}$ cycloalkyl.

8. The compound of any one of embodiments 1-7, or a pharmaceutically acceptable salt thereof, wherein R$^{a14}$ and R$^{a15}$ are each independently hydrogen; C$_{1-6}$ alkyl optionally substituted with one or more substituents independently selected from the group consisting of C$_{1-6}$ alkyl, C$_{2-6}$ alkenyl, C$_{3-10}$ cycloalkyl, —OH, —O(C$_{1-6}$ alkyl), —S(C$_{1-6}$ alkyl), and halo; C$_{2-6}$ alkenyl; C$_{3-10}$ cycloalkyl optionally substituted with one or more substituents independently selected from the group consisting of C$_{2-6}$ alkenyl, C$_{3-10}$ cycloalkyl, halo, cyano, —OH, —O(C$_{1-6}$ alkyl), =CR$^{1a1}$R$^{1a2}$, and C$_{1-6}$ alkyl optionally substituted with one or more substituents independently selected from the group consisting of —OH, —O(C$_{1-6}$ alkyl), and halo, wherein R$^{1a1}$ and R$^{1a2}$ are each independently hydrogen or C$_{1-6}$ alkyl; C$_{3-10}$ cycloalkenyl; or 3- to 12-membered heterocycloalkyl optionally substituted with one or more C$_{1-6}$ alkyl.

9. The compound of any one of embodiments 1-8, or a pharmaceutically acceptable salt thereof, wherein ring A is substituted with one or more substituents independently selected from the group consisting of fluoro, chloro, —OH, methyl, amino,

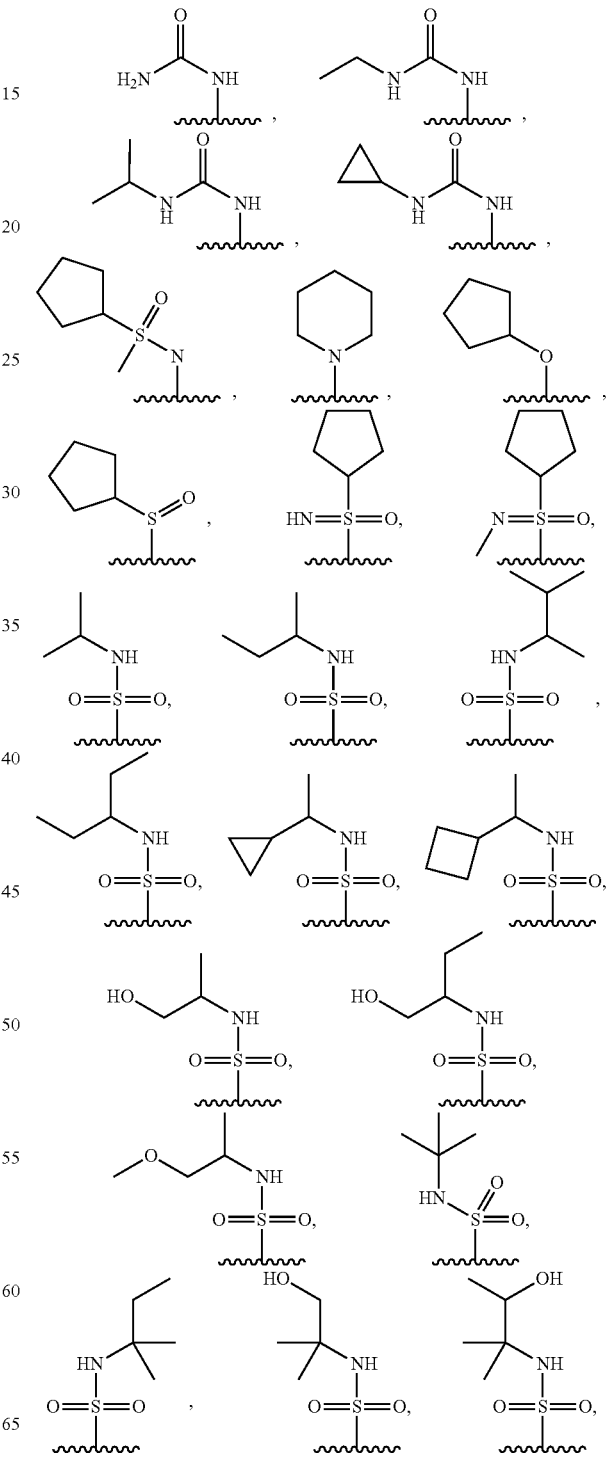

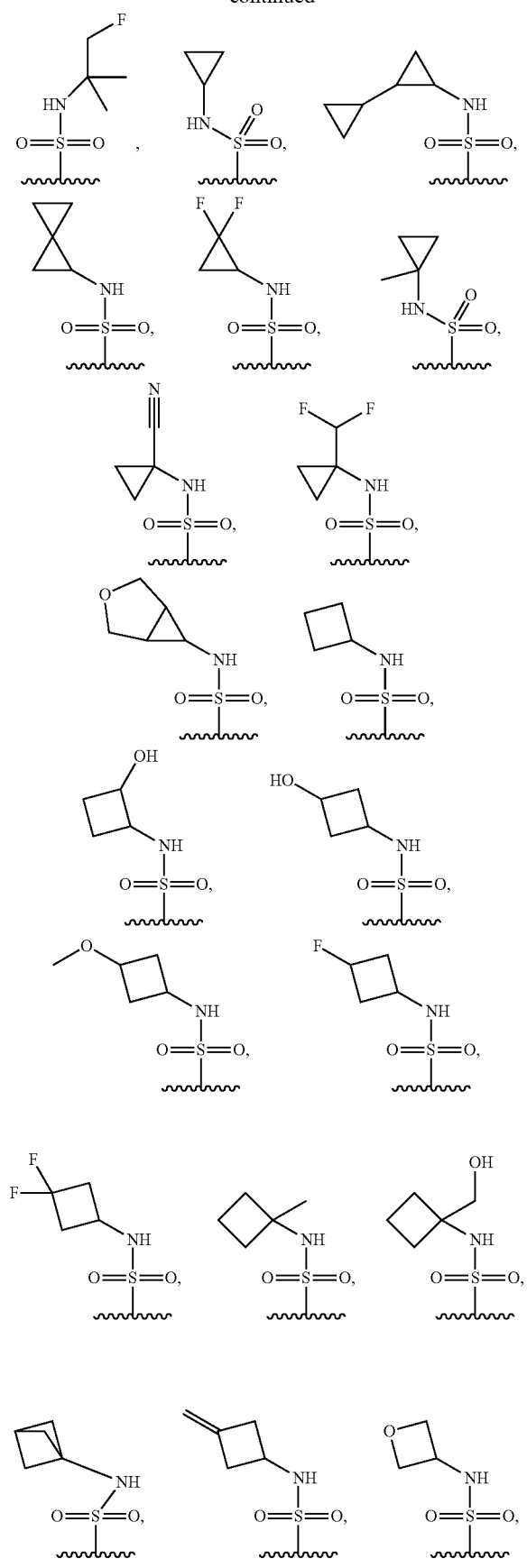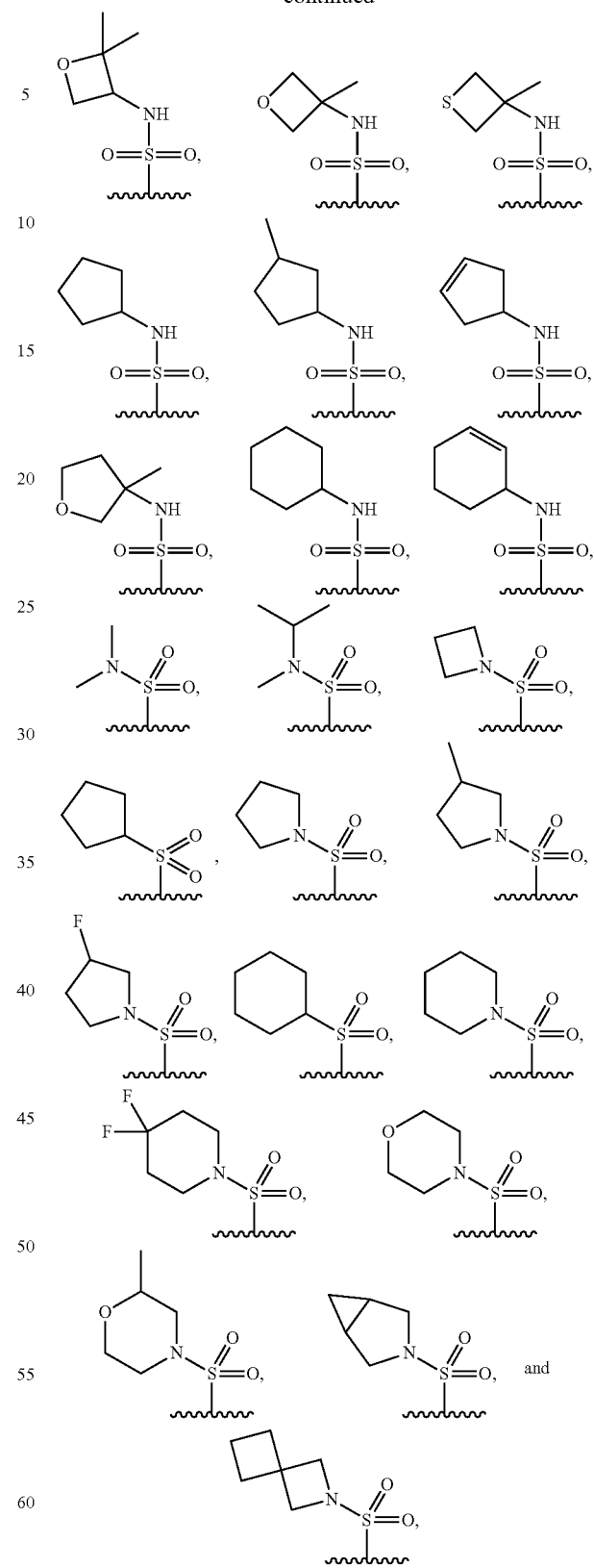
10. The compound of any one of embodiments 1-9, or a pharmaceutically acceptable salt thereof, wherein ring B is $C_{5-7}$ cycloalkyl.

11. The compound of any one of embodiments 1-9, or a pharmaceutically acceptable salt thereof, wherein ring B is 5- to 7-membered heterocycloalkyl.

12. The compound of any one of embodiments 1-9, or a pharmaceutically acceptable salt thereof, wherein ring B is

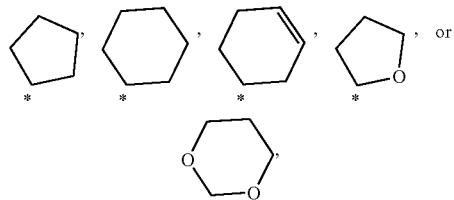

wherein * denotes the point of attachment to the rest of Formula (I).

13. The compound of any one of embodiments 1-9, or a pharmaceutically acceptable salt thereof, wherein

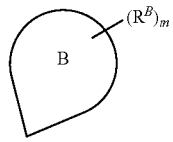

of Formula (I) is

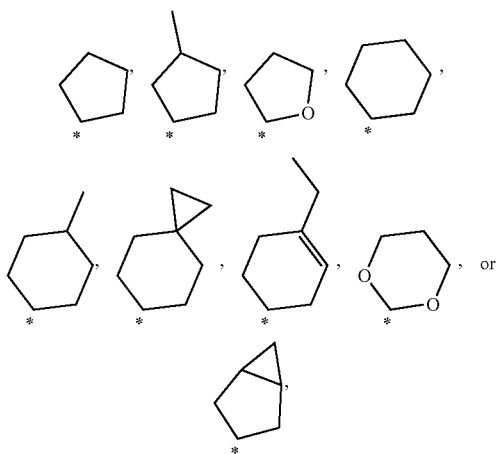

wherein * denotes the point of attachment to the rest of Formula (I).

14. The compound of any one of embodiments 1-13, or a pharmaceutically acceptable salt thereof, wherein $Y^1$ is $CR^{C1}$; $Y^2$ is $CR^{C2}$; $Y^3$ is $CR^{C3}$; and $Y^4$ is $CR^{C4}$.

15. The compound of any one of embodiments 1-13, or a pharmaceutically acceptable salt thereof, wherein $Y^1$ is N; $Y^2$ is $CR^{C2}$; $Y^3$ is $CR^{C3}$; and $Y^4$ is $CR^{C4}$.

16. The compound of any one of embodiments 1-13, or a pharmaceutically acceptable salt thereof, wherein $Y^1$ is $CR^{C1}$; $Y^2$ is N; $Y^3$ is $CR^{C3}$; and $Y^4$ is $CR^{C4}$.

17. The compound of any one of embodiments 1-16, or a pharmaceutically acceptable salt thereof, wherein $R^{C1}$, $R^{C3}$, and $R^{C4}$ are each independently hydrogen, halo, or —$NH_2$.

18. The compound of any one of embodiments 1-17, or a pharmaceutically acceptable salt thereof, wherein $R^{C2}$ is cyano, —OH, —$CH_2OH$, bromo, —$NO_2$,

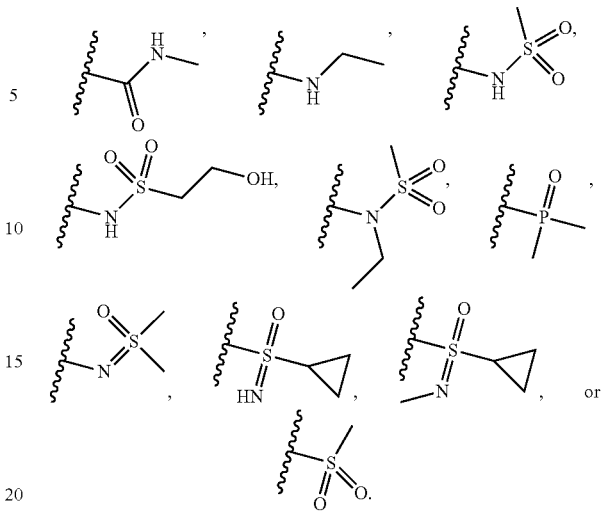

19. The compound of embodiment 1 or 2, or a pharmaceutically acceptable salt thereof, wherein the compound is selected from the group consisting of compounds of Table 1.

20. The compound of embodiment 1, or a pharmaceutically acceptable salt thereof, wherein the compound is selected from the group consisting of compounds of Table 2.

21. A pharmaceutical composition comprising a compound of any one of embodiments 1-18, or a pharmaceutically acceptable salt thereof, and a pharmaceutically acceptable carrier or excipient.

22. A method of inhibiting KIF18A comprising contacting a cell with an effective amount of a compound of any one of embodiments 1-20, or a pharmaceutically acceptable salt thereof, or a pharmaceutical composition of embodiment 21.

23. A method of treating a disease or condition mediated by KIF18A in a subject in need thereof, comprising administering to the subject a therapeutically effective amount of a compound of any one of embodiments 1-20, or a pharmaceutically acceptable salt thereof, or a pharmaceutical composition of embodiment 21.

24. A method of treating cancer in a subject in need thereof, comprising administering to the subject a therapeutically effective amount of a compound of any one of embodiments 1-20, or a pharmaceutically acceptable salt thereof, or a pharmaceutical composition of embodiment 21.

25. The method of embodiment 24, wherein the cancer is selected from the group consisting of carcinomas, cancer of the anus, bladder, breast, colon, small intestine, appendix, kidney, renal pelvis, ureter, urothelium, liver, lung, pleura, esophagus, head and neck, nasopharynx, oropharynx, hypopharynx, oral cavity, larynx, biliary tract, gall-bladder, ovary, testicle, germ cell, uterus, pancreas, stomach, cervix, thyroid, prostate, salivary gland, or skin, hematopoietic tumors of lymphoid lineage, hematopoietic tumors of myeloid lineage, hematopoietic tumors of any lineage, myeloma, tumors of mesenchymal origin including sarcomas, tumors of the central and peripheral nervous system, tumor of neuroendocrine origin, tumor of endocrine origin, small cell tumors, tumors of unknown primary, other tumors comprising retinoblastoma, melanoma, seminoma, teratocarcinoma, osteosarcoma, and other cancer-related disorders that are a consequence of cancer presence or progression.

26. A compound of Formula (I)

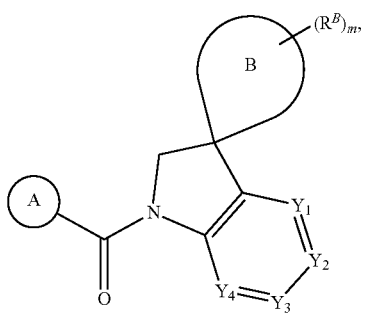

or a pharmaceutically acceptable salt thereof, wherein:
ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo;
R$^{a1}$-R$^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein R$^{1a1}$ and R$^{1a2}$ are each independently hydrogen or $C_{1-6}$ alkyl;
ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;
each R$^B$ group is independently halo, $C_{1-6}$ alkyl optionally substituted with one or more halo, or $C_{2-6}$ alkenyl; or two vicinal R$^B$ groups are taken together with the carbon atoms to which they are attached to form $C_{3-10}$ cycloalkyl; or two geminal R$^B$ groups are taken together with the carbon atom to which they are attached to form $C_{3-10}$ cycloalkyl;
m is 0, 1, 2, 3, or 4;
$Y^1$ is N or CR$^{C1}$;
$Y^2$ is N or CR$^{C2}$;
$Y^3$ is N or CR$^{C3}$;
$Y^4$ is N or CR$^{C4}$;
wherein no more than three of $Y^1$, $Y^2$, $Y^3$, and $Y^4$ are N;
R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, or $C_{1-6}$ alkyl optionally substituted with one or more substituents independently selected from the group consisting of halo and —OH;
R$^{c1}$-R$^{c15}$ are each independently hydrogen, $C_{3-10}$ cycloalkyl, or $C_{1-6}$ alkyl optionally substituted with one or more substituents independently selected from the group consisting of halo and —OH.

27. A compound of Formula (I-1)

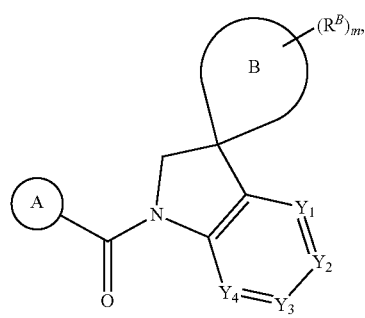

or a pharmaceutically acceptable salt thereof, wherein:
ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, and —(CR$^{a17}$R$^{a18}$)$_{0-1}$C(O)NR$^{a19}$R$^{a20}$.
R$^{a1}$-R$^{a20}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein R$^{1a1}$ and R$^{1a2}$ are each independently hydrogen or $C_{1-6}$ alkyl;
ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;
each R$^B$ group is independently halo, $C_{1-6}$ alkyl, or $C_{2-6}$ alkenyl; or two vicinal R$^B$ groups are taken together with the carbon atoms to which they are attached to form $C_{3-10}$ cycloalkyl; or two geminal R$^B$ groups are taken together with the carbon atom to which they are attached to form $C_{3-10}$ cycloalkyl;
m is 0, 1, 2, 3, or 4;
$Y^1$ is N or CR$^{C1}$;
$Y^2$ is N or CR$^{C2}$;
$Y^3$ is N or CR$^{C3}$;
$Y^4$ is N or CR$^{C4}$;
wherein no more than three of $Y^1$, $Y^2$, $Y^3$, and $Y^4$ are N;
R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$—S(O)$_2$R$^{c13}$, or $C_{1-6}$ alkyl optionally substituted with one or more substituents independently selected from the group consisting of halo and —OH;

$R^{c1}$-$R^{c13}$ are each independently hydrogen, $C_{3-10}$ cycloalkyl, or $C_{1-6}$ alkyl optionally substituted with one or more substituents independently selected from the group consisting of halo and —OH.

28. The compound of embodiment 26 or 27, or a pharmaceutically acceptable salt thereof, wherein the compound is not 4'-fluoro-1'-[3-(piperidine-1-sulfonyl)benzoyl]-1',2'-dihydrospiro[cyclopentane-1,3'-indole]; 3-cyclopropyl-1-[3-({4'-fluoro-1',2'-dihydrospiro[cyclopentane-1,3'-indol]-1'-yl}carbonyl)phenyl]urea; 1-[3-({4'-fluoro-1',2'-dihydrospiro[cyclopentane-1,3'-indol]-1'-yl}carbonyl)phenyl]-3-(propan-2-yl)urea; [4-({4'-fluoro-1',2'-dihydrospiro[cyclopentane-1,3'-indol]-1'-yl}carbonyl)phenyl]methanol; 4'-fluoro-1'-(1H-indole-5-carbonyl)-1',2'-dihydrospiro[cyclopentane-1,3'-indole]; N-[3-({4'-fluoro-1',2'-dihydrospiro[cyclopentane-1,3'-indol]-1'-yl}carbonyl)phenyl]pyrimidin-2-amine; 4'-fluoro-1'-[3-(morpholine-4-sulfonyl)benzoyl]-1',2'-dihydrospiro[cyclopentane-1,3'-indole]; [3-({4'-fluoro-1',2'-dihydrospiro[cyclopentane-1,3'-indol]-1'-yl}carbonyl)phenyl]urea; or salt of any of the foregoing.

29. The compound of embodiment 26 or 28, or a pharmaceutically acceptable salt thereof, wherein ring A is optionally substituted $C_{6-14}$ aryl.

30. The compound of embodiment 29, or a pharmaceutically acceptable salt thereof, wherein ring A is optionally substituted phenyl.

31. The compound of embodiment 26 or 28, or a pharmaceutically acceptable salt thereof, wherein ring A is optionally substituted 5- to 10-membered heteroaryl.

32. The compound of embodiment 31, or a pharmaceutically acceptable salt thereof, wherein ring A is indolyl, indazolyl, pyridinyl, thiophenyl, furanyl, pyrazolyl, pyrrolyl, oxazolyl, chromanyl, or quinolinyl, each optionally substituted.

33. The compound of any one of embodiments 26 and 28-32, or a pharmaceutically acceptable salt thereof, wherein $R^{a1}$ is hydrogen or $C_{1-6}$ alkyl; $R^{a2}$ and $R^{a3}$ are each independently hydrogen, $C_{1-6}$ alkyl, or $C_{3-10}$ cycloalkyl; $R^{a4}$ is hydrogen or $C_{1-6}$ alkyl; $R^{a5}$ is hydrogen or $C_{1-6}$ alkyl; $R^{a6}$ and $R^{ay}$ are each independently hydrogen, $C_{1-6}$ alkyl, or 5- to 12-membered heteroaryl optionally substituted with $C_{1-6}$ alkyl; $R^{a}$s and $R^{a9}$ are each independently hydrogen, $C_{1-6}$ alkyl, or $C_{3-10}$ cycloalkyl; $R^{a10}$ is $C_{3-10}$ cycloalkyl; $R^{a11}$ is $C_{3-10}$ cycloalkyl; $R^{a12}$ is hydrogen or $C_{1-6}$ alkyl; $R^{a13}$ is $C_{3-10}$ cycloalkyl; $R^{a16}$ is $C_{3-10}$ cycloalkyl or 3- to 12-membered heterocycloalkyl optionally substituted with one or more substituents independently selected from the group consisting of $C_{1-6}$ alkyl or halo; $R^{a17}$ and $R^{a18}$ are each independently hydrogen or $C_{1-6}$ alkyl; $R^{a19}$ and $R^{a20}$ are each independently hydrogen, $C_{1-6}$ alkyl, or $C_{3-10}$ cycloalkyl; $R^{a21}$ is $C_{3-10}$ cycloalkyl; and $R^{a22}$ is $C_{3-10}$ cycloalkyl.

34. The compound of any one of embodiments 26 and 28-33, or a pharmaceutically acceptable salt thereof, wherein $R^{a14}$ and $R^{a15}$ are each independently hydrogen; $C_{1-6}$ alkyl optionally substituted with one or more substituents independently selected from the group consisting of $C_{1-6}$ alkyl, $C_{2-6}$ alkenyl, $C_{3-10}$ cycloalkyl, —OH, —O($C_{1-6}$ alkyl), —S($C_{1-6}$ alkyl), and halo; $C_{2-6}$ alkenyl; $C_{3-10}$ cycloalkyl optionally substituted with one or more substituents independently selected from the group consisting of $C_{2-6}$ alkenyl, $C_{3-10}$ cycloalkyl, halo, cyano, —OH, —O($C_{1-6}$ alkyl), =$CR^{1a1}R^{1a2}$, and $C_{1-6}$ alkyl optionally substituted with one or more substituents independently selected from the group consisting of —OH, —O($C_{1-6}$ alkyl), and halo, wherein $R^{1a1}$ and $R^{1a2}$ are each independently hydrogen or $C_{1-6}$ alkyl; $C_{3-10}$ cycloalkenyl; or 3- to 12-membered heterocycloalkyl optionally substituted with one or more $C_{1-6}$ alkyl.

35. The compound of any one of embodiments 26 and 28-34, or a pharmaceutically acceptable salt thereof, wherein $R^{a14}$ is hydrogen and $R^{a15}$ is tert-butyl.

36. The compound of any one of embodiments 26 and 28-35, or a pharmaceutically acceptable salt thereof, wherein ring A is substituted with one or more substituents independently selected from the group consisting of fluoro, chloro, —OH, methyl, amino,

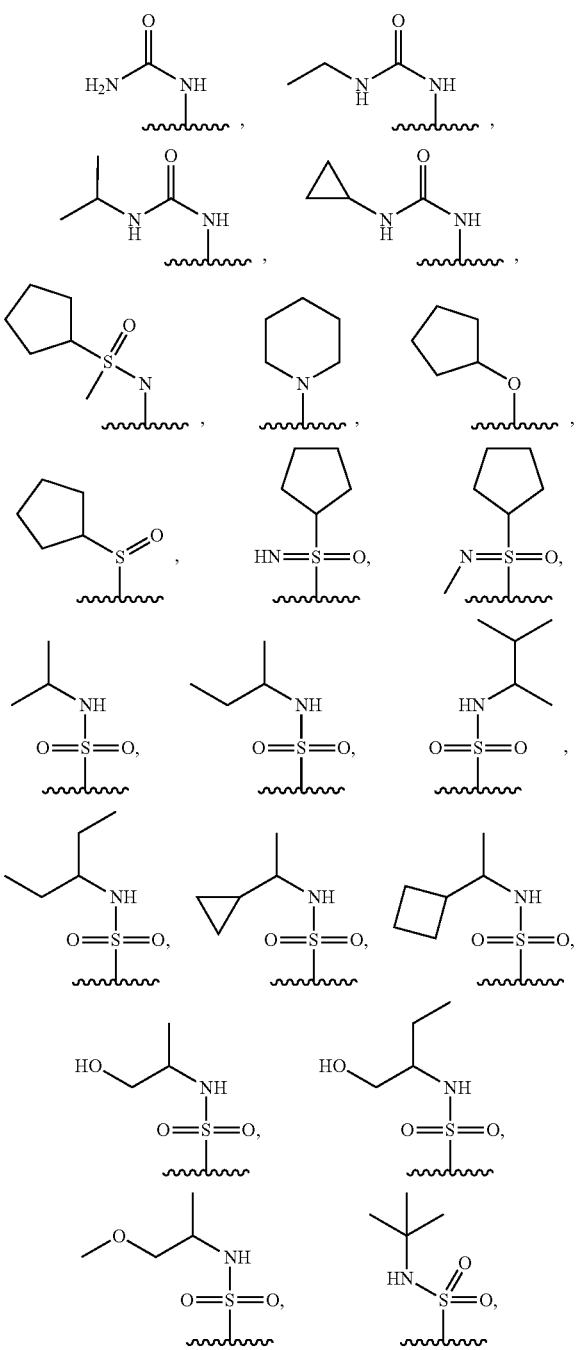

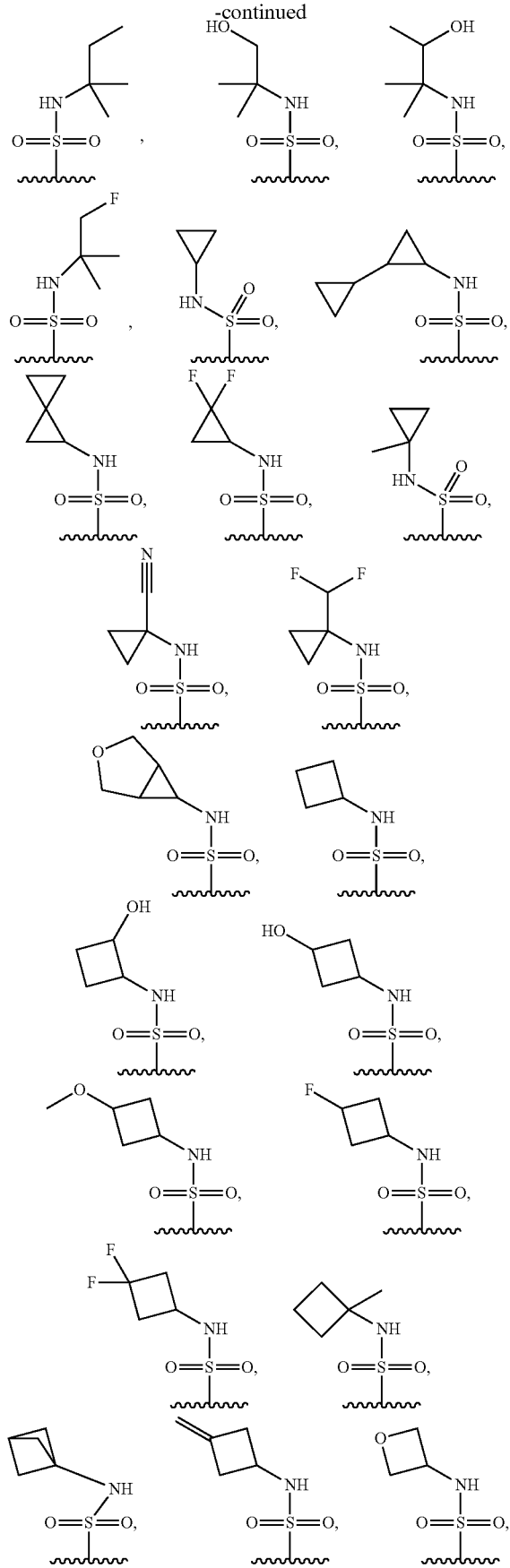
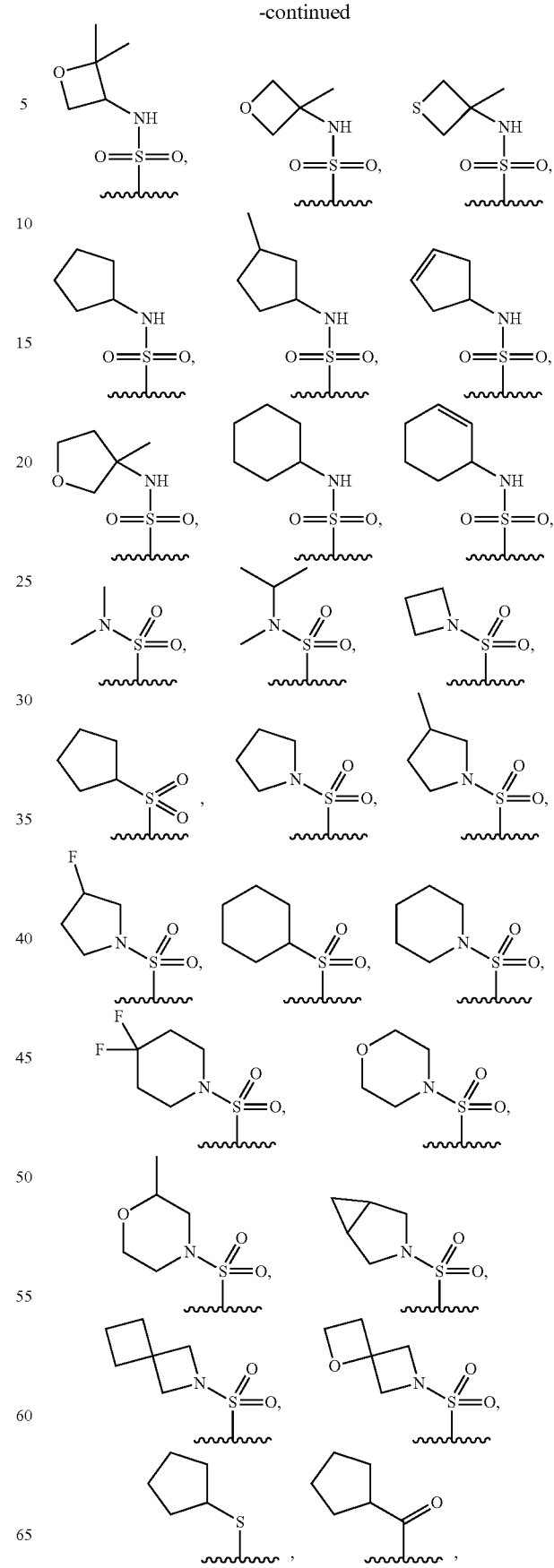

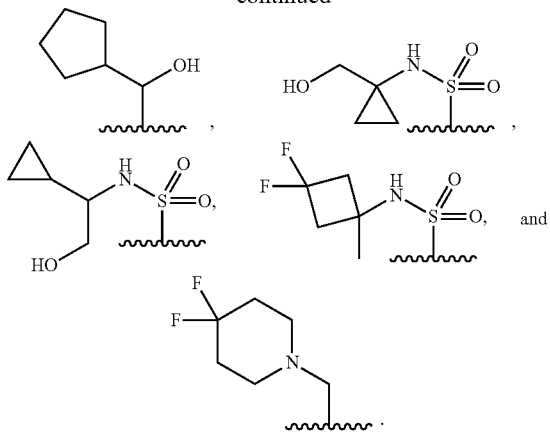

37. The compound of any one of embodiments 26 and 28-36, or a pharmaceutically acceptable salt thereof, wherein ring A is phenyl substituted with

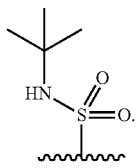

38. The compound of any one of embodiments 26 and 28-37, or a pharmaceutically acceptable salt thereof, wherein ring B is $C_{5-7}$ cycloalkyl.

39. The compound of any one of embodiments 26 and 28-37, or a pharmaceutically acceptable salt thereof, wherein ring B is 5- to 7-membered heterocycloalkyl.

40. The compound of any one of embodiments 26 and 28-37, or a pharmaceutically acceptable salt thereof, wherein ring B is

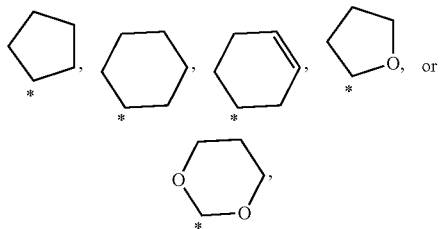

wherein* denotes the point of attachment to the rest of Formula (I).

41. The compound of any one of embodiments 26 and 28-37, or a pharmaceutically acceptable salt thereof, wherein

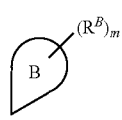

of Formula (I) is

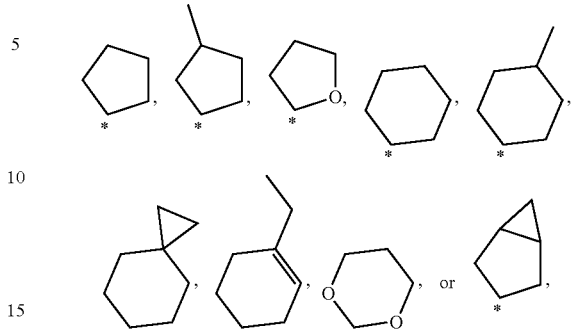

wherein * denotes the point of attachment to the rest of Formula (I).

42. The compound of embodiment 41, or a pharmaceutically acceptable salt thereof, wherein

of Formula (I) is

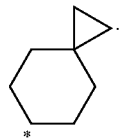

43. The compound of any one of embodiments 25 and 28-42, or a pharmaceutically acceptable salt thereof, wherein $Y^1$ is $CR^{C1}$; $Y^2$ is $CR^{C2}$; $Y^3$ is $CR^{C3}$; and $Y^4$ is $CR^{C4}$.

44. The compound of embodiment 43, or a pharmaceutically acceptable salt thereof, wherein $R^{C1}$, $R^{C3}$, and $R^{C4}$ are each independently hydrogen, halo, or —$NH_2$.

45. The compound of embodiment 43 or 44, or a pharmaceutically acceptable salt thereof, wherein $R^{C1}$, $R^{C3}$, and $R^{C4}$ are each hydrogen.

46. The compound of any one of embodiments 25 and 28-41, or a pharmaceutically acceptable salt thereof, wherein $Y^1$ is N; $Y^2$ is $CR^{C2}$; $Y^3$ is $CR^{C3}$; and $Y^4$ is $CR^{C4}$.

47. The compound of any one of embodiments 25 and 28-41, or a pharmaceutically acceptable salt thereof, wherein $Y^1$ is $CR^{C1}$; $Y^2$ is N; $Y^3$ is $CR^{C3}$; and $Y^4$ is $CR^{C4}$.

48. The compound of any one of embodiments 25 and 28-47, or a pharmaceutically acceptable salt thereof, wherein $R^{C2}$ is cyano, —OH, —$CH_2OH$, bromo, —$NO_2$,

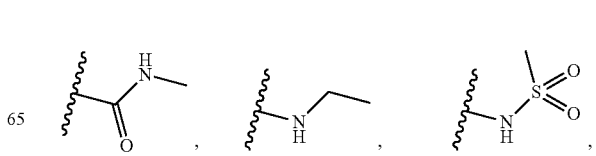

49. The compound of embodiment 48, or a pharmaceutically acceptable salt thereof, wherein $R^{C2}$ is

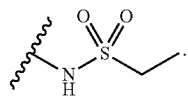 [SMILES: *NS(=O)(=O)CC]

50. The compound of embodiment 26 or 28, or a pharmaceutically acceptable salt thereof, wherein the compound is selected from the group consisting of compounds of Table 1.

51. The compound of embodiment 26, or a pharmaceutically acceptable salt thereof, wherein the compound is selected from the group consisting of compounds of Table 2.

52. A pharmaceutical composition comprising a compound of any one of embodiments 26-51, or a pharmaceutically acceptable salt thereof, and a pharmaceutically acceptable carrier or excipient.

53. A method of inhibiting KIF18A comprising contacting a cell with an effective amount of a compound of any one of embodiments 26-51, or a pharmaceutically acceptable salt thereof, or a pharmaceutical composition of embodiment 52.

54. A method of treating a disease or condition mediated by KIF18A in a subject in need thereof, comprising administering to the subject a therapeutically effective amount of a compound of any one of embodiments 26-51, or a pharmaceutically acceptable salt thereof, or a pharmaceutical composition of embodiment 52.

55. A method of treating cancer in a subject in need thereof, comprising administering to the subject a therapeutically effective amount of a compound of any one of embodiments 26-51, or a pharmaceutically acceptable salt thereof, or a pharmaceutical composition of embodiment 52.

56. The method of embodiment 55, wherein the cancer is selected from the group consisting of carcinomas, cancer of the anus, bladder, breast, colon, small intestine, appendix, kidney, renal pelvis, ureter, urothelium, liver, lung, pleura, esophagus, head and neck, nasopharynx, oropharynx, hypopharynx, oral cavity, larynx, biliary tract, gall-bladder, ovary, testicle, germ cell, uterus, pancreas, stomach, cervix, thyroid, prostate, salivary gland, or skin, hematopoietic tumors of lymphoid lineage, hematopoietic tumors of myeloid lineage, hematopoietic tumors of any lineage, myeloma, tumors of mesenchymal origin including sarcomas, tumors of the central and peripheral nervous system, tumor of neuroendocrine origin, tumor of endocrine origin, small cell tumors, tumors of unknown primary, other tumors comprising retinoblastoma, melanoma, seminoma, teratocarcinoma, osteosarcoma, and other cancer-related disorders that are a consequence of cancer presence or progression.

57. A compound of Formula (I)

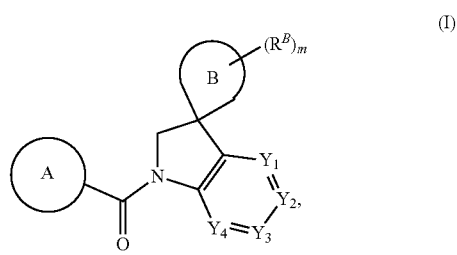

or a pharmaceutically acceptable salt thereof, wherein:
ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo;
$R^{a1}$-$R^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein R$^{1a1}$ and R$^{1a2}$ are each independently hydrogen or $C_{1-6}$ alkyl;
ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;
each $R^B$ group is independently halo, $C_{1-6}$ alkyl optionally substituted with one or more halo, or $C_{2-6}$ alkenyl; or two vicinal $R^B$ groups are taken together with the carbon atoms to which they are attached to form $C_{3-10}$ cycloalkyl; or two geminal $R^B$ groups are taken together with the carbon atom to which they are attached to form $C_{3-10}$ cycloalkyl;
m is 0, 1, 2, 3, or 4;
$Y^1$ is N or CR$^{C1}$;
$Y^2$ is N or CR$^{C2}$;
$Y^3$ is N or CR$^{C3}$;
$Y^4$ is N or CR$^{C4}$;
wherein no more than three of $Y^1$, $Y^2$, $Y^3$, and $Y^4$ are N;
$R^{C1}$-$R^{C4}$ are each independently hydrogen, halo, cyano, —OH, —NO$_2$, —C(O)NR$^{c1}$R$^{c2}$, —NR$^{c3}$R$^{c4}$, —NR$^{c5}$S (O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or C$_{1-6}$ alkyl optionally substituted with one or more substituents independently selected from the group consisting of halo and —OH;

R$^{c1}$-R$^{c18}$ are each independently hydrogen, C$_{3-10}$ cycloalkyl, or C$_{1-6}$ alkyl optionally substituted with one or more substituents independently selected from the group consisting of halo and —OH.

58. A compound of Formula (I-2)

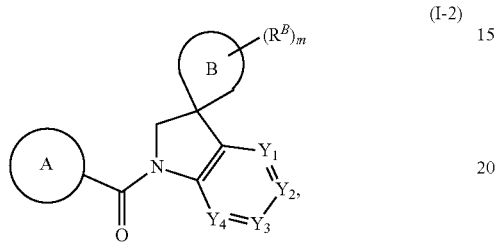

(I-2)

or a pharmaceutically acceptable salt thereof, wherein:
ring A is C$_{6-14}$ aryl or 5- to 12-membered heteroaryl, each optionally substituted with one or more substituents independently selected from the group consisting of halo, —OH, C$_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and C$_{1-6}$ alkyl substituted with one or more substituents independently selected from the group consisting of —OH, cyano, C$_{3-10}$ cycloalkyl, and 3- to 10-membered heterocycloalkyl optionally substituted with one or more halo;

R$^{a1}$-R$^{a22}$ are each independently hydrogen, C$_{1-6}$ alkyl, C$_{2-6}$ alkenyl, C$_{3-10}$ cycloalkyl, C$_{3-10}$ cycloalkenyl, 3- to 10-membered heterocycloalkyl, 3- to 10-membered heterocycloalkenyl, C$_{6-14}$ aryl, or 5- to 12-membered heteroaryl, each optionally substituted with one or more substituents independently selected from the group consisting of halo, cyano, —OH, —O(C$_{1-6}$ alkyl), C$_{2-6}$ alkenyl, C$_{3-10}$ cycloalkyl, —S(C$_{1-6}$ alkyl), =CR$^{1a1}$R$^{1a2}$, and C$_{1-6}$ alkyl optionally substituted with one or more substituents independently selected from the group consisting of halo, —OH, and —O(C$_{1-6}$ alkyl), wherein R$^{1a1}$ and R$^{1a2}$ are each independently hydrogen or C$_{1-6}$ alkyl;

ring B is C$_{5-7}$ cycloalkyl, C$_{5-7}$ cycloalkenyl, or 5- to 7-membered heterocycloalkyl wherein one or two of the ring atoms are each oxygen and the remaining ring atoms are each carbon;

each R$^B$ group is independently halo, C$_{1-6}$ alkyl optionally substituted with one or more halo, or C$_{2-6}$ alkenyl; or two vicinal R$^B$ groups are taken together with the carbon atoms to which they are attached to form C$_{3-10}$ cycloalkyl; or two geminal R$^B$ groups are taken together with the carbon atom to which they are attached to form C$_{3-10}$ cycloalkyl;

m is 0, 1, 2, 3, or 4;
Y$^1$ is N or CR$^{C1}$;
Y$^2$ is N or CR$^{C2}$;
Y$^3$ is N or CR$^{C3}$;
Y$^4$ is N or CR$^{C4}$;

wherein no more than three of Y$^1$, Y$^2$, Y$^3$, and Y$^4$ are N;
R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, or C$_{1-6}$ alkyl optionally substituted with one or more substituents independently selected from the group consisting of halo and —OH;

R$^{c1}$-R$^{c15}$ are each independently hydrogen, C$_{3-10}$ cycloalkyl, or C$_{1-6}$ alkyl optionally substituted with one or more substituents independently selected from the group consisting of halo and —OH.

59. A compound of Formula (I-1)

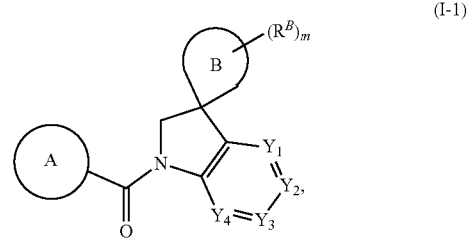

(I-1)

or a pharmaceutically acceptable salt thereof, wherein:
ring A is C$_{6-14}$ aryl or 5- to 12-membered heteroaryl, each optionally substituted with one or more substituents independently selected from the group consisting of halo, —OH, C$_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, and —(CR$^{a17}$R$^{a18}$)$_{0-1}$C(O)NR$^{a19}$R$^{a20}$;

R$^{a1}$-R$^{a20}$ are each independently hydrogen, C$_{1-6}$ alkyl, C$_{2-6}$ alkenyl, C$_{3-10}$ cycloalkyl, C$_{3-10}$ cycloalkenyl, 3- to 10-membered heterocycloalkyl, 3- to 10-membered heterocycloalkenyl C$_{6-14}$ aryl, or 5- to 12-membered heteroaryl, each optionally substituted with one or more substituents independently selected from the group consisting of halo, cyano, —OH, —O(C$_{1-6}$ alkyl), C$_{2-6}$ alkenyl, C$_{3-10}$ cycloalkyl, —S(C$_{1-6}$ alkyl), =CR$^{1a1}$R$^{1a2}$, and C$_{1-6}$ alkyl optionally substituted with one or more substituents independently selected from the group consisting of halo, —OH, and —O(C$_{1-6}$ alkyl), wherein R$^{1a1}$ and R$^{1a2}$ are each independently hydrogen or C$_{1-6}$ alkyl;

ring B is C$_{5-7}$ cycloalkyl, C$_{5-7}$ cycloalkenyl, or 5- to 7-membered heterocycloalkyl wherein one or two of the ring atoms are each oxygen and the remaining ring atoms are each carbon;

each R$^B$ group is independently halo, C$_{1-6}$ alkyl, or C$_{2-6}$ alkenyl; or two vicinal R$^B$ groups are taken together with the carbon atoms to which they are attached to form C$_{3-10}$ cycloalkyl; or two geminal R$^B$ groups are taken together with the carbon atom to which they are attached to form C$_{3-10}$ cycloalkyl;

m is 0, 1, 2, 3, or 4;
Y$^1$ is N or CR$^{C1}$;
Y$^2$ is N or CR$^{C2}$;
Y$^3$ is N or CR$^{C3}$;
Y$^4$ is N or CR$^{C4}$;
wherein no more than three of Y$^1$, Y$^2$, Y$^3$, and Y$^4$ are N;
R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)

(NR$^{c11}$)R$^{c12}$—S(O)$_2$R$^{c13}$, or C$_{1-6}$ alkyl optionally substituted with one or more substituents independently selected from the group consisting of halo and —OH; R$^{c1}$-R$^{c13}$ are each independently hydrogen, C$_{3-10}$ cycloalkyl, or C$_{1-6}$ alkyl optionally substituted with one or more substituents independently selected from the group consisting of halo and —OH.

60. The compound of embodiment 57 or 58, or a pharmaceutically acceptable salt thereof, wherein the compound is not 4'-fluoro-1'-[3-(piperidine-1-sulfonyl)benzoyl]-1',2'-dihydrospiro[cyclopentane-1,3'-indole]; 3-cyclopropyl-1-[3-({4'-fluoro-1',2'-dihydrospiro[cyclopentane-1,3'-indol]-1'-yl}carbonyl)phenyl]urea; 1-[3-({4'-fluoro-1',2'-dihydrospiro[cyclopentane-1,3'-indol]-1'-yl}carbonyl)phenyl]-3-(propan-2-yl)urea; [4-({4'-fluoro-1',2'-dihydrospiro[cyclopentane-1,3'-indol]-1'-yl}carbonyl)phenyl]methanol; 4'-fluoro-1'-(1H-indole-5-carbonyl)-1',2'-dihydrospiro[cyclopentane-1,3'-indole]; N-[3-({4'-fluoro-1',2'-dihydrospiro[cyclopentane-1,3'-indol]-1'-yl}carbonyl)phenyl]pyrimidin-2-amine; 4'-fluoro-1'-[3-(morpholine-4-sulfonyl)benzoyl]-1',2'-dihydrospiro[cyclopentane-1,3'-indole]; [3-({4'-fluoro-1',2'-dihydrospiro[cyclopentane-1,3'-indol]-1'-yl}carbonyl)phenyl]urea; or salt of any of the foregoing.

61. The compound of embodiment 57 or 60, or a pharmaceutically acceptable salt thereof, wherein ring A is optionally substituted C$_{6-14}$ aryl.

62. The compound of embodiment 61, or a pharmaceutically acceptable salt thereof, wherein ring A is optionally substituted phenyl.

63. The compound of embodiment 57 or 60, or a pharmaceutically acceptable salt thereof, wherein ring A is optionally substituted 5- to 10-membered heteroaryl.

64. The compound of embodiment 63, or a pharmaceutically acceptable salt thereof, wherein ring A is indolyl, indazolyl, pyridinyl, thiophenyl, furanyl, pyrazolyl, pyrrolyl, oxazolyl, chromanyl, or quinolinyl, each optionally substituted.

65. The compound of any one of embodiments 57 and 60-64, or a pharmaceutically acceptable salt thereof, wherein R$^{a1}$ is hydrogen or C$_{1-6}$ alkyl; R$^{a2}$ and R$^{a3}$ are each independently hydrogen, C$_{1-6}$ alkyl, or C$_{3-10}$ cycloalkyl; R$^{a4}$ is hydrogen or C$_{1-6}$ alkyl; R$^{a5}$ is hydrogen or C$_{1-6}$ alkyl; R$^{a6}$ and R$^{ay}$ are each independently hydrogen, C$_{1-6}$ alkyl, or 5- to 12-membered heteroaryl optionally substituted with C$_{1-6}$ alkyl; R$^{a}$s and R$^{a9}$ are each independently hydrogen, C$_{1-6}$ alkyl, or C$_{3-10}$ cycloalkyl; R$^{a10}$ is C$_{3-10}$ cycloalkyl; R$^{a11}$ is C$_{3-10}$ cycloalkyl; R$^{a12}$ is hydrogen or C$_{1-6}$ alkyl; R$^{a13}$ is C$_{3-10}$ cycloalkyl; R$^{a16}$ is C$_{3-10}$ cycloalkyl or 3- to 12-membered heterocycloalkyl optionally substituted with one or more substituents independently selected from the group consisting of C$_{1-6}$ alkyl or halo; R$^{a17}$ and R$^{a18}$ are each independently hydrogen or C$_{1-6}$ alkyl; R$^{a19}$ and R$^{a20}$ are each independently hydrogen, C$_{1-6}$ alkyl, or C$_{3-10}$ cycloalkyl; R$^{a21}$ is C$_{3-10}$ cycloalkyl; and R$^{a22}$ is C$_{3-10}$ cycloalkyl.

66. The compound of any one of embodiments 57 and 60-65, or a pharmaceutically acceptable salt thereof, wherein R$^{a14}$ and R$^{a15}$ are each independently hydrogen; C$_{1-6}$ alkyl optionally substituted with one or more substituents independently selected from the group consisting of C$_{1-6}$ alkyl, C$_{2-6}$ alkenyl, C$_{3-10}$ cycloalkyl, —OH, —O(C$_{1-6}$ alkyl), —S(C$_{1-6}$ alkyl), and halo; C$_{2-6}$ alkenyl; C$_{3-10}$ cycloalkyl optionally substituted with one or more substituents independently selected from the group consisting of C$_{2-6}$ alkenyl, C$_{3-10}$ cycloalkyl, halo, cyano, —OH, —O(C$_{1-6}$ alkyl), =CR$^{1a1}$R$^{1a2}$, and C$_{1-6}$ alkyl optionally substituted with one or more substituents independently selected from the group consisting of —OH, —O(C$_{1-6}$ alkyl), and halo, wherein R$^{1a1}$ and R$^{1a2}$ are each independently hydrogen or C$_{1-6}$ alkyl; C$_{3-10}$ cycloalkenyl; or 3- to 12-membered heterocycloalkyl optionally substituted with one or more C$_{1-6}$ alkyl.

67. The compound of any one of embodiments 57 and 60-66, or a pharmaceutically acceptable salt thereof, wherein R$^{a14}$ is hydrogen and R$^{a15}$ is tert-butyl.

68. The compound of any one of embodiments 57 and 60-67, or a pharmaceutically acceptable salt thereof, wherein ring A is substituted with one or more substituents independently selected from the group consisting of fluoro, chloro, —OH, methyl, amino,

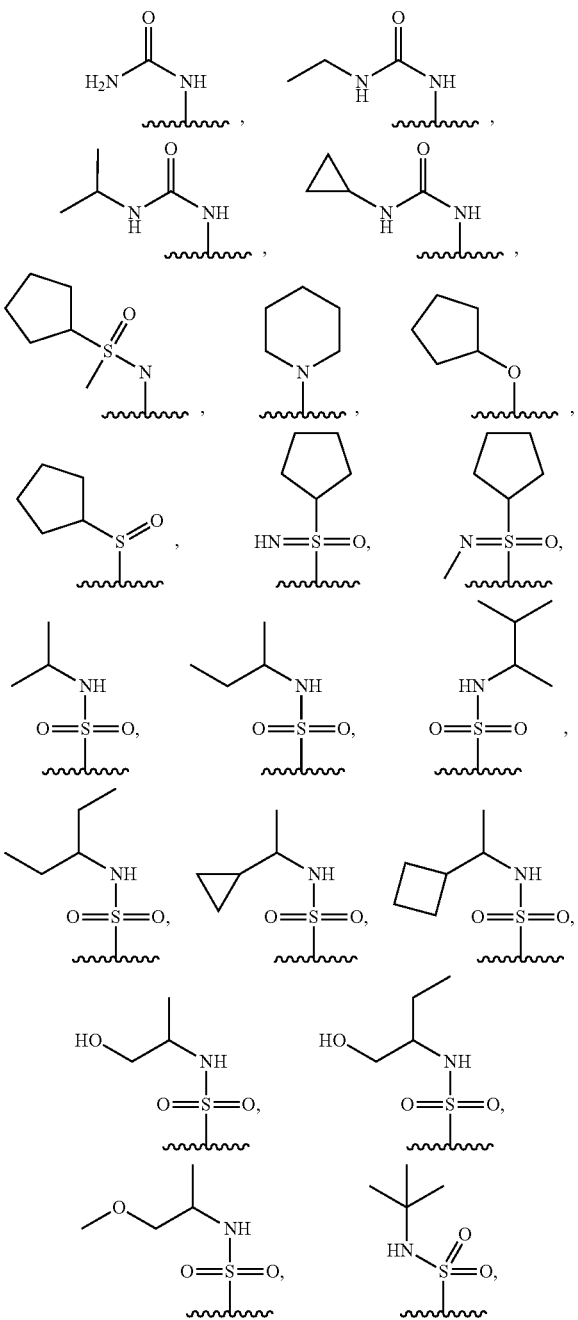

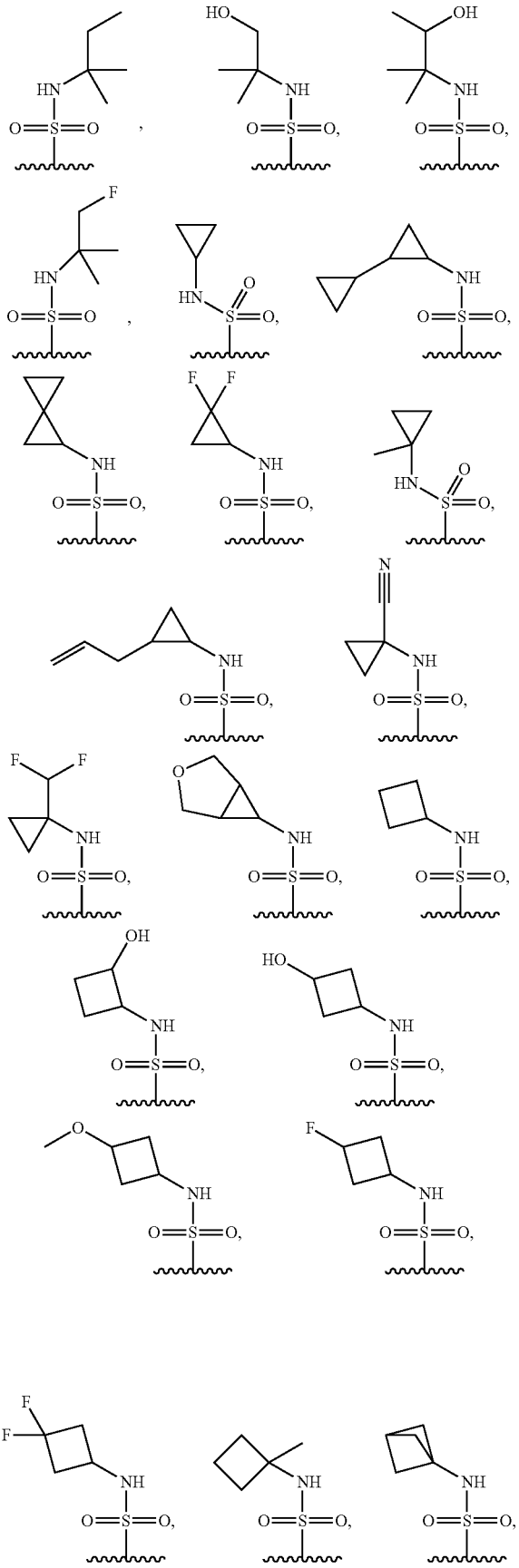
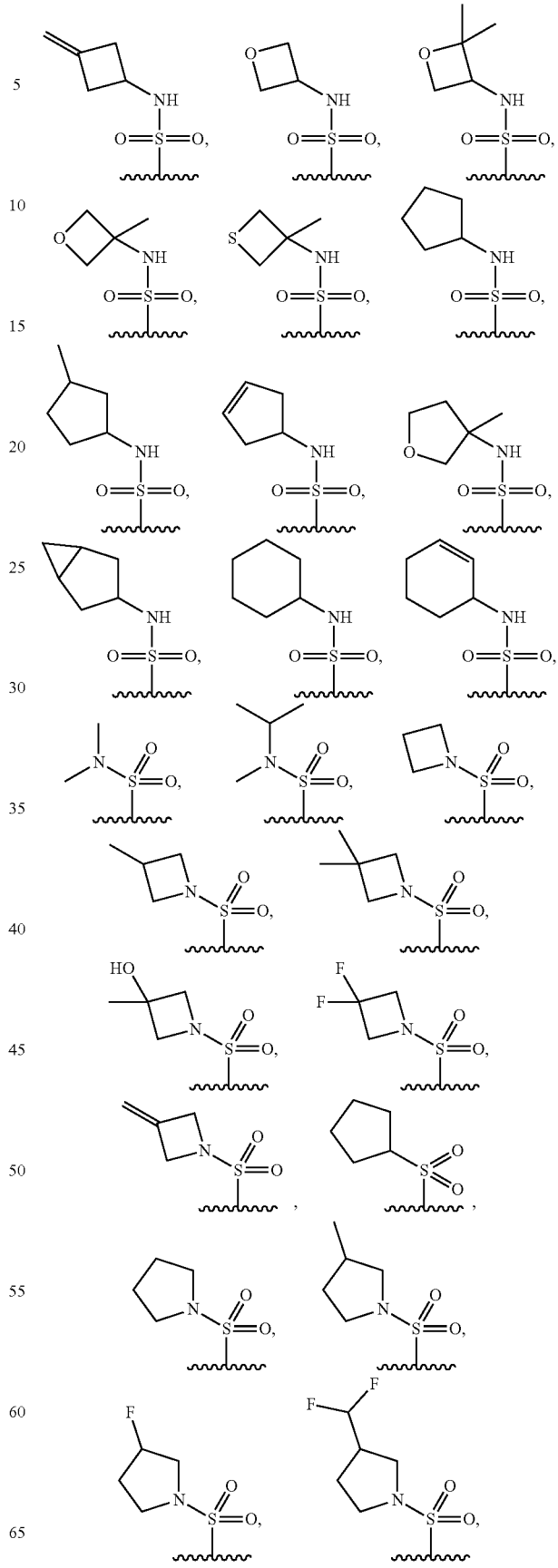

-continued

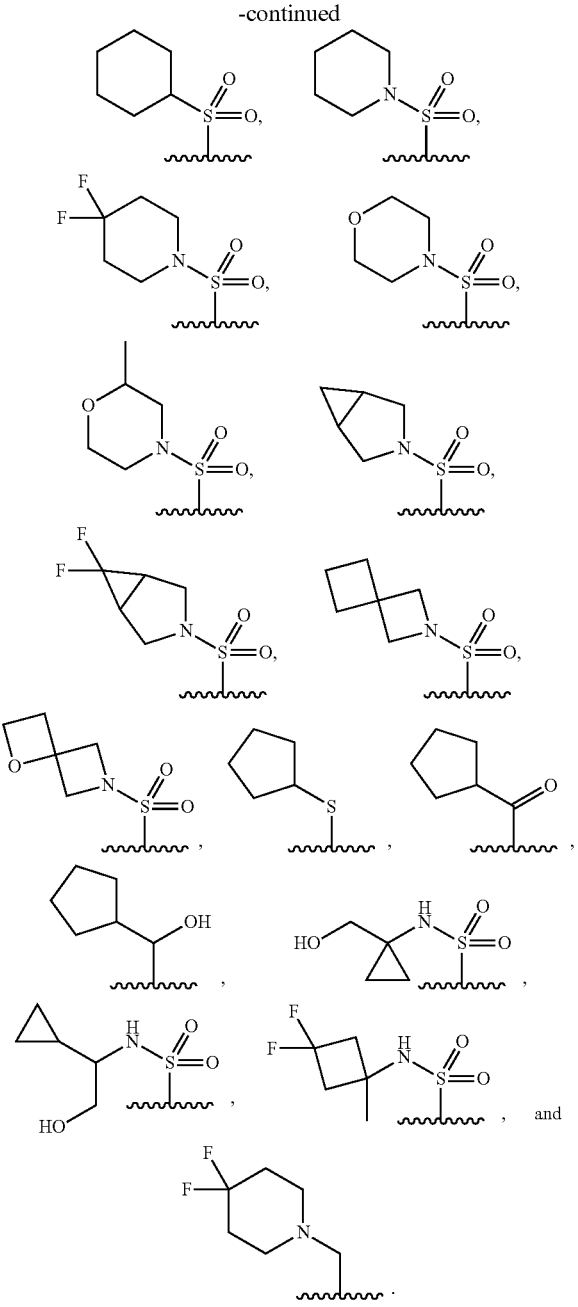

69. The compound of any one of embodiments 57 and 60-68, or a pharmaceutically acceptable salt thereof, wherein ring A is phenyl substituted with

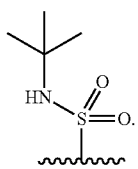

70. The compound of any one of embodiments 57 and 60-69, or a pharmaceutically acceptable salt thereof, wherein ring B is $C_{5-7}$ cycloalkyl.

71. The compound of any one of embodiments 57 and 60-69, or a pharmaceutically acceptable salt thereof, wherein ring B is 5- to 7-membered heterocycloalkyl.

72. The compound of any one of embodiments 57 and 60-69, or a pharmaceutically acceptable salt thereof, wherein ring B is

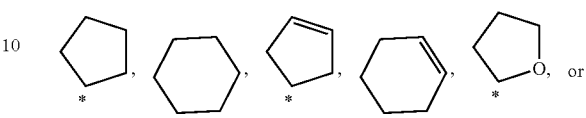

wherein * denotes the point of attachment to the rest of Formula (I).

73. The compound of any one of embodiments 57 and 60-69, or a pharmaceutically acceptable salt thereof, wherein

of Formula (I) is

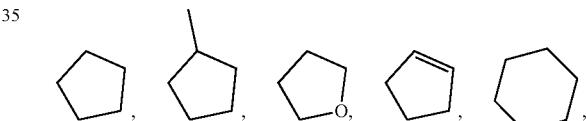

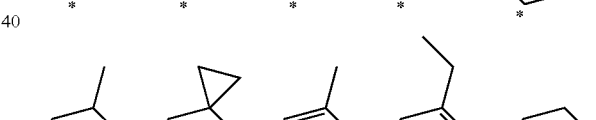

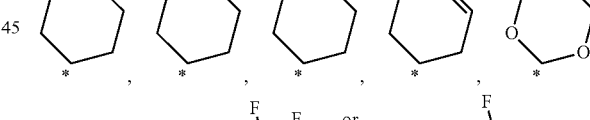

wherein* denotes the point of attachment to the rest of Formula (I).

74. The compound of embodiment 73, or a pharmaceutically acceptable salt thereof, wherein

of Formula (I) is

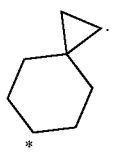

75. The compound of any one of embodiments 57 and 60-74, or a pharmaceutically acceptable salt thereof, wherein $Y^1$ is $CR^{C1}$; $Y^2$ is $CR^{C2}$; $Y^3$ is $CR^{C3}$; and $Y^4$ is $CR^{C4}$.

76. The compound of embodiment 75, or a pharmaceutically acceptable salt thereof, wherein $R^{C1}$, $R^{C3}$, and $R^{C4}$ are each independently hydrogen, halo, or —NH$_2$.

77. The compound of embodiment 75 or 76, or a pharmaceutically acceptable salt thereof, wherein $R^{C1}$, $R^{C3}$, and $R^{C4}$ are each hydrogen.

78. The compound of any one of embodiments 57 and 60-74, or a pharmaceutically acceptable salt thereof, wherein $Y^1$ is N; $Y^2$ is $CR^{C2}$; $Y^3$ is $CR^{C3}$; and $Y^4$ is $CR^{C4}$.

79. The compound of any one of embodiments 57 and 60-74, or a pharmaceutically acceptable salt thereof, wherein $Y^1$ is $CR^{C1}$; $Y^2$ is N; $Y^3$ is $CR^{C3}$; and $Y^4$ is $CR^{C4}$.

80. The compound of any one of embodiments 57 and 60-79, or a pharmaceutically acceptable salt thereof, wherein $R^{C2}$ is cyano, —OH, —CH$_2$OH, bromo, —NO$_2$,

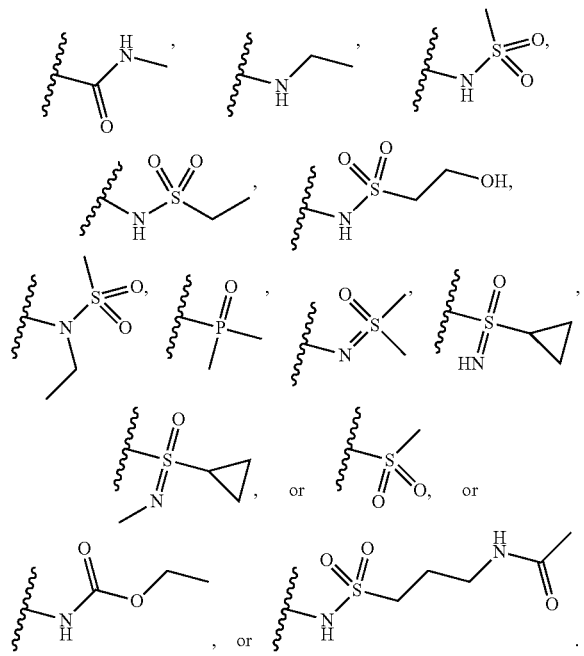

81. The compound of embodiment 80, or a pharmaceutically acceptable salt thereof, wherein $R^{C2}$ is

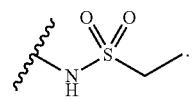 [SMILES: *NS(=O)(=O)CC]

82. The compound of embodiment 57 or 60, or a pharmaceutically acceptable salt thereof, wherein the compound is selected from the group consisting of compounds of Table 1.

83. The compound of embodiment 57, or a pharmaceutically acceptable salt thereof, wherein the compound is selected from the group consisting of compounds of Table 2.

84. A pharmaceutical composition comprising a compound of any one of embodiments 57-83, or a pharmaceutically acceptable salt thereof, and a pharmaceutically acceptable carrier or excipient.

85. A method of inhibiting KIF18A comprising contacting a cell with an effective amount of a compound of any one of embodiments 57-83, or a pharmaceutically acceptable salt thereof, or a pharmaceutical composition of embodiment 84.

86. A method of treating a disease or condition mediated by KIF18A in a subject in need thereof, comprising administering to the subject a therapeutically effective amount of a compound of any one of embodiments 57-83, or a pharmaceutically acceptable salt thereof, or a pharmaceutical composition of embodiment 84.

87. A method of treating cancer in a subject in need thereof, comprising administering to the subject a therapeutically effective amount of a compound of any one of embodiments 57-83, or a pharmaceutically acceptable salt thereof, or a pharmaceutical composition of embodiment 84.

88. The method of embodiment 87, wherein the cancer is selected from the group consisting of carcinomas, cancer of the anus, bladder, breast, colon, small intestine, appendix, kidney, renal pelvis, ureter, urothelium, liver, lung, pleura, esophagus, head and neck, nasopharynx, oropharynx, hypopharynx, oral cavity, larynx, biliary tract, gall-bladder, ovary, testicle, germ cell, uterus, pancreas, stomach, cervix, thyroid, prostate, salivary gland, or skin, hematopoietic tumors of lymphoid lineage, hematopoietic tumors of myeloid lineage, hematopoietic tumors of any lineage, myeloma, tumors of mesenchymal origin including sarcomas, tumors of the central and peripheral nervous system, tumor of neuroendocrine origin, tumor of endocrine origin, small cell tumors, tumors of unknown primary, other tumors comprising retinoblastoma, melanoma, seminoma, teratocarcinoma, osteosarcoma, and other cancer-related disorders that are a consequence of cancer presence or progression.

EXAMPLES

The following examples are offered to illustrate but not to limit the compositions, uses, and methods provided herein. The compounds are prepared using the general methods described above.

Abbreviations

BSA: bovine serum albumin
DAST: diaminosulfur trifluoride
dba: bibenzylidene acetone
DMF: dimethylformamide
EDCI: 1-ehthyl-3-(3-dimethylaminopropyl)carbodiimide
ESI MS: electrospray mass spectrometry
HATU: 1-[Bis(dimethylamino)methylene]-1H-1,2,3-triazolo[4,5-b]pyridinium 3-oxide hexafluorophosphate
HOBT: 1-hydroxybenzotriazole
HPLC: high-performance liquid chromatography
IC$_{50}$: 50% inhibitory concentration
LDA: lithium diisopropylamide
mCPBA: meta-chloroperoxybenzoic acid
MsCl: methanesulfonyl chloride MTBE: methyl t-butyl ether
NCS: N-chlorosuccinimide
NCI: N-iodosuccinimide
NMR: nuclear magnetic resonance
PE: petroleum ether
THF: tetrahydrofuran
TFA: trifluoroacetic acid
Xantphos: 4,5-bis(diphenylphosphino)-9,9-dimethylxanthene
Xphos Pd G4: dicyclohexyl-[2-[2,4,6-tri(propan-2-yl)phenyl]phenyl]phosphanium; methanesulfonic acid; N-methyl-2-phenylaniline; palladium (CAS: 1599466-81-5)

Synthesis of Intermediates

Synthesis of 3-(piperidin-1-ylsulfonyl)benzoic acid (A-01)

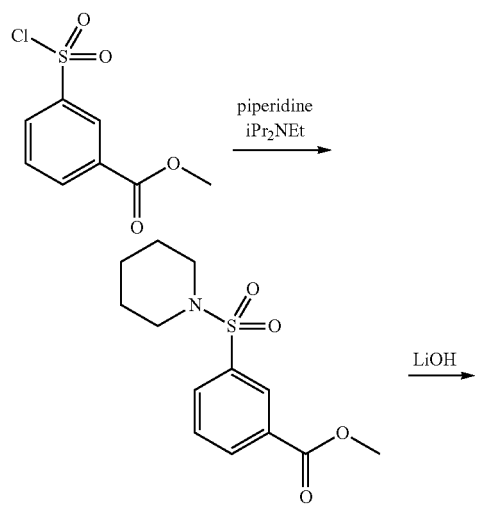

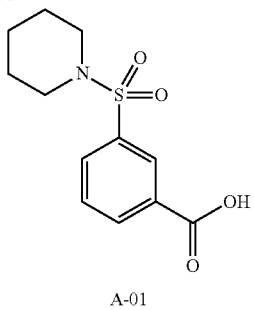

A-01

Step 1. A mixture of piperidine (0.25 mL, 2.6 mmol), $CH_2Cl_2$ (5.0 mL), $iPr_2NEt$ (1.3 mL, 7.7 mmol) and methyl 3-chlorosulfonylbenzoate (900 mg, 3.84 mmol, 1.5 eq) was stirred for 2 h, concentrated, poured into $H_2O$ (20 mL), and extracted with EtOAc (2×10 mL). The extracts were combined, washed with brine (10.0 mL), dried over $Na_2SO_4$, filtered, and concentrated to provide methyl 3-(1-piperidylsulfonyl) benzoate (0.95 g).

Step 2. A mixture of methyl 3-(1-piperidylsulfonyl) benzoate (0.90 g, 3.2 mmol), THF (6.0 mL), $H_2O$ (2.0 mL), and $LiOH·H_2O$ (0.67 g, 16 mmol) was stirred for 2 h, then was concentrated. The mixture was treated with HCl (4N) to bring the pH to 3, poured into $H_2O$ (10 mL), and extracted with EtOAc (2×10 mL). The extracts were combined, washed with brine (10 mL), dried over $Na_2SO_4$, filtered, and concentrated to provide 3-(1-piperidylsulfonyl) benzoic acid (A-01, 0.72 g). ESI MS m/z: 270.0 $(M+H)^+$.

Compounds in Table 3 were prepared in the same manner as A-01 from the indicated sulfonyl chloride and amine.

TABLE 3

| 4 | Structure | Sulfonyl Chloride | Amine |
|---|-----------|-------------------|-------|
| A-02 | 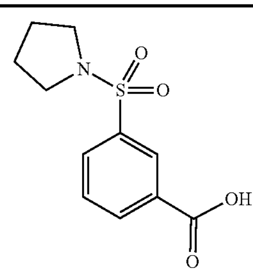 | | |
| A-03 | 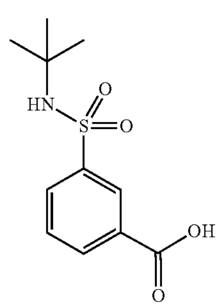 [SMILES: CC(C)(C)NS(=O)(=O)c1cccc(C(=O)O)c1] | | |

TABLE 3-continued

| 4 | Structure | Sulfonyl Chloride | Amine |
|---|---|---|---|
| A-04 | 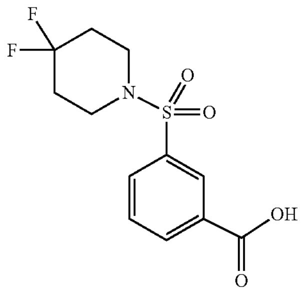 [SMILES: O=C(O)c1cccc(S(=O)(=O)N2CCC(F)(F)CC2)c1] | | |
| A-05 | 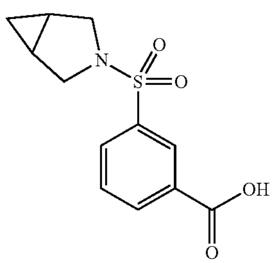 [SMILES: O=C(O)c1cccc(S(=O)(=O)N2CC3CC3C2)c1] | | |
| A-06 | 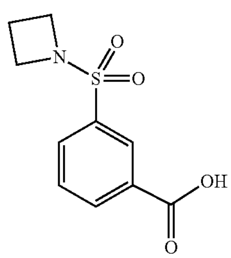 [SMILES: O=C(O)c1cccc(S(=O)(=O)N2CCC2)c1] | | |
| A-07 | 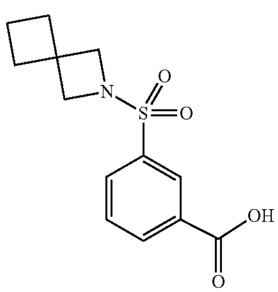 [SMILES: O=C(O)c1cccc(S(=O)(=O)N2CC3(CCC3)C2)c1] | | |
| A-08 | 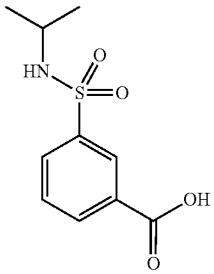 [SMILES: CC(C)NS(=O)(=O)c1cccc(C(=O)O)c1] | | |

TABLE 3-continued

| 4 | Structure | Sulfonyl Chloride | Amine |
|---|-----------|-------------------|-------|
| A-09 | 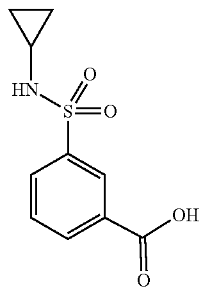 [SMILES: O=C(O)c1cccc(S(=O)(=O)NC2CC2)c1] | | |
| A-10 | 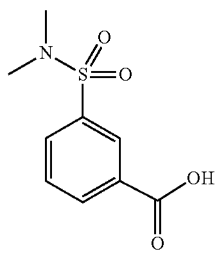 | | |
| A-11 | 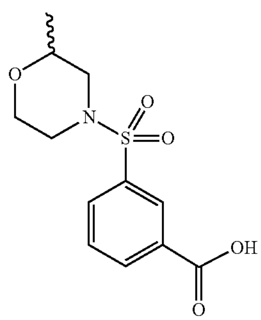 [SMILES: CC1CN(S(=O)(=O)c2cccc(C(=O)O)c2)CCO1] | | |
| A-12 | 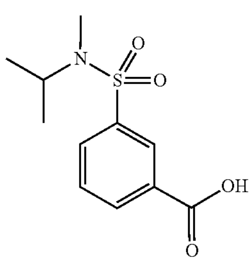 [SMILES: CC(C)N(C)S(=O)(=O)c1cccc(C(=O)O)c1] | | |
| A-13 | 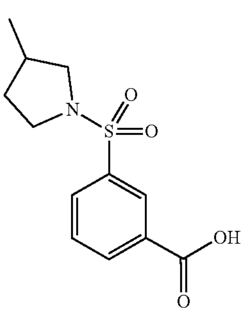 [SMILES: CC1CCN(S(=O)(=O)c2cccc(C(=O)O)c2)C1] | | |

TABLE 3-continued

| 4 | Structure | Sulfonyl Chloride | Amine |
|---|---|---|---|
| (S)-A-13 | 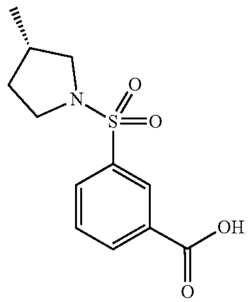 [SMILES: C[C@H]1CCN(S(=O)(=O)c2cccc(C(=O)O)c2)C1] | | |
| A-14 | 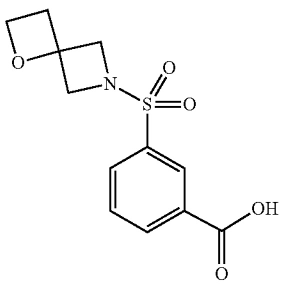 [SMILES: O=C(O)c1cccc(S(=O)(=O)N2CC3(CCO3)C2)c1] | | |
| A-15 | 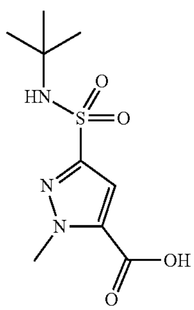 [SMILES: Cn1nc(S(=O)(=O)NC(C)(C)C)cc1C(=O)O] | | |
| A-16 | 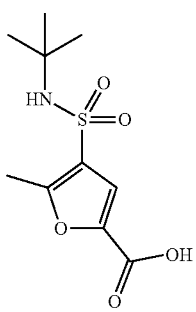 [SMILES: Cc1oc(C(=O)O)cc1S(=O)(=O)NC(C)(C)C] | | |
| A-17 | 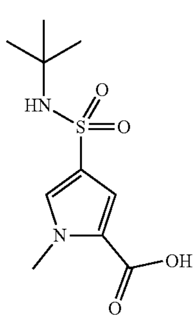 [SMILES: Cn1cc(S(=O)(=O)NC(C)(C)C)cc1C(=O)O] | | |

TABLE 3-continued

| 4 | Structure | Sulfonyl Chloride | Amine |
|---|---|---|---|
| A-18 | 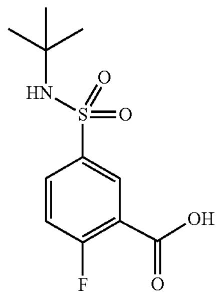 [SMILES: CC(C)(C)NS(=O)(=O)c1ccc(F)c(C(=O)O)c1] | | |
| A-19 | 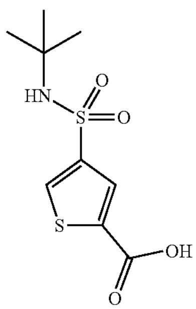 [SMILES: CC(C)(C)NS(=O)(=O)c1csc(C(=O)O)c1] | | |
| A-20 | 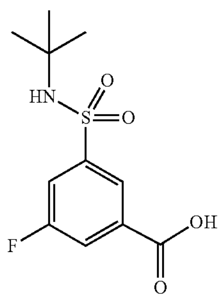 [SMILES: CC(C)(C)NS(=O)(=O)c1cc(F)cc(C(=O)O)c1] | | |
| A-21 | 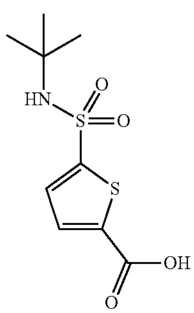 [SMILES: CC(C)(C)NS(=O)(=O)c1ccc(C(=O)O)s1] | | |
| A-22 | 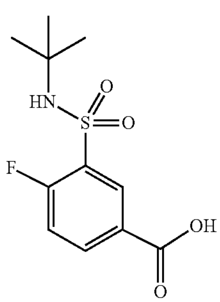 [SMILES: CC(C)(C)NS(=O)(=O)c1cc(C(=O)O)ccc1F] | | |

TABLE 3-continued

| 4 | Structure | Sulfonyl Chloride | Amine |
|---|---|---|---|
| A-23 | 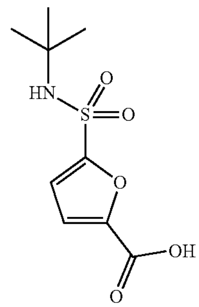 [SMILES: CC(C)(C)NS(=O)(=O)c1ccc(C(=O)O)o1] | | |
| A-24 | 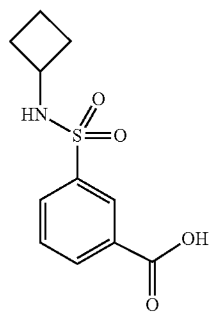 [SMILES: O=C(O)c1cccc(S(=O)(=O)NC2CCC2)c1] | | |
| A-25 | 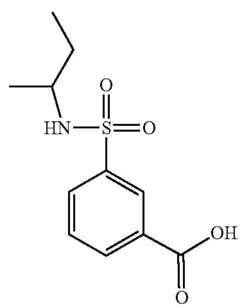 [SMILES: CCC(C)NS(=O)(=O)c1cccc(C(=O)O)c1] | | |
| A-26 | 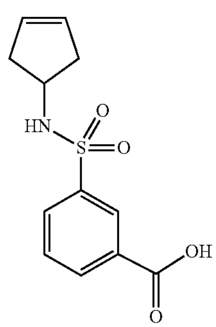 [SMILES: O=C(O)c1cccc(S(=O)(=O)NC2CC=CC2)c1] | | |
| A-27 | 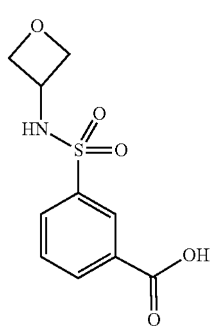 [SMILES: O=C(O)c1cccc(S(=O)(=O)NC2COC2)c1] | | |

TABLE 3-continued

| 4 | Structure | Sulfonyl Chloride | Amine |
|---|---|---|---|
| A-28 | 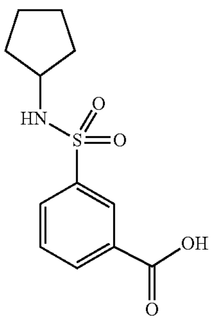 [SMILES: O=C(O)c1cccc(S(=O)(=O)NC2CCCC2)c1] | | |
| A-29 | 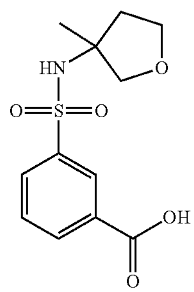 [SMILES: CC1(NS(=O)(=O)c2cccc(C(=O)O)c2)CCOC1] | | |
| A-30 | 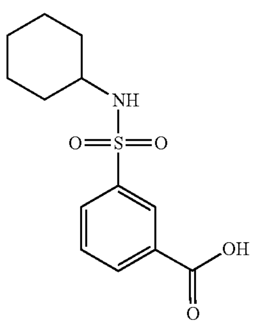 [SMILES: O=C(O)c1cccc(S(=O)(=O)NC2CCCCC2)c1] | | |
| A-31 | 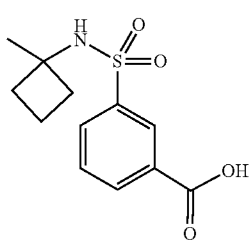 [SMILES: CC1(NS(=O)(=O)c2cccc(C(=O)O)c2)CCC1] | | |
| A-32 | 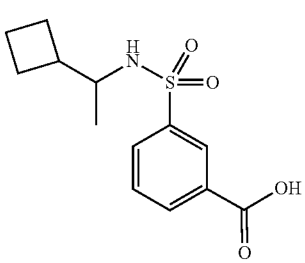 [SMILES: CC(NS(=O)(=O)c1cccc(C(=O)O)c1)C1CCC1] | | |

TABLE 3-continued

| 4 | Structure | Sulfonyl Chloride | Amine |
|---|---|---|---|
| A-33 | 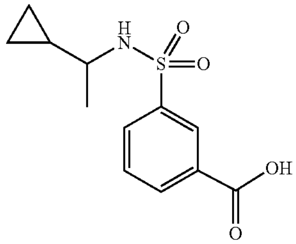 [SMILES: CC(NS(=O)(=O)c1cccc(C(=O)O)c1)C1CC1] | | · HCl |
| A-34 | 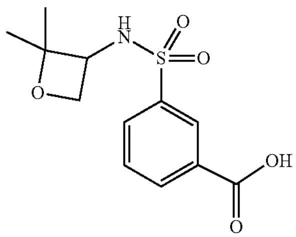 [SMILES: CC1(C)OCC1NS(=O)(=O)c1cccc(C(=O)O)c1] | | |
| A-35 | 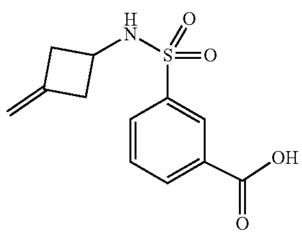 [SMILES: C=C1CC(NS(=O)(=O)c2cccc(C(=O)O)c2)C1] | | |
| A-36 | 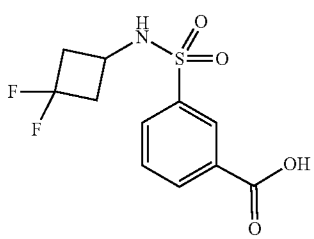 [SMILES: O=C(O)c1cccc(S(=O)(=O)NC2CC(F)(F)C2)c1] | | |
| A-37 | 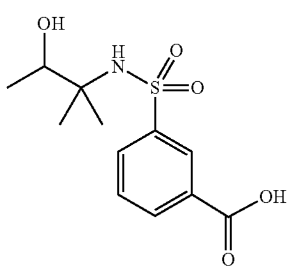 [SMILES: CC(O)C(C)(C)NS(=O)(=O)c1cccc(C(=O)O)c1] | | |
| A-38 | 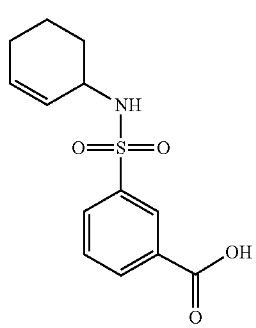 [SMILES: O=C(O)c1cccc(S(=O)(=O)NC2C=CCCC2)c1] | | |

TABLE 3-continued

| 4 | Structure | Sulfonyl Chloride | Amine |
|---|---|---|---|
| A-39 | 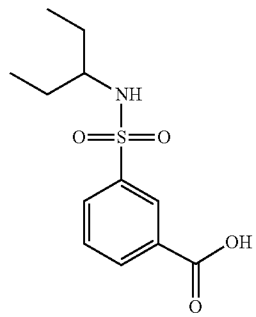 [SMILES: CCC(CC)NS(=O)(=O)c1cccc(C(=O)O)c1] | | |
| A-40 | 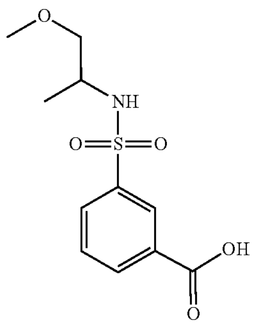 [SMILES: COCC(C)NS(=O)(=O)c1cccc(C(=O)O)c1] | | |
| A-41 | 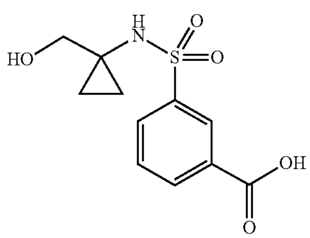 [SMILES: O=C(O)c1cccc(S(=O)(=O)NC2(CO)CC2)c1] | | |
| A-42 | 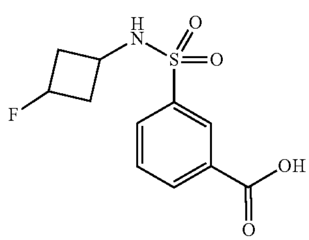 [SMILES: O=C(O)c1cccc(S(=O)(=O)NC2CC(F)C2)c1] | | |
| A-43 | 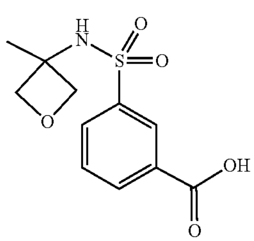 [SMILES: CC1(NS(=O)(=O)c2cccc(C(=O)O)c2)COC1] | | |
| A-44 | 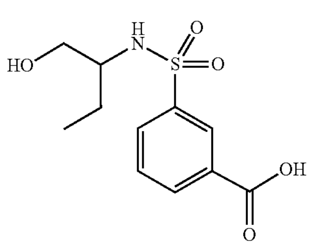 [SMILES: CCC(CO)NS(=O)(=O)c1cccc(C(=O)O)c1] | | |

TABLE 3-continued

| 4 | Structure | Sulfonyl Chloride | Amine |
|---|---|---|---|
| A-45 | 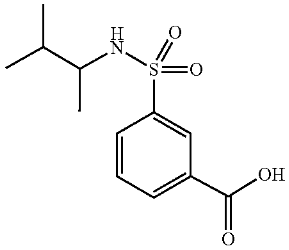 [SMILES: CC(C)C(C)NS(=O)(=O)c1cccc(C(=O)O)c1] | | |
| A-46 | 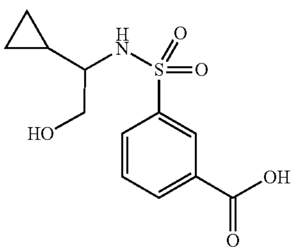 [SMILES: O=C(O)c1cccc(S(=O)(=O)NC(CO)C2CC2)c1] | | |
| A-47 | 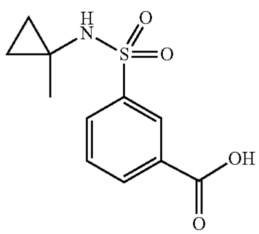 [SMILES: CC1(NS(=O)(=O)c2cccc(C(=O)O)c2)CC1] | | |
| A-48 | 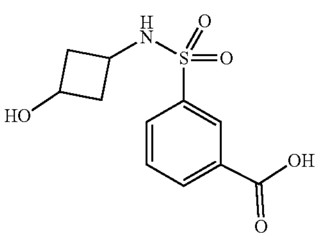 [SMILES: O=C(O)c1cccc(S(=O)(=O)NC2CC(O)C2)c1] | | |
| A-49 | 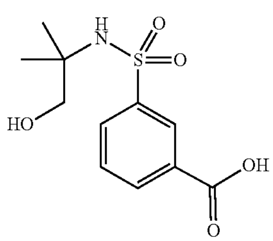 [SMILES: CC(C)(CO)NS(=O)(=O)c1cccc(C(=O)O)c1] | | |
| A-50 | 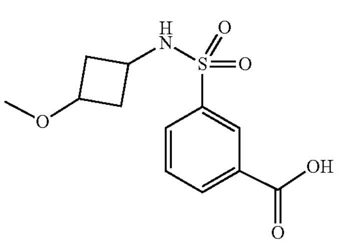 [SMILES: COC1CC(NS(=O)(=O)c2cccc(C(=O)O)c2)C1] | | |

TABLE 3-continued

| 4 | Structure | Sulfonyl Chloride | Amine |
|---|---|---|---|
| A-55 | *tert-butylamino sulfonyl thiophene-carboxylic acid structure* | 5-(chlorosulfonyl)thiophene-3-carboxylic acid methyl ester | tert-butylamine |
| A-56 | *cyclopropylaminosulfonyl benzoic acid structure* | methyl 3-(chlorosulfonyl)benzoate | cyclopropylamine |
| A-57 | *cyclopropylmethyl-cyclopropylaminosulfonyl benzoic acid structure* | methyl 3-(chlorosulfonyl)benzoate | (2-cyclopropylcyclopropyl)amine |
| A-58 | *6,6-difluoro-3-azabicyclo[3.1.0]hexane sulfonyl benzoic acid* | methyl 3-(chlorosulfonyl)benzoate | 6,6-difluoro-3-azabicyclo[3.1.0]hexane |
| (R)-A-59 | *(R)-3-fluoropyrrolidine sulfonyl benzoic acid structure* | methyl 3-(chlorosulfonyl)benzoate | (R)-3-fluoropyrrolidine |

US 12,084,420 B2
331                                                                                            332
TABLE 3-continued

| 4 | Structure | Sulfonyl Chloride | Amine |
|---|---|---|---|
| (S)-A-59 | 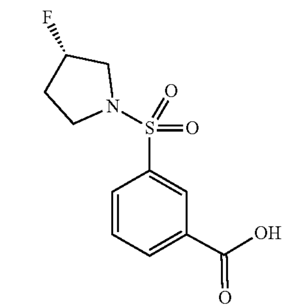 [SMILES: O=C(O)c1cccc(S(=O)(=O)N2CC[C@H](F)C2)c1] | | |
| A-60 | 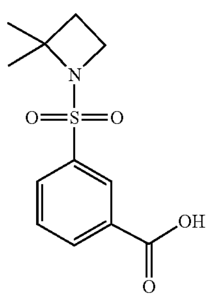 [SMILES: CC1(C)CCN1S(=O)(=O)c1cccc(C(=O)O)c1] | | |
| A-61 | 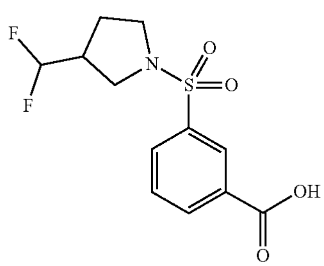 [SMILES: O=C(O)c1cccc(S(=O)(=O)N2CCC(C(F)F)C2)c1] | | |
| A-62 | 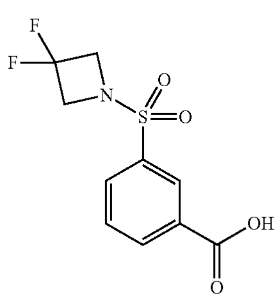 [SMILES: O=C(O)c1cccc(S(=O)(=O)N2CC(F)(F)C2)c1] | | F$_3$CCO$_2$H |
| A-63 | 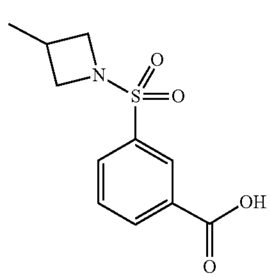 [SMILES: CC1CN(S(=O)(=O)c2cccc(C(=O)O)c2)C1] | | |

TABLE 3-continued
| 4 | Structure | Sulfonyl Chloride | Amine |
|---|-----------|-------------------|-------|
| A-64 | 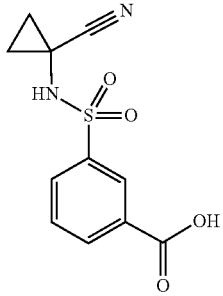 [SMILES: N#CC1(NS(=O)(=O)c2cccc(C(=O)O)c2)CC1] | 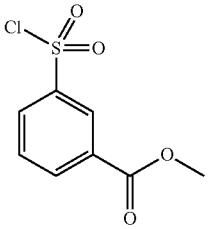 | 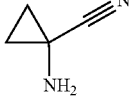 |
| A-65 | 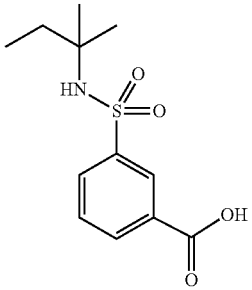 [SMILES: CCC(C)(C)NS(=O)(=O)c1cccc(C(=O)O)c1] | 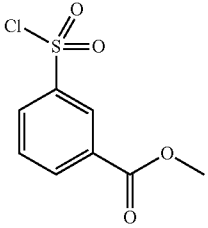 | 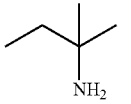 |
| A-66 | 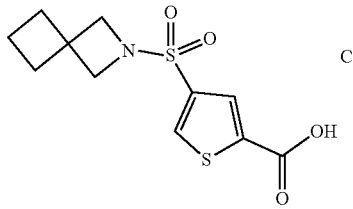 | 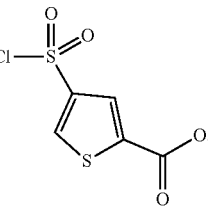 | 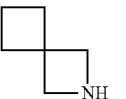 |
| A-67 | 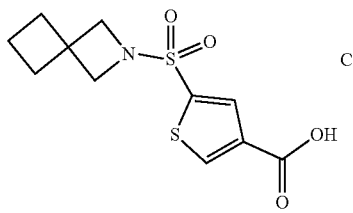 | 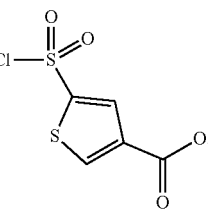 | 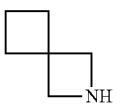 |
| A-68 | 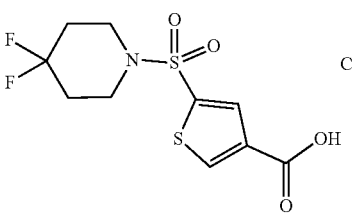 | 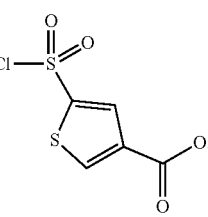 | 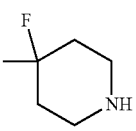 |
| A-69 | 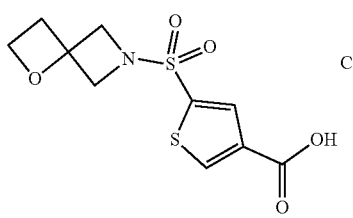 | 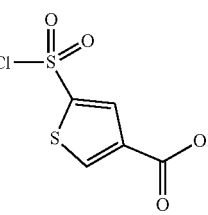 | 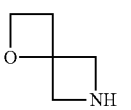 |

TABLE 3-continued

| 4 | Structure | Sulfonyl Chloride | Amine |
|---|---|---|---|
| A-70 | 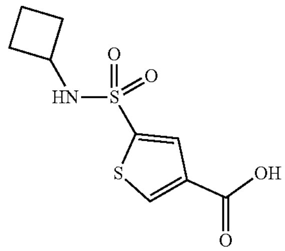 [SMILES: O=C(O)c1csc(S(=O)(=O)NC2CCC2)c1] | | |
| A-71 | 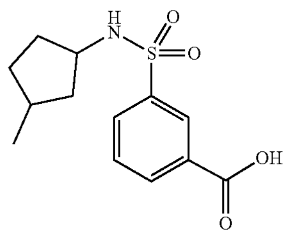 [SMILES: CC1CCC(NS(=O)(=O)c2cccc(C(=O)O)c2)C1] | | (with CF₃CO₂H) |
| A-73 | 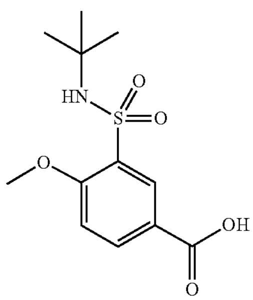 [SMILES: COc1ccc(C(=O)O)cc1S(=O)(=O)NC(C)(C)C] | | |
| A-74 | 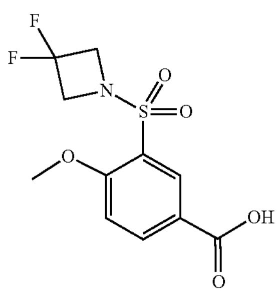 [SMILES: COc1ccc(C(=O)O)cc1S(=O)(=O)N1CC(F)(F)C1] | | (with F₃CCO₂H) |
| A-80 | 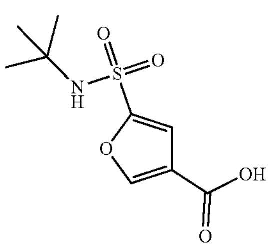 [SMILES: CC(C)(C)NS(=O)(=O)c1cc(C(=O)O)co1] | | |
| A-81 | 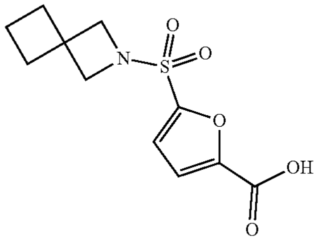 [SMILES: O=C(O)c1ccc(S(=O)(=O)N2CC3(CCC3)C2)o1] | | (with HCl) |

Synthesis of 3-(cyclopentylsulfinyl)benzoic acid
(A-51)

Synthesis of 3-(cyclopentylsulfonyl)benzoic acid
(A-52)

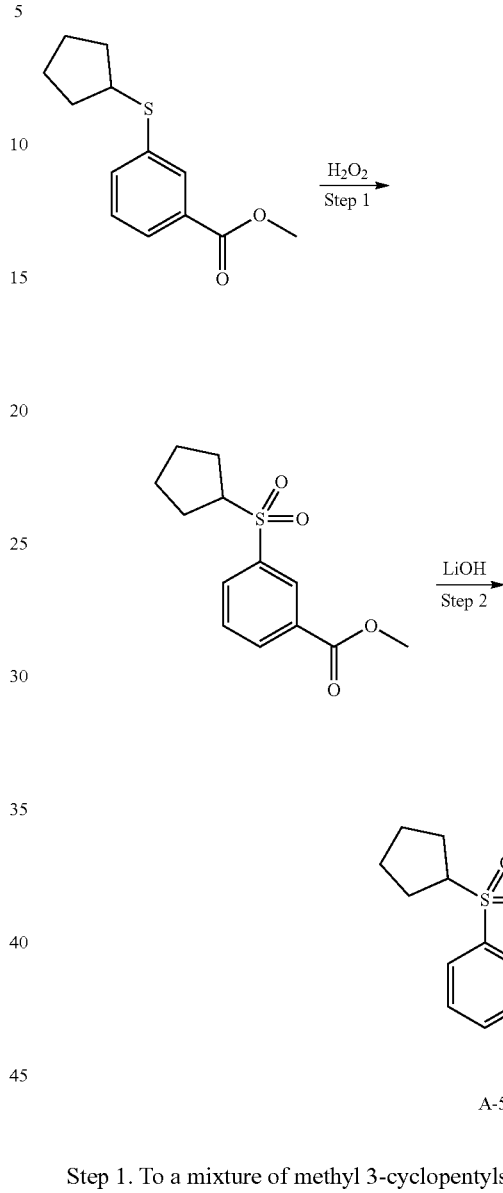

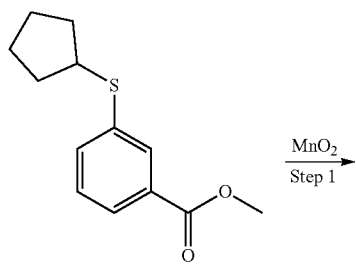

Step 1. A mixture of methyl 3-cyclopentylsulfanylbenzoate (0.50 g, 2.1 mmol), $CH_2Cl_2$ (25 mL), and $MnO_2$ (0.37 g, 4.2 mmol) was stirred at 20° C. for 16 h. The mixture was extracted with EtOAc (100 mL×3), and the extracts were combined, dried over $Na_2SO_4$, filtered, and concentrated. The residue was purified silica gel chromatography (0-100% EtOAc/Petroleum ether) to provide methyl 3-cyclopentylsulfinylbenzoate (0.52 g).

Step 2. A mixture of methyl 3-cyclopentylsulfinylbenzoate (0.50 g, 2.0 mmol), THF (10 mL), $H_2O$ (10 mL), and LiOH (95 mg, 4.0 mmol) was stirred at 25° C. for 2 h, and then was concentrated. The pH was adjusted to pH 3 with 2M HCl and the mixture was extracted with EtOAc (50 mL×3). The combined extracts were dried over $Na_2SO_4$, filtered, and concentrated to provide 3-cyclopentylsulfinylbenzoic acid (A-51, 83 mg).

Step 1. To a mixture of methyl 3-cyclopentylsulfanylbenzoate (0.50 g, 2.1 mmol) in HOAc (3.0 mL) was added $H_2O_2$ (30%, 1.2 mL, 13 mmol). The mixture was stirred at 80° C. for 12 h, $H_2O$ (20 mL) was added, and the mixture was extracted with EtOAc (10 mL×3). The extracts were combined, washed saturated $Na_2CO_3$ (20 mL×3), and aqueous of $Na_2SO_3$ (20 mL×3), and brine (30 mL). The extracts were dried over $Na_2SO_4$, filtered, and concentrated to provide methyl 3-cyclopentylsulfonylbenzoate (260 mg).

Step 2. A mixture of methyl 3-cyclopentylsulfonylbenzoate (0.28 g, 1.0 mmol), THF (5.0 mL), $H_2O$ (5 mL), and LiOH (50 mg, 2.1 mmol) was stirred at 25° C. for 2 h. The reaction mixture was extracted with MTBE (10 mL×2). The pH of the aqueous phase was adjusted to 3 with HCl and it was extracted with EtOAc (3×20 mL). The extracts were combined, washed with 20 mL of brine, dried over $Na_2SO_4$, filtered, and concentrated to provide 3-cyclopentylsulfonylbenzoic acid (0.29 g).

339
Synthesis of 3-(N-methylcyclopentanesulfonimidoyl)benzoic acid (A-53)

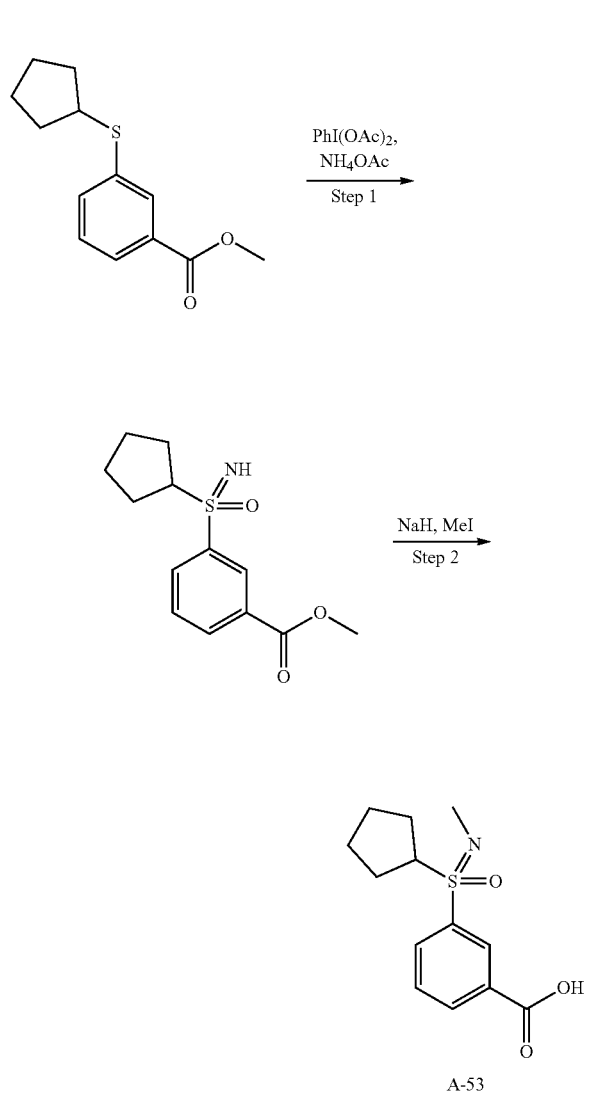

340
Synthesis of 3-(cyclopentanecarbonyl)benzoic acid (A-54)

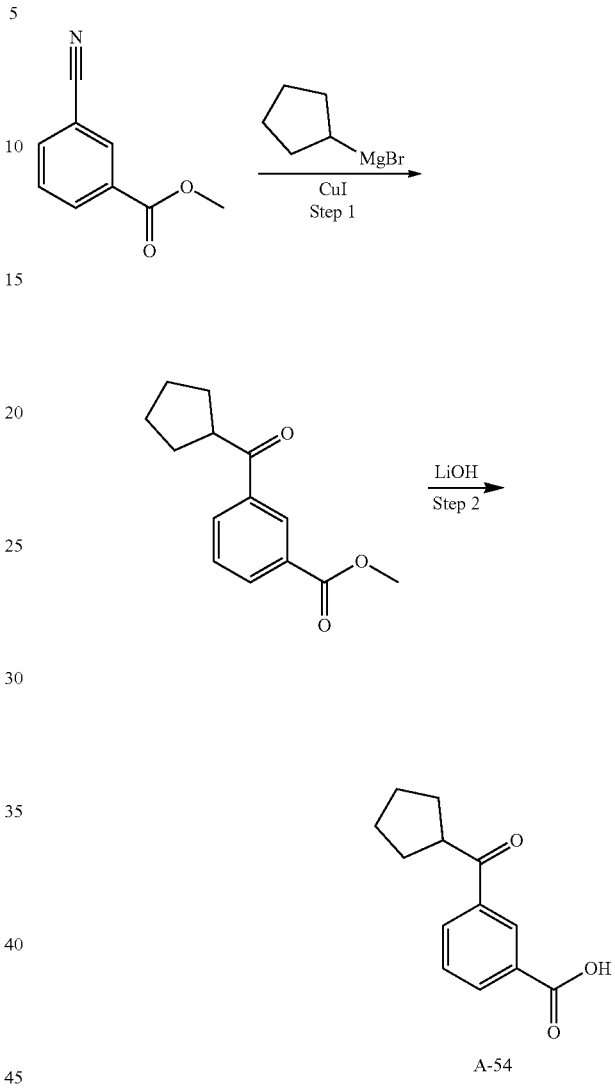

Step 1. To a mixture of methyl 3-cyclopentylsulfanylbenzoate (0.85 g, 3.6 mmol), EtOH (2 mL), and PhI(OAc)$_2$ (3.5 g, 11 mmol) was added NH$_4$OAc (1.1 g, 14 mmol). The mixture was stirred at 20° C. for 2 h, concentrated, combined with H$_2$O (30 mL), and extracted with EtOAc (2×30 mL). The combined extracts were washed with brine (10 mL), dried over Na$_2$SO$_4$, concentrated, and purified by silica chromatography (0-100% EtOAc in petroleum ether) to provide methyl 3-(cyclopentylsulfonimidoyl) benzoate (0.50 g).

Step 2. To a 0° C. mixture of methyl 3-(cyclopentylsulfonimidoyl) benzoate (0.25 g, 0.94 mmol) and DMF (2 mL) was added NaH (60% in mineral oil, 45 mg, 1.1). The mixture was stirred at 0° C. for 0.5 h, and MeI (64 μL, 1.0 mmol) was added. The mixture was stirred at 20° C. for 12 h, poured into H$_2$O (30 mL) and extracted with EtOAc (2×30 mL). The extracts were combined, washed with brine (10 mL), dried over Na$_2$SO$_4$, concentrated to provide 3-(S-cyclopentyl-N-methyl-sulfonimidoyl)benzoic acid (A-53, 0.25 g).

Step 1. To a −50° C. mixture of methyl 3-cyanobenzoate (1.0 g, 6.2 mmol), CuI (0.37 g, 1.9 mmol), and THF (30 mL) was slowly added cyclopentylmagnesium bromide (1 M in THF, 24 mL, 24 mmol). The mixture was stirred at −50° C. for 5 h, then at 20° C. for 1 h, and saturated aqueous NH$_4$Cl (10 mL) was added at 0° C. EtOAc (20 mL) was added, and the layers separated. The aqueous wash was extracted with EtOAc (10 mL), and extracts were combined, washed with brine (15 mL×2), dried over Na$_2$SO$_4$, filtered, concentrated, and purified by silica chromatography (0-20% EtOAc/petroleum ether) to provide methyl 3-(cyclopentanecarbonyl) benzoate (0.22 g).

Step 2. A degassed mixture of methyl 3-(cyclopentanecarbonyl) benzoate (0.22 g, 0.95 mmol), LiOH (0.11 g, 4.7 mmol), THF (0.9 mL), H$_2$O (0.3 mL) was stirred at 25° C. for 4 h. The mixture was concentrated, combined with H$_2$O (10 mL), and extracted with MTBE (2 mL). The pH of the aqueous phase was adjusted to between 2 and 3 with 2N HCl. The resulting precipitate was filtered and dried under vacuum to provide 3-(cyclopentanecarbonyl)benzoic acid (A-54, 120 mg).

Synthesis of 3-(cyclobutanecarbonyl)benzoic acid (A-77)

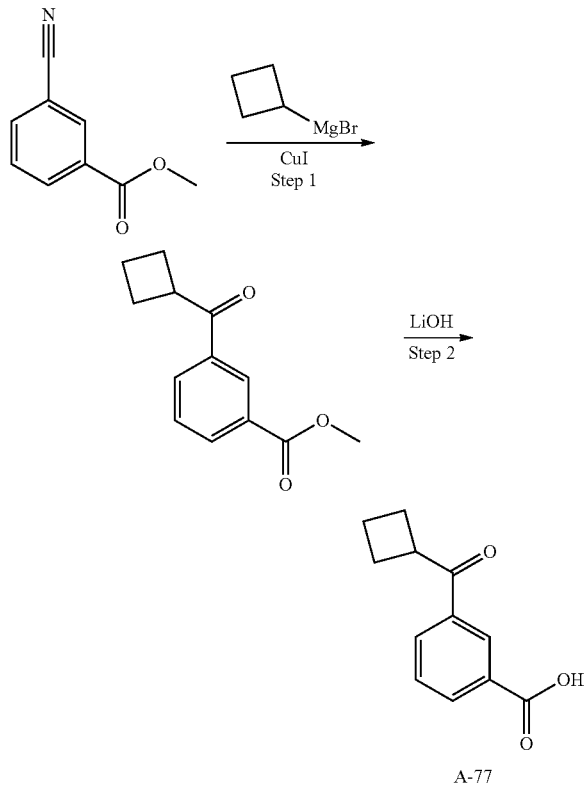

3-(Cyclobutanecarbonyl)benzoic acid was prepared from methyl 3-cyanobenzoate and cyclobutanemagnesium bromide in the same manner as A-54.

Synthesis of 3-(2-cyclobutylacetyl)benzoic acid (A-75)

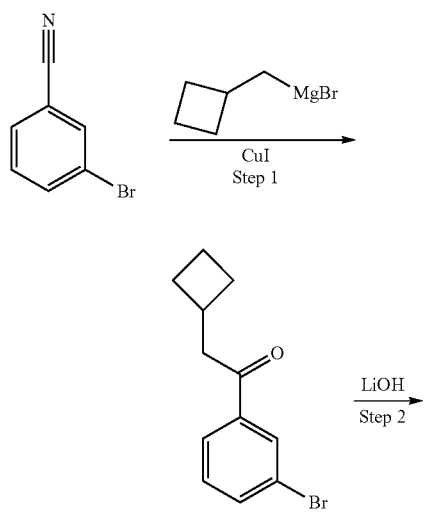

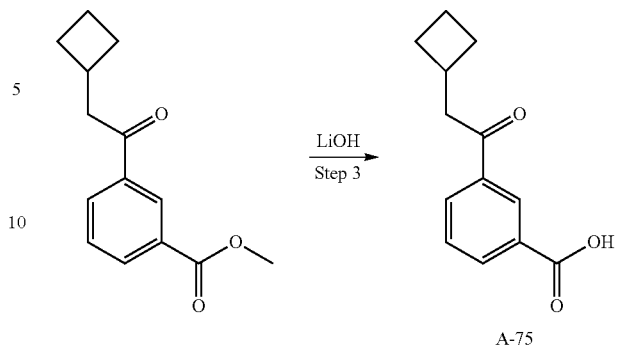

Step 1. To a mixture of 3-bromobenzonitrile (2.0 g, 11 mmol) and THF (10 mL) at −50° C. was added CuI (2.1 g, 11 mmol) and bromo(cyclobutylmethyl)magnesium (1 M, 13.2 mL). The mixture was stirred at −50° C. for 5 h then at 20° C. for 1 h. The mixture was poured into H$_2$O (20 mL) and extracted with EtOAc (2×20 mL). The combined extracts were washed with brine (20 mL), dried over Na2$_s$O$_4$, concentrated, purified by silica chromatography (0-20% EtOAC in PE) to provide 1-(3-bromophenyl)-2-cyclobutylethan-1-one (1.3 g).

Step 2. A mixture of 1-(3-bromophenyl)-2-cyclobutylethan-1-one (1.1 g, 4.4 mmol), MeOH (4 mL), DMF (16 mL), Et$_3$N (1.8 mL, 13 mmol), 3-diphenylphosphanylpropyl-(diphenyl)phosphane (0.36 g, 0.87 mmol), and Pd(OAc)$_2$ (0.20 g, 0.87 mmol) was stirred at 90° C. for 12 h under CO (50 psi). The mixture was poured to water (30 mL), extracted with EtOAc (2×30 mL), and the combined extracts were washed with brine (10 mL), dried over Na$_2$SO$_4$, concentrated, and purified by silica chromatography (0-20% EtOAc in PE) provide methyl 3-(2-cyclobutylacetyl)benzoate (0.80 g).

Step 3. A mixture of methyl 3-(2-cyclobutylacetyl)benzoate (0.50 g, 2.2 mmol), THF (0.6 mL), H$_2$O (0.2 mL), and LiOH (0.16 g, 6.7 mmol) was stirred at 20° C. for 2 h. The mixture was concentrated to remove THF, and HCl (0.5 M, 5 mL) was added. The mixture was extracted with EtOAc (2×30 mL) and the combined extracts were washed with brine (10 mL), dried over Na$_2$SO$_4$, and concentrated to provide 3-(2-cyclobutylacetyl)benzoic acid (0.36 g, 46% purity).

Synthesis of 3-(cyclopentyldifluoromethyl)benzoate (A-76)

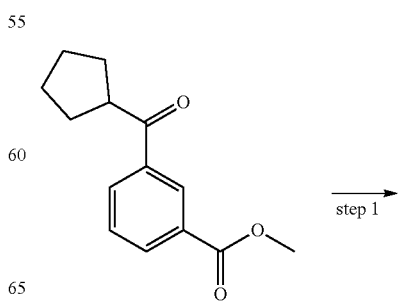

343

-continued

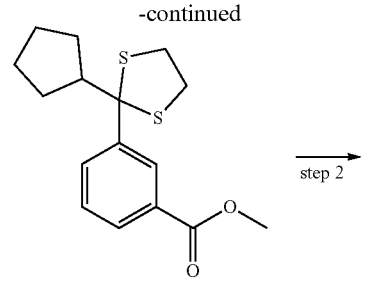

step 2 →

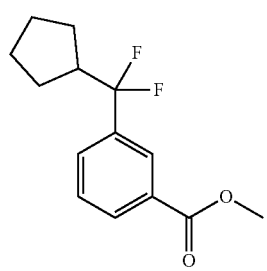

step 4 →

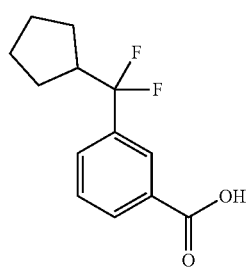

A-76

Step 1. To a mixture of methyl 3-(cyclopentanecarbonyl) benzoate (0.16 mg, 0.69 mmol) and CH$_2$Cl$_2$ (1 mL) was added BF$_3$·Et$_2$O (0.64 mL, 5.2 mmol) and ethane-1,2-dithiol (0.10 mL, 1.2 mmol). The mixture was stirred at 20° C. for 18 h, poured into water (20 mL), and extracted with CH$_2$Cl$_2$ (2×30 mL). The combined extracts were washed with brine (10 mL), dried Na$_2$SO$_4$, concentrated, purified by preparative TLC (10% EtOAc/PE) to provide methyl 3-(2-cyclopentyl-1,3-dithiolan-2-yl)benzoate (0.20 g).

Step 2. To a mixture of methyl 3-(2-cyclopentyl-1,3-dithiolan-2-yl)benzoate (0.20 g, 0.65 mmol) and CH$_2$Cl$_2$ (10 mL) was added NIS (0.29 g, 1.3 mmol) and pyridine hydrofluoride (0.33 mL, 2.6 mmol) at −70° C. The mixture was stirred at −70° C. for 0.5 h, poured into H$_2$O (10 mL) and extracted with EtOAc (2×10 mL). The combined extracts were washed with brine (10 mL), dried over Na$_2$SO$_4$, concentrated, and purified by preparative TLC (10% EtOAc in PE) to provide methyl 3-[cyclopentyl(difluoro)methyl]benzoate (80 mg).

Step 3. A mixture of methyl 3-[cyclopentyl(difluoro) methyl]benzoate (80 mg, 0.32 mmol), THF (3 mL), H$_2$O (1 mL), and LiOH (23 mg, 0.94 mmol) was stirred at 20° C. for 2 h. The mixture was concentrated, combined with HCl (0.5 M, 5 mL), and extracted with EtOAc (2×30 mL). The combined extract was washed with brine (10 mL), dried Na$_2$SO$_4$, concentrated, to provide 3-[cyclopentyl(difluoro) methyl]benzoic acid (A-76, 91 mg).

344

Synthesis of 3-(cyclopentanesulfonimidoyl)benzoic acid (A-72)

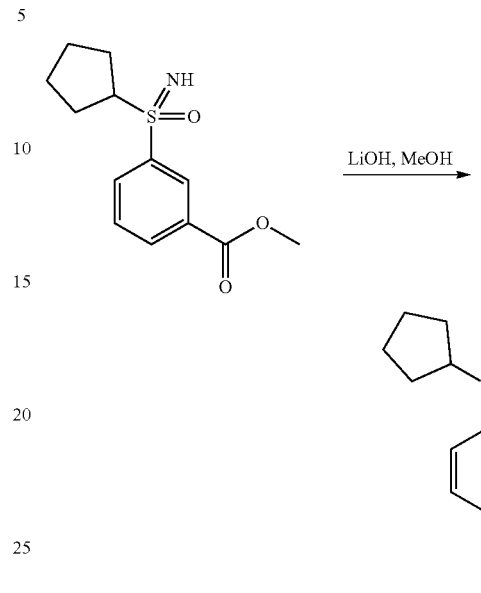

A mixture of methyl 3-(cyclopentylsulfonimidoyl)benzoate (0.80 g, 3.0 mmol), THF (18 mL), H$_2$O (6 mL), and LiOH·H$_2$O (0.38 g, 9.0 mmol) was stirred at 25° C. for 12 h, then was poured into water (20 mL) and =extracted with EtOAc (2×10 mL). The organic phase was washed with brine (20 mL), dried over Na$_2$SO$_4$, and concentrated to provide 3-(cyclopentanesulfonimidoyl)benzoic acid (A-72, 0.3 g). $^1$H NMR (DMSO-d$^6$, 400 MHz) δ ppm 13.72-13.06 (m, 1H), 8.40-8.38 (s, 1H), 8.20-8.17 (m, 1H), 8.13-8.09 (m, 1H), 7.76-7.72 (m, 1H), 3.68-3.60 (m, 1H), 1.91-1.70 (m, 4H), 1.62-1.47 (m, 4H).

Synthesis of 2-(cyclopentyl(hydroxy)methyl)isonicotinic acid (A-78)

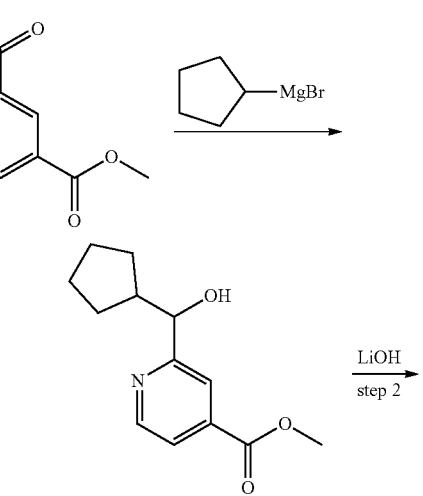

-continued

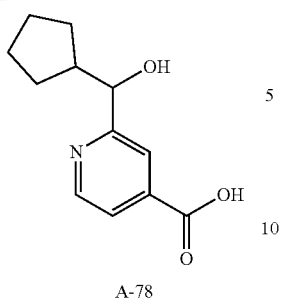

A-78

Step 1. To a −60° C. mixture of methyl 2-formylisonicotinate (1.0 g, 6.0 mmol) and THF (25 mL) was added cyclopentylmagnesium bromide (1 M, 7.3 mL) over 15 min. The resulting mixture was stirred at −60° C. for 1.75 h, poured into water (50 mL), and extracted with EtOAc (2×50 mL). The combined extracts were washed with brine (10 mL), dried over $Na_2SO_4$, concentrated, and purified by silica chromatography (0-100% EtOAc in PE) to provide methyl 2-(cyclopentyl(hydroxy)methyl)isonicotinate (0.20 g).

Step 2. A mixture of methyl 2-(cyclopentyl(hydroxy)methyl)isonicotinate (0.18 g, 0.77 mmol), THF (2 mL), and $H_2O$ (1 mL), and LiOH·$H_2O$ (96 mg, 2.0 mmol) was stirred at 25° C. for 2 h, poured into water (30 mL), and extracted with MTBE (2×20 mL). The aqueous layer was collected, and the pH was adjusted to 5 by the careful addition of 2N HCl. The mixture was concentrated to provide 2-(cyclopentyl(hydroxy)methyl)isonicotinic acid (A-78).

Synthesis of 3-((3,3-difluorocyclobutyl)sulfonyl)benzoic acid (A-82)

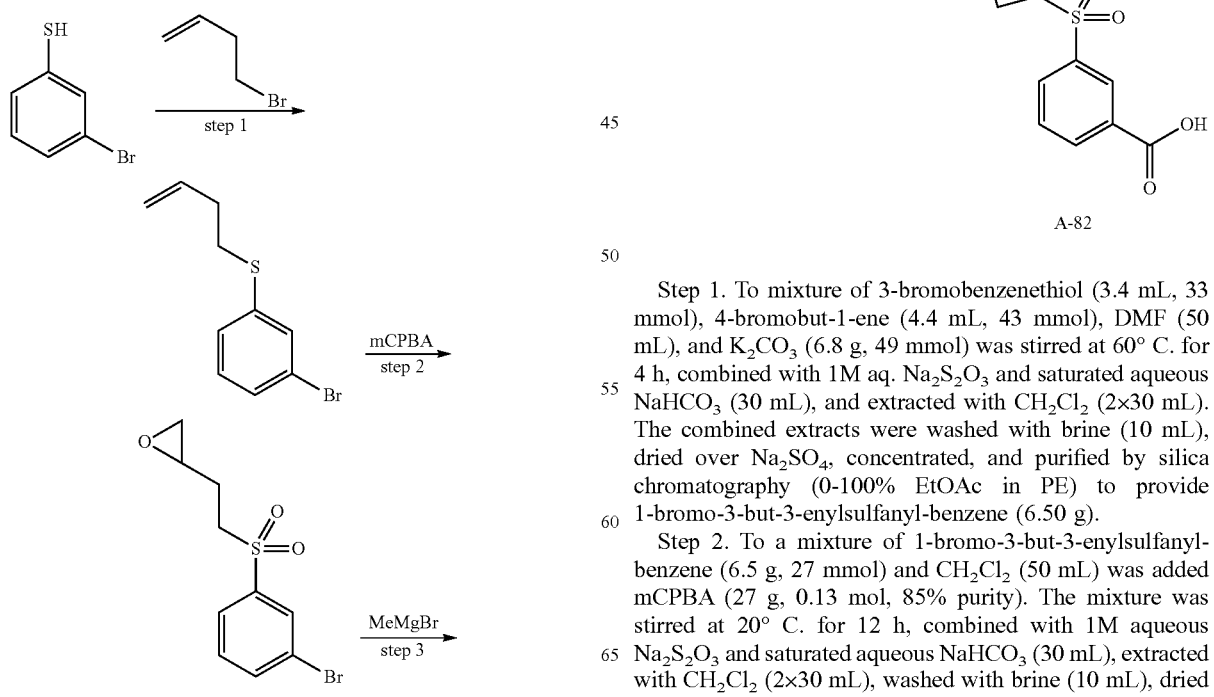

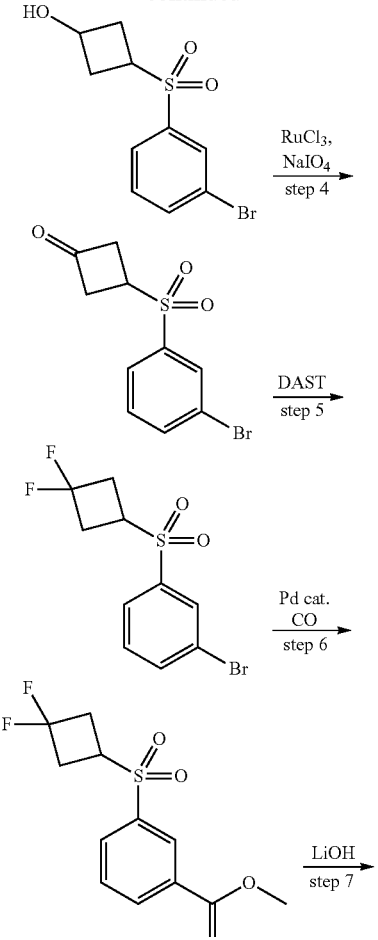

A-82

Step 1. To mixture of 3-bromobenzenethiol (3.4 mL, 33 mmol), 4-bromobut-1-ene (4.4 mL, 43 mmol), DMF (50 mL), and $K_2CO_3$ (6.8 g, 49 mmol) was stirred at 60° C. for 4 h, combined with 1M aq. $Na_2S_2O_3$ and saturated aqueous $NaHCO_3$ (30 mL), and extracted with $CH_2Cl_2$ (2×30 mL). The combined extracts were washed with brine (10 mL), dried over $Na_2SO_4$, concentrated, and purified by silica chromatography (0-100% EtOAc in PE) to provide 1-bromo-3-but-3-enylsulfanyl-benzene (6.50 g).

Step 2. To a mixture of 1-bromo-3-but-3-enylsulfanyl-benzene (6.5 g, 27 mmol) and $CH_2Cl_2$ (50 mL) was added mCPBA (27 g, 0.13 mol, 85% purity). The mixture was stirred at 20° C. for 12 h, combined with 1M aqueous $Na_2S_2O_3$ and saturated aqueous $NaHCO_3$ (30 mL), extracted with $CH_2Cl_2$ (2×30 mL), washed with brine (10 mL), dried over $Na_2SO_4$, concentrated, and purified by silica chromatography (0-100% EtOAc in PE) to provide 2-[2-(3-bromophenyl)sulfonylethyl]oxirane (5.1 g).

Step 3. To a mixture of 2-[2-(3-bromophenyl)sulfonylethyl]oxirane (5.1 g, 18 mmol) and THF (50 mL) was added MeMgBr (3 M, 23 mL, 69 mmol) at -70° C. The mixture was stirred at 20° C. for 12 h, poured into saturated aqueous NH₄Cl (20 mL), and extracted with EtOAc (2×20 mL). The combined extracts were washed with brine (10 mL), dried over Na₂SO₄, concentrated, and purified by silica chromatography (0-100% EtOAc in PE) to provide 3-(3-bromophenyl)sulfonylcyclobutanol (4.3 g).

Step 4. To a mixture of 3-(3-bromophenyl)sulfonylcyclobutanol (1.00 g, 3.4 mmol), H₂O (10 mL), MeCN (5 mL), and CH₂Cl₂ (5 mL) at 40° C. were added RuCl₃·H₂O (8 mg, 34 μmol) and NaIO₄ (3.7 g, 17 mmol). The mixture was stirred at 40° C. for 12 h, cold water (30 mL) was added, and the mixture was extracted with CH₂Cl₂ (2×30 mL). The combined extracts were washed with saturated aqueous NaHCO₃ and brine, dried over Na₂SO₄, concentrated, and purified by silica chromatography (0-100% EtOAc in PE) to provide 3-(3-bromophenyl)sulfonylcyclobutanone (0.64 g).

Step 5. To a mixture of 3-(3-bromophenyl)sulfonylcyclobutanone (0.64 g, 2.2 mmol) and CH₂Cl₂ (6 mL) was added DAST (0.88 mL, 6.6 mmol) over 0.5 h at -70° C. The mixture was stirred for 1 h, and then allowed to warm 20° C. and stirred for 16 h. The mixture was poured into saturated aqueous NaHCO₃ (10 mL) and the extracted with CH₂Cl₂ (2×10 mL), and the combined extracts were washed with brine (10 mL), dried over Na₂SO₄, concentrated, and purified by silica chromatography (0-100% EtOAc in PE) to provide 1-bromo-3-(3,3-difluorocyclobutyl)sulfonyl-benzene (0.60 g).

Step 6. CO gas was bubbled through a stirring mixture of 1-bromo-3-(3,3-difluorocyclobutyl)sulfonyl-benzene (0.55 g, 1.8 mmol), Et₃N (0.49 mL, 3.5 mmol), DMF (6 mL), MeOH (3 mL), bis(diphenylphosphino)propane (73 mg, 0.18 mmol), and Pd(OAc)₂ (40 mg, 0.18 mmol) for 5 mins and the mixture was then heated at 80° C. under a CO atmosphere at 15 psi for 12 h. The mixture was poured into water (30 mL), extracted with EtOAc (2×30 mL), and the combined extracts were washed with brine (10 mL), dried over Na₂SO₄, concentrated, and purified by silica chromatography (0-100% EtOAc in PE) to provide methyl 3-(3,3-difluorocyclobutyl)sulfonylbenzoate (0.44 g).

Step 7. A mixture of methyl 3-(3,3-difluorocyclobutyl)sulfonylbenzoate (0.44 g, 1.5 mmol), THF (5 mL), H₂O (1.5 mL), and LiOH·H₂O (0.25 g, 6.1 mmol) was stirred at 40° C. for 2 h, concentrated, combined with H₂O (30 mL), 2N HCl was added until the pH was between 3 and 4, and the resulting mixture was extracted with EtOAc (2×30 mL). The combined extracts were washed with brine (10 mL), dried over Na₂SO₄, and concentrated to provide 3-((3,3-difluorocyclobutyl)sulfonyl)benzoic acid (A-82, 0.33 g).

Synthesis of
5-(cyclopentylsulfonyl)thiophene-3-carboxylic acid
(A-83)

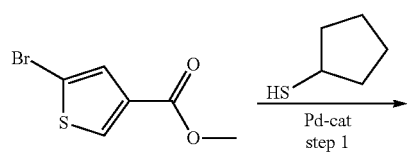

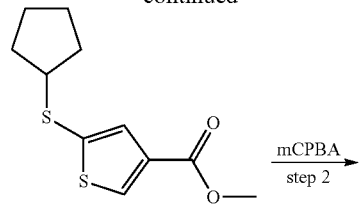

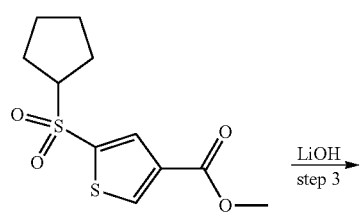

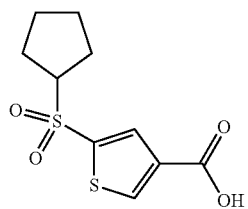

A-83

Step 1. A mixture of methyl 5-bromothiophene-3-carboxylate (1.0 g, 4.5 mmol), 1,4-dioxane (25 mL), iPr₂NEt (2.0 mL, 11 mmol), Pd₂(dba)₃ (0.41 g, 0.45 mmol), cyclopentanethiol (0.73 mL, 6.8 mmol), and Xantphos (0.26 g, 0.45 mmol) was stirred at 110° C. for 12 h. The mixture was poured into H₂O (20 mL), extracted with EtOAc (2×10 mL), and the combined extracts were washed with brine (20 mL), dried over Na₂SO₄, concentrated, and purified by silica chromatography (5-50% EtOAc in PE) to provide methyl 5-cyclopentylsulfanylthiophene-3-carboxylate (1.0 g).

Step 2. To a mixture of methyl 5-cyclopentylsulfanylthiophene-3-carboxylate (0.70 g, 2.9 mmol) and CH₂Cl₂ (20 mL) was added mCPBA (2.4 g, 12 mmol, 85% purity). The mixture was stirred at 20° C. for 12 h, poured into saturated Na₂SO₃ (10 mL), and extracted with EtOAc (2×5 mL). The combined extracts were washed with brine (10 mL), dried over anhydrous Na₂SO₄, concentrated, and purified by silica chromatography (5-50% EtOAc in PE) to provide methyl 5-cyclopentylsulfonylthiophene-3-carboxylate (0.70 g).

Step 3. A mixture methyl 5-cyclopentylsulfonylthiophene-3-carboxylate (0.71 g, 2.6 mmol), THF (9 mL), H₂O (3 mL), and LiOH·H₂O (0.32 g, 7.7 mmol) was stirred at 20° C. for 12 h, poured into H₂O (10 mL), and the pH was adjusted to 3-4 with HCl (2 N). The resulting mixture was extracted with EtOAc (2×5 mL). The extracts were combined, washed with brine (5 mL), dried over Na₂SO₄, concentrated, and purified by silica chromatography (5-50% EtOAc in PE) to provide 5-(cyclopentylsulfonyl)thiophene-3-carboxylic acid (A-83, 0.40 g).

Synthesis of 3-(cyano(cyclopentyl)methyl)benzoic acid (A-85)

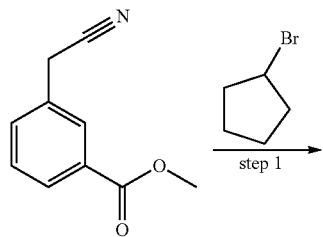

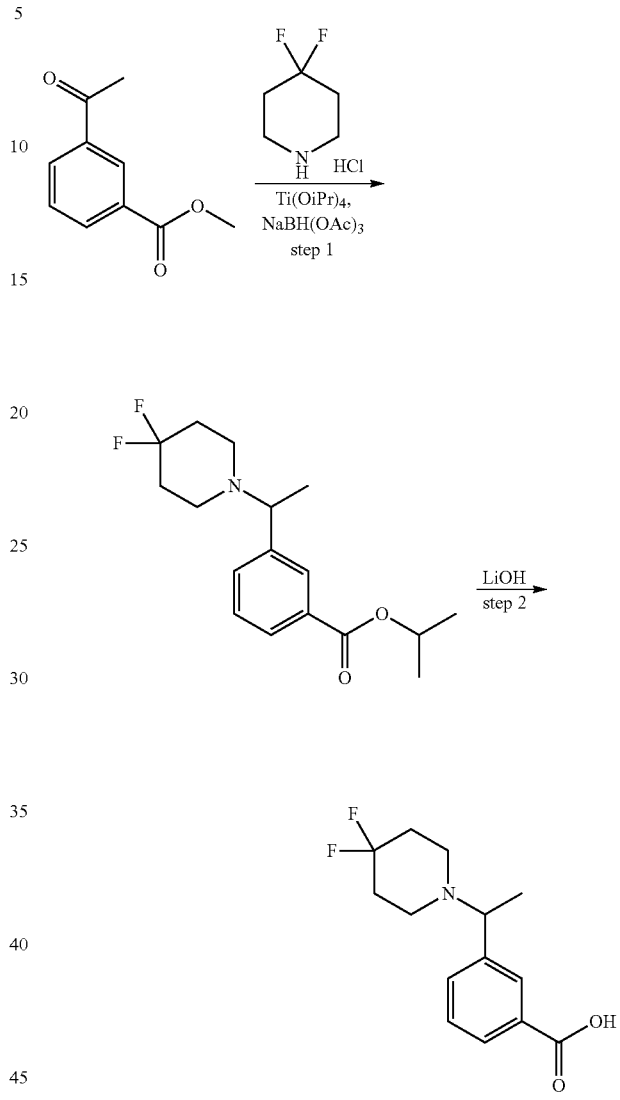

Step 1. To a mixture of methyl 3-(cyanomethyl)benzoate (0.10 g, 0.58 mmol) and DMF (2 mL) was added NaH (27 mg, 0.69 mmol, 285 uL, 60% purity, 1.2 eq) at 0° C. After stirring for 0.5 h, bromocyclopentane (0.12 mL, 1.1 mmol) was added dropwise at 0° C. The resulting mixture was stirred at 25° C. for 2 h, and saturated aqueous NH$_4$Cl (2 mL) and H$_2$O (10 mL) were added at 0° C. The mixture was extracted with EtOAc (10 mL×3), and the combined extracts were washed with brine (10 mL×3), dried over Na$_2$SO$_4$, filtered, concentrated, purified by silica chromatography (0-15% EtOAc in PE) to provide methyl 3-(cyano(cyclopentyl)methyl)benzoate (0.10 g).

Step 2. A mixture of methyl 3-(cyano(cyclopentyl)methyl)benzoate (0.10 g, 0.41 mmol), THF (3 mL), H$_2$O (3 mL), and LiOH·H$_2$O (35 mg, 0.82 mmol) was stirred at 20° C. for 4 h, concentrated, and the pH adjusted to 4 by the dropwise addition of 2M HCl. The mixture was extracted with EtOAc (20 mL×3), and the combined extracts were dried over Na$_2$SO$_4$, filtered, and concentrated to provide 3-(cyano(cyclopentyl)methyl)benzoic acid (A-85, 0.11 g).

Synthesis of 3-(1-(4,4-difluoropiperidin-1-yl)ethyl) benzoic acid (A-86)

Step 1. A mixture of methyl 3-acetylbenzoate (1.0 g, 5.6 mmol) and 4,4-difluoropiperidine hydrochloride (0.88 g, 5.6 mmol), 1,2-dichloroethane (20 mL), Ti(OiPr)$_4$ (6.6 mL, 23 mmol) and then was stirred at 80° C. for 12 h. NaBH(OAc)$_3$ (3.6 g, 17 mmol) was added and the mixture was stirred at 80° C. for 2 h, poured into water (20 mL), and extracted with EtOAc (2×20 mL). The combined extracts were washed with brine (10 mL), dried over Na$_2$SO$_4$, and concentrated to provide isopropyl 3-[1-(4,4-difluoro-1-piperidyl)ethyl]benzoate (1.5 g).

Step 2. A mixture of isopropyl 3-[1-(4,4-difluoro-1-piperidyl)ethyl]benzoate (1.4 g, 4.6 mmol) in THF (14 mL), MeOH (3.3 mL), and H$_2$O (3.3 mL), and LiOH (0.33 g, 14 mmol) was stirred at 25° C. for 2 h. The mixture was concentrated, combined with H$_2$O (28 mL) and washed with EtOAc (2×28 mL). The aqueous solution was treated with 2M HCl until a pH of 2, and the resulting mixture was concentrated to provide 3-[1-(4,4-difluoro-1-piperidyl)ethyl]benzoic acid (A-86, 0.91 g).

Synthesis of 6-((4,4-difluoropiperidin-1-yl)methyl) picolinic acid (A-87)

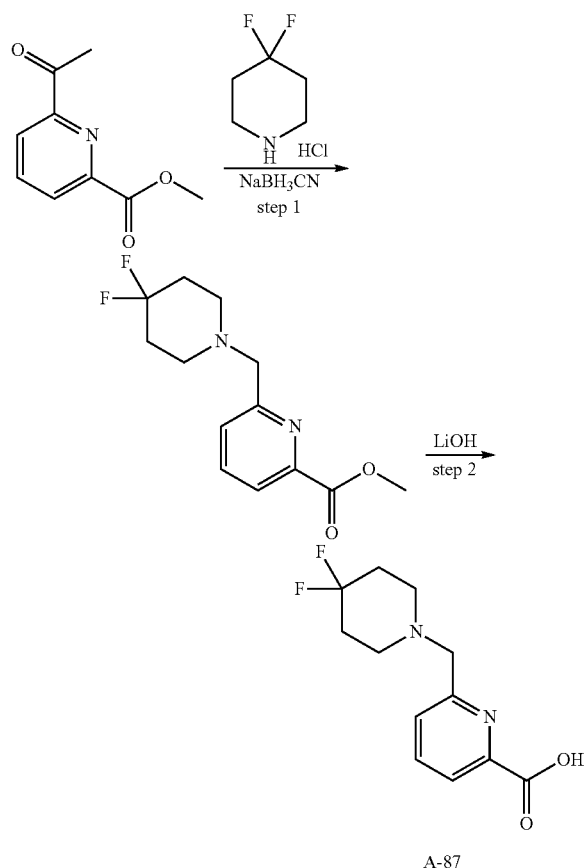

Step 1. A mixture of methyl 6-formylpyridine-2-carboxylate (0.50 g, 3.0 mmol) and 4,4-difluoropiperidine (477 mg, 3.0 mmol, 1.0 eq, HCl) in MeOH (10 mL) was added HOAc (545 mg, 9.1 mmol, 519 uL, 3.0 eq), NaOAc (745 mg, 9.1 mmol, 3.0 eq) and then was stirred at 25° C. for 1 hour. Then added NaBH$_3$CN (761 mg, 12.1 mmol, 4.0 eq), the mixture was stirred at 25° C. for 1 hour. The reaction was poured into water (10 mL) and the resulting mixture was extracted with EtOAc (2×10 mL). The organic phase was washed with brine (10 mL), dried over anhydrous Na$_2$SO$_4$, concentrated in vacuum to afford the compound methyl 6-[(4,4-difluoro-1-piperidyl)methyl]pyridine-2-carboxylate (500 mg, crude) as a yellow solid.

Synthesis of 3-((3,3-difluoropyrrolidin-1-yl)methyl) benzoic acid (A-92)

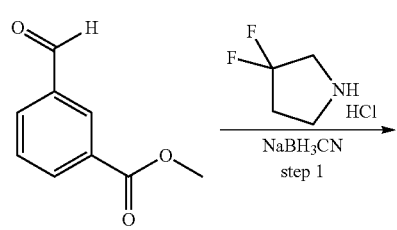

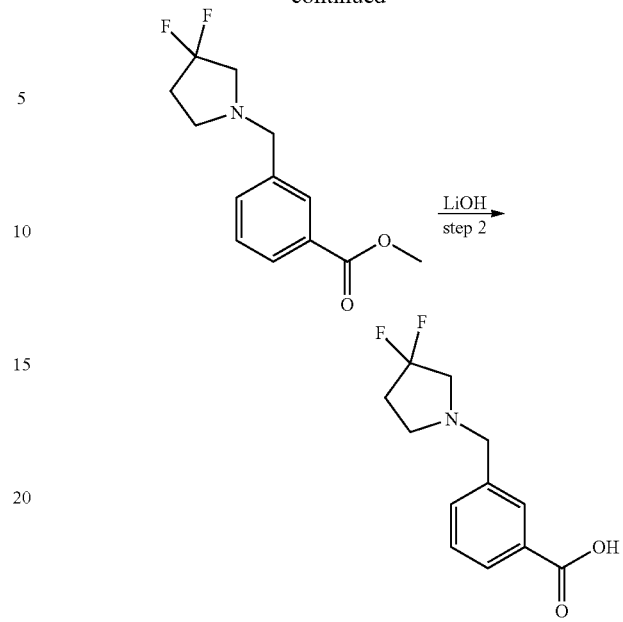

3-((3,3-difluoropyrrolidin-1-yl)methyl)benzoic acid (A-92) was prepared from methyl 3-formylbenzoate in the manner described for the synthesis of A-87.

Synthesis of 2-((4,4-difluoropiperidin-1-yl)methyl)-6-methylpyrimidine-4-carboxylic acid (A-88)

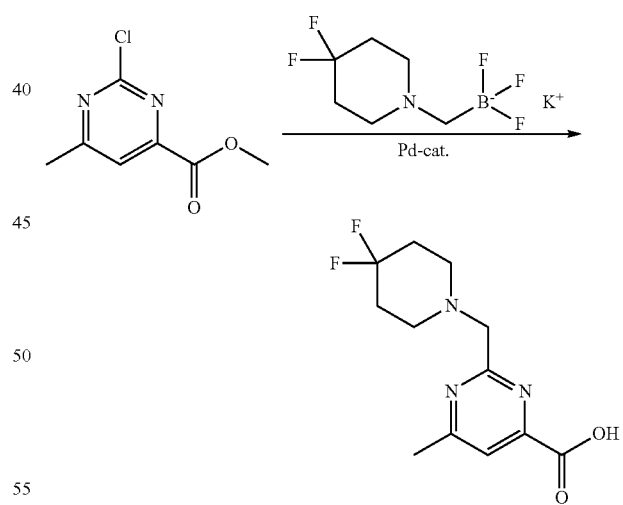

A mixture of potassium ((4,4-difluoropiperidin-1-yl)methyl)trifluoroborate (CAS: 1708960-44-4, 1.1 g, 4.6 mmol), methyl 2-chloro-6-methyl-pyrimidine-4-carboxylate (0.28 g, 1.5 mmol), H$_2$O (2 mL), THF (8 mL) Cs$_2$CO$_3$ (1.5 g, 4.6 mmol), and Xphos Pd G4 (65 mg, 76 μmol). The mixture was stirred at 80° C. for 12 h, diluted with water (10 mL), and extracted with EtOAc (10 mL×3). The combined extracts were washed with brine (10 mL), dried over Na$_2$SO$_4$, filtered, concentrated, and purified by preparative HPLC (C18, 1-10% MeCN in H$_2$O [formic acid]) to provide 2-((4,4-difluoropiperidin-1-yl)methyl)-6-methylpyrimidine-4-carboxylic acid (A-88, 50 mg).

Synthesis of 3-(isoxazolidin-2-ylmethyl)benzoic acid (A-89)

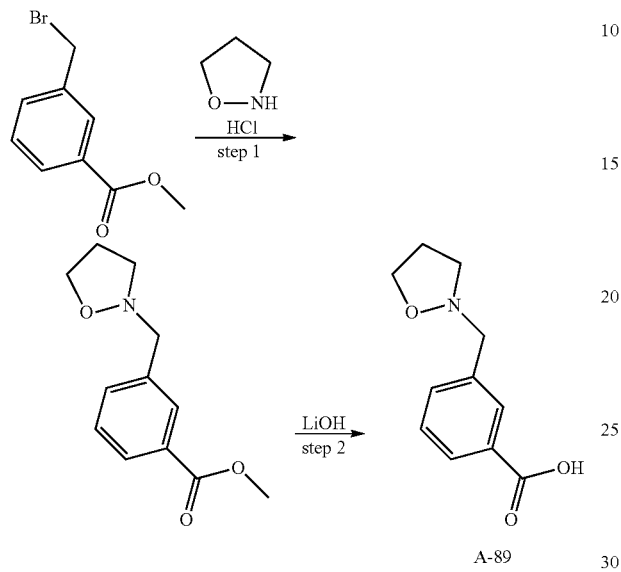

A-89

Step 1. A mixture of methyl 3-(bromomethyl)benzoate (0.30 g, 1.3 mmol), DMF (3 mL), isoxazolidine hydrochloride (0.14 g, 1.3), and iPr$_2$NEt (0.68 mL, 3.9 mmol) was stirred at 60° C. for 12 h. The mixture was combined with 0° C. H$_2$O (10 mL) and extracted with EtOAc (10 mL×2). The combined extracts were washed with H$_2$O (10 mL) and brine (10 mL), dried over Na$_2$SO$_4$, concentrated, and purified by silica chromatography (0-100% EtOAc in PE) to provide methyl 3-(isoxazolidin-2-ylmethyl)benzoate (0.17 g).

Step 2. A mixture of methyl 3-(isoxazolidin-3-ylmethyl)benzoate (0.17 g, 0.77 mmol), 1,4-dioxane (1.5 mL), H$_2$O (0.5 mL) and LiOH·H$_2$O (32 mg, 0.77 mmol) was stirred at 20° C. for 12 h, and H$_2$O (5 mL) and MTBE (10 mL). The aqueous phase was collected and the pH adjusted to 6.0 by addition of HCl (2 N). The aqueous phase was concentrated to provide 3-(isoxazolidin-3-ylmethyl)benzoic acid (A-89, 0.17 g, crude).

Synthesis of 3-((6,6-difluoro-3-azabicyclo[3.1.0]hexan-3-yl)methyl)benzoic acid (A-96)

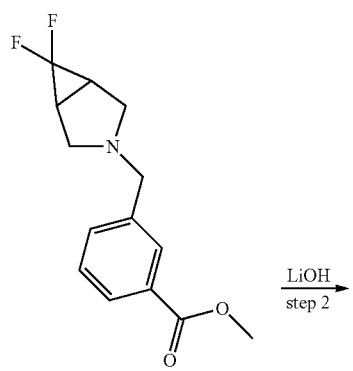

A-96

Synthesis of 3-((6,6-difluoro-3-azabicyclo[3.1.0]hexan-3-yl)methyl)benzoic acid (A-96) was prepared in the same manner as A-89 by substituting 6,6-difluoro-3-azabicyclo [3.1.0]hexane hydrochloride for isoxazolidine hydrochloride Synthesis of 3-(cyclopentylamino)benzoic acid (A-90)

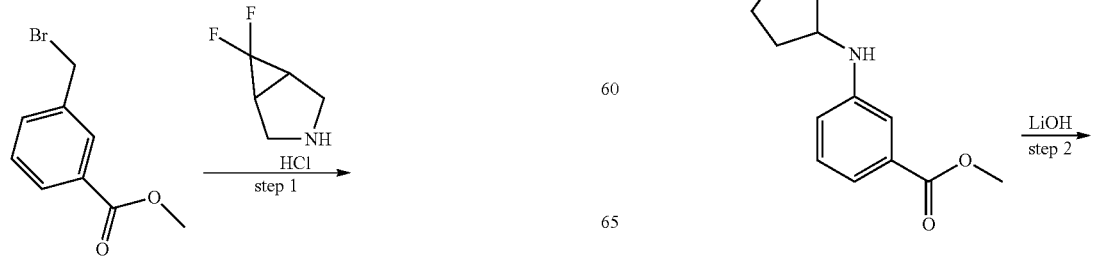

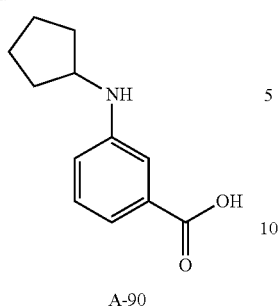

A-90

Step 1. A mixture of methyl 3-aminobenzoate (1.0 g, 6.6 mmol). cyclopentanone (2.9 mL, 33 mmol), MeOH (10 mL), and HOAc (0.38 mL, 6.6 mmol) was stirred for 3 hours, and NaBH$_3$CN (0.62 g, 9.9 mmol) was added in portions. The resulting mixture was stirred for 11 h, poured into water (50 mL), and extracted with EtOAc (2×25 mL). The extracts were washed with brine (10 mL), dried over Na$_2$SO$_4$, concentrated, and purified by silica chromatography (5-50% EtOAc in PE) to provide methyl 3-(cyclopentylamino)benzoate (1.33 g, 91.68% yield) as a white solid.

Step 2. A mixture of methyl 3-(cyclopentylamino)benzoate (0.10 g, 0.46 mmol), THF (0.9 mL), H$_2$O (0.3 mL), and LiOH·H$_2$O (96 mg, 2.3 mmol) was stirred at 60° C. for 6 h, poured into H$_2$O (10 mL), and the pH adjusted to 5-6 with HCl (2 N). The resulting mixture was extracted with EtOAc (2×5 mL), the extracts were washed with brine (5 mL), dried over Na$_2$SO$_4$, and concentrated to provide 3-(cyclopentylamino)benzoic acid (A-90, 53 mg).

Synthesis of 3-(cyclopentyl(methyl)amino)benzoic acid (A-91)

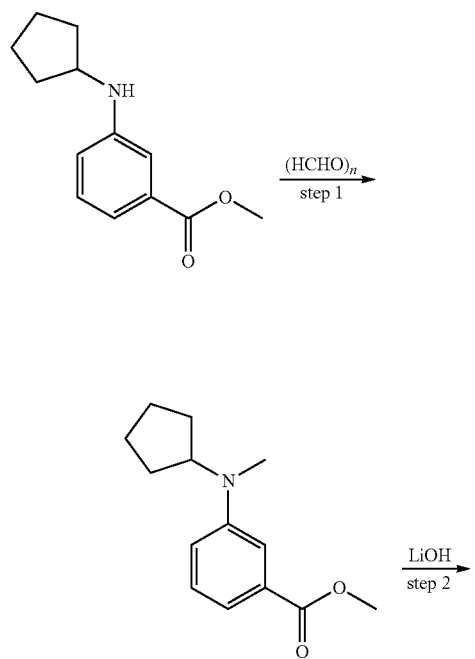

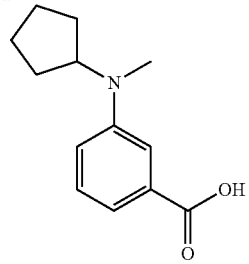

Step 1. To a mixture of methyl 3-(cyclopentylamino)benzoate (0.50 g, 2.0 mmol), paraformaldehyde (0.41 mg, 5 mmol), and dichloroethane (5 mL) was added HOAc (0.16 mL, 3.0 mmol) dropwise at 20° C. After stirring for 1 h, and NaBH(OAc)$_3$ (0.97 g, 5 mmol) and the mixture was stirred at 60° C. for 11 h. The reaction was poured into water (20 mL) and the resulting mixture was extracted with EtOAc (2×15 mL). The organic phase was washed with brine (10 mL), dried over Na$_2$SO$_4$, concentrated, and purified by silica chromatography (5-50% EtOAc in PE) to provide methyl 3-[cyclopentyl(methyl)amino]benzoate (0.42 g).

Step 2. A mixture of methyl 3-[cyclopentyl(methyl) amino]benzoate (0.23 g, 0.98 mmol), THF (3 mL), and H$_2$O (1 mL), and LiOH·H$_2$O (0.12 g, 3.0 mmol) was stirred at 60° C. for 2 h. The mixture was poured into water (10 mL), the pH adjusted to 3-4 with HCl (2 N), and was extracted with EtOAc (2×5 mL). The extracts were washed with brine (5 mL), dried over Na$_2$SO$_4$, and concentrated to provide 3-(cyclopentyl(methyl)amino)benzoic acid (A-91, 0.30 g).

Synthesis of 3-(3,3-difluorocyclobutane-1-carbonyl)benzoic acid (A-93)

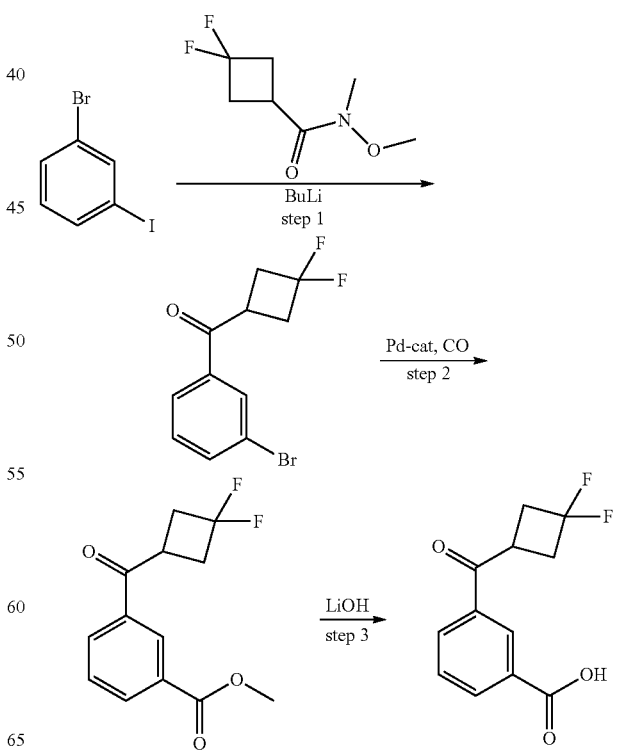

Step 1. To a −70° C. mixture of 1-bromo-3-iodo-benzene (1.3 mL, 10 mmol) and THF (20 mL), was added dropwise BuLi (1 M, 10 mL). The mixture was stirred for 30 min. and 3,3-difluoro-N-methoxy-N-methyl-cyclobutanecarboxamide (1.5 g, 8.4 mmol) in THF (10 mL) was added dropwise at −70° C. The resulting mixture was stirred at 20° C. for 1.5 h, poured into saturated aqueous NH$_4$Cl (10 mL), and extracted with EtOAc (2×10 mL). The combined extracts were washed with brine (10 mL), dried over Na$_2$SO$_4$, concentrated, and purified by silica chromatography (0-100% EtOAc in PE) to provide (3-bromophenyl)-(3,3-difluorocyclobutyl) methanone (1.1 g).

Step 2. A mixture of (3-bromophenyl)-(3,3-difluorocyclobutyl)methanone (1.0 g, 3.6 mmol), MeOH (5 mL), DMF (10 mL), Et$_3$N (1.5 mL, 11 mmol), 3-diphenylphosphanylpropyl (diphenyl)phosphane (0.30 g, 0.73 mmol), Pd(OAc)$_2$ (0.16 g, 0.73 mmol) was stirred at 80° C. for 12 h under CO (50 psi). The mixture was concentrated, poured into H$_2$O (10 mL), and extracted with EtOAc (2×10 mL). The combined extracts were washed with brine (10 mL), dried over Na$_2$SO$_4$, concentrated, and purified by preparative TLC (10% EtOAc in PE) to provide methyl 3-(3,3-difluorocyclobutanecarbonyl)benzoate (0.80 g).

Step 3. A mixture methyl 3-(3,3-difluorocyclobutanecarbonyl)benzoate (0.80 g, 3.2 mmol), THF (0.6 mL), H$_2$O (0.2 mL), and LiOH·H$_2$O (226 mg, 9.4 mmol, 3.0 eq) The mixture was stirred at 20° C. for 2 h, concentrated, and HCl (0.5 M, 5 mL) was added. The mixture was extracted with EtOAc (10 mL), and the extract was concentrated to provide 3-(3,3-difluorocyclobutane-1-carbonyl)benzoic acid (A-93, 0.50 g).

Synthesis of
3-(1-methylcyclobutane-1-carbonyl)benzoic acid
(A-94)

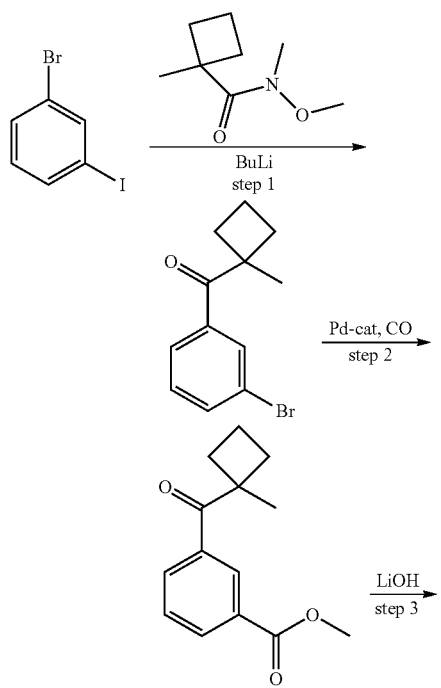

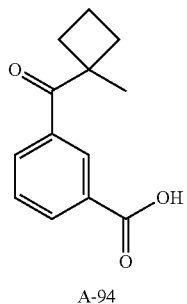

A-94

3-(1-methylcyclobutane-1-carbonyl)benzoic acid (A-94) was prepared in the same manner as A-93.

Synthesis of
4-(cyclopentanecarbonyl)thiophene-2-carboxylic acid (A-98)

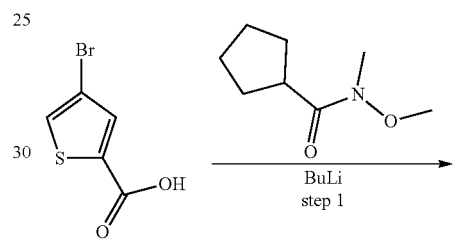

nBuLi (2.5 M, 3.9 mL, 2.5 eq) was added dropwise to 4-bromothiophene-2-carboxylic acid (0.80 g, 3.9 mmol) in THF (15 mL) over 5 min at −78° C. The mixture was stirred for 25 min, and N-methoxy-N-methyl-cyclopentanecarboxamide (0.91 g, 5.8 mmol) was added at −78° C. The resulting mixture was stirred at 20° C. for 12 h, combined with saturated NH$_4$Cl 1 mL at −78° C. and H$_2$O (5 mL) and extracted with EtOAc (10 mL×3). The combined extracts were washed with brine (10 mL), dried Na$_2$SO$_4$, filtered, concentrated, and purified by preparative HPLC (C18, 20-50% MeCN in H$_2$O [HCl]) to provide 4-(cyclopentanecarbonyl) thiophene-2-carboxylic acid (A-98, 10%).

Synthesis of 5-(cyclopentyl(hydroxy)methyl)furan-2-carboxylic acid (A-99)

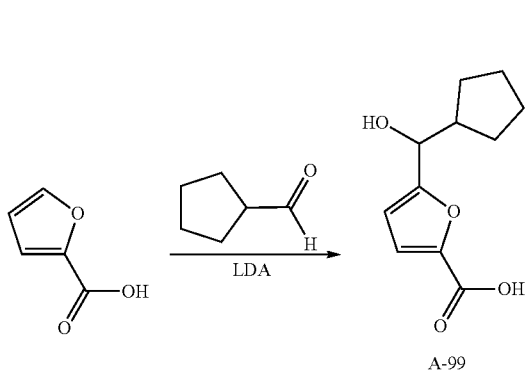

Synthesis of 3-(N-(3,3-difluorocyclobutyl)-N-methylsulfamoyl)benzoic acid (A-95)

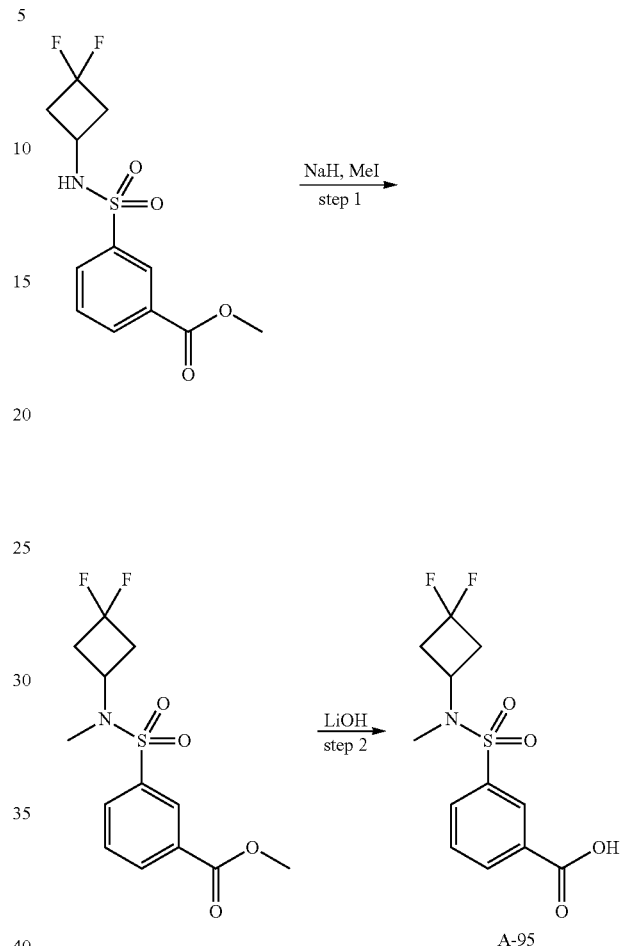

To a mixture of furan-2-carboxylic acid (2.0 g, 18 mmol) and THF (20 mL) was added dropwise LDA (2 M, 13 mL) at −70° C. The mixture was stirred 0.5 h, and cyclopentanecarbaldehyde (2.6 g, 27 mmol) in THF (20 mL) was added dropwise at −70° C. The resulting mixture was stirred at 20° C. for 1.5 h, poured into saturated NH$_4$Cl (10 mL), and the extracted with EtOAc (2×10 mL). The aqueous phase purified by preparative HPLC (0.1% FA condition) to provide 5-(cyclopentyl(hydroxy)methyl)furan-2-carboxylic acid (A-99, 0.38 g).

Compounds in Table 3.1 were prepared from furan-2-carboxylic acid and the indicated aldehyde in the manner described for the synthesis of A-99

TABLE 3.1

| Code | Compound | Aldehyde |
|---|---|---|
| A-100 | (structure) | (structure) |
| A-101 | (structure) | pivalaldehyde |

Step 1. To two mixtures of methyl 3-[(3,3-difluorocyclobutyl)sulfamoyl]benzoate (intermediate from synthesis of A-36, 0.30 & 0.10 g, 0.98 & 0.33 mmol) and DMF (4.0 & 1.3 mL) was added NaH (59 & 20 mg, 1.5 & 0.5 mmol, 60% purity) at 0° C. The mixtures were stirred for 30 min, MeI (73 & 24 μL, 1.2 & 0.4 mmol) was added, and the mixtures were stirred at 20° C. for 30 min. The mixtures were combined and poured into water (10 mL), extracted with EtOAc (10 mL×2), and the combined extracts were washed with brine (10 mL), dried over Na$_2$SO$_4$, concentrated, and purified by silica chromatography (10-100% EtOAc in PE) to provide methyl 3-[(3,3-difluorocyclobutyl)-methyl-sulfamoyl]benzoate (0.28 g).

Step 2. Two mixtures of methyl 3-[(3,3-difluorocyclobutyl)-methyl-sulfamoyl]benzoate (0.23 & 0.050 g, 0.72 & 0.16 mmol), THF (1.8 & 0.4 mL), H$_2$O (0.6 & 0.13 mL) was added LiOH·H$_2$O (91 & 20 mg, 2.2 & 0.48 mmol) were stirred at 20° C. for 4 h. The mixtures were combined, partially concentrated, and the pH adjusted to 3 by the addition of 2N HCl. The mixture was extracted with EtOAc (2×10 mL), and the combined extracts were washed with brine (10 mL), dried over Na$_2$SO$_4$, and concentrated to provide 3-(N-(3,3-difluorocyclobutyl)-N-methylsulfamoyl)benzoic acid (A-95, 0.29 g).

Synthesis of 3-((cyclobutylmethyl)(methyl)phosphoryl)benzoic acid (A-97)

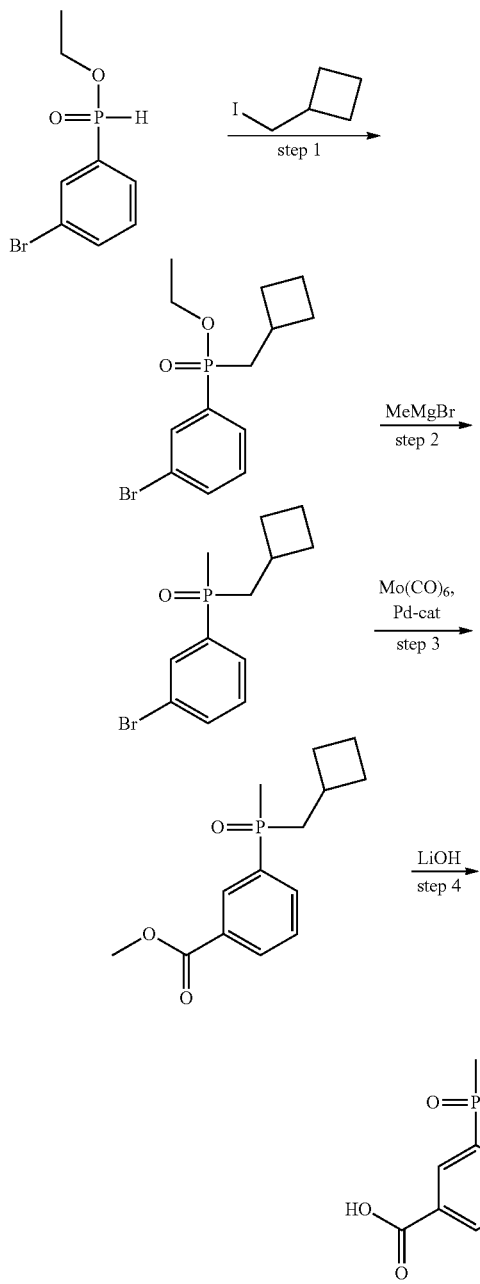

Step 1. To a mixture of 1-bromo-3-ethoxyphosphonoylbenzene (1.8 g, 7.2 mmol) and DMF (20 mL) was added NaH (0.87 g, 22 mmol, 60% purity) at 0° C. The mixture was stirred for 30 min and iodomethylcyclobutane (1.6 mL, 14 mmol) was added. The mixture was stirred at 0-20° C. for 60 min, poured into saturated $NH_4Cl$ (20 mL), and extracted with EtOAc (2×10 mL). The combined extracts were washed with brine (10 mL), dried over $Na_2SO_4$, concentrated, and purified by silica chromatography (5-50% EtOAc in PE) to provide 1-bromo-3-[cyclobutylmethyl(ethoxy)phosphoryl]benzene (0.85 g).

Step 2. To a 0° C. mixture of 1-bromo-3-[cyclobutylmethyl(ethoxy)phosphoryl]benzene (0.68 g, 2.1 mmol) and THF (6 mL) was added MeMgBr (3 M, 6.4 mL) was stirred at 20° C. for 4 h, poured into saturated $NH_4Cl$ (20 mL), and extracted with EtOAc (2×15 mL). The combined extracts were washed with brine (10 mL), dried over $Na_2SO_4$, concentrated, and purified by silica chromatography (5-50% EtOAc in PE) to provide 1-bromo-3-[cyclobutylmethyl(methyl)phosphoryl]benzene (0.56 g).

Step 3. A mixture of 1-bromo-3-[cyclobutylmethyl(methyl)phosphoryl]benzene (0.49 g, 1.7 mmol), MeOH (4 mL), 1,4-dioxane (4 mL), $Mo(CO)_6$ (0.11 g, 0.43 mmol), $K_3PO_4$ (0.36 g, 1.7 mmol), DMAP (0.10 g, 0.85 mmol), Xantphos (99 mg, 0.17 mmol), and $Pd(OAc)_2$ (19 mg, 85 µmol) was stirred at 120° C. for 3 h. The reaction was poured into water (20 mL) and the resulting mixture was extracted with EtOAc (2×15 mL). The organic phase was washed with brine (10 mL), dried over $Na_2SO_4$, concentrated, and purified by silica chromatography (5-10% MeOH in $CH_2Cl_2$) to provide methyl 3-[cyclobutylmethyl(methyl)phosphoryl]benzoate (0.34 g).

Step 4. A mixture of methyl 3-[cyclobutylmethyl(methyl)phosphoryl]benzoate (0.32 g, 1.2 mmol), THF (3 mL), $H_2O$ (1 mL), and $LiOH·H_2O$ (0.15 g, 3.6 mmol) was stirred for 12 h, poured into $H_2O$ (10 mL), and HCl (2 N) added to adjust the pH to 3-4, and extracted with EtOAc (2×5 mL). The combined extracts were washed with brine (5 mL), dried over $Na_2SO_4$, and concentrated to provide 3-((cyclobutylmethyl)(methyl)phosphoryl)benzoic acid (A-97, 0.17 g).

Synthesis of 4-(difluoromethyl)cyclohexane-1-carbaldehyde

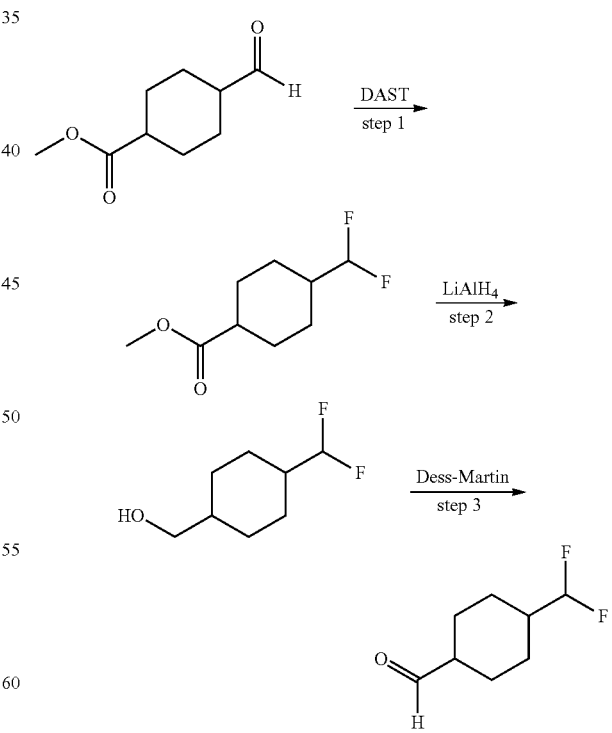

Step 1. To a 0° C. mixture of methyl 4-formylcyclohexanecarboxylate (5.0 g, 29 mmol) and $CH_2Cl_2$ (50 mL) was added slowly DAST (12 mL, 88 mmol). The mixture was stirred at 20° C. for 12 h, poured into saturated aqueous of NaHCO$_3$ (30 mL), and extracted with CH$_2$Cl$_2$ (2×80 mL). The combined extracts were washed with brine (30 mL), dried over Na$_2$SO$_4$, concentrated, purified by silica chromatography (5-17% EtOAc in petroleum ether) to provide methyl 4-(difluoromethyl)cyclohexanecarboxylate (3.2 g).

Step 2. A solution of 4-(difluoromethyl)cyclohexanecarboxylate (3.2 g, 17 mmol) in THF (10 mL) was slowly added to LiAlH$_4$ (1.3 g, 33 mmol) in THF (20 mL) and then stirred at 25° C. for 2 h. H$_2$O (1.3 mL), aqueous NaOH (85%, 1.3 mL), and additional H$_2$O (1.3 mL) were added and the mixture was filtered. The filtrate was concentration to provide [4-(difluoromethyl) cyclohexyl] methanol (1.80 g).

Step 3. To a mixture of [4-(difluoromethyl)cyclohexyl] methanol (1.6 g, 9.7 mmol), NaHCO$_3$ (6.6 g, 78 mmol), and CH$_2$Cl$_2$ (50 mL) was added Dess-Martin periodinane (8.3 g, 20 mmol). The mixture was stirred at 25° C. for 2, then was poured into a mixture of saturated aqueous of NaHCO$_3$ (15 mL) and saturated aqueous of Na$_2$SO$_3$ (15 mL). The resulting mixture was filtered and extracted with CH$_2$Cl$_2$ (2×30 mL). The combined extracts were washed with brine (10 mL), dried over Na$_2$SO$_4$, concentrated, and purified by silica chromatography (5-17% EtOAc in petroleum ether) to provide 4-(difluoromethyl)cyclohexanecarbaldehyde (1.4 g).

trated, and purified by silica chromatography (13-50% EtOAc in PE) to ethyl 4-hydroxy-4-methyl-cyclohexanecarboxylate (2.20 g).

Step 2. To a solution of ethyl 4-hydroxy-4-methyl-cyclohexanecarboxylate (2.4 g, 13 mmol) and CH$_2$Cl$_2$ (1 mL) was added DAST (1.7 mL, 13 mmol). The mixture was stirred at −40° C. for 1 h, poured into 1M Na$_2$HCO$_3$ (20 mL), and extracted with EtOAc (2×20 mL). The combined extracts were washed with brine (15 mL), dried over Na$_2$SO$_4$, concentrated, and purified by silica chromatography (15-50% EtOAc in PE) to provide ethyl 4-fluoro-4-methyl-cyclohexanecarboxylate (1.60 g).

Step 3. To a 0° C. mixture of ethyl 4-fluoro-4-methyl-cyclohexanecarboxylate (1.4 g, 7.4 mmol) and THF (30 mL) was added LiAlH$_4$ (0.57 g, 15 mmol). The mixture was stirred at 0° C. for 2 h, and 0.56 mL of H$_2$O, 0.56 mL of 15% aqueous NaOH, and an additional 1.7 mL of H$_2$O. The mixture was filtered, the filtrate was concentrated, added to H$_2$O (10 mL), and extracted with EtOAc (2×15 mL). The combined extracts were washed with brine (15 mL), dried over Na$_2$SO$_4$, and concentrated to provide (4-fluoro-4-methyl-cyclohexyl)methanol (0.80 g).

Step 4. A mixture of (4-fluoro-4-methyl-cyclohexyl) methanol (0.70 mg, 4.8 mmol), CH$_2$Cl$_2$ (20 mL), NaHCO$_3$ (3.2 g, 38 mmol), and Dess-Martin periodinane (4.1 g, 9.6 mmol) was stirred at 25° C. for 2 hours. The mixture was poured into saturated NaHCO$_3$ (5 mL) and saturated Na$_2$SO$_3$ (5 mL) and the resulting mixture was filtered and extracted with CH$_2$Cl$_2$ (2×10 mL). The combined extracts were washed with brine (10 mL), dried over Na$_2$SO$_4$, and concentrated to provide 4-fluoro-4-methyl-cyclohexanecarbaldehyde (0.60 mg).

Synthesis of 4-fluoro-4-methylcyclohexane-1-carbaldehyde

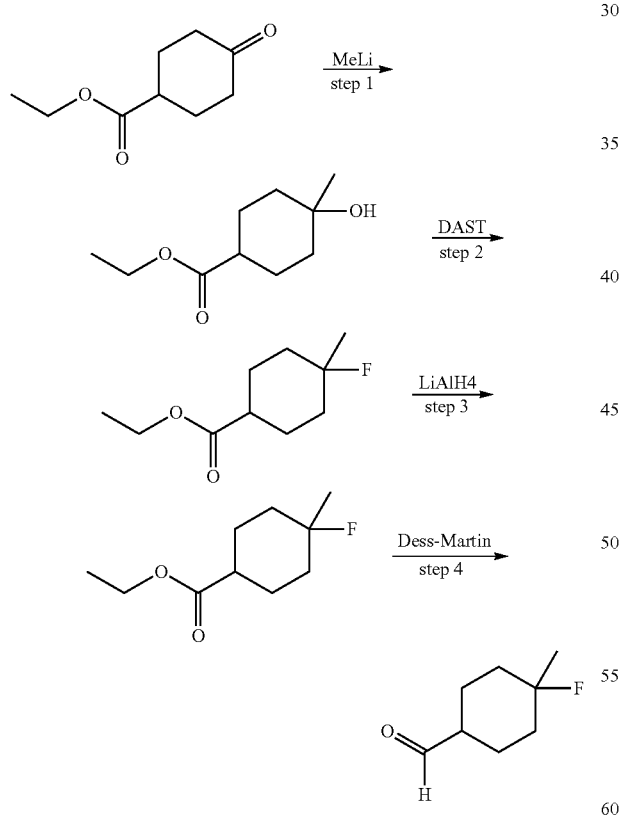

Synthesis of 5"-nitrodispiro[cyclopropane-1,1'-cyclohexane-4',3"-indoline] (B-01)

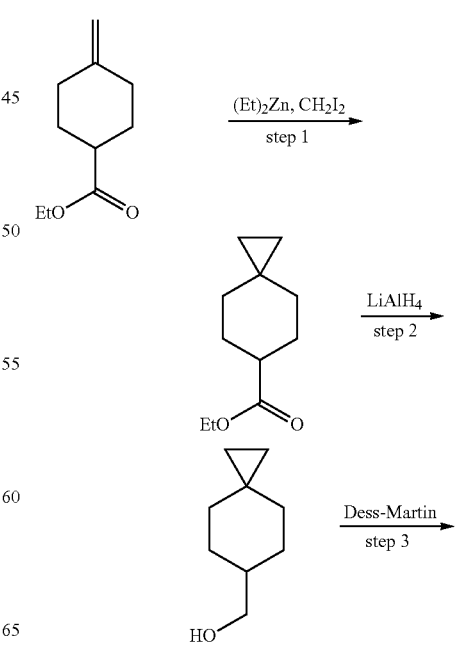

Step 1. To a mixture of ethyl 4-oxocyclohexanecarboxylate (4.7 mL, 29 mmol) in THF (30 mL) was slowly added MeLi (1 M, 41 mL) at −60° C. The mixture was stirred at −60° C. for 1 h, poured into NH$_4$Cl (20 mL), and extracted with EtOAc (2×20 mL). The combined extracts were washed with brine (20 mL), dried over Na$_2$SO$_4$, concen- -continued

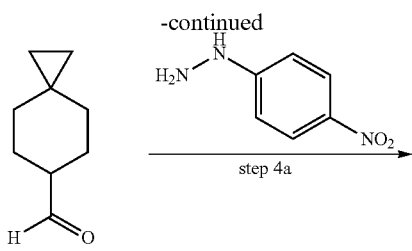

step 4a

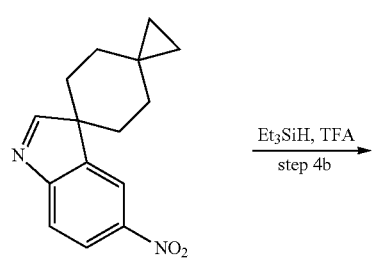

Et₃SiH, TFA
step 4b

B-01

Step 1. To a mixture of ZnEt₂ (1 M in hexanes, 180 mL), CH₂Cl₂ (200 mL) at 0° C. under N₂ was added slowly CH₂I₂ (26 mL, 320 mmol), in CH₂Cl₂ (60 mL). The mixture was stirred at 0° C. for 30 min and ethyl 4-methylenecyclohexanecarboxylate (12 g, 71 mmol) in CH₂Cl₂ (50 mL) was slowly added. The mixture was stirred at 20° C. for 12 h, cooled to 0° C., and saturated NH₄Cl (100 mL) was added. The organic phase separated, washed with water (50 mL×2), brine (50 mL), dried over Na₂SO₄, filtered, concentrated, and purified by silica chromatography (1-10% CH₂C₂ in petroleum ether) to afford the compound ethyl spiro[2.5]octane-6-carboxylate (10 g).

Step 2. To a mixture of ethyl spiro[2.5]octane-6-carboxylate (10 g, 55 mmol), THF (300 mL) at 0° C. under N₂ was added LiAlH₄ (3.1 g, 81 mmol) in portions. The mixture was stirred at 0° C. for 1 h, then at 22° C. for another 1 h. Aqueous 2M NaOH (3.0 mL) was slowly added to the stirring mixture, followed by Na₂SO₄ (30 g). The suspension was filtered, and the filtrate was concentrated to provide spiro[2.5]octan-6-ylmethanol (7.5 g). $^1$H NMR (DMSO-d$^6$, 400 MHz) δ 3.51 (d, J=6.38 Hz, 2H), 1.82-1.68 (m, 4H), 1.53 (tdt, J=14.71, 6.38, 3.24 Hz, 1H), 1.40-1.29 (m, 1H), 1.12-1.07 (m, 2H), 0.96-0.84 (m, 2H), 0.35-0.24 (m, 2H), 0.23-0.12 (m, 2H).

Step 3. To a mixture of spiro[2.5]octan-6-ylmethanol (7.5 g, 54 mmol) and CH₂Cl₂ (250 mL) was added Dess-Martin periodinane (28 g, 66 mmol) at 0° C. The mixture was stirred for 5 h as the temperature was allowed to rise to 25° C. The mixture was filtered through celite and the filter solid was washed with CH₂Cl₂ (50 mL×3). The filtrate was concentrated and purified by silica chromatography (0-10% EtOAc in petroleum ether) to provide spiro[2.5]octane-6-carbaldehyde (7.30 g). $^1$H NMR (DMSO-d$^6$, 400 MHz) δ 9.68 (d, J=1.25 Hz, 1H), 2.35-2.23 (m, 1H), 1.97-1.85 (m, 2H), 1.70-1.51 (m, 4H), 1.12-1.03 (m, 2H), 0.35-0.27 (m, 2H), 0.26-0.18 (m, 2H).

Step 4. a) A mixture of (4-nitrophenyl)hydrazine (1.8 g, 12 mmol), TFA (4.5 mL, 61 mmol), CH₂Cl₂ (40 mL), and spiro[2.5]octane-6-carbaldehyde (2.0 g, 15 mmol) was stirred at 40° C. for 15 h. b) Additional TFA (6.3 mL, 85 mmol), CH₂Cl₂, and Et₃SiH (6.3 mL, 4.6 mmol) were added at 0° C. and the mixture stirred at 25° C. for 2 h, then was concentrated and purified by silica chromatography (0-15% [1:1 Me-THF in EtOAc] in petroleum ether) to provide 5''-nitrodispiro[cyclopropane-1,1'-cyclohexane-4',3''-indoline] (B-01, 0.88 g).

Synthesis of spiro[cyclopentane-1,3'-indoline]
(B-02)

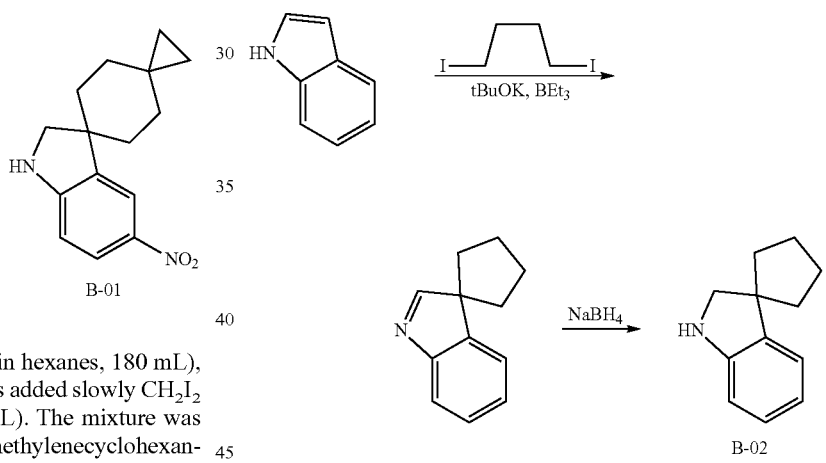

B-02

To a mixture of 1H-indole (1.0 g, 8.5 mmol) and THF (25 mL) was added dropwise t-BuOK (1 M in THF, 20 mL) and the mixture was stirred at 20° C. for 0.5 h. Et₃B (1 M in THF, 17 mL) was added and the mixture was stirred for 0.5 h. 1,4-diiodobutane (1.2 mL, 9.4 mmol) was added and the mixture was stirred at 70° C. for 13 h. MeOH (10 mL) and NaBH₄ (0.97 g, 26 mmol) were added and the mixture stirred at 20° C. for 12 h. The mixture was concentrated, combined with EtOAc (20 mL) and 2 N HCl (20 mL). The pH was adjusted to 9 by the slow addition of saturated aqueous NaHCO₃. The phases were separated, and the aqueous wash was extracted with EtOAc (2×30 mL). The extracts were combined, washed with brine (10 mL), dried over Na₂SO₄, filtered, and concentrated to provide spiro[cyclopentane-1,3'-indoline] (B-02). $^1$H NMR: (DMSO-d6, 400 MHz) δ 6.98 (dd, J=7.32, 0.81 Hz, 1H), 6.90 (td, J=7.57, 1.25 Hz, 1H), 6.55 (td, J=7.35, 0.94 Hz, 1H), 6.49 (d, J=7.75 Hz, 1H), 5.43 (s, 1H), 3.22 (s, 2H), 1.84-1.62 (m, 8H).

Compounds in Table 4 were prepared from the indole and dihalide in the manner described for B-02.

TABLE 4

| Code | Structure | indole | Amine |
|------|-----------|--------|-------|
| B-03 | 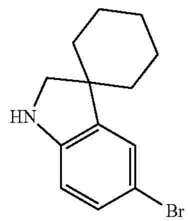 [SMILES: Brc1ccc2c(c1)C1(CCCCC1)CN2] | | |
| B-04 | 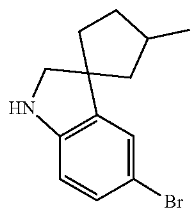 | | |
| B-05 | 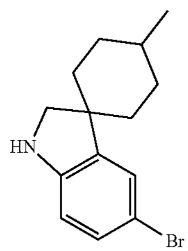 [SMILES: CC1CCC2(CC1)CNc1ccc(Br)cc12] | | |
| B-16 | 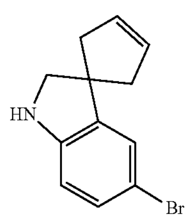 [SMILES: Brc1ccc2c(c1)C1(CC=CC1)CN2] | | |

Synthesis of dispiro[cyclopropane-1,1'-cyclohexane-4',3"-indoline] (B-06)

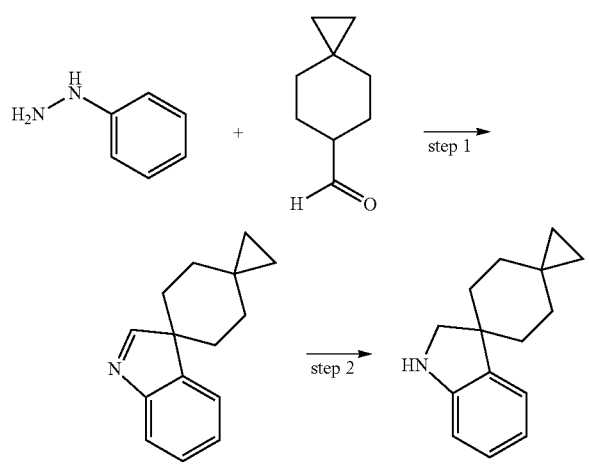

Step 1. Dispiro[cyclopropane-1,1'-cyclohexane-4',3"-indole] was prepared from phenylhydrazine and spiro[2.5]octane-6-carbaldehyde in the manner described in Step 4a of the synthesis of B-01.

Step 2. To a mixture of dispiro[cyclopropane-1,1'-cyclohexane-4',3"-indole] (1.0 g, 4.7 mmol) in MeOH (15 mL) and THF (15 mL) at 0° C. was added NaBH$_3$CN (0.90 g, 14 mmol) in portions. The mixture was stirred at 20° C. for 12 h and NaBH$_3$CN (0.50 g) and THF (15 mL) was added, and the mixture was stirred at 40° C. for 2 h. The reaction mixture was concentrated and purified by chromatography (silica, 0-15% [1:1 THF/EtOAc] in petroleum ether) to afford dispiro[cyclopropane-1,1'-cyclohexane-4',3"-indoline] (B-06, 0.64 g).

Compounds in Table 5 were prepared from the hydrazine and the aldehyde indicated by the method described for the synthesis of B-06.

TABLE 5
| Code | Structure | Hydrazine | Aldehyde |
|---|---|---|---|
| B-07 | 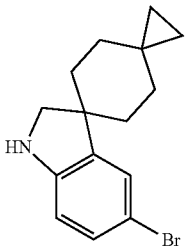 [SMILES: Brc1ccc2c(c1)C1(CCC3(CC3)CC1)CN2] | 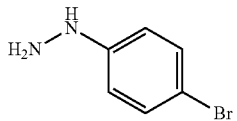 | 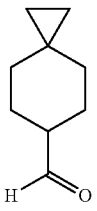 |
| B-08 | 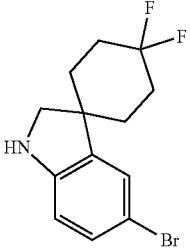 | 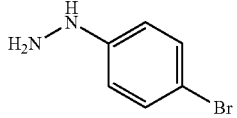 | 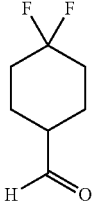 |
| B-09 | 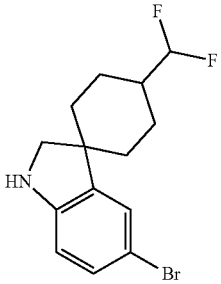 [SMILES: FC(F)C1CCC2(CC1)CNc1ccc(Br)cc12] | 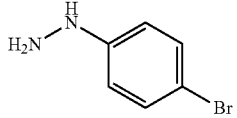 |  |
| B-17 | 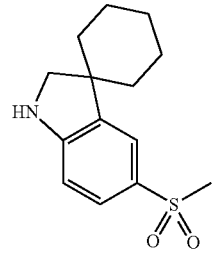 [SMILES: CS(=O)(=O)c1ccc2c(c1)C1(CCCCC1)CN2] | 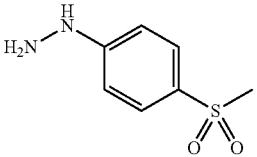 | 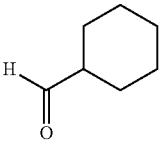 |
| B-18 | 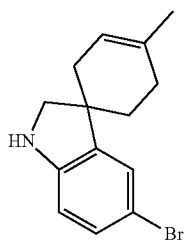 | 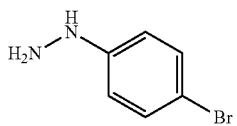 | 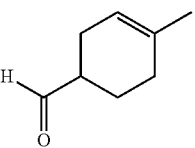 |

TABLE 5-continued

| Code | Structure | Hydrazine | Aldehyde |
|---|---|---|---|
| B-19/B-20 | 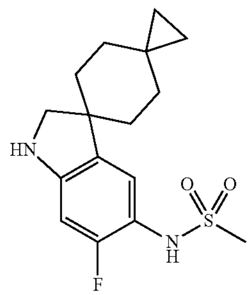 [SMILES: CS(=O)(=O)Nc1cc2c(cc1F)NCC21CCC2(CC2)CC1] | | |
| B-21 | 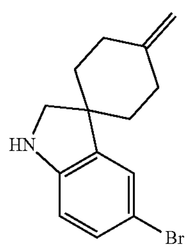 | | |
| B-22 | 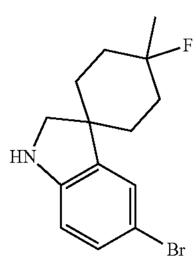 [SMILES: CC1(F)CCC2(CC1)CNc1ccc(Br)cc12] | | |
| B-24 | 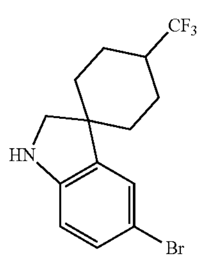 [SMILES: FC(F)(F)C1CCC2(CC1)CNc1ccc(Br)cc12] | | |

Synthesis of tert-butyl 5"-bromodispiro[cyclopropane-1,1'-cyclohexane-4',3"-indoline]-1"-carboxylate (B-10) and N-(dispiro[cyclopropane-1,1'-cyclohexane-4',3"-indolin]-5"-yl)-2-hydroxyethane-1-sulfonamide (B-11)

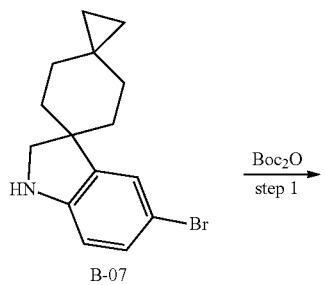

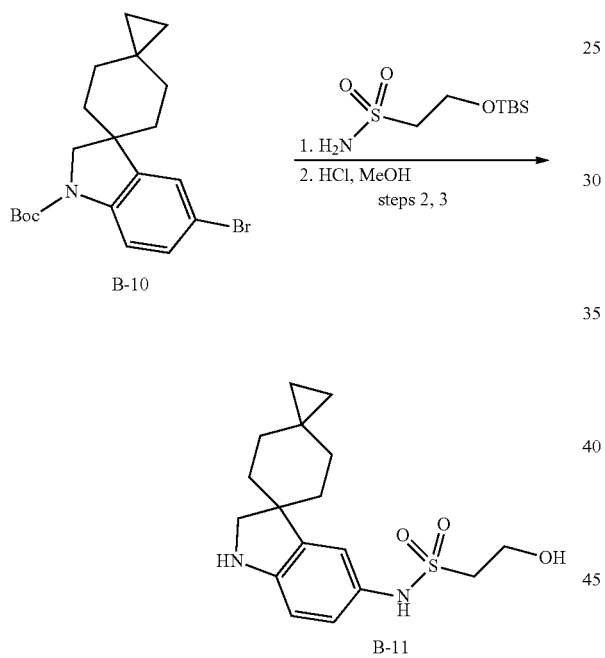

Step 1. A mixture of B-07 (0.2 M, 3.4 mL) and Boc₂O (0.30 g, 1.4 mmol), MeCN (10 mL), and Et₃N (0.40 mL, 2.9 mmol) was stirred at 25° C. for 12 h. The mixture was concentrated and purified by silica chromatography (0-20% MTBE in petroleum ether) to provide tert-butyl 5"-bromo-1",2"-dihydrodispiro[cyclopropane-1,1'-cyclohexane-4',3"-indole]-1"-carboxylate (B-10, 0.23 g).

Step 2. a) To a mixture of tert-butyl 5"-bromo-1",2"-dihydrodispiro[cyclopropane-1,1'-cyclohexane-4',3"-indole]-1"-carboxylate (0.11 g, 0.27 mmol) and 2-[(tert-butyldimethylsilyl)oxy]ethane-1-sulfonamide (0.21 g, 0.88 mmol), and DMF (8.0 mL) was added CuI (57 mg, 0.30 mmol), K₃PO₄ (0.21 g, 0.99 mmol), and N¹,N²-dimethylcyclohexane-1,2-diamine (48 mg, 0.34 mmol). The reaction mixture was stirred at 140° C. in a microwave reactor for 3 h. The reaction mixture was diluted with water 30 mL and extracted with 1:1 EtOAc/THF (15 mL×2). The extracts were combined, washed with H₂O (10 mL×3) and brine (10 mL), dried over Na₂SO₄, filtered, concentrated, and purified by silica chromatography (0-10% [1:1 THF/EtOAc] in petroleum ether) to provide 2-[(tert-butyldimethylsilyl)oxy]-N-{1",2"-dihydrodispiro[cyclopropane-1,1'-cyclohexane-4',3"-indol]-5"-yl}ethane-1-sulfonamide (70 mg).

Step 3. A mixture of 2-[(tert-butyldimethylsilyl)oxy]-N-{1",2"-dihydrodispiro[cyclopropane-1,1'-cyclohexane-4', 3"-indol]-5"-yl}ethane-1-sulfonamide (60 mg, 0.11 mmol), MeOH (1.0 mL), and HCl (4 M in MeOH, 1.0 mL) was stirred at 25° C. for 5 h. The mixture was concentrated to provide N-{1",2"-dihydrodispiro[cyclopropane-1,1'-cyclohexane-4',3"-indol]-5"-yl}-2-hydroxyethane-1-sulfonamide hydrochloride (B-11, 47 mg).

Separation of B-24 into Diastereomers

Indoline B-24 was separated into the (1s,4s) and (1r,4r) isomers by silica chromatography (0-100% EtOAc in PE). The configurations were not determined, and the first eluting isomer is B-24a and the second eluting isomer is B-24b.

Synthesis of tert-butyl 5'-bromospiro[cyclohexane-1,3'-indoline]-1'-carboxylate (B-12) and N-(spiro[cyclohexane-1,3'-indolin]-5'-yl)methanesulfonamide (B-13)

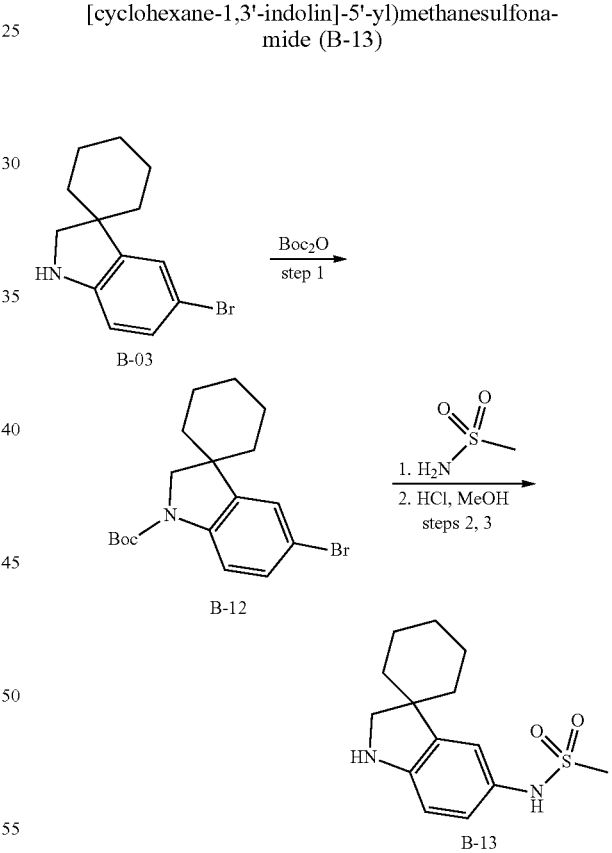

tert-Butyl 5'-bromospiro[cyclohexane-1,3'-indoline]-1'-carboxylate (B-12) and N-(spiro[cyclohexane-1,3'-indolin]-5'-yl)methanesulfonamide (B-13) were prepared from B-03 in the same manner as B-10 and B-11.

Intermediates in Table 5.1 were prepared from the indicated indolines and sulfonamides in the manner described for the synthesis of B-11.

TABLE 5.1

| Code | Structure | Sulfonamide | indoline |
|---|---|---|---|
| B-14 | 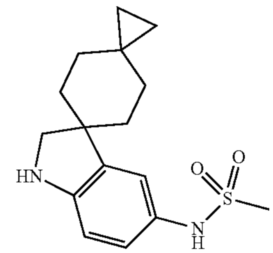 [SMILES: CS(=O)(=O)Nc1ccc2c(c1)C1(CCC3(CC3)CC1)CN2] | methanesulfonamide | B-07 |
| B-23 | 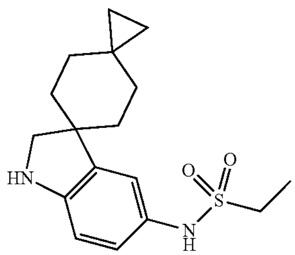 [SMILES: CCS(=O)(=O)Nc1ccc2c(c1)C1(CCC3(CC3)CC1)CN2] | ethanesulfonamide | B-07 |

Synthesis of spiro[cyclohexane-1,3'-indolin]-5'-ol hydrochloride (B-15)

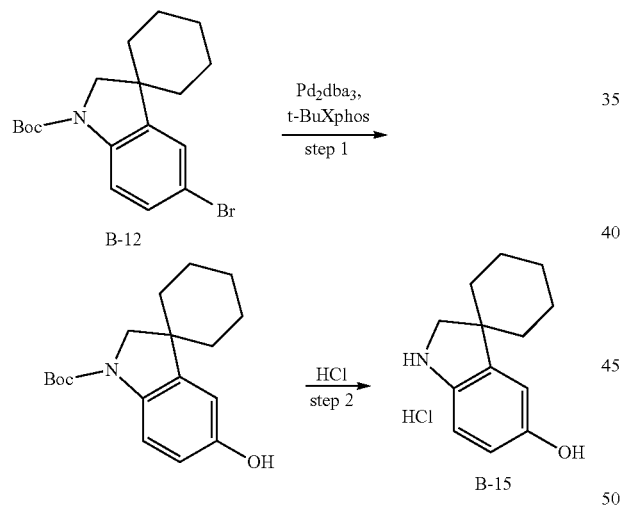

Step 1. A mixture of B-12 (0.35 g, 0.96 mmol), NMP (8 mL), H₂O (4 mL), was KOH (0.16 g, 2.9 mmol), Pd₂(dba)₃ (88 mg, 96 μmol), di-tert-butyl-[2-(2,4,6-triisopropylphenyl)phenyl]phosphane (81 mg, 0.19 mmol) was stirred at 110° C. for 12 h, diluted with 10 mL of water, and extracted with EtOAc (5 mL×3). The combined extracts were washed with brine (5 mL), dried over Na₂SO₄, filtered, concentrated, and purified by preparative TLC (SiO₂, 25% EtOAc in petroleum ether) to provide tert-butyl 5'-hydroxyspiro[cyclohexane-1,3'-indoline]-1'-carboxylate (80 mg).

Step 2. A mixture of tert-butyl tert-butyl 5'-hydroxyspiro[cyclohexane-1,3'-indoline]-1-carboxylate (80 mg, 0.26 mmol) and 1M HCl in EtOAc (2.0 mL) was stirred at 25° C. for 2 h, and was concentrated to provide spiro[cyclohexane-1,3'-indolin]-5'-ol hydrochloride (B-15; 60 mg).

Synthesis of 3-(5"-(methylsulfonamido)dispiro[cyclopropane-1,1'-cyclohexane-4',3"-indoline]-1"-carbonyl)benzenesulfonyl chloride (C-01)

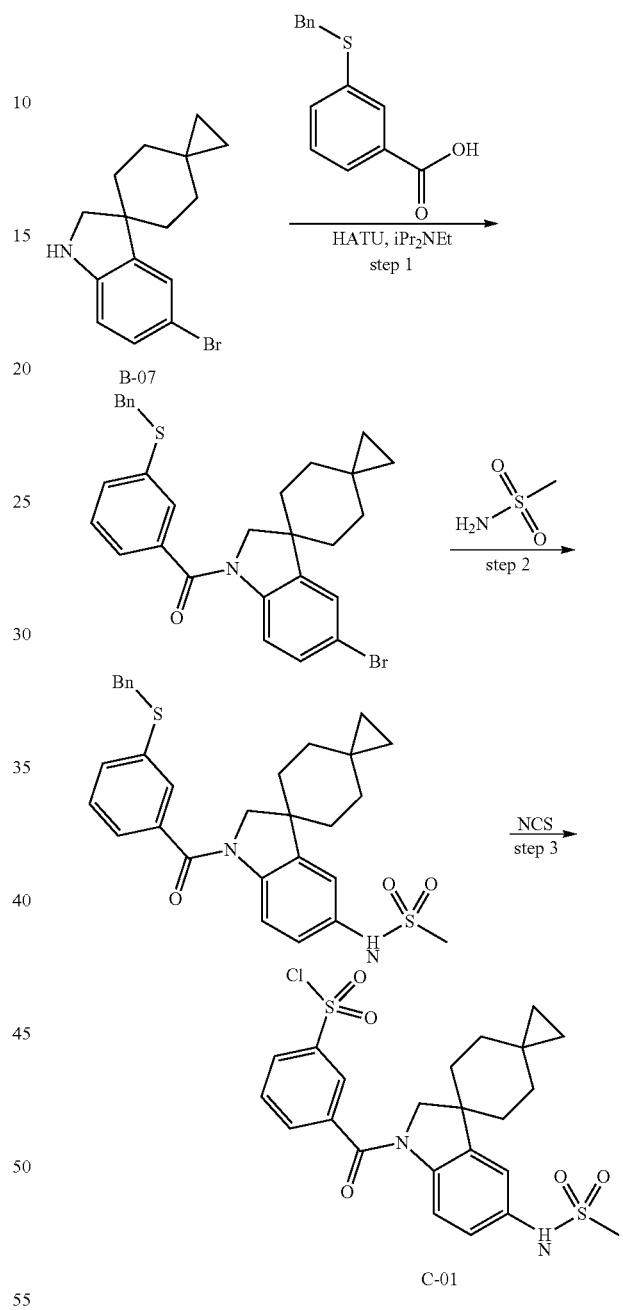

Step 1. A mixture of 3-benzylsulfanylbenzoic acid (1.5 g, 6.1 mmol), DMF (10 mL), HATU (4.7 g, 13 mmol), and iPr₂NEt (3.2 mL, 18 mmol) was stirred at 25° C. for 15 min and B-07 (1.8 g, 6.1 mmol) was added. The mixture was stirred at 25° C. for 2 h, then was diluted with EtOAc (50 mL), washed with water (30 mL×3) and brine (30 mL), dried over Na₂SO₄, filtered, concentrated, and purified by silica chromatography (8-10% EtOAc in petroleum ether) to provide (3-(benzylthio)phenyl)(5"-bromodispiro[cyclopropane-1,1'-cyclohexane-4',3"-indolin]-1"-yl)methanone (3.0 g).

Step 2. A mixture of (3-(benzylthio)phenyl)(5"-bromodispiro[cyclopropane-1,1'-cyclohexane-4',3"-indolin]-1"-yl)methanone (2.0 g, 3.9 mmol), DMF (10 mL), methanesulfonamide (1.1 g, 12 mmol), K$_3$PO$_4$ (2.5 g, 12 mmol), N$^1$,N$^2$-dimethylcyclohexane-1,2-diamine (0.55 g, 3.9 mmol), and CuI (0.74 g, 3.9 mmol) was stirred at 160° C. for 2 h. The mixture was diluted with EtOAc (30 mL), washed with H$_2$O (30 mL×3) and brine (30 mL), dried over Na$_2$SO$_4$, filtered, concentrated, and purified by silica chromatography (29-31% EtOAc in petroleum ether) to provide N-(1"-(3-(benzylthio)benzoyl)dispiro[cyclopropane-1,1'-cyclohexane-4',3"-indolin]-5"-yl)methanesulfonamide (1.84 g).

Step 3. A mixture of N-(1"-(3-(benzylthio)benzoyl)dispiro[cyclopropane-1,1'-cyclohexane-4',3"-indolin]-5"-yl)methanesulfonamide (1.0 g, 1.9 mmol), NCS (0.50 g, 3.8 mmol), HOAc (1.8 mL), and H$_2$O (0.2 mL) was stirred at 30° C. for 2 h. The mixture was diluted with EtOAc (50 mL), washed with H$_2$O (30 mL×3), saturated aqueous NaHCO$_3$ (30 mL), and brine (30 mL) before being dried over Na$_2$SO$_4$, filtered, concentrated, and purified by silica chromatography (25-35% EtOAc in petroleum ether) to provide 3-(5"-(methylsulfonamido)dispiro[cyclopropane-1,1'-cyclohexane-4',3"-indoline]-1"-carbonyl)benzenesulfonyl chloride (C-01, 0.36 g).

Compounds in Table 5.2 were prepared from the indicated carboxylic acid and indoline in the same manner as described for C-01.

TABLE 5.2

| Code | Structure | Carboxylic Acid | Indoline |
|------|-----------|-----------------|----------|
| C-03 | 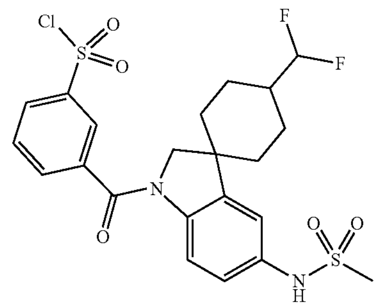 [SMILES: CS(=O)(=O)Nc1ccc2c(c1)C1(CCC(C(F)F)CC1)CN2C(=O)c1cccc(S(=O)(=O)Cl)c1] | | B-09 |
| C-04 | 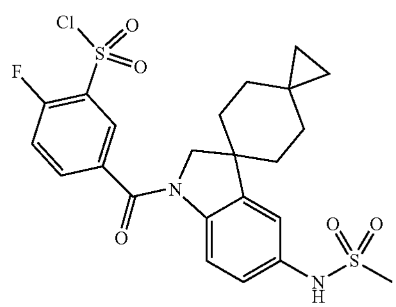 [SMILES: CS(=O)(=O)Nc1ccc2c(c1)C1(CCC3(CC3)CC1)CN2C(=O)c1ccc(F)c(S(=O)(=O)Cl)c1] | | B-07 |
| C-05 | 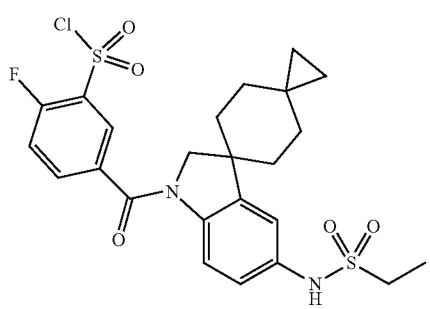 [SMILES: CCS(=O)(=O)Nc1ccc2c(c1)C1(CCC3(CC3)CC1)CN2C(=O)c1ccc(F)c(S(=O)(=O)Cl)c1] | | B-23 |

Synthesis of 2-methoxy-5-(5"-(methylsulfonamido) dispiro[cyclopropane-1,1'-cyclohexane-4',3"-indoline]-1"-carbonyl)benzenesulfonyl chloride (C-02)

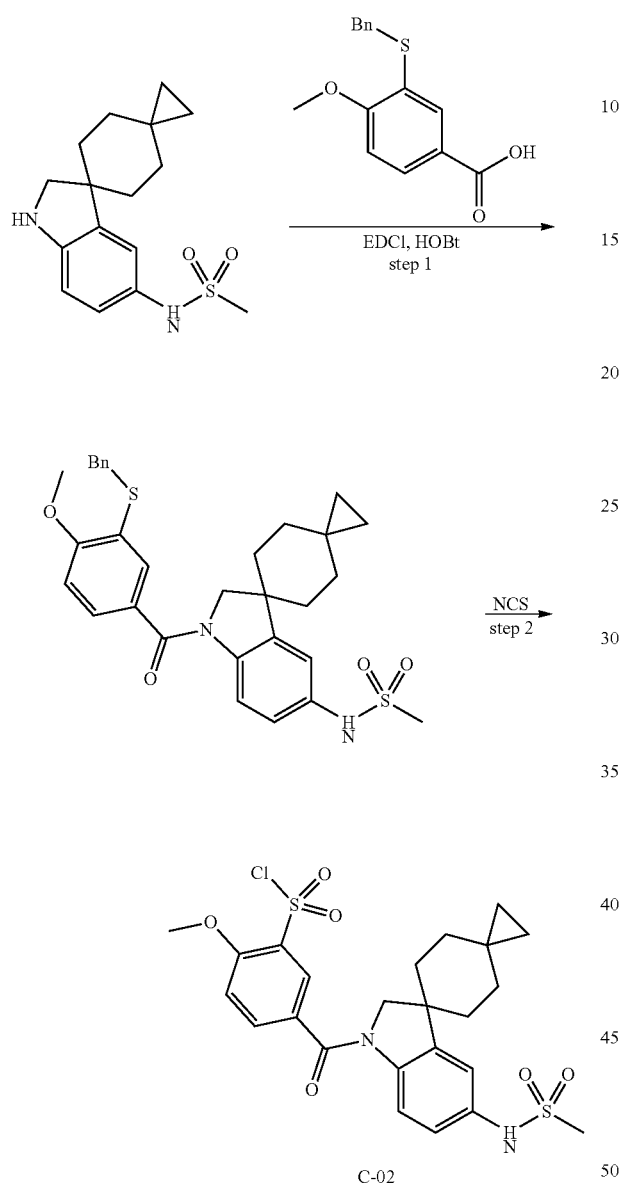

C-02

Step 1. A mixture of 3-benzylsulfanyl-4-methoxy-benzoic acid (0.32 mg, 1.2 mmol), B-14 (0.22 g, 0.73 mmol), DMF (3 mL), HOBt (0.26 g, 1.9 mmol), EDCI (0.37 g, 1.9 mmol), Et₃N (0.54 mL, 3.9 mmol) was stirred at 25° C. for 2 h. The reaction was poured into H₂O (30 mL), extracted with EtOAc (2×30 mL), and the combined extracts were washed with brine (10 mL), dried over Na₂SO₄, concentrated, and purified by silica chromatography (40-45% EtOAc in PE) to provide N-(1"-(3-(benzylthio)-4-methoxybenzoyl)dispiro[cyclopropane-1,1'-cyclohexane-4',3"-indolin]-5"-yl)methanesulfonamide (0.22 g).

Step 2. A mixture of N-(1"-(3-(benzylthio)-4-methoxybenzoyl)dispiro[cyclopropane-1,1'-cyclohexane-4',3"-indolin]-5"-yl)methanesulfonamide (0.22 g, 0.36 mmol), NCS (0.14 g, 1.1 mmol), H₂O (0.05 mL), and HOAc (0.45 mL) was stirred at 25° C. for 2 h. The mixture was poured into H₂O (10 mL) and saturated NaHCO₃ (10 mL), extracted with EtOAc (2×30 mL), and the combined extracts were washed with brine (10 mL), dried over Na₂SO₄, and concentrated to provide 2-methoxy-5-(5"-(methylsulfonamido) dispiro[cyclopropane-1,1'-cyclohexane-4',3"-indoline]-1"-carbonyl)benzenesulfonyl chloride (C-02, 0.20 g).

Synthetic Example S-001

Synthesis of (3-((4,4-difluoropiperidin-1-yl)sulfonyl)phenyl)(4'-fluorospiro[cyclopentane-1,3'-indolin]-1'-yl)methanone (Compound 1)

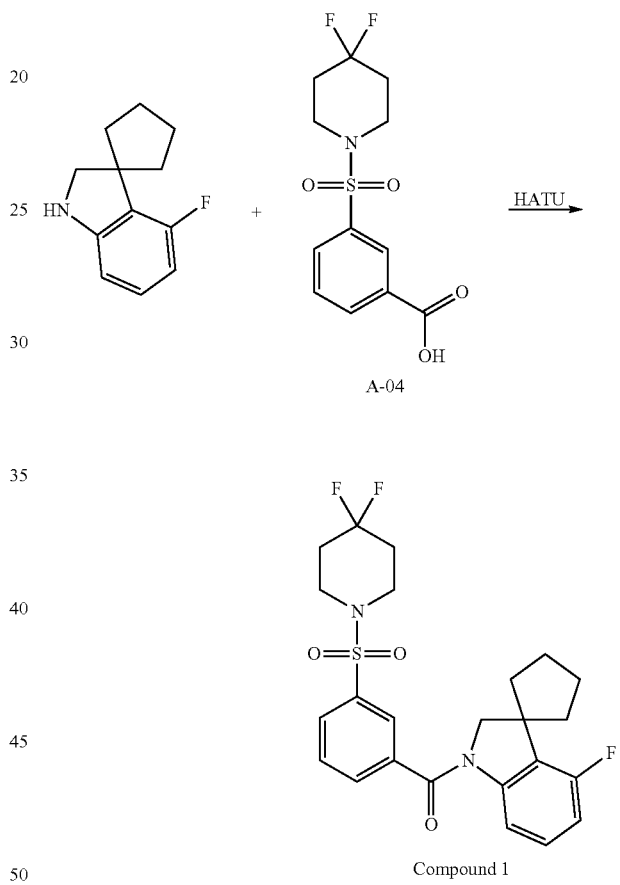

Compound 1

A mixture of 3-[(4,4-difluoro-1-piperidyl)sulfonyl]benzoic acid (88 mg, 0.28 mmol), DMF (1.5 mL), Et₃N (0.11 mL, 0.78 mmol), and HATU (0.20 g, 0.52 mmol) was stirred at 20° C. for 30 min, and 4'-fluorospiro[cyclopentane-1,3'-indoline] (50 mg, 0.26 mmol) in DMF (1.0 mL) was added. The resulting mixture was stirred at 20° C. for 3.5 h, concentrated, and purified by prep-HPLC (45-75% MeCN in H₂O [10 mM NH₄HCO₃]) to afford (3-((4,4-difluoropiperidin-1-yl)sulfonyl)phenyl)(4'-fluorospiro[cyclopentane-1,3'-indolin]-1'-yl)methanone (Compound 1) (35 mg). ESI MS m/z: 479.2 (M+H).

Compounds in Table 6 were prepared from the carboxylic acid and indoline analog indicated by the method described for the synthesis of Compound 1 (Synthetic Example S-001).

TABLE 6

| Compound | Structure | Carboxylic Acid | Indoline |
|---|---|---|---|
| Compound 2 | 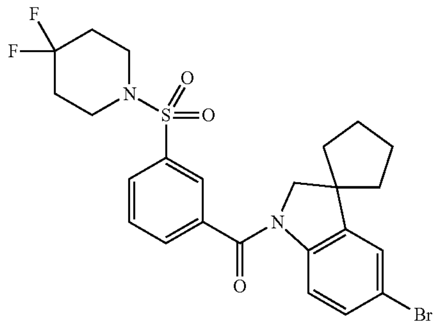 [SMILES: O=C(c1cccc(S(=O)(=O)N2CCC(F)(F)CC2)c1)N1CC2(CCCC2)c2cc(Br)ccc21] | A-04 | |
| Compound 3 | 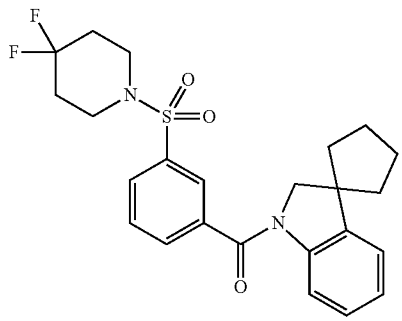 [SMILES: O=C(c1cccc(S(=O)(=O)N2CCC(F)(F)CC2)c1)N1CC2(CCCC2)c2ccccc21] | A-04 | B-02 |
| Compound 4 | 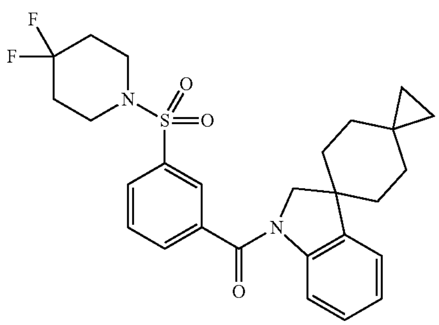 [SMILES: O=C(c1cccc(S(=O)(=O)N2CCC(F)(F)CC2)c1)N1CC2(CCC3(CC3)CC2)c2ccccc21] | A-04 | B-06 |
| Compound 5 | 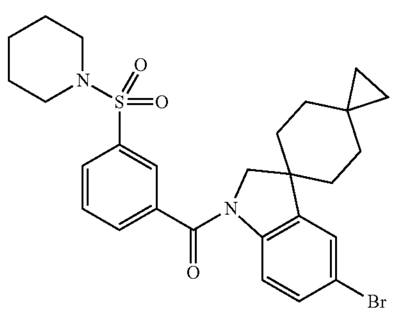 [SMILES: O=C(c1cccc(S(=O)(=O)N2CCCCC2)c1)N1CC2(CCC3(CC3)CC2)c2cc(Br)ccc21] | A-01 | B-07 |
| Compound 6 | 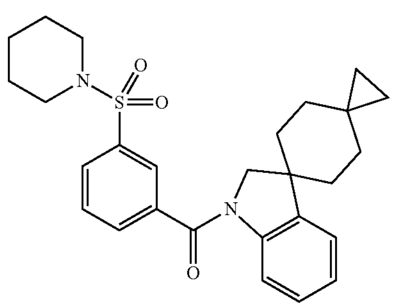 [SMILES: O=C(c1cccc(S(=O)(=O)N2CCCCC2)c1)N1CC2(CCC3(CC3)CC2)c2ccccc21] | A-01 | B-06 |

TABLE 6-continued

| Compound | Structure | Carboxylic Acid | Indoline |
|---|---|---|---|
| Compound 7 | 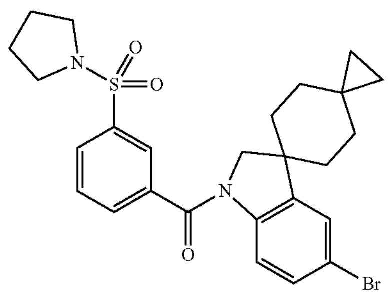 [SMILES: O=C(c1cccc(S(=O)(=O)N2CCCC2)c1)N1CC2(CCC3(CC3)CC2)c2cc(Br)ccc21] | A-02 | B-07 |
| Compound 8 | 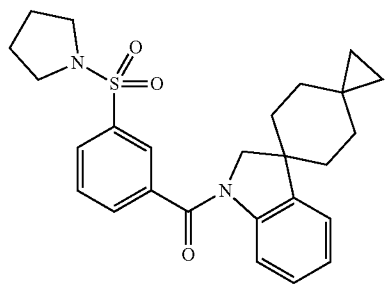 [SMILES: O=C(c1cccc(S(=O)(=O)N2CCCC2)c1)N1CC2(CCC3(CC3)CC2)c2ccccc21] | A-02 | B-06 |
| Compound 9 | 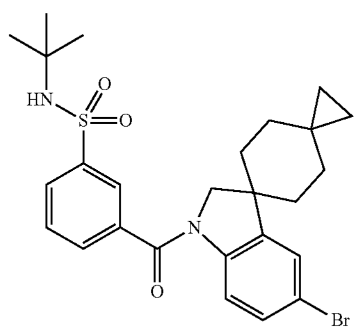 [SMILES: CC(C)(C)NS(=O)(=O)c1cccc(C(=O)N2CC3(CCC4(CC4)CC3)c3cc(Br)ccc32)c1] | A-03 | B-07 |
| Compound 10 | 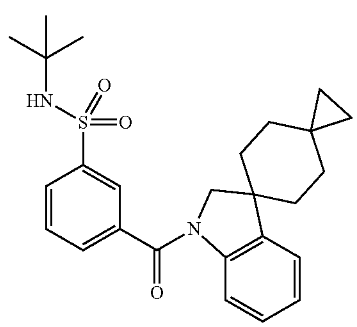 [SMILES: CC(C)(C)NS(=O)(=O)c1cccc(C(=O)N2CC3(CCC4(CC4)CC3)c3ccccc32)c1] | A-03 | B-06 |
| Compound 11 | 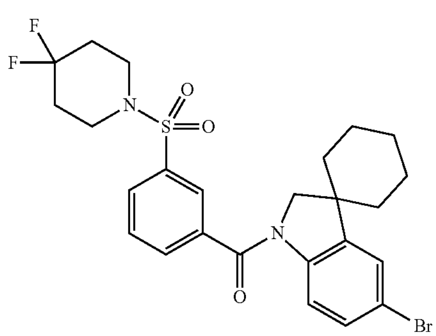 [SMILES: O=C(c1cccc(S(=O)(=O)N2CCC(F)(F)CC2)c1)N1CC2(CCCCC2)c2cc(Br)ccc21] | A-03 | B-03 |

TABLE 6-continued

| Compound | Structure | Carboxylic Acid | Indoline |
|---|---|---|---|
| Compound 12 | 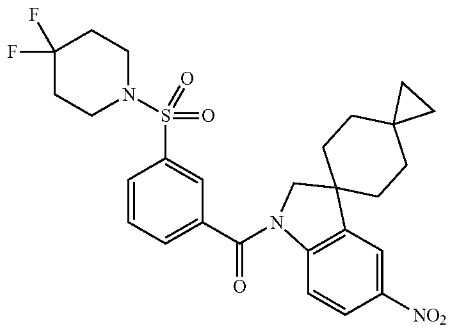 [SMILES: O=C(c1cccc(S(=O)(=O)N2CCC(F)(F)CC2)c1)N1CC2(CCC3(CC3)CC2)c2cc([N+](=O)[O-])ccc21] | A-04 | B-01 |
| Compound 13 | 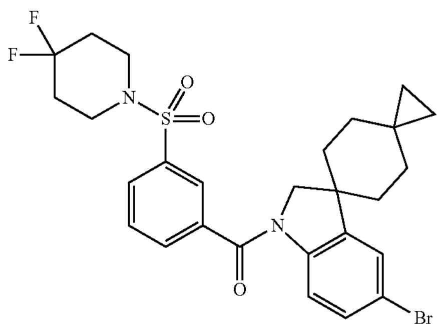 [SMILES: O=C(c1cccc(S(=O)(=O)N2CCC(F)(F)CC2)c1)N1CC2(CCC3(CC3)CC2)c2cc(Br)ccc21] | A-04 | B-07 |
| Compound 14 | 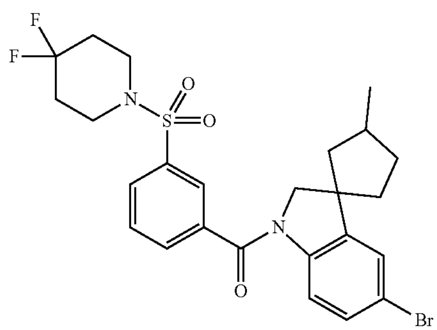 [SMILES: CC1CCC2(C1)CN(C(=O)c1cccc(S(=O)(=O)N3CCC(F)(F)CC3)c1)c1ccc(Br)cc12] | A-04 | B-04 |
| Compound 15 | 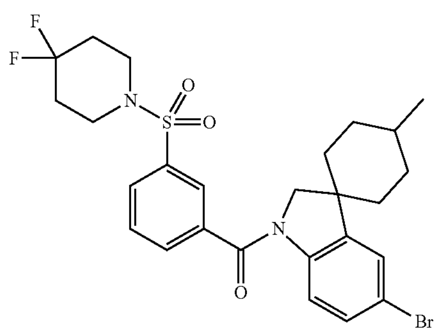 [SMILES: CC1CCC2(CC1)CN(C(=O)c1cccc(S(=O)(=O)N3CCC(F)(F)CC3)c1)c1ccc(Br)cc12] | A-04 | B-05 |
| Compound 16 | 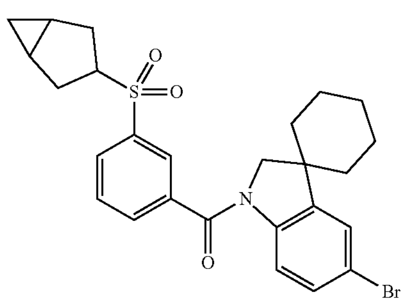 [SMILES: O=C(c1cccc(S(=O)(=O)C2CC3CC3C2)c1)N1CC2(CCCCC2)c2cc(Br)ccc21] | A-05 | B-03 |

TABLE 6-continued

| Compound | Structure | Carboxylic Acid | Indoline |
|---|---|---|---|
| Compound 17 | 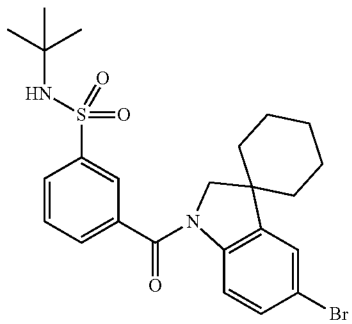 [SMILES: CC(C)(C)NS(=O)(=O)c1cccc(C(=O)N2CC3(CCCCC3)c3cc(Br)ccc32)c1] | A-03 | B-03 |
| Compound 126 | 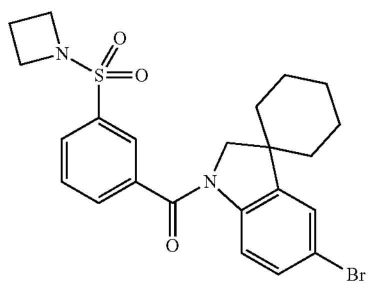 [SMILES: O=C(c1cccc(S(=O)(=O)N2CCC2)c1)N1CC2(CCCCC2)c2cc(Br)ccc21] | A-06 | B-03 |
| Compound 128 | 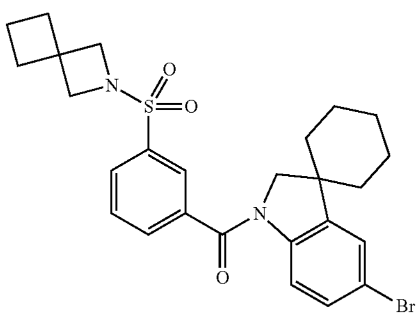 [SMILES: O=C(c1cccc(S(=O)(=O)N2CC3(CCC3)C2)c1)N1CC2(CCCCC2)c2cc(Br)ccc21] | A-07 | B-03 |
| Compound 130 | 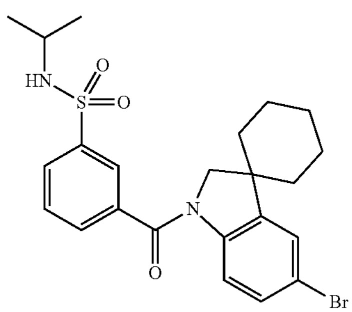 [SMILES: CC(C)NS(=O)(=O)c1cccc(C(=O)N2CC3(CCCCC3)c3cc(Br)ccc32)c1] | A-08 | B-03 |
| Compound 132 | 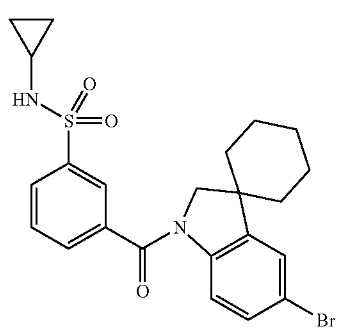 [SMILES: O=C(c1cccc(S(=O)(=O)NC2CC2)c1)N1CC2(CCCCC2)c2cc(Br)ccc21] | A-09 | B-03 |

TABLE 6-continued

| Compound | Structure | Carboxylic Acid | Indoline |
|---|---|---|---|
| Compound 135 | 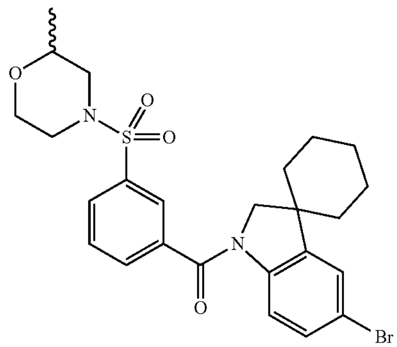 [SMILES: CC1CN(S(=O)(=O)c2cccc(C(=O)N3CC4(CCCCC4)c4cc(Br)ccc43)c2)CCO1] | A-11 | B-03 |
| Compound 138 | 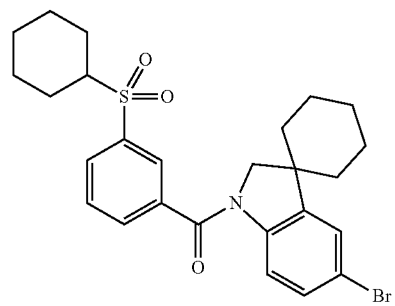 [SMILES: O=C(c1cccc(S(=O)(=O)C2CCCCC2)c1)N1CC2(CCCCC2)c2cc(Br)ccc21] | | B-03 |
| | | CAS: 1096908-69-8 | |
| Compound 139 | 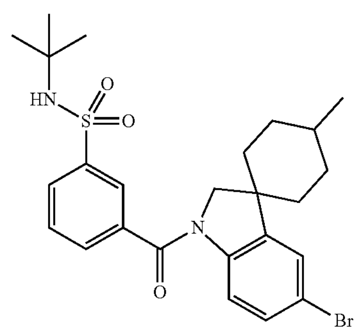 [SMILES: CC1CCC2(CC1)CN(C(=O)c1cccc(S(=O)(=O)NC(C)(C)C)c1)c1ccc(Br)cc12] | A-03 | B-05 |
| Compound 142 | 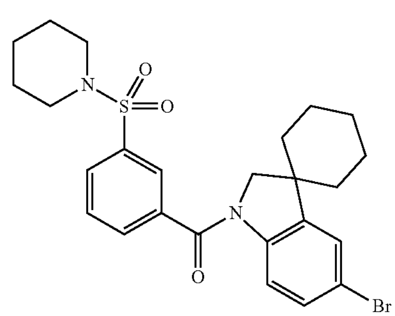 [SMILES: O=C(c1cccc(S(=O)(=O)N2CCCCC2)c1)N1CC2(CCCCC2)c2cc(Br)ccc21] | A-01 | B-03 |

TABLE 6-continued

| Compound | Structure | Carboxylic Acid | Indoline |
|---|---|---|---|
| Compound 143 | 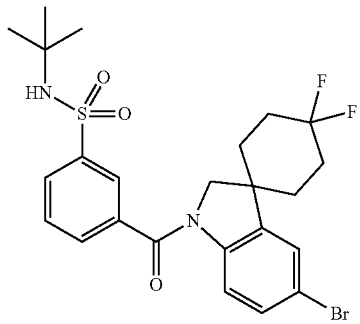 [SMILES: CC(C)(C)NS(=O)(=O)c1cccc(C(=O)N2CC3(CCC(F)(F)CC3)c3cc(Br)ccc32)c1] | A-03 | B-08 |
| Compound 150 | 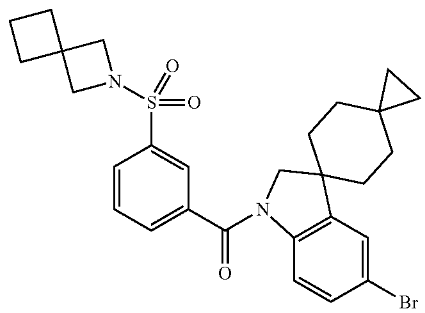 | A-07 | B-07 |
| Compound 152 | 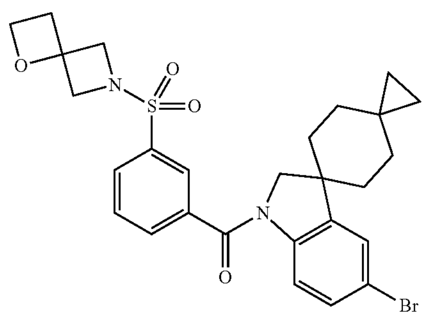 [SMILES: O=C(c1cccc(S(=O)(=O)N2CC3(CCO3)C2)c1)N1CC2(CCC3(CC3)CC2)c2cc(Br)ccc21] | A-14 | B-07 |
| Compound 154 | 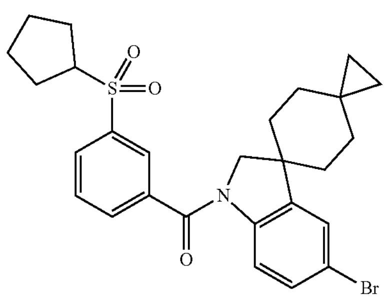 | A-52 | B-07 |
| Compound 158 | 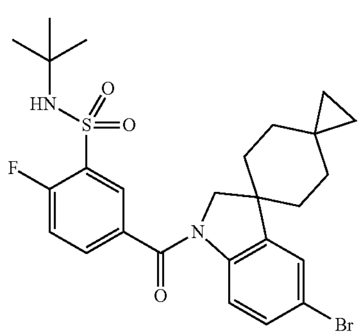 [SMILES: CC(C)(C)NS(=O)(=O)c1cc(C(=O)N2CC3(CCC4(CC4)CC3)c3cc(Br)ccc32)ccc1F] | A-22 | B-07 |

TABLE 6-continued

| Compound | Structure | Carboxylic Acid | Indoline |
| --- | --- | --- | --- |
| Compound 161 | 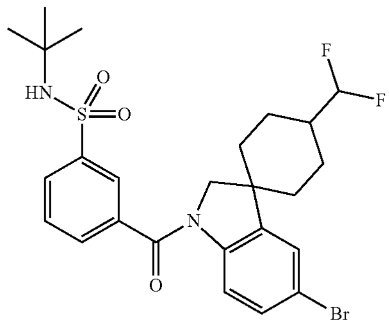 [SMILES: CC(C)(C)NS(=O)(=O)c1cccc(C(=O)N2CC3(CCC(C(F)F)CC3)c3cc(Br)ccc32)c1] | A-03 | B-09 |
| Compound 167 | 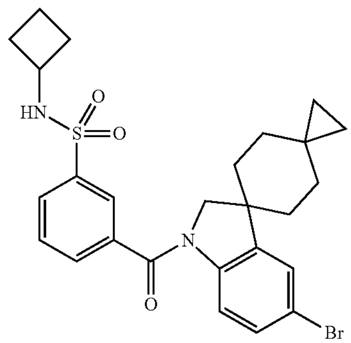 [SMILES: O=C(c1cccc(S(=O)(=O)NC2CCC2)c1)N1CC2(CCC3(CC3)CC2)c2cc(Br)ccc21] | A-24 | B-07 |
| Compound 169 | 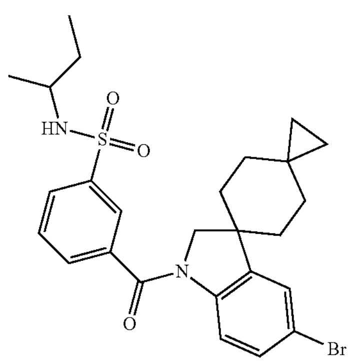 [SMILES: CCC(C)NS(=O)(=O)c1cccc(C(=O)N2CC3(CCC4(CC4)CC3)c3cc(Br)ccc32)c1] | A-25 | B-07 |
| Compound 171 | 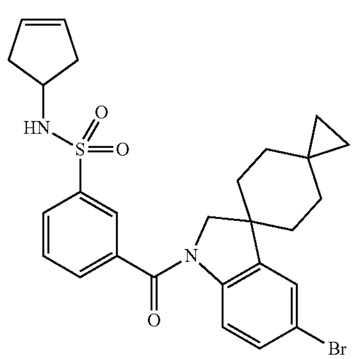 [SMILES: O=C(c1cccc(S(=O)(=O)NC2CC=CC2)c1)N1CC2(CCC3(CC3)CC2)c2cc(Br)ccc21] | A-26 | B-07 |

TABLE 6-continued

| Compound | Structure | Carboxylic Acid | Indoline |
|---|---|---|---|
| Compound 173 | 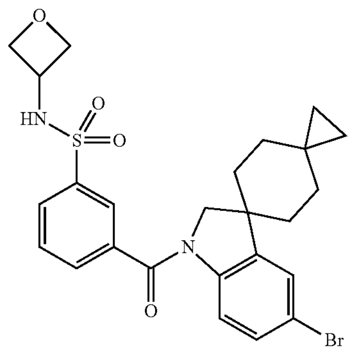 [SMILES: O=C(c1cccc(S(=O)(=O)NC2COC2)c1)N1CC2(CCC3(CC3)CC2)c2cc(Br)ccc21] | A-27 | B-07 |
| Compound 175 | 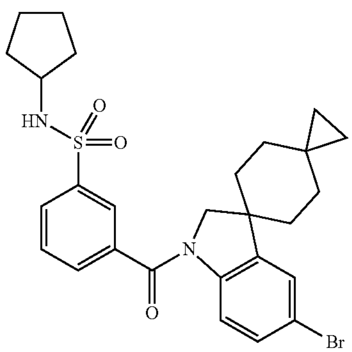 [SMILES: O=C(c1cccc(S(=O)(=O)NC2CCCC2)c1)N1CC2(CCC3(CC3)CC2)c2cc(Br)ccc21] | A-28 | B-07 |
| Compound 177 | 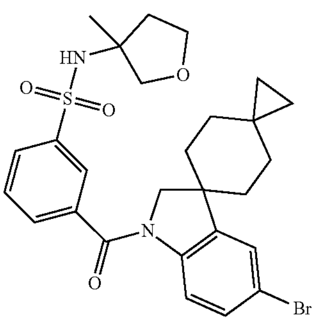 [SMILES: CC1(NS(=O)(=O)c2cccc(C(=O)N3CC4(CCC5(CC5)CC4)c4cc(Br)ccc43)c2)CCOC1] | A-29 | B-07 |
| Compound 179 | 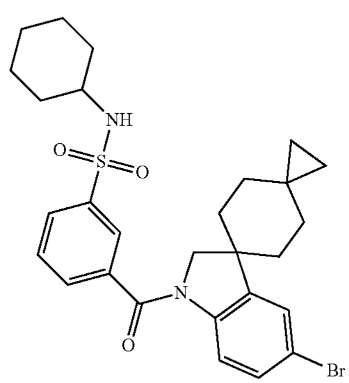 [SMILES: O=C(c1cccc(S(=O)(=O)NC2CCCCC2)c1)N1CC2(CCC3(CC3)CC2)c2cc(Br)ccc21] | A-30 | B-07 |

TABLE 6-continued

| Compound | Structure | Carboxylic Acid | Indoline |
|---|---|---|---|
| Compound 181 | 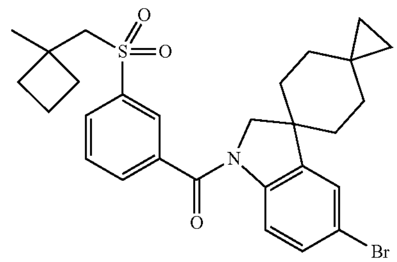 [SMILES: CC1(CS(=O)(=O)c2cccc(C(=O)N3CC4(CCC5(CC5)CC4)c4cc(Br)ccc43)c2)CCC1] | A-31 | B-07 |
| Compound 183 | 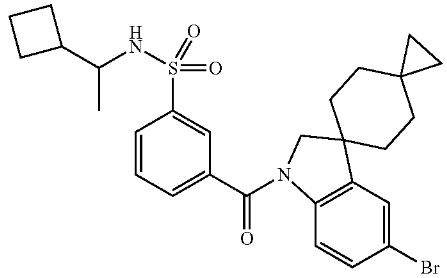 [SMILES: CC(NS(=O)(=O)c1cccc(C(=O)N2CC3(CCC4(CC4)CC3)c3cc(Br)ccc32)c1)C1CCC1] | A-32 | B-07 |
| Compound 185 | 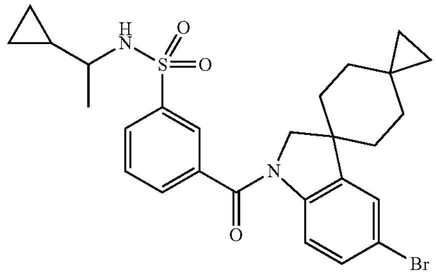 [SMILES: CC(NS(=O)(=O)c1cccc(C(=O)N2CC3(CCC4(CC4)CC3)c3cc(Br)ccc32)c1)C1CC1] | A-33 | B-07 |
| Compound 187 | 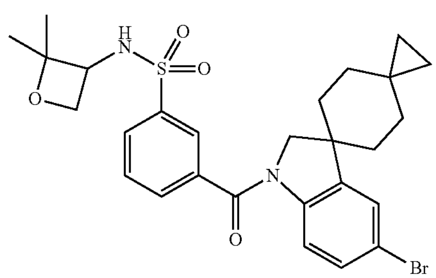 [SMILES: CC1(C)OCC1NS(=O)(=O)c1cccc(C(=O)N2CC3(CCC4(CC4)CC3)c3cc(Br)ccc32)c1] | A-34 | B-07 |
| Compound 189 | 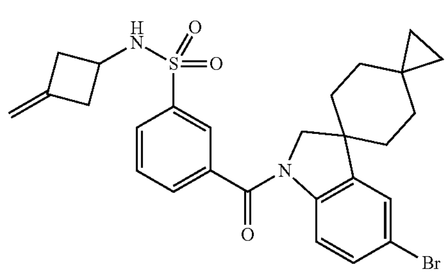 [SMILES: C=C1CC(NS(=O)(=O)c2cccc(C(=O)N3CC4(CCC5(CC5)CC4)c4cc(Br)ccc43)c2)C1] | A-35 | B-07 |

TABLE 6-continued
| Compound | Structure | Carboxylic Acid | Indoline |
|---|---|---|---|
| Compound 191 | 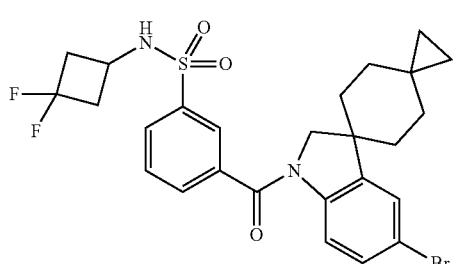 | A-36 | B-07 |
| Compound 193 | 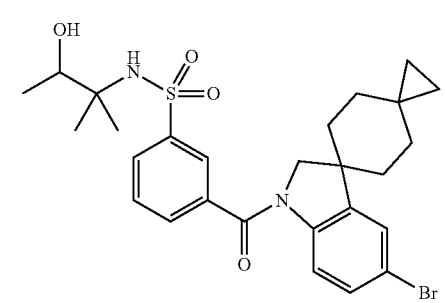 [SMILES: CC(O)C(C)(C)NS(=O)(=O)c1cccc(C(=O)N2CC3(CCC4(CC4)CC3)c3cc(Br)ccc32)c1] | A-37 | B-07 |
| Compound 195 | 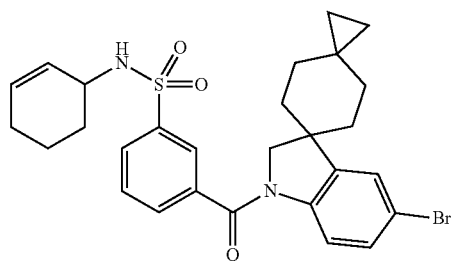 [SMILES: O=C(c1cccc(S(=O)(=O)NC2C=CCCC2)c1)N1CC2(CCC3(CC3)CC2)c2cc(Br)ccc21] | A-38 | B-07 |
| Compound 197 | 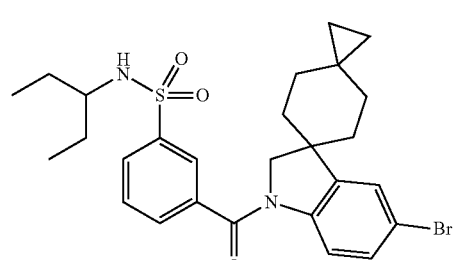 | A-39 | B-07 |
| Compound 199 | 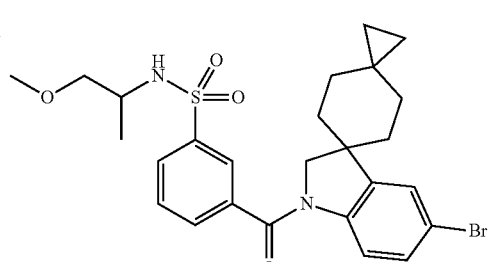 | A-40 | B-07 |

TABLE 6-continued

| Compound | Structure | Carboxylic Acid | Indoline |
|---|---|---|---|
| Compound 201 | 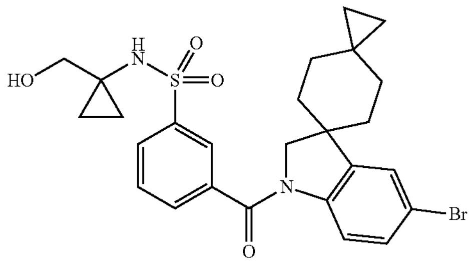 [SMILES: O=C(c1cccc(S(=O)(=O)NC2(CO)CC2)c1)N1CC2(CCC3(CC3)CC2)c2cc(Br)ccc21] | A-41 | B-07 |
| Compound 203 | 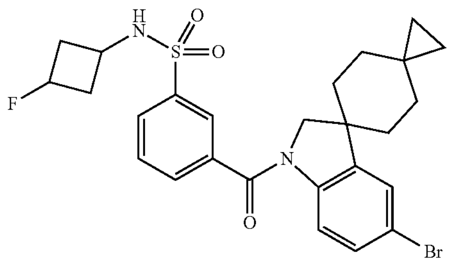 [SMILES: O=C(c1cccc(S(=O)(=O)NC2CC(F)C2)c1)N1CC2(CCC3(CC3)CC2)c2cc(Br)ccc21] | A-42 | B-07 |
| Compound 205 | 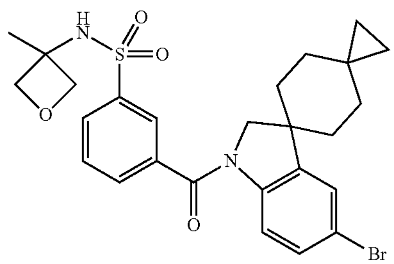 [SMILES: CC1(NS(=O)(=O)c2cccc(C(=O)N3CC4(CCC5(CC5)CC4)c4cc(Br)ccc43)c2)COC1] | A-43 | B-07 |
| Compound 207 | 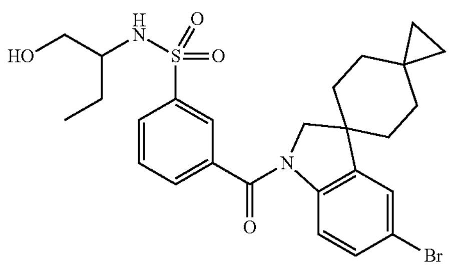 [SMILES: CCC(CO)NS(=O)(=O)c1cccc(C(=O)N2CC3(CCC4(CC4)CC3)c3cc(Br)ccc32)c1] | A-44 | B-07 |
| Compound 209 | 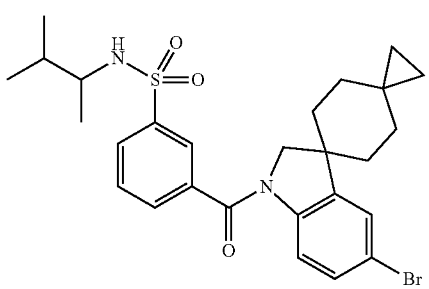 [SMILES: CC(C)C(C)NS(=O)(=O)c1cccc(C(=O)N2CC3(CCC4(CC4)CC3)c3cc(Br)ccc32)c1] | A-45 | B-07 |
| Compound 211 | 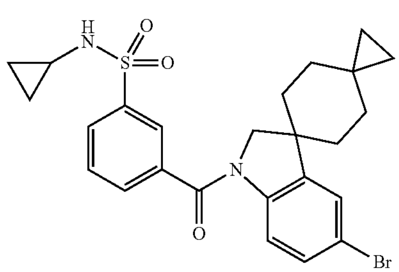 [SMILES: O=C(c1cccc(S(=O)(=O)NC2CC2)c1)N1CC2(CCC3(CC3)CC2)c2cc(Br)ccc21] | A-09 | B-07 |

TABLE 6-continued

| Compound | Structure | Carboxylic Acid | Indoline |
| --- | --- | --- | --- |
| Compound 213 | 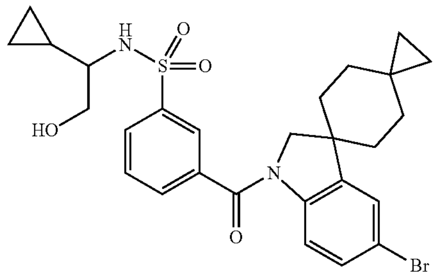 [SMILES: O=C(c1cccc(S(=O)(=O)NC(CO)C2CC2)c1)N1CC2(CCC3(CC3)CC2)c2cc(Br)ccc21] | A-46 | B-07 |
| Compound 215 | 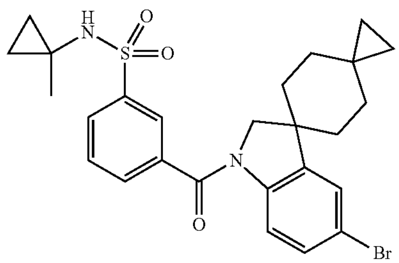 [SMILES: CC1(NS(=O)(=O)c2cccc(C(=O)N3CC4(CCC5(CC5)CC4)c4cc(Br)ccc43)c2)CC1] | A-47 | B-07 |
| Compound 217 | 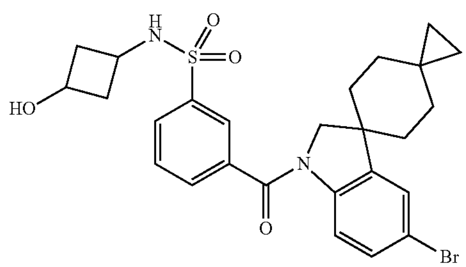 [SMILES: O=C(c1cccc(S(=O)(=O)NC2CC(O)C2)c1)N1CC2(CCC3(CC3)CC2)c2cc(Br)ccc21] | A-48 | B-07 |
| Compound 219 | 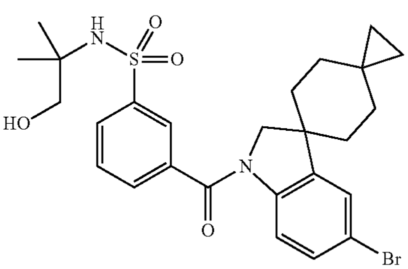 [SMILES: CC(C)(CO)NS(=O)(=O)c1cccc(C(=O)N2CC3(CCC4(CC4)CC3)c3cc(Br)ccc32)c1] | A-49 | B-07 |
| Compound 221 | 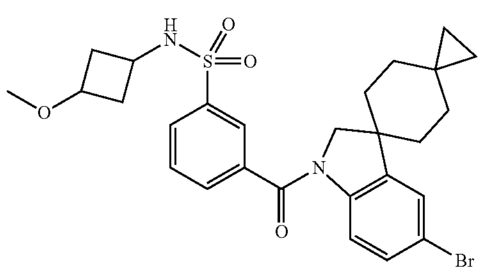 [SMILES: COC1CC(NS(=O)(=O)c2cccc(C(=O)N3CC4(CCC5(CC5)CC4)c4cc(Br)ccc43)c2)C1] | A-50 | B-07 |

TABLE 6-continued

| Compound | Structure | Carboxylic Acid | Indoline |
|---|---|---|---|
| Compound 232 | 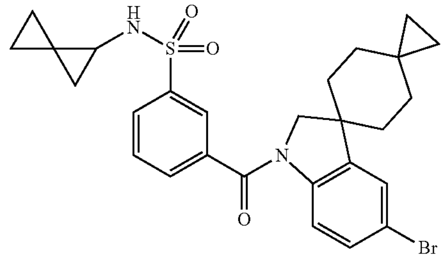 [SMILES: O=C(c1cccc(S(=O)(=O)NC2CC23CC3)c1)N1CC2(CCC3(CC3)CC2)c2cc(Br)ccc21] | A-56 | B-07 |
| Compound 234 | 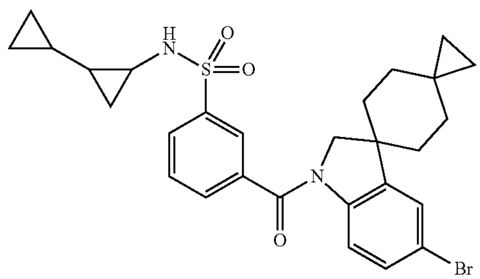 [SMILES: O=C(c1cccc(S(=O)(=O)NC2CC2C2CC2)c1)N1CC2(CCC3(CC3)CC2)c2cc(Br)ccc21] | A-57 | B-07 |
| Compound 236 | 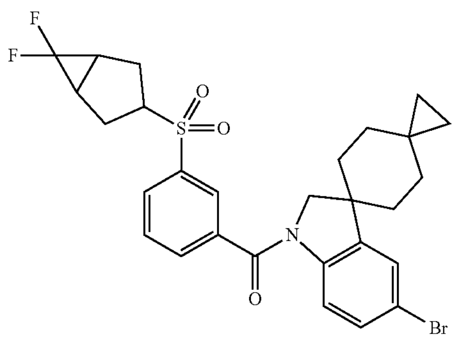 [SMILES: O=C(c1cccc(S(=O)(=O)C2CC3C(C2)C3(F)F)c1)N1CC2(CCC3(CC3)CC2)c2cc(Br)ccc21] | A-58 | B-07 |
| (R)-Compound 238 | 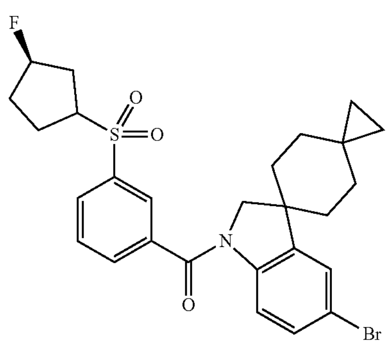 [SMILES: O=C(c1cccc(S(=O)(=O)C2CC[C@@H](F)C2)c1)N1CC2(CCC3(CC3)CC2)c2cc(Br)ccc21] | (R)-A-59 | B-07 |
| (S)-Compound 238 | 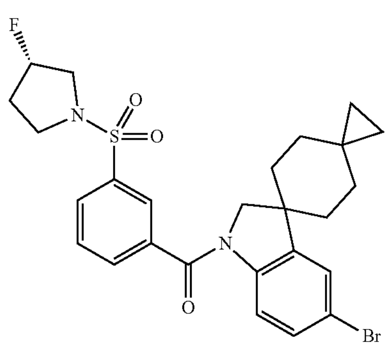 [SMILES: O=C(c1cccc(S(=O)(=O)N2CC[C@H](F)C2)c1)N1CC2(CCC3(CC3)CC2)c2cc(Br)ccc21] | (S)-A-59 | B-07 |

TABLE 6-continued

| Compound | Structure | Carboxylic Acid | Indoline |
|---|---|---|---|
| Compound 242 | 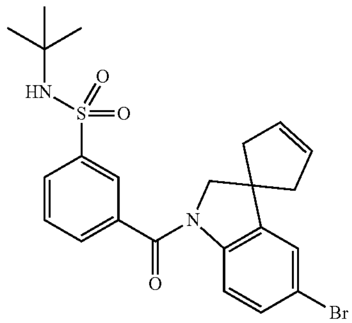 [SMILES: CC(C)(C)NS(=O)(=O)c1cccc(C(=O)N2CC3(CC=CC3)c3cc(Br)ccc32)c1] | A-03 | B-16 |
| Compound 244 | 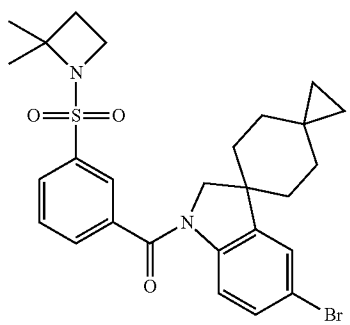 [SMILES: CC1(C)CCN1S(=O)(=O)c1cccc(C(=O)N2CC3(CCC4(CC4)CC3)c3cc(Br)ccc32)c1] | A-60 | B-07 |
| Compound 246 | 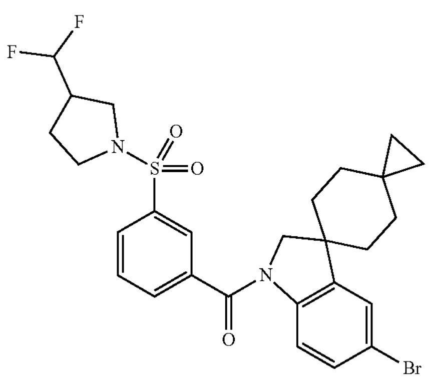 [SMILES: O=C(c1cccc(S(=O)(=O)N2CCC(C(F)F)C2)c1)N1CC2(CCC3(CC3)CC2)c2cc(Br)ccc21] | A-61 | B-07 |
| Compound 248 | 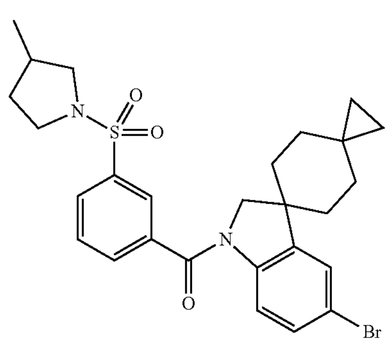 [SMILES: CC1CCN(S(=O)(=O)c2cccc(C(=O)N3CC4(CCC5(CC5)CC4)c4cc(Br)ccc43)c2)C1] | A-13 | B-07 |

TABLE 6-continued

| Compound | Structure | Carboxylic Acid | Indoline |
|---|---|---|---|
| (S)-Compound 248 | 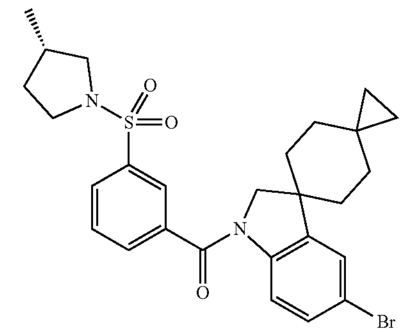 [SMILES: C[C@H]1CCN(S(=O)(=O)c2cccc(C(=O)N3CC4(CCC5(CC5)CC4)c4cc(Br)ccc43)c2)C1] | (S)-A-13 | B-07 |
| Compound 250 | 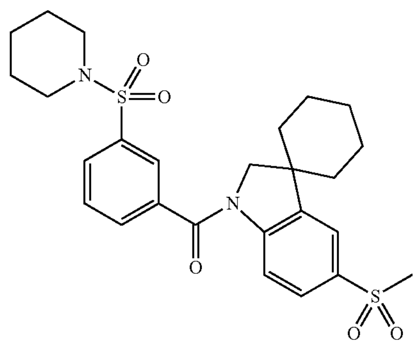 [SMILES: CS(=O)(=O)c1ccc2c(c1)C1(CCCCC1)CN2C(=O)c1cccc(S(=O)(=O)N2CCCCC2)c1] | A-01 | B-17 |
| Compound 251 | 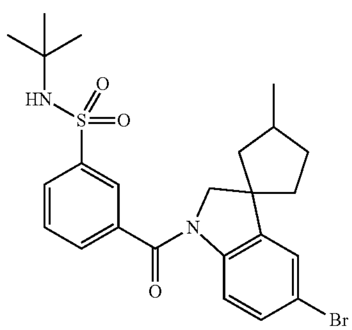 [SMILES: CC1CCC2(C1)CN(C(=O)c1cccc(S(=O)(=O)NC(C)(C)C)c1)c1ccc(Br)cc12] | A-09 | B-04 |
| Compound 253 | 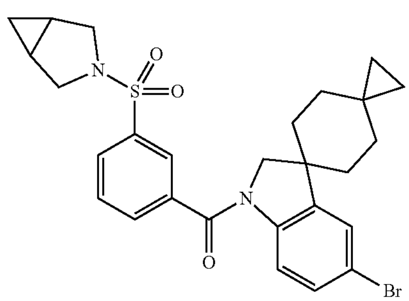 [SMILES: O=C(c1cccc(S(=O)(=O)N2CC3CC3C2)c1)N1CC2(CCC3(CC3)CC2)c2cc(Br)ccc21] | A-05 | B-07 |
| Compound 256 | 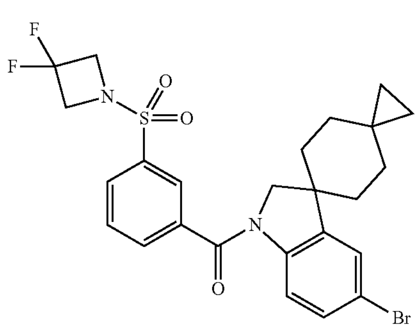 [SMILES: O=C(c1cccc(S(=O)(=O)N2CC(F)(F)C2)c1)N1CC2(CCC3(CC3)CC2)c2cc(Br)ccc21] | A-62 | B-07 |

TABLE 6-continued

| Compound | Structure | Carboxylic Acid | Indoline |
|---|---|---|---|
| Compound 259 | 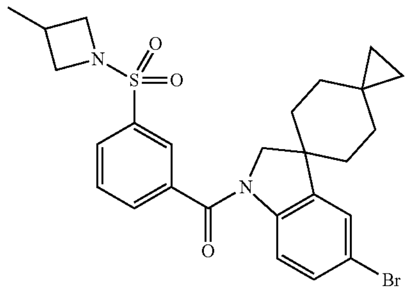 [SMILES: CC1CN(S(=O)(=O)c2cccc(C(=O)N3CC4(CCC5(CC5)CC4)c4cc(Br)ccc43)c2)C1] | A-63 | B-07 |
| Compound 263 | 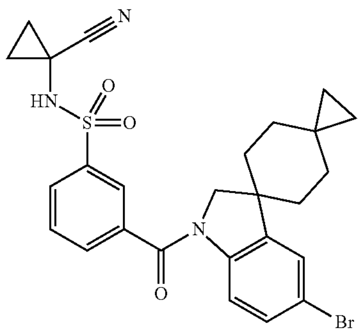 [SMILES: N#CC1(NS(=O)(=O)c2cccc(C(=O)N3CC4(CCC5(CC5)CC4)c4cc(Br)ccc43)c2)CC1] | A-64 | B-07 |
| Compound 265 | 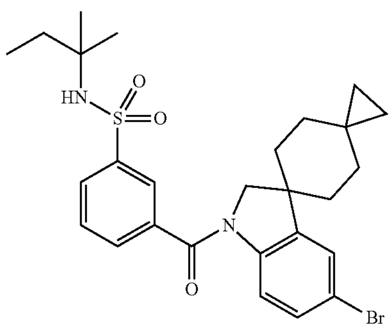 [SMILES: CCC(C)(C)NS(=O)(=O)c1cccc(C(=O)N2CC3(CCC4(CC4)CC3)c3cc(Br)ccc32)c1] | A-65 | B-07 |
| Compound 267 | 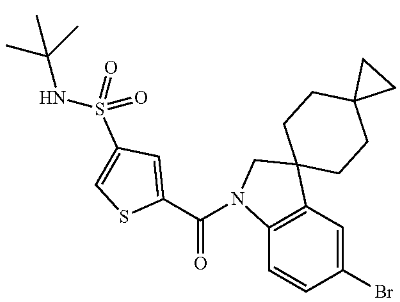 [SMILES: CC(C)(C)NS(=O)(=O)c1csc(C(=O)N2CC3(CCC4(CC4)CC3)c3cc(Br)ccc32)c1] | A-19 | B-07 |
| Compound 271 | 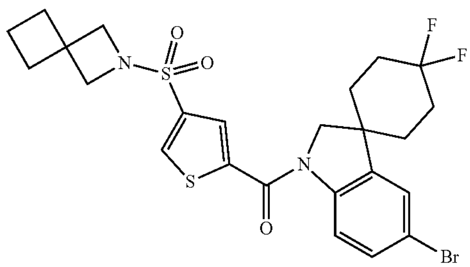 [SMILES: O=C(c1cc(S(=O)(=O)N2CC3(CCC3)C2)cs1)N1CC2(CCC(F)(F)CC2)c2cc(Br)ccc21] | A-65 | B-08 |

TABLE 6-continued

| Compound | Structure | Carboxylic Acid | Indoline |
| --- | --- | --- | --- |
| Compound 273 | 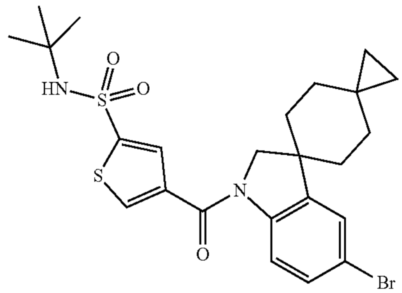 [SMILES: CC(C)(C)NS(=O)(=O)c1cc(C(=O)N2CC3(CCC4(CC4)CC3)c3cc(Br)ccc32)cs1] | A-55 | B-07 |
| Compound 276 | 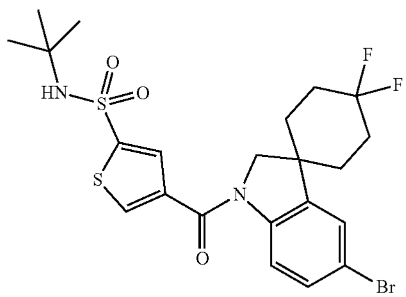 [SMILES: CC(C)(C)NS(=O)(=O)c1cc(C(=O)N2CC3(CCC(F)(F)CC3)c3cc(Br)ccc32)cs1] | A-55 | B-08 |
| Compound 278 | 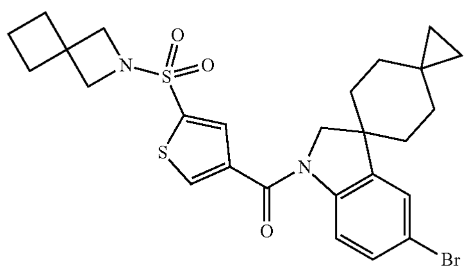 [SMILES: O=C(c1csc(S(=O)(=O)N2CC3(CCC3)C2)c1)N1CC2(CCC3(CC3)CC2)c2cc(Br)ccc21] | A-67 | B-07 |
| Compound 280 | 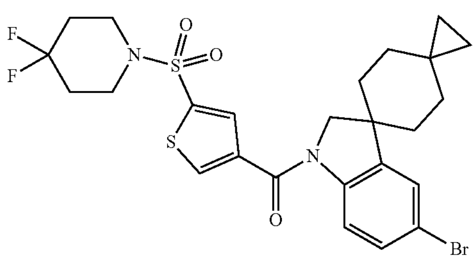 [SMILES: O=C(c1csc(S(=O)(=O)N2CCC(F)(F)CC2)c1)N1CC2(CCC3(CC3)CC2)c2cc(Br)ccc21] | A-68 | B-07 |
| Compound 282 | 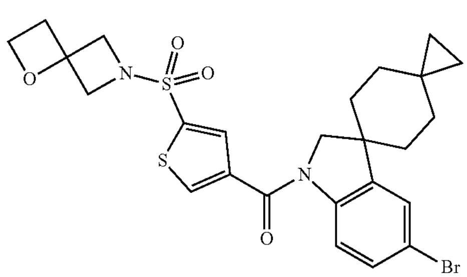 [SMILES: O=C(c1csc(S(=O)(=O)N2CC3(CCO3)C2)c1)N1CC2(CCC3(CC3)CC2)c2cc(Br)ccc21] | A-69 | B-07 |

TABLE 6-continued
| Compound | Structure | Carboxylic Acid | Indoline |
|---|---|---|---|
| Compound 286 | 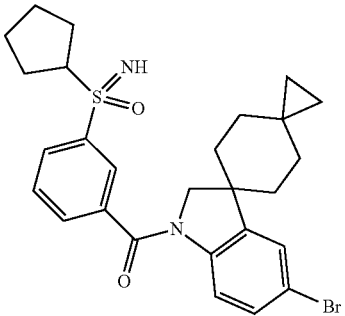 [SMILES: N=S(=O)(c1cccc(C(=O)N2CC3(CCC4(CC4)CC3)c3cc(Br)ccc32)c1)C1CCCC1] | A-72 | B-07 |
| Compound 288 | 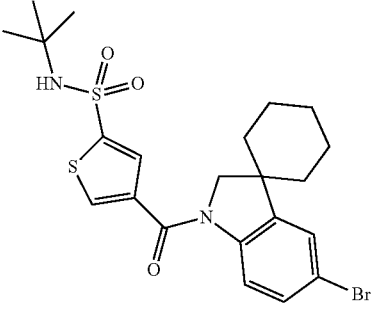 [SMILES: CC(C)(C)NS(=O)(=O)c1cc(C(=O)N2CC3(CCCCC3)c3cc(Br)ccc32)cs1] | A-55 | B-03 |
| Compound 290 | 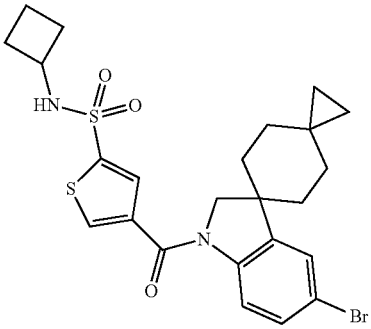 [SMILES: O=C(c1csc(S(=O)(=O)NC2CCC2)c1)N1CC2(CCC3(CC3)CC2)c2cc(Br)ccc21] | A-70 | B-07 |
| Compound 294 | 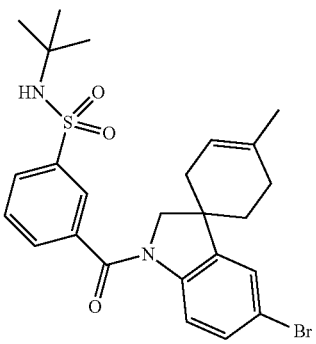 [SMILES: CC1=CCC2(CC1)CN(C(=O)c1cccc(S(=O)(=O)NC(C)(C)C)c1)c1ccc(Br)cc12] | A-09 | B-18 |

TABLE 6-continued

| Compound | Structure | Carboxylic Acid | Indoline |
| --- | --- | --- | --- |
| Compound 296 | 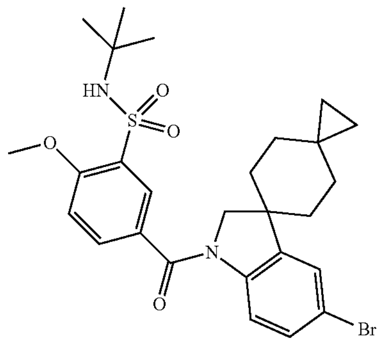 [SMILES: COc1ccc(C(=O)N2CC3(CCC4(CC4)CC3)c3cc(Br)ccc32)cc1S(=O)(=O)NC(C)(C)C] | A-73 | B-07 |
| Compound 307 & Compound 308 | | A-09 | B-19/B-20 |
| Compound 323 | 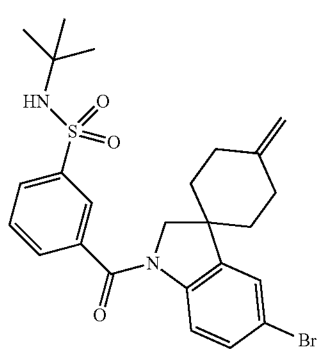 [SMILES: C=C1CCC2(CC1)CN(C(=O)c1cccc(S(=O)(=O)NC(C)(C)C)c1)c1ccc(Br)cc12] | A-09 | B-21 |

TABLE 6-continued

| Compound | Structure | Carboxylic Acid | Indoline |
|---|---|---|---|
| Compound 325 | 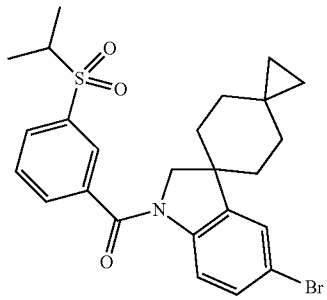 [SMILES: CC(C)S(=O)(=O)c1cccc(C(=O)N2CC3(CCC4(CC4)CC3)c3cc(Br)ccc32)c1] | | B-07 |
| Compound 328 | 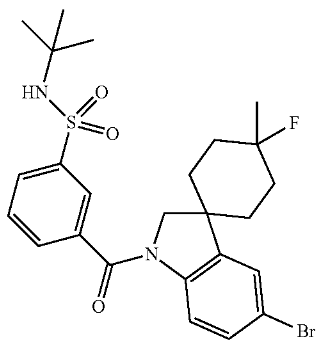 [SMILES: CC1(F)CCC2(CC1)CN(C(=O)c1cccc(S(=O)(=O)NC(C)(C)C)c1)c1ccc(Br)cc12] | | B-22 |
| Compound 360a | 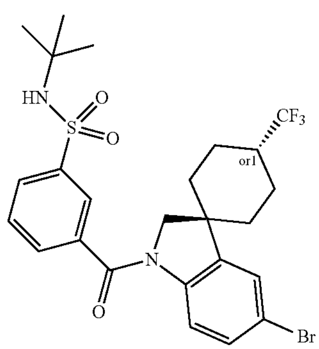 [SMILES: CC(C)(C)NS(=O)(=O)c1cccc(C(=O)N2C[C@]3(CC[C@H](C(F)(F)F)CC3)c3cc(Br)ccc32)c1] | | B-24a |
| Compound 360b | 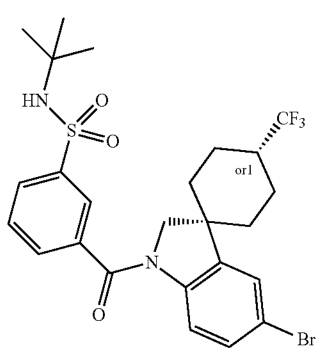 [SMILES: CC(C)(C)NS(=O)(=O)c1cccc(C(=O)N2C[C@]3(CC[C@@H](C(F)(F)F)CC3)c3cc(Br)ccc32)c1] | | B-24b |

421

Synthetic Example S-002

Synthesis of N-(1'-(3-((4,4-difluoropiperidin-1-yl)sulfonyl)benzoyl)spiro[cyclopentane-1,3'-indolin]-5'-yl)methanesulfonamide (Compound 18)

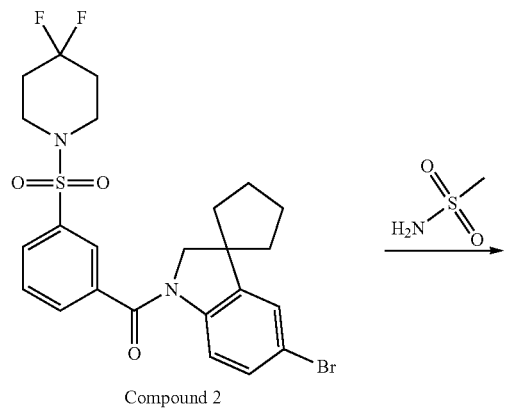
Compound 2

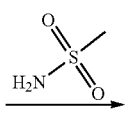

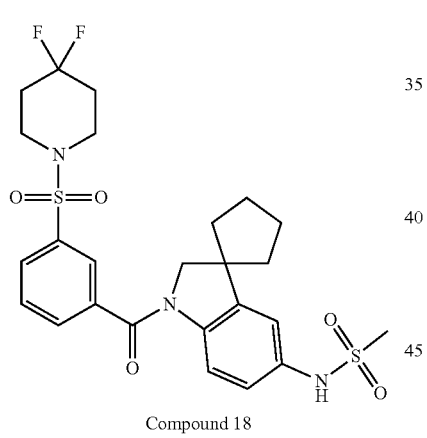
Compound 18

A degassed mixture of Compound 2 (50 mg, 93 μmol), methanesulfonamide (13 mg, 0.14 mmol), CuI (9.0 mg, 46 μmol), K$_3$PO$_4$ (59 mg, 0.28 mmol), N$^1$,N$^2$-dimethylcyclohexane-1,2-diamine (7.0 mg, 46 μmol), and DMF (2.0 mL) was stirred at 150° C. for 2 h in a microwave reactor. The mixture was combined with H$_2$O (30 mL) and extracted with EtOAc (2×30 mL). The extracts were combined, washed with brine (10 mL), dried over Na$_2$SO$_4$, concentrated, and purified by prep-HPLC (35-0% H$_2$O [10 mM NH$_4$CO$_3$] in MeCN) to provide N-(1'-(3-((4,4-difluoropiperidin-1-yl)sulfonyl)benzoyl)spiro[cyclopentane-1,3'-indolin]-5'-yl)methanesulfonamide (Compound 18, 8.6 mg).

422

Synthetic Example S-002a

Synthesis of N-(tert-butyl)-3-(5"-(ethylsulfonamido)dispiro[cyclopropane-1,1'-cyclohexane-4',3"-indoline]-1"-carbonyl)benzenesulfonamide (Compound 134)

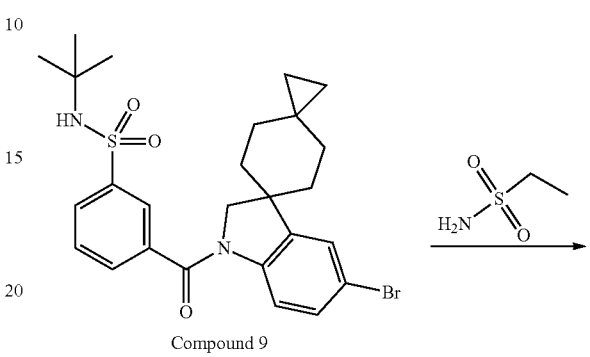
Compound 9

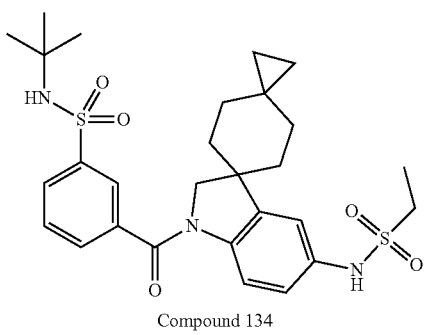
Compound 134

A degassed mixture of Compound 2 (1.0 g, 1.9 mmol), ethanesulfonamide (0.60 g, 5.5 mmol), CuI (0.37 g, 1.9 mmol), K$_3$PO$_4$ (1.3 g, 6.0 mmol), N$^1$,N$^2$-dimethylcyclohexane-1,2-diamine (0.27 g, 1.9 mmol), and DMF (14 mL) was stirred at 150° C. for 3 h. The mixture was combined with H$_2$O (40 mL). The resulting precipitate was filtered, washed with H$_2$O (5 mL×3), dissolved in EtOAc (50 mL), washed with water (20 mL×2), dried over Na$_2$SO$_4$, concentrated, and purified by prep-HPLC (50-20% H$_2$O [0.100 formic acid] in MeCN) to provide N-(tert-butyl)-3-(5"-(ethyl sulfonamido)dispiro[cyclopropane-1,1'-cyclohexane-4',3"-indoline]-1"-carbonyl)benzenesulfonamide (Compound 134, 1.3 g).

Compounds in Table 7 were prepared from the indicated bromoindoline and primary sulfonamide in the same manner as Compound 18.

TABLE 7

| Compound | Structure | Bromide | Sulfonamide |
|---|---|---|---|
| Compound 19 | (structure) | Compound 11 | methanesulfonamide (H₂N-S(=O)₂-CH₃) |
| Compound 20 | (structure) | Compound 5 | methanesulfonamide |
| Compound 21 | (structure) | Compound 7 | methanesulfonamide |
| Compound 22 | (structure) | Compound 9 | methanesulfonamide |

TABLE 7-continued

| Compound | Structure | Bromide | Sulfonamide |
|---|---|---|---|
| Compound 23 | (structure) | Compound 14 | (structure) |
| Compound 24 | (structure) | Compound 15 | (structure) |
| Compound 25 | (structure) | Compound 16 | (structure) |
| Compound 26 | (structure) | Compound 17 | (structure) |

TABLE 7-continued

| Compound | Structure | Bromide | Sulfonamide |
|---|---|---|---|
| Compound 45 | 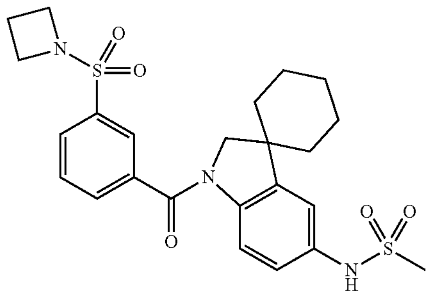 [SMILES: CS(=O)(=O)Nc1ccc2c(c1)C1(CCCCC1)CN2C(=O)c1cccc(S(=O)(=O)N2CCC2)c1] | Compound 126 | H₂N-S(=O)(=O)-CH₃ |
| Compound 46 | 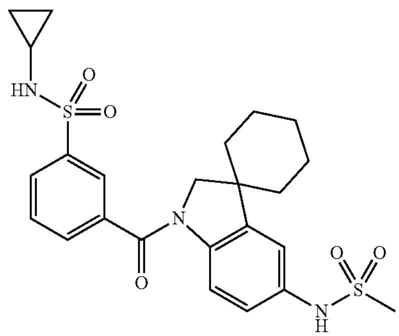 [SMILES: CS(=O)(=O)Nc1ccc2c(c1)C1(CCCCC1)CN2C(=O)c1cccc(S(=O)(=O)NC2CC2)c1] | Compound 132 | H₂N-S(=O)(=O)-CH₃ |
| Compound 48 | 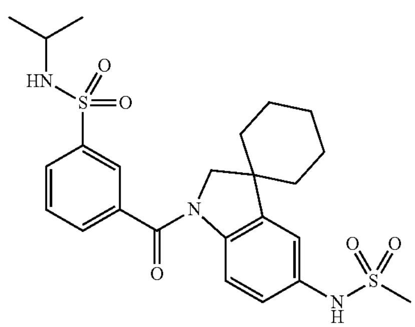 [SMILES: CC(C)NS(=O)(=O)c1cccc(C(=O)N2CC3(CCCCC3)c3cc(NS(C)(=O)=O)ccc32)c1] | Compound 130 | H₂N-S(=O)(=O)-CH₃ |
| Compound 70 | 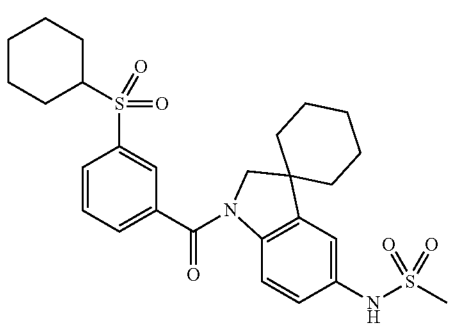 [SMILES: CS(=O)(=O)Nc1ccc2c(c1)C1(CCCCC1)CN2C(=O)c1cccc(S(=O)(=O)C2CCCCC2)c1] | Compound 138 | H₂N-S(=O)(=O)-CH₃ |

TABLE 7-continued

| Compound | Structure | Bromide | Sulfonamide |
|---|---|---|---|
| Compound 71 | 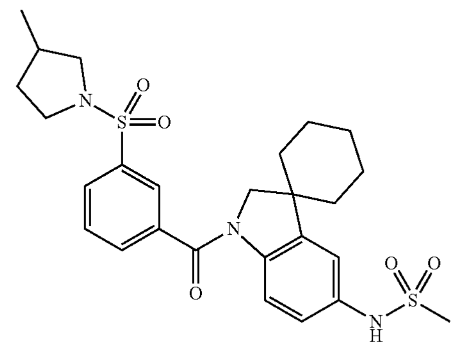 [SMILES: CC1CCN(S(=O)(=O)c2cccc(C(=O)N3CC4(CCCCC4)c4cc(NS(C)(=O)=O)ccc43)c2)C1] | Compound 137 | H₂N-S(=O)₂-CH₃ |
| Compound 83 | 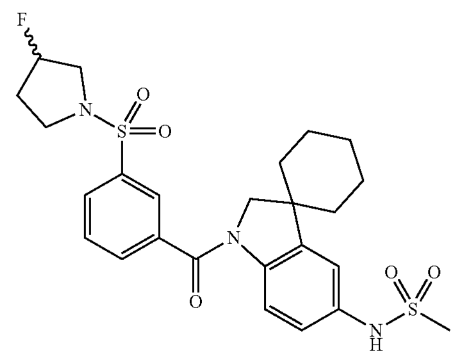 [SMILES: CS(=O)(=O)Nc1ccc2c(c1)C1(CCCCC1)CN2C(=O)c1cccc(S(=O)(=O)N2CCC(F)C2)c1] | Compound 136 | H₂N-S(=O)₂-CH₃ |
| Compound 107 | 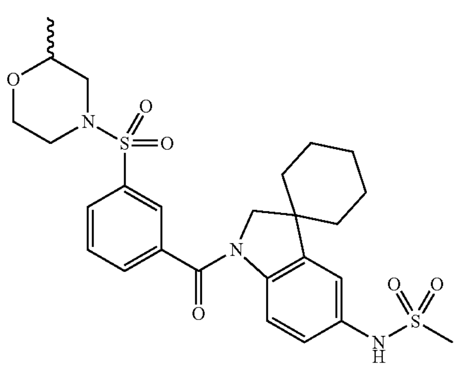 [SMILES: CC1CN(S(=O)(=O)c2cccc(C(=O)N3CC4(CCCCC4)c4cc(NS(C)(=O)=O)ccc43)c2)CCO1] | Compound 135 | H₂N-S(=O)₂-CH₃ |
| Compound 129 | 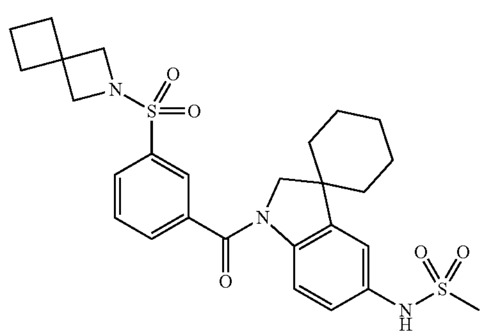 [SMILES: CS(=O)(=O)Nc1ccc2c(c1)C1(CCCCC1)CN2C(=O)c1cccc(S(=O)(=O)N2CC3(CCC3)C2)c1] | Compound 128 | H₂N-S(=O)₂-CH₃ |

TABLE 7-continued

| Compound | Structure | Bromide | Sulfonamide |
|---|---|---|---|
| Compound 140 | 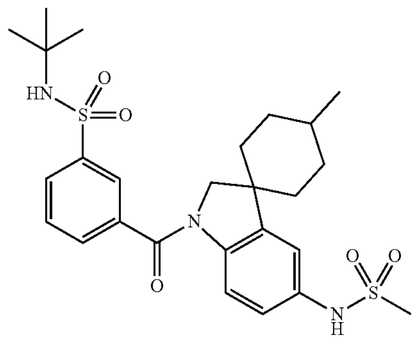 [SMILES: CC1CCC2(CC1)CN(C(=O)c1cccc(S(=O)(=O)NC(C)(C)C)c1)c1ccc(NS(C)(=O)=O)cc12] | Compound 139 | H₂N-S(=O)₂-CH₃ |
| Compound 144 | 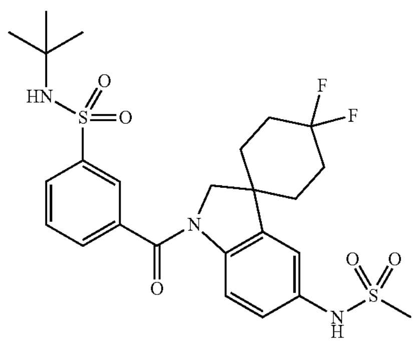 | Compound 143 | H₂N-S(=O)₂-CH₃ |
| Compound 151 | 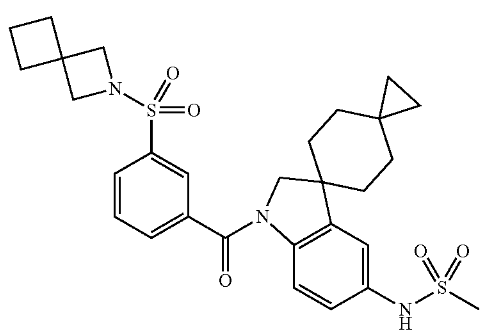 [SMILES: CS(=O)(=O)Nc1ccc2c(c1)C1(CCC3(CC3)CC1)CN2C(=O)c1cccc(S(=O)(=O)N2CC3(CCC3)C2)c1] | Compound 150 | H₂N-S(=O)₂-CH₃ |
| Compound 153 | 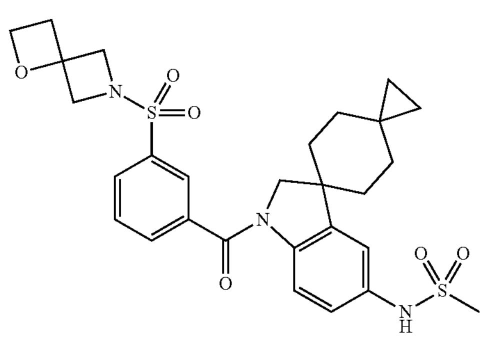 | Compound 151 | H₂N-S(=O)₂-CH₃ |

TABLE 7-continued

| Compound | Structure | Bromide | Sulfonamide |
|---|---|---|---|
| Compound 155 | 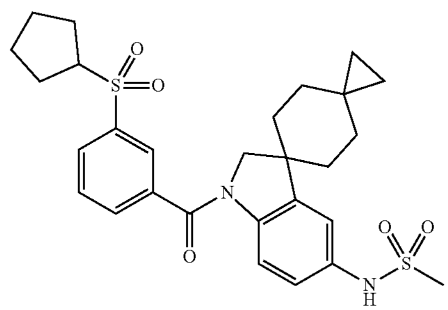 [SMILES: CS(=O)(=O)Nc1ccc2c(c1)C1(CCC3(CC3)CC1)CN2C(=O)c1cccc(S(=O)(=O)C2CCCC2)c1] | Compound 154 | H₂N-S(=O)(=O)-CH₃ |
| Compound 159 | 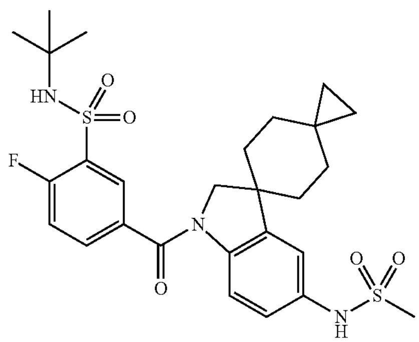 [SMILES: CC(C)(C)NS(=O)(=O)c1cc(C(=O)N2CC3(CCC4(CC4)CC3)c3cc(NS(C)(=O)=O)ccc32)ccc1F] | Compound 158 | H₂N-S(=O)(=O)-CH₃ |
| Compound 160 | 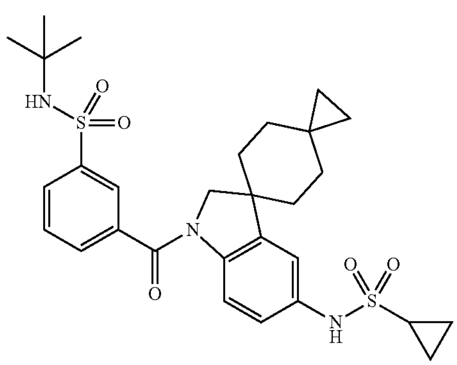 [SMILES: CC(C)(C)NS(=O)(=O)c1cccc(C(=O)N2CC3(CCC4(CC4)CC3)c3cc(NS(=O)(=O)C4CC4)ccc32)c1] | Compound 9 | H₂N-S(=O)(=O)-CH₃ |
| Compound 162 | 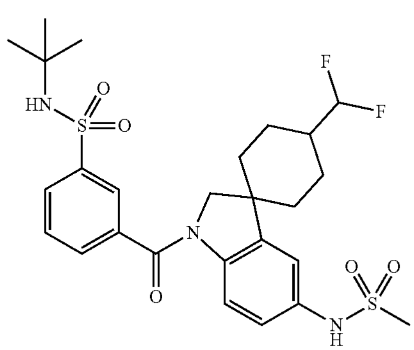 [SMILES: CC(C)(C)NS(=O)(=O)c1cccc(C(=O)N2CC3(CCC(C(F)F)CC3)c3cc(NS(C)(=O)=O)ccc32)c1] | Compound 161 | H₂N-S(=O)(=O)-CH₃ |

TABLE 7-continued

| Compound | Structure | Bromide | Sulfonamide |
|---|---|---|---|
| Compound 168 | 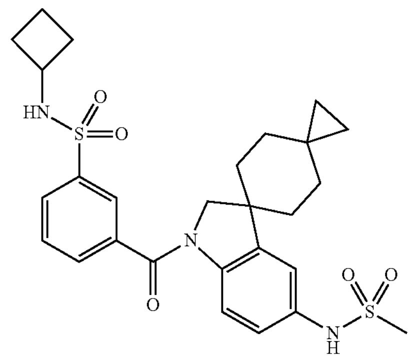 [SMILES: CS(=O)(=O)Nc1ccc2c(c1)C1(CCC3(CC3)CC1)CN2C(=O)c1cccc(S(=O)(=O)NC2CCC2)c1] | Compound 167 | methanesulfonamide |
| Compound 170 | 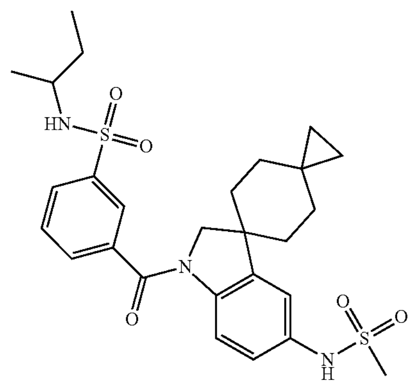 [SMILES: CCC(C)NS(=O)(=O)c1cccc(C(=O)N2CC3(CCC4(CC4)CC3)c3cc(NS(C)(=O)=O)ccc32)c1] | Compound 168 | methanesulfonamide |
| Compound 172 | 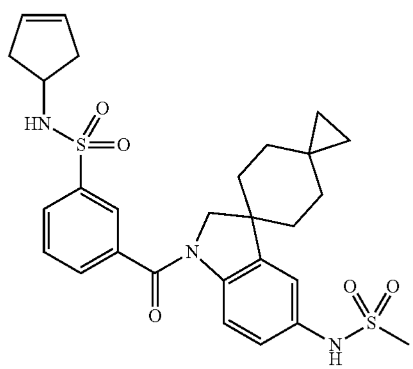 [SMILES: CS(=O)(=O)Nc1ccc2c(c1)C1(CCC3(CC3)CC1)CN2C(=O)c1cccc(S(=O)(=O)NC2CC=CC2)c1] | Compound 171 | methanesulfonamide |
| Compound 174 | 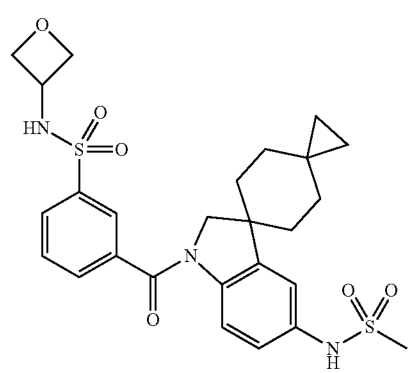 [SMILES: CS(=O)(=O)Nc1ccc2c(c1)C1(CCC3(CC3)CC1)CN2C(=O)c1cccc(S(=O)(=O)NC2COC2)c1] | Compound 173 | methanesulfonamide |

TABLE 7-continued

| Compound | Structure | Bromide | Sulfonamide |
|---|---|---|---|
| Compound 176 | 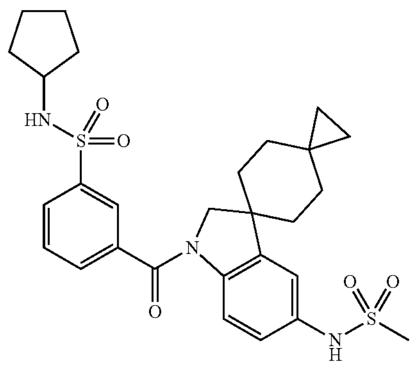 [SMILES: CS(=O)(=O)Nc1ccc2c(c1)C1(CCC3(CC3)CC1)CN2C(=O)c1cccc(S(=O)(=O)NC2CCCC2)c1] | Compound 175 | H₂N-S(=O)(=O)-CH₃ |
| Compound 178 | 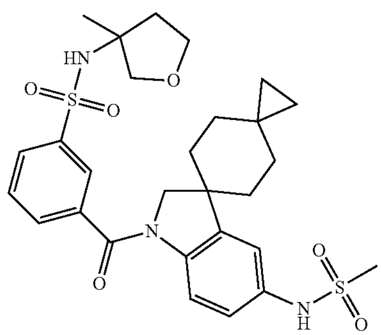 [SMILES: CC1(NS(=O)(=O)c2cccc(C(=O)N3CC4(CCC5(CC5)CC4)c4cc(NS(C)(=O)=O)ccc43)c2)CCOC1] | Compound 177 | H₂N-S(=O)(=O)-CH₃ |
| Compound 180 | 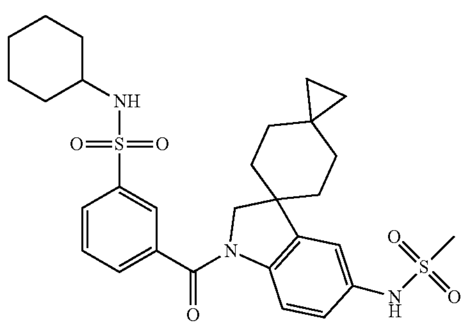 [SMILES: CS(=O)(=O)Nc1ccc2c(c1)C1(CCC3(CC3)CC1)CN2C(=O)c1cccc(S(=O)(=O)NC2CCCCC2)c1] | Compound 179 | H₂N-S(=O)(=O)-CH₃ |
| Compound 182 | 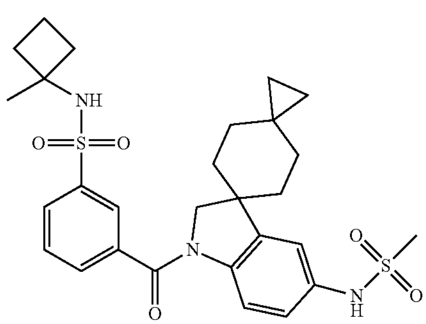 [SMILES: CC1(NS(=O)(=O)c2cccc(C(=O)N3CC4(CCC5(CC5)CC4)c4cc(NS(C)(=O)=O)ccc43)c2)CCC1] | Compound 181 | H₂N-S(=O)(=O)-CH₃ |

TABLE 7-continued

| Compound | Structure | Bromide | Sulfonamide |
|---|---|---|---|
| Compound 184 | 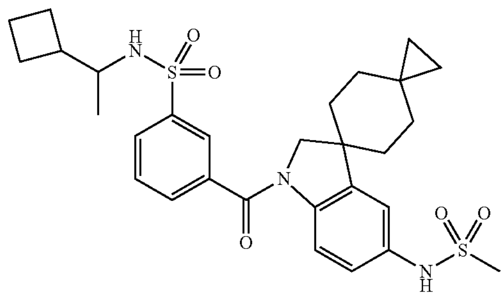 [SMILES: CC(NS(=O)(=O)c1cccc(C(=O)N2CC3(CCC4(CC4)CC3)c3cc(NS(C)(=O)=O)ccc32)c1)C1CCC1] | Compound 183 | methanesulfonamide (H₂N-S(=O)₂-CH₃) |
| Compound 186 | 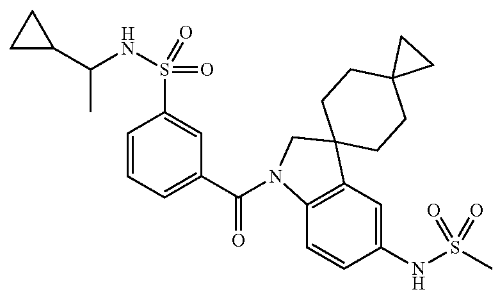 [SMILES: CC(NS(=O)(=O)c1cccc(C(=O)N2CC3(CCC4(CC4)CC3)c3cc(NS(C)(=O)=O)ccc32)c1)C1CC1] | Compound 185 | methanesulfonamide (H₂N-S(=O)₂-CH₃) |
| Compound 188 | 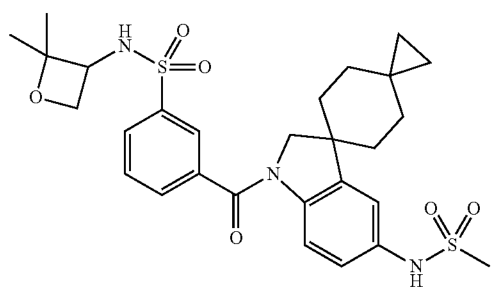 | Compound 187 | methanesulfonamide (H₂N-S(=O)₂-CH₃) |
| Compound 190 | 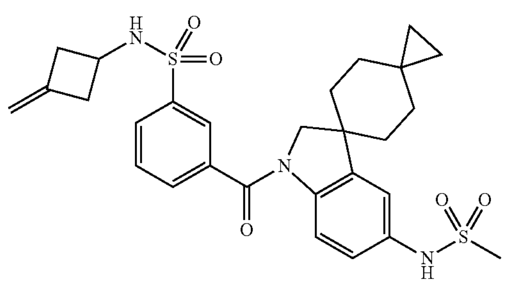 | Compound 189 | methanesulfonamide (H₂N-S(=O)₂-CH₃) |
| Compound 192 | 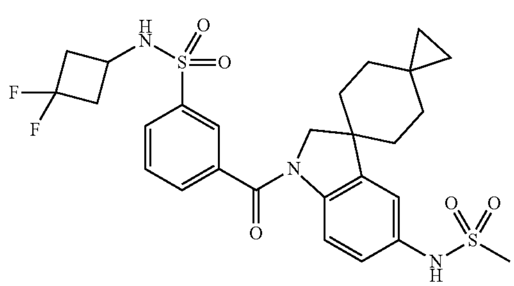 [SMILES: CS(=O)(=O)Nc1ccc2c(c1)C1(CCC3(CC3)CC1)CN2C(=O)c1cccc(S(=O)(=O)NC2CC(F)(F)C2)c1] | Compound 191 | methanesulfonamide (H₂N-S(=O)₂-CH₃) |

TABLE 7-continued

| Compound | Structure | Bromide | Sulfonamide |
|---|---|---|---|
| Compound 194 | 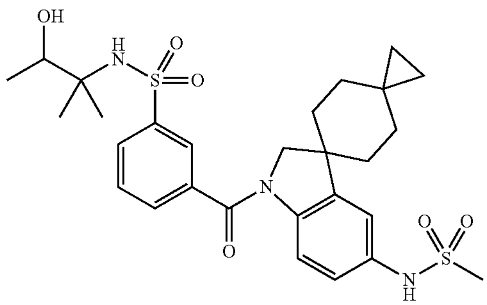 [SMILES: CC(O)C(C)(C)NS(=O)(=O)c1cccc(C(=O)N2CC3(CCC4(CC4)CC3)c3cc(NS(C)(=O)=O)ccc32)c1] | Compound 193 | H₂NS(=O)(=O)CH₃ |
| Compound 196 | 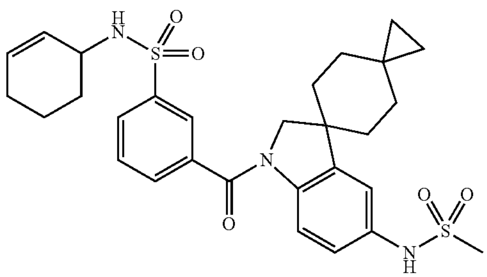 [SMILES: CS(=O)(=O)Nc1ccc2c(c1)C1(CCC3(CC3)CC1)CN2C(=O)c1cccc(S(=O)(=O)NC2C=CCCC2)c1] | Compound 195 | H₂NS(=O)(=O)CH₃ |
| Compound 198 | 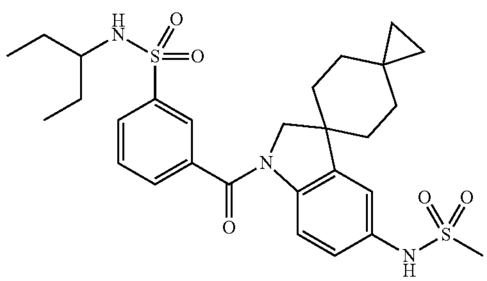 [SMILES: CCC(CC)NS(=O)(=O)c1cccc(C(=O)N2CC3(CCC4(CC4)CC3)c3cc(NS(C)(=O)=O)ccc32)c1] | Compound 197 | H₂NS(=O)(=O)CH₃ |
| Compound 200 | 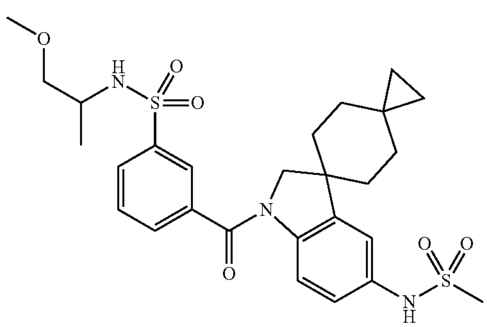 | Compound 199 | H₂NS(=O)(=O)CH₃ |
| Compound 202 | 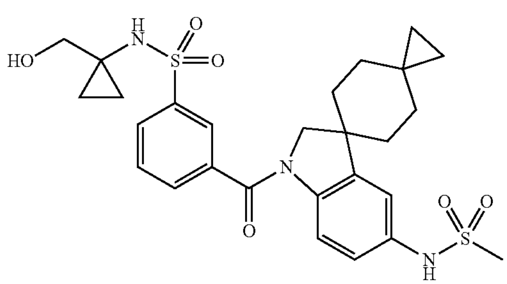 [SMILES: CS(=O)(=O)Nc1ccc2c(c1)C1(CCC3(CC3)CC1)CN2C(=O)c1cccc(S(=O)(=O)NC2(CO)CC2)c1] | Compound 201 | H₂NS(=O)(=O)CH₃ |

TABLE 7-continued

| Compound | Structure | Bromide | Sulfonamide |
|---|---|---|---|
| Compound 204 | 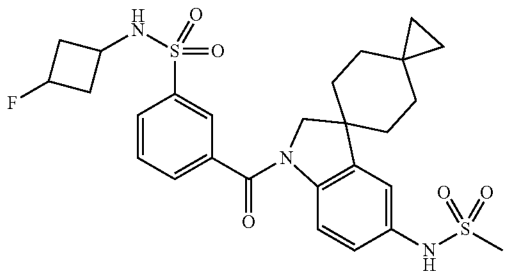 [SMILES: CS(=O)(=O)Nc1ccc2c(c1)C1(CCC3(CC3)CC1)CN2C(=O)c1cccc(S(=O)(=O)NC2CC(F)C2)c1] | Compound 203 | methanesulfonamide (H₂N-SO₂-CH₃) |
| Compound 206 | 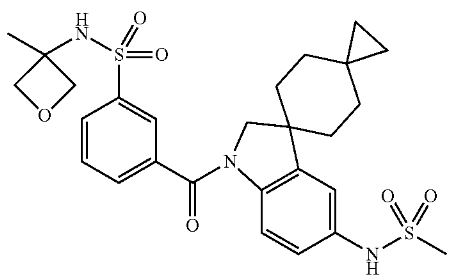 | Compound 205 | methanesulfonamide (H₂N-SO₂-CH₃) |
| Compound 208 | 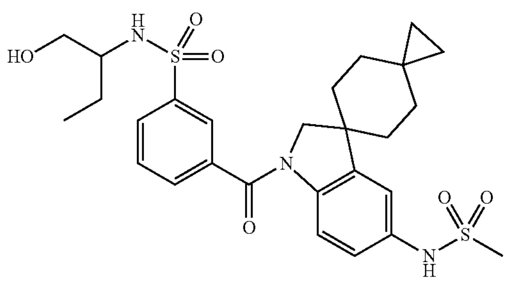 [SMILES: CCC(CO)NS(=O)(=O)c1cccc(C(=O)N2CC3(CCC4(CC4)CC3)c3cc(NS(C)(=O)=O)ccc32)c1] | Compound 207 | methanesulfonamide (H₂N-SO₂-CH₃) |
| Compound 210 | 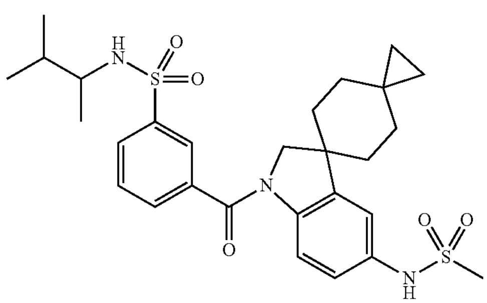 [SMILES: CC(C)C(C)NS(=O)(=O)c1cccc(C(=O)N2CC3(CCC4(CC4)CC3)c3cc(NS(C)(=O)=O)ccc32)c1] | Compound 209 | methanesulfonamide (H₂N-SO₂-CH₃) |
| Compound 212 | 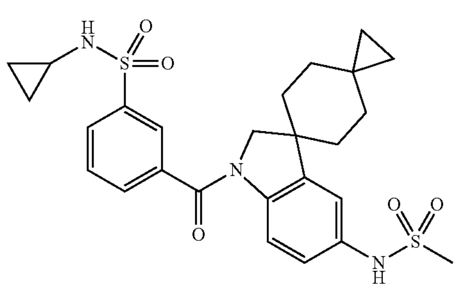 [SMILES: CS(=O)(=O)Nc1ccc2c(c1)C1(CCC3(CC3)CC1)CN2C(=O)c1cccc(S(=O)(=O)NC2CC2)c1] | Compound 211 | methanesulfonamide (H₂N-SO₂-CH₃) |

TABLE 7-continued

| Compound | Structure | Bromide | Sulfonamide |
|---|---|---|---|
| Compound 214 | 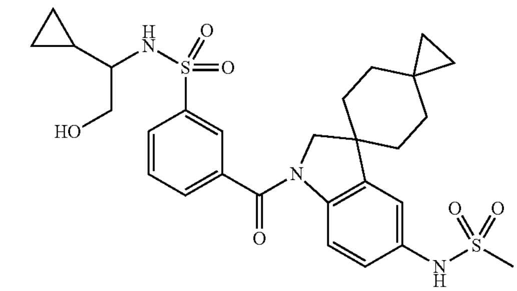 [SMILES: CS(=O)(=O)Nc1ccc2c(c1)C1(CCC3(CC3)CC1)CN2C(=O)c1cccc(S(=O)(=O)NC(CO)C2CC2)c1] | Compound 213 | methanesulfonamide (H$_2$N-S(=O)$_2$-CH$_3$) |
| Compound 216 | 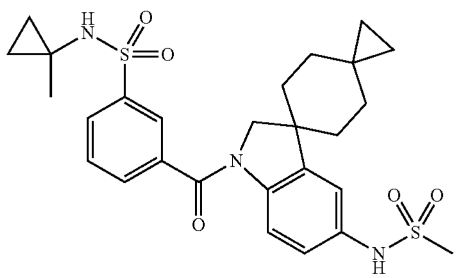 [SMILES: CC1(NS(=O)(=O)c2cccc(C(=O)N3CC4(CCC5(CC5)CC4)c4cc(NS(C)(=O)=O)ccc43)c2)CC1] | Compound 215 | methanesulfonamide |
| Compound 218 | 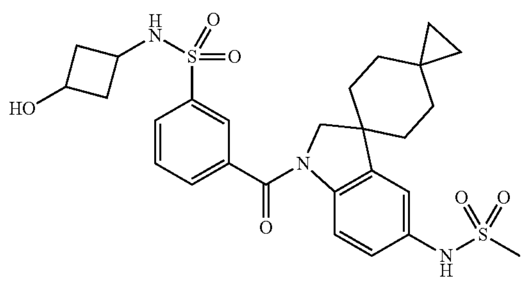 [SMILES: CS(=O)(=O)Nc1ccc2c(c1)C1(CCC3(CC3)CC1)CN2C(=O)c1cccc(S(=O)(=O)NC2CC(O)C2)c1] | Compound 217 | methanesulfonamide |
| Compound 220 | 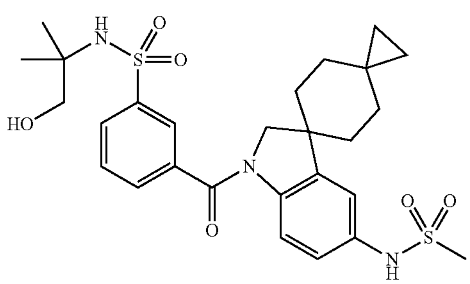 [SMILES: CC(C)(CO)NS(=O)(=O)c1cccc(C(=O)N2CC3(CCC4(CC4)CC3)c3cc(NS(C)(=O)=O)ccc32)c1] | Compound 219 | methanesulfonamide |
| Compound 222 | 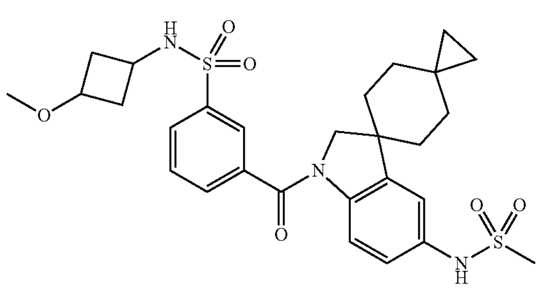 | Compound 221 | methanesulfonamide |

TABLE 7-continued

| Compound | Structure | Bromide | Sulfonamide |
|---|---|---|---|
| Compound 233 | 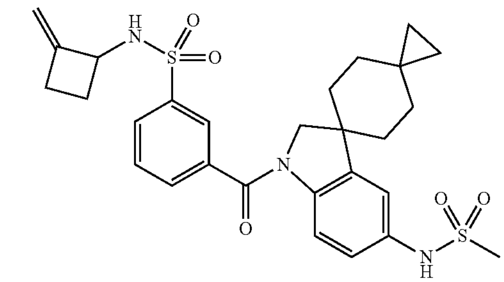 | Compound 232 | methanesulfonamide (H₂N-SO₂-CH₃) |
| Compound 235 | 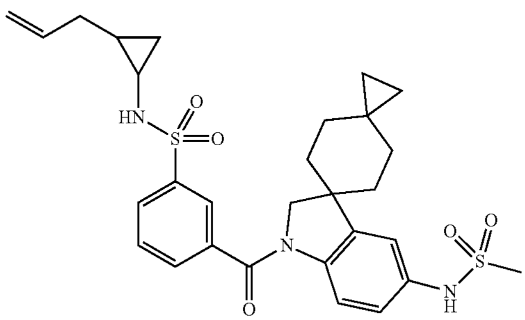 [SMILES: C=CCC1CC1NS(=O)(=O)c1cccc(C(=O)N2CC3(CCC4(CC4)CC3)c3cc(NS(C)(=O)=O)ccc32)c1] | Compound 234 | methanesulfonamide (H₂N-SO₂-CH₃) |
| Compound 237 | 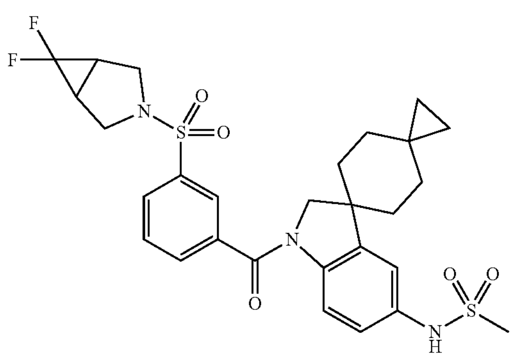 [SMILES: CS(=O)(=O)Nc1ccc2c(c1)C1(CCC3(CC3)CC1)CN2C(=O)c1cccc(S(=O)(=O)N2CC3C(C2)C3(F)F)c1] | Compound 236 | methanesulfonamide (H₂N-SO₂-CH₃) |
| (R)-Compound 239 | 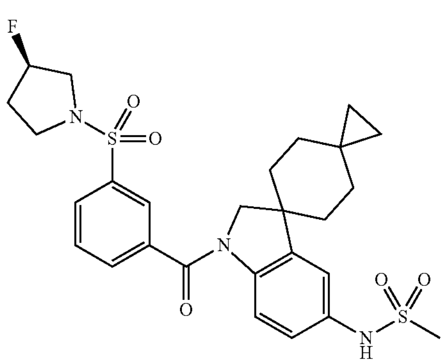 [SMILES: CS(=O)(=O)Nc1ccc2c(c1)C1(CCC3(CC3)CC1)CN2C(=O)c1cccc(S(=O)(=O)N2CC[C@@H](F)C2)c1] | (R)-Compound 238 | methanesulfonamide (H₂N-SO₂-CH₃) |

TABLE 7-continued

| Compound | Structure | Bromide | Sulfonamide |
|---|---|---|---|
| (S)-Compound 239 | 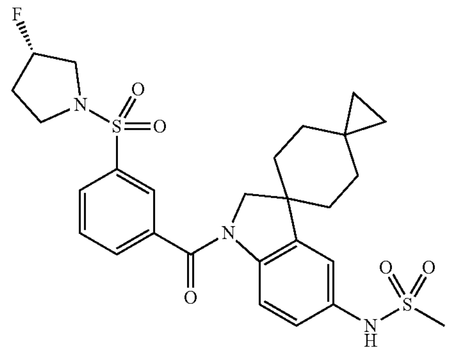 [SMILES: CS(=O)(=O)Nc1ccc2c(c1)C1(CCC3(CC3)CC1)CN2C(=O)c1cccc(S(=O)(=O)N2CC[C@H](F)C2)c1] | (S)-Compound 238 | H₂N-S(=O)(=O)-CH₃ |
| Compound 243 | 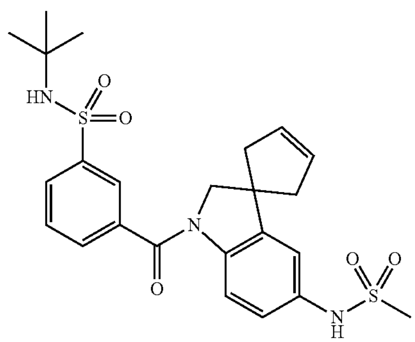 [SMILES: CC(C)(C)NS(=O)(=O)c1cccc(C(=O)N2CC3(CC=CC3)c3cc(NS(C)(=O)=O)ccc32)c1] | Compound 242 | H₂N-S(=O)(=O)-CH₃ |
| Compound 245 | 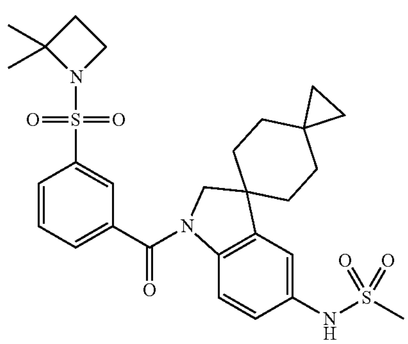 | Compound 244 | H₂N-S(=O)(=O)-CH₃ |
| Compound 247 | 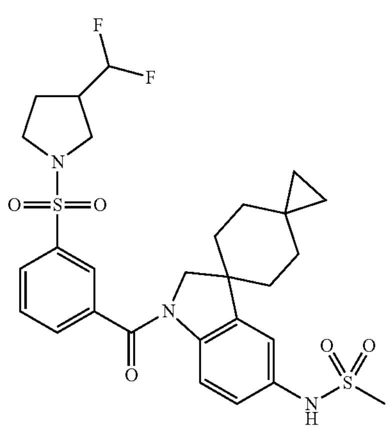 [SMILES: CS(=O)(=O)Nc1ccc2c(c1)C1(CCC3(CC3)CC1)CN2C(=O)c1cccc(S(=O)(=O)N2CCC(C(F)F)C2)c1] | Compound 246 | H₂N-S(=O)(=O)-CH₃ |

TABLE 7-continued

| Compound | Structure | Bromide | Sulfonamide |
|---|---|---|---|
| Compound 249 | 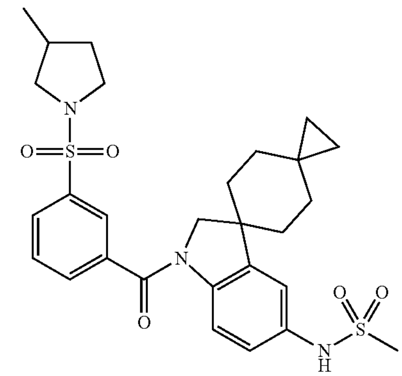 | Compound 248 | methanesulfonamide (H₂N-S(=O)₂-CH₃) |
| (S)-Compound 249 | 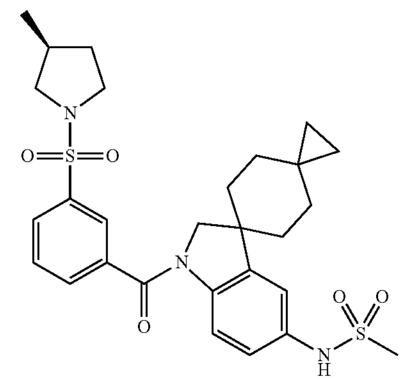 | (S)-Compound 248 | methanesulfonamide (H₂N-S(=O)₂-CH₃) |
| Compound 252 | 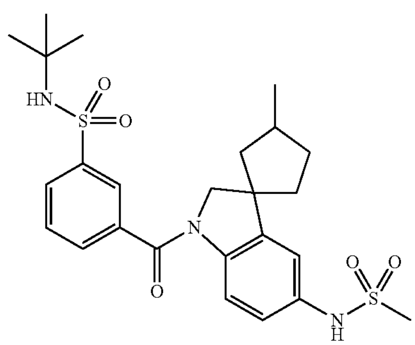 [SMILES: CC1CCC2(C1)CN(C(=O)c1cccc(S(=O)(=O)NC(C)(C)C)c1)c1ccc(NS(C)(=O)=O)cc12] | Compound 251 | methanesulfonamide (H₂N-S(=O)₂-CH₃) |
| Compound 254 | 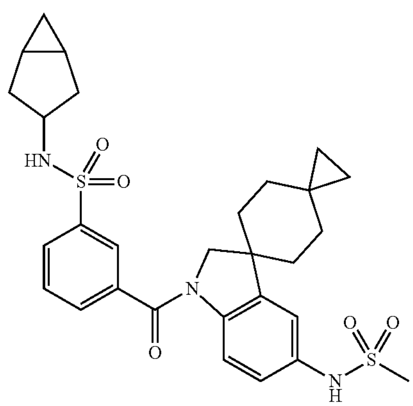 [SMILES: CS(=O)(=O)Nc1ccc2c(c1)C1(CCC3(CC3)CC1)CN2C(=O)c1cccc(S(=O)(=O)NC2CC3CC3C2)c1] | Compound 253 | methanesulfonamide (H₂N-S(=O)₂-CH₃) |

TABLE 7-continued

| Compound | Structure | Bromide | Sulfonamide |
|---|---|---|---|
| Compound 257 | 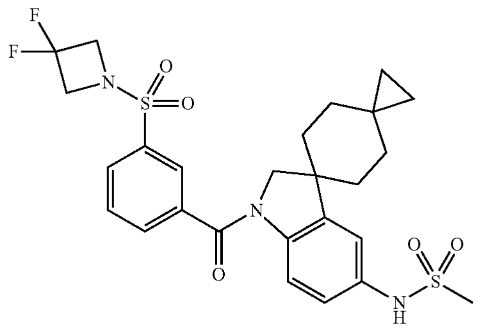 [SMILES: CS(=O)(=O)Nc1ccc2c(c1)C1(CCC3(CC3)CC1)CN2C(=O)c1cccc(S(=O)(=O)N2CC(F)(F)C2)c1] | Compound 256 | methanesulfonamide |
| Compound 260 | 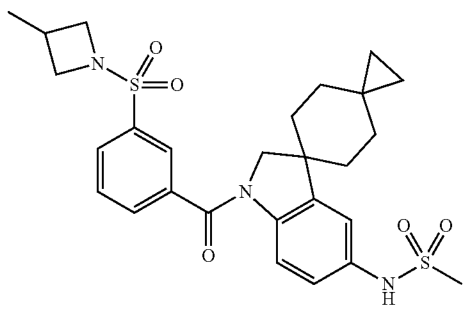 | Compound 259 | methanesulfonamide |
| Compound 261 | 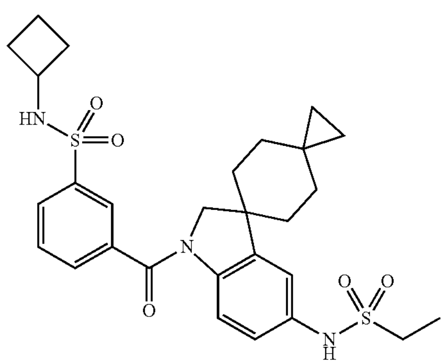 [SMILES: CCS(=O)(=O)Nc1ccc2c(c1)C1(CCC3(CC3)CC1)CN2C(=O)c1cccc(S(=O)(=O)NC2CCC2)c1] | Compound 167 | ethanesulfonamide |
| Compound 264 | 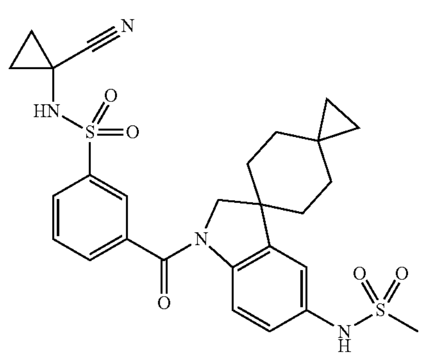 [SMILES: CS(=O)(=O)Nc1ccc2c(c1)C1(CCC3(CC3)CC1)CN2C(=O)c1cccc(S(=O)(=O)NC2(C#N)CC2)c1] | Compound 263 | methanesulfonamide |

TABLE 7-continued

| Compound | Structure | Bromide | Sulfonamide |
|---|---|---|---|
| Compound 266 | 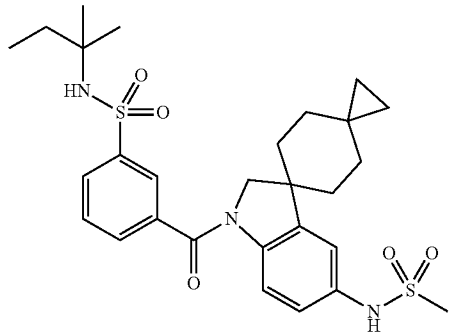 [SMILES: CCC(C)(C)NS(=O)(=O)c1cccc(C(=O)N2CC3(CCC4(CC4)CC3)c3cc(NS(C)(=O)=O)ccc32)c1] | Compound 265 | methanesulfonamide (H₂N-S(=O)₂-CH₃) |
| Compound 268 | 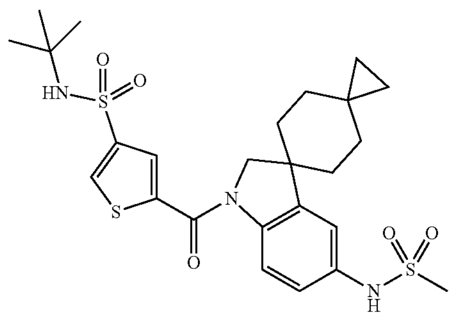 [SMILES: CC(C)(C)NS(=O)(=O)c1csc(C(=O)N2CC3(CCC4(CC4)CC3)c3cc(NS(C)(=O)=O)ccc32)c1] | Compound 267 | methanesulfonamide (H₂N-S(=O)₂-CH₃) |
| Compound 269 | 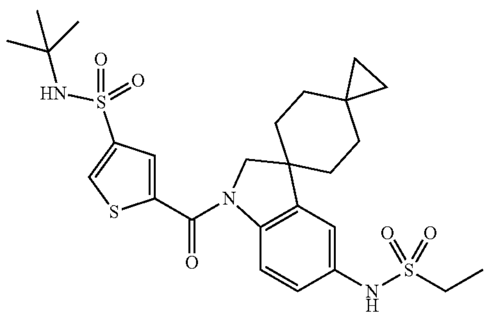 [SMILES: CCS(=O)(=O)Nc1ccc2c(c1)C1(CCC3(CC3)CC1)CN2C(=O)c1cc(S(=O)(=O)NC(C)(C)C)cs1] | Compound 267 | ethanesulfonamide (H₂N-S(=O)₂-CH₂CH₃) |
| Compound 272 | 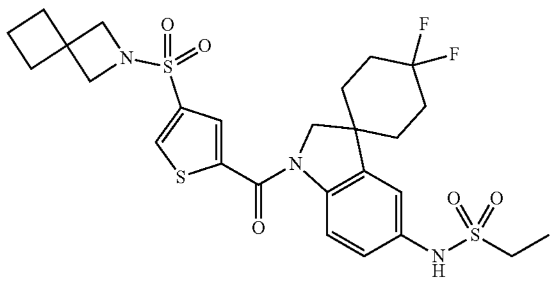 [SMILES: CCS(=O)(=O)Nc1ccc2c(c1)C1(CCC(F)(F)CC1)CN2C(=O)c1cc(S(=O)(=O)N2CC3(CCC3)C2)cs1] | Compound 271 | ethanesulfonamide (H₂N-S(=O)₂-CH₂CH₃) |
| Compound 275 | 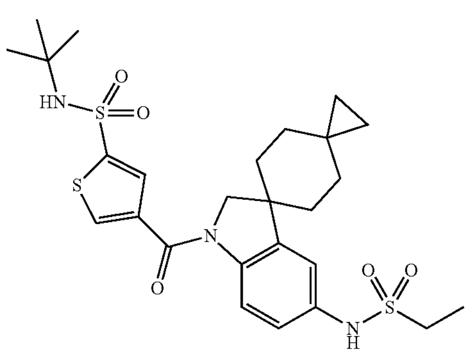 [SMILES: CCS(=O)(=O)Nc1ccc2c(c1)C1(CCC3(CC3)CC1)CN2C(=O)c1csc(S(=O)(=O)NC(C)(C)C)c1] | Compound 273 | ethanesulfonamide (H₂N-S(=O)₂-CH₂CH₃) |

TABLE 7-continued
| Compound | Structure | Bromide | Sulfonamide |
|---|---|---|---|
| Compound 277 | 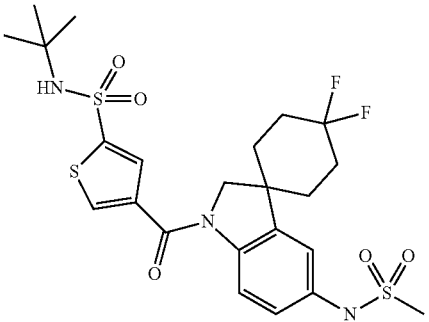 | Compound 275 | 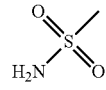 |
| Compound 279 | 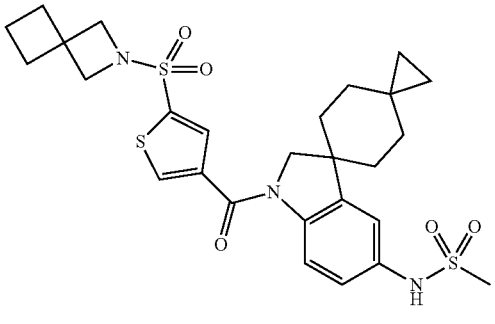 [SMILES: CS(=O)(=O)Nc1ccc2c(c1)C1(CCC3(CC3)CC1)CN2C(=O)c1csc(S(=O)(=O)N2CC3(CCC3)C2)c1] | Compound 278 | 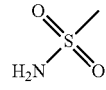 |
| Compound 281 | 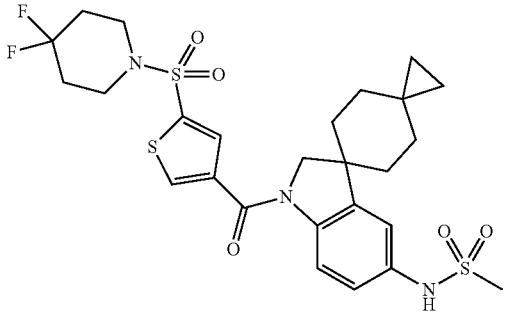 [SMILES: CS(=O)(=O)Nc1ccc2c(c1)C1(CCC3(CC3)CC1)CN2C(=O)c1csc(S(=O)(=O)N2CCC(F)(F)CC2)c1] | Compound 280 | 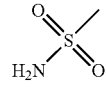 |
| Compound 283 | 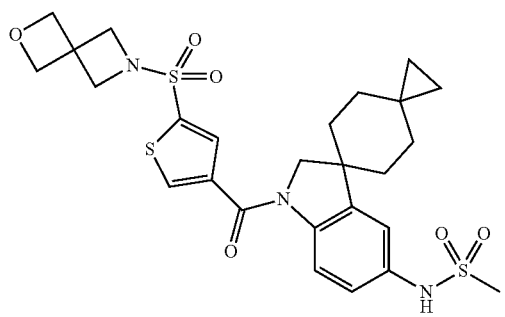 [SMILES: CS(=O)(=O)Nc1ccc2c(c1)C1(CCC3(CC3)CC1)CN2C(=O)c1csc(S(=O)(=O)N2CC3(COC3)C2)c1] | Compound 282 | 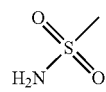 |

TABLE 7-continued

| Compound | Structure | Bromide | Sulfonamide |
|---|---|---|---|
| Compound 287 | 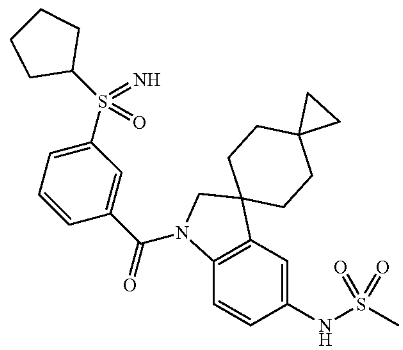 [SMILES: CS(=O)(=O)Nc1ccc2c(c1)C1(CCC3(CC3)CC1)CN2C(=O)c1cccc(S(=N)(=O)C2CCCC2)c1] | Compound 287 | methanesulfonamide (H₂N-SO₂-CH₃) |
| Compound 291 | 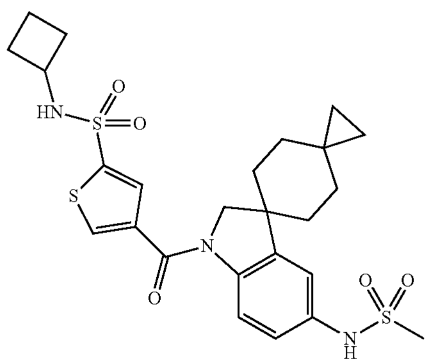 [SMILES: CS(=O)(=O)Nc1ccc2c(c1)C1(CCC3(CC3)CC1)CN2C(=O)c1csc(S(=O)(=O)NC2CCC2)c1] | Compound 290 | methanesulfonamide (H₂N-SO₂-CH₃) |
| Compound 292 | 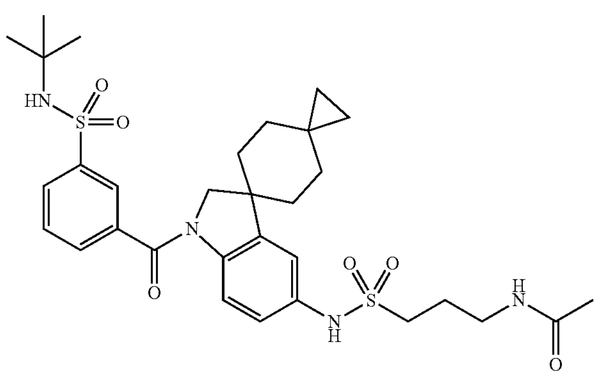 [SMILES: CC(=O)NCCCS(=O)(=O)Nc1ccc2c(c1)C1(CCC3(CC3)CC1)CN2C(=O)c1cccc(S(=O)(=O)NC(C)(C)C)c1] | Compound 9 | N-(3-sulfamoylpropyl)acetamide |
| Compound 293 | 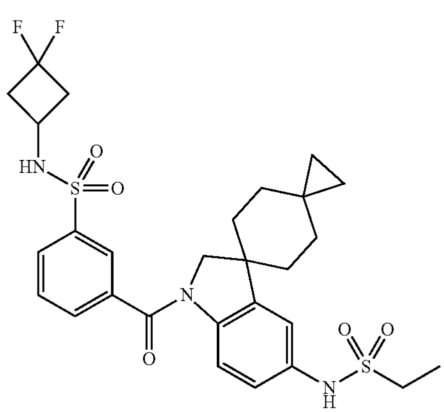 [SMILES: CCS(=O)(=O)Nc1ccc2c(c1)C1(CCC3(CC3)CC1)CN2C(=O)c1cccc(S(=O)(=O)NC2CC(F)(F)C2)c1] | Compound 191 | ethanesulfonamide (H₂N-SO₂-CH₂CH₃) |

TABLE 7-continued

| Compound | Structure | Bromide | Sulfonamide |
|---|---|---|---|
| Compound 295 | 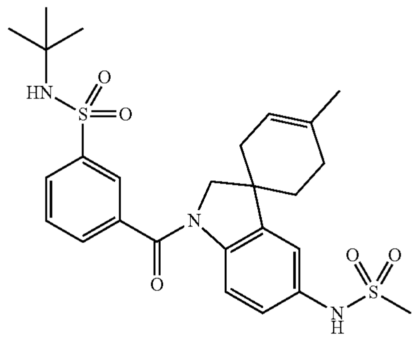 [SMILES: CC1=CCC2(CC1)CN(C(=O)c1cccc(S(=O)(=O)NC(C)(C)C)c1)c1ccc(NS(C)(=O)=O)cc12] | Compound 294 | methanesulfonamide (H₂N-SO₂-CH₃) |
| Compound 300 | 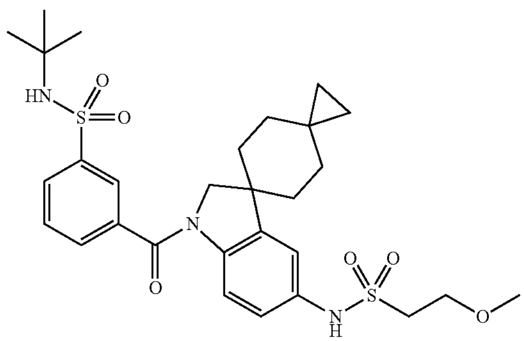 [SMILES: COCCS(=O)(=O)Nc1ccc2c(c1)C1(CCC3(CC3)CC1)CN2C(=O)c1cccc(S(=O)(=O)NC(C)(C)C)c1] | Compound 9 | 2-methoxyethanesulfonamide |
| Compound 320 | 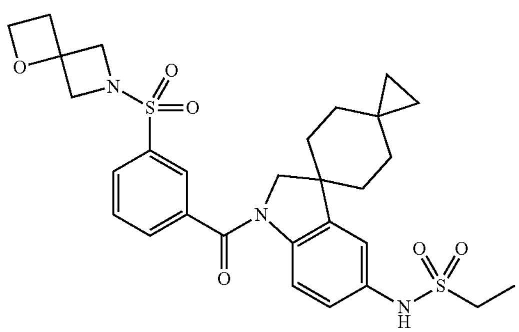 [SMILES: CCS(=O)(=O)Nc1ccc2c(c1)C1(CCC3(CC3)CC1)CN2C(=O)c1cccc(S(=O)(=O)N2CC3(CCO3)C2)c1] | Compound 152 | ethanesulfonamide |
| Compound 324 | 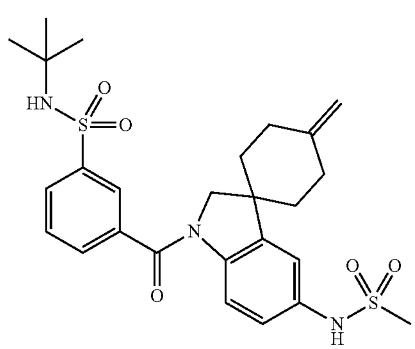 [SMILES: C=C1CCC2(CC1)CN(C(=O)c1cccc(S(=O)(=O)NC(C)(C)C)c1)c1ccc(NS(C)(=O)=O)cc12] | Compound 323 | methanesulfonamide |

TABLE 7-continued

| Compound | Structure | Bromide | Sulfonamide |
|---|---|---|---|
| Compound 326 | 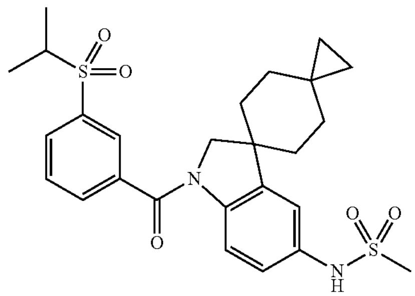 [SMILES: CC(C)S(=O)(=O)c1cccc(C(=O)N2CC3(CCC4(CC4)CC3)c3cc(NS(C)(=O)=O)ccc32)c1] | Compound 325 | methanesulfonamide (H₂N-S(=O)₂-CH₃) |
| Compound 327 | 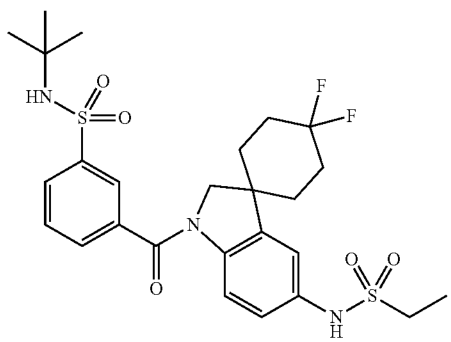 [SMILES: CCS(=O)(=O)Nc1ccc2c(c1)C1(CCC(F)(F)CC1)CN2C(=O)c1cccc(S(=O)(=O)NC(C)(C)C)c1] | Compound 143 | methanesulfonamide (H₂N-S(=O)₂-CH₃) |
| Compound 329 | 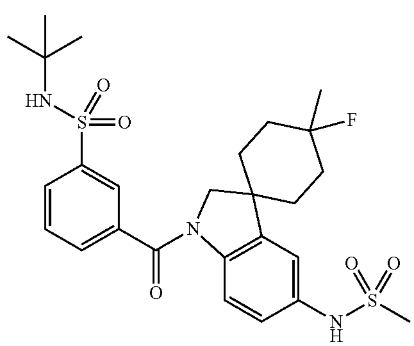 [SMILES: CC1(F)CCC2(CC1)CN(C(=O)c1cccc(S(=O)(=O)NC(C)(C)C)c1)c1ccc(NS(C)(=O)=O)cc12] | Compound 328 | methanesulfonamide (H₂N-S(=O)₂-CH₃) |
| Compound 333 | 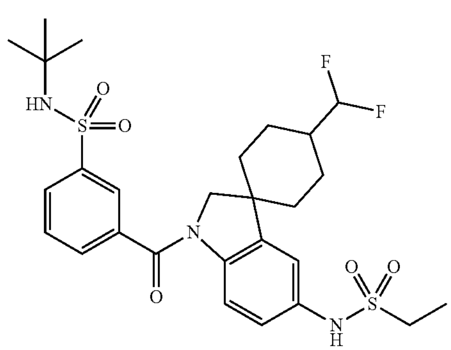 [SMILES: CCS(=O)(=O)Nc1ccc2c(c1)C1(CCC(C(F)F)CC1)CN2C(=O)c1cccc(S(=O)(=O)NC(C)(C)C)c1] | Compound 161 | ethanesulfonamide (H₂N-S(=O)₂-CH₂CH₃) |

TABLE 7-continued

| Compound | Structure | Bromide | Sulfonamide |
|---|---|---|---|
| Compound 361a | 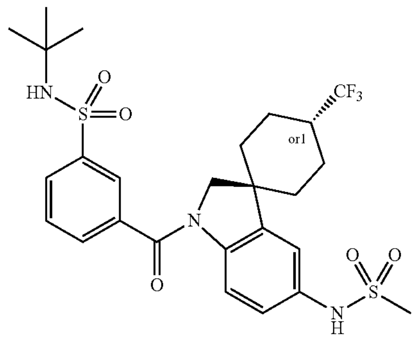 [SMILES: CC(C)(C)NS(=O)(=O)c1cccc(C(=O)N2C[C@]3(CC[C@H](C(F)(F)F)CC3)c3cc(NS(C)(=O)=O)ccc32)c1] | Compound | $H_2N-S(=O)_2-CH_3$ (methanesulfonamide) |
| Compound 361b | 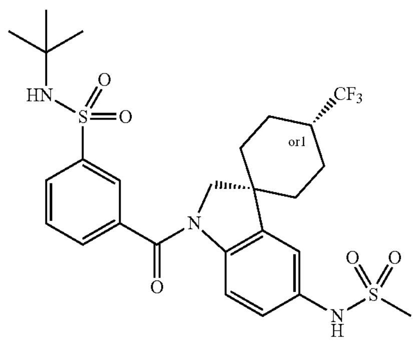 [SMILES: CC(C)(C)NS(=O)(=O)c1cccc(C(=O)N2C[C@]3(CC[C@@H](C(F)(F)F)CC3)c3cc(NS(C)(=O)=O)ccc32)c1] | Compound | $H_2N-S(=O)_2-CH_3$ (methanesulfonamide) |

Synthesis of N-(tert-butyl)-3-(6"-fluoro-5"-(methylsulfonamido)dispiro[cyclopropane-1,1'-cyclohexane-4',3"-indoline]-1"-carbonyl)benzenesulfonamide and N-(tert-butyl)-3-(4"-fluoro-5"-(methylsulfonamido)dispiro[cyclopropane-1,1'-cyclohexane-4',3"-indoline]-1"-carbonyl)benzenesulfonamide

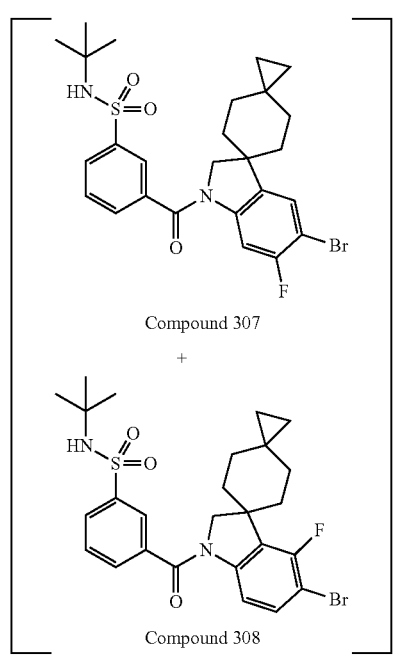

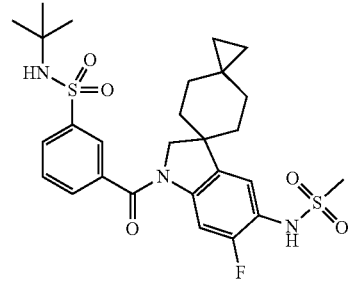

Compound 309

+

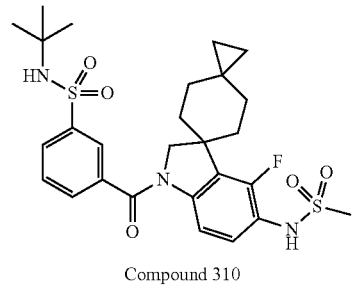

Compound 310

A ~3/1 mixture Compound 307 and Compound 308 (0.55 g, 1.0 mmol), methanesulfonamide (0.29 g, 3.0 mmol), CuI (0.11 g, 0.60 mmol), DMF (5 mL), N1,N2-dimethylcyclohexane-1,2-diamine (85 mg, 0.60 mmol) and K₃PO₄ (0.64 g, 3.0 mmol) was stirred at 160° C. for 2 h. The mixture was concentrated, combined with H₂O (10 mL), extracted with EtOAc (2×10 mL), and the combined extracts were washed with brine (10 mL), dried over Na₂SO₄, concentrated, and purified by preparative HPLC (35-65% MeCN/H₂O [formic acid]) to provide N-(tert-butyl)-3-(6"-fluoro-5"-(methylsulfonamido)dispiro[cyclopropane-1,1'-cyclohexane-4',3"-indoline]-1"-carbonyl)benzenesulfonamide (Compound 309, 23.2 mg) and N-(tert-butyl)-3-(4"-fluoro-5"-(methylsulfonamido)dispiro[cyclopropane-1,1'-cyclohexane-4',3"-indoline]-1"-carbonyl)benzenesulfonamide (Compound 310, 5.1 mg).

Synthetic Example S-002b

Synthesis of N-(tert-butyl)-2-methoxy-5-(5"-(methylsulfonamido)dispiro[cyclopropane-1,1'-cyclohexane-4',3"-indoline]-1"-carbonyl)benzenesulfonamide (Compound 297) and N-(tert-butyl)-2-hydroxy-5-(5"-(methylsulfonamido)dispiro[cyclopropane-1,1'-cyclohexane-4',3"-indoline]-1"-carbonyl)benzenesulfonamide (Compound 298)

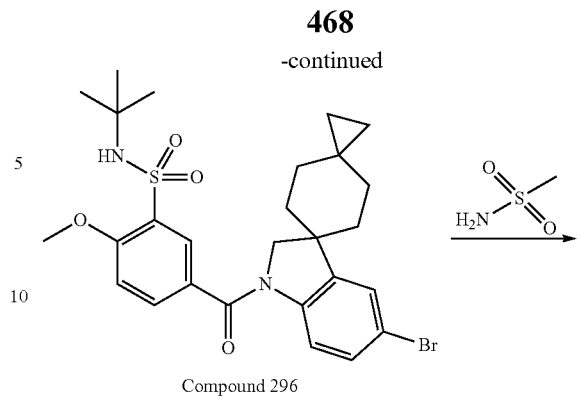

Compound 296

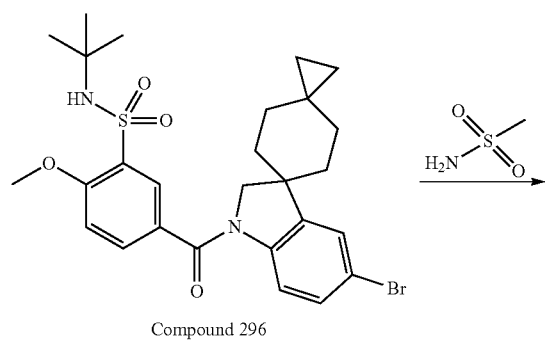

Compound 296

-continued

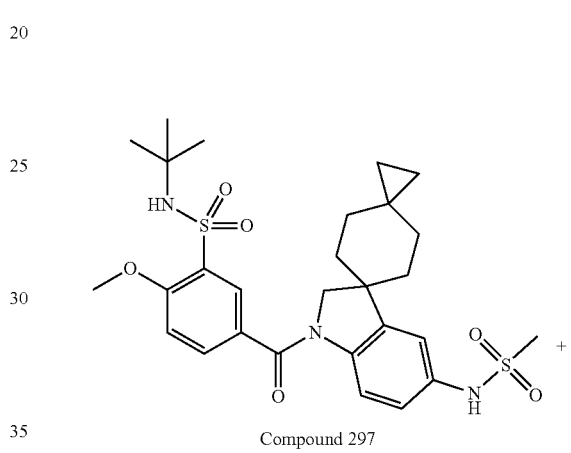

Compound 297

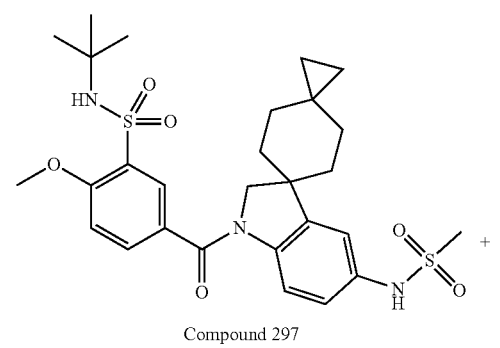

Compound 297

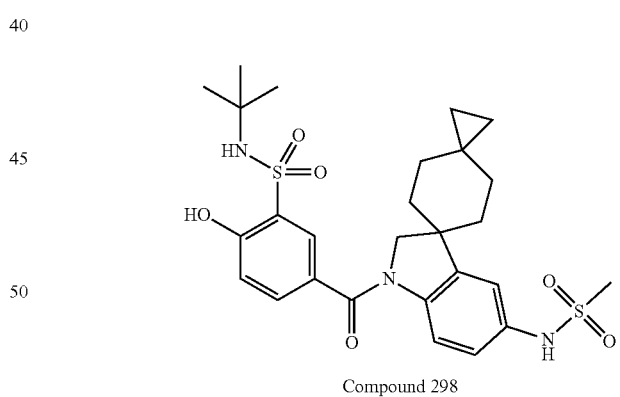

Compound 298

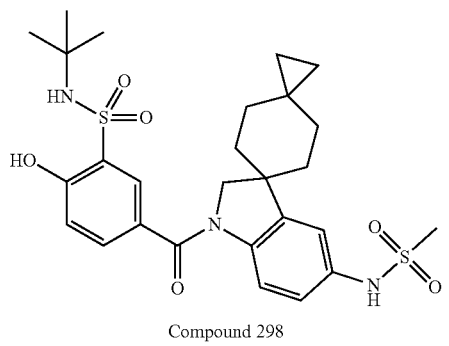

Compound 298

A mixture of Compound 296 (0.10 g, 0.18 mmol), methanesulfonamide (51 mg, 0.53 mmol), CuI (34 mg, 0.18 mmol), $K_3PO_4$ (0.11 g, 0.53 mmol), $N^1,N^2$-dimethylcyclohexane-1,2-diamine (25 mg, 0.18 mmol), and DMF (2 mL) was stirred as 150° C. for 1.5 h. The mixture was then poured into 30 mL of $H_2O$, extracted with EtOAc (2×30 mL) and the extracts were washed with brine (10 mL), dried over $Na_2SO_4$, filtered, concentration and purified by reverse-phase HPLC (C18, 30-60% MeCN/water [0.1 mM formic acid]) to provide 13 mg of Compound 297 and 26 mg of Compound 298.

Synthetic Example S-003

Synthesis of N-(1'-(3-((4,4-difluoropiperidin-1-yl)sulfonyl)benzoyl)spiro[cyclopentane-1,3'-indolin]-5'-yl)-2-hydroxyethane-1-sulfonamide (Compound 27)

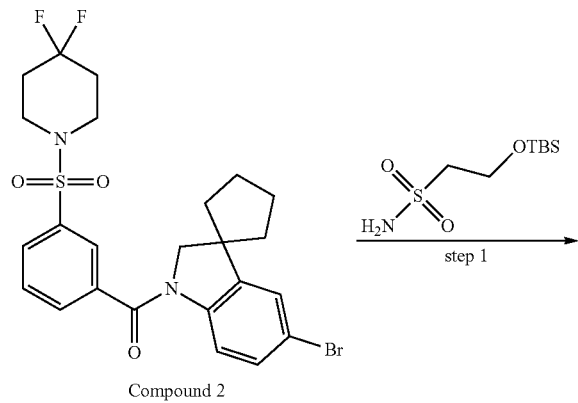

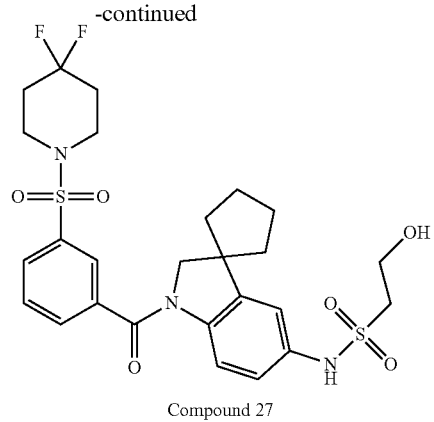

Compound 27

Step 1. A degassed mixture of Compound 2 (50 mg, 93 µmol), 2-((tert-butyldimethylsilyl)oxy)ethane-1-sulfonamide (33 mg, 0.14 mmol), CuI (9 mg, 46 µmol), $K_3PO_4$ (59 mg, 0.28 mmol) and $N^1,N^2$-dimethylcyclohexane-1,2-diamine (7 mg, 46 µmol), and DMF (2.0 mL) was stirred at 150° C. for 2 h in a microwave reactor. The mixture was poured into water $H_2O$ (30 mL) and extracted with EtOAc (2×30 mL). The extracts were combined, washed with brine (10 mL), dried over $Na_2SO_4$, and concentrated to provide 2-((tert-butyldimethylsilyl)oxy)-N-(1'-(3-((4,4-difluoropiperidin-1-yl)sulfonyl)benzoyl)spiro[cyclopentane-1,3'-indolin]-5'-yl)ethane-1-sulfonamide (65 mg).

Step 2. A mixture of 2-((tert-butyldimethylsilyl)oxy)-N-(1'-(3-((4,4-difluoropiperidin-1-yl)sulfonyl)benzoyl)spiro[cyclopentane-1,3'-indolin]-5'-yl)ethane-1-sulfonamide (65 mg, 93 µmol), MeOH (5.0 mL), and HCl (2M, 5.0 mL) was stirred at 20° C. for 1 h, concentrated, aqueous saturated $NaHCO_3$ was added to bring the pH to 9. The mixture was extracted with EtOAc (2×30 mL) and the extracts were combined, washed with brine (10 mL), dried over $Na_2SO_4$, concentrated, and purified by prep-HPLC (30-60% MeCN in $H_2O$ [10 mM $NH_4HCO_3$]) to provide N-(1'-(3-((4,4-difluoropiperidin-1-yl)sulfonyl)benzoyl)spiro[cyclopentane-1,3'-indolin]-5'-yl)-2-hydroxyethane-1-sulfonamide (Compound 27, 8.5 mg).

Compounds in Table 7.1 were prepared from the indicated bromoindoline and 2-[(tert-butyldimethylsilyl)oxy]ethane-1-sulfonamide in the same manner as Compound 29.

TABLE 7.1

| Compound | Structure | Bromoindole |
|---|---|---|
| Compound 148 | 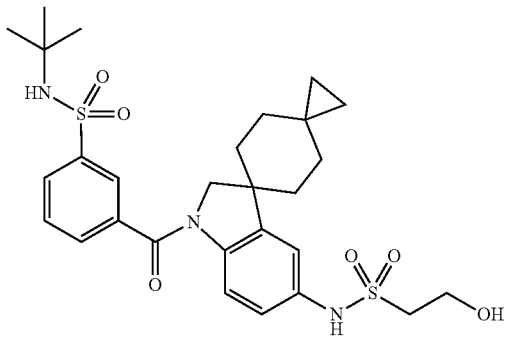 [SMILES: CC(C)(C)NS(=O)(=O)c1cccc(C(=O)N2CC3(CCC4(CC4)CC3)c3cc(NS(=O)(=O)CCO)ccc32)c1] | Compound 9 |

TABLE 7.1-continued

| Compound | Structure | Bromoindole |
|---|---|---|
| Compound 227 | 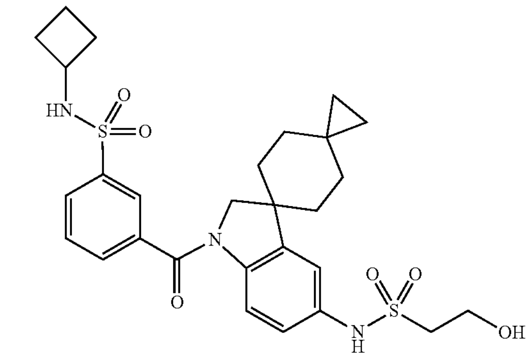 [SMILES: O=C(c1cccc(S(=O)(=O)NC2CCC2)c1)N1CC2(CCC3(CC3)CC2)c2cc(NS(=O)(=O)CCO)ccc21] | Compound 167 |
| Compound 228 | 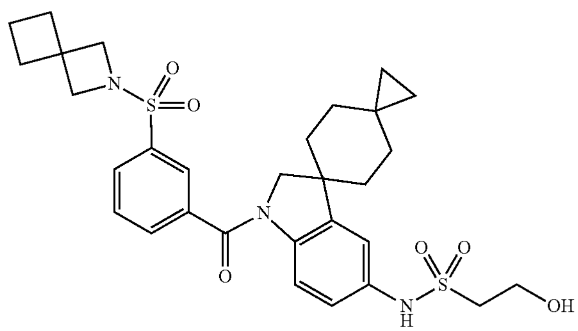 [SMILES: O=C(c1cccc(S(=O)(=O)N2CC3(CCC3)C2)c1)N1CC2(CCC3(CC3)CC2)c2cc(NS(=O)(=O)CCO)ccc21] | Compound 150 |
| Compound 229 | 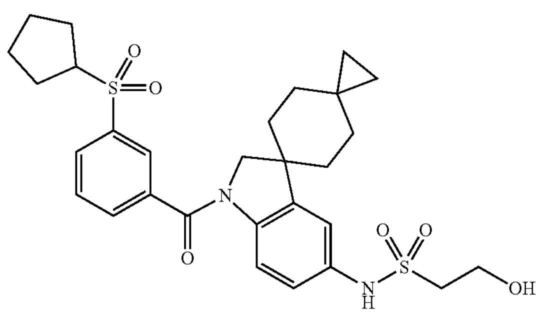 [SMILES: O=C(c1cccc(S(=O)(=O)C2CCCC2)c1)N1CC2(CCC3(CC3)CC2)c2cc(NS(=O)(=O)CCO)ccc21] | Compound 154 |
| Compound 230 | 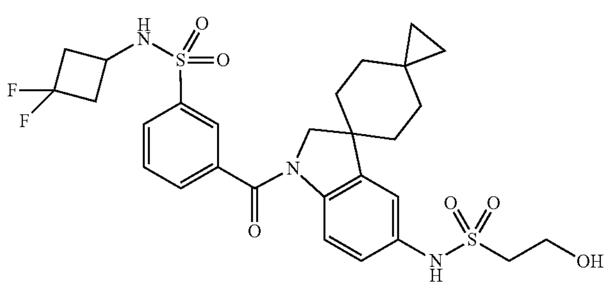 [SMILES: O=C(c1cccc(S(=O)(=O)NC2CC(F)(F)C2)c1)N1CC2(CCC3(CC3)CC2)c2cc(NS(=O)(=O)CCO)ccc21] | Compound 191 |
| Compound 274 | 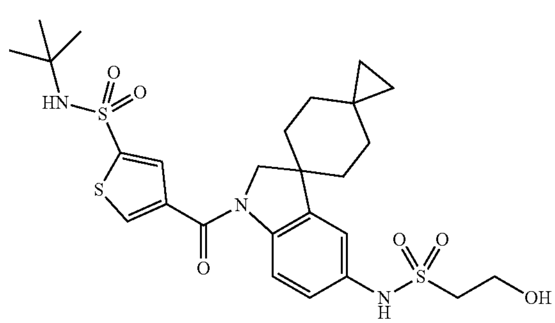 [SMILES: CC(C)(C)NS(=O)(=O)c1cc(C(=O)N2CC3(CCC4(CC4)CC3)c3cc(NS(=O)(=O)CCO)ccc32)cs1] | Compound 273 |

TABLE 7.1-continued
| Compound | Structure | Bromoindole |
|---|---|---|
| Compound 289 | 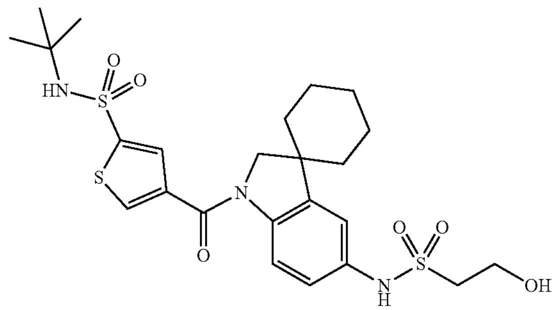 [SMILES: CC(C)(C)NS(=O)(=O)c1cc(C(=O)N2CC3(CCCCC3)c3cc(NS(=O)(=O)CCO)ccc32)cs1] | Compound 288 |
| Compound 368 | 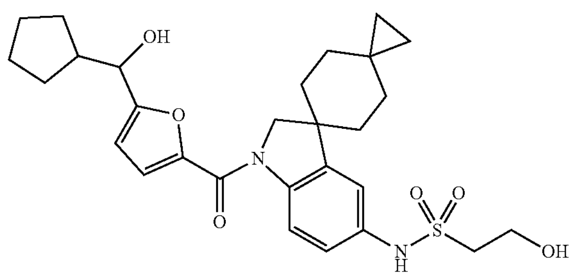 [SMILES: O=C(c1ccc(C(O)C2CCCC2)o1)N1CC2(CCC3(CC3)CC2)c2cc(NS(=O)(=O)CCO)ccc21] | Compound 366 |
| Compound 371 | 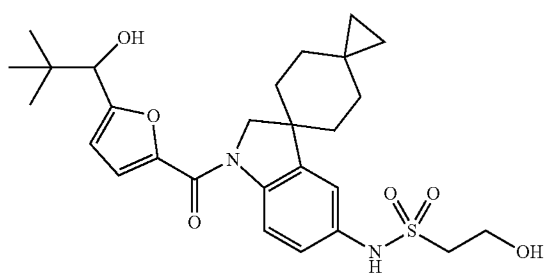 [SMILES: CC(C)(C)C(O)c1ccc(C(=O)N2CC3(CCC4(CC4)CC3)c3cc(NS(=O)(=O)CCO)ccc32)o1] | Compound 370 |
Synthetic Example S-004
Synthesis of N-(1"-(3-((4,4-difluoropiperidin-1-yl)sulfonyl)benzoyl)dispiro[cyclopropane-1,1'-cyclohexane-4',3"-indolin]-5"-yl)methanesulfonamide (Compound 28)
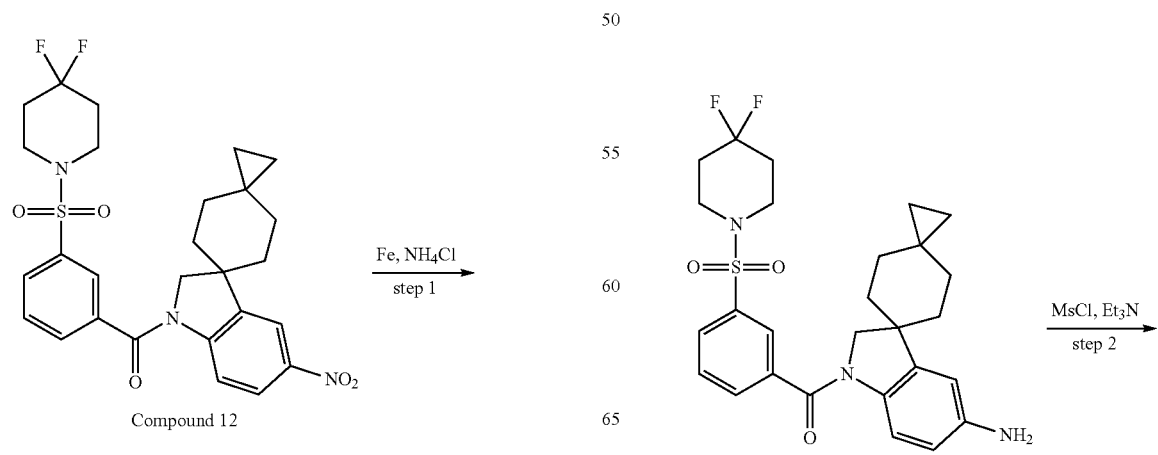

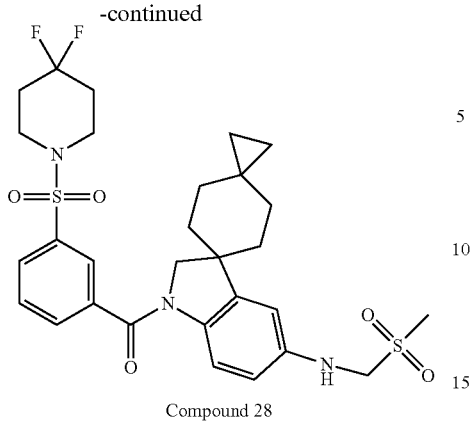

Compound 28

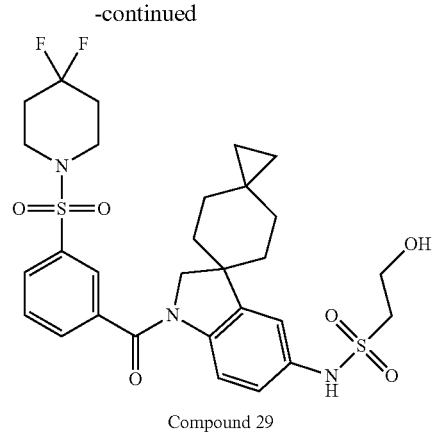

Compound 29

Step 1. To a mixture of Compound 12 (0.18 g, 0.33 mmol), and Fe (0.20 g, 3.6 mmol), EtOH (10 mL), THF (10 mL), and H₂O (4.0 mL) was added NH₄Cl (0.2 g, 3.7 mmol) and the mixture was stirred at 80° C. for 3 h. The mixture was filtered through celite, and the filter cake was washed with THF (10 mL×2) and MeOH (10 mL×2). The filtrate was concentrated to ~20 mL, diluted with EtOAc (30 mL), washed with H₂O (15 mL×2), brine (15 mL), dried over Na₂SO₄, filtered, and concentrated to (5"-aminodispiro[cyclopropane-1,1'-cyclohexane-4',3"-indolin]-1"-yl)(3-((4,4-difluoropiperidin-1-yl)sulfonyl)phenyl)methanone (0.17 g).

Step 2. To a mixture of (5"-aminodispiro[cyclopropane-1,1'-cyclohexane-4',3"-indolin]-1"-yl)(3-((4,4-difluoropiperidin-1-yl)sulfonyl)phenyl)methanone (0.15 g, 0.29 mmol), and Et₃N (88 0.12 mL, 0.87 mmol), and CH₂Cl₂ (14 mL) was added slowly a mixture of methanesulfonyl chloride (68 μg, 0.87 mmol) and CH₂Cl₂ (1.0 mL) and the mixture was stirred at 20° C. for 2 h. The reaction mixture was poured into ice-water and extracted with CH₂Cl₂ (15 mL) and the extract was washed with H₂O (5.0 mL×2) and brine (5.0 mL), dried over Na₂SO₄, filtered, concentrated, and purified by prep-HPLC (40-70% MeCN in water [0.1% formic acid]) to provide N-(1"-(3-((4,4-difluoropiperidin-1-yl)sulfonyl)benzoyl)dispiro[cyclopropane-1,1'-cyclohexane-4',3"-indolin]-5"-yl)methanesulfonamide (Compound 28, 55 mg).

Synthetic Example S-005

N-(1"-(3-((4,4-difluoropiperidin-1-yl)sulfonyl)benzoyl)dispiro[cyclopropane-1,1'-cyclohexane-4',3"-indolin]-5"-yl)-2-hydroxyethane-1-sulfonamide (Compound 29)

A mixture of A-04 (16 mg, 53 μmol), DMF (1.0 mL), HATU (46 mg, 0.12 mmol) and iPr₂NEt (18 μg, 0.10 mmol) was stirred at 25° C. for 15 min and a mixture of N-{1", 2"-dihydrodispiro[cyclopropane-1,1'-cyclohexane-4',3"-indol]-5"-yl}-2-hydroxyethane-1-sulfonamide (42 mg, 48 μmol), iPr₂NEt (89 μg, 0.51 μmol), and DMF (1.0 mL) was added. After stirring at 25° C. for 5 h, the mixture was filtered and the filtrate was concentrated and purified by prep-HPLC (20-60% MeCN in H₂O [0.1% formic acid]) to provide N-(1"-(3-((4,4-difluoropiperidin-1-yl)sulfonyl)benzoyl)dispiro[cyclopropane-1,1'-cyclohexane-4',3"-indolin]-5"-yl)-2-hydroxyethane-1-sulfonamide (Compound 29, 2 mg).

Synthetic Example S-006

Synthesis of (3-((4,4-difluoropiperidin-1-yl)sulfonyl)phenyl)(5"-(ethylamino)dispiro[cyclopropane-1,1'-cyclohexane-4',3"-indolin]-1"-yl)methanone (Compound 30)

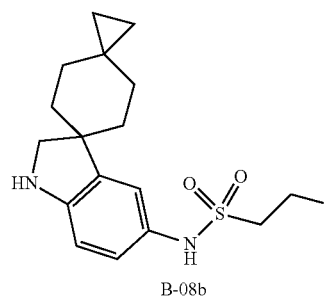

B-08b

A-04, HATU →

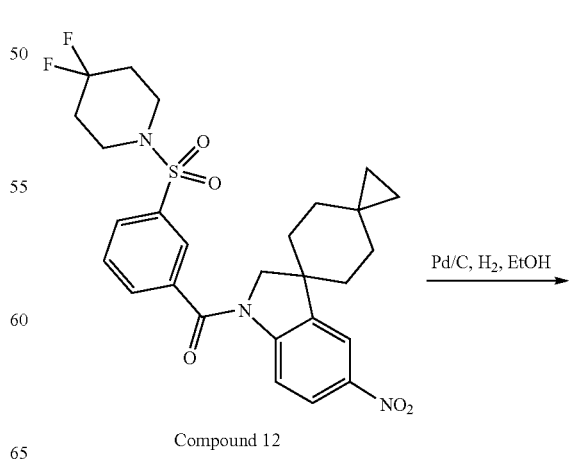

Compound 12

Pd/C, H₂, EtOH →

Compound 31 was isolated as a side-product during the purification of Compound 22: prep-HPLC (40-60% MeCN in H₂O [10 mM NH₄HCO₃]).

Synthetic Example S-008

Preparation of N,N-dimethyl-3-(5'-(methylsulfonamido)spiro[cyclohexane-1,3'-indoline]-1'-carbonyl)benzenesulfonamide (Compound 42)

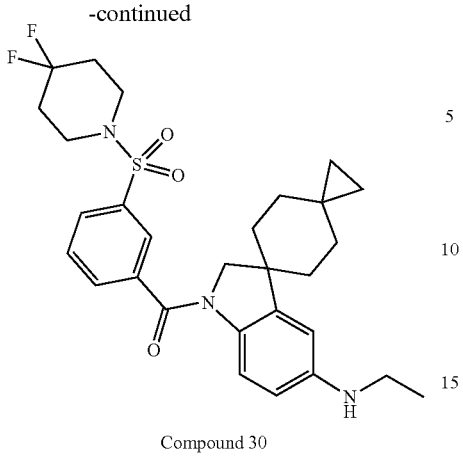

A mixture of Compound 12 (0.15 g, 0.28 mmol), Pd/C (0.15 g, 10%) and EtOH (15 mL) was stirred under H₂ (15 psi) at 25° C. for 12 h. The mixture was flushed with N₂, filtered through celite, and the filtrate was concentrated and the minor product was isolated by prep-HPLC (45-80% MeCN in H₂O [10 mM NH₄HCO₃]), and further by prep-HPLC (35-75% MeCN in H₂O [0.1% formic acid]) to provide (3-((4,4-difluoropiperidin-1-yl)sulfonyl)phenyl)(5"-(ethylamino)dispiro[cyclopropane-1,1'-cyclohexane-4',3"-indolin]-1"-yl)methanone (Compound 30, 7.9 mg).

Synthetic Example S-007

Isolation of N-(tert-butyl)-3-(4-ethyl-5'-(methylsulfonamido)spiro[cyclohexane-1,3'-indolin]-3-en-1'-carbonyl)benzenesulfonamide (Compound 31)

To a mixture of A-10 (50 mg, 0.22 mmol) and DMF (3 mL) were added HATU (0.12 g, 0.33 mmol) and iPr₂NEt (0.11 mL, 0.65 mmol). After 20 min, B-13 (73 mg, 0.26 mmol) was added and the mixture was stirred at 60° C. for 2 h, concentrated, and purified by prep-HPLC (45-65% MeCN in H₂O (0.1 M HCl)) to provide N,N-dimethyl-3-(5'-(methylsulfonamido)spiro[cyclohexane-1,3'-indoline]-1'-carbonyl)benzenesulfonamide (Compound 42, 50 mg).

Compounds in Table 7.2 were prepared from the indicated indoline and carboxylic acid in the same manner as Compound 42.

TABLE 7.2

| Compound | Structure | Indoline | Carboxylic acid |
|---|---|---|---|
| Compound 166 | (structure) | B-15 | A-14 |
| Compound 55 | (structure) | B-13 | A-12 |
| Compound 43 | (structure) | B-13 | A-51 |
| Compound 49 | (structure) | B-13 | (structure) |
| Compound 50 | (structure) | B-13 | A-52 |

TABLE 7.2-continued

| Compound | Structure | Indoline | Carboxylic acid |
|---|---|---|---|
| Compound 57 | 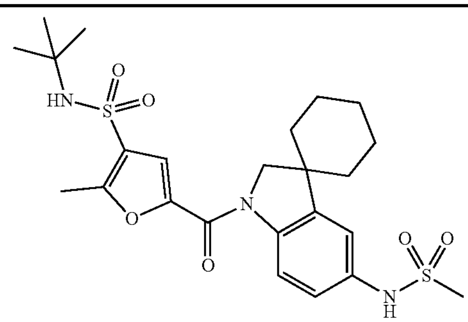 | B-13 | A-16 |
| Compound 59 | 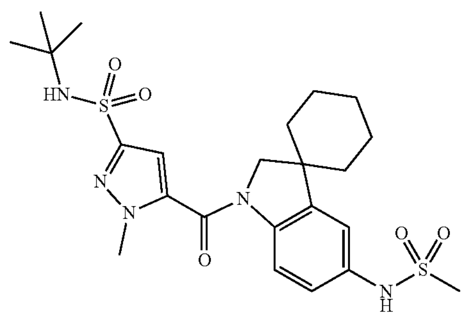 [SMILES: Cn1nc(S(=O)(=O)NC(C)(C)C)cc1C(=O)N1CC2(CCCCC2)c2cc(NS(C)(=O)=O)ccc21] | B-13 | A-15 |
| Compound 60 | 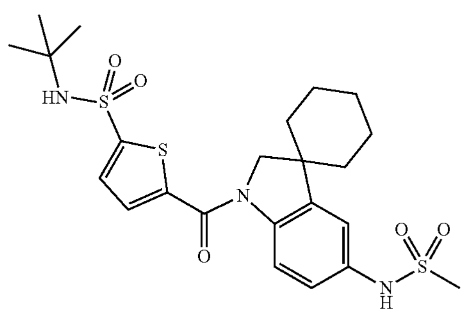 [SMILES: CC(C)(C)NS(=O)(=O)c1ccc(C(=O)N2CC3(CCCCC3)c3cc(NS(C)(=O)=O)ccc32)s1] | B-13 | A-21 |
| Compound 67 | 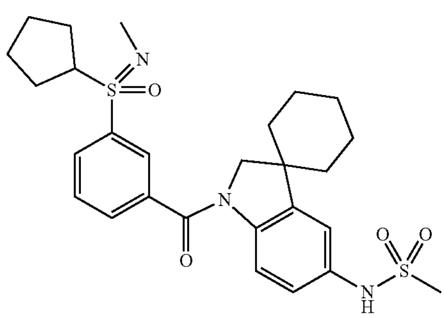 [SMILES: CN=S(=O)(c1cccc(C(=O)N2CC3(CCCCC3)c3cc(NS(C)(=O)=O)ccc32)c1)C1CCCC1] | B-13 | A-53 |
| Compound 95 | 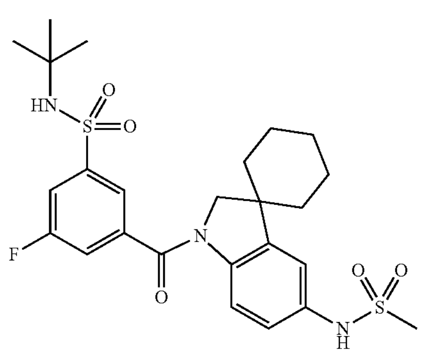 [SMILES: CC(C)(C)NS(=O)(=O)c1cc(F)cc(C(=O)N2CC3(CCCCC3)c3cc(NS(C)(=O)=O)ccc32)c1] | B-13 | A-20 |

TABLE 7.2-continued

| Compound | Structure | Indoline | Carboxylic acid |
|---|---|---|---|
| Compound 96 | 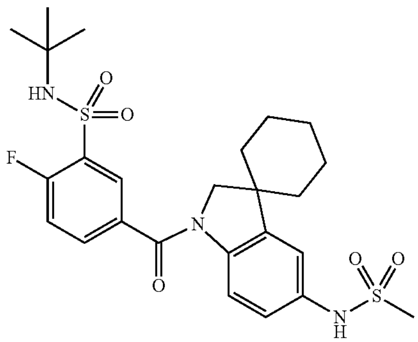 [SMILES: CC(C)(C)NS(=O)(=O)c1cc(C(=O)N2CC3(CCCCC3)c3cc(NS(C)(=O)=O)ccc32)ccc1F] | B-13 | A-22 |
| Compound 97 | 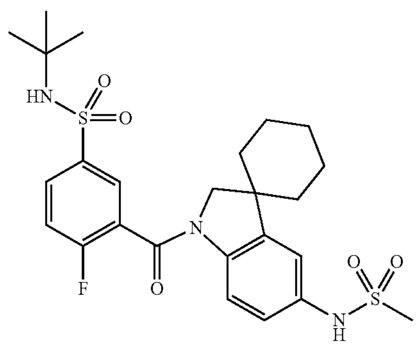 [SMILES: CC(C)(C)NS(=O)(=O)c1ccc(F)c(C(=O)N2CC3(CCCCC3)c3cc(NS(C)(=O)=O)ccc32)c1] | B-13 | A-18 |
| Compound 145 | 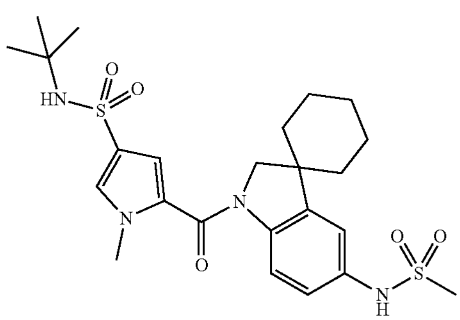 [SMILES: Cn1cc(S(=O)(=O)NC(C)(C)C)cc1C(=O)N1CC2(CCCCC2)c2cc(NS(C)(=O)=O)ccc21] | B-13 | A-17 |
| Compound 146 | 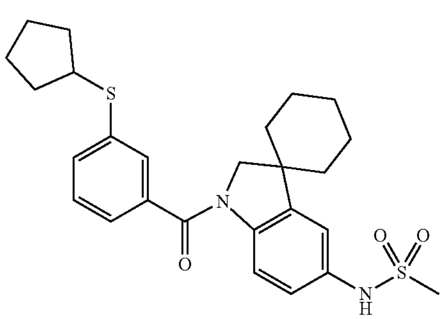 [SMILES: CS(=O)(=O)Nc1ccc2c(c1)C1(CCCCC1)CN2C(=O)c1cccc(SC2CCCC2)c1] | B-13 | |

TABLE 7.2-continued

| Compound | Structure | Indoline | Carboxylic acid |
|---|---|---|---|
| Compound 147 | 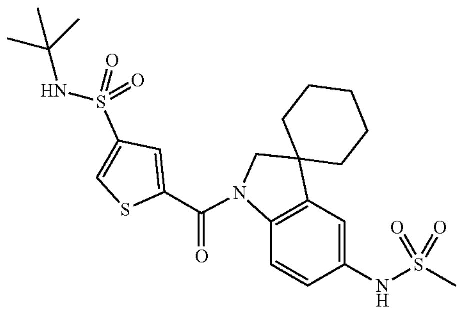 [SMILES: CC(C)(C)NS(=O)(=O)c1csc(C(=O)N2CC3(CCCCC3)c3cc(NS(C)(=O)=O)ccc32)c1] | B-13 | A-19 |
| Compound 149 | 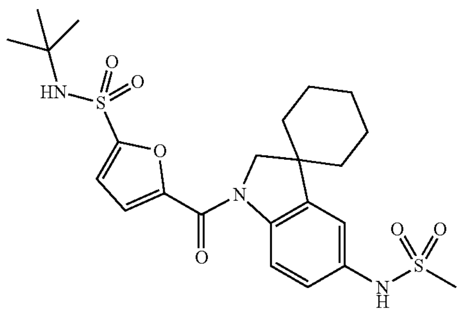 [SMILES: CC(C)(C)NS(=O)(=O)c1ccc(C(=O)N2CC3(CCCCC3)c3cc(NS(C)(=O)=O)ccc32)o1] | B-13 | A-23 |
| Compound 156 | 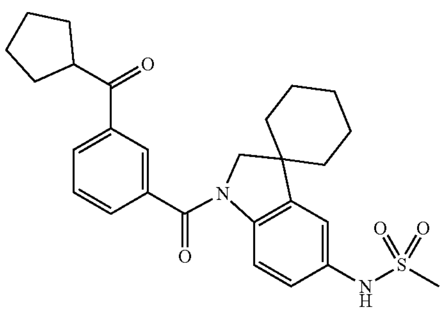 [SMILES: CS(=O)(=O)Nc1ccc2c(c1)C1(CCCCC1)CN2C(=O)c1cccc(C(=O)C2CCCC2)c1] | B-13 | A-54 |
| Compound 163 | 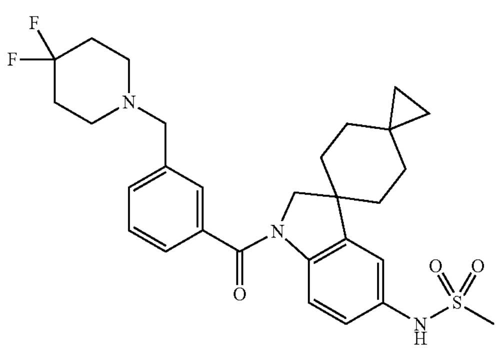 [SMILES: CS(=O)(=O)Nc1ccc2c(c1)C1(CCC3(CC3)CC1)CN2C(=O)c1cccc(CN2CCC(F)(F)CC2)c1] | B-14 | CAS: 1783412-42-9 |
| Compound 164 | 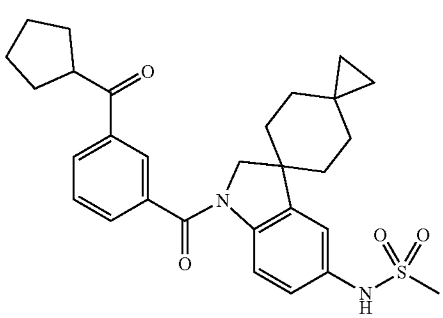 [SMILES: CS(=O)(=O)Nc1ccc2c(c1)C1(CCC3(CC3)CC1)CN2C(=O)c1cccc(C(=O)C2CCCC2)c1] | B-14 | A-54 |

TABLE 7.2-continued

| Compound | Structure | Indoline | Carboxylic acid |
|---|---|---|---|
| Compound 231 | 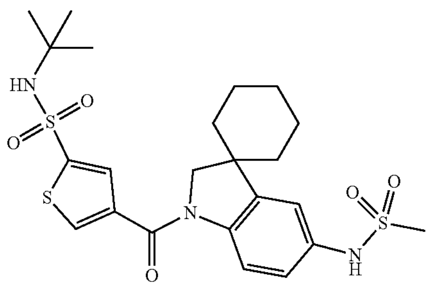 [SMILES: CC(C)(C)NS(=O)(=O)c1cc(C(=O)N2CC3(CCCCC3)c3cc(NS(C)(=O)=O)ccc32)cs1] | B-09 | A-55 |
| Compound 240 | 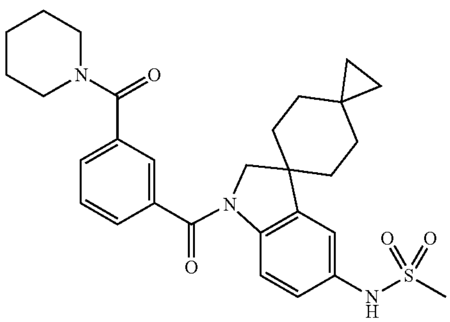 [SMILES: CS(=O)(=O)Nc1ccc2c(c1)C1(CCC3(CC3)CC1)CN2C(=O)c1cccc(C(=O)N2CCCCC2)c1] | B-13 | A-01 |
| Compound 241 | 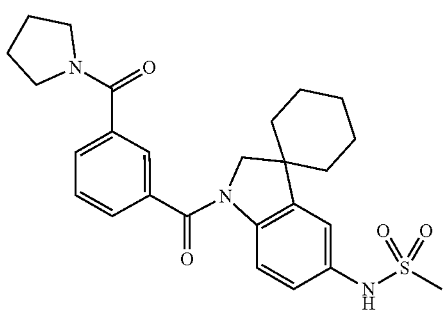 [SMILES: CS(=O)(=O)Nc1ccc2c(c1)C1(CCCCC1)CN2C(=O)c1cccc(C(=O)N2CCCC2)c1] | B-13 | A-02 |
| Compound 262 | 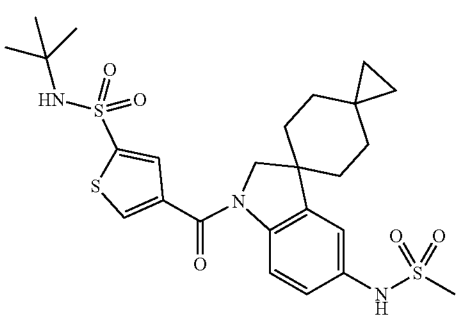 [SMILES: CC(C)(C)NS(=O)(=O)c1cc(C(=O)N2CC3(CCC4(CC4)CC3)c3cc(NS(C)(=O)=O)ccc32)cs1] | B-14 | A-55 |

TABLE 7.2-continued

| Compound | Structure | Indoline | Carboxylic acid |
|---|---|---|---|
| Compound 270 | 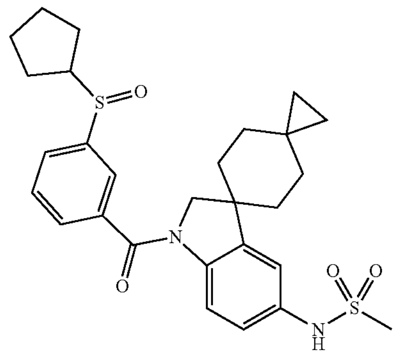 [SMILES: CS(=O)(=O)Nc1ccc2c(c1)C1(CCC3(CC3)CC1)CN2C(=O)c1cccc(S(=O)C2CCCC2)c1] | B-14 | A-51 |
| Compound 284 | 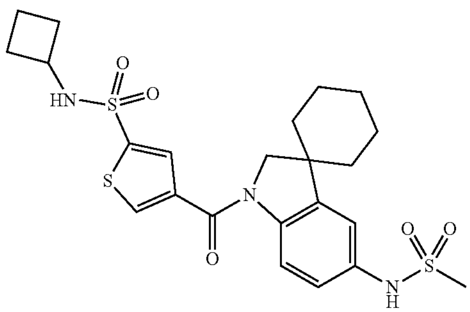 [SMILES: CS(=O)(=O)Nc1ccc2c(c1)C1(CCCCC1)CN2C(=O)c1csc(S(=O)(=O)NC2CCC2)c1] | B-13 | A-70 |
| Compound 285 | 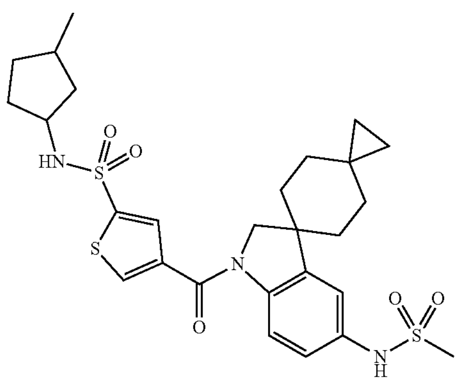 [SMILES: CC1CCC(NS(=O)(=O)c2cc(C(=O)N3CC4(CCC5(CC5)CC4)c4cc(NS(C)(=O)=O)ccc43)cs2)C1] | B-14 | A-71 |
| Compound 299 | 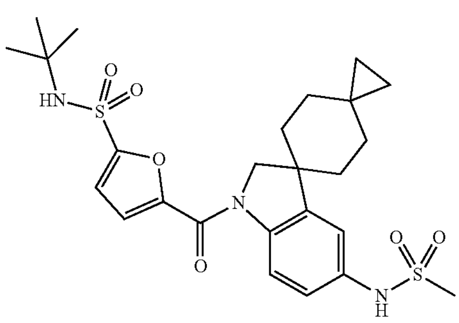 [SMILES: CC(C)(C)NS(=O)(=O)c1ccc(C(=O)N2CC3(CCC4(CC4)CC3)c3cc(NS(C)(=O)=O)ccc32)o1] | B-14 | A-23 |

TABLE 7.2-continued

| Compound | Structure | Indoline | Carboxylic acid |
|---|---|---|---|
| Compound 302 | 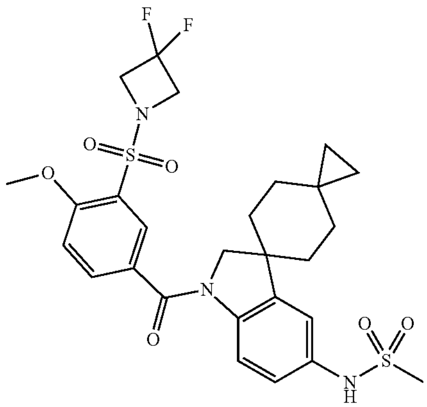 | B-14 | A-74 |
| Compound 304 | 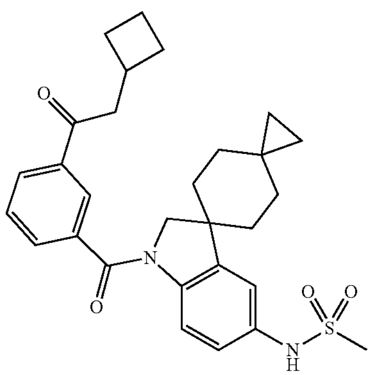 [SMILES: CS(=O)(=O)Nc1ccc2c(c1)C1(CCC3(CC3)CC1)CN2C(=O)c1cccc(C(=O)CC2CCC2)c1] | B-14 | A-75 |
| Compound 306 | 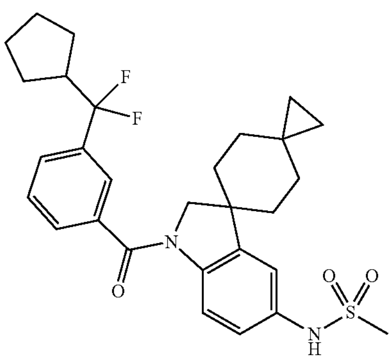 [SMILES: CS(=O)(=O)Nc1ccc2c(c1)C1(CCC3(CC3)CC1)CN2C(=O)c1cccc(C(F)(F)C2CCCC2)c1] | B-14 | A-76 |
| Compound 312 | 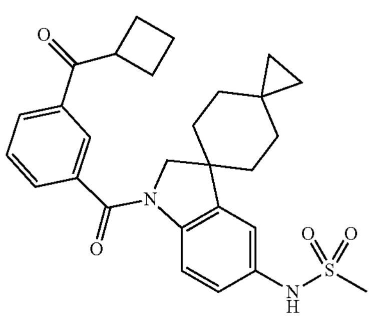 [SMILES: CS(=O)(=O)Nc1ccc2c(c1)C1(CCC3(CC3)CC1)CN2C(=O)c1cccc(C(=O)C2CCC2)c1] | B-14 | A-77 |

TABLE 7.2-continued

| Compound | Structure | Indoline | Carboxylic acid |
|---|---|---|---|
| Compound 316 | 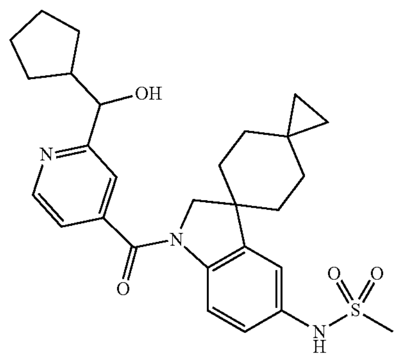 [SMILES: CS(=O)(=O)Nc1ccc2c(c1)C1(CCC3(CC3)CC1)CN2C(=O)c1ccnc(C(O)C2CCCC2)c1] | B-14 | A-78 |
| Compound 317 | 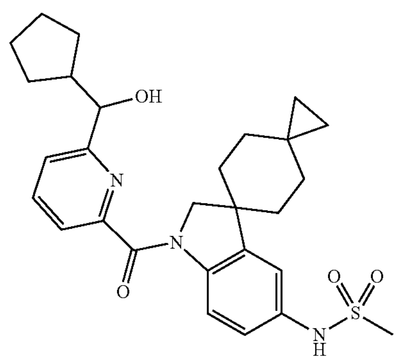 [SMILES: CS(=O)(=O)Nc1ccc2c(c1)C1(CCC3(CC3)CC1)CN2C(=O)c1cccc(C(O)C2CCCC2)n1] | B-14 | A-79 |
| Compound 318 | 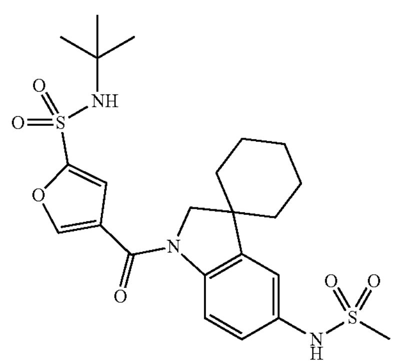 [SMILES: CC(C)(C)NS(=O)(=O)c1cc(C(=O)N2CC3(CCCCC3)c3cc(NS(C)(=O)=O)ccc32)co1] | B-13 | A-80 |
| Compound 321 | 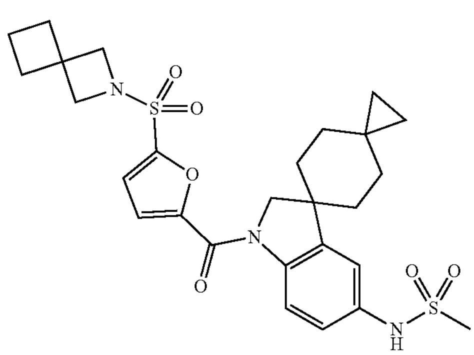 [SMILES: CS(=O)(=O)Nc1ccc2c(c1)C1(CCC3(CC3)CC1)CN2C(=O)c1ccc(S(=O)(=O)N2CC3(CCC3)C2)o1] | B-14 | A-81 |

TABLE 7.2-continued

| Compound | Structure | Indoline | Carboxylic acid |
|---|---|---|---|
| Compound 322 | 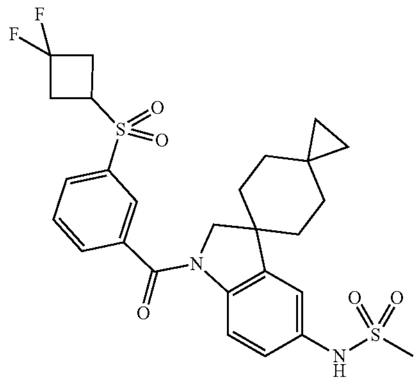 [SMILES: CS(=O)(=O)Nc1ccc2c(c1)C1(CCC3(CC3)CC1)CN2C(=O)c1cccc(S(=O)(=O)C2CC(F)(F)C2)c1] | B-14 | A-82 |
| Compound 330 | 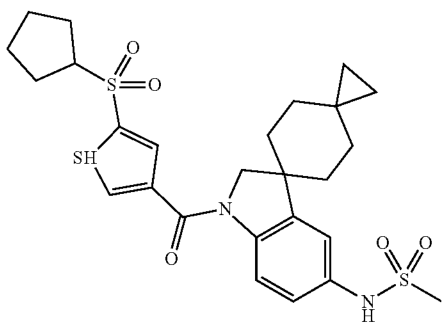 [SMILES: CS(=O)(=O)Nc1ccc2c(c1)C1(CCC3(CC3)CC1)CN2C(=O)c1csc(S(=O)(=O)C2CCCC2)c1] | B-14 | A-83 |
| Compound 334 | 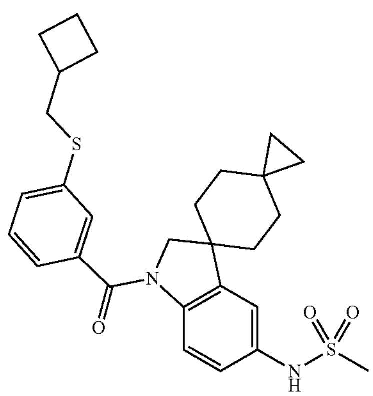 [SMILES: CS(=O)(=O)Nc1ccc2c(c1)C1(CCC3(CC3)CC1)CN2C(=O)c1cccc(SCC2CCC2)c1] | B-14 | A-84 CAS: 1468983-59-6 |
| Compound 339 | 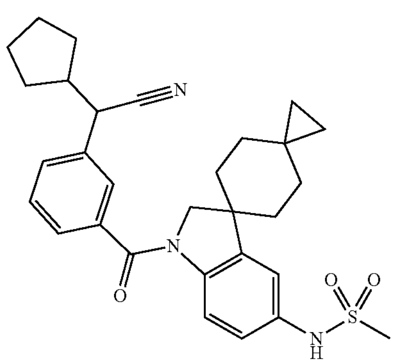 [SMILES: CS(=O)(=O)Nc1ccc2c(c1)C1(CCC3(CC3)CC1)CN2C(=O)c1cccc(C(C#N)C2CCCC2)c1] | B-14 | A-85 |

TABLE 7.2-continued

| Compound | Structure | Indoline | Carboxylic acid |
|---|---|---|---|
| Compound 343 | 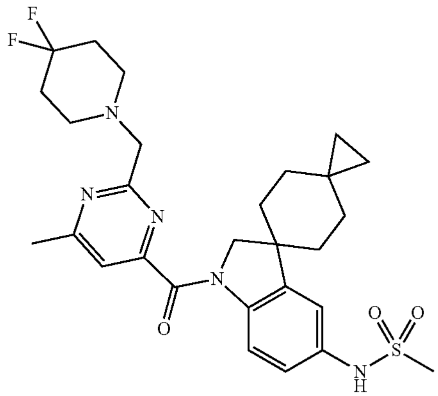 [SMILES: Cc1cc(C(=O)N2CC3(CCC4(CC4)CC3)c3cc(NS(C)(=O)=O)ccc32)nc(CN2CCC(F)(F)CC2)n1] | B-14 | A-88 |
| Compound 362 | 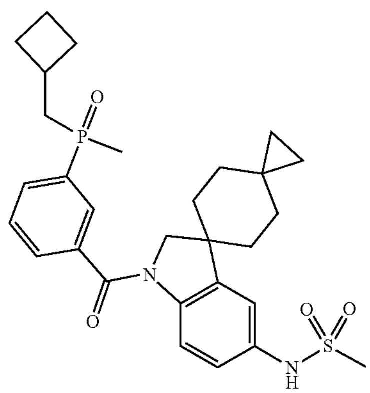 [SMILES: CP(=O)(CC1CCC1)c1cccc(C(=O)N2CC3(CCC4(CC4)CC3)c3cc(NS(C)(=O)=O)ccc32)c1] | B-14 | A-97 |

Preparation of N-(1"-(3-(1-(4,4-difluoropiperidin-1-yl)ethyl)benzoyl)dispiro[cyclopropane-1,1'-cyclohexane-4',3"-indolin]-5"-yl)methanesulfonamide (Compound 341)

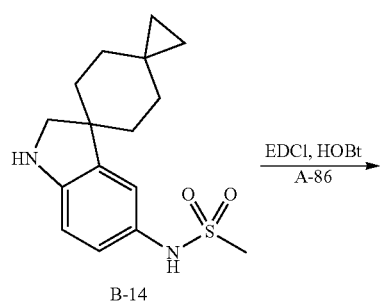

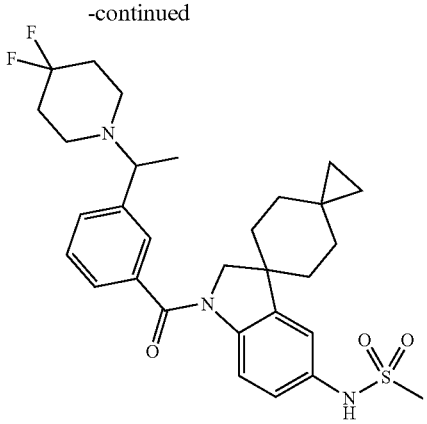

Compound 341

A mixture of A-86 (0.55 g, 2.0 mmol), DMF (5.5 mL), Et₃N (0.85 mL, 6.1 mmol), EDCI (1.4 g, 7.1 mmol), HOBt (0.96 g, 7.1 mmol) was stirred at 20° C. for 0.5 h, and then B-14 (0.25 g, 0.81 mmol) was added. The mixture was stirred at 20° C. for 12 h, poured into H₂O (16 mL), and extracted with EtOAc (2×16 mL). The combined extracts were washed with brine (10 mL), dried over Na₂SO₄, concentrated, and purified by preparative HPLC (C18, 20-55% MeCN in H₂O [formic acid]) provide N-(1"-(3-(1-(4,4-difluoropiperidin-1-yl)ethyl)benzoyl)dispiro[cyclopropane-1,1'-cyclohexane-4',3"-indolin]-5"-yl)methanesulfonamide (Compound 341, 30 mg).

Compounds in Table 7.3 were prepared from the indicated indoline and carboxylic acid in the same manner as Compound 341.

TABLE 7.3

| Code | Structure | Carboxylic Acid | Indoline |
|---|---|---|---|
| Example 344 | 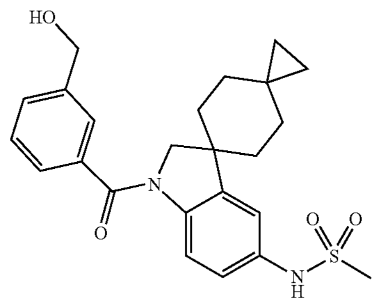 [SMILES: CS(=O)(=O)Nc1ccc2c(c1)C1(CCC3(CC3)CC1)CN2C(=O)c1cccc(CO)c1] | | B-14 |
| Compound 346 | 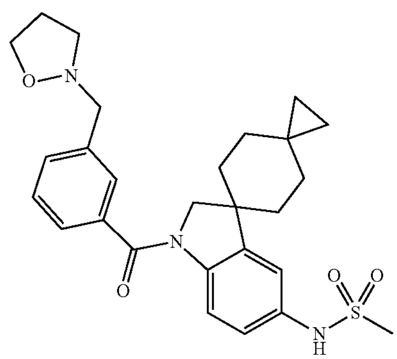 [SMILES: CS(=O)(=O)Nc1ccc2c(c1)C1(CCC3(CC3)CC1)CN2C(=O)c1cccc(CN2CCCO2)c1] | A-89 | B-14 |
| Compound 347 | 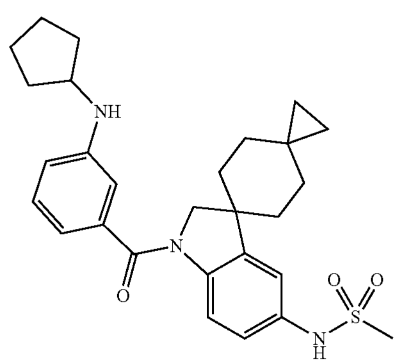 [SMILES: CS(=O)(=O)Nc1ccc2c(c1)C1(CCC3(CC3)CC1)CN2C(=O)c1cccc(NC2CCCC2)c1] | A-90 | B-14 |
| Compound 348 | 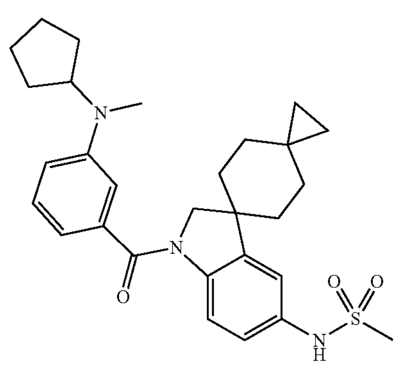 [SMILES: CN(c1cccc(C(=O)N2CC3(CCC4(CC4)CC3)c3cc(NS(C)(=O)=O)ccc32)c1)C1CCCC1] | A-91 | B-14 |

TABLE 7.3-continued

| Code | Structure | Carboxylic Acid | Indoline |
|---|---|---|---|
| Compound 349 | 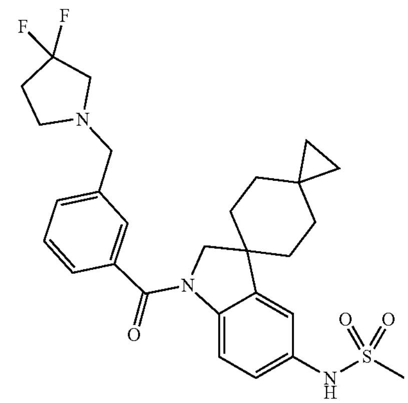 [SMILES: CS(=O)(=O)Nc1ccc2c(c1)C1(CCC3(CC3)CC1)CN2C(=O)c1cccc(CN2CCC(F)(F)C2)c1] | A-92 | B-14 |
| Compound 350 | 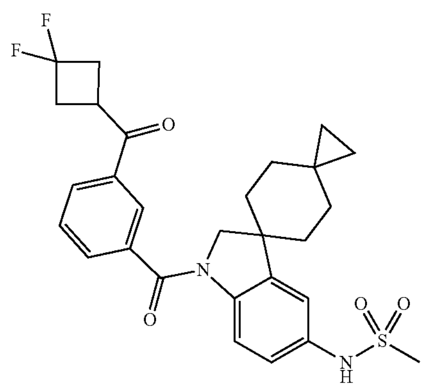 [SMILES: CS(=O)(=O)Nc1ccc2c(c1)C1(CCC3(CC3)CC1)CN2C(=O)c1cccc(C(=O)C2CC(F)(F)C2)c1] | A-93 | B-14 |
| Compound 353 | 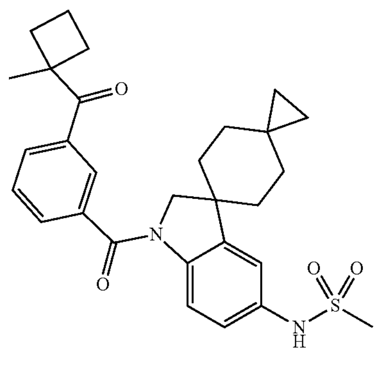 | A-94 | B-14 |

TABLE 7.3-continued

| Code | Structure | Carboxylic Acid | Indoline |
|---|---|---|---|
| Compound 356 | 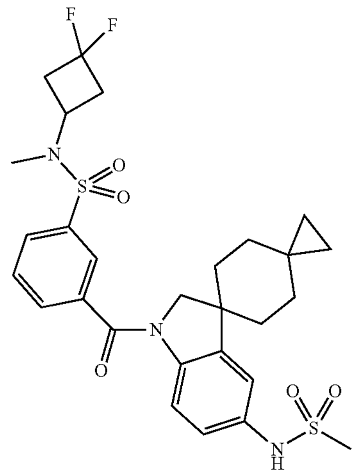 | A-95 | B-14 |
| Compound 358 | 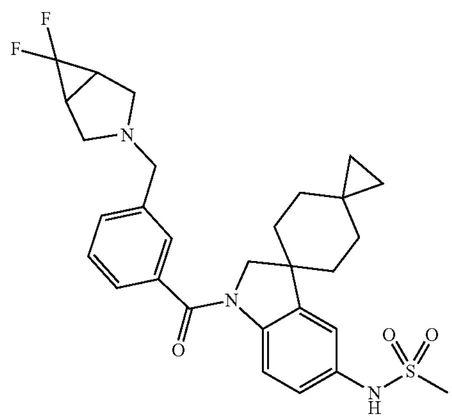 [SMILES: CS(=O)(=O)Nc1ccc2c(c1)C1(CCC3(CC3)CC1)CN2C(=O)c1cccc(CN2CC3C(C2)C3(F)F)c1] | A-96 | B-14 |
| Compound 359 | 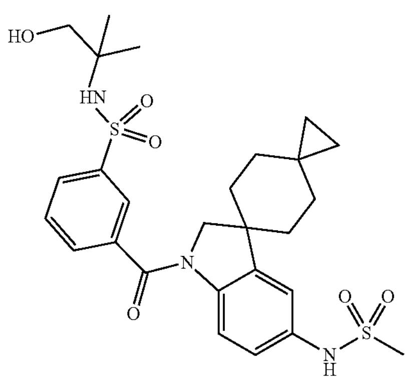 [SMILES: CC(C)(CO)NS(=O)(=O)c1cccc(C(=O)N2CC3(CCC4(CC4)CC3)c3cc(NS(C)(=O)=O)ccc32)c1] | A-49 | B-23 |
| Compound 363 | 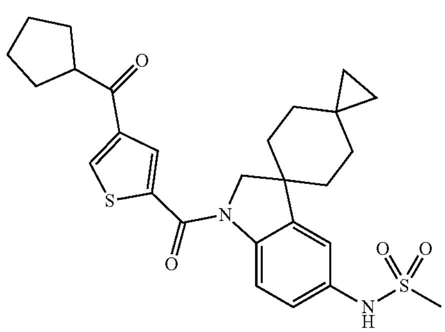 [SMILES: CS(=O)(=O)Nc1ccc2c(c1)C1(CCC3(CC3)CC1)CN2C(=O)c1cc(C(=O)C2CCCC2)cs1] | A-98 | B-14 |

TABLE 7.3-continued

| Code | Structure | Carboxylic Acid | Indoline |
|---|---|---|---|
| Compound 366 | 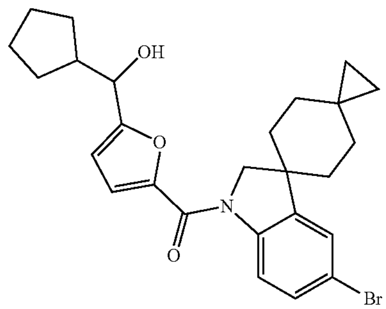 [SMILES: O=C(c1ccc(C(O)C2CCCC2)o1)N1CC2(CCC3(CC3)CC2)c2cc(Br)ccc21] | A-99 | B-07 |
| Compound 367 | 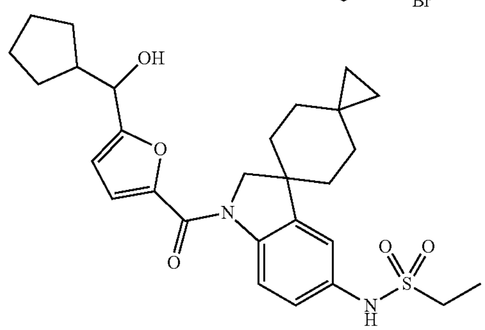 | A-99 | B-23 |
| Compound 368 | 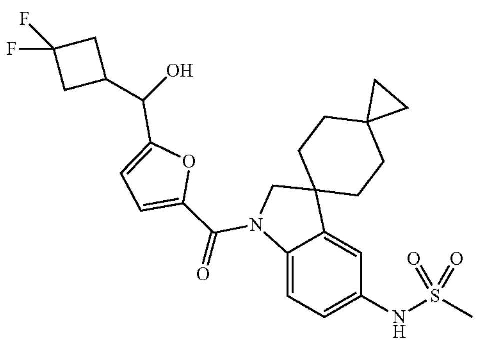 [SMILES: CS(=O)(=O)Nc1ccc2c(c1)C1(CCC3(CC3)CC1)CN2C(=O)c1ccc(C(O)C2CC(F)(F)C2)o1] | A-100 | B-14 |
| Compound 370 | 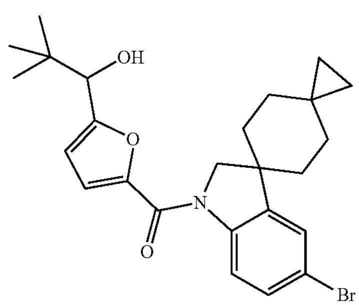 [SMILES: CC(C)(C)C(O)c1ccc(C(=O)N2CC3(CCC4(CC4)CC3)c3cc(Br)ccc32)o1] | A-101 | B-07 |
| Compound 372 | 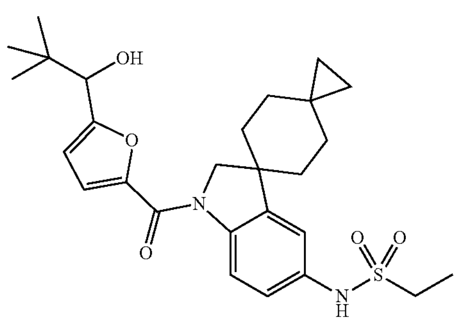 [SMILES: CCS(=O)(=O)Nc1ccc2c(c1)C1(CCC3(CC3)CC1)CN2C(=O)c1ccc(C(O)C(C)(C)C)o1] | A-101 | B-23 |

TABLE 7.3-continued

| Code | Structure | Carboxylic Acid | Indoline |
|---|---|---|---|
| Compound 373 | 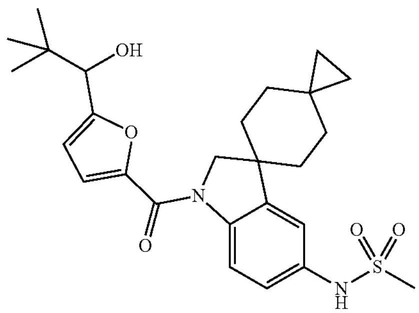 [SMILES: CC(C)(C)C(O)c1ccc(C(=O)N2CC3(CCC4(CC4)CC3)c3cc(NS(C)(=O)=O)ccc32)o1] | A-101 | B-14 |

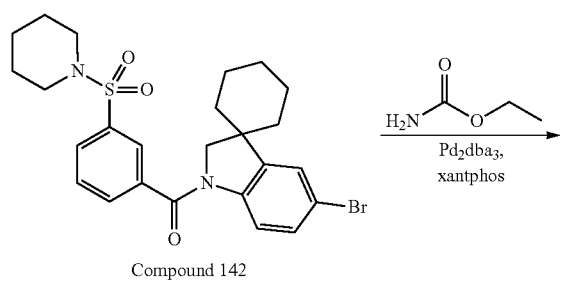

Synthetic Example S-009

Preparation of ethyl (1'-(3-(piperidin-1-ylsulfonyl)benzoyl)spiro[cyclohexane-1,3'-indolin]-5'-yl)carbamate (Compound 141)

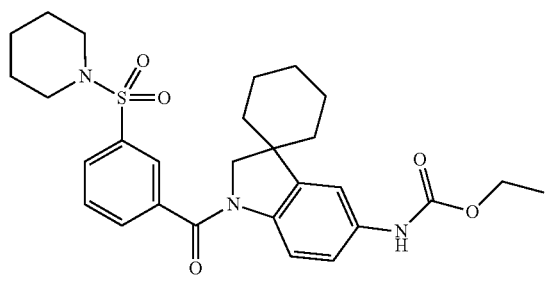

A mixture of Compound 142 (0.20 g, 0.39 mmol), dioxane (10 mL), $Cs_2CO_3$ (0.38 g, 1.2 mmol), $Pd_2(dba)_3$ (35 mg, 39 μmol), Xantphos (22 mg, 39 μmol) and ethyl carbamate (52 mg, 0.58 mmol) was stirred at 110° C. for 12 h. The mixture was concentrated and purified by preparative HPLC (70-90% MeCN in $H_2O$ [0.1 M HCl]) to provide ethyl (1'-(3-(piperidin-1-ylsulfonyl)benzoyl)spiro[cyclohexane-1,3'-indolin]-5'-yl)carbamate (Compound 141, 21 mg).

Synthetic Example S-010

Preparation of N-(1'-(3-(cyclopentyl(hydroxy)methyl)benzoyl)spiro[cyclohexane-1,3'-indolin]-5'-yl)methanesulfonamide (Compound 157)

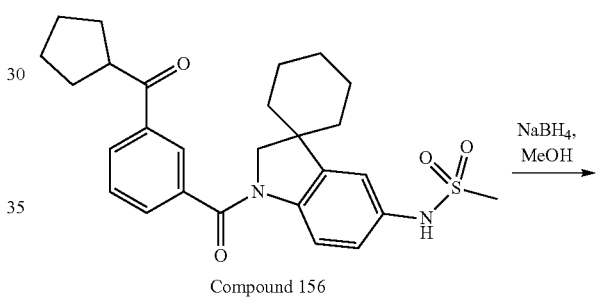

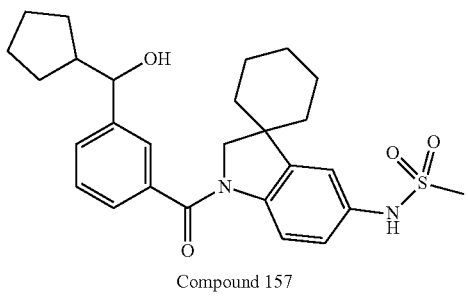

A degassed mixture of Compound 156 (0.10 g, 0.21 mmol), $NaBH_4$ (16 mg, 0.42 mmol), and MeOH (2 mL) was stirred under an $N_2$ atmosphere at 0° C. for 3 h. The mixture was concentrated and extracted with EtOAc (10 mL). The extract was washed with water (5 mL×2) and brine (3 mL), dried over $Na_2SO_4$, filtered, concentrated, and purified by preparative HPLC (42-72% MeCN in $H_2O$ [0.1% formic acid]) to provide N-(1'-(3-(cyclopentyl (hydroxy) methyl) benzoyl) spiro[cyclohexane-1,3'-indolin]-5'-yl) methanesulfonamide (Compound 157, 20 mg).

Compounds in Table 7.4 were prepared from the indicated ketone in the manner described for the synthesis of Compound 157.

TABLE 7.4

| Compound | Structure | Ketone |
|---|---|---|
| Compound 165 | 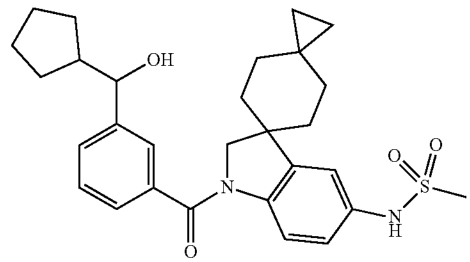 [SMILES: CS(=O)(=O)Nc1ccc2c(c1)C1(CCC3(CC3)CC1)CN2C(=O)c1cccc(C(O)C2CCCC2)c1] | Compound 164 |
| Compound 305 | 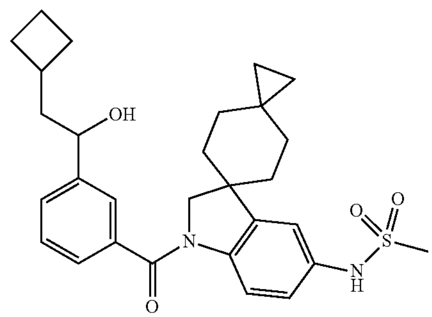 [SMILES: CS(=O)(=O)Nc1ccc2c(c1)C1(CCC3(CC3)CC1)CN2C(=O)c1cccc(C(O)CC2CCC2)c1] | Compound 304 |
| Compound 313 | 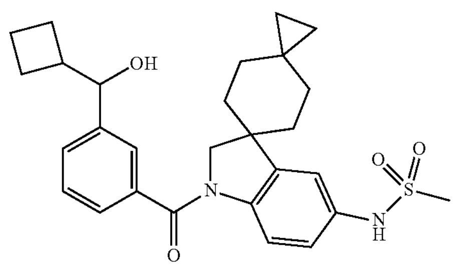 [SMILES: CS(=O)(=O)Nc1ccc2c(c1)C1(CCC3(CC3)CC1)CN2C(=O)c1cccc(C(O)C2CCC2)c1] | Compound 312 |
| Compound 351 | 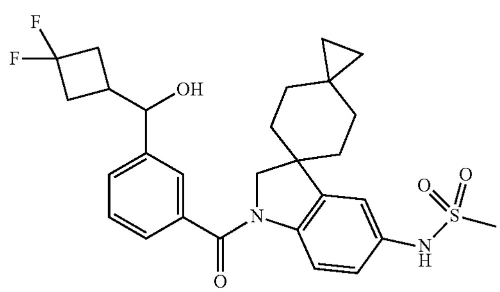 [SMILES: CS(=O)(=O)Nc1ccc2c(c1)C1(CCC3(CC3)CC1)CN2C(=O)c1cccc(C(O)C2CC(F)(F)C2)c1] | Compound 350 |
| Compound 354 | 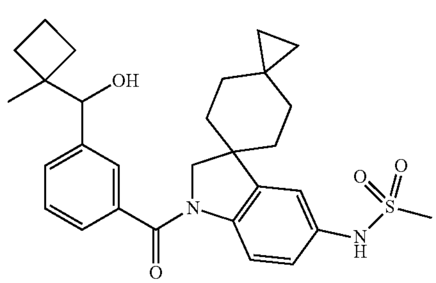 | Compound 353 |

TABLE 7.4-continued

| Compound | Structure | Ketone |
|---|---|---|
| Compound 364 | 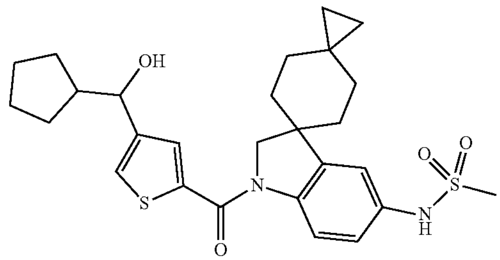 [SMILES: CS(=O)(=O)Nc1ccc2c(c1)C1(CCC3(CC3)CC1)CN2C(=O)c1cc(C(O)C2CCCC2)cs1] | Compound 363 |

Synthetic Example S-011

Preparation of N-(bicyclo[1.1.1]pentan-1-yl)-3-(5"-(methylsulfonamido)dispiro[cyclopropane-1,1'-cyclohexane-4',3"-indoline]-1"-carbonyl)benzenesulfonamide

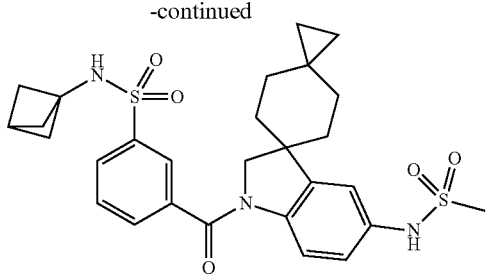

Compound 223

To a mixture of bicyclo[1.1.1]pentan-1-amine (16 mg, 196 μmol), $CH_2Cl_2$ (1.0 mL) was added $Et_3N$ (82 μg, 0.59 mmol) and C-01 (100 mg, 0.20 mmol). The resulting mixture was stirred at 25° C. for 1 h, then was concentrated and partitioned between $H_2O$ (30 mL) and EtOAc (2×30 mL). The extracts were combined, washed with brine (10 mL), dried over $Na_2SO_4$, concentrated, and purified by preparative HPLC (35-65% MeCN in $H_2O$ [0.1% formic acid]) to provide N-(bicyclo[1.1.1]pentan-1-yl)-3-(5"-(methylsulfonamido)dispiro[cyclopropane-1,1'-cyclohexane-4',3"-indoline]-1"-carbonyl)benzenesulfonamide (Compound 223, 15 mg).

Compounds in Table 7.5 were prepared from the indicated sulfonyl chloride and amine in the same manner as Compound 223.

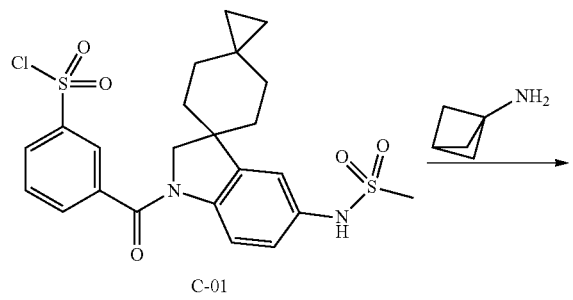

C-01

TABLE 7.5

| Compound | Structure | Sulfonyl chloride | amine |
|---|---|---|---|
| Compound 224 | 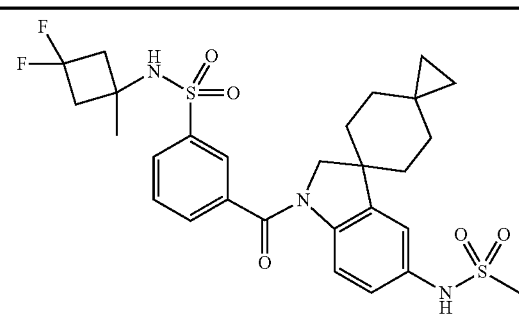 | C-01 | |

TABLE 7.5-continued

| Compound | Structure | Sulfonyl chloride | amine |
|---|---|---|---|
| Compound 225 | 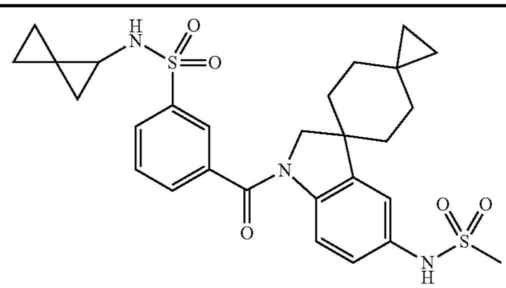 | C-01 | cyclopropylmethyl-NH₂ (cyclopropyl amine shown) |
| Compound 226 | 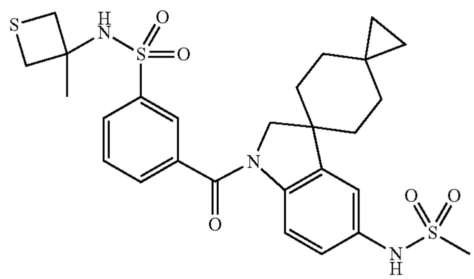 [SMILES: CC1(NS(=O)(=O)c2cccc(C(=O)N3CC4(CCC5(CC5)CC4)c4cc(NS(C)(=O)=O)ccc43)c2)CSC1] | C-01 | 3-methylthietan-3-amine |
| Compound 255 | 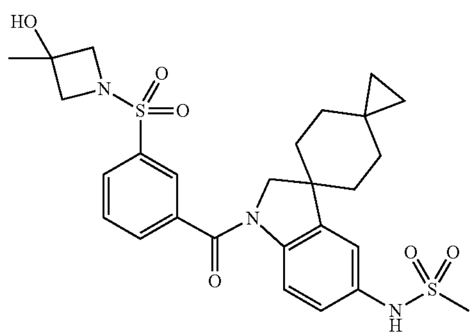 | C-01 | HCl · 3-hydroxy-3-methylcyclobutan-1-amine |
| Compound 258 | 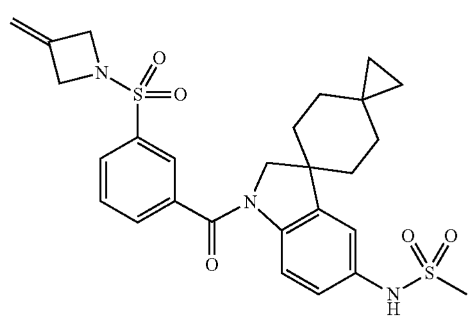 | C-01 | 3-methyleneazetidine · F₃CCO₂H |
| Compound 311 | 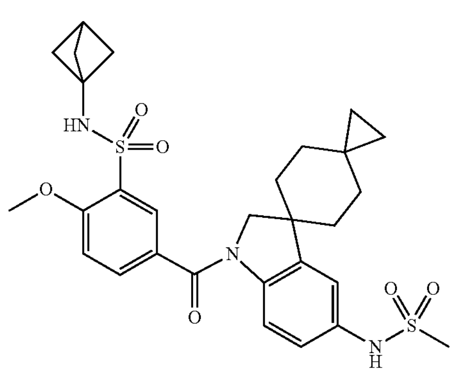 | C-02 | bicyclo[1.1.1]pentan-1-amine · HCl |

TABLE 7.5-continued

| Compound | Structure | Sulfonyl chloride | amine |
|---|---|---|---|
| Compound 336 | 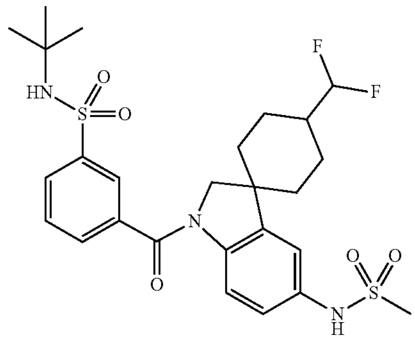 [SMILES: CC(C)(C)NS(=O)(=O)c1cccc(C(=O)N2CC3(CCC(C(F)F)CC3)c3cc(NS(C)(=O)=O)ccc32)c1] | C-03 | |
| Compound 337 | 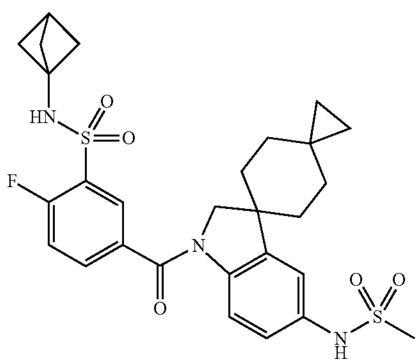 [SMILES: CS(=O)(=O)Nc1ccc2c(c1)C1(CCC3(CC3)CC1)CN2C(=O)c1ccc(F)c(S(=O)(=O)NC23CC(C2)C3)c1] | C-04 | |
| Compound 340 | 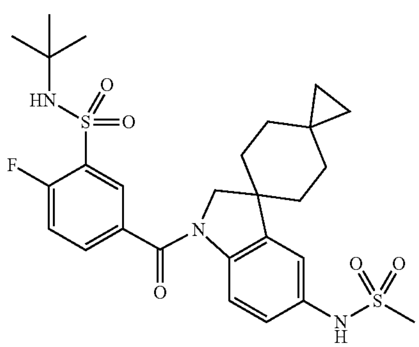 [SMILES: CC(C)(C)NS(=O)(=O)c1cc(C(=O)N2CC3(CCC4(CC4)CC3)c3cc(NS(C)(=O)=O)ccc32)ccc1F] | C-05 | |

Synthetic Example S-012

Preparation of N-(1'-(5-(cyclopentyl(hydroxy)methyl)thiophene-3-carbonyl)dispiro[cyclopropane-1,1'-cyclohexane-4',3"-indolin]-5"-yl)methanesulfonamide (Compound 301)

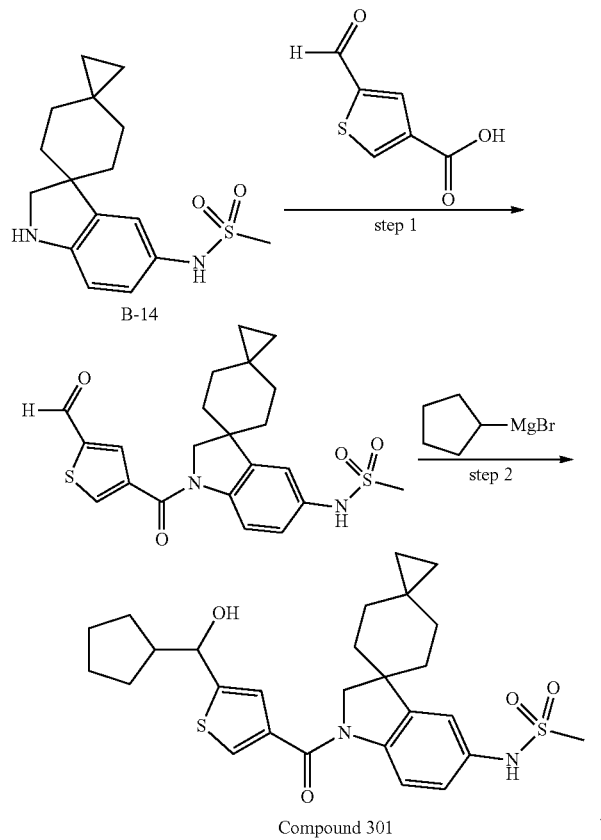

Preparation of N-(1"-(5-(cyclopentyl(hydroxy)methyl)furan-2-carbonyl)dispiro[cyclopropane-1,1'-cyclohexane-4',3"-indolin]-5"-yl)methanesulfonamide (Compound 352)

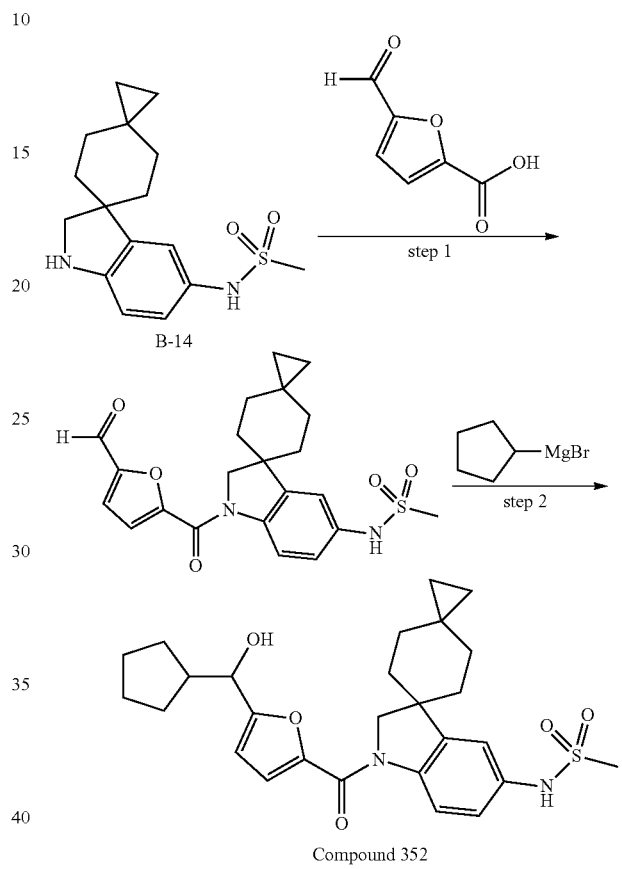

Step 1. To a mixture of 5-formylthiophene-3-carboxylic acid (0.12 mg, 0.74 mmol) and DMF (1.5 mL) was added HATU (0.42 g, 1.1 mmol), and iPr$_2$NEt (0.39 mL, 2.2 mmol). After stirring for 30 min, B-14 (0.27 mg, 0.88 mmol) was added and the mixture was stirred at 80° C. for 1.5 h, diluted with H$_2$O (4 mL), and extracted with EtOAc (10 mL×3). The combined extracts were washed with brine (30 mL), dried over Na$_2$SO$_4$, filtered, concentrated, and purified by silica chromatography (0-100% EtOAc/PE) to provide N-(1"-(5-formylthiophene-3-carbonyl)dispiro[cyclopropane-1,1'-cyclohexane-4',3"-indolin]-5"-yl)methanesulfonamide (0.31 g). $^1$H NMR (400 MHz, DMSO-d$^6$) 6 ppm 10.00-9.91 (m, 1H) 8.14 (s, 1H) 8.08-7.96 (m, 1H) 7.26-7.19 (m, 2H) 7.15-7.00 (m, 1H) 4.08 (d, J=6.58 Hz, 2H) 2.98 (s, 3H) 1.27-1.24 (m, 8H) 0.36-0.28 (m, 4H).

Step 2. To a mixture of N-(1"-(5-formylthiophene-3-carbonyl)dispiro[cyclopropane-1,1'-cyclohexane-4',3"-indolin]-5"-yl)methanesulfonamide (0.25 g, 0.56 mmol) and THF (3 mL) was added bromo(cyclopentyl)magnesium (1 M, 2.8 mL). The mixture was stirred at −70° C. for 2, slowly poured into ice (5 mL), and extracted with EtOAc (10 ml×3). The combined extracts were washed with brine (30 mL), dried over Na$_2$SO$_4$, concentrated, and purified by preparative HPLC (C18, 45%-75% MeCN in H$_2$O [NH$_4$HCO$_3$]) to provide N-(1"-(5-(cyclopentyl(hydroxy)methyl)thiophene-3-carbonyl)dispiro[cyclopropane-1,1'-cyclohexane-4',3"-indolin]-5"-yl)methanesulfonamide (Compound 301, 3.5 mg).

Step 1. A mixture of 5-formylfuran-2-carboxylic acid (0.20 g, 1.4 mmol), DMF (3 mL), EDCI (0.55 g, 2.9 mmol), HOBt (0.39 g, 2.9 mmol), and iPr$_2$Net (0.75 mL, 4.3 mmol) was stirred at 20° C. for 30 min., and B-14 (0.44 g, 1.4 mmol) in DMF (0.5 mL) was added dropwise at 20° C. The mixture was stirred at 20° C. for 12 h, poured into water (20 mL), and extracted with EtOAc (2×20 mL). The combined extracts were washed with brine (20 mL), dried over Na$_2$SO$_4$, concentrated, purified by silica chromatography (10-50% EtOAc in PE) to provide N-(1"-(3-formylbenzoyl)dispiro[cyclopropane-1,1'-cyclohexane-4',3"-indolin]-5"-yl)methanesulfonamide (0.23 g).

Step 2. To a mixture of N-(1"-(3-formylbenzoyl)dispiro[cyclopropane-1,1'-cyclohexane-4',3"-indolin]-5"-yl)methanesulfonamide (0.20 g, 0.37 mmol) and THF (3 mL) was added bromo(cyclopentyl)magnesium (1 M, 0.47 mL). The mixture was stirred at −60° C. for 0.5 h, poured into saturated NH$_4$Cl (5 mL), and extracted with EtOAc (2×10 mL). The combined extracts were washed with brine (10 mL), dried over Na$_2$SO$_4$, concentrated, purified by preparative HPLC (C18, 30-70% MeCN in H$_2$O [formic acid]) to provide N-(1"-(5-(cyclopentyl(hydroxy)methyl)furan-2-carbonyl)dispiro[cyclopropane-1,1'-cyclohexane-4',3"-indolin]-5"-yl)methanesulfonamide (Compound 352, 7.0 mg).

Synthetic Example S-013

Preparation of N-(1"-(3-((3,3-difluoroazetidin-1-yl)sulfonyl)-4-hydroxybenzoyl)dispiro[cyclopropane-1,1'-cyclohexane-4',3"-indolin]-5"-yl)methanesulfonamide (Compound 303)

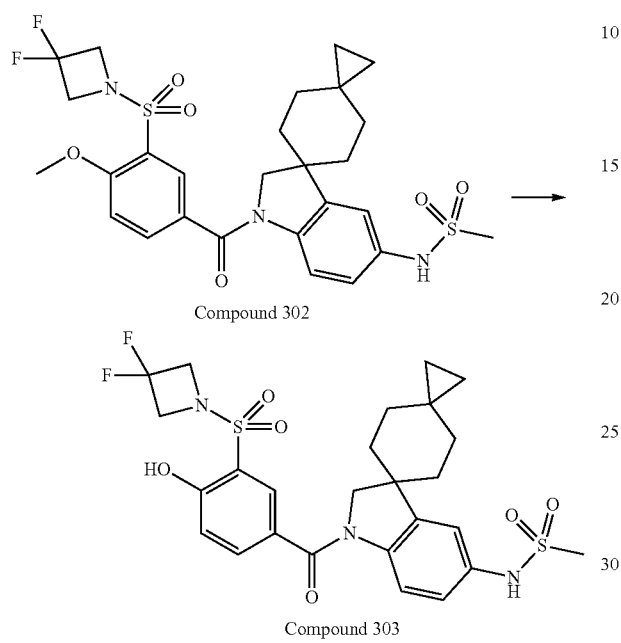

Compound 302

Compound 303

Two mixtures of Compound 302 (90 & 40 mg, 0.15 & 0.067 mmol), DMF (3 & 1.3 mL), LiCl (19 & 8.5 mg, 0.45 & 0.20 mmol) were stirred at 160° C. for 4 h. The mixtures were combined and poured into H₂O (10 mL) and extracted with EtOAc (2×10 mL). The combined extracts were washed with brine (10 mL), dried over Na₂SO₄, concentrated, and purified by preparative HPLC (C18, 15-55% MeCN in H₂O [NH₄HCO₃]) to provide N-(1"-(3-((3,3-difluoroazetidin-1-yl)sulfonyl)-4-hydroxybenzoyl)dispiro[cyclopropane-1,1'-cyclohexane-4',3"-indolin]-5"-yl)methanesulfonamide (Compound 303, 10 mg).

Synthetic Example S-014

Preparation of N-(1"-(3-(2-(3,3-difluoroazetidin-1-yl)-1-hydroxyethyl)benzoyl)dispiro[cyclopropane-1,1'-cyclohexane-4',3"-indolin]-5"-yl)methanesulfonamide (Compound 314)

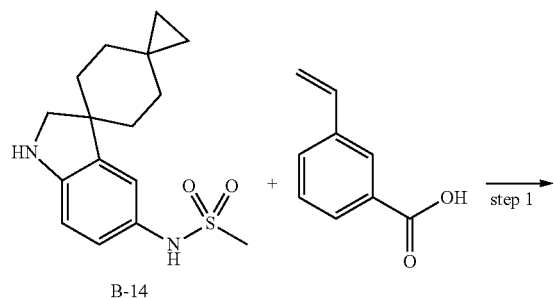

B-14

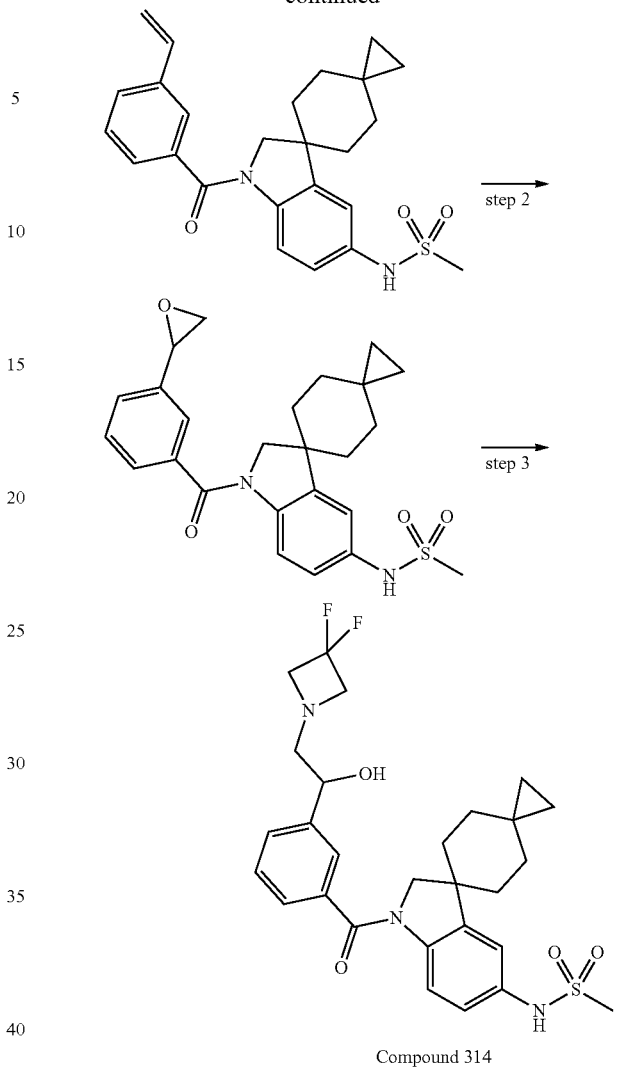

Compound 314

Step 1. A mixture of 3-vinylbenzoic acid (0.13 g, 0.89 mmol), DMF (3 mL), B-14 (0.30 mg, 0.98 mmol), HOBt (0.24 mg, 1.8 mmol), EDCI (0.34 g, 1.8 mmol), Et₃N (0.37 mL, 2.7 mmol) was stirred at 20° C. for 2 h then poured into water (30 mL) and extracted with EtOAc (2×30 mL). The combined extracts were washed with brine (10 mL), dried over Na₂SO₄, concentrated, and purified by silica chromatography (0-40% EtOAc in PE) to provide N-(1"-(3-vinylbenzoyl)dispiro[cyclopropane-1,1'-cyclohexane-4',3"-indolin]-5"-yl)methanesulfonamide (0.30 g).

Step 2. To a mixture of N-(1"-(3-vinylbenzoyl)dispiro[cyclopropane-1,1'-cyclohexane-4',3"-indolin]-5"-yl)methanesulfonamide (0.15 g, 0.34 mmol) and CH₂Cl₂ (1 mL) was added m-CPBA (0.14 g, 0.60 mmol, 85% purity) at 0° C. The mixture was stirred at 20° C. for 12 h, poured into Na₂SO₃ (1M, 30 mL), and extracted with EtOAc (2×30 mL). The combined extracts were washed with brine (10 mL), dried over Na₂SO₄, concentrated, and purified by silica chromatography (0-30% EtOAc in PE) to provide N-(1"-(3-(oxiran-2-yl)benzoyl)dispiro[cyclopropane-1,1'-cyclohexane-4',3"-indolin]-5"-yl)methanesulfonamide (0.10 g).

Step 3. A mixture of 3,3-difluoroazetidine hydrochloride (39 mg, 0.30 mmol), iPr₂NEt (0.10 mL, 0.60 mmol), EtOH (1 mL), and N-(1"-(3-(oxiran-2-yl)benzoyl)dispiro[cyclopropane-1,1'-cyclohexane-4',3"-indolin]-5"-yl)methanesulfonamide (90 mg, 0.20 mmol) was stirred at 80° C. for 12 h. The mixture was concentrated and purified by preparative HPLC (35-65% MeCN in H₂O [formic acid]) to provide N-(1"-(3-(2-(3,3-difluoroazetidin-1-yl)-1-hydroxyethyl)benzoyl)dispiro[cyclopropane-1,1'-cyclohexane-4',3"-indolin]-5"-yl)methanesulfonamide (Compound 314, 22 mg).

Preparation of N-(1"-(3-(2-(4,4-difluoropiperidin-1-yl)-1-hydroxyethyl)benzoyl)dispiro[cyclopropane-1,1'-cyclohexane-4',3"-indolin]-5"-yl)methanesulfonamide (Compound 315)

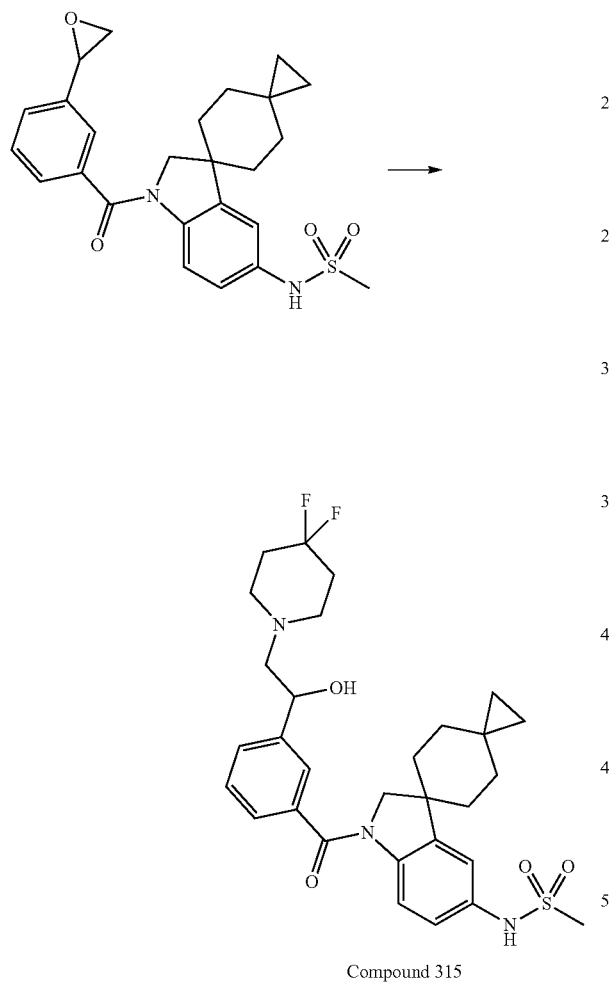

Compound 315

(Compound 315) was prepared from N-(1"-(3-vinylbenzoyl)dispiro[cyclopropane-1,1'-cyclohexane-4',3"-indolin]-5"-yl)methanesulfonamide and 3,3-difluoropiperidine hydrochloride by the method described for Compound 314.

Synthetic Example S-015

Preparation of N-(1"-(3-((piperidin-1-ylimino)methyl)benzoyl)dispiro[cyclopropane-1,1'-cyclohexane-4',3"-indolin]-5"-yl)methanesulfonamide (Compound 318)

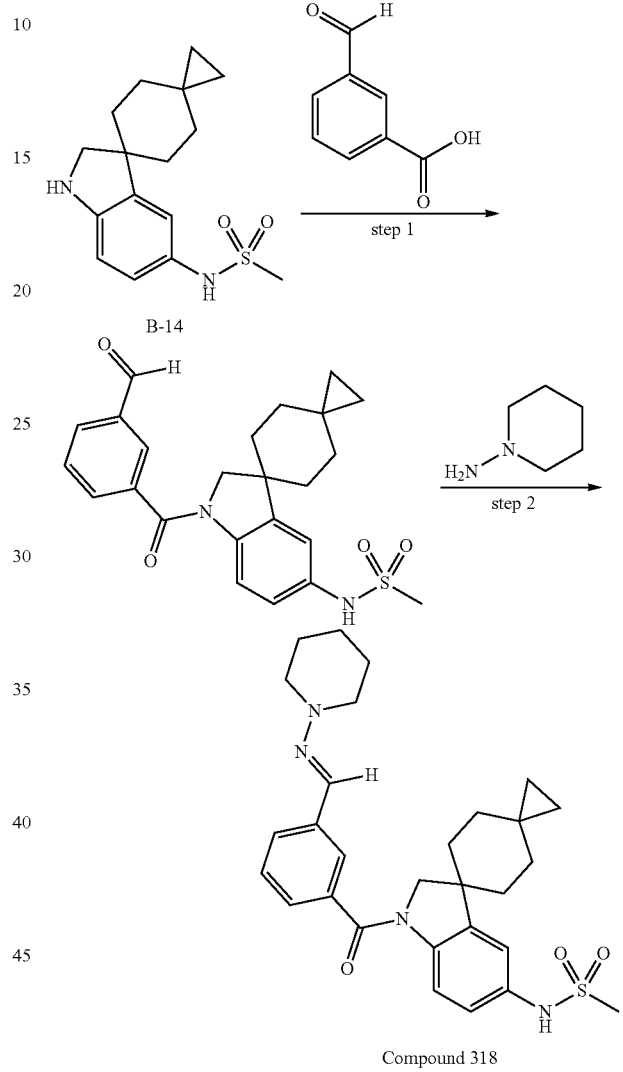

Compound 318

Step 1. Three mixtures of 3-formylbenzoic acid (0.20, 0.10, and 0.10 g, 1.3, 0.65, and 0.65 mmol), THF (10, 5, and 5 mL), EDCI (0.51, 0.25, and 0.25 g, 2.7, 1.4, and 1.4 mmol), HOBt (0.36, 0.18, and 0.18 g, 2.7. 1.4, and 1.4 mmol), Et₃N (0.56, 0.28, and 0.28 mL, 4.0, 2.0, and 2.0 mmol) were stirred at this 20° C. for 0.5 h, and then B-14 (0.41, 0.21, 0.21 g, 1.3, 0.65, and 0.65 mmol) was added to the mixtures and they were stirred at 20° C. for 12 h. The mixtures were combined, poured into water (20 mL), and extracted with CH₂Cl₂ (2×20 mL). The combined extracts were washed with brine (10 mL), dried over Na₂SO₄, concentrated, and purified by silica chromatography (20-100% EtOAc in PE) to provide N-(1"-(3-formylbenzoyl)dispiro[cyclopropane-1,1'-cyclohexane-4',3"-indolin]-5"-yl)methanesulfonamide (0.36 g).

Step 2. A mixture of N-(1"-(3-formylbenzoyl)dispiro[cyclopropane-1,1'-cyclohexane-4',3"-indolin]-5"-yl)methanesulfonamide (0.31 g, 0.73 mmol), EtOAc (3 mL), TFA (81 µg, 1.1 mmol), and piperidin-1-amine (0.47 g, 4.4 mmol) was stirred at 80° C. for 12 h. The mixture was concentrated, added to water (30 mL), and extracted with EtOAc (2×30 mL), and the combined extracts were washed with brine (10 mL), dried over Na₂SO₄, concentrated, and purified by preparative HPLC (C18, 40-80% MeCN in H₂O [formic acid]) to provide N-(1"-(3-((piperidin-1-ylimino)methyl)benzoyl)dispiro[cyclopropane-1,1'-cyclohexane-4',3"-indolin]-5"-yl)methanesulfonamide (0.17 g).

Synthetic Example S-016

Preparation of N-(1"-(3-(1-cyclopentyl-1-hydroxyethyl)benzoyl)dispiro[cyclopropane-1,1'-cyclohexane-4',3"-indolin]-5"-yl)methanesulfonamide (Compound 331)

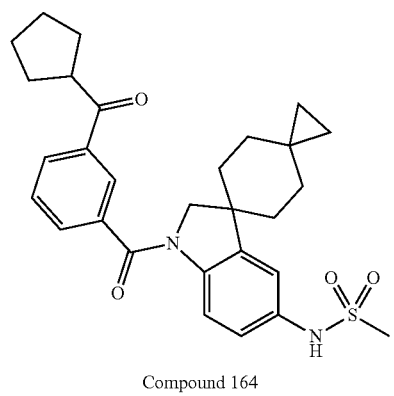

Compound 164

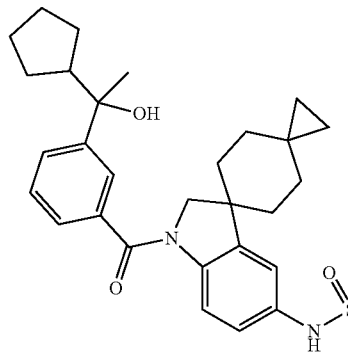

Compound 331

To Compound 164 (50 mg, 99 µmol) in THF (1 mL) was added MeMgBr (3 M, 99 uL, 0.30 mmol) at 0° C. The mixture was stirred at 20° C. for 2 h, poured into H₂O (3 mL), concentrated, and purified by preparative HPLC (40-80% MeCN in H₂O [formic acid]) to provide N-(1"-(3-(1-cyclopentyl-1-hydroxyethyl)benzoyl)dispiro[cyclopropane-1,1'-cyclohexane-4',3"-indolin]-5"-yl)methanesulfonamide (Compound 331, 6 mg).

Synthetic Example S-017

Preparation of N-(tert-butyl)-3-(5"-(1-hydroxyethyl)dispiro[cyclopropane-1,1'-cyclohexane-4',3"-indoline]-1"-carbonyl)benzenesulfonamide (Compound 332)

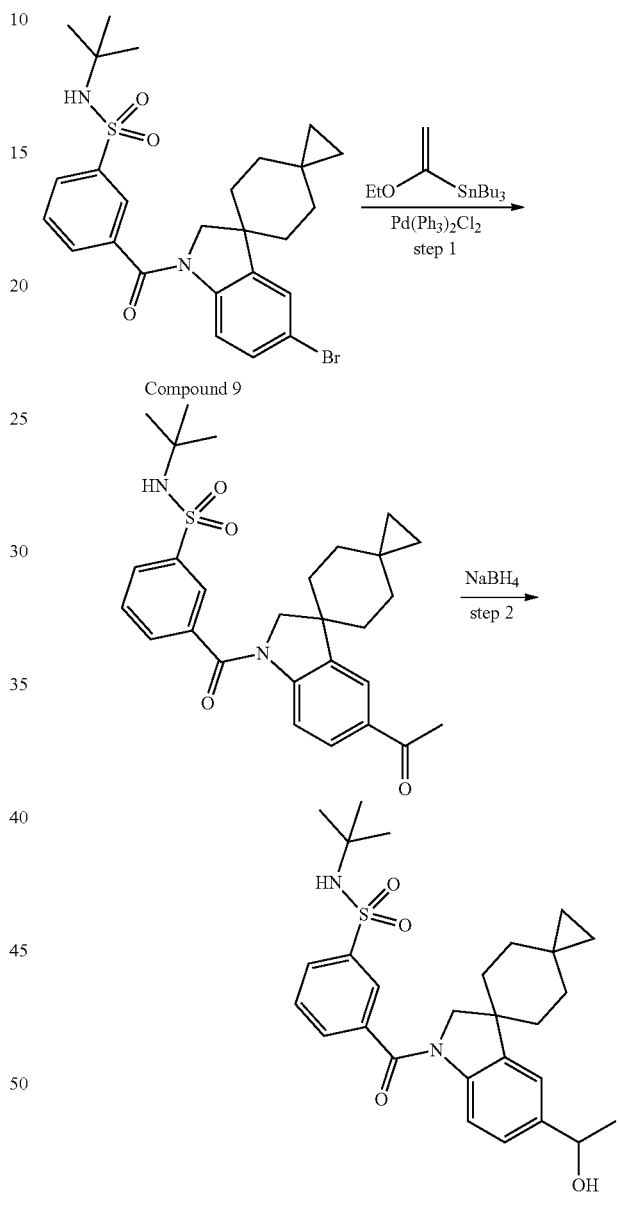

Step 1. A degassed mixture of Compound 9 (0.20 g, 0.38 mmol), tributyl(1-ethoxyvinyl)stannane (0.19 mL, 0.56 mmol), Pd(PPh₃)₂Cl₂ (53 mg, 75 µmol), CsF (0.11 g, 0.75 mmol), and dioxane (4 mL) was stirred at 130° C. for 2 h under an N₂ atmosphere. A solution of KF (0.10 g) in H₂O (20 mL) and the mixture was stirred at 20° C. for 0.5 h. The mixture was extracted with EtOAc (20×2 mL), and the combined extracts were washed with brine (10 mL), dried over Na₂SO₄, filtered, concentrated, and purified by silica chromatography (0-50% EtOAc in PE) to provide 3-(5"- acetyldispiro[cyclopropane-1,1'-cyclohexane-4',3"-indoline]-1"-carbonyl)-N-(tert-butyl)benzenesulfonamide (0.11 g).

Step 1. To a mixture of 3-(5"-acetyldispiro[cyclopropane-1,1'-cyclohexane-4',3"-indoline]-1"-carbonyl)-N-(tert-butyl)benzenesulfonamide (0.11 g, 0.22 mmol) and MeOH (10 mL) was added NaBH₄ (25 mg, 0.67 mmol) slowly at 0° C. The mixture was stirred at 0° C. for 3 h, poured into saturated NH₄Cl (20 mL), and extracted with EtOAc (2×10 mL). The combined extracts were washed with brine (10 mL), dried over Na₂SO₄, concentrated, and purified by preparative HPLC (C18, 45-75% MeCN in H₂O [formic acid]) to provide N-(tert-butyl)-3-(5"-(1-hydroxyethyl)dispiro[cyclopropane-1,1'-cyclohexane-4',3"-indoline]-1"-carbonyl)benzenesulfonamide (Compound 332, 25 mg).

Synthetic Example S-018

Preparation of N-(1"-(3-((cyclobutylmethyl)sulfonyl)benzoyl)dispiro[cyclopropane-1,1'-cyclohexane-4',3"-indolin-5"-yl)methanesulfonamide (Compound 335)

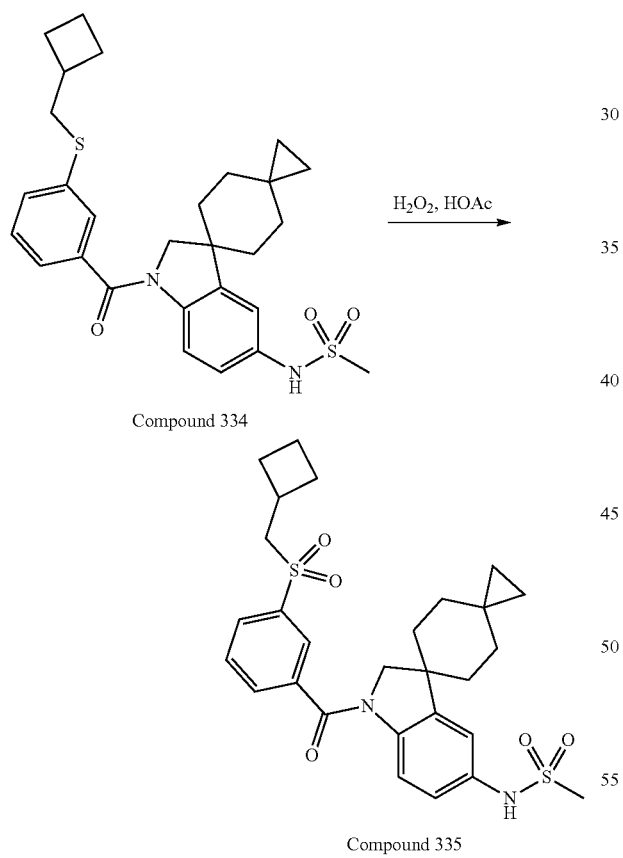

A mixture of Compound 334 (0.20 g, 0.39 mmol), HOAc (2 mL), and 30% H₂O₂ (0.11 mL, 1.2 mmol) was stirred at 20° C. for 2 h. The mixture was combined with saturated Na₂SO₃ (20 mL) and H₂O (30 mL) and extracted with EtOAc (2×30 mL). The combined extracts were washed with brine (10 mL), dried over Na₂SO₄, concentrated, and purified by preparative HPLC (C18, 35-65% MeCN in H₂O [formic acid]) to provide N-(1"-(3-((cyclobutylmethyl)sulfonyl)benzoyl)dispiro[cyclopropane-1,1'-cyclohexane-4',3"-indolin]-5"-yl)methanesulfonamide (Compound 335, 76 mg, 35.40% yield, 99.00% purity) as a white solid.

Synthetic Example S-019

Preparation of N-(tert-butyl)-3-(5"-(2,2,2-trifluoro-1-hydroxyethyl)dispiro[cyclopropane-1,1'-cyclohexane-4',3"-indoline]-1"-carbonyl)benzenesulfonamide (Compound 338)

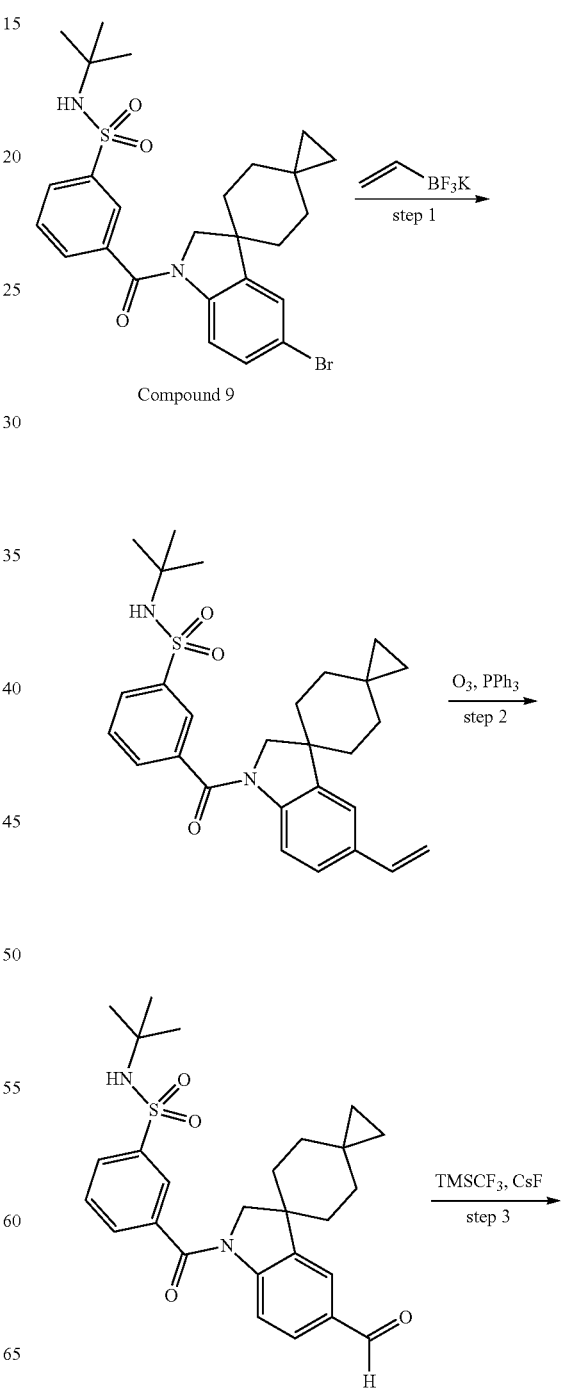

527
-continued

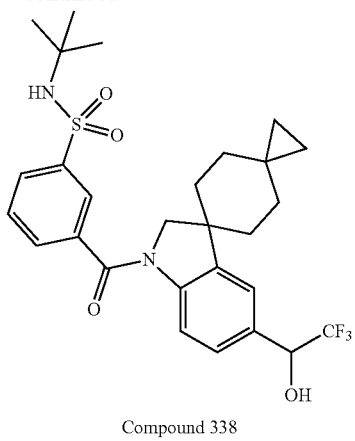

Compound 338

Step 1. A degassed mixture of Compound 9 (0.50 g, 0.94 mmol) and KBF$_3$ (vinyl) (0.63 g, 4.7 mmol), K$_2$CO$_3$ (0.65 g, 4.7 mmol), PdCl$_2$ (0.12 g, 0.66 mmol), and DMSO (5 mL) was stirred at 100° C. for 3 h under an N$_2$ atmosphere. The mixture was poured into H$_2$O (20 mL, extracted with CH$_2$Cl$_2$ (2×20 mL), and the combined extracts were washed with brine (10 mL), dried over Na$_2$SO$_4$, concentrated, purified by silica chromatography (30-50% EtOAc in PE) to provide N-(tert-butyl)-3-(5"-vinyldispiro[cyclopropane-1,1'-cyclohexane-4',3"-indoline]-1"-carbonyl)benzenesulfonamide (0.32 mg).

Step 2. A mixture of N-(tert-butyl)-3-(5"-vinyldispiro [cyclopropane-1,1'-cyclohexane-4',3"-indoline]-1"-carbonyl)benzenesulfonamide (0.32 g, 0.67 mmol), CH$_2$Cl$_2$ (10 mL), and MeOH (10 mL) was treated with O3 (32 mg, 669 umol, 1.0 eq) for 0.5 hour at 0° C. The solution was purged with O2 (21 mg, 669 umol, 1.0 eq) for 0.5 hour at 0° C., then stirred with PPh$_3$ (0.35 g, 1.3 mmol) for 1 h at 20° C., poured into H$_2$O (20 mL), and extracted with CH$_2$Cl$_2$ (2×20 mL). The combined extracts were washed with brine (10 mL), dried over Na$_2$SO$_4$, concentrated, and purified by silica chromatography (30-50% EtOAc in PE) to provide N-(tert-butyl)-3-(5"-formyldispiro[cyclopropane-1,1'-cyclohexane-4',3"-indoline]-1"-carbonyl)benzenesulfonamide (0.25 g).

Step 3. To a mixture of N-(tert-butyl)-3-(5"-formyldispiro [cyclopropane-1,1'-cyclohexane-4',3"-indoline]-1"-carbonyl)benzenesulfonamide (0.15 g, 0.31 mmol) and DMF (2 mL) were added TMSCF$_3$ (89 mg, 0.62 mmol) and CsF (95 mg, 0.62 mmol) at 50° C. The mixture was stirred at 50° C. for 12 h, concentrated, added to H$_2$O (30 mL), and extracted with EtOAc (2×30 mL). The combined extracts were washed with brine (10 mL), dried over Na$_2$SO$_4$, concentrated, and purified by preparative HPLC(C18, 35-75% MeCN in H$_2$O [formic acid]) to provide N-(tert-butyl)-3-(5"-(2,2,2-trifluoro-1-hydroxyethyl)dispiro[cyclopropane-1, 1'-cyclohexane-4',3"-indoline]-1"-carbonyl)benzenesulfonamide (Compound 338, 11 mg).

528

Synthetic Example S-20

Preparation of N-(1"-(3-((3,3-difluoroazetidin-1-yl)methyl)benzoyl)dispiro[cyclopropane-1,1'-cyclohexane-4',3"-indolin]-5"-yl)methanesulfonamide (Compound 345)

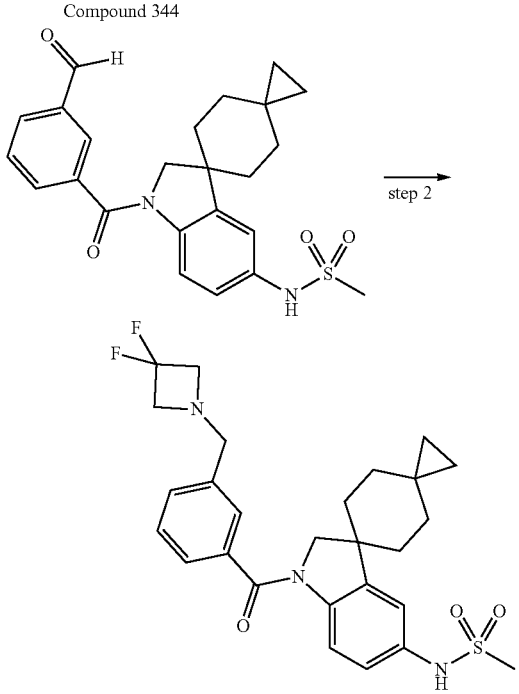

Compound 345

Step 1. A mixture of Compound 344 (0.28 g, 0.64 mmol), CH$_2$Cl$_2$ (5 mL), and PCC (0.27 g, 1.3 mmol) was stirred at 20° C. for 2 h, diluted with CH$_2$Cl$_2$ (10 mL), washed with H$_2$O (5 mL), saturated aqueous NaHCO$_3$ (5 mL), brine (5 mL), then dried over Na$_2$SO$_4$, concentrated, and purified by flash silica chromatography (0-50% EtOAc in PE) to provide N-(1"-(3-formylbenzoyl)dispiro[cyclopropane-1,1'-cyclohexane-4',3"-indolin]-5"-yl)methanesulfonamide (0.18 g).

Step 2. A mixture of N-(1"-(3-formylbenzoyl)dispiro[cyclopropane-1,1'-cyclohexane-4',3"-indolin]-5"-yl)methanesulfonamide (0.10 g, 0.23 mmol), MeOH (1 mL), THF (1 mL), 3,3-difluoroazetidine hydrochloride (44 mg, 0.34 mmol), and HOAc (26 µL, 0.46 mmol) was stirred at 20° C. for 2 h and NaBH$_3$CN (43 mg, 0.68 mmol) was added and the mixture was stirred at 20° C. for 10 h. The mixture was treated with H$_2$O (5 mL) at 0° C. and extracted with CH$_2$Cl$_2$ (10 mL). The combined extracts were washed with H₂O (10 mL) and brine (10 mL), dried over Na₂SO₄, concentrated, and purified by preparative HPLC (C18, 25-65% MeCN in H₂O [formic acid]) to provide N-(1"-(3-((3,3-difluoroazetidin-1-yl)methyl)benzoyl)dispiro[cyclopropane-1,1'-cyclohexane-4',3"-indolin]-5"-yl)methanesulfonamide (Compound 345, 6 mg).

Synthetic Example S-21

Preparation of 2-methyl-N-(3-(5"-(methylsulfonamido)dispiro[cyclopropane-1,1'-cyclohexane-4',3"-indoline]-1"-carbonyl)phenyl)propane-2-sulfonamide (Compound 355)

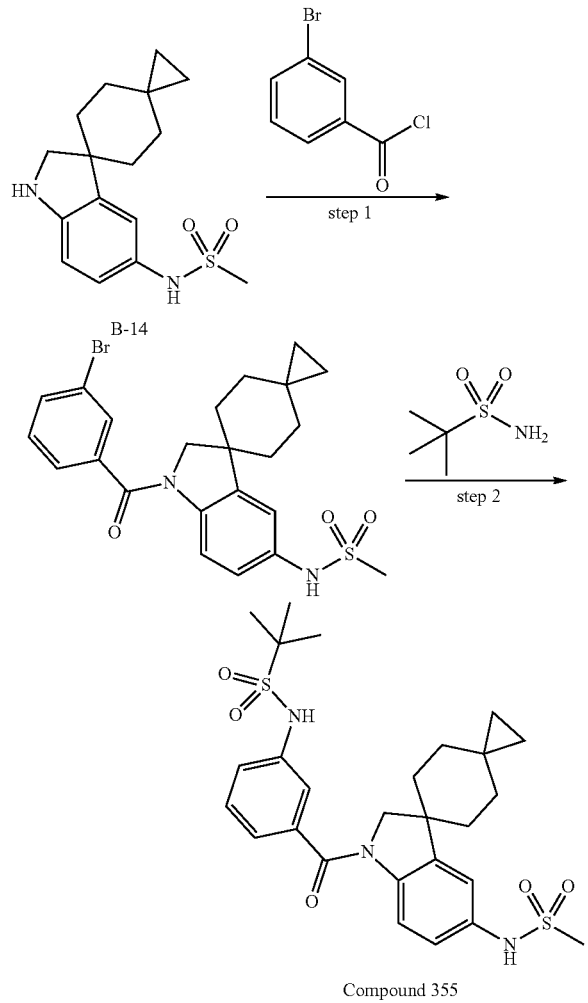

Compound 355

Step 1. A mixture of B-14 (0.20 g, 0.65 mmol), CH₂Cl₂ (4 mL), iPr₂NEt (0.34 mL, 2.0 mmol) and 3-bromobenzoyl chloride (0.10 mL, 0.78 mmol) was stirred at 20° C. for 1 h and then concentration and poured into water (5 mL). The resulting mixture was extracted with EtOAc (10 mL×2) and the combined extracts were washed with brine (10 mL), dried over Na₂SO₄, concentrated, and purified by silica chromatography (10-100% EtOAc in PE) to provide N-(1"-(3-bromobenzoyl)dispiro[cyclopropane-1,1'-cyclohexane-4',3"-indolin]-5"-yl)methanesulfonamide (0.21 g).

Step 2. A degassed mixture of N-(1"-(3-bromobenzoyl)dispiro[cyclopropane-1,1'-cyclohexane-4',3"-indolin]-5"-yl)methanesulfonamide (0.10 g, 0.20 mmol), 2-methylpropane-2-sulfonamide (0.11 g, 0.82 mmol), CuI (78 mg, 0.41 mmol), N₁,N₂-dimethylcyclohexane-1,2-diamine dihydrochloride (88 mg, 0.41 mmol), K₃PO₄ (0.13 g, 0.61 mmol), and DMF (2 mL) was stirred at 160° C. for 2 h under an N₂ atmosphere. The mixture was poured into water (10 mL), extracted with EtOAc (10 mL×2), and the combined extracts were washed with brine (10 mL), dried over Na₂SO₄, concentrated, and purified by preparative HPLC (C18, 35-65% MeCN in H₂O [NH₄CO₃]) to provide 2-methyl-N-(3-(5"-(methylsulfonamido)dispiro[cyclopropane-1,1'-cyclohexane-4',3"-indoline]-1"-carbonyl)phenyl)propane-2-sulfonamide (Compound 355, 16 mg).

Synthetic Example S-22

Preparation of N-(1"-(3-(1-hydroxy-3,3-dimethylbutyl)benzoyl)dispiro[cyclopropane-1,1'-cyclohexane-4',3"-indolin]-5"-yl)methanesulfonamide (Compound 357)

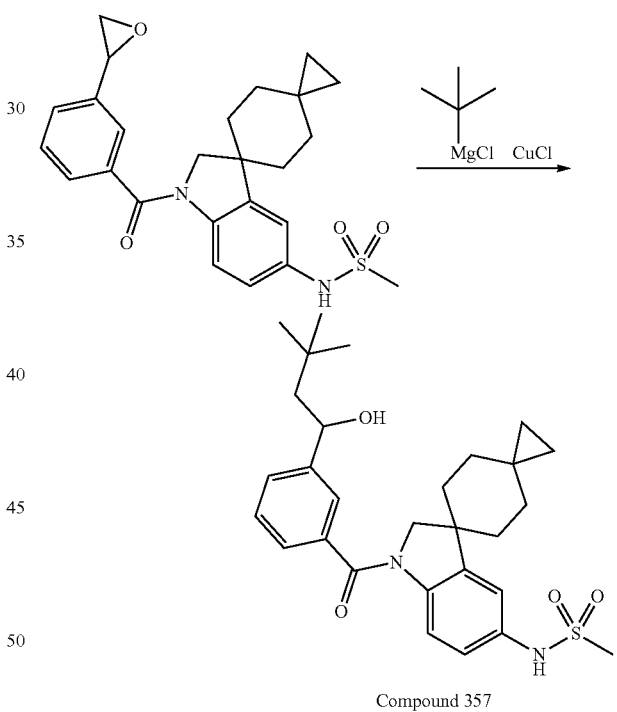

Compound 357

To mixture of N-(1"-(3-(oxiran-2-yl)benzoyl)dispiro[cyclopropane-1,1'-cyclohexane-4',3"-indolin]-5"-yl)methanesulfonamide (50 mg, 0.11 mmol), CuCl₂ (15 mg, 0.11 mmol), LiCl (5 mg, 0.11 mmol), and THF (1 mL) was added dropwise t-BuMgCl (1 M, 0.44 mL). The mixture was stirred at 20° C. for 2 h, poured into saturated aqueous NH₄Cl (20 mL), and extracted with EtOAc (2×20 mL). The combined extracts were washed with brine (10 mL), dried over Na₂SO₄, concentrated, and purified by preparative HPLC (C18, 45-85% MeCN in H₂O [formic acid]) to provide N-(1"-(3-(1-hydroxy-3,3-dimethylbutyl)benzoyl)dispiro[cyclopropane-1,1'-cyclohexane-4',3"-indolin]-5"-yl)methanesulfonamide (8.0 mg).

Synthetic Example S-23

Preparation of N-(tert-butyl)-3-(5"-((2-fluoroethyl)sulfonamido)dispiro[cyclopropane-1,1'-cyclohexane-4',3"-indoline]-1"-carbonyl)benzenesulfonamide (Compound 365)

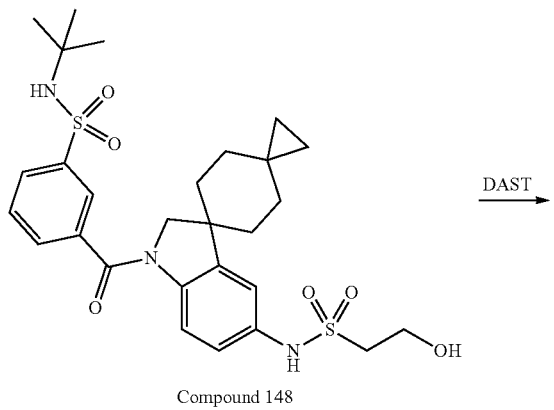

Compound 148

DAST →

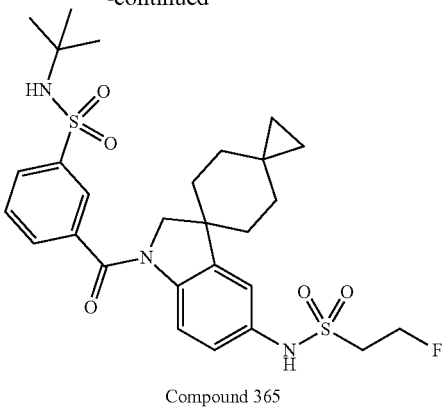

Compound 365

To a mixture of Compound 148 (50 mg, 87 μmol) in $CH_2Cl_2$ (1.5 mL) was added DAST (23 μL, 0.18 mmol) at 0° C. The mixture was stirred at 20° C. for 1 h under $N_2$, poured into $H_2O$ (30 mL), and extracted with EtOAc (2×30 mL). The combined extracts were washed with brine (10 mL), dried over $Na_2SO_4$, concentrated, purified by preparative HPLC (C18, 45-75% MeCN in $H_2O$ [formic acid]) to provide N-(tert-butyl)-3-(5"-((2-fluoroethyl)sulfonamido)dispiro[cyclopropane-1,1'-cyclohexane-4',3"-indoline]-1"-carbonyl)benzenesulfonamide (Compound 365, 13 mg).

Table 7c describes the chromatography separation of isomers for specific examples.

TABLE 7c

| Compound | Conditions | First | Purity % | Second | Purity % |
|---|---|---|---|---|---|
| 24 | Chiralpak AD (250 mm × 30 mm, 10 μm) 15-40% [0.1% $NH_3/H_2O$ in iPrOH] in supercritical $CO_2$ | 24a | 100% (er) | 24b | 99.5% (er) |
| 140 | Chiralpak AD (250 mm × 30 mm, 10 μm) 45-75% [0.1% $NH_3/H_2O$ in EtOH] in supercritical $CO_2$ | 140a | 100% | 140b | 99.5% |
| 162 | Phenomenex Luna C18 (200 × 40 mm, 10 μm) 30-60% MeCN in $H_2O$ [0.1M formic acid] | 162a | 100% | 162b | 100% |
| 165 | Chiralpak AD (250 mm × 30 mm, 10 μm) 35% [0.1% $NH_3/H_2O$ in EtOH] in supercritical $CO_2$ | 165a | >99.5% (er) | 165b | 98.9% (er) |
| 249 | Chiralpak OD (250 mm × 30 mm, 10 μm) 45% [0.1% $NH_3/H_2O$ in iPrOH] in supercritical $CO_2$ | (R)-249 | 100% (er) | (S)-249 | 98.9% (er) |
| 287 | Regis (S,S)-Whelk-O ®1 (250 mm × 25 mm, 10 μm) 60% EtOH in supercritical $CO_2$ | 287a | 99.7% (er) | 287b | 97.8% (er) |
| 305 | Chiralcel OD (250 mm × 30 mm, 10 μm) 44% [0.1% $NH_3/H_2O$ in EtOH] in supercritical $CO_2$ | 305a | 99.7% (er) | 205b | 99.0% (er) |
| 313 | Chiralpak AD (250 mm × 30 mm, 10 μm) 35% [0.1% $NH_3/H_2O$ in EtOH] in supercritical $CO_2$ | 313a | >99.5% (er) | 313b | 99.2% (er) |
| 316 | Chiralcel OD (250 mm × 30 mm, 10 μm) 45% [0.1% $NH_3/H_2O$ in iPrOH] in supercritical $CO_2$ | 316a | >99.5% (er) | 316b | 99.7% (er) |
| 317 | Chiralcel OD (250 mm × 30 mm, 10 μm) 40% [0.1% $NH_3/H_2O$ in iPrOH] in supercritical $CO_2$ | 317a | >99.5% (er) | 317b | 98.7 (er) |

TABLE 7c-continued

| Compound | Conditions | First | Purity % | Second | Purity % |
|---|---|---|---|---|---|
| 333 | Phenomenex Luna C18 (100 × 40 mm, 3 μm) 20-60% MeCN in H$_2$O [0.1M formic acid] | 333a | 100% | 333b | 100% |
| 336 | Phenomenex Luna C18 (200 × 40 mm, 10 μm) 45-80% MeCN in H$_2$O [0.1M formic acid] | 336a | 100% | 336b | 100% |
| 338 | Chiralpak AD (250 mm × 30 mm, 10 μm) 27-75% [0.1% NH$_3$/H$_2$O in EtOH] in supercritical CO$_2$ | 338a | >99.9% (er) | 338b | 99.2% (er) |
| 341 | Chiralpak AD (250 mm × 30 mm, 10 μm) 25% [0.1% NH$_3$/H$_2$O in iPrOH] in supercritical CO$_2$ | 341a | >99.9% (er) | 341b | 99.8% (er) |
| 351 | Chiralpak IC (250 mm × 30 mm, 10 μm) 50% [0.1% NH$_3$/H$_2$O in iPrOH] in supercritical CO$_2$ | 351a | 99.9% (er) | 351a | 99.2% (er) |
| 352 | Chiralpak AD (250 mm × 30 mm, 10 μm) 40% [0.1% NH$_3$/H$_2$O in EtOH] in supercritical CO$_2$ | 352a | >99.9% (er) | 352b | >99.95% (er) |
| 367 | Chiralpak AD (250 mm × 30 mm, 10 μm) 40% [0.1% NH$_3$/H$_2$O in EtOH] in supercritical CO$_2$ | 367a | >99.9% (er) | 367b | >99.9% (er) |
| 368 | Chiralpak AD (250 mm × 30 mm, 10 μm) 40% [0.1% NH$_3$/H$_2$O in EtOH] in supercritical CO$_2$ | 368a | >99.9% (er) | 368b | >99.9% (er) |
| 371 | Chiralpak AD (250 mm × 30 mm, 10 μm) 22% [0.1% NH$_3$/H$_2$O in EtOH] in supercritical CO$_2$ | 371a | >99.9% (er) | 371b | 98.6% (er) |
| 372 | Chiralcel OJ (250 mm × 30 mm, 10 μm) 30% [0.1% NH$_3$/H$_2$O in MeOH] in supercritical CO$_2$ | 372a | >99.9% (er) | 372b | 99.9% (er) |
| 373 | Chiralpak AD (250 mm × 30 mm, 10 μm) 30% [0.1% NH$_3$/H$_2$O in EtOH] in supercritical CO$_2$ | 373a | >99.9% (er) | 373b | 99.3% (er) |

TABLE 8

| Compound | ESI MS (M/z) | NMR summary (400 MHz) ppm |
|---|---|---|
| Compound 1 | 479.2 (M + H) | (DMSO-d$^6$) δ 7.98 (dt, J = 15.13, 7.44 Hz, 4H), 7.86-7.77 (m, 1H), 7.29 (br s, 1H), 6.94 (br t, J = 8.94 Hz, 1H), 3.85 (br s, 2H), 3.33 (s, 1H), 3.15 (br d, J = 5.00 Hz, 4H), 2.14-1.96 (m, 6H), 1.86 (br s, 2H), 1.77 (br s, 2H), 1.56 (br s, 2H). |
| Compound 2 | | (DMSO-d$^6$) δ 8.11-7.89 (m, 3H), 7.85-7.77 (m, 1H), 7.51 (d, J = 2.00 Hz, 2H), 3.82 (br s, 2H), 3.21-3.09 (m, 4H), 2.16-1.98 (m, 4H), 1.91-1.70 (m, 6H), 1.66-1.43 (m, 2H) |
| Compound 3 | 461.1 (M + H)$^+$ | (DMSO-d$^6$) δ 8.33-7.83 (m, 3H), 7.45-6.95 (m, 3H), 3.85-3.72 (m, 2H), 3.12 (br d, J = 4.88 Hz, 4H), 2.13-1.98 (m, 4H), 1.87-1.69 (m, 6H), 1.65-1.48 (m, 2H). |
| Compound 4 | 501.1 (M + H)$^+$ | (DMSO-d$^6$) δ 7.88-8.27 (m, 4 H) 7.77-7.85 (m, 1 H) 7.31 (br d, J = 7.82 Hz, 1 H) 6.98-7.30 (m, 1 H) 6.98-7.30 (m, 1 H) 3.89 (br s, 2 H) 3.13 (br s, 4 H) 2.01-2.12 (m, 4 H) 1.36-1.90 (m, 6 H) 0.85 (br d, J = 10.64 Hz, 2 H) 0.26 (br s, 4 H) |
| Compound 6 | 465.1 (M + H)$^+$ | (DMSO-d$^6$) δ 8.21-7.86 (m, 4H) 7.83-7.73 (m, 1H), 7.31 (d, J = 7.88 Hz, 2H) 7.11 (br d, J = 2.25 Hz, 1H), 3.92 (br s, 2 H) 2.98-2.88 (m, 4H), 1.77-1.62 (m, 5 H), 1.55 (br s, 5H), 1.41-1.32 (m, 2H), 0.93-0.79 (m, 2H), 0.33-0.20 (m, 4H). |
| Compound 8 | 451.1 (M + H)$^+$ | (DMSO-d$^6$) δ 8.22-7.85 (m, 4H), 7.80-7.73 (m, 1H), 7.30 (d, J = 8.38 Hz, 2H), 7.10 (m, 1H), 3.95-3.82 (m, 2H), 3.18 (br s, 4H), 1.79-1.50 (m, 10H), 0.93-0.78 (m, 4H), 0.34-0.17 (m, 4H). |
| Compound 9 | | (DMSO-d$^6$) δ 8.04 (s, 1H), 7.99 (d, J = 7.2 Hz 2H), 7.85 (d, J = 7.2 Hz, 1H), 7.73-7.69 (t, J = 7.2 Hz, 1H), 7.67 (s, 1H), 7.51 (s, 1H), 7.41 (br s, 1H), 3.90 (s, 2H), 1.77-1.74 (m, 2H), 1.65-1.62 (m, 4H), 1.11 (s, 9H), 0.84-0.81 (br d, J = 12.8 Hz, 2H), 0.26 (m, 4H) |

TABLE 8-continued

| Compound | ESI MS (M/z) | NMR summary (400 MHz) ppm |
|---|---|---|
| Compound 10 | 453.1 (M + H)+ | (DMSO-d6) δ 8.19-7.92 (m, 3H) 7.83 (br d, J = 5.63 Hz, 1H) 7.75-7.60 (m, 2H), 7.31 (d, J = 8.25 Hz, 2H), 7.10 (br s, 1H), 3.92-3.83 (m, 2H), 1.81-1.55 (m, 6H), 1.10 (s, 9H) 0.88-0.81 (m, 2H), 0.26 (br s, 4H) |
| Compound 15 | 567.0 (M + H)+ | (DMSO-d6) δ 8.12-7.91 (m, 4H), 7.87-7.76 (m, 1H), 7.66 (s, 1H), 7.53-7.35 (m, 1H), 3.92-3.75 (m, 2H), 3.19-3.06 (m, 4H), 2.15-1.99 (m, 4H), 1.85-1.77 (m, 1H), 1.71-1.31 (m, 8H), 1.04 (br d, J = 6.8 Hz, 1H), 0.90-0.73 (m, 3H) |
| Compound 18 | 554.0 (M + H)+ | (CD3OD) δ 8.23-7.96 (m, 3H), 7.93 (br d, J = 5.63 Hz, 1H), 7.85-7.77 (m, 1H), 7.32-6.96 (m, 2H), 4.09-3.83 (m, 2H), 3.26 (br s, 4H), 2.96 (br s, 3H), 2.18-2.04 (m, 4H), 1.89 (br s, 6H), 1.80-1.57 (m, 2H). |
| Compound 19 | 568.1 (M + H)+ | (DMSO-d6) δ 9.57 (br s, 1H), 8.09-8.08 (m, 1H), 8.10-7.89 (m, 4H), 7.87-7.75 (m, 1H), 7.11 (s, 2H), 3.84 (br s, 2H), 3.13 (br s, 4H), 2.94 (s, 3H), 2.14-1.97 (m, 4H), 1.77-1.45 (m, 8H), 1.24 (br s, 1H), 1.13 (br d, J = 14.26 Hz, 1H) |
| Compound 20 | 558.1 (M + H)+ | (DMSO-d6) δ 9.58 (br d, J = 2.13 Hz, 1H), 8.12-7.84 (m, 4H), 7.82-7.75 (m, 1H), 7.13 (d, J = 1.75 Hz, 2H), 3.92 (br s, 2H), 2.94 (s, 7H), 1.72-1.49 (m, 10H), 1.37 (br d, J = 5.00 Hz, 2H), 0.96-0.79 (m, 2H), 0.35-0.19 (m, 4H). |
| Compound 21 | 544.1 (M + H)+ | (DMSO-d6) δ 9.58 (br s, 1H), 8.11-7.89 (m, 4H), 7.82-7.73 (m, 1H), 7.18-7.03 (m, 2H), 3.90 (br d, J = 2.88 Hz, 2H), 3.22-3.16 (m, 4H), 2.94 (s, 3H), 1.74-1.49 (m, 10H), 0.94-0.80 (m, 2H), 0.28 (br s, 4H). |
| Compound 22 | 546.1 (M + H)+ | (DMSO-d6) δ 9.58 (br s, 1H), 8.11-7.91 (m, 3H), 7.88-7.67 (m, 1H), 7.74-7.59 (m, 2H), 7.14 (d, J = 1.88 Hz, 2H) 3.88 (br d, J = 1.63 Hz, 2H), 2.94 (s, 3H), 1.74-1.49 (m, 6H), 1.11 (s, 9H), 0.94-0.80 (m, 2H), 0.34-0.18 (m, 4H). |
| Compound 23 | 568.1 (M + H)+ | (DMSO-d6) δ 9.67-9.54 (m, 1H), 8.17-7.89 (m, 4H), 7.86-7.73 (m, 1H), 7.02 (br d, J = 3.5 Hz, 2H), 3.96-3.75 (m, 2H), 3.22-3.06 (m, 4H), 2.95 (s, 3H), 2.16-2.01 (m, 6H), 1.99-1.90 (m, 2H), 1.85-1.77 (m, 1H), 1.72-1.61 (m, 1H), 1.47-1.28 (m, 1H), 1.20-1.08 (m, 1H), 1.07-0.92 (m, 3H) |
| Compound 24 | 582.1 (M + H)+ | (DMSO-d6) δ 9.24-9.51 (m, 1H), 7.72-8.05 (m, 4H), 7.35-7.42 (m, 1H), 7.19-6.99 (m, 2H), 3.95-3.70 (m, 2H), 3.28-3.18 (m, 3H), 2.99-2.91 (m, 4H), 2.17-1.98 (m, 4H), 1.77-1.57 (m, 6H), 1.52-1.35 (m, 2H), 1.04 (d, J = 6.7 Hz, 1H), 0.91-0.76 ppm (m, 3H) |
| Compound 24a | 582.1 (M + H)+ | (DMSO-d6) δ 9.52 (s, 1H), 8.15-7.89 (m, 4H), 7.86-7.73 (m, 1H), 7.35 (d, J = 1.9 Hz, 1H), 7.22-7.03 (m, 1H), 3.88-3.67 (m, 2H), 3.19-3.07 (m, 4H), 2.95 (s, 3H), 2.14-2.00 (m, 5H), 1.81-1.70 (m, 2H), 1.66-1.57 (m, 1H), 1.54-1.34 (m, 6H), 1.06-0.96 (m, 3H) |
| Compound 24b | 582.1 (M + H)+ | (DMSO-d6) δ 9.65-9.54 (m, 1H), 8.12-7.89 (m, 4H), 7.84-7.77 (m, 1H), 7.09 (d, J = 1.9 Hz, 2H), 3.95-3.75 (m, 2H), 3.19-3.09 (m, 4H), 2.94 (s, 3H), 2.13-1.96 (m, 5H), 1.74-1.52 (m, 7H), 1.47-1.37 (m, 2H), 0.87-0.75 (m, 3H) |
| Compound 25 | 530.1 (M + H)+ | (DMSO-d6) δ 8.32-8.09 (m, 1H), 8.03-7.87 (m, 2H), 7.80 (br d, J = 7.25 Hz, 1H), 7.74-7.63 (m, 1H), 7.19-7.12 (m, 1H), 7.10-6.93 (m, 1H), 6.49-6.37 (m, 1H), 3.99-3.70 (m, 2H), 3.63-3.49 (m, 2H), 3.22-3.08 (m, 2H), 3.04-2.93 (m, 3H), 1.80-1.62 (m, 8H), 1.50-1.44 (m, 2H), 1.38-1.23 (m, 2H), 0.66-0.56 (m, 1H), 0.39-0.31 (m, 1H) |
| Compound 26 | 520.1 (M + H)+ | (DMSO-d6) δ 8.32-7.92 (m, 3H), 7.81-7.70 (m, 1H), 7.68-7.57 (m, 1H), 7.21-7.11 (m, 1H), 7.08-6.90 (m, 1H), 6.65-6.43 (m, 1H), 4.85-4.51 (m, 1H), 4.06-3.65 (m, 2H), 3.07-2.91 (m, 3H), 1.71 (br d, J = 11.88 Hz, 10H), 1.28-1.21 (m, 9H) |
| Compound 27 | 558.1 (M + H)+ | (DMSO-d6) δ 8.10 (br d, J = 2.13 Hz, 4H), 7.84-7.69 (m, 1H), 7.21-6.94 (m, 2H), 3.91-3.76 (m, 2H), 3.73 (br t, J = 6.57 Hz, 2H), 3.19-3.05 (m, 6H), 2.14-1.99 (m, 4H), 1.92-1.69 (m, 6H), 1.63-1.44 (m, 2H). |
| Compound 28 | 594.1 (M + H)+ | (DMSO-d6) δ 9.68-9.48 (m, 1H), 8.21-7.88 (m, 1H), 8.15-7.88 (m, 3H), 7.86-7.74 (m, 1H), 7.13 (br d, J = 1.75 Hz, 2H), 4.02-3.79 (m, 2H), 3.13 (br s, 4H), 3.02-2.84 (m, 3H), 2.17-1.97 (m, 3H), 2.15-1.96 (m, 1H), 1.76-1.62 (m, 1H), 1.74-1.48 (m, 1H), 1.67 (br s, 4H), 0.93-0.78 (m, 2H), 0.27 (br s, 3H), 0.37-0.12 (m, 1H) |
| Compound 29 | 624.0 (M + H)+ | (DMSO-d6) δ 8.17 (br d, J = 7.25 Hz, 1H), 8.03-7.89 (m, 2H), 7.84 (br d, J = 7.50 Hz, 1H), 7.75-7.67 (m, 1H), 7.25 (d, J = 1.88 Hz, 1H), 7.20-6.99 (m, 1H), 6.67 (br s, 1H), 4.13 (br t, J = 4.88 Hz, 1H), 3.89 (br s, 2H), 3.25 (br s, 6H), 2.51 (br s, 1H), 2.18-2.03 (m, 4H), 1.90-1.80 (m, 2H), 1.69 (br d, J = 12.26 Hz, 4H), 0.94 (br d, J = 11.76 Hz, 2H), 0.32 (br s, 4H) |
| Compound 30 | 544.1 (M + H)+ | (DMSO-d6) δ 8.39-8.30 (m, 1H), 8.01-7.83 (m, 3H), 7.82-7.75 (m, 1H), 8.02-7.73 (m, 1H), 6.49 (d, J = 2.13 Hz, 1H), 6.44 (br d, J = 8.00 Hz, 1H), 5.50-5.39 (m, 1H), 3.84-3.75 (m, 1H), 3.79 (s, 1H), 3.16-3.09 (m, 1H), 3.16-3.08 (m, 1H), 3.13 (br s, 2H), 3.07-2.98 (m, 2H), 2.14-1.98 (m, 4H), 1.75-1.47 (m, 6H), 1.16 (br t, J = 7.00 Hz, 2H), 1.22-1.03 (m, 1H), 0.83 (br d, J = 12.76 Hz, 2H), 0.41-0.16 (m, 1H), 0.23 (br d, J = 6.13 Hz, 3H) |

TABLE 8-continued

| Compound | ESI MS (M/z) | NMR summary (400 MHz) ppm |
|---|---|---|
| Compound 31 | 546.1 (M + H)+ | (DMSO-d6) δ 7.92-8.02 (m, 2H), 7.81-7.74 (m, 1H), 7.72-7.64 (m, 1H), 7.38 (br s, 1H), 7.12 (s, 1H), 7.05 (br s, 1H), 5.39 (br s, 1H), 3.84-3.67 (m, 2H), 2.92 (s, 3H), 2.29-2.10 (m, 2H), 1.90-2.08 (m, 4H), 1.88-1.77 (m, 1H), 1.69-1.59 (m, 1H), 1.15 (s, 9H), 0.98-0.94 (m, 3H) |
| Compound 32 | 622.2 (M + H)+ | (CDCl3) δ 8.38-8.11 (m, 1H), 7.97 (br s, 1H), 7.93 (br d, J = 7.75 Hz, 1H), 7.84 (br d, J = 7.51 Hz, 1H), 7.76-7.65 (m, 1H), 7.26-7.08 (m, 2H), 4.06-3.81 (m, 2H), 3.73 (br d, J = 6.91 Hz, 2H), 3.26 (br t, J = 5.30 Hz, 4H), 2.90 (s, 3H), 2.18-2.03 (m, 4H), 1.92-1.79 (m, 2H), 1.72 (br d, J = 11.80 Hz, 4H), 1.16 (br t, J = 7.03 Hz, 3H), 0.96 (br s, 2H), 0.33 (s, 4H) |
| Compound 42 | 492.0 (M + H)+ | (DMSO-d6) δ 9.77-9.41 (m, 1H), 8.15-7.83 (m, 4H), 7.82-7.75 (m, 1H), 7.15-7.00 (m, 2H), 3.93-3.79 (m, 2H), 2.98-2.88 (m, 3H), 2.64 (s, 6H), 1.79-1.43 (m, 7H), 1.38-0.89 (m, 3H) |
| Compound 43 | 501.1 (M + H)+ | (DMSO-d6) δ 9.58 (br s, 1H), 8.14-7.97 (m, 1H), 7.95-7.85 (m, 1H), 7.81 (br d, J = 7.1 Hz, 1H), 7.78-7.67 (m, 2H), 7.19-6.96 (m, 2H), 3.95-3.79 (m, 2H), 3.39-3.29 (m, 1H), 2.99-2.90 (m, 3H), 1.97-1.78 (m, 3H), 1.67-1.39(m, 12H), 1.34-1.05 (m, 3H) |
| Compound 45 | 504.1 (M + H)+ | (DMSO-d6) δ 8.31-8.10 (br s, 1H), 8.09-7.95 (m, 2H), 7.85 (br d, J = 7.6 Hz, 1H), 7.75-7.71 (m, 1H), 7.16 (s, 1H), 7.10-6.90 (br s, 1H), 6.36 (br s, 1H), 4.25-3.68 (m, 6H), 2.99 (s, 3H), 2.20-2.07 (m, 2H), 1.88-1.62 (m, 7H), 1.40-1.10 (m, 3H |
| Compound 46 | 504.2 (M + H)+ | (DMSO-d6) δ 9.73-9.40 (m, 1H), 8.18-7.82 (m, 5H), 7.81-7.72 (m, 1H), 7.23-7.00 (m, 2H), 3.99-3.79 (m, 2H), 3.05-2.86 (m, 3H), 2.22-2.12 (m, 1H), 1.74-1.47 (m, 7H), 1.35-1.01 (m, 3H), 0.55-0.44 (m, 2H), 0.41-0.31 (m, 2H) |
| Compound 48 | 506.0 (M + H)+ | (DMSO-d6) δ 9.58 (br s, 1H), 8.35-7.91 (m, 3H), 7.90-7.80 (m, 1H), 7.77-7.63 (m, 2H), 7.20-6.92 (m, 2H), 3.97-3.65 (m, 2H), 3.06-2.81 (m, 3H), 1.75-1.59 (m, 4H), 1.58-1.40 (m, 3H), 1.35-1.04 (m, 3H), 1.02-0.87 (m, 6H) |
| Compound 49 | 516.1 (M + H)+ | (DMSO-d6) δ 9.68-9.49 (brs, 1H), 8.08-8.02 (m, 3H), 7.93-7.85 (m, 1H), 7.76-7.72 (m, 1H), 7.11-6.99 (m, 2H), 4.30 (s, 1H), 3.90-3.79 (m, 2H), 3.72-3.63 (m, 1H), 3.42 (m, 1H), 2.93 (s, 3H), 1.94-1.70 (m, 4H), 1.64-1.52 (m, 12H), 1.27 (m, 1H), 1.24-1.23 (m, 1H) |
| Compound 50 | 517.0 (M + H)+ | (CDCl3) δ 8.40-7.95 (m, 3H), 7.90-7.81 (m, 1H), 7.77-7.67 (m, 1H), 7.20-7.12 (m, 1H), 7.11-6.9 (m, 1H), 6.36-6.24 (m, 1H), 4.15-3.75 (m, 2H), 3.59-3.48 (m, 1H), 3.01-2.98 (m, 3H), 2.15-2.01 (m, 2H), 1.98-1.64 (m, 14H), 1.31-1.22 (m, 2H) |
| Compound 55 | 520.1 (M + H)+ | (DMSO-d6) δ 9.67-9.51 (m, 1H), 8.10-7.87 (m, 3H), 7.78-7.70 (m, 1H), 7.23-6.99 (m, 2H), 4.15-4.02 (m, 1H), 3.94-3.77 (m, 2H), 3.02-2.86 (m, 3H), 2.79-2.64 (m, 3H), 1.77-1.47 (m, 7H), 1.34-1.03 (m, 3H), 0.98-0.81 (m, 6H) |
| Compound 57 | 524.2 (M + H)+ | (DMSO-d6) δ 9.60 (brs, 1H), 7.99 (m, 1H), 7.61 (s, 1H), 7.36 (s, 1H), 7.12 (d, J = 2.0 Hz, 2H), 7.07-7.05 (m, 1H), 4.21 (s, 2H), 2.95 (s, 3H), 2.58 (s, 3H), 1.73-1.49 (m, 6H), 1.44-1.26 (m, 4H), 1.24-1.13 (m, 9H) |
| Compound 59 | 541.3 (M + NH4)+ | (DMSO-d6) δ 9.69-9.55 (m, 1H), 8.15-7.97 (m, 1H), 7.66-7.60 (m, 1H), 7.27-7.17 (m, 1H), 7.13 (s, 1H), 7.13 (s, 1H), 4.04 (s, 2H), 4.00 (s, 3H), 2.95 (s, 3H), 1.78-1.59 (m, 5H), 1.55-1.43 (m, 2H), 1.37-1.21 (m, 3H), 1.17 (s, 9H) |
| Compound 60 | 526.0 (M + H)+ | (CDCl3) δ 8.10-8.01 (brs, 1H), 7.60 (d, J = 3.6 Hz, 1H), 7.50 (br d, J = 3.2 Hz, 1H), 7.18 (s, 1H), 7.04-7.02 (d, J = 8.0 Hz, 1H), 6.52 (s, 1H), 4.76 (s, 1H), 4.16 (s, 2H), 3.00 (s, 3H), 1.78-1.65 (m, 8H), 1.59 (m, 1H), 1.35 (s, 9H), 1.26 (s, 1H) |
| Compound 67 | 530.1 (M + H)+ | (CDCl3) δ 8.25-8.00 (m, 3H), 7.91 (d, J = 7.63 Hz, 1H) 7.83-7.72 (m, 1 H), 7.16-7.08 (m, 1H), 6.54-6.35 (m, 1H), 3.94-3.74 (m, 2H), 2.98-2.93 (m, 2H), 2.36-2.11 (m, 3H), 1.72-1.55 (m, 10H), 1.50-0.92 (m, 5H) |
| Compound 70 | 531.1 (M + H)+ | (DMSO-d6) δ 9.58 (br s, 1H), 8.15-7.85 (m, 4H), 7.85-7.76 (m, 1H), 7.2-6.92 (m, 2H), 3.85 (br s, 2H), 3.30 (br s, 1H), 2.94 (s, 3H), 2.00-1.89 (m, 2H), 1.78-1.70 (m, 2H), 1.70-1.47 (m, 8H), 1.34-1.05 (m, 8H) |
| Compound 71 | 532.1 (M + H)+ | (DMSO-d6) δ 9.64-9.52 (m, 1H), 8.18-7.84 (m, 4H), 7.82-7.72 (m, 1H), 7.16-7.02 (m, 2H), 3.93-3.76 (m, 2H), 3.25-3.14 (m, 2H), 2.94 (s, 3H), 2.78-2.62 (m, 2H), 2.11-1.95 (m, 1H), 1.92-1.79 (m, 1H), 1.72-1.44 (m, 7H), 1.35-1.02 (m, 4H), 0.84-0.74 (m, 3H |
| Compound 83 | 536.1 (M + H)+ | (CDCl3) δ 8.36-8.07 (m, 1H), 8.06-7.90 (m, 2H), 7.88-7.77 (m, 1H), 7.74-7.60 (m, 1H), 7.22-6.90 (m, 2H), 6.69-6.38 (m, 1H), 5.31-5.02 (m, 1H), s3.85 (br d, J = 3.25 Hz, 2H), 3.69-3.48 (m, 3H), 3.42-3.21 (m, 1H), 2.99 (br s, 3H), 2.27-2.14 (m, 1H), 2.09-1.88 (m, 1H), 1.71 (br d, J = 11.01 Hz, 7H), 1.38-1.02 (m, 3H) |
| Compound 95 | 538.0 (M + H)+ | (DMSO-d6) δ 9.60 (s, 1H), 8.06-7.96 (m, 1H), 7.91-7.85 (m, 1H), 7.80-7.74 (m, 3H), 7.15-7.06 (m, 2H), 3.82 (m, 2H), 2.94 (s, 3H), 1.62-1.52 (m, 8H), 1.28-1.21 (m, 2H), 1.13 (s, 9H) |
| Compound 96 | 538.1 (M + H)+ | (CDCl3) δ 8.15-8.10 (m, 1H), 7.87-7.79 (m, 1H), 7.35-7.31 (m, 1H), 7.21-7.15 (m, 2H), 7.00 (m, 1H), 6.24 (s, 1H), 4.79 (s, 1H), 3.91-3.80 (m, 2H), 2.99 (s, 3H), 1.76-1.62 (m, 7H), 1.35-1.31 (m, 1H), 1.27 (s, 9H), 1.25 (m, 2H) |

TABLE 8-continued

| Compound | ESI MS (M/z) | NMR summary (400 MHz) ppm |
|---|---|---|
| Compound 97 | 538.0 (M + H)+ | (DMSO-d6) δ 8.08-8.03 (m, 3H), 7.66-7.59 (m, 2H), 7.15-7.11 (m, 2H), 3.70 (s, 2H), 2.99-2.94 (m, 3H), 1.64-1.61 (m, 9H), 1.26-1.22 (m, 1H), 1.13 (s, 9H) |
| Compound 107 | 548.0 (M + H)+ | (DMSO-d6) δ 9.58 (br s, 1H), 8.15-7.85 (m, 4H), 7.84-7.78 (m, 1H), 7.17-7.01 (m, 2H), 3.95-3.79 (m, 3H), 3.63-3.45 (m, 4H), 2.94 (s, 3H), 2.33-2.27 (m, 1H), 1.97 (t, J = 11.13 Hz, 1H), 1.72-1.47 (m, 7H), 1.32-1.11 (m, 2H), 1.05 (d, J = 6.00 Hz, 3H) |
| Compound 129 | 544.0 (M + H)+ | (DMSO-d6) δ 9.79-9.43 (m, 1H), 8.17-7.90 (m, 4H), 7.89-7.75 (m, 1H), 7.24-6.92 (m, 2H), 3.97-3.81 (m, 2H), 3.77-3.62 (m, 4H), 2.94 (s, 3H), 1.92-1.78 (m, 4H), 1.73-1.58 (m, 6H), 1.58-1.45 (m, 3H), 1.33-1.20 (m, 1H), 1.16-1.02 (m, 1H) |
| Compound 134 | 560.1 (M + H)+ | (DMSO-d6) δ 9.69 (br s, 1H), 8.03-7.96 (m, 3H), 7.84 (br s, 1H), 7.73-7.69 (m, 2H), 7.14-7.12 (m, 2H), 3.87 (s, 2H), 3.05-3.03 (m, 2H), 1.64-157 (m, 6H), 1.20-1.16 (t, J = 7.2 Hz, 3H), 1.10 (s, 9H), 0.88~0.85 (m, 2H), 0.27 (br s, 4H) |
| Compound 140 | 534.1 (M + H)+ | (DMSO-d6) δ 9.68-9.49 (m, 1H), 8.10-7.92 (m, 3H), 7.89-7.77 (m, 1H), 7.77-7.62 (m, 2H), 7.39-7.31 (m, 1H), 7.16-7.02 (m, 1H), 3.88-3.72 (m, 2H), 2.95 (d, J = 3.88 Hz, 3H), 1.83-1.33 (m, 9H), 1.13-1.09 (m, 9H), 0.88-0.74 (m, 3H) |
| Compound 141 | 526.2 (M + H)+ | (DMSO-d6) δ 9.52-9.67 (m, 1H), 8.08-7.85 (m, 4H), 7.79 (s, 1H), 7.51-7.45 (m, 1H), 7.32-7.18 (m, 1H), 4.16-4.06 (m, 2H), 3.98-3.80 (m, 2H), 2.93 (br s, 4H), 1.54 (br s, 11H), 1.42-1.29 (m, 3H), 1.27-1.23 (m, 3H), 1.22-0.99 (m, 2H) |
| Compound 144 | 556.2 (M + H)+ | (DMSO-d6) δ 9.52-9.51 (brs, 1H), 8.03-7.97 (m, 3H), 7.83 (m, 1H), 7.83-7.61 (m, 2H), 7.11 (brs, 2H), 4.00 (s, 2H), 2.95 (s, 3H), 2.04-2.03 (m, 2H), 1.82 (m, 6 H), 1.15 (s, 9H) |
| Compound 145 | 523.1 (M + H)+ | (DMSO-d6) δ 9.56 (s, 1H), 7.85-7.82 (m, 1H), 7.48 (s, 1H), 7.10 (m, 2H), 7.04-7.02 (dd, J = 8.69, 1.81 Hz, 1H), 6.91 (s, 1H), 4.09 (s, 2H), 3.77 (s, 3H), 2.93 (s, 3H), 1.68-1.62 (m, 5H), 1.59-1.49 (m, 2H), 1.31-1.25 (m, 3H), 1.16 (s, 9H) |
| Compound 146 | 485.1 (M + H)+ | (CDCl3) δ 8.48-7.92 (m, 1H), 7.50-7.46 (m, 2H), 7.39-7.32 (m, 2H), 7.14 (s, 1H), 7.09-6.88 (m, 1H), 6.44 (s, 1H), 4.02-3.82 (br s, 2H), 2.97 (m, 1H), 2.09-2.92 (m, 3H), 2.09-2.00 (m, 2H), 1.79-1.62 (m, 14H), 1.19-1.14 (m, 2H) |
| Compound 147 | 524.1 (M − H)− | (DMSO-d6) δ 9.61 (s, 1H), 8.35 (d, J = 1.25 Hz, 1H), 7.97-7.93 (m, 2H), 7.65 (s, 1H), 7.14-7.04 (m, 2H), 4.21 (s, 2H), 2.95 (s, 3H), 1.74-1.52 (m, 8H), 1.34-1.26 (m, 2H), 1.14 (s, 9H) |
| Compound 148 | 576.1 (M + H)+ | (DMSO-d6) δ 8.02-7.96 (m, 2H), 7.84-7.82 (m, 1H), 7.77-7.69 (m, 2H), 7.14-7.09 (m, 2H), 3.90 (s, 2H), 3.75-3.71 (t, J = 6.4 Hz, 2H), 3.19-3.16 (m, 2H), 1.65-1.54 (m, 6H), 1.11 (s, 9H), 1.10 (s, 1H), 0.97-0.86 (m, 2H), 0.38-0.18 (m, 4H) |
| Compound 149 | 510.1 (M + H)+ | (DMSO-d6) δ 9.62 (s, 1H), 8.17 (s, 1H), 8.03-8.01 (m, 1H), 7.39 (d, J = 3.6 Hz, 1H), 7.21 (d, J = 3.6 Hz, 1H), 7.14 (d, J = 2.4 Hz, 1H), 7.08-7.06 (dd, J = 8.69, 2.06 Hz, 1H), 4.24 (s, 2H), 2.96 (s, 3H), 1.68-1.65 (m, 5H), 1.56-1.52 (m, 3H), 1.34-1.38 (m, 2H), 1.20 (s, 9H) |
| Compound 151 | 570.1 (M + H)+ | (DMSO-d6) δ 9.58 (s, 1H), 8.06-7.0 (m, 5H), 7.13-7.11 (m, 2H), 3.91 (s, 2H), 3.72 (s, 4H), 2.94 (s, 3H), 1.85-1.83 (m, 4H), 1.68-1.55 (m, 8H), 0.88-0.85 (m, 2H), 0.28-0.23 (m, 4H) |
| Compound 153 | 572.1 (M + H)+ | (DMSO-d6) δ 9.59-9.57 (br s, 1H), 8.04-7.96 (m, 4H), 7.81-7.85 (m, 1H), 7.14 (m, 2H), 4.28-4.25 (br t, J = 7.2 Hz, 2H), 4.09 (d, J = 10.8 Hz, 2H), 3.90 (s, 2H), 3.76 (br d, J = 10.8 Hz, 2H), 2.94 (s, 3H), 2.65-2.53 (m, 2H), 1.68-1.60 (m, 6H), 0.87-0.85 (m, 2H), 0.27 (br s, 4H) |
| Compound 155 | 543.1 (M + H)+ | (DMSO-d6) δ 9.66-9.57 (br s, 1H), 8.12-8.03 (m, 3H), 7.82-7.78 (m, 1H), 7.13-7.09 (m, 2H), 3.94-3.85 (m, 3H), 2.94 (s, 3H), 1.93-1.83 (m, 4H), 1.66-1.57 (m, 10H), 0.88-0.85 (m, 2H), 0.27-0.22 (br s, 4H). |
| Compound 157 | 483.4 (M + H)+ | (DMSO-d6) δ 9.54 (br s, 1H), 8.03-8.00 (m, 1H), 7.51-7.42 (m, 4H), 7.10 (m, 2H), 5.24 (d, J = 4.4 Hz, 1H), 4.37 (br dd, J = 7.50, 4.50 Hz, 1H), 3.86 (br s, 2H), 2.93 (s, 3H), 2.09-2.07 (m, 1H), 1.64-1.44 (m, 13H), 1.28-1.22 (m, 5 H) |
| Compound 159 | 564.1 (M + H)+ | (DMSO-d6) δ 9.57 (br s, 1H), 8.03-7.98 (m, 3H), 7.59-7.54 (m, 1H), 7.12-7.07 (m, 2H), 3.89 (s, 2H), 2.93 (s, 3H), 1.69-1.61 (m, 4H), 1.14 (s, 9H), 0.88-0.85 (m, 2H), 0.27 (br s, 4H |
| Compound 160 | 572.2 (M + H)+ | (DMSO-d6) δ 9.60 (br s, 1H), 8.04-7.95 (m, 3H), 7.84 (d, J = 1.2 Hz, 1H), 7.73-7.69 (m, 2H), 7.16-7.12 (m, 2H), 3.88 (s, 2H), 3.32 (s, 1H), 1.66-1.56 (m, 6H), 1.10 (s, 9H), 0.91-0.87 (m, 6H), 0.27 (br s, 4H) |
| Compound 162a | 570.1 (M + H)+ | (DMSO-d6) δ 9.60 (s, 1H), 8.07-7.96 (m, 2H), 7.89-7.79 (m, 1H), 7.73-7.70 (m, 1H), 7.66(m, 1H), 7.12-7.06 (m, 2H), 5.98-5.70 (m, 1H), 3.89 (s, 2H), 2.95 (s, 3H), 1.92-1.83 (m, 1H), 1.77-1.60 (m, 6H), 1.10-1.05 (m, 11H |
| Compound 162b | 570.1 (M + H)+ | (DMSO-d6) δ 9.68 (br s, 1H), 8.04-8.00 (m, 2H), 7.99-7.97 (m, 1H), 7.95-7.81 (m, 2H), 7.37 (s, 1H), 7.23-7.09 (m, 1H), 6.29-5.99 (m, 1H), 3.79 (s, 2H), 2.94 (m, 3H), 1.91-1.80 (m, 3H), 1.66-1.53 (m, 6H), 1.11 (s, 9H) |

TABLE 8-continued

| Compound | ESI MS (M/z) | NMR summary (400 MHz) ppm |
|---|---|---|
| Compound 163 | 544.2 (M + H)+ | (DMSO-d6) δ 11.57-11.53 (br s, 1H), 9.58 (s, 1H), 8.04-7.61 (m, 5H), 7.59-7.11 (m, 2H), 4.45 (s, 2H), 3.95 (s, 2H), 3.45-3.37 (m, 2H), 3.14-3.13 (m, 2H), 2.94 (s, 3H), 2.49-2.32 (m, 4H), 1.66 (m, 6H), 0.89-0.87 (m, 2H), 0.28 (br s, 4H) |
| Compound 164 | 507.1 (M + H)+ | (DMSO-d6) δ = 9.68-9.37 (m, 1H), 8.25-8.06 (m, 3H), 7.86-7.84 m, 1H), 7.66 (t, J = 7.7 Hz, 1H), 7.18-6.97 (m, 2H), 3.91-3.80 (m, 3H), 2.94 (s, 3H), 1.89 (m, 2H), 1.77-1.51 (m, 12H), 0.96-0.87 (m, 2H), 0.27 (br s, 4H) |
| Compound 165 | 509.2 (M + H)+ | (DMSO-d6) δ 9.67 (bs s, 1H), 8.24-8.00 (m, 1H), 7.48-7.42 (m, 4H), 7.19-7.03 (m, 2H), 5.25 (d, J = 4.8 Hz, 1H), 4.66 (m, 1H), 3.98 (s, 2H), 2.93 (s, 3H), 2.07 (m, 1H), 1.77-1.45 (m, 12H), 1.35-1.14 (m, 2H), 0.93-0.86 (m, 2H), 0.27 (br s, 4H) |
| Compound 165a | 509.2 (M + H)+ | (DMSO-d6) δ 9.68 (br s, 1H), 8.24 (m, 1H), 7.63-7.26 (m, 4H), 7.29-6.80 (m, 2H), 5.25 (s, 1H), 4.47-4.43 (m, 1H), 3.96-3.83 (m, 2H), 2.93 (s, 3H), 2.12-2.05 (m, 1H), 1.78-1.36 (m, 12H), 1.31-1.23 (m, 2H), 0.89-0.86 (m, 2H), 0.39-0.16 (m, 4H |
| Compound 165b | 509.3 (M + H)+ | (DMSO-d6) δ 9.71 (br s, 1H), 8.22-7.85 (m, 1H), 7.52-7.42 (m, 4H), 7.11-6.90 (m, 2H), 5.26 (d, J = 4.8 Hz, 1H), 4.38-4.35 (m, 1H), 3.96 (s, 2H), 2.93 (s, 3H), 2.11-2.07 (m, 1H), 1.65-1.45 (m, 12H), 1.35-1.18 (m, 2H), 0.89-0.86 (m, 2H), 0.44-0.07 (m, 4H) |
| Compound 166 | 455.1 (M + H)+ | (DMSO-d6) δ 9.39-9.19 (brs, 1H), 7.91-7.84 (m, 3H), 7.78-7.74 (m, 1H), 6.67 (d, J = 2.0 Hz, 2H), 3.80 (s, 2H), 2.92 (m, 4H), 1.75-1.59 (m, 11H), 1.53 (m, 2H), 1.37-0.98 (m, 3H) |
| Compound 168 | 544.1 (M + H)+ | (DMSO-d6) δ 9.58 (br s, 1H), 8.11-8.09 (m, 1H), 7.97-7.86 (m, 4H), 7.74-7.70 (m, 1H), 7.13 (m, 2H), 3.95 (s, 2H), 3.70-3.62 (m, 1H), 2.94 (m, 3H), 1.81-1.96 (m, 2H), 1.74-1.45 (m, 10H), 0.88-0.85 (m, 2H), 0.13-0.36 ppm (m, 4H) |
| Compound 170 | 546.1 (M + H)+ | (DMSO-d6) δ 9.56 (brs, 1 H), 7.95-7.92 (m, 2 H), 7.85 (m, 1 H), 7.84-7.66 (m, 2 H), 7.13 (m, 2 H), 3.88 (s, 2 H), 3.11-3.15 (m, 1 H), 2.94 (s, 3 H), 1.65-1.28 (m, 6 H), 1.22-1.28 (m, 2 H), 0.90-0.86 (m, 5 H), 0.71-0.68 (m, 2 H), 0.27 (m, 4 H) |
| Compound 172 | 556.0 (M + H)+ | (DMSO-d6) δ 9.57 (s, 1 H), 8.04-7.87 (m, 5 H), 7.70-7.79 (m, 1 H), 7.14-7.10 (m, 2 H), 5.57-5.54 (m, 2 H), 3.89-3.81 (m, 3 H), 2.94 (s, 3 H), 2.35-2.32 (m, 3 H), 1.99-2.15 (m, 2 H), 1.65-1.51 (m, 6 H), 0.87-0.85 (m, 2 H), 0.21-0.18 (m, 4 H) |
| Compound 174 | 546.0 (M + H)+ | (DMSO-d6) δ 9.70-9.33 (br s, 1H), 9.01-8.45 (m, 1H), 8.10-7.91 (m, 4H), 7.64-7.83 (m, 1H), 7.14-6.97 (m, 2H), 4.36-4.58 (m, 3H), 4.13-4.33 (m, 2H), 3.73-4.00 (s, 2H), 2.94 (s, 3H), 1.81-1.49 (m, 5H), 0.99-0.79 (m, 2H), 0.39-0.05 (br s, 4H) |
| Compound 176 | 558.1 (M + H)+ | (DMSO-d6) δ 9.58 (br s, 1H), 8.11-7.85 (m, 3H), 7.80-7.78 (m, 1H), 7.75-7.71 (m, 2H), 7.10-7.18 (m, 1H), 3.98 (br s, 2H), 3.39-3.57 (m, 1H), 2.94 (s, 3H), 1.77-1.53 (m, 10H), 1.44-1.18 (m, 4H), 0.88-0.85 (m, 2H), 0.27-0.14 (m, 4H) |
| Compound 178 | 574.1 (M + H)+ | (DMSO-d6) δ 9.57 (s, 1 H) 8.06-7.97 (m, 4 H), 7.79-7.94 (m, 1 H), 7.74-7.72 (m, 1 H), 7.13 (m, 2 H), 3.86 (s, 2 H), 3.64-3.73 (m, 4 H), 2.94 (s, 3 H), 2.06-2.16 (m, 1 H), 1.73-1.58 (m, 7 H) 1.19 (s, 3 H), 0.77-1.00 (m, 2 H) 0.27 (s, 4 H) |
| Compound 180 | 572.1 (M + H)+ | (DMSO-d6) δ 9.57 (s, 1 H), 7.99-7.78 (m, 5 H), 7.73-7.69 (m, 1 H), 7.13 (m, 2 H), 3.87 (br s, 2 H), 2.94 (s, 3 H), 1.64-1.54 (m, 10 H), 1.48-1.49 (m, 1 H), 0 1.24-1.09 (m, 6 H), 0.86 (m, 2 H), 0.26-0.23 (m, 4 H) |
| Compound 182 | 558.1 (M + H)+ | (DMSO-d6) δ 9.58 (s, 1H), 8.13-8.00 (m, 4H), 7.97-7.95 (m, 1H), 7.84 (m, 1H), 7.14-6.99 (m, 2H), 3.89 (s, 2H), 2.95 (s, 3H), 2.08 (m, 2H), 1.65-1.62 (m, 10H), 1.28 (s, 3H), 0.88-0.85 (m, 2H), 0.15-0.36 (m, 4H) |
| Compound 184 | 572.1 (M + H)+ | (DMSO-d6) δ 9.59 (br s, 1 H), 8.09-7.93 (m, 3 H), 7.86 (m, 1 H), 7.74-7.70 (m, 1 H), 7.65 (d, J = 8.0 Hz, 1 H), 7.14-7.11 (m, 2 H), 3.88 (br s, 2 H), 3.08 (m, 1 H), 2.95 (s, 3 H), 2.21-2.09 (m, 1 H), 1.75-1.56 (m, 11H), 1.47-1.33 (m, 1 H), 0.88-0.85 (m, 2 H), 0.78 (d, J = 6.4 Hz, 3 H), 0.26 (m, 4 H) |
| Compound 186 | 558.1 (M + H)+ | (DMSO-d6) δ 9.59 (br s, 1 H), 8.11-7.94 (m, 3 H), 7.87 (d, J = 8.0 Hz, 2 H), 7.74-7.70 (m, 1 H), 7.13 (m, 2 H), 3.88 (s, 2 H), 2.95 (s, 3 H), 2.71-2.59 (m, 1 H), 1.76-1.48 (m, 6 H), 1.00 (d, J = 6.4 Hz, 3 H), 0.89-0.85 (m, 2 H), 0.72 (m, 1 H), 0.21-0.39 (m, 5 H), 0.05-0.20 (m, 2 H), 0.11 (m, 1 H) |
| Compound 188 | 574.1 (M + H)+ | (DMSO-d6) δ 9.59 (br s, 1H), 8.63 (m, 1 H), 7.95-7.94 (m, 4 H), 7.76-7.72 (m, 1 H), 7.15-7.14 (m, 2 H), 4.29 (s, 1 H), 4.05 (s, 2 H), 3.89 (s, 2H), 2.95 (s, 3 H), 1.72-1.57 (m, 6 H), 1.19 (s, 3 H), 1.11 (s, 3 H), 0.89-0.87 (m, 2 H), 0.33-0.18 (br s, 4 H) |
| Compound 190 | 556.1 (M + H)+ | (CDCl3) 8.33 (m, 1H), 8.15 (m, 1H), 7.81-7.79 (m, 1H), 7.70-7.66 (t, J = 7.2 Hz, 1H), 7.21 (m, 1H), 7.05-7.10 (m, 1H), 6.62 (s, 1H), 4.83 (s, 2H), 4.82-4.77 (m, 1H), 3.93-3.88 (br s, 2H), 3.02 (s, 3H), 2.96-2.91 (m, 2H).2.60-2.55 (m, 2H), 1.82-1.80 (m, 3H), 1.71-1.68 (m, 3H), 0.97-0.92 (m, 2H), 0.33 (s, 4H) |
| Compound 192 | 580.1 (M + H)+ | (DMSO-d6) δ 9.54 (br s, 1 H), 8.42-7.93 (m, 4 H), 7.78-7.75 (m, 1 H), 7.14-6.96 (m, 2 H), 3.96 (s, 2 H), 3.58-3.71 (m, 1 H), 2.95 (s, 3 H), 2.74-2.42 (m, 2 H), 2.46-2.34 (m, 2 H), 1.82-1.61 (m, 6 H), 0.95-0.87 (m, 2 H), 0.37 (m, 4 H) |

TABLE 8-continued

| Compound | ESI MS (M/z) | NMR summary (400 MHz) ppm |
|---|---|---|
| Compound 194 | 574.2 (M − H)⁻ | (MeOD) 8.19-8.00 (m, 3 H), 7.82 (m, 1 H), 7.74-7.70 (m, 2 H), 7.21-7.08 (m, 2 H), 3.95 (br s, 1H), 3.71-3.65 (m, 1 H) 2.94 (s, 3H) 1.84 (m, 2 H) 1.70 (m, 4 H) 1.14-1.11 (m, 8 H) 095-0.89 (m, 3 H) 0.32 (s, 4 H). |
| Compound 196 | 570.1 (M + H)⁺ | (DMSO-d⁶) δ 9.59 (br s, 1 H), 8.10-7.94 (m, 4 H), 7.87 (m, 1 H), 7.76-7.72 (m, 1 H), 7.14-7.15 (m, 2 H), 5.71-5.68 (m, 1 H), 5.25-5.22 (m, 1 H), 3.90 (br s, 2 H), 3.71 (br s, 1 H), 2.95 (s, 3 H), 1.87 (m, 2 H), 1.67-1.57 (m, 8 H), 1.39 (m, 2 H), 0.88-0.85 (d, J = 9.6 Hz, 2 H), 0.28-0.26 (m, 4 H) |
| Compound 198 | 560.1 (M + H)⁺ | (DMSO-d⁶) δ 9.59 (br s, 1 H), 8.11-7.90 (m, 3 H), 7.85 (m, 1 H), 7.74-7.64 (m, 2 H), 7.14-7.13 (m, 2 H), 3.88 (br s, 2 H), 2.98 (m, 1 H), 2.95 (s, 3 H), 1.74-1.66 (m, 6 H), 1.36-1.28 (m, 2 H), 1.26-1.23 (m, 2 H), 0.85-0.80 (m, 2 H), 0.67-0.65 (m, 6 H), 0.28-0.26 (m, 4H) |
| Compound 200 | 562.1 (M + H)⁺ | (DMSO-d⁶) δ 9.59 (br s, 1 H), 8.11-7.95 (m, 3 H), 7.85-7.83 (m, 2 H), 7.77-7.70 (m, 1 H), 7.14 (m, 2 H), 3.90 (s, 2 H), 3.17-3.16 (m, 1 H), 3.12 (m, 1 H), 3.10 (s, 3 H), 2.95 (s, 3 H), 1.67-1.66 (m, 6 H), 0.92-0.86 (m, 5 H), 0.27 (m, 4 H) |
| Compound 202 | 560.1 (M + H)⁺ | (DMSO-d⁶) δ 8.12-8.11(m, 1H), 8.07-8.05 (m, 1H), 7.79 (br d, J = 7.2 Hz, 1H), 7.68-7.64 (m, 1H), 7.18 (s, 1H), 6.37 (s, 1H), 5.49 (s, 1H), 3.92-3.86 (m, 2H), 3.40 (s, 2H), 3.00 (s, 3H), 1.83-1.80 (m, 2H), 1.71-1.58 (m, 4H), 0.95-0.92 (m, 2H), 0.88-0.85 (m, 2H) 0.70-0.67 (m, 2H) 0.32 (br s, 4H) |
| Compound 204 | 562.2 (M + H)⁺ | (DMSO-d⁶) δ 9.58 (br s, 1 H), 8.18-8.16 (br d, J = 7.6 Hz, 1 H), 7.96-7.92 (m, 4 H), 7.76-7.72 (t, J = 8.0 Hz, 1 H), 7.14-7.08 (m, 2 H), 4.73-4.54 (m, 1 H), 3.88 (br s, 2 H), 3.23-3.27 (m, 1 H), 2.94 (s, 3 H), 2.45-2.41 (m, 2 H) 1.95-1.96 (m, 2 H) 1.79-1.50 (m, 6 H), 0.88-0.86 (m, 2 H) 0.275 (br s, 4 H) |
| Compound 206 | 560.1 (M + H)⁺ | (DMSO-d⁶) δ 9.58-9.41 (br s, 1 H) 8.58-8.53 (br s, 1 H), 8.19-7.89 (m, 4 H), 7.76-7.72 (m, 1 H), 7.13 (m, 2 H), 4.55 (d, J = 6.0 Hz, 2 H), 4.13 (d, J = 6.0 Hz, 2 H), 3.88 (br s, 2 H) 2.94 (s, 3 H) 1.66-1.57 (m, 6 H), 1.41 (s, 3 H), 0.88-0.75 (m, 2 H) 0.27 (br s, 4 H) |
| Compound 208 | 562.1 (M + H)⁺ | (DMSO-d⁶) δ 9.61 (br.s, 1 H), 8.11-7.93 (m, 3 H), 7.86 (m, 1 H), 7.73-7.65 (m, 2 H), 7.13-7.09 (m, 2 H), 4.60-4.70 (t, J = 4.8 Hz, 1 H), 3.87 (br s, 2 H), 3.29-3.27 (m, 1 H), 3.18-3.15 (m, 1 H), 2.96 (m, 1 H), 2.94 (s, 3H), 1.65-1.51 (m, 7 H), 1.12-1.29 (m, 1 H), 0.98-0.86 (m, 2 H), 0.69-0.59 (m, 3 H), 0.27 (br s, 4 H) |
| Compound 210 | 560.1 (M + H)⁺ | (DMSO-d⁶) δ 9.58 (br s, 1 H), 7.99 (s, 1 H), 7.95 (d, J = 7.8 Hz, 1 H), 7.86 (br d, J = 5.9 Hz, 1 H), 7.73 (t, J = 24.0 Hz, 1 H), 7.61 (d, J = 8.3 Hz, 1 H), 7.03-7.18 (m, 2 H), 3.88 (s, 2 H), 2.98-3.07 (m, 1 H), 2.95 (s, 3 H), 1.50-1.72 (m, 7 H), 0.87 (br d, J = 11.9 Hz, 2 H), 0.74-0.81 (m, 9 H), 0.21-0.34 (m, 4 H) |
| Compound 212 | 530.2 (M + H)⁺ | (DMSO-d⁶) δ 9.58-9.53 (m, 1 H), 8.07-8.04 (s, 1 H), 8.01-7.97 (m, 3 H), 7.78-7.74 (m, 1 H), 7.14-7.08 (m, 2 H), 3.98 (br s, 2 H), 2.94 (s, 3 H), 2.16-2.10 (m, 1 H), 1.77-1.52 (m, 6 H), 0.92-0.87 (m, 2 H), 0.42-0.55 (m, 2 H), 0.34-0.41 (m, 2 H), 0.27 (br s, 4 H) |
| Compound 214 | 574.1 (M + H)⁺ | (DMSO-d⁶) δ 9.69-9.43 (br s, 1 H), 8.15-7.94 (m, 3 H), 7.84-7.79 (m, 2 H), 7.71-7.67 (m, 1 H), 7.14 (m, 1 H), 4.61 (br s, 1 H), 3.89 (br s, 2 H), 3.38-3.52 (m, 2 H), 2.94 (s, 3 H), 2.58-2.63 (m, 1 H), 1.66 (m, 6 H), 0.87-0.81 (m, 3 H), 0.27 (br s, 6 H), 0.15-0.09 (m, 2 H). |
| Compound 216 | 544.1 (M + H)⁺ | (DMSO-d⁶) δ 9.58 (br.s, 1 H), 8.20 (s, 1 H), 8.05-7.87 (m, 3 H), 7.76-7.72 (m, 1 H), 7.13-7.09 (m, 1 H), 7.10 (s, 1H), 3.88 (s, 2 H), 2.94 (s, 3 H), 1.46-1.76 (m, 6 H), 1.07 (s, 3 H), 0.89-0.86 (m, 2 H), 0.63-0.60 (m, 2 H), 0.41-0.38 (m, 2 H), 0.27 (br s, 4 H) |
| Compound 218 | 560.1 (M + H)⁺ | (DMSO-d⁶) δ 9.58 (s, 1 H), 8.09-7.90 (m, 4 H), 7.66-7.80 (m, 1 H), 7.14-7.10 (m, 1 H), 7.15 (s, 1 H), 5.00-4.91 (m, 1 H), 3.89-3.62 (m, 3 H), 3.25-3.07 (m, 1 H), 2.95 (s, 3 H), 2.06 (m, 1 H), 1.83-2.01 (m, 2 H), 1.66-1.51 (m, 7 H), 0.96-0.87 (m, 2 H), 0.22 (br s, 4 H) |
| Compound 220 | 562.1 (M + H)⁺ | (DMSO-d⁶) δ 9.60 (br s, 1 H), 8.09-7.91 (m, 3 H), 7.84 (m, 1 H), 7.75-7.62 (m, 1 H), 7.51 (s, 1 H), 7.13-7.09 (m, 2 H), 4.79 (t, J = 6.0 Hz, 1 H), 3.89 (s, 2 H), 3.21 (d, J = 5.6 Hz, 2 H), 2.94 (s, 3 H), 1.74-1.50 (m, 6 H), 0.96-1.08 (m, 6 H), 0.93-0.80 (m, 2 H), 0.27 (brs, 4 H) |
| Compound 222 | 574.1 (M + H)⁺ | (DMSO-d⁶) δ 9.58 (br. s, 1 H), 8.07-7.95 (m, 2 H), 7.94-7.88 (m, 3 H), 7.75-7.71 (m, 1H) 7.14-7.11 (m, 1 H), 3.88-3.80 (br s, 2 H), 3.41-3.32 (m, 1 H), 3.00 (s, 3 H), 2.90 (s, 3 H), 2.27-2.25 (m, 2 H), 2.04-1.88 (m, 1 H), 1.66-1.56 (m, 8 H), 0.89-0.86 (d, J = 10.4 Hz, 2 H), 0.27 (br s, 4 H) |
| Compound 223 | 556.1 (M + H)⁺ | (DMSO-d⁶) δ 9.57 (brs, 1H), 8.71 (s, 1H), 7.99-7.88 (m, 4H), 7.74-7.72 (m, 1H), 7.13-7.07 (m, 2H), 3.89 (s, 2H), 2.94 (s, 3H), 2.28 (s, 1H), 1.71-1.65 (m, 12H), 0.88-0.85 (m, 2H), 0.26 (br d, J = 6.50 Hz, 3H) |

TABLE 8-continued

| Compound | ESI MS (M/z) | NMR summary (400 MHz) ppm |
|---|---|---|
| Compound 224 | 594.2 (M + H)+ | (CDCl$_3$) δ 8.02-8.15 (m, 3 H), 7.79 (br d, J = 7.13 Hz, 1 H), 7.65-7.69 (m, 1 H), 7.20 (s, 1 H), 7.00-7.09 (m, 1 H), 6.45 (s, 1 H), 5.08 (br s, 1 H) 3.88-3.95 (m, 2 H), 3.00 (s, 3 H) 2.84-2.98 (m, 2 H) 2.55-2.63 (m, 2 H) 1.68-1.96 (m, 6 H), 1.49 (s, 3 H), 0.91-0.94 (m, 2 H), 0.32 (br s, 4 H) |
| Compound 225 | 556.1 (M + H)+ | (DMSO-d$^6$) δ 9.56 (brs, 1H), 8.07-7.93 (m, 5H), 7.77 (d, J = 7.6, 1H), 7.14-7.04 (m, 2H), 3.90 (br s, 2H), 3.26-3.30 (m, 2H), 2.94 (s, 3H), 1.76-152 (m, 6H), 0.99-1.10 (m, 1H), 0.88 (br d, J = 10.9 Hz, 2H), 0.77-0.82 (m, 1H), 0.65-0.76 (m, 4H), 0.27 (br s, 4H) |
| Compound 226 | 576.1 (M + H)+ | (DMSO-d$^6$) δ 9.57 (s, 1 H) 8.38-8.48 (s, 1 H) 7.94-8.10 (m, 2 H) 7.83-7.93 (m, 1 H) 7.70-7.80 (m, 1 H) 7.01-7.19 (m, 2 H) 3.80-3.96 (s, 2 H) 3.48-3.60 (m, 2 H) 2.88-3.00 (s, 3 H) 2.68-2.74 (m, 2 H) 2.11-2.22 (m, 1 H) 1.85-1.95 (m, 1 H) 1.46-1.78 (m, 9 H) 1.35-1.43 (m, 1 H) 1.12-1.30 (m, 1 H) 0.80-0.95 (m, 2 H) 0.18-0.34 (br s, 4 H) |
| Compound 227 | 574.1 (M + H)+ | (DMSO-d$^6$) δ 7.99-7.91 (m, 2 H), 7.83 (br d, J = 7.70 Hz, 2H), 7.75-7.66 (m, 2H), 7.19 (d, J = 1.83 Hz, 1 H), 7.07 (br d, J = 8.19 Hz, 1 H), 3.90 (s, 2 H), 3.78 (t, J = 6.60 Hz, 4 H), 3.05 (s, 2 H), 1.97-1.93 (m, 2 H), 1.69-1.48 (m, 10 H), 0.96 (br d, J = 13.20 Hz, 2 H), 0.54-0.09 (m, 4 H) |
| Compound 228 | 600.1 (M + H)+ | (DMSO-d$^6$) δ 8.04-7.94 (m, 4H), 7.84-7.80 (m, 1H), 7.14-7.10 (m, 2H), 3.91 (ms, 2H), 3.78-3.72 (m, 6H), 3.24-3.18 (m, 2H), 1.87-1.83 (m, 4 H), 1.68-1.55 (m, 8H), 0.87-0.83 (m, 2H), 0.28-0.23 (m, 4H) |
| Compound 229 | 573.1 (M + H)+ | (DMSO-d$^6$) δ 9.52-9.65 (m, 1 H), 7.94-8.16 (m, 4 H), 7.76-7.86 (m, 1 H), 7.04-7.18 (m, 2 H), 4.95 (m, 1 H), 3.81-3.95 (m, 3 H), 3.73 (br t, J = 6.32 Hz, 2 H), 3.18 (br t, J = 6.44 Hz, 2 H), 1.77-1.92 (m, 4 H), 1.50-1.72 (m, 10 H), 0.88 (br d, J = 9.26 Hz, 2 H), 0.28 (br s, 4 H) |
| Compound 230 | 610.1 (M + H)+ | (DMSO-d$^6$) δ 8.51-8.22 (m, 1 H), 8.22-7.84 (m, 4 H), 7.82-7.68 (m, 1 H), 7.24-6.96 (m, 2 H), 3.97-3.81 (m, 2 H), 3.79-3.70 (m, 2 H), 3.68-3.59 (m, 1 H), 3.23-3.13 (m, 2 H), 2.80-2.64 (m, 2 H), 2.38-2.29 (m, 2 H), 1.78-1.46 (m, 6 H), 0.97-0.77 (m, 2 H), 0.37-0.12 (m, 4 H) |
| Compound 231 | 534.2 (M + H)+ | (DMSO-d$^6$) δ 9.58 (s, 1 H) 8.36 (s, 1 H) 7.81-7.91 (m, 2 H) 7.01-7.15 (m, 2 H) 4.02 (s, 2 H) 2.94 (s, 3 H) 1.52-1.67 (m, 7 H) 1.22-1.30 (m, 3 H) 1.19 (s, 9 H) |
| Compound 233 | 558.1 (M + H)+ | (DMSO-d$^6$) δ 9.57 (s, 1H), 8.27-8.44 (m, 1H), 7.71-8.12 (m, 4H), 7.64-7.80 (m, 1H), 6.92-7.23(m, 2H), 4.69 (br d, J = 1.6 Hz, 1H), 4.55 (br s, 1H), 4.23-4.39 (m, 1H), 3.77-4.00(m, 2H), 2.95 (s, 3H), 2.17-2.34 (m, 2H), 1.84-2.02 (m, 1H), 1.46-1.75 (m, 7H), 0.76-0.98 (m, 2H), 0.15-0.38 (m, 4H) |
| Compound 235 | 570.1 (M + H)+ | (DMSO-d$^6$) δ 8.09 (br s, 1H), 8.04 (d, J = 7.88 Hz, 1H), 7.79 (br d, J = 7.63 Hz, 1H), 7.71-7.63 (m, 1H), 7.21 (s, 2H), 6.28 (br s, 1H), 5.67 (ddt, J = 9.82, 3.60, 1.67, 1.67 Hz, 1H), 5.56-5.48 (m, 1H), 4.59 (d, J = 8.25 Hz, 1H), 4.03-3.78 (m, 2H), 3.65-3.50 (m, 1H), 3.00 (s, 3H), 2.32-2.20 (m, 1H), 2.09 (br d, J = 2.38 Hz, 2H), 1.93-1.63 (m, 8H), 1.26 (s, 1H), 1.02-0.77 (m, 3H), 0.32 (br s, 4H) |
| Compound 237 | 592.1 (M + H)+ | (DMSO-d$^6$) δ 8.15-8.65 (br s, 1H), 7.95-8.00 (m, 2H), 7.83 (d, J = 8.0 Hz 3H), 7.66-7.70 (m, 1H), 7.20 (s, 1H), 7.00 (m, 1H), 6.27 (s, 1H), 3.88-3.90 (m, 2H), 3.67 (s , 4H), 3.00 (s, 3H), 2.29 (d, J = 11.6 Hz, 2H), 1.80-1.82 (m, 3H), 1.71 (m, 3H), 0.92-0.4 (m, 2H), 3.19 (s, 4H) |
| (R)-Compound 239 | 562.1 (M + H)+ | (DMSO-d$^6$) δ 8.15-8.30 (br s, 1H), 7.98-8.02 (m, 2H), 7.83 (d, J = 7.2 Hz, 1H), 7.67-7.71 (m, 1H), 7.19 (s, 1H), 7.10 (m, 1H), 6.45 (s, 1H), 5.10-5.23 (d, J = 53.2 Hz, 2H), 3.89 (m, 2H), 3.59-3.63 (m, 3H), 3.31-3.32 (m, 1H), 2.15-2.25 (m, 1H), 1.98 (m, 2H), 1.71 (m, 2H), 0.91-0.93 (m, 2H), 0.31 (s , 4H) |
| (S)-Compound 239 | 562.1 (M + H)+ | (CDCl$_3$) δ 8.12-8.34 (m, 2H), 7.97-8.09 (m, 1H), 7.81-7.88 (m, 1H), 7.67-7.74 (m, 1H), 7.18-7.25 (m, 1H), 6.96-7.15 (m, 1H), 6.25-6.40 (m, 1H), 5.01-5.35 (m, 1H), 3.75-4.17 (m, 2H), 3.59-3.66 (m, 2H), 3.47-3.58 (m, 1H), 3.28-3.39 (m, 1H), 2.98-3.04 (m, 3H), 2.16-2.27 (m, 1H), 1.97 (br s, 1H), 1.86-1.95 (m, 1H), 1.77-1.85 (m, 2H), 1.65-1.76 (m, 3H), 0.88-1.00 (m, 2H), 0.24-0.42 (br s, 4H |
| Compound 240 | 532.1 (M + H)+ | (DMSO-d$^6$) δ 9.59 (s, 1 H) 7.83-8.11 (m, 3 H) 7.75-7.82 (m, 1 H) 6.91-7.21 (m, 2 H) 3.76-4.00 (s, 2 H) 2.79-3.06 (m, 7 H) 1.61-1.43(m, 13 H) 1.03-1.30 (m, 4 H) |
| Compound 241 | 518.1 (M + H)+ | (DMSO-d$^6$) δ 9.59 (1 H, br s) ) 7.81-8.40 (m, 4 H) 7.72-7.80 (m, 1 H) 6.78-7.25 (m, 2 H) 3.85 (m, 2 H) 3.19 (br s, 4 H) 2.80-3.03 (m, 3 H) 1.41-1.90 (m, 11 H) 0.93-1.38 (m, 3 H) |
| Compound 243 | 504.0 (M + H)+ | (DMSO-d$^6$) δ 9.61 (s, 1H), 8.00 (s, 1H), 7.95 (d, J = 7.9 Hz, 1H), 7.82 (d, J = 7.4 Hz, 1H), 7.72-7.66 (m, 1H), 7.65 (s, 1H), 7.16 (d, J = 2.0 Hz, 2H), 5.72 (s, 2H), 3.93 (s, 2H), 2.94 (s, 3H), 2.60 (s, 4H), 1.09 (s, 9H) |

TABLE 8-continued

| Compound | ESI MS (M/z) | NMR summary (400 MHz) ppm |
|---|---|---|
| Compound 245 | 558.2 (M + H)+ | (DMSO-d$^6$) δ 9.49-9.56 (m, 1 H), 7.91-7.98 (m, 3 H), 7.73-7.74 (m, 1 H), 6.99-7.12 (m, 2 H), 3.88-3.90 (br s, 2 H), 3.65-3.80 (m, 2 H), 2.91 (s, 3 H), 1.93-2.08 (m, 2 H), 1.56-1.75 (m, 6 H), 1.33 (s, 6 H), 0.85-0.90 (m, 2 H), 0.18-0.35 (m, 4 H) |
| Compound 247 | 562.1 (M + H)+ | (DMSO-d$^6$) δ 8.12-8.34 (m, 1H), 7.97-8.09 (m, 2H), 7.81-7.88 (m, 1H), 7.67-7.74 (m, 1H), 7.18-7.25 (m, 1H), 6.96-7.15 (m, 1H), 6.25-6.40 (m, 1H), 5.01-5.35 (m, 1H), 3.75-4.17 (m, 2H), 3.59-3.66 (m, 2H), 3.47-3.58 (m, 1H), 3.28-3.39 (m, 1H), 2.98-3.04 (m, 3H), 2.16-2.27 (m, 1H), 1.97 (br s, 1H), 1.86-1.95 (m, 1H), 1.77-1.85 (m, 2H), 1.65-1.76 (m, 3H), 0.88-1.00 (m, 2H), 0.24-0.42 (br s, 4H) |
| Compound 249 | 558.1 (M + H)+ | (DMSO-d$^6$) δ 9.58 (s, 1 H) 7.87-8.18 (m, 4 H) 7.75-7.82 (m, 1 H) 7.14 (d, J = 2.00 Hz, 2 H) 3.90 (br s, 2 H) 3.41 (dd, J = 9.82, 7.19 Hz, 1 H) 3.30 (br s, 1 H) 3.16-3.26 (m, 1 H) 2.95 (s, 3 H) 2.72 (dd, J = 9.88, 7.50 Hz, 1 H) 1.99-2.09 (m, 1 H) 1.87 (td, J = 11.73, 6.69 Hz, 1 H) 1.46-1.76 (m, 6 H) 1.23-1.35 (m, 1 H) 0.88 (br d, J = 11.76 Hz, 2 H) 0.80 (d, J = 6.63 Hz, 3 H) 0.28 (br d, J = 5.63 Hz, 4 H) |
| Compound 250 | 517.1 (M + H)+ | (DMSO-d$^6$) δ 8.22-7.93 (m, 3H), 7.91 (m, 1H), 7.86-7.74 (m, 3H), 3.96 (s, 2H), 3.40 (s , 4H), 2.99-2.82 (m, 4H), 1.76-1.60 (m, 6H), 1.54 (s, 5H), 1.38 (d, J = 4.0 Hz, 2H), 1.33-1.09 (m, 3H) |
| Compound 252 | 520.1 (M + H)+ | (DMSO-d$^6$) δ 9.57 (br s, 1 H), 7.92-8.04 (m, 2 H), 7.82 (br d, J = 6.85 Hz, 1 H), 7.63-7.74 (m, 2 H), 7.01-7.16 (m, 2 H), 3.77-3.91 (m, 2 H), 2.94 (s, 3 H), 1.85-1.99 (m, 2 H), 1.62-1.84 (m, 2 H), 1.30-1.42 (m, 2 H), 1.20-1.27 (m, 2 H), 1.11 (s, 9 H), 0.92-1.04 (m, 3 H), 0.81-0.90 (m, 1 H). |
| Compound 254 | 556.1 (M + H)+ | (DMSO-d$^6$) δ 9.54-9.63 (br s, 1 H), 7.89-8.11 (m, 3 H), 7.75-7.83 (m, 1 H), 7.04-7.18 (m, 2 H), 3.86-3.97 (s, 2 H), 3.42 (br d, J = 9.26 Hz, 2 H), 3.11-3.21 (s, 2 H), 2.90-2.98 (s, 3 H), 1.57-1.74 (m, 6 H), 1.45-1.54 (m, 2 H), 0.81-0.96 (m, 2 H), 0.46-0.56 (m, 1 H), 0.19-0.37 (m, 4 H), −0.24-0.14 (m, 1 H). |
| Compound 255 | 560.1 (M + H)+ | (DMSO-d$^6$) δ 9.54-9.63 (s, 1 H), 7.93-8.12 (m, 4 H), 7.79-7.88 (m, 1 H), 7.13 (s, 2 H), 5.64 (s, 1 H), 3.92 (br s, 2 H), 3.50-3.66 (m, 4 H), 2.94 (s, 3 H), 1.68 (s, 6 H), 1.16 (s, 3 H), 0.80-0.95 (m, 2 H), 0.27 (br s, 4 H). |
| Compound 257 | 566.0 (M + H)+ | (DMSO-d$^6$) δ 9.57 (br s, 1 H) 8.13-8.02 (m, 3 H) 7.83 (t, J = 7.60, 1 H) 7.11 (d, J = 1.60 Hz, 2 H) 4.32 (t, J = 12.80 Hz, 4 H) 3.83-3.82 (m, 2 H) 2.92 (s, 3 H) 1.67-1.61 (m, 6 H) 0.84-0.80 (m, 2 H) 0.26-0.22 (m, 4 H) |
| Compound 258 | 542.1 (M + H)+ | (DMSO-d$^6$) δ 9.58 (br s, 1 H), 8.20-7.94 (m, 4 H), 7.89-7.81 (m, 1 H), 7.14 (s, 2 H), 4.95 (s, 2H), 4.41 (br s, 4 H), 4.00-3.82 (m, 2H), 2.94 (s, 3 H), 1.77-1.49(m, 6H), 0.97-0.80(m, 2 H), 0.38-0.19 (m, 4H) |
| Compound 260 | 544.1 (M + H)+ | (DMSO-d$^6$) δ 9.57 (br s , 1 H), 8.14-7.91 (m, 4 H), 7.86-7.82 (m, 1 H), 7.13 (J = 2.0 Hz, br d, 2 H), 3.92-3.86 (m, 4 H), 3.29-3.26 (m, 2 H), 2.94 (s, 3 H), 2.52-2.51 (m, 1 H), 1.68 (br s , 6 H), 0.86 (J = 6.8 Hz, br d, 5 H), 0.27-0.24 (m, 4 H) |
| Compound 261 | 558.7 (M + H)+ | (DMSO-d$^6$) δ 9.43-9.95 (br s, 1H), 8.08-8.18 (m, 1H), 7.81-8.00 (m, 3H), 7.66-7.78 (m, 1H), 7.05-7.20 (m, 2H), 3.81-3.95 (s, 2H), 3.57-3.75 (m, 1H), 3.00-3.11 (m, 2H), 1.83-1.94 (m, 2H), 1.43-1.76 (m, 10H), 1.15-1.22 (m, 3H), 0.82-0.91 (m, 2H), 0.19-0.33 (m, 4H) |
| Compound 262 | 552.1 (M + H)+ | (DMSO-d$^6$) δ 9.54-9.74 (br s, 1 H) 8.40 (s, 1 H) 7.69-8.19 (m, 3 H) 6.94-7.24 (m, 2 H) 4.06 (s, 2 H) 2.89 (s, 3 H) 1.69-1.76 (m, 6 H) 1.19 (s, 9 H) 0.89-0.90 (m, 2 H) 0.24 (s, 4 H) |
| Compound 264 | 555.1 (M + H)+ | (DMSO-d$^6$) δ 9.57 (br s, 1 H) 9.28 (br s, 1 H) 8.03-7.97 (m, 4 H) 7.82-7.78 (m, 1 H) 7.14-7.12 (m, 2 H) 3.91 (br s, 2 H) 2.95 (s, 3 H) 1.65 (br s, 6 H) 1.44-1.35 (m, 4 H) 0.83 (br s, 2 H) 0.25 (br s, 4H) |
| Compound 266 | 559.2 (M + H)+ | (CD$_3$OD) δ 9.60 (brs, 1 H) 7.94-8.03 (m, 2 H) 7.83 (m, 1 H) 7.69-7.73 (m, 1 H) 7.57 (m, 1 H) 6.98-7.23 (m, 2 H) 3.88 (s, 2 H) 2.94 (s, 3 H) 1.57-1.65 (m, 6 H) 1.36-1.50 (m, 2 H) 1.04 (s, H) 0.85-0.88 (m, 2 H) 0.71-0.74 (m, 3 H) 0.27 (m, 4 H) |
| Compound 268 | 552.1 (M + H)+ | (DMSO-d$^6$) δ 9.60 (br s, 1H), 8.36 (s, 1H), 7.87-8.14 (m, 2H), 7.55-7.80 (m, 1H), 7.01-7.27 (m, 2H), 4.27 (s, 2H), 2.96 (s, 3H), 1.62-1.92 (m, 6H), 1.17 (s, 9H), 0.86-1.02 (m, 2H), 0.31 ppm (br s, 4H) |
| Compound 269 | 566.1 (M + H)+ | (DMSO-d$^6$) δ 9.69 (br s, 1H), 8.35 (s, 1H), 7.96 (m, 2H), 7.65 (s, 1H), 7.01-7.24 (m, 2H), 4.19-4.38 (m, 2H), 3.05 (q, 2H), 1.62-1.89 (m, 6H), 1.07-1.29 (m, 12H), 0.92 (br d, J = 13.0 Hz, 2H), 0.31 (br s, 4H) |
| Compound 270 | 527.1 (M + H)+ | (DMSO-d$^6$) δ 9.64-9.54 (m, 1H), 8.20-8.00 (m, 1H), 7.92-7.80 (m, 2H), 7.78-7.66 (m, 2H), 7.19-7.07 (m, 2H), 3.99-3.79 (s, 2H), 2.97-2.91 (s, 3H), 1.94-1.75 (m, 4H), 1.72-1.64 (m, 4H), 1.61-1.49 (m, 6H), 1.44-1.36 (m, 1H), 0.92-0.83 (m, 2H), 0.32-0.21 (m, 4H) |
| Compound 272 | 600.0 (M + H)+ | (DMSO-d$^6$) δ 9.81-9.58 (m, 1 H), 8.57 (s, 1 H), 8.11-7.82 (m, 2 H), 7.24-7.01 (m, 2 H), 4.58-4.31 (s, 2 H), 3.86-3.71 (m, 6 H), 3.14-2.99 (m, 2 H), 2.16-1.99 (m, 2H), 1.96-1.84 (m, 8 H), 1.67-1.61 (m, 2H), 1.30-1.13 (m, 3 H) |

TABLE 8-continued

| Compound | ESI MS (M/z) | NMR summary (400 MHz) ppm |
|---|---|---|
| Compound 274 | 582.1 (M + H)+ | (DMSO-d6) δ 9.58 (br s, 1 H) 8.38 (s, 1 H) 8.08-7.94 (m, 1 H) 7.93-7.80 (m, 2 H) 7.18-7.01 (m, 2 H) 4.93 (br d, J = 2.00 Hz, 1 H) 4.07 (s, 2 H) 3.73 (br d, J = 2.00 Hz, 2 H) 3.19 (t, J = 6.75 Hz , 2 H) 1.78-1.58 (m, 6 H) 1.20 (s, 9 H) 0.89 (br d, J = 10.51 Hz, 2 H) 0.29 (s, 4 H) |
| Compound 275 | 566.1 (M + H)+ | (DMSO-d6) δ 9.66 (br s, 1 H) 8.37 (s, 1 H) 8.07 (m, 1 H), 7.92-7.82 (m, 2 H) 7.13 (d, J = 1.97 Hz, 2 H) 4.06 (s, 2 H) 3.03 (m, 2 H), 1.80-1.58 (m, 6 H), 1.21-1.15 (m, 12 H), 0.88 (br d, J = 10.74 Hz, 2 H), 0.29 (s, 4 H) |
| Compound 277 | 562.0 (M + H)+ | (DMSO-d6) δ 9.59 (s, 1H), 8.41 (s, 1H), 8.19-7.95 (m, 1H), 7.93-7.82 (m, 2H), 7.18-7.01 (m, 2H), 4.18 (s, 2H), 2.96 (s, 3H), 2.14-1.73 (m, 8H), 1.20 (s, 9H) |
| Compound 279 | 576.1 (M + H)+ | (DMSO-d6) δ 9.58 (br s, 1 H), 8.56 (s, 1 H), 8.03 (br s, 2 H), 7.18-7.04 (m, 2 H), 4.07 (s, 2 H), 3.82 (s, 4 H), 2.95 (s, 3 H), 1.99-1.89 (m, 4 H), 1.68 (br s, 8 H), 0.88 (br d, J = 5.63 Hz, 2 H), 0.36-0.21 (m, 4 H) |
| Compound 281 | 600.0 (M + H)+ | (DMSO-d6) δ 9.67-9.49 (m, 1H), 8.65-8.52 (m, 1H), 8.14-7.91 (m, 2H), 7.21-7.01 (m, 2H), 4.20-4.05 (m, 2H), 3.22-3.11 (m, 4H), 2.96-2.82 (m, 3H), 2.22-2.06 (m, 4H), 1.80-1.59 (m, 6H), 0.93-0.82 (m, 2H), 0.41-0.20 (m, 4H) |
| Compound 283 | 578.0 (M + H)+ | (DMSO-d6) δ 9.69-9.51 (m, 1H), 8.56 (br s, 1H, ), 8.18-8.01 (m, 2H), 7.19-7.00 (m, 2H), 4.31 (t, J = 7.4 Hz, 2H, ), 4.18 (d, J = 11.0 Hz, 2H, ), 4.06 (s, 2H, s), 3.85 (d, J = 10.9 Hz, 2H, ), 2.94 (s, 3H), 2.72 (br t, J = 7.4 Hz, 2H), 1.85-1.60 (m, 6H), 0.96-0.82 (m, 2H), 0.28 (s, 4H) |
| Compound 284 | 524.0 (M + H)+ | (DMSO-d6) δ 9.61-9.52 (m, 1H), 8.50-8.22 (m, 2H), 8.12-7.73 (m, 2H), 7.16-6.90 (m, 2H), 4.11-3.92 (m, 2H), 3.81-3.66 (m, 1H), 3.00-2.87 (m, 3H), 2.08-1.93 (m, 2H), 1.87-1.74 (m, 2H), 1.68-1.46 (m, 10H), 1.36-1.12 (m, 3H) |
| Compound 285 | 572.2 (M + H)+ | (DMSO-d6) δ 9.59 (s, 1 H) 8.15-7.91 (m, 3 H) 7.90-7.79 (m, 2 H) 7.77-7.70 (m, 1 H) 7.14 (m, 2 H) 3.89 (s, 2 H) 3.64-3.43 (m, 1 H) 2.95 (s, 3 H) 2.05-1.91 (m, 1 H) 1.84-1.45 (m, 9 H) 1.38-1.05 (m, 2 H) 0.99-0.79 (m, 6 H) 0.27 (br d, J = 9.13 Hz, 4 H) |
| Compound 287 | 542.1 (M + H)+ | (DMSO-d6) δ 9.60-9.54 (m, 1 H) 8.11-8.01 (m, 3 H) 7.93-7.84 (m, 1 H) 7.78-7.71 (m, 1 H) 7.15-7.11 (m, 2 H) 4.30-4.26 (s, 1 H) 3.96-3.83 (s, 2 H) 3.73-3.62 (m, 1 H) 2.99-2.90 (s, 3 H) 1.95-1.83 (m, 2 H) 1.74-1.63 (m, 6 H) 1.62-1.46 (m, 6 H) 0.96-0.80 (m, 2 H) 0.34-0.20 (m, 4 H) |
| Compound 289 | 556.0 (M + H)+ | (DMSO-d6) δ 9.59 (s, 1H), 8.36 (br s, 1H), 8.12-7.94 (m, 1H), 7.94-7.77 (m, 2H), 7.12 (d, J = 1.8 Hz, 1H), 7.10-6.96 (m, 1H), 5.28-4.60 (m, 1H), 4.01 (s, 2H), 3.73 (t, J = 6.7 Hz, 2H), 3.18 (t, J = 6.7 Hz, 2H), 1.65 (br d, J = 11.7 Hz, 5H), 1.58-1.44 (m, 2H), 1.33-1.23 (m, 3H), 1.19 (s, 9H) |
| Compound 291 | 550.0 (M + H)+ | (DMSO-d6) δ 9.71-9.45 (m, 1 H), 8.44-8.28 (m, 2 H), 7.85 (br s, 2 H), 7.17-7.02 (m, 2 H), 4.06 (s, 2 H), 3.76 (br s, 1 H), 2.94 (s, 3 H), 2.08-1.96 (m, 2 H), 1.91-1.48 (m, 11 H), 0.88 (br d, J = 8.38 Hz, 2 H), 0.29 (br s, 4 H) |
| Compound 292 | 631.2 (M + H)+ | (DMSO-d6) δ 8.20-7.97 (m, 3 H), 7.89-7.76 (m, 1 H), 7.75-7.62 (m, 1 H), 7.25-7.02 (m, 2 H), 4.06-3.84 (m, 2 H), 3.27-3.17 (m, 2 H), 3.15-2.96 (m, 2 H), 2.05-1.80 (m, 7 H), 1.78-1.50 (m, 4 H), 1.33-1.11 (m, 9 H), 1.06-0.82 (m, 2 H), 0.47-0.09 (m, 4 H) |
| Compound 293 | 594.1 (M + H)+ | (DMSO-d6) δ 9.86-9.44 (m, 1 H), 8.55-8.22 (m, 1 H), 8.11-7.86 (m, 4 H), 7.80-7.69 (m, 1 H), 7.20-7.01 (m, 1 H), 3.97-3.78 (m, 2 H), 3.70-3.55 (m, 1 H), 3.10-2.97 (m, 2 H), 2.80-2.67 (m, 2 H), 2.43-2.35 (m, 2 H), 1.76-1.49 (m, 6 H), 1.27-1.10 (m, 3 H), 0.97-0.76 (m, 2 H), 0.37-0.14 (m, 4 H) |
| Compound 295 | 532.1 (M + H)+ | (DMSO-d6) δ 9.62 (br s, 1 H), 8.08-7.92 (m, 3 H), 7.80 (br d, J = 6.63 Hz, 1 H), 7.74-7.63 (m, 2 H), 7.10 (d, J = 1.75 Hz, 2 H), 5.34 (br s, 1 H), 3.86-3.75 (m, 1 H), 3.74-3.61 (m, 1 H), 2.94 (s, 3 H), 2.22-2.04 (m, 2 H), 2.02-1.89 (m, 2 H), 1.87-1.75 (m, 1 H), 1.72-1.52 (m, 4 H), 1.09 (s, 9 H) |
| Compound 297 | 576.1 (M + H)+ | (DMSO-d6) δ 9.65-9.46 (m, 1 H) 8.03-7.93 (m, 1 H) 7.87 (br d, J = 7.50 Hz, 1 H) 7.37-7.28 (m, 1 H) 7.25-7.18 (m, 1 H) 7.15-7.10 (m, 1 H) 7.04 (br d, J = 8.88 Hz, 1 H) 4.00 (s, 3 H) 3.93 (s, 2 H) 2.98-2.89 (m, 3 H) 1.74-1.56 (m, 6 H) 1.10 (s, 9 H) 0.93-0.82 (m, 2 H) 0.36-0.20 (m, 4 H) |
| Compound 298 | 562.1 (M + H)+ | (DMSO-d6) δ 11.64-10.86 (m, 1 H) 9.64-9.45 (m, 1 H) 7.99-7.82 (m, 1 H) 7.74-7.54 (m, 1 H) 7.23-6.81 (m, 4 H) 4.03-3.85 (s, 2 H) 3.03-2.86 (s, 3 H) 1.75-1.56 (m, 6 H) 1.13 (s, 9 H) 0.97-0.81 (m, 2 H) 0.37-0.16 (m, 4 H) |
| Compound 299 | 536.1 (M + H)+ | (DMSO-d6) δ 9.71-9.10 (m, 1 H) 8.43-8.31 (m, 1 H) 8.13-7.95 (m, 1 H) 7.47-7.28 (m, 1 H) 7.23-6.99 (m, 3 H) 4.40-4.17 (s, 2 H) 3.03-2.86 (s, 3 H) 1.99-1.78 (m, 2 H) 1.75-1.56 (m, 4 H) 1.26-1.13 (s, 9 H) 0.99-0.82 (m, 2 H) 0.42-0.17 (s, 4 H) |

TABLE 8-continued

| Compound | ESI MS (M/z) | NMR summary (400 MHz) ppm |
|---|---|---|
| Compound 301 | 515.1 (M + H)⁺ | (DMSO-d⁶) δ 9.08-8.37 (m, 1 H) 8.02-7.90 (m, 1 H) 7.29-7.20 (m, 1 H) 7.14-6.99 (m, 2 H) 5.73-5.64 (m, 1 H) 4.65-4.53 (m, 1 H) 4.13-3.97 (m, 2 H) 2.96-2.90 (m, 3 H) 2.19-2.09 (m, 1 H) 1.86-1.37 (m, 14 H) 0.95-0.84 (m, 2 H) 0.34-0.23 (m, 4 H) |
| Compound 302 | 596.0 (M + H)⁺ | (DMSO-d⁶) δ 9.66-9.49 (m, 1 H, m) 8.14-7.92(m, 2 H) 7.42 (d, J = 8.55 Hz, 1 H) 7.17-6.93 (m, 2 H) 4.57-4.33 (m, 4 H) 4.09-4.00 (m, 5 H) 2.93 (s, 3 H) 1.76-1.53 (m, 6 H) 0.95-0.78 (m, 2 H) 0.36-0.17 (m, 4 H) |
| Compound 303 | 582.0 (M + H)⁺ | (DMSO-d⁶) δ 11.64-11.90 (m, 1 H) 9.43-9.61 (m, 1 H) 7.69-7.95 (m, 2 H) 6.93-7.18 (m, 3 H) 4.43 (t, J = 12.88 Hz, 4 H) 3.95 (s, 2 H) 2.93 (s, 3 H) 1.55-1.76 (m, 6 H) 0.76-1.01 (m, 2 H) 0.28 (s, 4H) |
| Compound 305 | 509.3 (M + H)⁺ | (DMSO-d⁶) δ 9.62 (s, 1H), 8.19-7.87 (m, 1H), 7.55-7.39 (m, 4H), 7.16-6.94 (m, 2H), 5.18 (d, J = 4.3 Hz, 1H), 4.56-4.45 (m, 1H), 3.96-3.84 (m, 2H), 2.94 (s, 3H), 2.35-2.20 (m, 1H), 1.97-1.47 (m, 14H), 0.89 (br d, J = 11.3 Hz, 2H), 0.27 (br d, J = 5.5 Hz, 4H) |
| Compound 306 | 529.1 (M + H)⁺ | (DMSO-d⁶) δ 9.56 (br s, 1H), 8.22-7.92 (m, 1H), 7.83-7.57 (m, 4H), 7.19-6.95 (m, 2H), 3.89 (br s, 2H), 2.94 (s, 3H), 2.86-2.71 (m, 1H), 1.79-1.45 (m, 14H), 0.89 (br d, J = 12.0 Hz, 2H), 0.28 (br s, 4H) |
| Compound 309 | 564.1 (M + H)⁺ | (DMSO-d⁶) δ 9.70-9.33 (m, 1H), 8.08-8.03 (m, 1H), 7.99 (br d, J = 7.8 Hz, 1H), 7.91-7.78 (m, 1H), 7.76-7.67 (m, 2H), 7.32-7.17 (m, 1H), 3.92 (br s, 2H), 3.07-2.91 (m, 3H), 1.82-1.47 (m, 6H), 1.19-1.03 (m, 9H), 0.93-0.75 (m, 2H), 0.37-0.15 (m, 4H) |
| Compound 310 | 564.1 (M + H)⁺ | (DMSO-d⁶) δ 9.81-9.25 (m, 1 H), 8.09-8.02 (m, 1 H), 8.02-7.95 (m, 1 H), 7.90-7.80 (m, 1 H), 7.76-7.62 (m, 2 H), 7.32-7.11 (m, 1 H), 4.03-3.86 (s, 2 H), 3.02-2.89 (s, 3 H), 2.05-1.95 (m, 2 H), 1.82-1.49 (m, 4 H), 1.11 (s, 9 H), 0.89-0.70 (m, 2 H), 0.33-0.14 (m, 4 H) |
| Compound 311 | 586.1 (M + H)⁺ | (CDCl₃) δ 8.16 (br s, 1 H) 7.89 (br d, J = 7.88 Hz, 1 H) 7.21 (s, 1 H) 7.17 (d, J = 8.63 Hz, 1H) 7.10-6.86 (m, 1 H) 6.53-6.42 (m, 1 H) 5.62 (br d, J = 3.25 Hz, 1 H) 4.09 (s, 3 H) 3.99 (br s, 2 H) 2.99 (s, 3 H) 2.33 (s, 1 H) 1.91-1.64 (m, 12 H) 0.92 (br d, J = 11.51 Hz, 2 H) 0.31 (s, 4H) |
| Compound 312 | 495.1 (M + H)⁺ | (DMSO-d⁶) δ 9.54 (br s, 1 H, ) 8.24-7.41 (m, 5 H) 7.11-6.80 (m, 2 H) 5.26 (d, J = 4.50 Hz, 1 H) 4.49 (dd, J = 6.88, 4.75 Hz, 1 H) 3.89 (br s, 2 H) 2.93 (s, 3 H) 2.61-2.78 (m, 1 H) 2.32-1.74 (m, 4 H, m) 1.71-1.65 (m, 8 H) 0.91-0.88 (m, 2 H) 0.28 (br s, 4 H) |
| Compound 313 | 495.1 (M + H)⁺ | (DMSO-d⁶) δ 9.54 (br s, 1 H, ) 8.24-7.41 (m, 5 H) 7.11-6.80 (m, 2 H) 5.26 (d, J = 4.50 Hz, 1 H) 4.49 (dd, J = 6.88, 4.75 Hz, 1 H) 3.89 (br s, 2 H) 2.93 (s, 3 H) 2.61-2.78 (m, 1 H) 2.32-1.74 (m, 4 H, m) 1.71-1.65 (m, 8 H) 0.91-0.88 (m, 2 H) 0.28 (br s, 4 H) |
| Compound 314 | 546.1 (M + H)⁺ | (DMSO-d⁶) δ 9.55 (br s, 1 H), 7.59-7.41 (m, 4 H), 7.13 (d, J = 1.88 Hz, 2 H), 5.40 (d, J = 4.50 Hz, 1 H), 4.69-4.60 (m, 1 H), 3.89 (br s, 2 H), 3.66-3.49 (m, 4 H), 2.94 (s, 3 H), 2.75 (m, 2 H), 1.73-1.54 (m, 6 H), 0.95-0.84 (m, 2 H), 0.28 (br s, 4 H) |
| Compound 315 | 574.1 (M + H)⁺ | (DMSO-d⁶) δ 8.46 (br d, J = 1.59 Hz, 1 H) 7.38-7.62 (m, 5 H) 7.17 (d, J = 2.20 Hz, 1 H) 7.03 (m, 1 H) 4.98 (br s, 1 H) 4.79 (m, 1 H) 3.90 (s, 2 H) 2.90-2.96 (m, 3 H) 2.65-2.56 (m, 6 H)1.83-1.99 (m, 4 H) 1.56-1.80 (m, 6 H) 0.92-1.04 (m, 2 H) 0.24-0.38 (m, 4H) |
| Compound 316 | 510.6 (M + H)⁺ | (DMSO-d⁶) δ 9.64 (br d, J = 5.26 Hz, 1H), 8.69-8.57 (d, 1H), 8.11-7.98 (m, 1H), 7.66-7.54 (s, 1H), 7.45 (m, 1H), 7.16 (m, 2H), 5.46 (d, 1H), 4.57-4.46 (t, 1H), 3.75 (m, 2H), 2.95 (s, 3H), 1.70-1.36 (m, 15H), 0.91-0.80 (m, 2H), 0.32-0.21 (m, 4H) |
| Compound 317 | 510.3 (M + H)⁺ | (DMSO-d⁶) δ 9.56 (s, 1 H), 8.14 (d, J = 8.38 Hz, 1 H), 8.01-7.93 (m, 1 H), 7.74-7.66 (m, 1 H), 7.62 (d, J = 7.63 Hz, 1 H), 7.18-7.04 (m, 2 H), 5.45 (d, J = 5.00 Hz, 1 H), 4.53-4.44 (m, 1 H), 4.35 (d, J = 11.2 Hz, 1 H), 4.12 (d, J = 11.6 Hz, 1 H), 2.95 (s, 3 H), 2.43-2.35 (m, 1 H), 1.74-1.39 (m, 14 H), 0.95-0.79 (m, 2 H), 0.36-0.21 (m, 4 H) |
| Compound 318 | 521.2 (M + H)⁺ | (DMSO-d⁶) δ 9.66-9.46 (m, 1 H), 8.15-7.90 (m, 1 H), 7.78-7.62 (m, 3 H), 7.54-7.38 (m, 2 H), 6.38-7.97 (m, 2 H), 4.01-3.83 (m, 2 H), 3.20-3.07 (s, 4 H), 3.00-2.87 (m, 3 H), 1.83-1.43 (m, 12 H), 0.98-0.80 (m, 2 H), 0.38-0.14 (m, 4 H) |
| Compound 319 | 510.1 (M + H)⁺ | (DMSO-d⁶) δ 9.60 (s, 1H), 8.58 (s, 1H), 8.05 (s, 2H), 7.37 (s, 1H), 7.12 (d, J = 2.1 Hz, 1H), 7.06 (brd J = 8.5 Hz, 1H), 4.09 (s, 2H), 2.95 (s, 3H), 1.65 (br d, J = 10.5 Hz, 5H), 1.54 (br t, J = 11.4 Hz, 2H), 1.45-1.23 (m, 3H), 1.18 (s, 9H). |
| Compound 320 | 586.1 (M + H)⁺ | (DMSO-d⁶) δ 9.78-9.56 (m, 1H), 8.15-7.91 (m, 4H), 7.87-7.77 (m, 1H), 7.21-6.97 (m, 2H), 4.26 (br t, J = 7.4 Hz, 2H), 4.09 (br d, J = 10.5 Hz, 2H), 3.89 (br s, 2H), 3.79-3.68 (m, 2H), 3.12-3.00 (m, 2H), 2.71-2.60 (m, 2H), 1.78-1.51 (m, 6H), 1.27-1.14 (m, 3H), 0.86 (br d, J = 4.5 Hz, 2H), 0.39-0.14 (m, 4H) |

TABLE 8-continued

| Compound | ESI MS (M/z) | NMR summary (400 MHz) ppm |
|---|---|---|
| Compound 321 | 560.1 (M + H)+ | (DMSO-d6) δ 9.69-9.57 (m, 1 H) 8.14-8.00 (m, 1 H) 7.58-7.51 (m, 1 H) 7.50-7.43 (m, 1 H) 7.21-7.02 (m, 2 H) 4.51-4.24 (m, 2 H) 3.98-3.79 (m, 4 H) 3.00-2.92 (m, 3 H) 2.01-1.91 (m, 4 H) 1.90-1.78 (m, 2 H) 1.75 (br d, J = 2.88 Hz, 6 H) 0.97-0.88 (m, 2 H) 0.43-0.21 (m, 4H) |
| Compound 322 | 565.0 (M + H)+ | (DMSO-d6) δ 9.68-9.41 (m, 1 H) 8.23-7.94 (m, 4 H) 7.88-7.76 (m, 1 H) 7.21-7.03 (m, 2 H) 4.35-4.17 (m, 1 H) 4.01-3.78 (m, 2 H) 3.12-2.86 (m, 7 H) 1.85-1.44 (m, 6 H) 1.04-0.75 (m, 2 H) 0.42-0.11 (m, 4H) |
| Compound 323 | | (DMSO-d6) δ 8.08-7.94 (m, 2 H) 7.89-7.78 (m, 1 H) 7.76-7.69 (m, 1 H) 7.69-7.62 (m, 1 H) 7.54-7.45 (m, 1 H) 7.45-7.30 (m, 1 H) 4.69 (s, 1H) 4.01-3.87 (m, 2 H) 3.30 (s, 1H) 2.29-2.15 (m, 2 H) 2.05-1.88 (m, 6 H) 1.13-1.06 (m, 9 H) |
| Compound 324 | 532.1 (M + H)+ | (DMSO-d6) δ 9.61 (br s, 1 H) 8.12-7.92 (m, 2 H) 7.90-7.76 (m, 1 H) 7.75-7.64 (m, 2 H) 7.18-7.03 (m, 1 H) 5.35 (br d, J = 10.08 Hz, 1 H) 4.77-4.64 (m, 1 H) 4.03-3.65 (m, 2 H) 2.95 (s, 3 H) 2.31-1.75 (m, 6H) 1.67-1.53 (m, 2 H) 1.13-1.07 (m, 9 H) |
| Compound 325 | | (DMSO-d6) δ 8.45-7.95 (m, 4H), 7.90-7.74 (m, 1H), 7.57-7.26 (m, 2H), 3.91 (br s, 2H), 3.60-3.45 (m, 1H), 1.84-1.53 (m, 6H), 1.25-1.13 (m, 6H), 0.94-0.73 (m, 2H), 0.26 (br s, 4H) |
| Compound 326 | 517.1 (M + H)+ | (DMSO-d6) δ 9.74-9.46 (m, 1H), 8.19-7.93 (m, 4H), 7.82 (t, J = 7.8 Hz, 1H), 7.26-6.96 (m, 2H), 4.10-3.81 (m, 2H), 3.61-3.43 (m, 1H), 2.94 (s, 3H), 1.82-1.47 (m, 6H), 1.29-1.04 (m, 6H), 0.97-0.78 (m, 2H), 0.27 (br s, 4H) |
| Compound 327 | 570.0 (M + H)+ | (DMSO-d6) δ 9.69 (br s, 1H), 8.23-7.93 (m, 3H), 7.91-7.79 (m, 1H), 7.76-7.59 (m, 2H), 7.24-7.01 (m, 2H), 4.12-3.89 (m, 2H), 3.07 (q, J = 7.0 Hz, 2H), 2.04 (br s, 2H), 1.82 (br d, J = 11.9 Hz, 6H), 1.27-1.16 (m, 3H), 1.13 (s, 9H) |
| Compound 329 | 552.2 (M + H)+ | (CD3OD) δ 8.41-7.98 (m, 3 H) 7.66-7.88 (m, 2 H) 7.03-7.34 (m, 2 H) 3.83-4.09 (m, 2 H) 2.95 (s, 3 H) 1.99-2.15 (m, 2 H) 1.73-1.96 (m, 3 H) 1.44-1.70 (m, 4 H) 1.30-1.39 (m, 2 H) 1.17-1.25 (m, 9H) |
| Compound 330 | 549.3 (M + H)+ | (DMSO-d6) δ 9.53-9.62 (m, 1 H) 8.55-8.67 (m, 1 H) 7.94-8.16 (m, 2 H) 7.00-7.18 (m, 2 H) 4.05-4.11 (m, 2 H) 3.87-3.98 (m, 1 H) 2.90-2.98 (m, 3 H) 1.90-1.99 (m, 4 H) 1.51-1.82 (m, 12 H) 0.25-0.34 (m, 4 H) |
| Compound 331 | 523.2 (M + H)+ | (CDCl3) δ 9.73-9.43 (m, 1H), 8.30-7.83 (m, 1H), 7.75-7.53 (m, 2H), 7.51-7.31 (m, 2H), 7.23-6.88 (m, 2H), 4.87 (s, 1H), 4.07-3.77 (m, 2H), 2.93 (s, 3H), 2.29-2.15 (m, 1H), 1.78-1.33 (m, 15H), 1.31-1.01 (m, 2H), 0.98-0.80 (m, 2H), 0.42-0.13 (m, 4H) |
| Compound 332 | 497.3 (M + H)+ | (DMSO-d6) δ 8.11-7.90 (m, 3 H) 7.87-7.79 (m, 1 H) 7.75-7.67 (m, 2 H) 7.29 (s, 2 H) 5.14 (br d, J = 2.25 Hz, 1 H) 4.71 (br d, J = 3.13 Hz, 1 H) 3.88 (br d, J = 8.76 Hz, 2 H) 1.83-1.54 (m, 6 H) 1.35-1.25 (m, 3H) 1.11 (s, 9 H) 0.92-0.77 (m, 2 H) 0.33-0.19 (m, 4H) |
| Compound 333a | 584.1 (M + H)+ | (DMSO-d6) δ 9.77-9.61 (m, 1 H) 8.10-7.92 (m, 3 H) 7.82 (br s, 3 H) 7.19-7.03 (m, 2 H) 6.05-5.04 (m, 1 H) 3.92-3.75 (m, 2 H) 3.11-2.97 (m, 2 H) 2.01-1.55 (m, 7 H) 1.25 (br s, 14 H) |
| Compound 333b | 584.1 (M + H)+ | (DMSO-d6) δ 9.71-9.59 (m, 1 H) 8.08-7.91 (m, 3 H) 7.87-7.63 (m, 3 H) 7.42-7.35 (m, 1 H) 7.20-7.01 (m, 1 H) 6.28-5.96 (m, 1 H) 3.82-3.74 (m, 1 H) 3.08-3.00 (m, 2 H) 1.96-1.77 (m, 2 H) 1.97-1.49 (m, 9 H) 1.25-1.06 (m, 12 H) |
| Compound 335 | 543.1 (M + H)+ | (DMSO-d6) δ 9.65-9.52 (m, 1 H), 8.17-7.92 (m, 4 H), 7.84-7.75 (m, 1 H), 7.20-7.04 (m, 2 H), 4.00-3.79 (m, 2 H), 3.60-3.49 (m, 2 H), 3.01-2.88 (m, 3 H), 1.94-1.46 (m, 13 H), 0.95-0.79 (m, 2 H), 0.26 (br d, J = 8.76 Hz, 4 H) |
| Compound 336a | 580.1 (M + H)+ | (DMSO-d6) δ 9.71-9.53 (m, 1 H), 8.81-8.69 (m, 1 H) 8.10-7.67(m, 5 H) 7.17-6.99 (m, 2 H) 6.03-5.65 (m, 1 H) 3.92-3.73 (m, 2 H) 2.97-2.93 (m, 3 H) 2.26 (s, 1 H) 1.79-1.60 (m, 13 H) 1.12-0.91 (m, 2H) |
| Compound 336b | 580.1 (M + H)+ | (DMSO-d6) δ 9.67-9.42 (m, 1 H), 8.83-8.64 (m, 1 H) 8.15-7.65 (m, 5 H), 7.40-7.34 (m, 1 H) 7.18-7.00 (m, 1 H) 6.33-5.97 (m, 1 H) 3.88-3.72 (m, 2 H) 2.97-2.93 (m, 3 H) 2.30-2.29 (m, 1 H) 1.85-1.53 (m, 15 H) |
| Compound 337 | 574.1 (M + H)+ | (DMSO-d6) δ 9.65-9.50 (m, 1 H), 9.15-9.00 (m, 1 H) 8.05-7.95 (m, 2 H) 7.60 (dd, J = 9.88, 8.63 Hz, 1 H) 7.19-7.00 (m, 2 H) 3.91 (br s, 2 H) 2.94 (s, 3 H) 2.29 (s, 1 H) 1.75 (s, 6 H) 1.71-1.54 (m, 6 H) 0.92-0.80 (m, 2 H) 0.26 (br d, J = 6.75 Hz, 4 H) |
| Compound 338 | 551.1 (M + H)+ | (DMSO-d6) δ 8.13-7.95 (m, 2 H), 7.90-7.79 (m, 1 H), 7.76-7.64 (m, 2 H), 7.45-7.26 (m, 2 H), 6.87-6.74 (m, 1 H), 5.22-5.08 (s, 1 H), 4.01-3.82 (s, 2 H), 1.84-1.49 (m, 6 H), 1.19-1.03 (m, 9 H), 0.93-0.79 (m, 2 H), 0.38-0.16 (m, 4 H) |
| Compound 339 | 518.1 (M + H)+ | (DMSO-d6) δ 9.62-9.52 (m, 1H), 8.16-7.93 (m, 1H), 7.71-7.50 (m, 4H), 7.18-7.03 (m, 2H), 4.31-4.22 (m, 1H), 3.96-3.84 (m, 2H), 3.35 (s, 1H), 2.99-2.91 (m, 3H), 2.46-2.31 (m, 1H), 1.81-1.74 (m, 1H), 1.65 (br s, 6H), 1.60-1.39 (m, 5H), 1.32-1.20 (m, 1H), 0.94-0.82 (m, 2H), 0.37-0.19 (m, 4H) |

TABLE 8-continued

| Compound | ESI MS (M/z) | NMR summary (400 MHz) ppm |
|---|---|---|
| Compound 340 | 578.1 (M + H)+ | (DMSO-d6) δ 9.72-9.60 (m, 1 H), 8.11-7.88 (m, 3 H), 7.62-7.50 (m, 1 H), 7.18-6.99 (m, 2 H), 3.97-3.80 (s, 2 H), 3.11-2.97 (s, 2 H), 1.75-1.50 (m, 6 H), 1.25-1.08 (m, 12 H), 0.93-0.79 (m, 2 H), 0.37-0.18 (m, 4 H) |
| Compound 341 | 558.1 (M + H)+ | (DMSO-d6) δ 9.86-9.10 (m, 1 H) 8.54-7.75 (m, 1 H) 7.56-7.42 (m, 4 H) 7.21-6.80 (m, 2 H) 3.99-3.85 (m, 2 H) 3.83-3.54 (m, 1 H) 3.50-3.38 (m, 2 H) 2.95-2.92 (m, 3 H) 1.95-1.86 (m, 4 H) 1.77-1.49 (m, 8 H) 1.39-1.33 (m, 3 H) 0.92-0.82 (m, 2 H) 0.32-0.23 (m, 4 H) |
| Compound 342 | 545.1 (M + H)+ | (DMSO-d6) δ 9.66-9.54 (m, 1H), 8.20-8.09 (m, 1H), 8.04-7.93 (m, 1H), 7.73 (br d, J = 7.6 Hz, 1H), 7.65-7.53 (m, 1H), 7.20-7.03 (m, 2H), 4.27-4.16 (m, 2H), 3.79-3.72 (m, 2H), 3.02-2.86 (s, 3H), 2.69-2.55 (m, 4H), 2.05-1.91 (m, 4H), 1.75-1.57 (m, 6H), 0.95-0.85 (m, 2H), 0.39-0.19 (m, 4H) |
| Compound 343 | 560.1 (M + H)+ | (CD3OD) δ 8.18 (d, J = 8.63 Hz, 1 H) 7.68 (s, 1 H) 7.26-7.12 (m, 2 H) 4.28-4.05 (m, 4 H) 3.12-2.91 (m, 7 H) 2.67 (s, 3 H) 2.25-2.06 (m, 4 H) 1.92-1.64 (m, 6 H) 0.95 (br d, J = 12.76 Hz, 2 H) 0.42-0.27 (m, 4 H) |
| Compound 345 | 516.2 (M + H)+ | (CD3OD) δ δ 8.07 (m, 1H), 7.56-7.53 (m, 4H), 7.20-7.10 (m, 2H), 4.03-3.90(m, 4H), 3.82-3.72 (m, 4H), 2.92 (s, 3H), 1.85-1.61 (m, 6 H), 0.97-0.94 (m, 2H), 0.26 (brs, 4H) |
| Compound 346 | 496.1 (M + H)+ | (DMSO-d6) δ 9.83 (s, 1H), 8.03-8.00 (br s, 1H), 7.50-7.43 (m, 4H), 7.12-6.97 (m, 2H), 4.01 (s, 2H), 3.71-3.90(m, 2H), 3.02-2.97 (m, 1H), 2.93 (s, 3), 2.81 (m, 1 H), 2.22-2.19 (m, 2H), 1.65 (m, 6H), 0.94-0.88 (m, 2H), 0.27 (br s, 4H) |
| Compound 347 | 494.1 (M + H)+ | (DMSO-d6) δ 9.54-9.48 (m, 1 H) 7.20-7.10 (m, 2 H) 7.07-6.94 (m, 1 H) 6.72-6.62 (m, 3 H) 5.88-5.81 (m, 1 H) 3.93-3.86 (m, 2 H) 3.76-3.66 (m, 1 H) 2.94-2.91 (m, 3 H) 1.96-1.86 (m, 2 H) 1.73-1.59 (m, 8 H) 1.58-1.51 (m, 2 H) 1.48-1.39 (m, 2 H) 0.99-0.84 (m, 2 H) 0.32-0.24 (m, 4 H) |
| Compound 348 | 508.1 (M + H)+ | (DMSO-d6) δ 9.29-8.82 (s, 1 H), 7.65-7.44 (s, 1 H), 7.31-7.24 (m, 1 H), 7.18-7.13 (m, 1 H), 7.02-6.99 (m, 1 H), 6.97-6.90 (m, 2 H), 6.80-6.74 (m, 1 H), 4.26-4.16 (m, 1 H), 3.94-3.87 (s, 2 H), 2.94-2.91 (s, 3 H), 2.80-2.76 (s, 3 H), 1.89-1.79 (m, 2 H), 1.75-1.55 (m, 12 H), 1.02-0.94 (m, 2 H), 0.35-0.25 (m, 4 H) |
| Compound 349 | 530.1 (M + H)+ | (DMSO-d6) δ 9.26 (s, 1 H), 7.56-7.45 (m, 5 H), 7.17 (d, J = 2.20 Hz, 1 H), 7.03 (dd, J = 8.50, 1.77 Hz, 1 H), 3.90 (s, 2 H), 3.74 (s, 2 H), 2.94 (s, 3 H), 2.93-2.89 (m, 2 H), 2.81-2.75 (m, 2 H), 2.31-2.21 (m, 2 H), 1.75-1.61 (m, 6 H), 0.97 (br d, J = 13.33 Hz, 2 H), 0.32-0.26 (m, 4 H) |
| Compound 351 | 531.1 (M + H)+ | (DMSO-d6) δ 9.35-9.17 (m, 1H), 7.61-7.39 (m, 5H), 7.17 (d, J = 2.1 Hz, 1H), 7.06-6.96 (m, 1H), 5.48-5.35 (m, 1H), 4.70-4.57 (m, 1H), 3.97-3.82 (m, 2H), 2.93 (s, 3H), 2.45-2.33 (m, 3H), 1.80-1.55 (m, 6H), 0.97 (br d, J = 13.3 Hz, 2H), 0.43-0.23 (m, 4H) |
| Compound 352 | 499.1 (M + H)+ | (DMSO-d6) δ 9.63-9.48 (m, 1 H) 8.02 (br d, J = 7.13 Hz, 1 H) 7.23 (d, J = 3.38 Hz, 1 H) 7.14-7.10 (m, 1 H) 7.06 (dd, J = 8.76, 2.00 Hz, 1 H) 6.48 (d, J = 3.38 Hz, 1 H) 5.51 (d, J = 5.25 Hz, 1 H) 4.48-4.35 (m, 1 H) 4.35-4.23 (m, 2 H) 2.94 (s, 3 H) 2.35-2.25 (m, 1 H) 1.88-1.68 (m, 7H) 1.61-1.19 (m, 7 H) 0.92 (br d, J = 13.26 Hz, 2 H) 0.32 (s, 4 H) |
| Compound 353 | | (DMSO-d6) δ 11.68 (s, 1 H) 9.55 (br s, 1 H) 8.11-7.76 (m, 3 H) 7.70-7.55 (m, 1 H) 7.20-6.97 (m, 2 H) 3.91 (br s, 2 H) 3.84-3.72 (m, 1 H) 3.32 (s, 2 H) 2.93 (s, 3 H) 2.58-2.55 (m, 1 H) 2.14-1.90 (m, 4 H) 1.71-1.60 (br s, 6 H) 1.55 (br s, 3 H) 0.95-0.80 (m, 2 H) 0.27 (br s, 4 H) |
| Compound 354 | 509.2 (M + H)+ | (DMSO-d6) δ 9.53 (s, 1 H) 8.0 (br m, 1 H) 7.58-7.30 (m, 4 H) 7.20-6.87 (m, 2 H) 5.32 (d, J = 4.0 Hz, 1H) 4.47 (d, J = 3.6 Hz, 1 H) 3.89 (br s, 2 H) 2.93 (s, 3 H) 2.30-2.18 (m, 2 H) 1.93-1.78 (m, 1 H) 1.75-1.25 (m, 9 H) 0.95 (s, 3H) 0.85-0.75 (m, 2 H) 0.28 (br s, 4H) |
| Compound 355 | 546.1 (M + H)+ | (DMSO-d6) δ 9.50-9.11 (m, 1 H) 7.70-7.39 (m, 4 H) 7.27-7.22 (m, 1 H) 7.18-7.15 (m, 1 H) 7.07-7.01 (m, 1 H) 3.95-3.84 (m, 2 H) 2.97-2.91 (m, 3 H) 1.79-1.61 (m, 6 H) 1.34-1.30 (m, 9 H) 1.02-0.91 (m, 2 H) 0.37-0.21 (m, 4 H) |
| Compound 356 | 594.0 (M + H)+ | (DMSO-d6) δ 9.69-9.35 (m, 1 H) 8.13-7.90 (m, 3 H) 7.83-7.73 (m, 1 H) 7.20-7.05 (m, 2 H) 4.02-3.80 (m, 2 H) 3.00-2.90 (m, 3 H) 2.83-2.63 (m, 7 H) 1.78-1.48 (m, 6 H) 0.96-0.80 (m, 2 H) 0.42-0.11 (m, 4 H) |
| Compound 357 | 511.3 (M + H)+ | (DMSO-d6) δ 9.58-9.50 (m, 1 H) 8.11-7.91 (m, 1 H) 7.54-7.39 (m, 4 H) 7.17-6.98 (m, 2 H) 5.09 (d, J = 4.63 Hz, 1 H) 4.72 (m, 1 H) 3.89 br s, 2 H) 2.97-2.90 (m, 3 H) 1.73-1.41 (m, 8 H) 0.94 (s, 9 H) 0.91-0.84 (m, 2 H) 0.32-0.21 (m, 4 H) |
| Compound 358 | 542.1 (M + H)+ | (DMSO-d6) δ 9.53 (brs 1H), 8.06-7.99 (m, 1H), 7.53-7.44 (m, 4H), 7.15 (s, 1H), 7.12-7.04 (m, 1H), 3.96 (s, 2H), 3.89 (s, 2H), 3.03-2.96 (m, 2H), 2.85-2.80 (m, 2H), 2.33-2.30 (m, 6H), 0.96-0.88 (m, 2H), 0.38-0.28 (m, 4H) |
| Compound 359 | 576.1 (M + H)+ | (DMSO-d6) δ 9.79-9.47 (m, 1 H) 8.18-7.95 (m, 2 H) 7.88-7.78 (m, 1 H) 7.76-7.63 (m, 1 H) 7.57-7.40 (m, 1 H) 7.22-6.99 (m, 2 H) 4.87-4.61 (m, 1 H) 4.05-3.77 (m, 2 H) 3.29-3.14 (m, 2 H) |

TABLE 8-continued

| Compound | ESI MS (M/z) | NMR summary (400 MHz) ppm |
|---|---|---|
| Compound 361a | 588.1 (M + H)+ | 3.11-2.94 (m, 2 H) 1.96-1.45 (m, 6 H) 1.29-1.14 (m, 3 H) 1.12-0.96 (m, 6 H) 0.95-0.81 (m, 2 H) 0.47-0.07 (m, 4 H) (DMSO-d6) δ 9.64 (s, 1 H) 8.13-8.02 (m, 1 H) 7.98 ( d, J = 8 Hz, 1 H) 7.82 ( d, J = 6 Hz, 1 H) 7.75-7.70 (m, 1 H) 7.67 (s, 1 H) 7.13 (d, J = 2 Hz, 2 H) 3.86 ( s, 2 H) 2.95 (s, 3 H) 2.45 (d, J = 1.2 Hz, 1 H) 1.90-1.61 (m, 6 H) 1.22-1.02 (m, 11 H) |
| Compound 361b | 588.1 (M + H)+ | (DMSO-d6) δ 9.68 (s, 1 H) 8.06-7.92 (m, 2 H) 7.83 (d, J = 6.8 Hz, 1 H) 7.74-7.64 (m, 2 H) 7.37 (d, J = 1.8 Hz, 1 H) 7.25-7.00 (m, 1 H) 3.78 (s, 2 H) 2.95 (s, 3 H) 2.46-2.29 (m, 1 H) 1.89-1.52 (m, 8 H) 1.11 (s, 9 H) |
| Compound 362 | 541.2 (M + H)+ | (DMSO-d6) δ 9.19 (s, 1 H) 7.95-7.84 (m, 2 H) 7.80-7.50 (m, 3 H) 7.20-7.15 (m, 1 H) 7.10-6.98 (m, 1 H) 3.99-3.85 (m, 2 H) 3.06-3.01 (m, 1 H) 2.98-2.90 (m, 3 H) 2.23-1.99 (m, 3 H) 1.91-1.49 (m, 14 H) 1.01-0.90 (m, 2 H) 0.36-0.23 (m, 4 H) |
| Compound 364 | 515.1 (M + H)+ | (DMSO-d6) δ 9.52 (br s, 1 H) 7.94 (br d, J = 5.38 Hz, 1 H) 7.73 (s, 1 H) 7.59 (s, 1 H) 7.13 (d, J = 2.00 Hz, 1 H) 7.06 (dd, J = 8.63, 2.13 Hz, 1 H) 5.23 (d, J = 5.13 Hz, 1 H) 4.42 (dd, J = 7.19, 5.32 Hz, 1 H) 4.26 (s, 2 H) 2.94 (s, 3 H) 2.24-2.09 (m, 1 H) 1.88-1.63 (m, 7 H) 1.60-1.36 (m, 6 H) 1.34-1.17 (m, 1 H) 0.93 (br d, J = 12.13 Hz, 2 H) 0.32 (s, 4 H) |
| Compound 365 | 568.3 (M + H)+ | (DMSO-d6) δ 9.92-9.74 (m, 1 H) 8.09-7.93 (m, 2 H) 7.83 (br d, J = 4.75 Hz, 1 H) 7.75-7.63 (m, 2 H) 7.16-7.05 (m, 2 H) 4.80 (t, J = 5.19 Hz, 1 H) 4.69 (t, J = 5.19 Hz, 1 H) 3.88 (br s, 2 H) 3.58-3.43 (m, 2H) 1.72-1.49 (m, 6H) 1.11 (s, 9 H) 0.88 (br d, J = 11.26 Hz, 2 H) 0.27 (br s, 4 H) |
| Compound 367 | 513.3 (M + H)+ | (DMSO-d6) δ 9.62 (s, 1 H) 8.01 (br d, J = 8.50 Hz, 1 H) 7.22 (d, J = 3.50 Hz, 1 H) 7.14 (d, J = 2.13 Hz, 1 H) 7.06 (m, 1 H) 6.48 (d, J = 3.38 Hz, 1 H) 5.50 (d, J = 5.50 Hz, 1 H) 4.41 (m, 1 H) 4.36-4.25 (m, 2 H) 3.04 (m, 2 H) 2.37-2.24 (m, 1 H) 1.90-1.62 (m, 7 H) 1.62-1.42 (m, 6 H) 1.38-1.26 (m, 1 H) 1.19 (t, J = 7.38 Hz, 3 H) 0.93 (br d, J = 13.26 Hz, 2 H) 0.32 (s, 4 H) |
| Compound 368 | 529.2 (M + H)+ | (DMSO-d6) δ 9.63-9.47 (m, 1 H) 8.01 (br d, J = 9.38 Hz, 1 H) 7.23 (d, J = 3.50 Hz, 1 H) 7.14 (d, J = 2.25 Hz, 1 H) 7.06 (m, 1 H) 6.48 (d, J = 3.38 Hz, 1 H) 5.50 (d, J = 5.50 Hz, 1 H) 4.92 (br t, J = 7.13 Hz, 1 H) 4.41 (m, 1 H) 4.31 (d, J = 2.25 Hz, 2 H) 3.74 (br t, J = 6.07 Hz, 2 H) 3.19 (t, J = 6.75 Hz, 2 H) 1.92-1.45 (m, 13 H) 1.39-1.21 (m, 1 H) 1.01-0.85 (m, 2 H) 0.33 (s, 4 H) |
| Compound 369 | 521.0 (M + H)+ | (DMSO-d6) δ 9.54 (br d, J = 3.25 Hz, 1 H) 8.06-7.97 (1 H, m) 7.25 (d, J = 3.38 Hz, 1 H) 7.13 (d, J = 2.13 Hz, 1 H) 7.06 (m, 1 H) 6.53 (d, J = 3.63 Hz, 1 H) 5.90 (d, J = 5.75 Hz, 1 H) 4.70-4.61 (m, 1 H) 4.29 (s, 2 H, ) 2.94 (s, 3 H) 2.54-2.64 (m, 5 H) 1.81-1.96 (m, 2 H) 1.76-1.62 (m, 4 H) 0.93 (br d, J = 13.76 Hz, 2 H) 0.32 (s, 4 H) |
| Compound 370 | | (DMSO-d6) δ 8.15-7.92 (m, 1 H) 7.51-7.46 (m, 1 H) 7.43-7.35 (m, 1 H) 7.31-7.25 (m, 1 H) 6.58-6.33 (m, 1 H) 5.65-5.40 (m, 1 H) 4.35-4.32 (m, 2 H) 2.04-1.73 (m, 5 H) 1.70-1.33 (m, 3 H) 0.94 (s, 9 H) 0.38-0.24 (m, 4 H) |
| Compound 371 | 517.3 (M + H)+ | (DMSO-d6) δ 9.70-9.42 (m, 1 H) 8.15-7.94 (m, 1 H) 7.31-7.18 (m, 1 H) 7.16-7.10 (m, 1 H) 7.08-6.97 (m, 1 H) 6.52-6.39 (m, 1 H) 5.58-5.45 (m, 1 H) 5.03-4.81 (m, 1 H) 4.38-4.24 (m, 3 H) 3.83-3.63 (m, 2 H) 3.24-3.11 (m, 2 H) 1.93-1.77 (m, 2 H) 1.76-1.58 (m, 4 H) 0.98-0.91 (m, 11 H) 0.39-0.25 (m, 4 H) |
| Compound 372 | 501.1 (M + H)+ | (DMSO-d6) δ 9.62 (s, 1H), 8.03 (br d, J = 8.6 Hz, 1H), 7.31-6.91 (m, 3H), 6.47 (d, J = 3.4 Hz, 1H), 5.51 (d, J = 4.9 Hz, 1H), 4.38-4.22 (m, 3H), 3.13-2.98 (m, 2H), 1.93-1.57 (m, 6H), 1.19 (t, J = 7.3 Hz, 3H), 1.06-0.86 (m, 11H), 0.32 (s, 4H) |
| Compound 373 | 487.3 (M + H)+ | 9.55 (s, 1 H) 8.05 (br d, J = 8.58 Hz, 1H) 7.31-7.20 (m, 1H) 7.15-7.00 (m, 2 H) 6.47 (d, J = 3.46 Hz, 1 H) 5.52 (d, J = 4.89 Hz, 1 H) 4.39-4.24 (m, 3 H) 2.94 (s, 3 H) 1.93-1.58 (m, 6 H) 1.00-0.83 (m, 11 H) 0.38-0.26 (m, 4 H) |

Biological Assays
Inhibition of KIF18A Microtubule-Dependent ATPase Activity:

Test compounds were plated in a 3× dilution scheme in a 384-well plate. Assay buffer: 80 mM PIPES (pH 6.9), 1 mM MgCl$_2$, 75 mM KCl, 1 mM EGTA, 1 mM DTT, 0.01% BSA, 0.005% Tween-20, 1 µM Taxol in H$_2$O. To 50 nL of compound in DMSO was added 2.5 µL of enzyme mix [4 nM hKIF18A (1-374) in assay buffer]. After incubation at room temperature for 30 min, 2.5 µL of microtubule mix was added [0.2 mg/mL pre-formed microtubules, 2.0 mM ATP in assay buffer], the plate was centrifuged for 30 s and then incubated at 28° C. for 60 min. 5 µL of Promega® ADP-Glo Max R1 was added, the plate was centrifuged for 30 s, and the mixture incubated for 4 h at room temperature. 10 µL of Promega® ADP-Glo Max R2 was added, the plate centrifuged for 30 s, and incubated for 60 min at room temperature. Luminescence was measured with an Envision plate reader, and % Inhibition was calculated for each well as: ([max−min]−[test−min])/[max−min]. IC$_{50}$ values were calculated from concentration vs. % Inhibition data via a four-parameter variable slope model.

Table 9 indicates that compounds as provided herein are potent inhibitors of KIF18a. As a comparison, the data for AMG650 (2-{6-azaspiro[2.5]octan-6-yl}-N-[2-(4,4-difluoropiperidin-1-yl)-6-methylpyrimidin-4-yl]-4-(2-hydroxyethanesulfonamido)benzamide) is 17 nM.

Binding Kinetics to KIF18a-Microtubule Complex

Compound binding kinetics parameters ($k_{on}$ and $k_{off}$) were determined by the method of global progress curve analysis (GPCA). KIF18A (0.25 nM) was incubated for up to 24 hr with serially diluted compound in the assay buffer containing 80 mM PIPES, pH 6.9, 1 mM ATP, 0.1 mg/ml preformed microtubule from porcine brain (Cytoskeleton), 1 mM $MgCl_2$, 1 μM Taxol, 75 mM KCl, 1 mM EGTA, 1 mM DTT, 0.01% BSA and 0.005% Tween-20. ADP product levels were determined by the Promega® ADP-Glo assay. The time/dose-dependent progress curves were then globally fit to a Michaelis-Menten kinetics model with 1-step slow binding inhibition to derive both on-rate $k_{on}$ and off-rate $k_{off}$ values (Zhang, R., Wong, K. (2017): "High performance enzyme kinetics of turnover, activation and inhibition for translational drug discovery", Expert Opinion on Drug Discovery, 2017 January; 12(1):17-37. doi: 10.1080/17460441.2017.1245721).

Results from the binding kinetics assay are summarized in Table 10. The data in Table 10 indicate that compounds as provided herein can achieve sub-nanomolar potency with small off-rates, or very long dissociation half-life ($\ln(2)/k_{off}$). As a comparison, the data for AMG650 (2-{6-azaspiro[2.5]octan-6-yl}-N-[2-(4,4-difluoropiperidin-1-yl)-6-methylpyrimidin-4-yl]-4-(2-hydroxyethanesulfonamido)benzamide) are: $k_{on}$=0.059 $nM^{-1}h^{-1}$; $k_{off}$=0.21 $h^{-1}$, dissociation $t_{1/2}$=4.1 h; $K_i$=3.4 nM.

Cell Viability of KIF18a-Sensitive Cell Lines

Cell lines were seeded as follows 24 hours before compound treatment: HCC15 (Korean Cell Line Bank) 600 cell/well, 95 μL of RPMI-1640 media supplemented with 100 units/mL penicillin, 100 units/mL streptomycin and 10% FBS; NIH:OVCAR-3 (ATCC), 1000 cell/well, 95 μL of RPMI-1640 media supplemented with 100 units/mL penicillin, 100 units/mL streptomycin, 0.01 mg/mL bovine insulin, and 20% FBS; JIMT-1 (Addexbio) 1000 cell/well, 95 μL of DMEM media supplemented with 100 units/mL penicillin, 100 units/mL streptomycin, and 10% FBS.

Test compounds were added to cells in a 20× dilution scheme by adding 5 μL of serially diluted compound to the plate, and the treated cells were incubated for an additional 7 days in a 37° C., 5% $CO_2$ incubator. DMSO was used as the negative control (0% effect), and wells omitting cells were used as the positive control (100% effect). The cells were incubated for seven days, and cell viability determined via the Promega Cell Titre-Glo® Assay kit. Luminescence units were converted to ATP concentrations via an ATP standard curve (10 point, 2-fold dilution from 5 uM). % Inhibition was calculated for each well as: ([max−min]−[test−min])/[max−min]. $IC_{50}$ values were calculated from concentration vs. % Inhibition data via a four-parameter variable slope model. Results from the biological assay are summarized in Table 10.

Table 11 indicates that compounds as provided herein potently inhibit cell growth or induce cell killing for KIF18a-sensitive cancer cell lines. As a comparison, the data for AMG650 (2-{6-azaspiro[2.5]octan-6-yl}-N-[2-(4,4-difluoropiperidin-1-yl)-6-methylpyrimidin-4-yl]-4-(2-hydroxyethanesulfonamido)benzamide) are: HCC-15, 0.066 μM; JIMT-1 0.13 μM; NIH: OVCAR3 0.10 μM.

TABLE 9

Summary of biochemical assay data

| Compound | $IC_{50}$ (μM) |
| --- | --- |
| Compound 1 | 1.6 |
| Compound 3 | 1.6 |
| Compound 4 | 0.36 |
| Compound 6 | 0.58 |
| Compound 8 | 0.94 |
| Compound 9 | 1.0 |
| Compound 10 | 0.27 |
| Compound 15 | 0.78 (n = 1) |
| | 0.74 (n = 2) |
| Compound 18 | 0.079 |
| Compound 19 | 0.032 |
| Compound 20 | 0.013 |
| Compound 21 | 0.019 |
| Compound 22 | 0.011 (n = 3) |
| | 0.0094 (n = 10) |
| Compound 23 | 0.023 |
| Compound 24 | 0.010 |
| Compound 24a | 0.011 |
| Compound 24b | 0.014 |
| Compound 25 | 0.12 |
| Compound 26 | 0.067 |
| Compound 27 | 0.083 |
| Compound 28 | 0.010 |
| Compound 29 | 0.022 |
| Compound 30 | 0.18 |
| Compound 31 | 0.039 |
| Compound 32 | 0.078 |
| Compound 42 | 1.3 |
| Compound 43 | 0.089 |
| Compound 45 | 0.27 |
| Compound 46 | 0.12 |
| Compound 48 | 0.10 |
| Compound 49 | 0.13 |
| Compound 50 | 0.072 |
| Compound 55 | 0.14 |
| Compound 57 | 1.1 |
| Compound 59 | 1.0 |
| Compound 60 | 1.2 |
| Compound 67 | 0.46 |
| Compound 70 | 0.030 |
| Compound 71 | 0.086 |
| Compound 83 | 0.13 |
| Compound 95 | 0.17 |
| Compound 96 | 0.10 |
| Compound 97 | 0.85 |
| Compound 107 | 0.47 |
| Compound 129 | 0.045 |
| Compound 134 | 0.016 |
| Compound 140 | 0.013 |
| Compound 141 | 1.1 |
| Compound 144 | 0.051 |
| Compound 145 | 0.29 |
| Compound 146 | 0.19 |
| Compound 147 | 0.043 |
| Compound 148 | 0.012 |
| Compound 149 | 0.078 |
| Compound 151 | 0.0068 |
| Compound 153 | 0.018 |
| Compound 155 | 0.0074 |
| Compound 157 | 0.058 |
| Compound 159 | 0.019 |
| Compound 160 | 0.020 |
| Compound 162a | 0.015 |
| Compound 162b | 0.037 |
| Compound 163 | 0.020 |
| Compound 164 | 0.12 |
| Compound 165 | 0.015 |
| Compound 165a | 0.0088 |
| Compound 165b | 0.010 |
| Compound 166 | 1.1 |
| Compound 168 | 0.0055 |
| Compound 170 | 0.015 |
| Compound 172 | 0.0055 |
| Compound 174 | 0.056 |
| Compound 176 | 0.0056 |
| Compound 178 | 0.017 |
| Compound 180 | 0.011 |

TABLE 9-continued

Summary of biochemical assay data

| Compound | IC$_{50}$ (μM) |
|---|---|
| Compound 182 | 0.0073 |
| Compound 184 | 0.033 |
| Compound 186 | 0.012 |
| Compound 188 | 0.075 |
| Compound 190 | 0.0048 |
| Compound 192 | 0.010 |
| Compound 194 | 0.050 |
| Compound 196 | 0.010 |
| Compound 198 | 0.026 |
| Compound 200 | 0.072 |
| Compound 202 | 0.053 |
| Compound 204 | 0.013 |
| Compound 206 | 0.027 |
| Compound 208 | 0.064 |
| Compound 210 | 0.016 |
| Compound 212 | 0.012 |
| Compound 214 | 0.08 |
| Compound 216 | 0.0093 |
| Compound 218 | 0.10 |
| Compound 220 | 0.025 |
| Compound 222 | 0.10 |
| Compound 223 | 0.0067 |
| Compound 224 | 0.023 |
| Compound 225 | 0.0075 |
| Compound 226 | 0.013 |
| Compound 227 | 0.0072 |
| Compound 228 | 0.0046 |
| Compound 229 | 0.0062 |
| Compound 230 | 0.014 |
| Compound 231 | 0.0087 |
| Compound 233 | 0.012 |
| Compound 235 | 0.022 |
| Compound 237 | 0.011 |
| (R)-Compound 239 | 0.0093 |
| (S)-Compound 239 | 0.015 |
| Compound 240 | 0.040 |
| Compound 241 | 0.18 |
| Compound 243 | 0.14 |
| Compound 245 | 0.034 |
| Compound 247 | 0.021 |
| Compound 249 | 0.0090 |
| (R)-Compound 249 | 0.011 |
| (S)-Compound 249 | 0.016 |
| Compound 250 | 0.67 |
| Compound 252 | 0.034 |
| Compound 254 | 0.010 |
| Compound 255 | 0.063 |
| Compound 257 | 0.0083 |
| Compound 258 | 0.014 |
| Compound 260 | 0.012 |
| Compound 261 | 0.0093 |
| Compound 262 | 0.0059 |
| Compound 264 | 0.035 |
| Compound 266 | 0.016 |
| Compound 268 | 0.077 |
| Compound 269 | 0.079 |
| Compound 270 | 0.110 |
| Compound 272 | 0.038 |
| Compound 274 | 0.0060 |
| Compound 275 | 0.0080 |
| Compound 277 | 0.041 |
| Compound 279 | 0.0063 |
| Compound 281 | 0.013 |
| Compound 283 | 0.018 |
| Compound 284 | 0.026 |
| Compound 285 | 0.011 |
| Compound 287 | 0.017 |
| Compound 287a | 0.034 |
| Compound 287b | 0.012 |
| Compound 289 | 0.017 |
| Compound 291 | 0.0058 |
| Compound 292 | 0.022 |
| Compound 293 | 0.017 |
| Compound 295 | 0.038 |
| Compound 297 | 0.017 |
| Compound 298 | 0.0084 |
| Compound 299 | 0.014 |
| Compound 300 | 0.031 |
| Compound 301 | 0.021 |
| Compound 302 | 0.019 |
| Compound 303 | 0.0082 |
| Compound 305 | 0.0089 |
| Compound 305a | 0.0081 |
| Compound 305b | 0.0068 |
| Compound 306 | 0.033 |
| Compound 309 | 0.0065 |
| Compound 310 | 0.0066 |
| Compound 311 | 0.0052 |
| Compound 313 | 0.020 |
| Compound 313a | 0.019 |
| Compound 313b | 0.015 |
| Compound 314 | 0.028 |
| Compound 315 | 0.053 |
| Compound 316 | 0.018 |
| Compound 316a | 0.021 |
| Compound 316b | 0.016 |
| Compound 317 | 0.011 |
| Compound 317a | 0.011 |
| Compound 317b | 0.010 |
| Compound 318 | 0.93 |
| Compound 319 | 1.2 |
| Compound 320 | 0.018 |
| Compound 321 | 0.0063 |
| Compound 322 | 0.021 |
| Compound 324 | 0.021 |
| Compound 326 | 0.050 |
| Compound 327 | 0.044 |
| Compound 329 | 0.072 |
| Compound 330 | 0.012 |
| Compound 331 | 0.035 |
| Compound 332 | 0.15 |
| Compound 333a | 0.018 |
| Compound 333b | 0.033 |
| Compound 335 | 0.0093 |
| Compound 336a | 0.0085 |
| Compound 336b | 0.017 |
| Compound 337 | 0.0088 |
| Compound 338 | 0.049 |
| Compound 338a | 0.048 |
| Compound 338b | 0.083 |
| Compound 339 | 0.024 |
| Compound 340 | 0.018 |
| Compound 341 | 0.025 |
| Compound 341a | 0.030 |
| Compound 341b | 0.024 |
| Compound 342 | 0.020 |
| Compound 343 | 0.81 |
| Compound 345 | 0.058 |
| Compound 346 | 0.31 |
| Compound 347 | 0.28 |
| Compound 348 | 0.19 |
| Compound 349 | 0.045 |
| Compound 351 | 0.0088 |
| Compound 351a | 0.0087 |
| Compound 351b | 0.012 |
| Compound 352 | 0.0050 |
| Compound 352a | 0.0040 |
| Compound 352b | 0.0033 |
| Compound 354 | 0.014 |
| Compound 355 | 0.025 |
| Compound 356 | 0.051 |
| Compound 357 | 0.011 |
| Compound 358 | 0.028 |
| Compound 359 | 0.016 |
| Compound 361a | 0.015 |
| Compound 361b | 0.10 |
| Compound 362 | 0.035 |
| Compound 364 | 0.0051 |
| Compound 365 | 0.013 |
| Compound 367a | 0.0039 |
| Compound 367b | 0.0048 |
| Compound 368a | 0.0030 |

TABLE 9-continued

Summary of biochemical assay data

| Compound | IC$_{50}$ (µM) |
|---|---|
| Compound 368b | 0.0035 |
| Compound 369 | 0.0071 |
| Compound 371a | 0.030 |
| Compound 371b | 0.040 |
| Compound 372a | 0.037 |
| Compound 372b | 0.035 |
| Compound 373a | 0.20 |
| Compound 373b | 0.17 |
| Compound 1' | 2.6 |
| Compound 2' | 0.92 |

TABLE 10

Summary of kinetic assay data

| Compound | k$_{on}$ (nM$^{-1}$h$^{-1}$)$^a$ | k$_{off}$ (h$^{-1}$)$^b$ | disc. t$_{1/2}$ (h)$^c$ | K$_I$ (nM)$^d$ |
|---|---|---|---|---|
| Compound 19 | 0.051 | 0.096 | 7.2 | 1.8 |
| Compound 22 | 0.038 | 0.018 | 38 | 0.55 |
| Compound 24b | 0.052 | 0.015 | 45 | 0.29 |
| Compound 24a | 0.080 | 0.043 | 16 | 0.54 |
| Compound 70 | 0.036 | 0.23 | 3.0 | 6.5 |
| Compound 129 | 0.044 | 0.28 | 2.5 | 6.3 |
| Compound 134 | 0.054 | 0.018 | 40 | 0.34 |
| Compound 140a | 0.047 | 0.024 | 29 | 0.50 |
| Compound 140b | 0.058 | 0.080 | 8.7 | 1.4 |
| Compound 144 | 0.015 | 0.14 | 5.2 | 9.3 |
| Compound 148 | 0.049 | 0.014 | 48 | 0.29 |
| Compound 151 | 0.096 | 0.011 | 61 | 0.12 |
| Compound 155 | 0.11 | 0.11 | 6.5 | 2.0 |
| Compound 159 | 0.026 | 0.022 | 32 | 0.83 |
| Compound 160 | 0.038 | 0.021 | 33 | 0.54 |
| Compound 162a | 0.029 | 0.055 | 13 | 1.9 |
| Compound 165a | 0.043 | 0.18 | 3.8 | 4.2 |
| Compound 165b | 0.043 | 0.17 | 4.2 | 3.9 |
| Compound 182 | 0.11 | 0.029 | 24 | 0.26 |
| Compound 192 | 0.052 | 0.033 | 21 | 0.64 |
| Compound 229 | 0.061 | 0.018 | 39 | 0.29 |
| Compound 223 | 0.023 | 0.088 | 7.9 | 0.26 |
| Compound 237 | 0.082 | 0.036 | 19 | 0.44 |
| (R)-Compound 239 | 0.060 | 0.086 | 8.1 | 1.4 |
| Compound 257 | 0.066 | 0.067 | 10 | 0.96 |
| Compound 262 | 0.032 | 0.103 | 6.7 | 0.31 |
| Compound 269 | 0.020 | 0.080 | 8.7 | 4.0 |
| Compound 297 | 0.037 | 0.014 | 49 | 0.38 |
| Compound 298 | 0.071 | 0.027 | 26 | 0.38 |
| Compound 305a | 0.35 | 1.3 | 0.56 | 3.5 |
| Compound 305b | 0.38 | 1.4 | 0.49 | 3.7 |
| Compound 317a | 0.033 | 0.33 | 2.1 | 10 |
| Compound 317b | 0.059 | 0.35 | 2.0 | 5.9 |
| Compound 320 | 0.027 | 0.015 | 45 | 0.57 |
| Compound 322 | 0.037 | 0.12 | 5.7 | 3.3 |
| Compound 333a | 0.028 | 0.013 | 53 | 0.47 |
| Compound 333b | 0.014 | 0.011 | 63 | 0.77 |
| Compound 351a | 0.070 | 0.41 | 1.7 | 5.8 |
| Compound 352a | 0.10 | 0.38 | 1.8 | 3.7 |
| Compound 352b | 0.080 | 0.25 | 2.8 | 3.1 |

$^a$on-rate from binding kinetics assay,
$^b$off-rate from binding kinetics assay,
$^c$dissociation half-life ln(2)/k$_{off}$.
$^d$K$_I$ determined from binding kinetic assay k$_{off}$/k$_{on}$

TABLE 11

Summary of cellular assay data

| Compound | HCC-15 IC$_{50}$ (µM) | JIMT-1 IC$_{50}$ (µM) | NIH-OVCAR3 IC$_{50}$ (µM) |
|---|---|---|---|
| Compound 4 | 2.1 | | |
| Compound 10 | 2.2 | | |
| Compound 18 | 0.16 | | |
| Compound 19 | 0.092 | | |
| Compound 20 | 0.025 | | |
| Compound 21 | 0.055 | | |
| Compound 22 | 0.011 | 0.0078 | 0.0097 |
| Compound 24 | 0.023 | | |
| Compound 24a | 0.26 | | |
| Compound 24b | 0.032 | | |
| Compound 26 | 0.069 | | |
| Compound 27 | 0.14 | | |
| Compound 28 | 0.024 | | |
| Compound 29 | 0.33 | | |
| Compound 30 | 3.5 | 2.3 | 1.43 |
| Compound 43 | 0.49 | | |
| Compound 70 | 0.59 | | |
| Compound 134 | 0.0051 | 0.0040 | 0.0051 |
| Compound 140 | 0.038 | | |
| Compound 140a | 0.010 | | |
| Compound 140b | 0.045 | | |
| Compound 148 | 0.036 | | |
| Compound 151 | 0.013 | | |
| Compound 153 | 0.044 | | |
| Compound 157 | 0.60 | 0.44 | 0.72 |
| Compound 159 | 0.021 | 0.015 | 0.022 |
| Compound 160 | 0.0075 | 0.0054 | 0.0080 |
| Compound 163 | 0.14 | 0.12 | 0.19 |
| Compound 165a | 0.068 | 0.045 | 0.059 |
| Compound 165b | 0.046 | 0.038 | 0.057 |
| Compound 168 | 0.028 | | |
| Compound 172 | 0.032 | | |
| Compound 182 | 0.015 | | |
| Compound 192 | 0.51 | 0.50 | 0.41 |
| Compound 223 | 0.021 | 0.015 | 0.020 |
| Compound 229 | 0.011 | 0.011 | 0.013 |
| Compound 257 | 0.021 | 0.012 | 0.021 |
| Compound 287b | 0.097 | 0.064 | 0.033 |
| Compound 297 | 0.011 | 0.0098 | 0.010 |
| Compound 305a | 0.074 | 0.052 | 0.090 |
| Compound 305b | 0.060 | 0.040 | 0.069 |
| Compound 309 | 0.012 | 0.0094 | 0.012 |
| Compound 310 | 0.011 | 0.0079 | 0.0091 |
| Compound 320 | 0.021 | 0.014 | 0.020 |
| Compound 322 | 0.043 | 0.032 | 0.040 |
| Compound 333a | 0.022 | 0.024 | 0.017 |
| Compound 352a | 0.034 | 0.040 | 0.045 |
| Compound 352b | 0.019 | 0.019 | 0.027 |
| Compound 355 | 0.094 | 0.12 | 0.11 |
| Compound 2' | 2.6 | | |

Assessment of In Vivo Activity

OVCAR-3 (ATCC) tumor cells were maintained in vitro in RPMI-1640 medium supplemented with 20% fetal bovine serum, 0.01 mg/mL bovine insulin and 1% Anti-Anti at 37° C. in an atmosphere of 5% $CO_2$ in air. HCC15 (DSMZ) tumor cells were maintained in vitro in RPMI 1640 medium supplemented with 10% fetal bovine serum and 1% Anti-Anti at 37° C. in an atmosphere of 5% $CO_2$ in air.

The tumor cells were sub-cultured twice weekly. The cells growing in an exponential growth phase were harvested and counted for tumor inoculation.

Tumor cells (10×10$^6$) in 0.2 mL of PBS mixed with Matrigel (50:50) were inoculated subcutaneously on the right flank of each mouse. When the average tumor volume reached 110-175 mm$^3$, animals were randomized into groups of 10 and treatment started. OVCAR-3 cells were implanted in Balb/C nude mice, and HCC15 cell were implanted in SCID Beige mice.

Compounds were dosed once or twice a day (12 h) orally. Tumor Growth Inhibition (TGI) was calculated using the formula: TGI (%)=[1−(T_N−T_0)/(V_N−V_0)]×100; $T_N$ is the average tumor volume of a treatment group at the indicated timepoint, $T_0$ is the average tumor volume of the treatment group on treatment day 0, $V_N$ is the average tumor volume of the vehicle control group at the indicated timepoint, and $V_0$ is the average tumor volume of the vehicle group on treatment day 0. P value was calculated based on tumor size by One-Way ANOVA with GraphPad Prism 9.4.0 compared with the vehicle group, respectively. **** indicates p<0.0001.

Figure 1B:
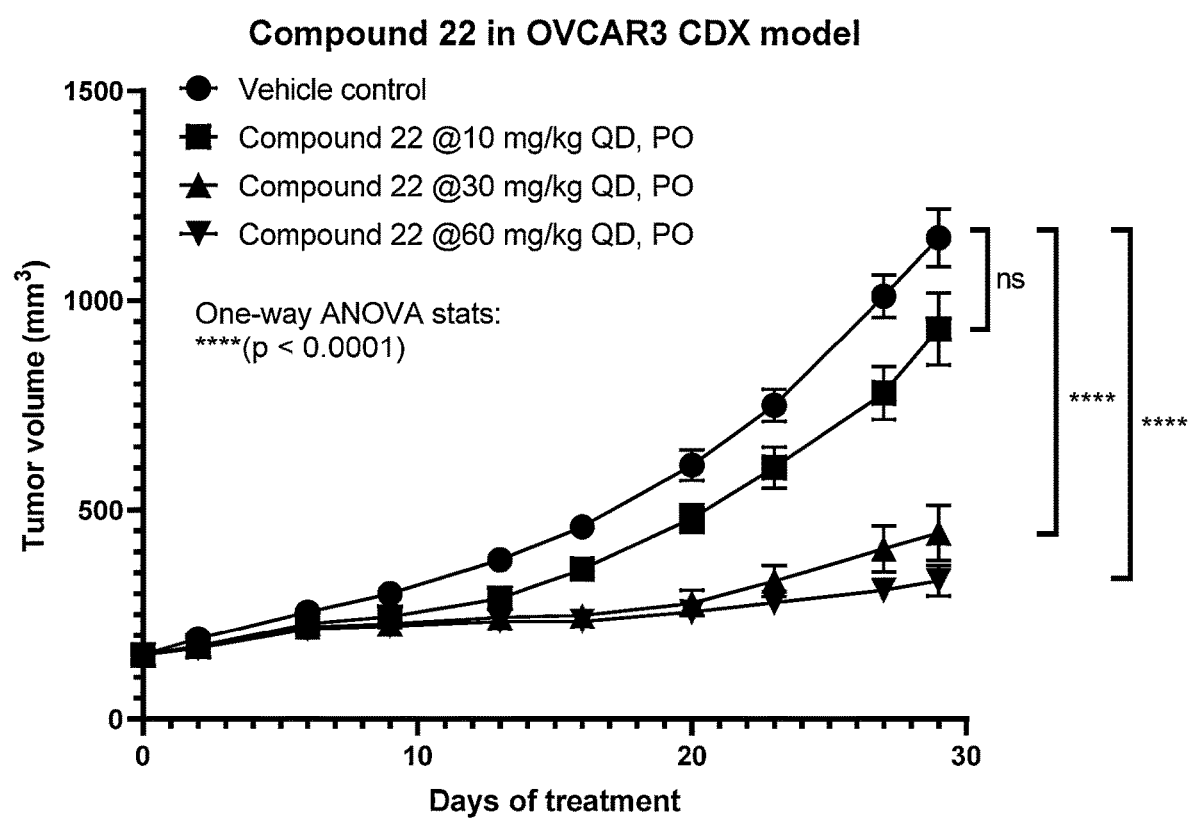
Figure 1C:
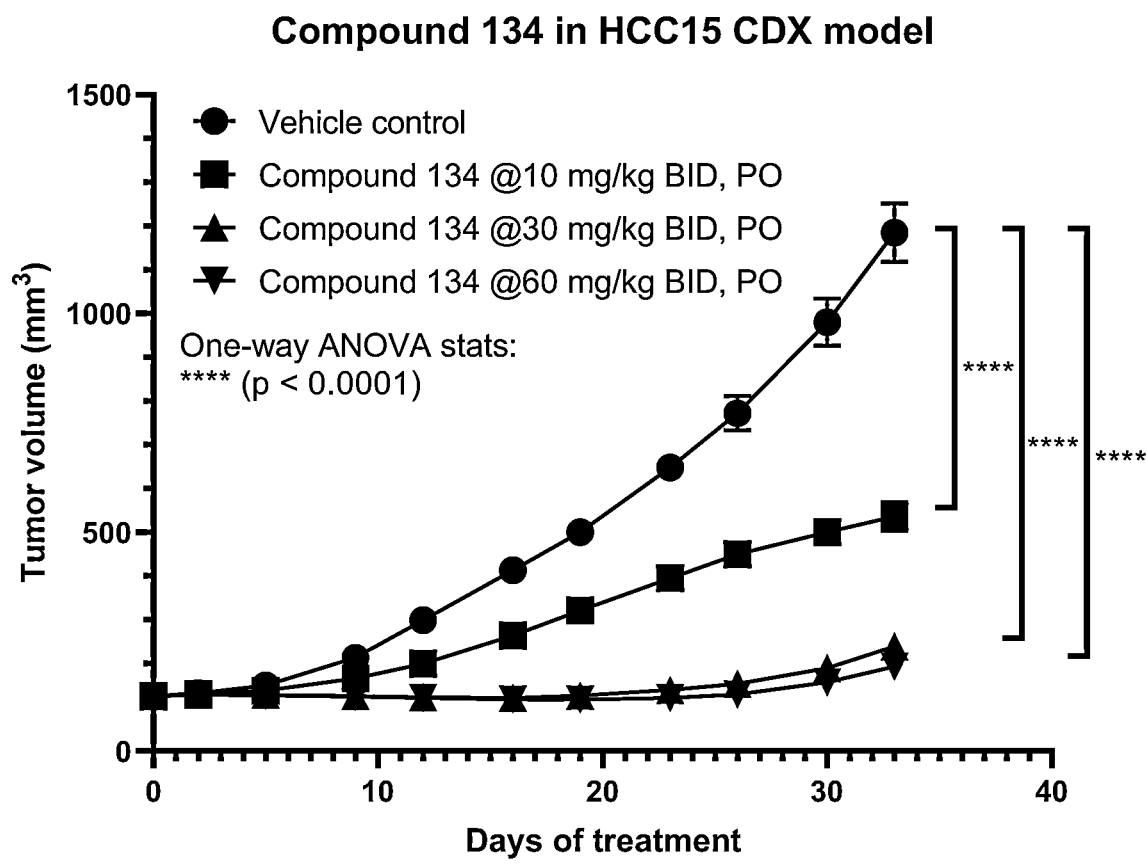
Figure 1D:
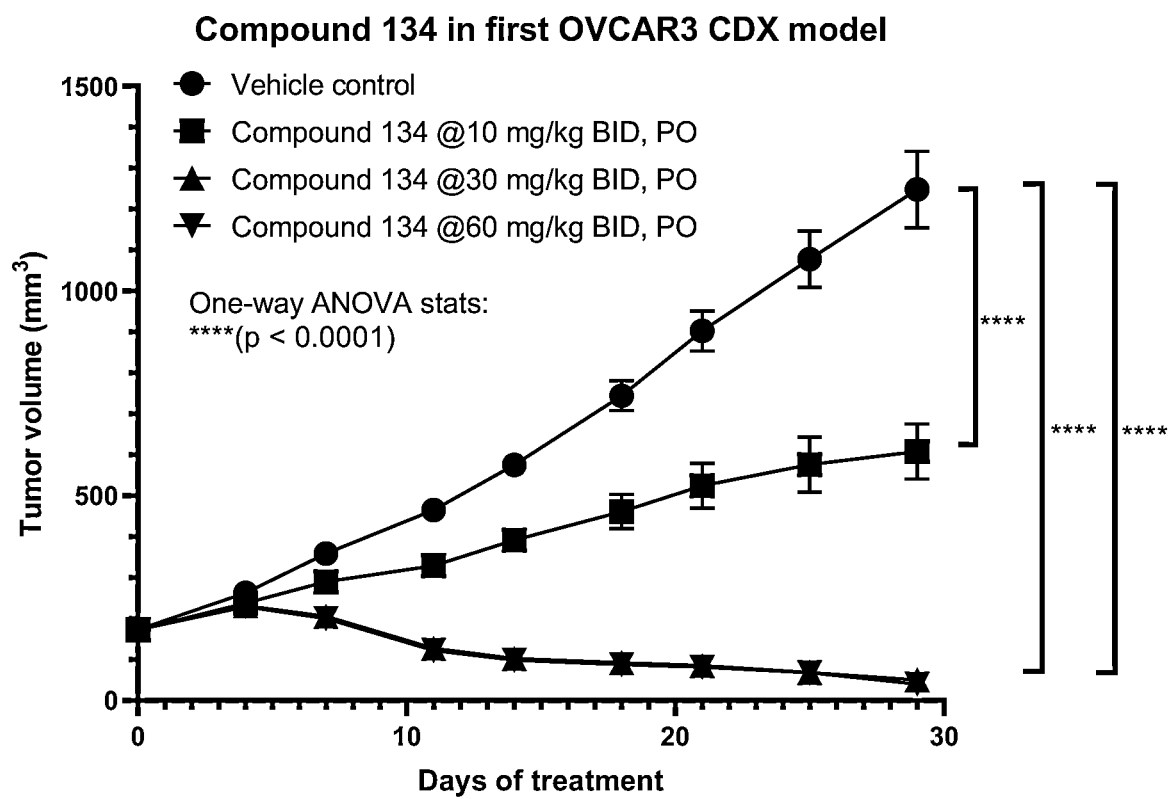
Figure 1E:
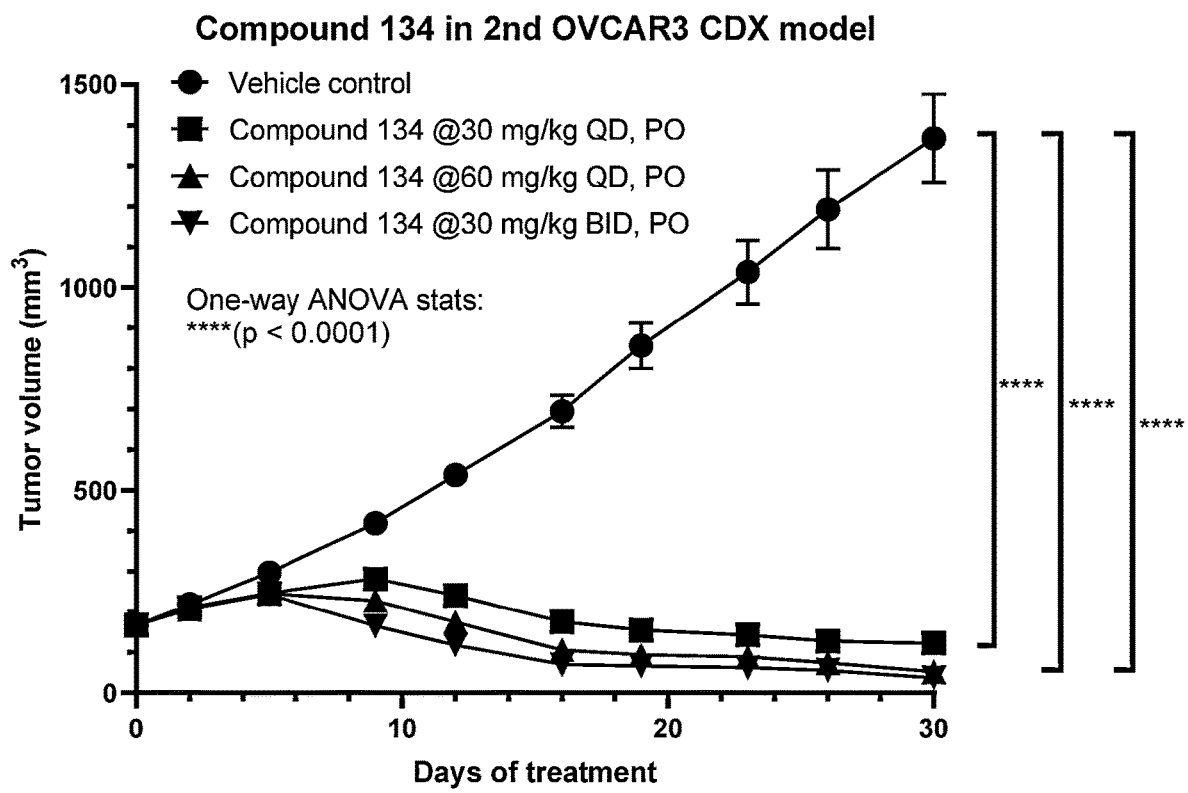

The tumor volume of vehicle- and compound-treated mice as a function of time after start of treatment and the results of treatments with selected compounds on SCID Beige mice or nude mice implanted with HCC15 or OVCAR-3 are shown in FIGS. 1A-1E. The TGI calculated for treatments with selected compounds are shown in Table 12.

TABLE 12

| Compound | Model | Subfigure | Dose | TGI |
|---|---|---|---|---|
| Compound 22 | HCC15 | 1A | 10 mg/kg BID PO | 30 ± 15% |
| Compound 22 | HCC15 | 1A | 30 mg/kg BID PO | 72 ± 6% |
| Compound 22 | HCC15 | 1A | 60 mg/kg BID PO | 82 ± 9% |
| Compound 22 | OVCAR3 | 1B | 10 mg/kg QD PO | 24 ± 26% |
| Compound 22 | OVCAR3 | 1B | 30 mg/kg QD PO | 72 ± 17% |
| Compound 22 | OVCAR3 | 1B | 60 mg/kg QD PO | 82 ± 10% |
| Compound 134 | HCC15 | 1C | 10 mg/kg BID PO | 61 ± 10% |
| Compound 134 | HCC15 | 1C | 30 mg/kg BID PO | 89 ± 7% |
| Compound 134 | HCC15 | 1C | 60 mg/kg BID PO | 94 ± 5% |
| Compound 134 | OVCAR3 | 1D | 10 mg/kg BID PO | 60 ± 17% |
| Compound 134 | OVCAR3 | 1D | 30 mg/kg BID PO | 111 ± 1% |
| Compound 134 | OVCAR3 | 1D | 60 mg/kg BID PO | 112 ± 1% |
| Compound 134 | OVCAR3 | 1E | 30 mg/kg QD PO | 104 ± 7% |
| Compound 134 | OVCAR3 | 1E | 60 mg/kg QD PO | 109 ± 2% |
| Compound 134 | OVCAR3 | 1R | 30 mg/kg BID PO | 110 ± 1% |

What is claimed is:

1. A compound of Formula (I):

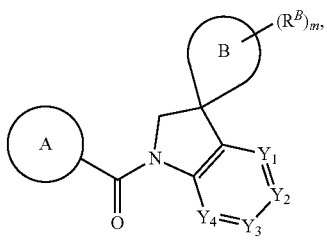

(I)

or a pharmaceutically acceptable salt thereof, wherein:
ring A is $C_{6-14}$ aryl optionally substituted with one or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and $C_{1-6}$ alkyl substituted with one or more substituents independently selected from the group consisting of —OH, cyano, $C_{3-10}$ cycloalkyl, and 3- to 10-membered heterocycloalkyl optionally substituted with one or more halo;
$R^{a1}$-$R^{a22}$ are each independently hydrogen, $C_{1-6}$ alkyl, $C_{2-6}$ alkenyl, $C_{3-10}$ cycloalkyl, $C_{3-10}$ cycloalkenyl, 3- to 10-membered heterocycloalkyl, 3- to 10-membered heterocycloalkenyl, $C_{6-14}$ aryl, or 5- to 12-membered heteroaryl, each optionally substituted with one or more substituents independently selected from the group consisting of halo, cyano, —OH, —O($C_{1-6}$ alkyl), $C_{2-6}$ alkenyl, $C_{3-10}$ cycloalkyl, —S($C_{1-6}$ alkyl), =CR$^{1a1}$R$^{1a2}$, and $C_{1-6}$ alkyl optionally substituted with one or more substituents independently selected from the group consisting of halo, —OH, and —O($C_{1-6}$ alkyl), wherein $R^{1a1}$ and $R^{1a2}$ are each independently hydrogen or $C_{1-6}$ alkyl;
ring B is $C_{5-7}$ cycloalkyl, $C_{5-7}$ cycloalkenyl, or 5- to 7-membered heterocycloalkyl wherein one or two of the ring atoms are each oxygen and the remaining ring atoms are each carbon;
each $R^B$ group is independently halo, $C_{1-6}$ alkyl optionally substituted with one or more halo, or $C_{2-6}$ alkenyl; or two vicinal $R^B$ groups are taken together with the carbon atoms to which they are attached to form $C_{3-10}$ cycloalkyl; or two geminal $R^B$ groups are taken together with the carbon atom to which they are attached to form $C_{3-10}$ cycloalkyl;
m is 0, 1, 2, 3, or 4;
$Y^1$ is N or CR$^{C1}$;
$Y^2$ is N or CR$^{C2}$;
$Y^3$ is N or CR$^{C3}$;
$Y^4$ is N or CR$^{C4}$;
wherein no more than three of $Y^1$, $Y^2$, $Y^3$, and $Y^4$ are N;
$R^{C1}$, $R^{C3}$, and $R^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or $C_{1-6}$ alkyl optionally substituted with one or more substituents independently selected from the group consisting of halo and —OH;
$R^{C2}$ is halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or $C_{1-6}$ alkyl optionally substituted with one or more substituents independently selected from the group consisting of halo and —OH; and
$R^{c1}$-$R^{c18}$ are each independently hydrogen, $C_{3-10}$ cycloalkyl, or $C_{1-6}$ alkyl optionally substituted with one or more substituents independently selected from the group consisting of halo and —OH.

2. A compound of Formula (I-3):

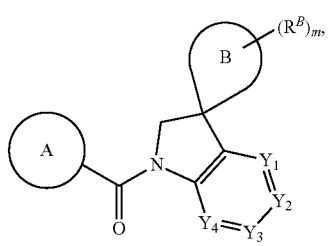

(I-3)

or a pharmaceutically acceptable salt thereof, wherein:
ring A is $C_{6-14}$ aryl or 5- to 12-membered heteroaryl, each optionally substituted with one or more substituents independently selected from the group consisting of halo, —OH, $C_{1-6}$ alkyl, 3- to 10-membered heterocycloalkyl, —NR$^{a1}$C(O)NR$^{a2}$R$^{a3}$, —NR$^{a4}$C(O)OR$^{a5}$, —NR$^{a6}$R$^{a7}$, —N=S(O)R$^{a8}$R$^{a9}$, —OR$^{a10}$, —S(O)

R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, and C$_{1-6}$ alkyl substituted with one or more substituents independently selected from the group consisting of —OH, cyano, C$_{3-10}$ cycloalkyl, and 3- to 10-membered heterocycloalkyl optionally substituted with one or more halo;

R$^{a1}$-R$^{a22}$ are each independently hydrogen, C$_{1-6}$ alkyl, C$_{2-6}$ alkenyl, C$_{3-10}$ cycloalkyl, C$_{3-10}$ cycloalkenyl, 3- to 10-membered heterocycloalkyl, 3- to 10-membered heterocycloalkenyl, C$_{6-14}$ aryl, or 5- to 12-membered heteroaryl, each optionally substituted with one or more substituents independently selected from the group consisting of halo, cyano, —OH, —O(C$_{1-6}$ alkyl), C$_{2-6}$ alkenyl, C$_{3-10}$ cycloalkyl, —S(C$_{1-6}$ alkyl), —CR$^{1a1}$R$^{1a2}$, and C$_{1-6}$ alkyl optionally substituted with one or more substituents independently selected from the group consisting of halo, —OH, and —O(C$_{1-6}$ alkyl), wherein R$^{1a1}$ and R$^{1a2}$ are each independently hydrogen or C$_{1-6}$ alkyl;

ring B is C$_{5-7}$ cycloalkyl, C$_{5-7}$ cycloalkenyl, or 5- to 7-membered heterocycloalkyl wherein one or two of the ring atoms are each oxygen and the remaining ring atoms are each carbon;

m is 2;

the two R$^B$ groups are attached to the same carbon atom on ring B and are taken together with the carbon atom to which they are attached to form C$_{3-7}$ cycloalkyl;

Y$^1$ is N or CR$^{C1}$;
Y$^2$ is N or CR$^{C2}$;
Y$^3$ is N or CR$^{C3}$;
Y$^4$ is N or CR$^{C4}$;

wherein no more than three of Y$^1$, Y$^2$, Y$^3$, and Y$^4$ are N;

R$^{C1}$-R$^{C4}$ are each independently hydrogen, halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or C$_{1-6}$ alkyl optionally substituted with one or more substituents independently selected from the group consisting of halo and —OH; and R$^{c1}$-R$^{c18}$ are each independently hydrogen, C$_{3-10}$ cycloalkyl, or C$_{1-6}$ alkyl optionally substituted with one or more substituents independently selected from the group consisting of halo and —OH.

3. The compound of claim 1, or a pharmaceutically acceptable salt thereof, wherein ring A is optionally substituted phenyl.

4. The compound of claim 1, which is a compound of Formula (Ia1):

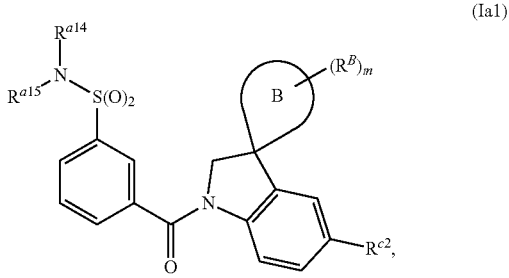

(Ia1)

or a pharmaceutically acceptable salt thereof, wherein:
R$^{a14}$ and R$^{a15}$ are each independently hydrogen, C$_{1-6}$ alkyl, C$_{2-6}$ alkenyl, C$_{3-10}$ cycloalkyl, C$_{3-10}$ cycloalkenyl, 3- to 10-membered heterocycloalkyl, 3- to 10-membered heterocycloalkenyl, C$_{6-14}$ aryl, or 5- to 12-membered heteroaryl, each optionally substituted with one or more substituents independently selected from the group consisting of halo, cyano, —OH, —O(C$_{1-6}$ alkyl), C$_{2-6}$ alkenyl, C$_{3-10}$ cycloalkyl, —S(C$_{1-6}$ alkyl), =CR$^{1a1}$R$^{1a2}$, and C$_{1-6}$ alkyl optionally substituted with one or more substituents independently selected from the group consisting of halo, —OH, and —O(C$_{1-6}$ alkyl), wherein R$^{1a1}$ and R$^{1a2}$ are each independently hydrogen or C$_{1-6}$ alkyl;

ring B is C$_{5-7}$ cycloalkyl, C$_{5-7}$ cycloalkenyl, or 5- to 7-membered heterocycloalkyl wherein one or two of the ring atoms are each oxygen and the remaining ring atoms are each carbon;

each R$^B$ group is independently halo, C$_{1-6}$ alkyl optionally substituted with one or more halo, or C$_{2-6}$ alkenyl; or two vicinal R$^B$ groups are taken together with the carbon atoms to which they are attached to form C$_{3-10}$ cycloalkyl; or two geminal R$^B$ groups are taken together with the carbon atom to which they are attached to form C$_{3-10}$ cycloalkyl;

m is 0, 1, 2, 3, or 4;

R$^{C2}$ is halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or C$_{1-6}$ alkyl optionally substituted with one or more substituents independently selected from the group consisting of halo and —OH; and R$^{c1}$-R$^{c18}$ are each independently hydrogen, C$_{3-10}$ cycloalkyl, or C$_{1-6}$ alkyl optionally substituted with one or more substituents independently selected from the group consisting of halo and —OH.

5. The compound of claim 4, or a pharmaceutically acceptable salt thereof, wherein R$^{C2}$ is halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, N=S(O)R$^{c9}$R$^{c10}$, —S(O)(NR$^{c11}$)R$^{c12}$, —S(O)$_2$R$^{c13}$, or C$_{1-6}$ alkyl optionally substituted with one or more substituents independently selected from the group consisting of halo and —OH; and R$^{c1}$-R$^{c13}$ are each independently hydrogen, C$_{3-10}$ cycloalkyl, or C$_{1-6}$ alkyl optionally substituted with one or more substituents independently selected from the group consisting of halo and —OH.

6. The compound of claim 4, or a pharmaceutically acceptable salt thereof, wherein R$^{C2}$ is —NR$^{c5}$S(O)$_2$R$^{c6}$, and R$^{c5}$ and R$^{c6}$ are each independently hydrogen, C$_{3-10}$ cycloalkyl, or C$_{1-6}$ alkyl optionally substituted with one or more substituents independently selected from the group consisting of halo and —OH.

7. The compound of claim 1, which is a compound of Formula (Ia2):

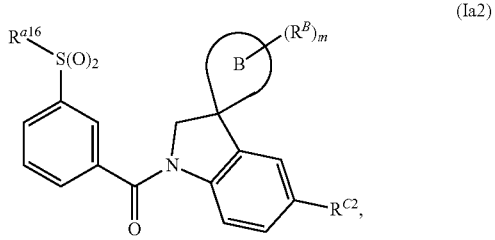

(Ia2)

or a pharmaceutically acceptable salt thereof, wherein:

R$^{a16}$ is hydrogen, C$_{1-6}$ alkyl, C$_{2-6}$ alkenyl, C$_{3-10}$ cycloalkyl, C$_{3-10}$ cycloalkenyl, 3- to 10-membered heterocycloalkyl, 3- to 10-membered heterocycloalkenyl, C$_{6-14}$ aryl, or 5- to 12-membered heteroaryl, each optionally substituted with one or more substituents independently selected from the group consisting of halo, cyano, —OH, —O(C$_{1-6}$ alkyl), C$_{2-6}$ alkenyl, C$_{3-10}$ cycloalkyl, —S(C$_{1-6}$ alkyl), —CR$^{1a1}$R$^{1a2}$, and C$_{1-6}$ alkyl optionally substituted with one or more substituents independently selected from the group consisting of halo, —OH, and —O(C$_{1-6}$ alkyl), wherein R$^{1a1}$ and R$^{1a2}$ are each independently hydrogen or C$_{1-6}$ alkyl;

ring B is C$_{5-7}$ cycloalkyl, C$_{5-7}$ cycloalkenyl, or 5- to 7-membered heterocycloalkyl wherein one or two of the ring atoms are each oxygen and the remaining ring atoms are each carbon;

each R$^B$ group is independently halo, C$_{1-6}$ alkyl optionally substituted with one or more halo, or C$_{2-6}$ alkenyl; or two vicinal R$^B$ groups are taken together with the carbon atoms to which they are attached to form C$_{3-10}$ cycloalkyl; or two geminal R$^B$ groups are taken together with the carbon atom to which they are attached to form C$_{3-10}$ cycloalkyl;

m is 0, 1, 2, 3, or 4; and

R$^{C2}$ is halo, cyano, —OH, —NO$_2$, —C(O)NR$^{c1}$R$^{c2}$, —NR$^{c3}$R$^{c4}$, —NR$^{c5}$S(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, or C$_{1-6}$ alkyl optionally substituted with one or more substituents independently selected from the group consisting of halo and —OH;

R$^{c1}$-R$^{c18}$ are each independently hydrogen, C$_{3-10}$ cycloalkyl, or C$_{1-6}$ alkyl optionally substituted with one or more substituents independently selected from the group consisting of halo and —OH.

8. The compound of claim 1, or a pharmaceutically acceptable salt thereof, wherein R$^{a14}$ and R$^{a15}$ are each independently hydrogen; C$_{1-6}$ alkyl optionally substituted with one or more substituents independently selected from the group consisting of C$_{1-6}$ alkyl, C$_{2-6}$ alkenyl, C$_{3-10}$ cycloalkyl, —OH, —O(C$_{1-6}$ alkyl), —S(C$_{1-6}$ alkyl), and halo; C$_{2-6}$ alkenyl; C$_{3-10}$ cycloalkyl optionally substituted with one or more substituents independently selected from the group consisting of C$_{2-6}$ alkenyl, C$_{3-10}$ cycloalkyl, halo, cyano, —OH, —O(C$_{1-6}$ alkyl), =CR$^{1a1}$R$^{1a2}$, and C$_{1-6}$ alkyl optionally substituted with one or more substituents independently selected from the group consisting of —OH, —O(C$_{1-6}$ alkyl), and halo, wherein R$^{1a1}$ and R$^{1a2}$ are each independently hydrogen or C$_{1-6}$ alkyl; C$_{3-10}$ cycloalkenyl; or 3- to 12-membered heterocycloalkyl optionally substituted with one or more C$_{1-6}$ alkyl.

9. The compound of claim 8, or a pharmaceutically acceptable salt thereof, wherein R$^{a14}$ is hydrogen and R$^{a15}$ is tert-butyl.

10. The compound of claim 1, or a pharmaceutically acceptable salt thereof, wherein ring A is substituted with one or more substituents independently selected from the group consisting of fluoro, chloro, —OH, methyl, amino,

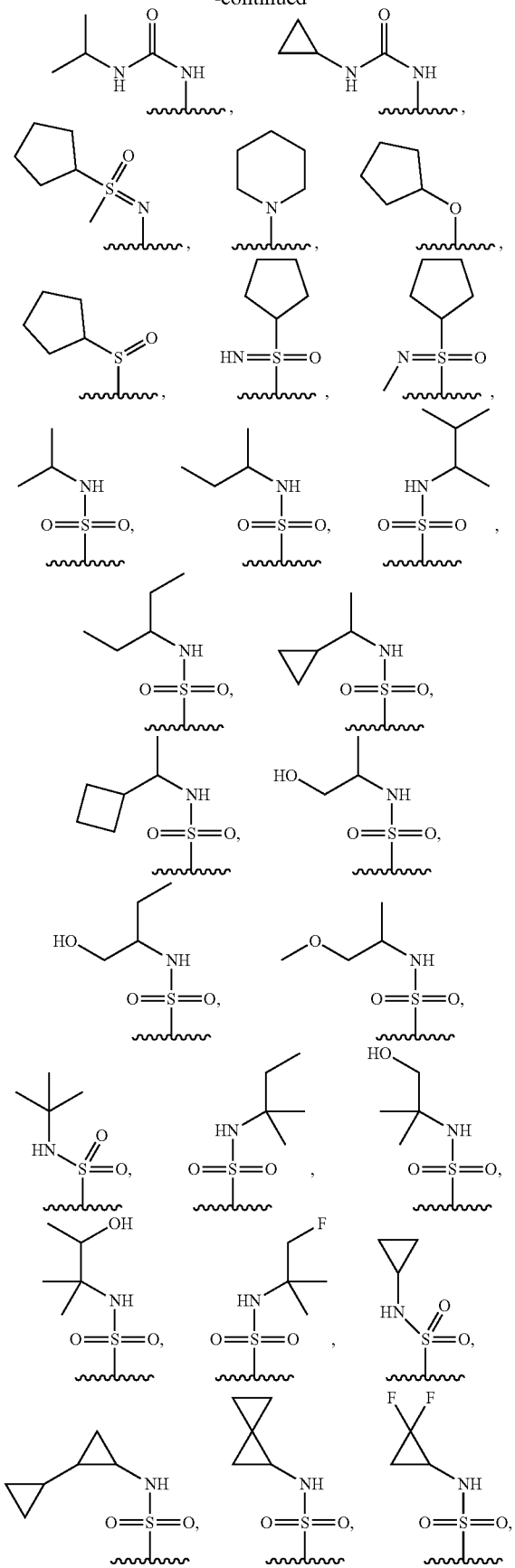

571
-continued
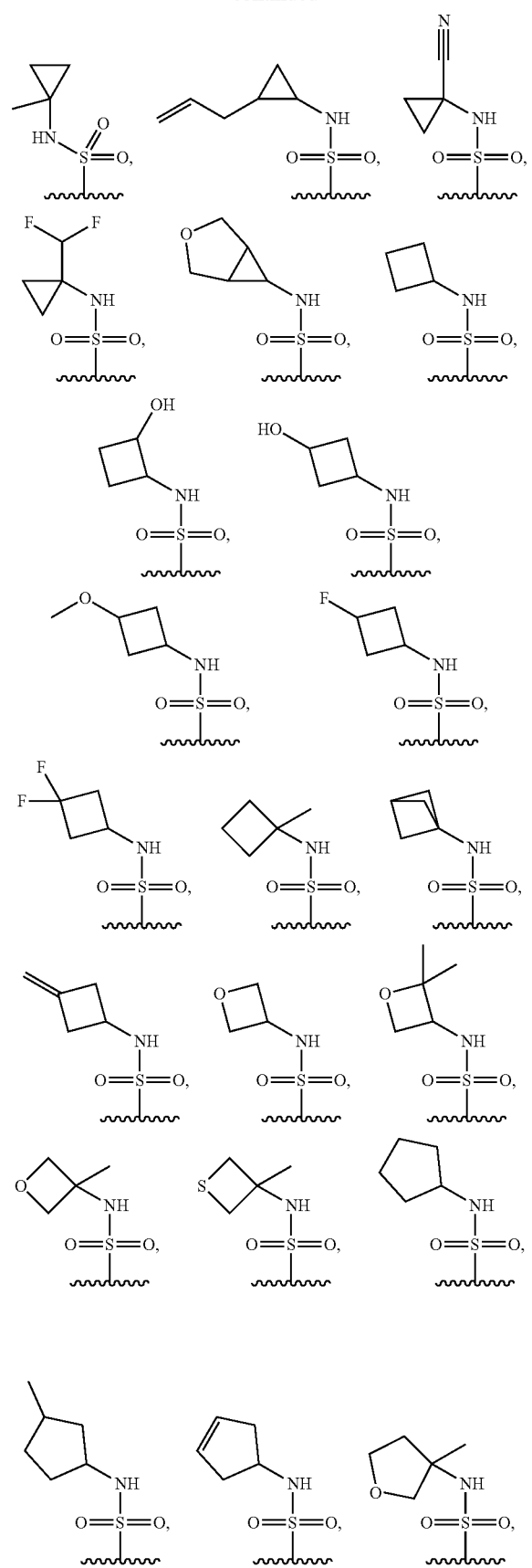
572
-continued
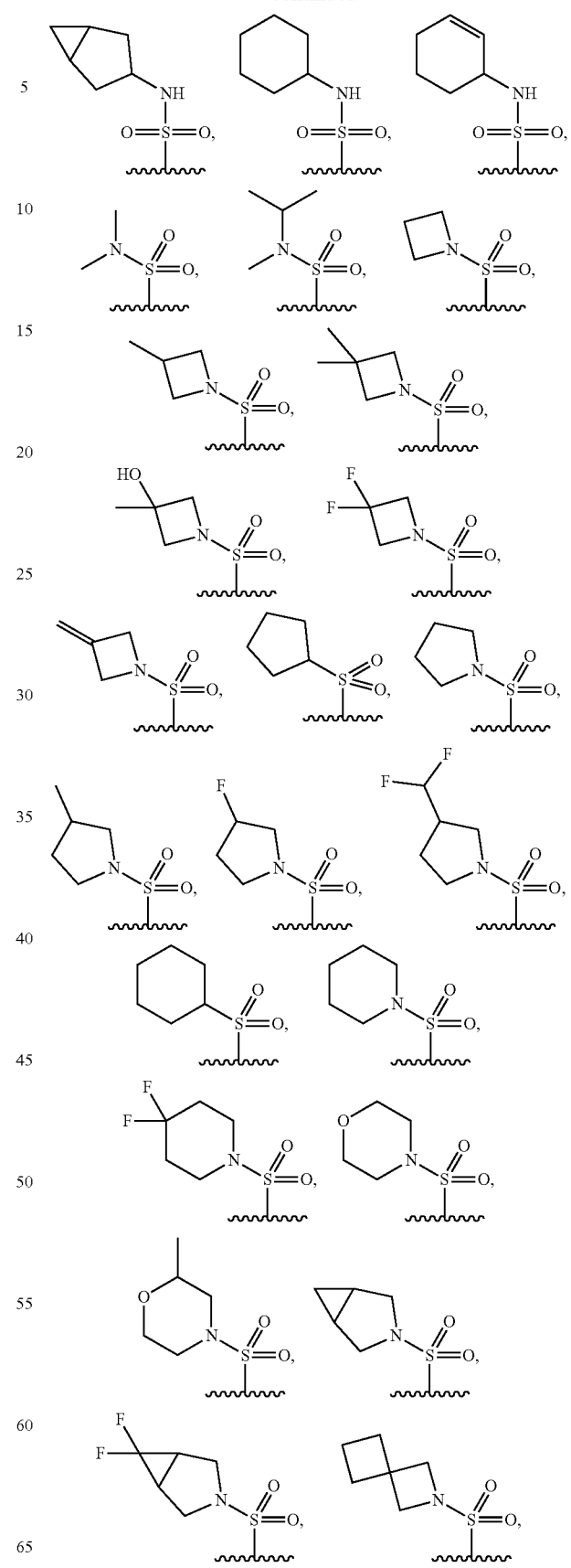

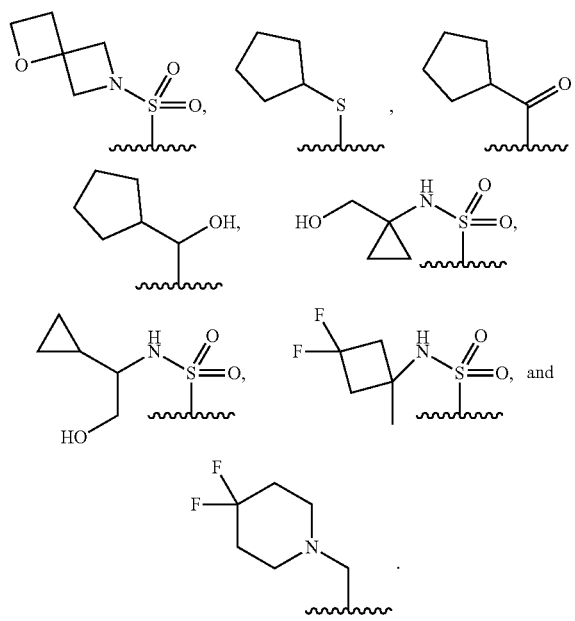

11. The compound of claim 1, or a pharmaceutically acceptable salt thereof, wherein ring A is phenyl substituted with

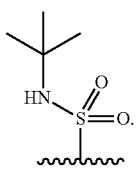

12. The compound of claim 1, or a pharmaceutically acceptable salt thereof, wherein

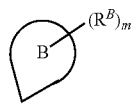

of Formula (I) is

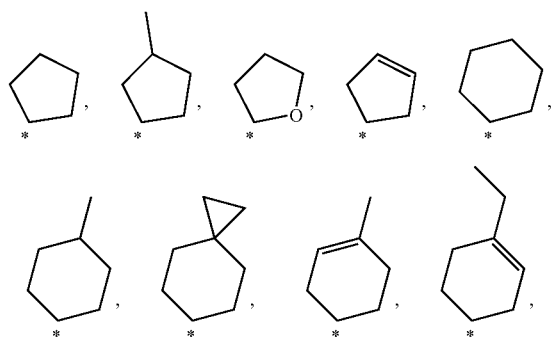

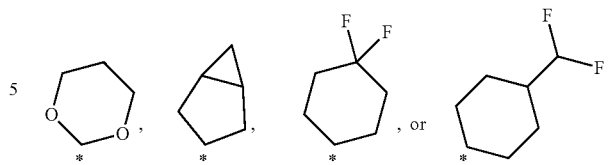

wherein * denotes the point of attachment to the rest of Formula (I).

13. The compound of claim 1, or a pharmaceutically acceptable salt thereof, wherein $Y^1$ is $CR^{C1}$; $Y^2$ is $CR^{C2}$; $Y^3$ is $CR^{C3}$; and $Y^4$ is $CR^{C4}$, wherein $R^{C1}$, $R^{C3}$, and $R^{C4}$ are each independently hydrogen, halo, or —NH$_2$.

14. The compound of claim 1, or a pharmaceutically acceptable salt thereof, wherein $R^{C2}$ is cyano, —OH, —CH$_2$OH, bromo, —NO$_2$,

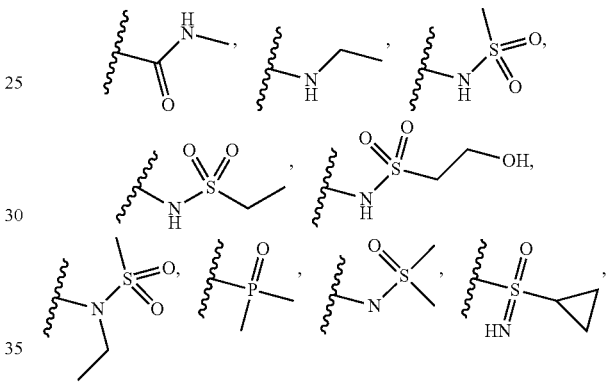

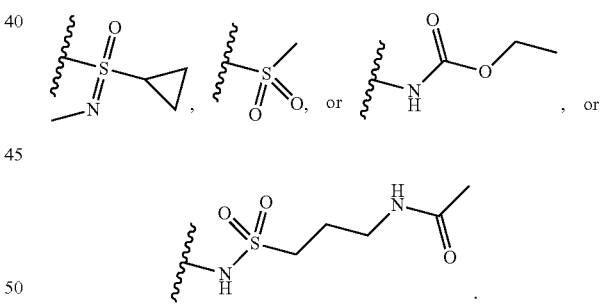

15. A compound of Formula (II):

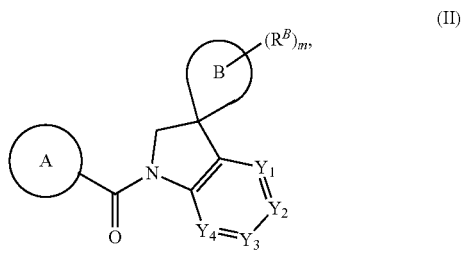

(II)

or a pharmaceutically acceptable salt thereof, wherein:
ring A is

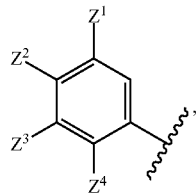

(i)

wherein $Z^1$, $Z^2$, $Z^3$, and $Z^4$ are each independently hydrogen or $R^D$, wherein $R^D$ is halo, —OH, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, —P(O)(R$^{a23}$)(R$^{a24}$), —C=NR$^{a25}$, or C$_{1-6}$ alkyl substituted with one or more substituents independently selected from the group consisting of —OH, cyano, C$_{3-10}$ cycloalkyl, and 3- to 10-membered heterocycloalkyl optionally substituted with one or more halo or C$_{1-3}$ alkyl,
provided that
(1) when $Z^4$ is hydrogen, then at least one of $Z^1$ and $Z^3$ is $R^D$; and
(2) when $Z^4$ is $R^D$, then $Z^1$ is $R^D$, or

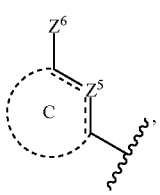

(ii)

wherein
⟍⟋ is a single bond or a double bond,
$Z^5$ is C—H, N, O, S, or N—X, wherein X is H or C$_{1-6}$alkyl;
$Z^6$ is —NR$^{a26}$C(O)NR a27 R$^{a28}$, —NR$^{a29}$C(O)OR$^{a30}$, —N=S(O)R$^{a31}$R$^{a32}$, —S(O)R$^{a33}$, —S(O)(NR$^{a34}$)R$^{a35}$, —S(O)$_2$NR$^{a36}$R$^{a37}$, —S(O)$_2$R$^{a38}$, —SR$^{a39}$, 3- to 10-membered heterocycloalkyl, —C(O)R$^{a40}$, or —CH(Z$^7$)(Z$^8$), wherein $Z^7$ is hydrogen or —OH, and $Z^8$ is C$_{1-6}$ alkyl, C$_{3-10}$ cycloalkyl optionally substituted with one or more halo, or 3- to 10-membered heterocycloalkyl optionally substituted with one or more halo, and
ring C is 5- to 6-membered heteroaryl optionally substituted with one or more $R^E$ substituents, wherein each $R^E$ substituent is independently selected from the group consisting of halo, —OH, and C$_{1-6}$ alkyl, or two $R^E$ substituents are taken, together with the atoms to which they are attached, to form C$_{5-6}$ cycloalkyl, C$_{5-6}$ cycloalkenyl, 5- to 6-membered heterocycloalkyl, 5- to 6-membered heterocycloalkenyl, or 5- to 6-membered heteroaryl;

$R^{a4}$-$R^{a40}$ are each independently hydrogen, C$_{1-6}$ alkyl, C$_{2-6}$ alkenyl, C$_{3-10}$ cycloalkyl, C$_{3-10}$ cycloalkenyl, 3- to 10-membered heterocycloalkyl, 3- to 10-membered heterocycloalkenyl, C$_{6-14}$ aryl, or 5- to 12-membered heteroaryl, each optionally substituted with one or more substituents independently selected from the group consisting of halo, cyano, —OH, —O(C$_{1-6}$ alkyl), C$_{2-6}$ alkenyl, C$_{3-10}$ cycloalkyl, —S(C$_{1-6}$ alkyl), =CR$^{1a1}$R$^{1a2}$, and C$_{1-6}$ alkyl optionally substituted with one or more substituents independently selected from the group consisting of halo, —OH, and —O(C$_{1-6}$ alkyl), wherein R$^{1a1}$ and R$^{1a2}$ are each independently hydrogen or C$_{1-6}$ alkyl;

ring B is C$_{5-7}$ cycloalkyl, C$_{5-7}$ cycloalkenyl, or 5- to 7-membered heterocycloalkyl wherein one or two of the ring atoms are each oxygen and the remaining ring atoms are each carbon;

each $R^B$ group is independently halo or C$_{1-6}$ alkyl optionally substituted with one or more halo; or two vicinal $R^B$ groups are taken together with the carbon atoms to which they are attached to form C$_{3-10}$ cycloalkyl; or two geminal $R^B$ groups are taken together with the carbon atom to which they are attached to form C$_{3-10}$ cycloalkyl; or two geminal $R^B$ groups are taken together to form a =CR$^{1a3}$R$^{1a4}$ group, wherein R$^{1a3}$ and R$^{1a4}$ are each independently hydrogen or C$_{1-6}$ alkyl;

m is 0, 1, 2, 3, or 4;

$Y^1$ is N or CR$^{C1}$;

$Y^2$ is N or CR$^{C2}$;

$Y^3$ is N or CR$^{C3}$;

$Y^4$ is N or CR$^{C4}$;

wherein no more than three of $Y^1$, $Y^2$, $Y^3$, and $Y^4$ are N;

$R^{C1}$-$R^{C4}$ are each independently hydrogen or $R^F$, wherein $R^F$ is halo, cyano, —OH, —NO$_2$, —C(O)NR$^{c1}$R$^{c2}$, —NR$^{c3}$R$^{c4}$, —NRCS(O)$_2$R$^{c6}$, —P(O)R$^{c7}$R$^{c8}$, —N=S(O)R$^{c9}$R$^{c10}$, —S(O)(NR$^{c11}$)R$^{c12}$, —S(O)$_2$R$^{c13}$, —NR$^{c14}$C(O)OR$^{c15}$, —NR$^{c16}$S(O)$_2$(CH$_2$)$_{1-6}$NR$^{c17}$C(O)R$^{c18}$, —O—S(O)$_2$R$^{c19}$, or C$_{1-6}$ alkyl substituted with one or more substituents independently selected from the group consisting of halo and —OH, and $R^{c1}$-$R^{c19}$ are each independently hydrogen, C$_{3-10}$ cycloalkyl, or C$_{1-6}$ alkyl optionally substituted with one or more substituents independently selected from the group consisting of halo, —O(C$_{1-6}$ alkyl), —NHC(O)(C$_{1-6}$ alkyl), and —OH;

provided that (1) when ring B is unsubstituted cyclopentyl, then ring A is

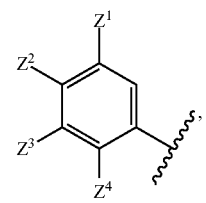

wherein at least one of $Z^1$-$Z^4$ is —S(O)$_2$-(3- to 10-membered heterocycloalkyl) substituted with one or more halo, (2) when ring B is unsubstituted cyclohexyl and ring A is

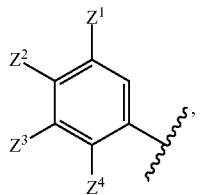

then at least one of $R^{C1}$-$R^{C4}$ is $R^F$, and (3) when ring B is 5- to 7-membered heterocycloalkyl optionally substituted with 1-4 $R^B$, then ring A is

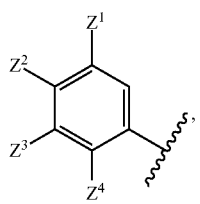

wherein at least one of $Z^1$-$Z^4$ is —S(O)$_2$-(3- to 10-membered heterocycloalkyl) optionally substituted with one or more halo.

16. The compound of claim 15, or a pharmaceutically acceptable salt thereof, wherein ring A is

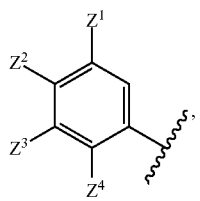

wherein $Z^4$ is hydrogen, and at least one of $Z^1$ and $Z^3$ is $R^D$, wherein $R^D$ is halo, —OH, —NR$^{a4}$C(O)OR$^{a5}$, —NR$^{a6}$R$^{a7}$, —N=S(O)R$^{a8}$R$^{a9}$, —OR$^{a10}$, —S(O)R$^{a11}$, —S(O)(NR$^{a12}$)R$^{a13}$, —S(O)$_2$NR$^{a14}$R$^{a15}$, —S(O)$_2$R$^{a16}$, —(CR$^{a17}$R$^{a18}$)$_{0-1}$C(O)NR$^{a19}$R$^{a20}$, —SR$^{a21}$, —C(O)R$^{a22}$, —P(O)(R$^{a23}$)(R$^{a24}$), —C=NR$^{a25}$, or C$_{1-6}$ alkyl substituted with one or more substituents independently selected from the group consisting of —OH, cyano, C$_{3-10}$ cycloalkyl, and 3- to 10-membered heterocycloalkyl optionally substituted with one or more halo or C$_{1-3}$ alkyl.

17. The compound of claim 15, or a pharmaceutically acceptable salt thereof, wherein one or more of $Z^1$-$Z^4$ is selected from the group consisting of fluoro, chloro, —OH, —NH$_2$, —CH$_2$OH,

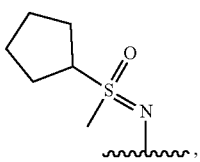 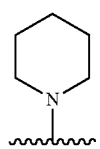 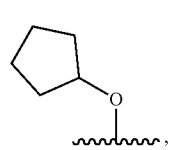

-continued

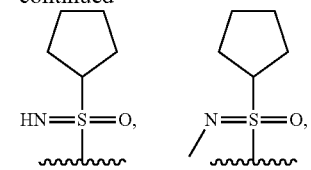

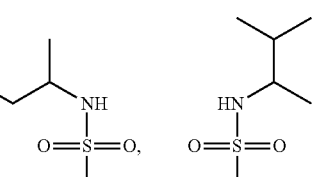

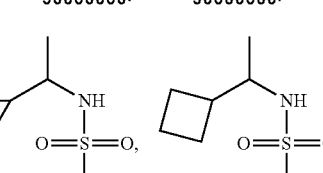

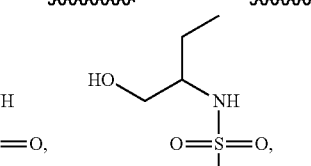

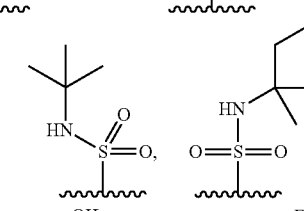

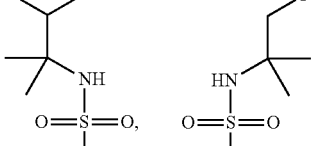

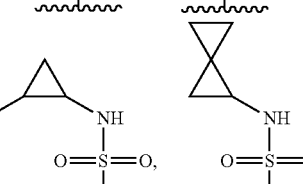

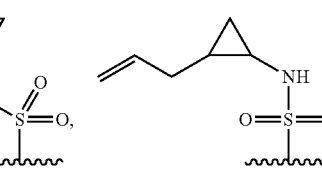

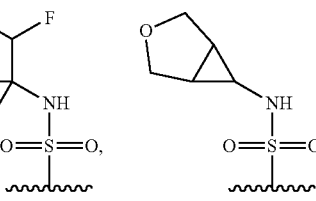

579
-continued
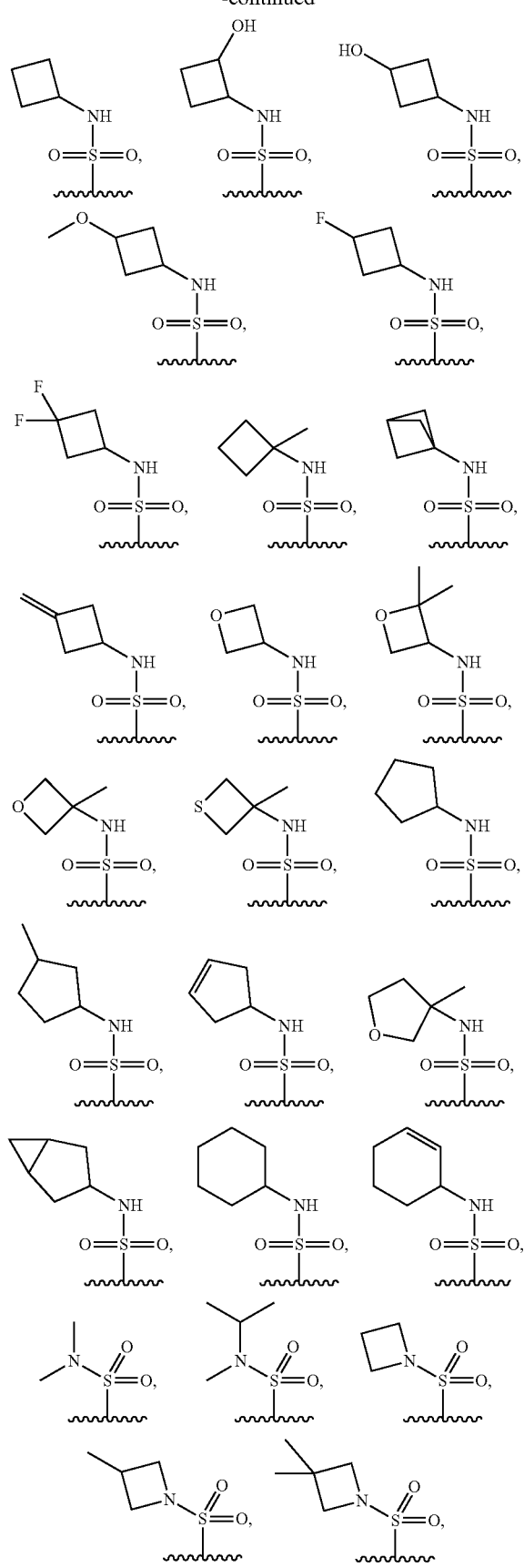
580
-continued
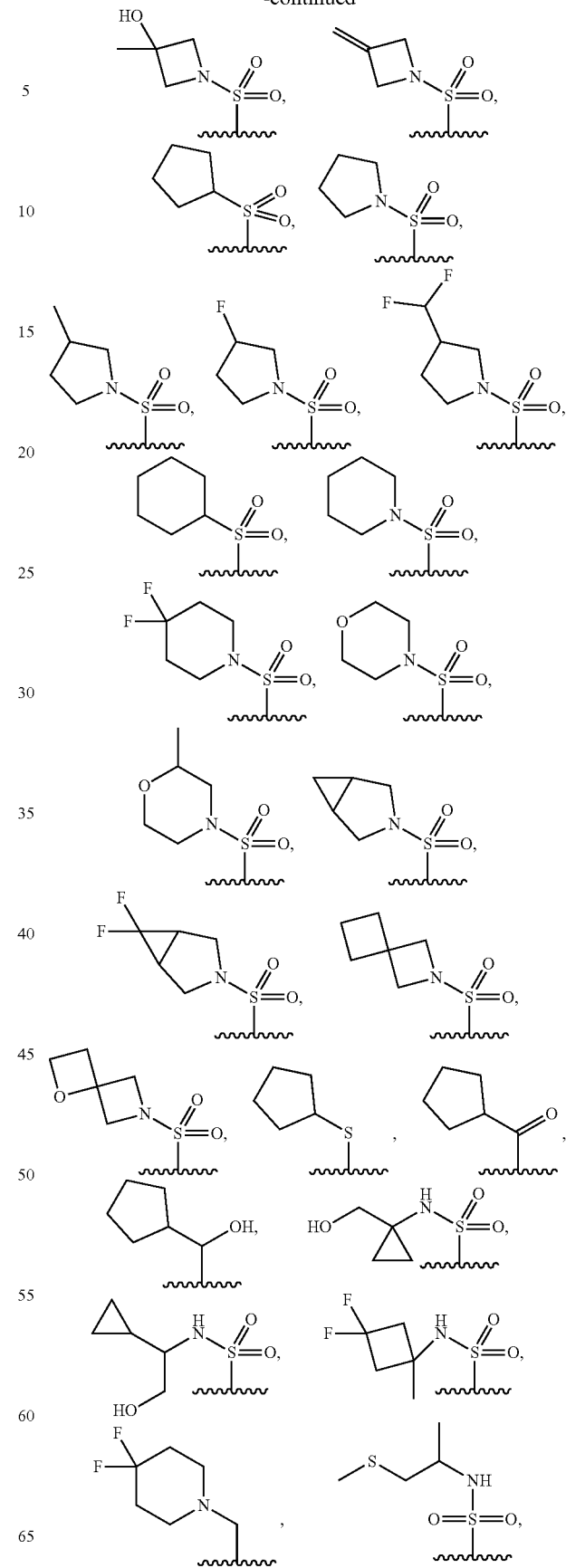

581
-continued
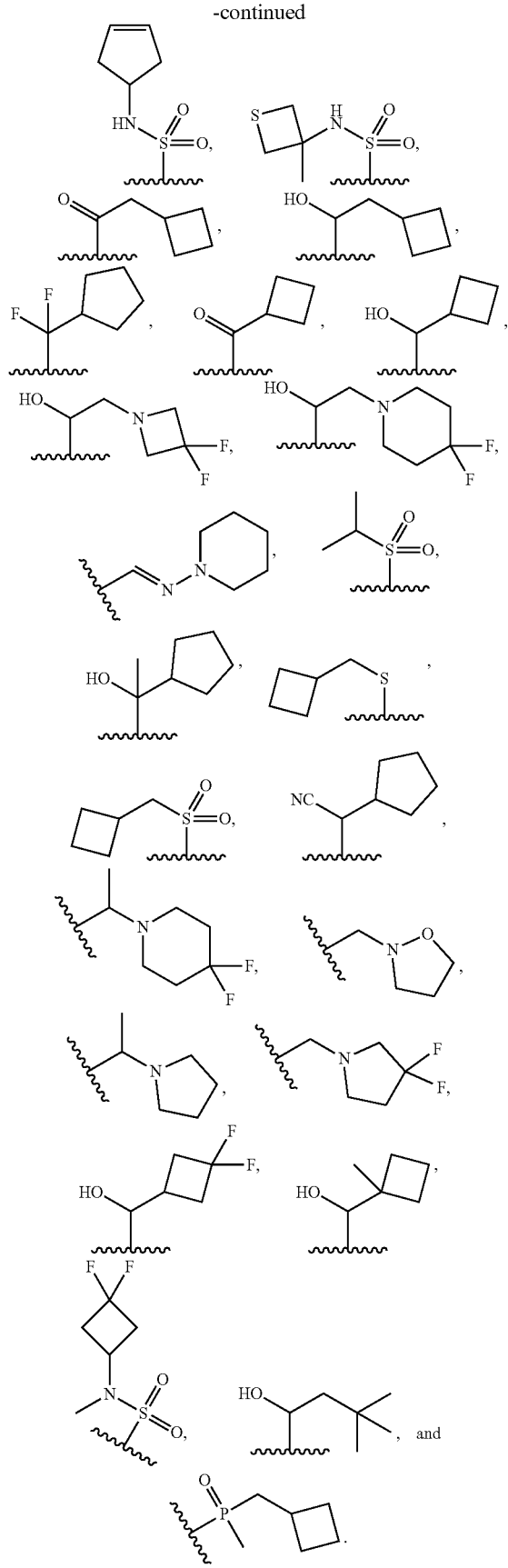
582
18. The compound of claim 15, or a pharmaceutically acceptable salt thereof, wherein one of $Z^1$-$Z^4$ is
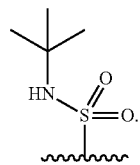
19. The compound of claim 15, or a pharmaceutically acceptable salt thereof, wherein
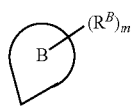
of Formula (II) is
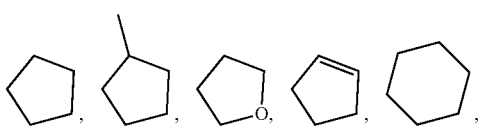
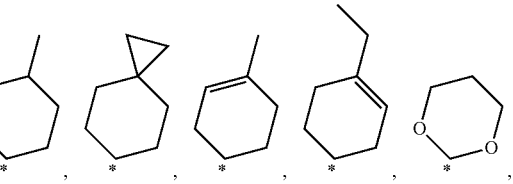
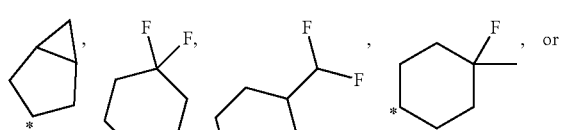
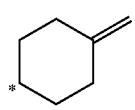
wherein * denotes the point of attachment to the rest of Formula (II).
20. The compound of claim 19, or a pharmaceutically acceptable salt thereof, wherein
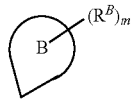

of Formula (II) is

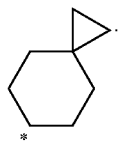

21. The compound of claim 15, or a pharmaceutically acceptable salt thereof, wherein $Y^1$ is $CR^{C1}$; $Y^2$ is $CR^{C2}$; $Y^3$ is $CR^{C3}$; and $Y^4$ is $CR^{C4}$, wherein $R^{C1}$, $R^{C3}$, and $R^{C4}$ are each independently hydrogen, halo, or —NH$_2$.

22. The compound of claim 15, or a pharmaceutically acceptable salt thereof, wherein $R^{C2}$ is cyano, —OH, —CH$_2$OH, fluro, bromo, —NO$_2$,

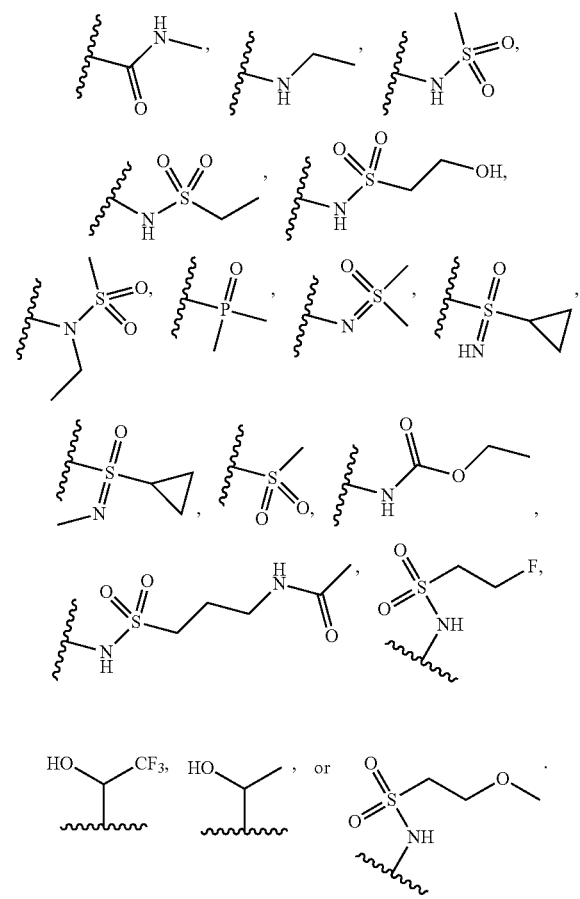

23. The compound of claim 22, or a pharmaceutically acceptable salt thereof, wherein $R^{C2}$ is

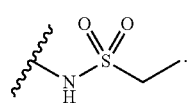 [SMILES: *NS(=O)(=O)CC]

24. A compound, or a pharmaceutically acceptable salt thereof, wherein the compound is selected from the group consisting of:

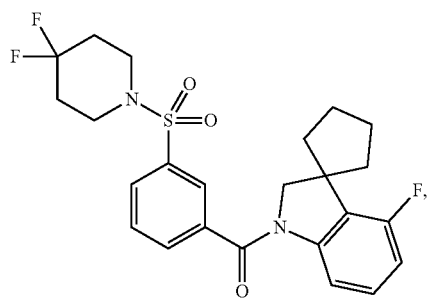

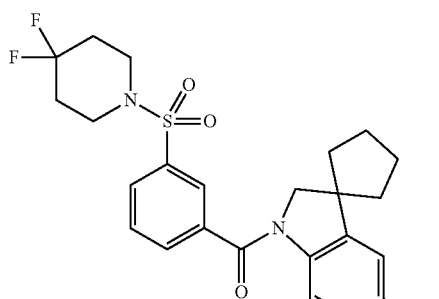

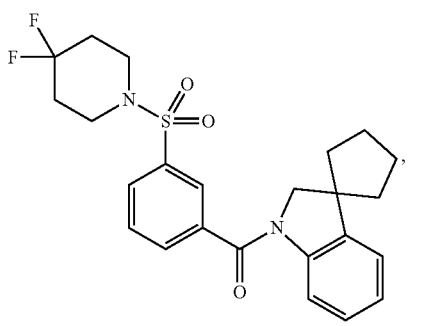

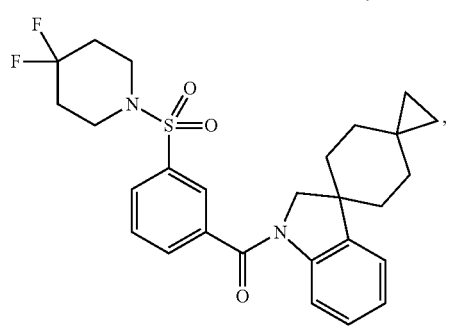

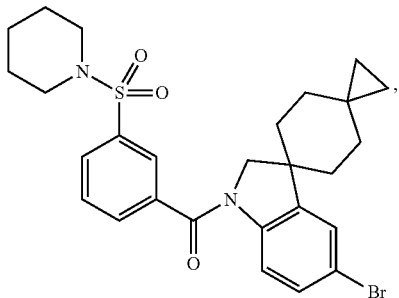

585
-continued
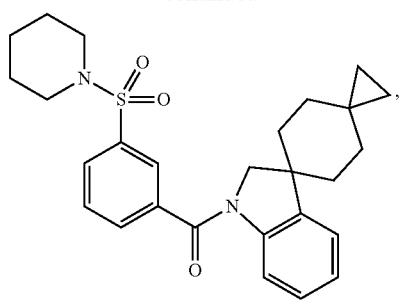
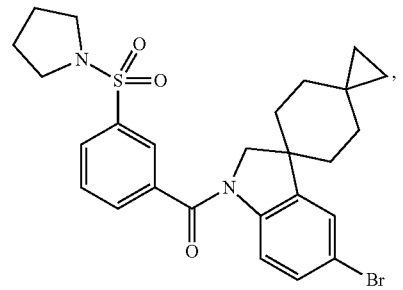
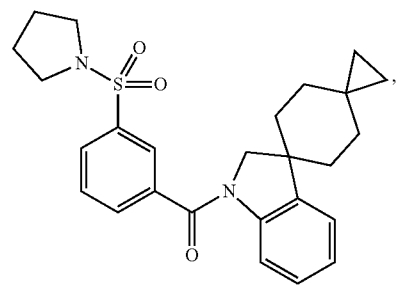
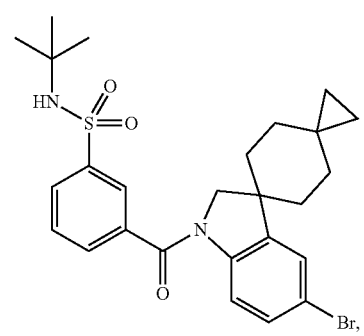
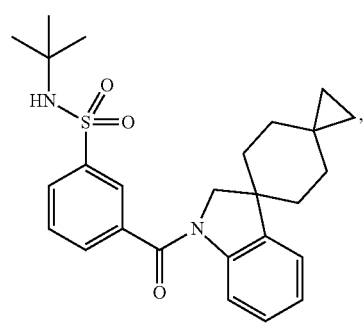
586
-continued
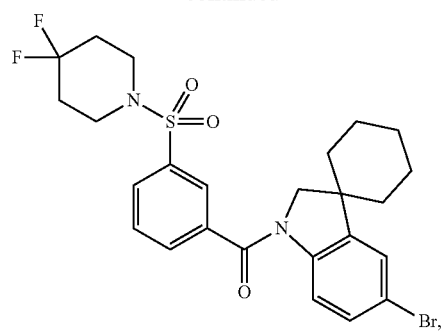
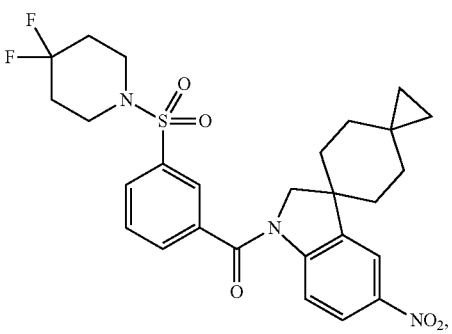
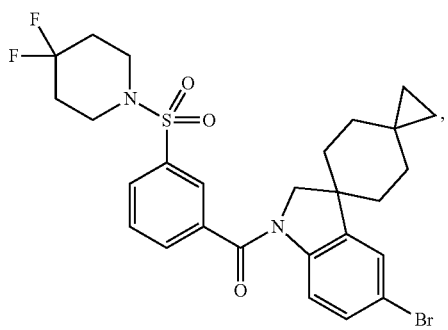
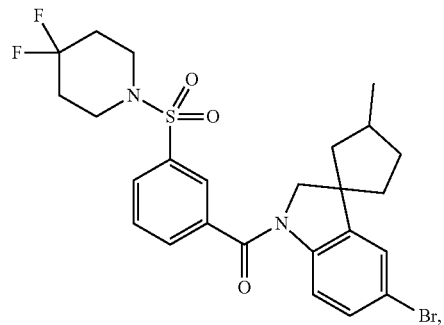
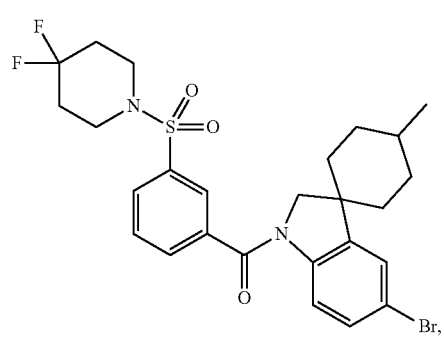

587
-continued
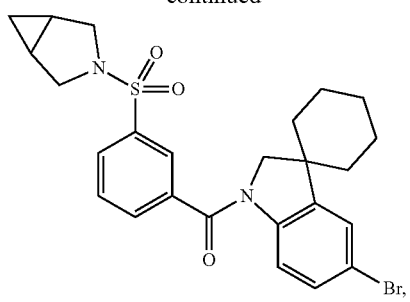
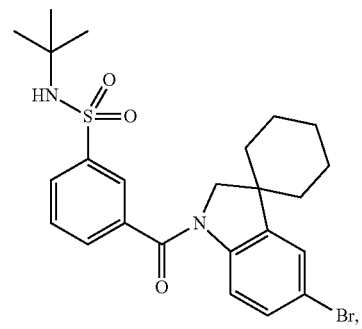
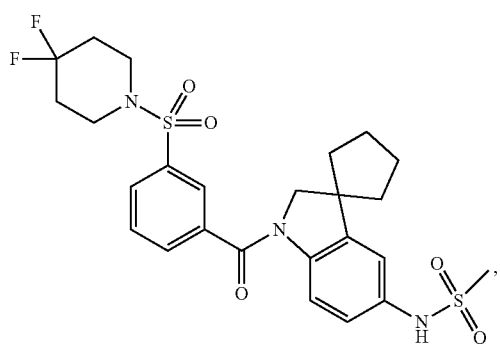
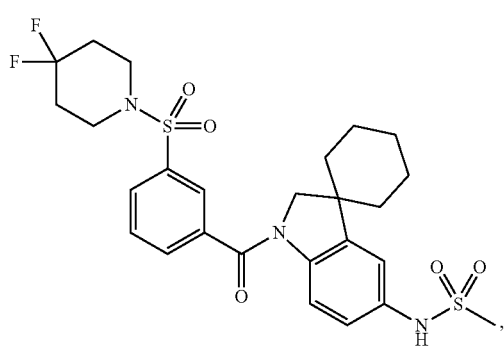
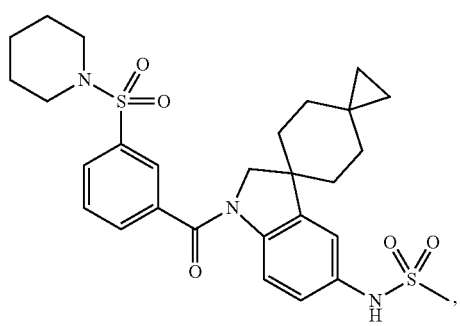
588
-continued
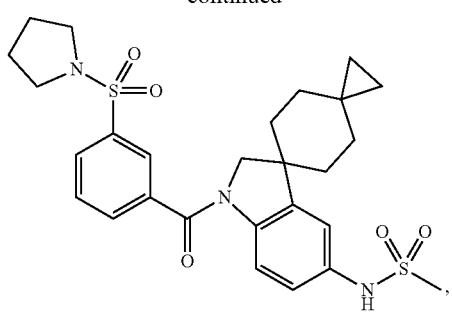
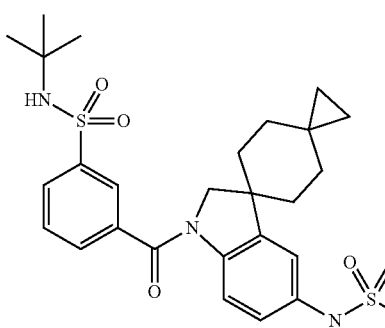
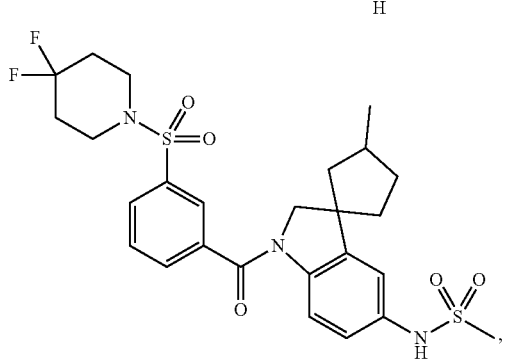
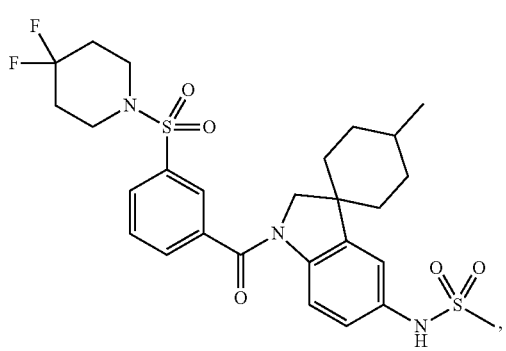
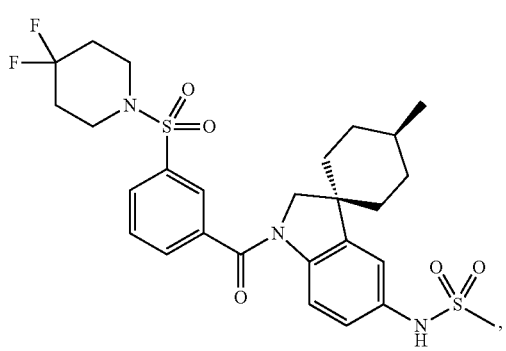

589
-continued
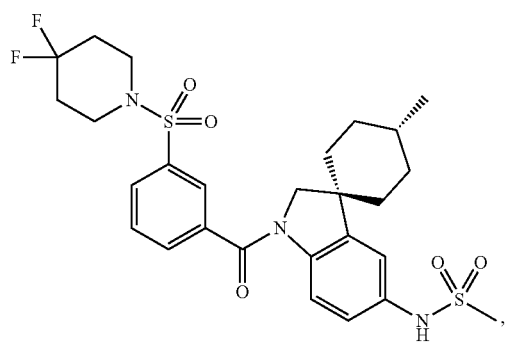
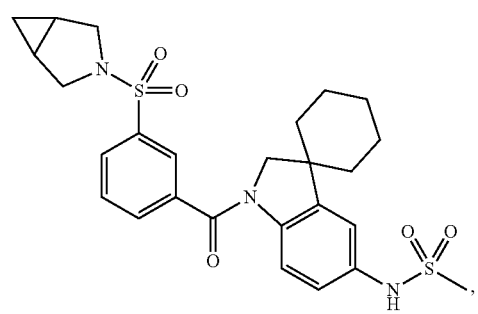
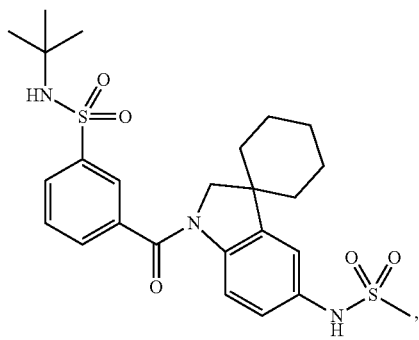
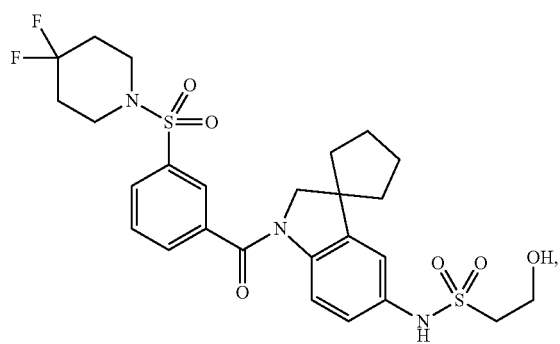
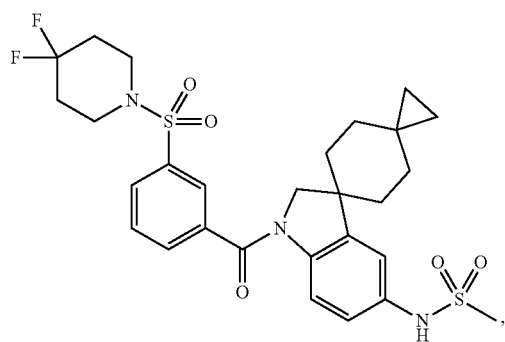
590
-continued
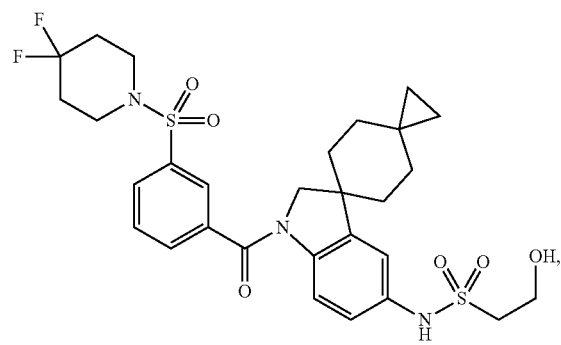
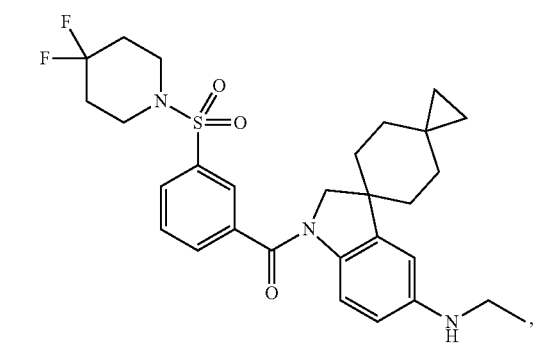
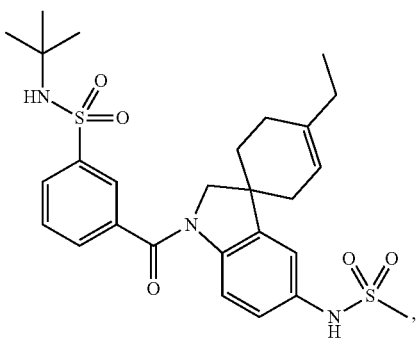
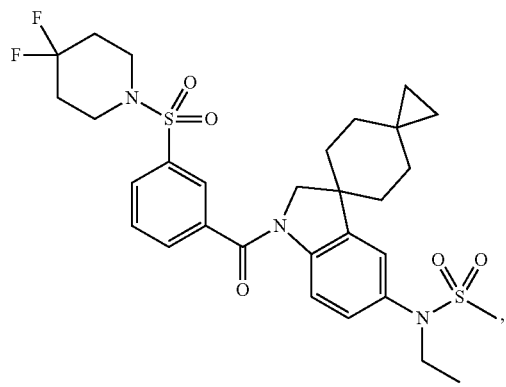
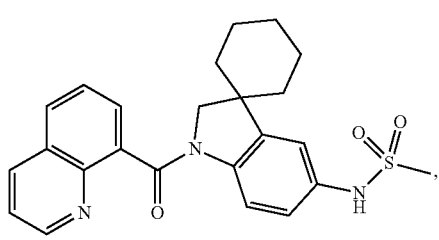

591
-continued
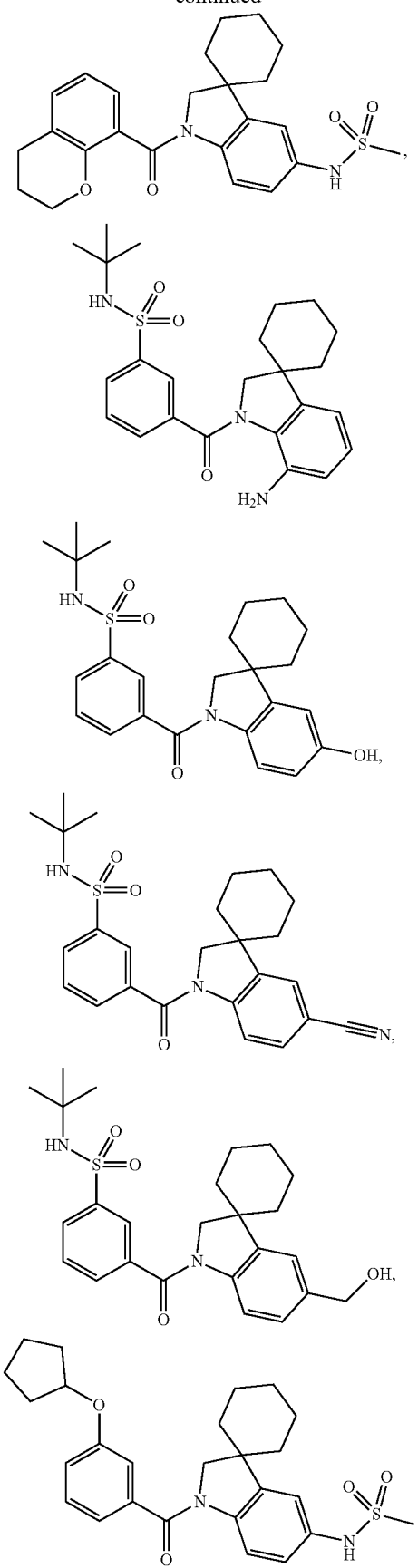
592
-continued
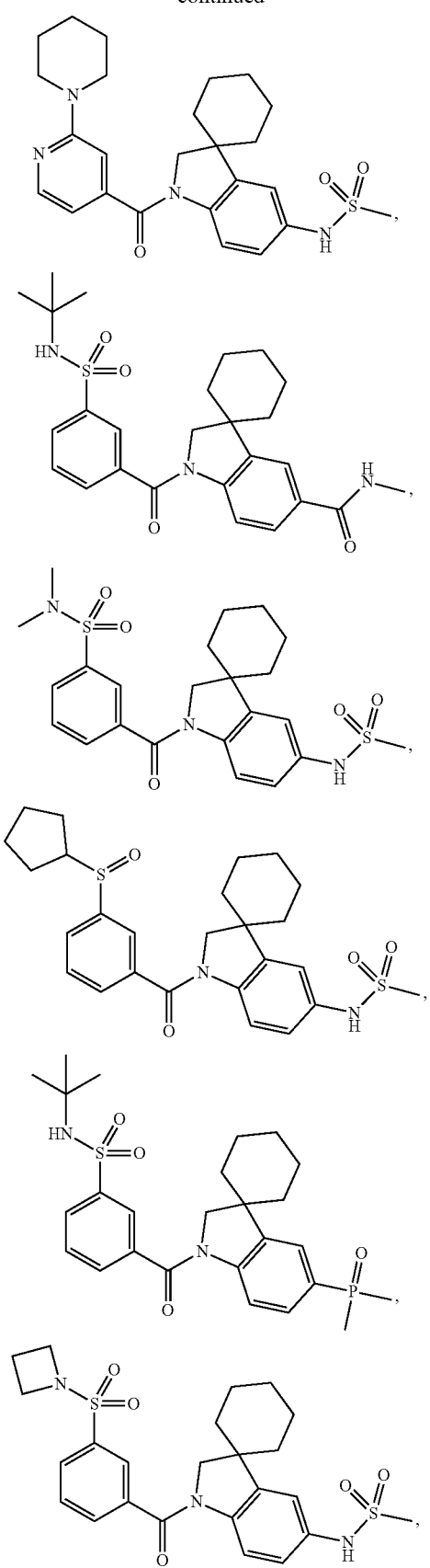

593
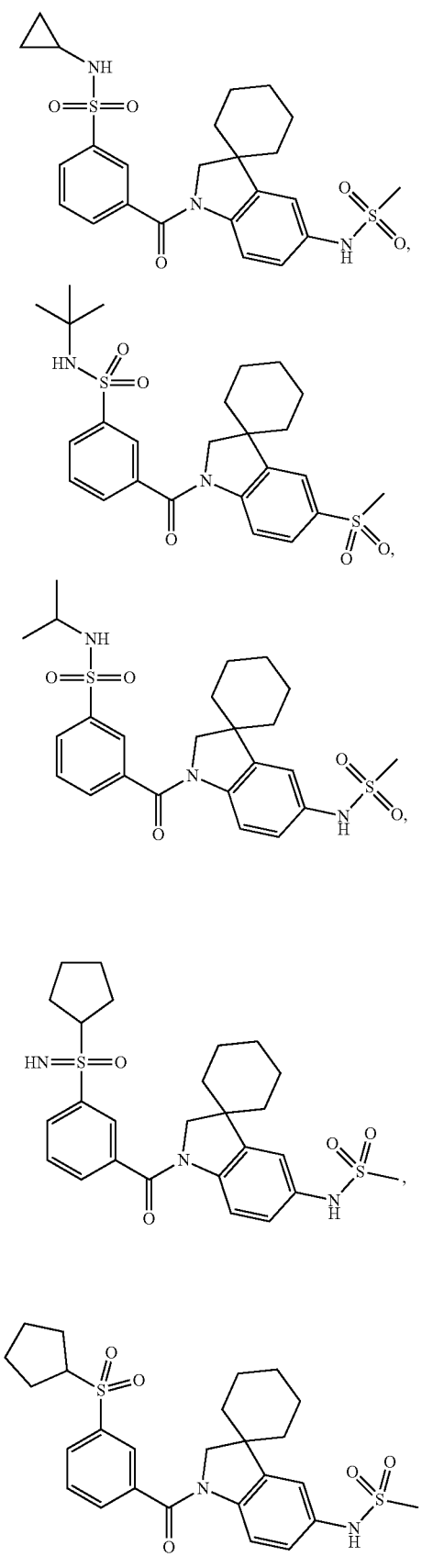
594
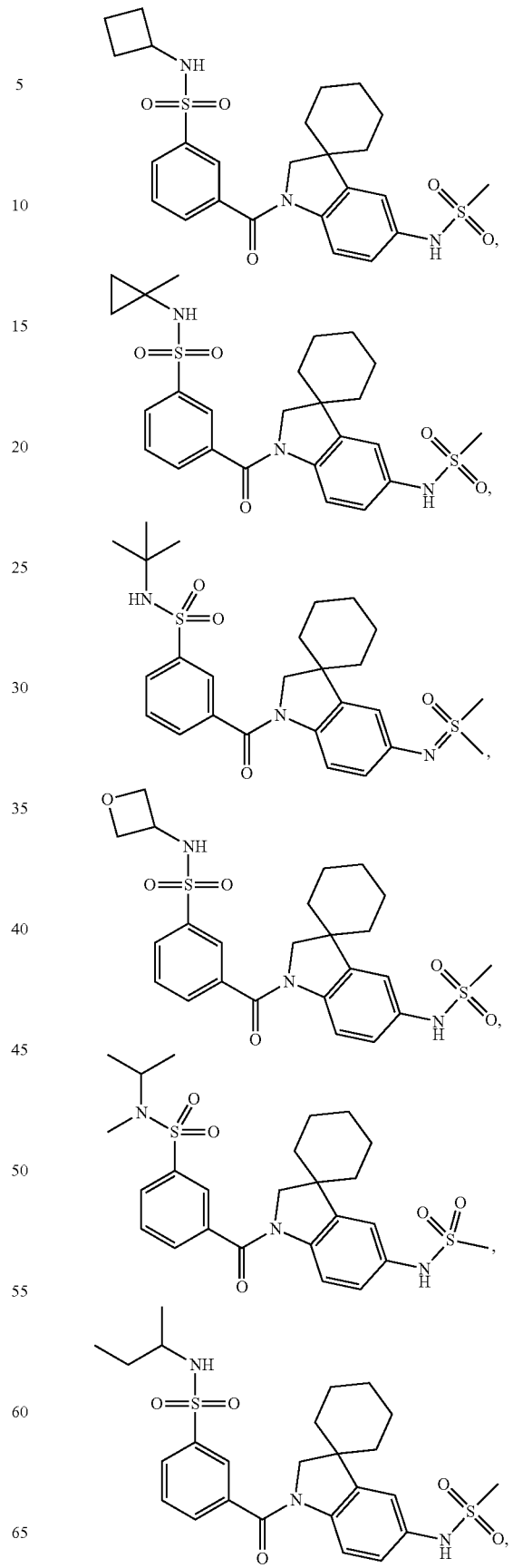

595
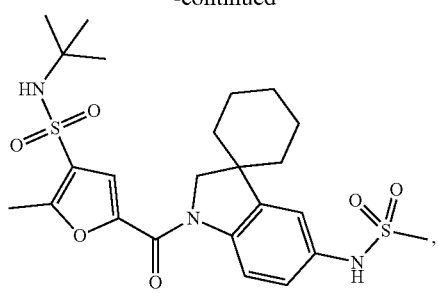
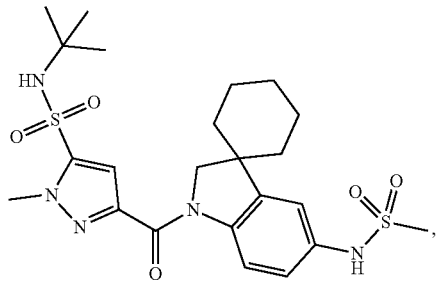
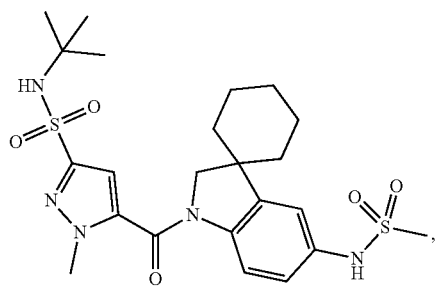
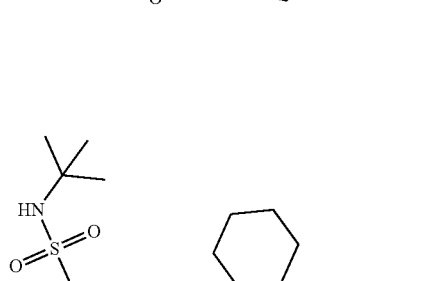
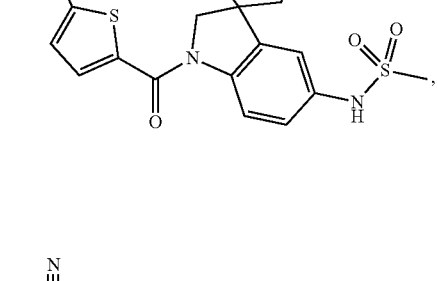
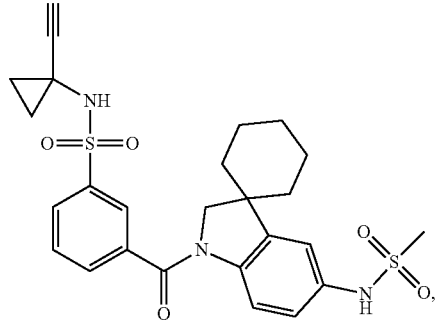
596
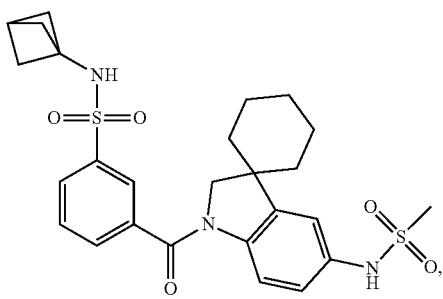
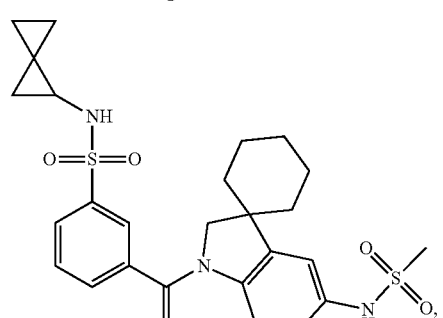
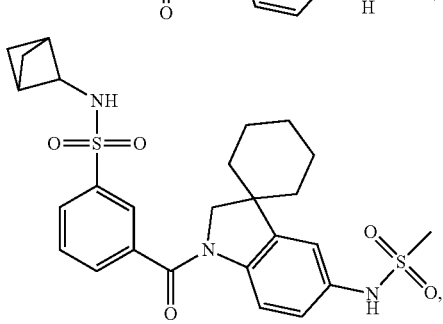
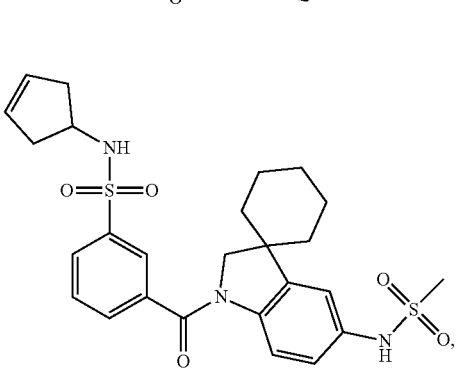
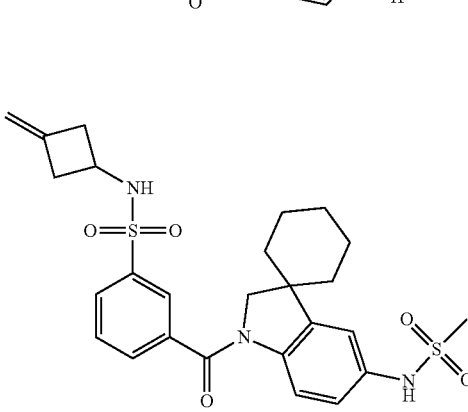

597
-continued
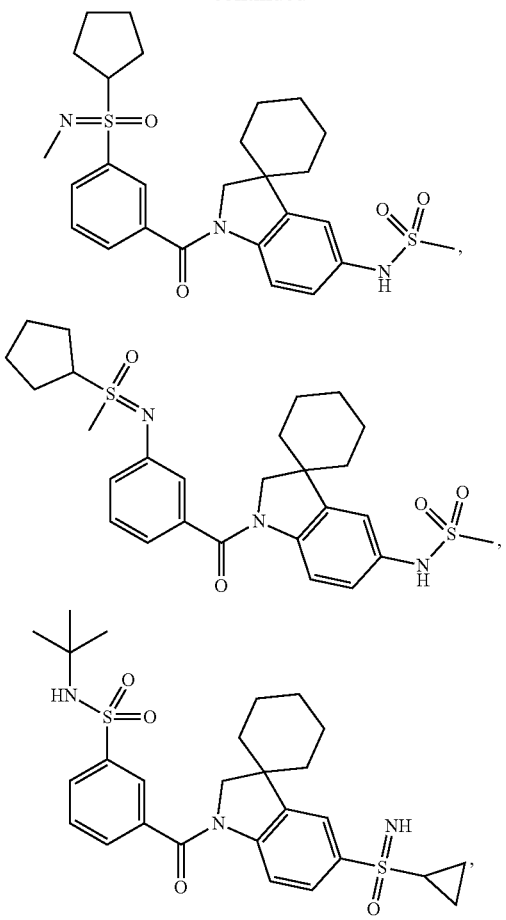
598
-continued
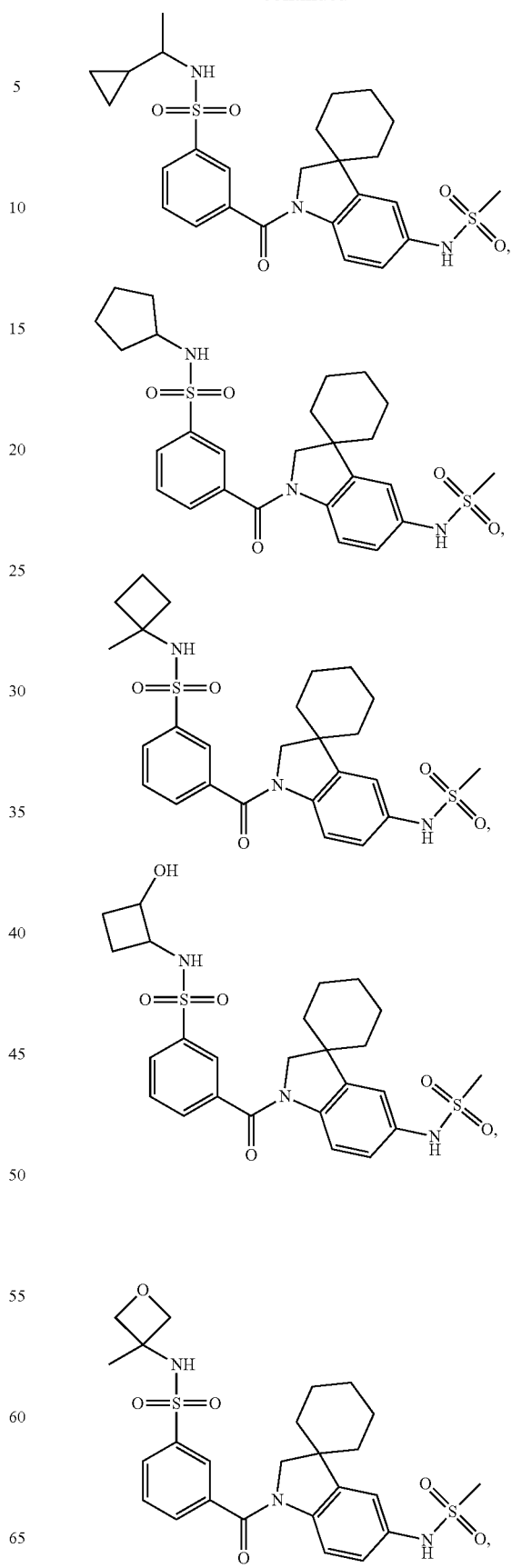

599
-continued
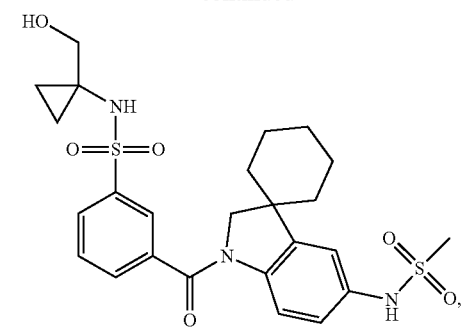
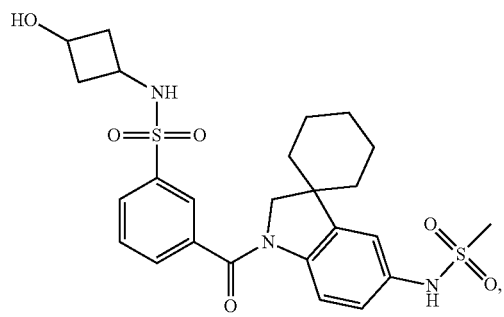
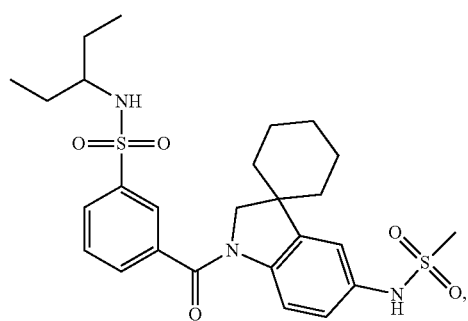
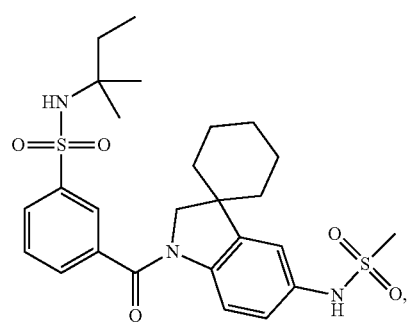
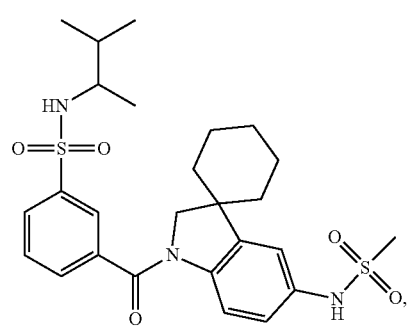
600
-continued
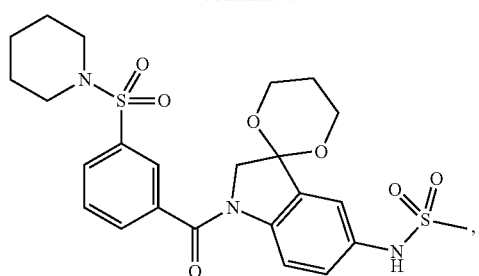
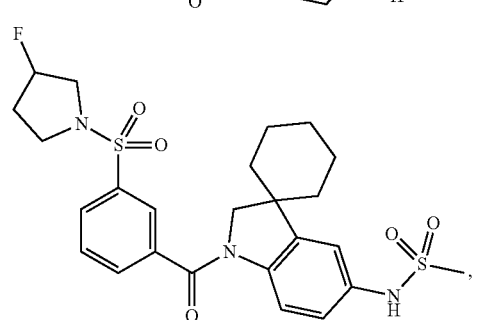
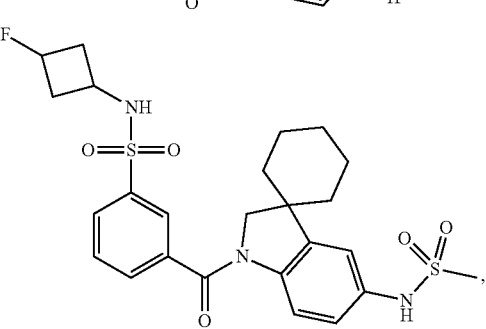
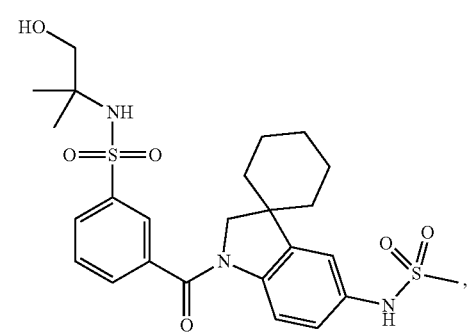
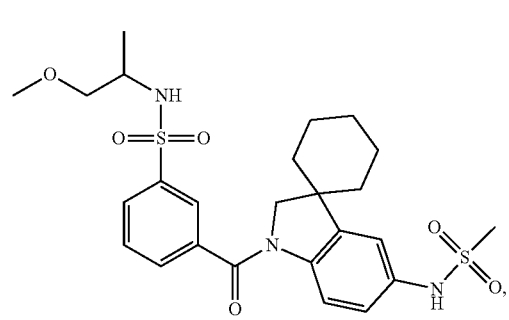

601
-continued
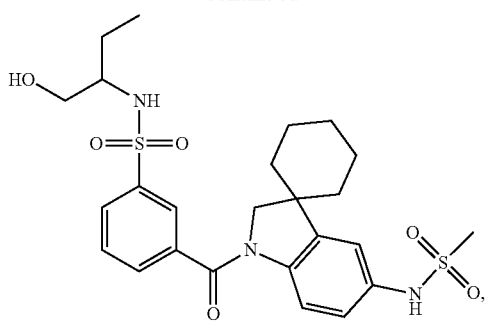
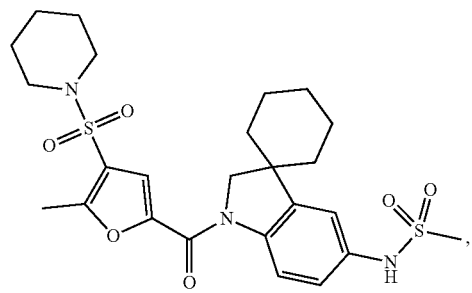
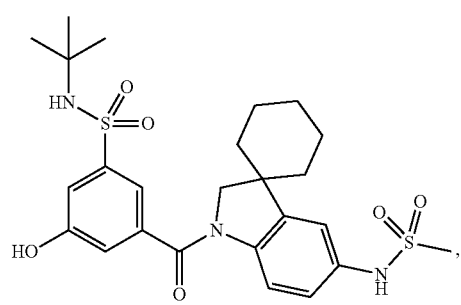
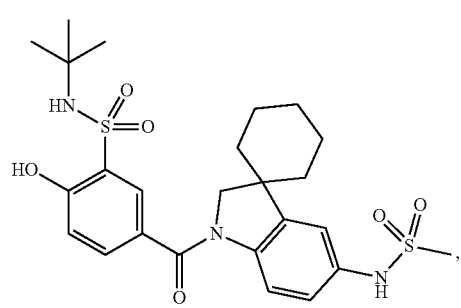
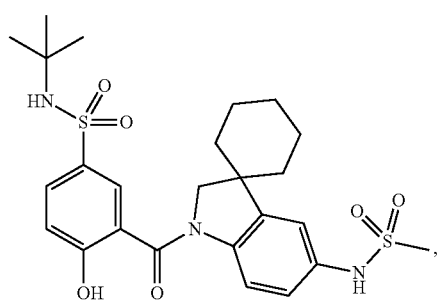
602
-continued
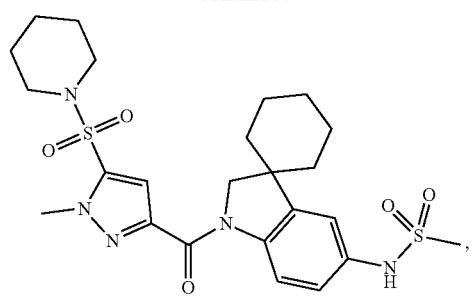
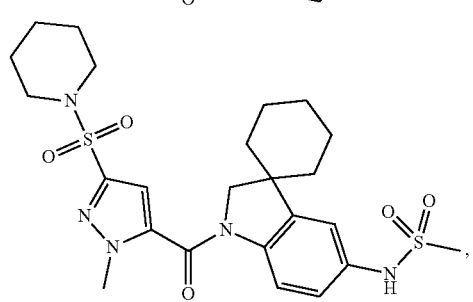
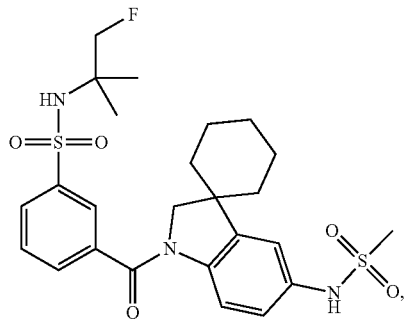
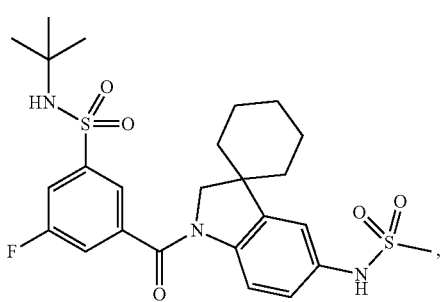
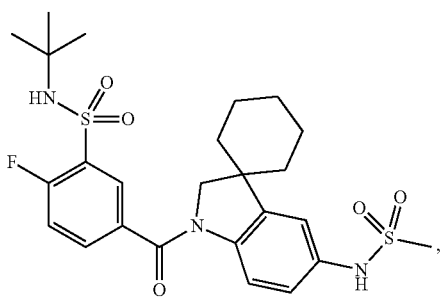

603
-continued
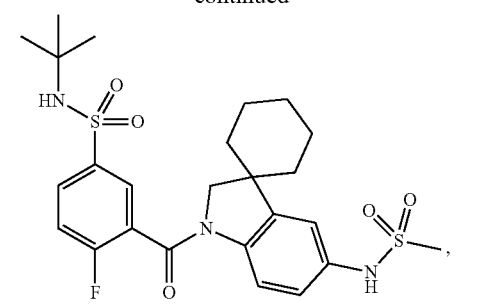
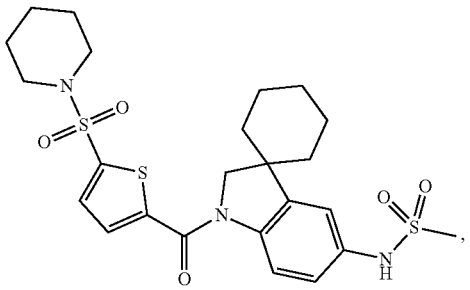
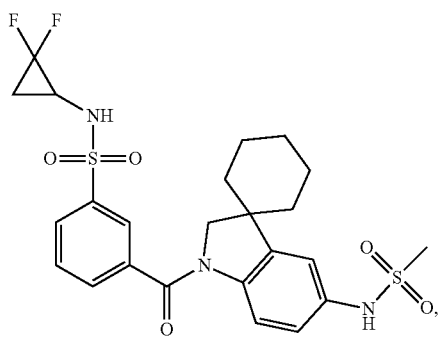
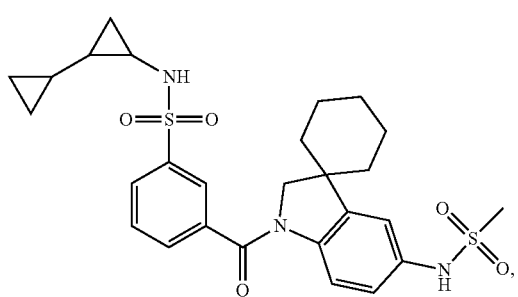
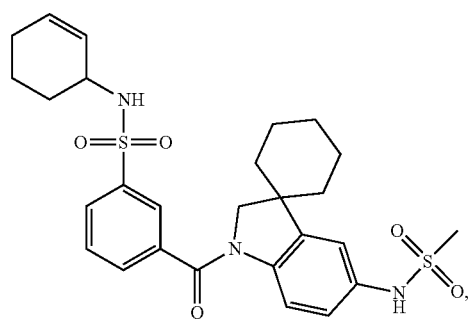
604
-continued
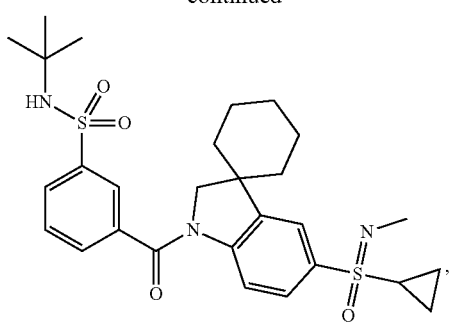
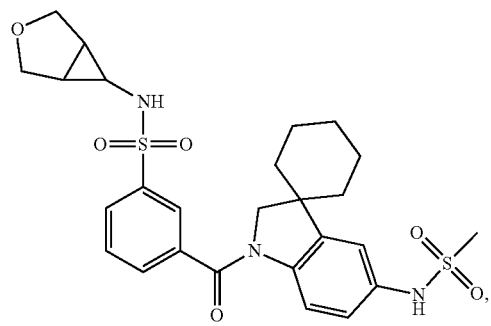
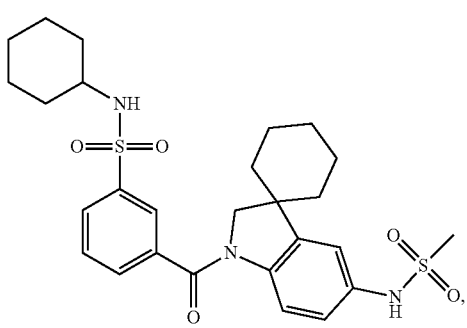
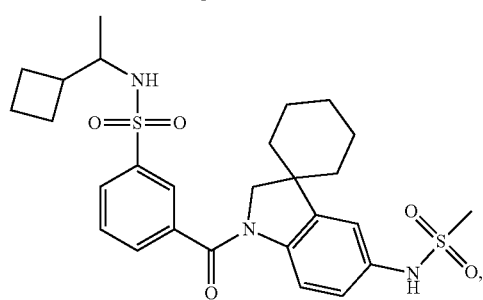
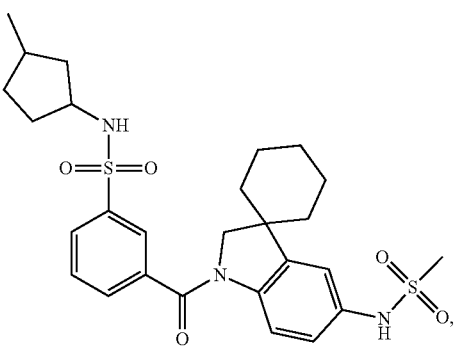

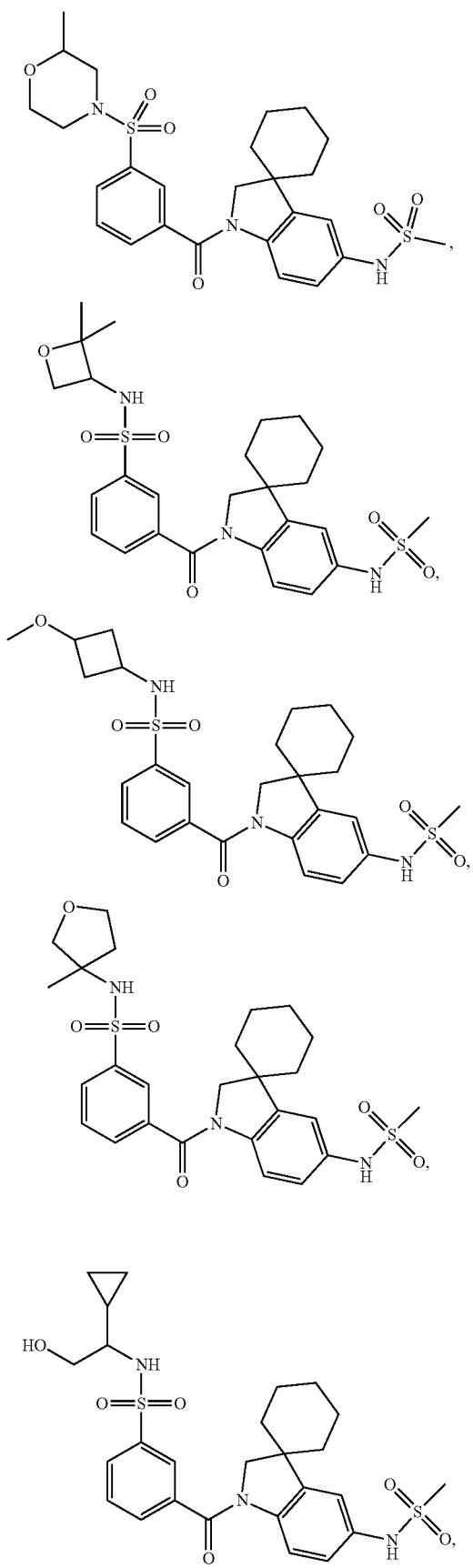
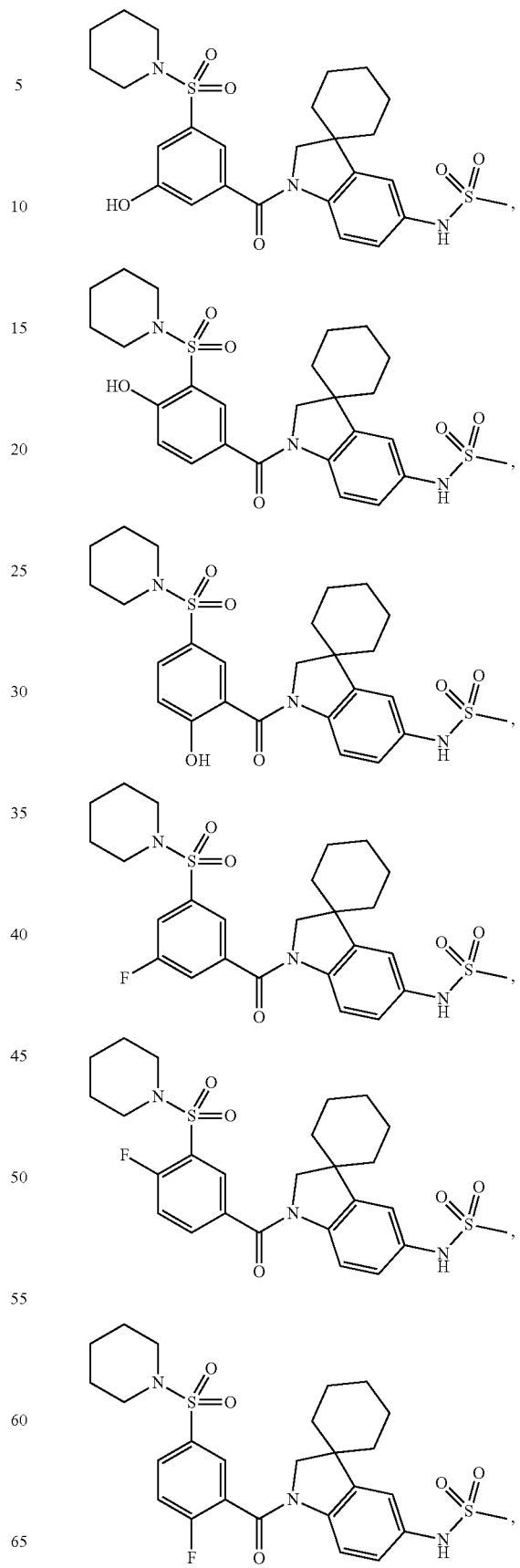

607
-continued
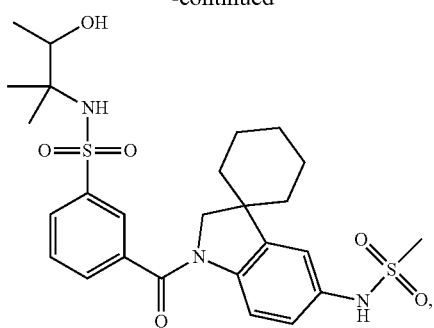
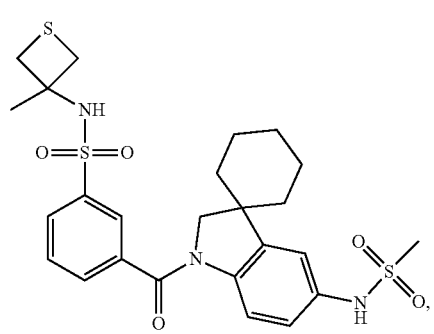
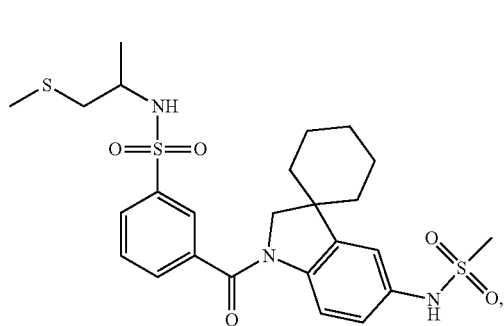
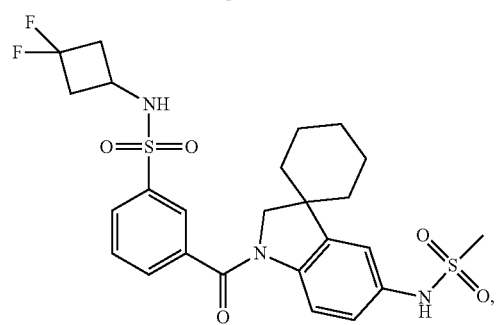
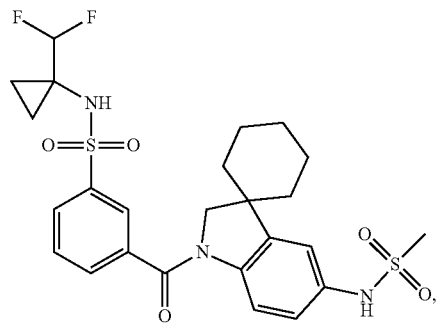
608
-continued
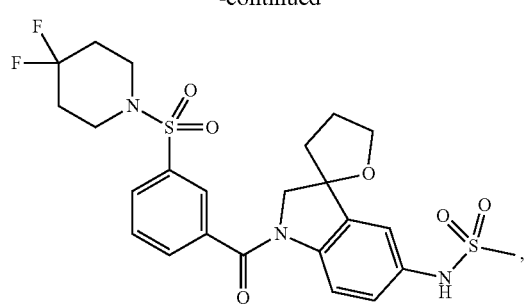
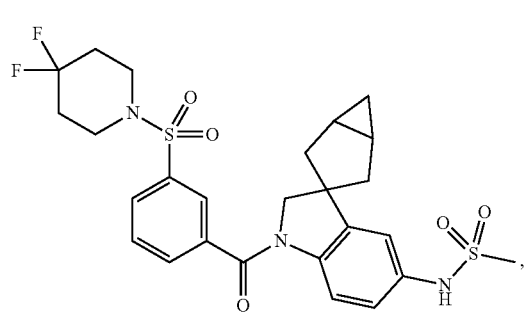
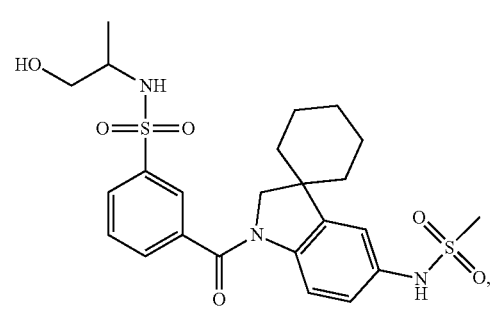
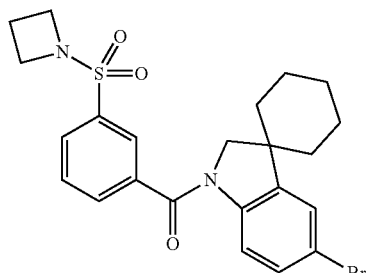
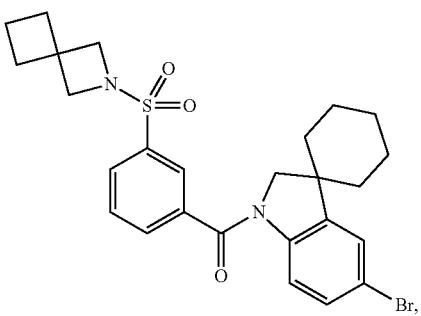

609
-continued
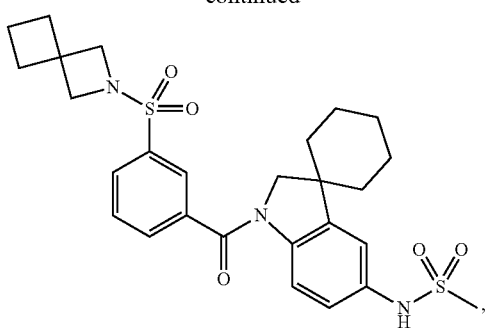
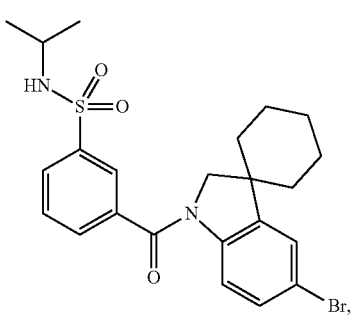
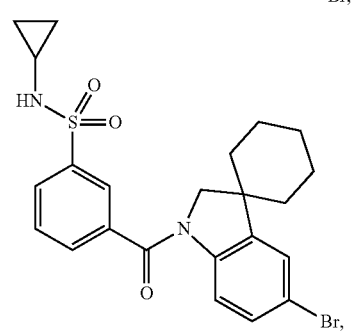
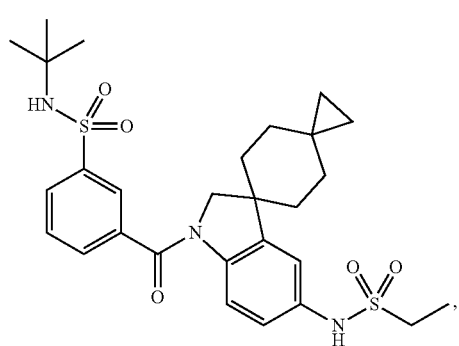
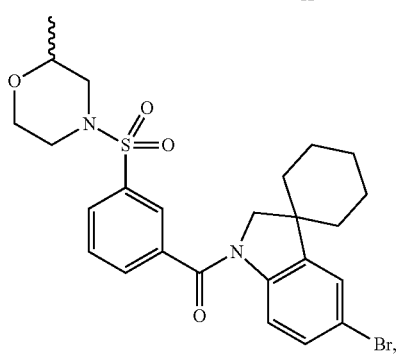
610
-continued
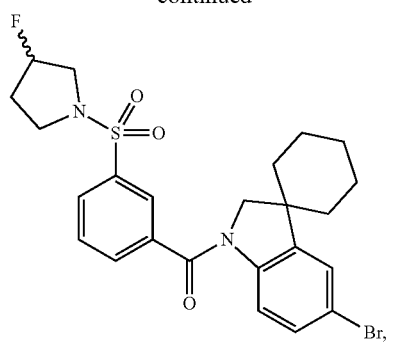
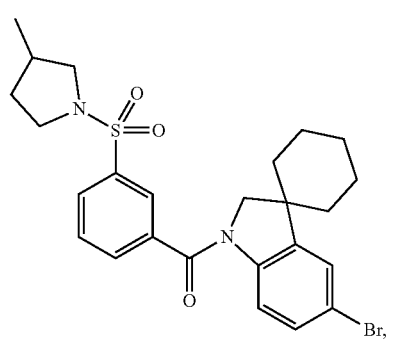
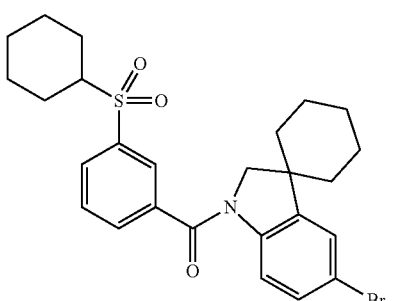
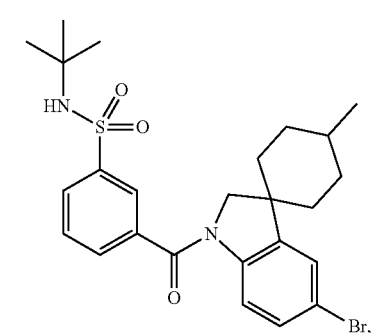
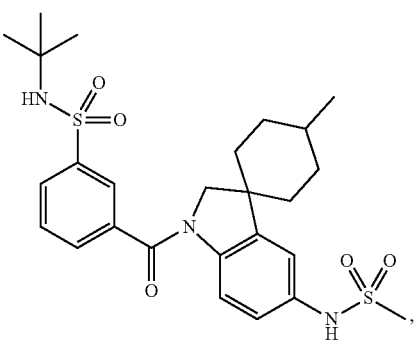

611
-continued
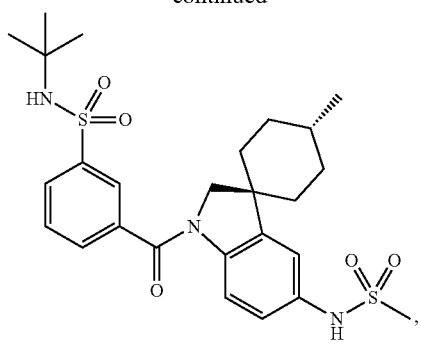
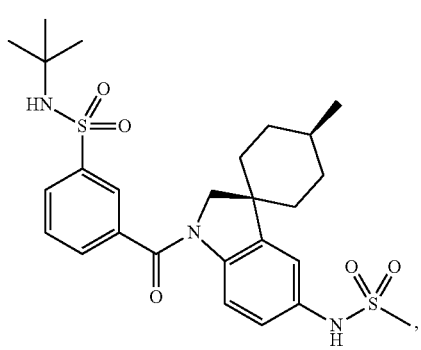
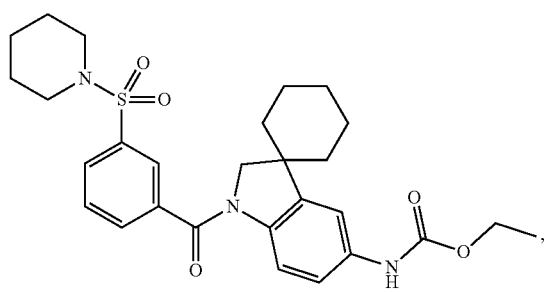
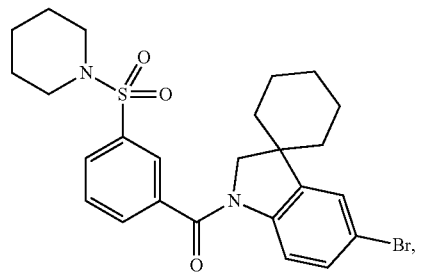
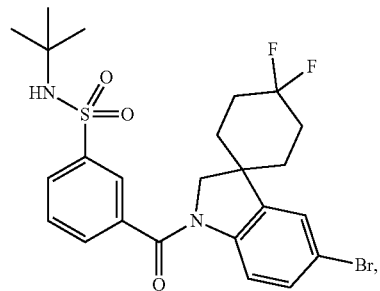
612
-continued
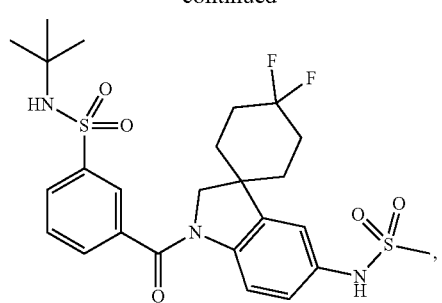
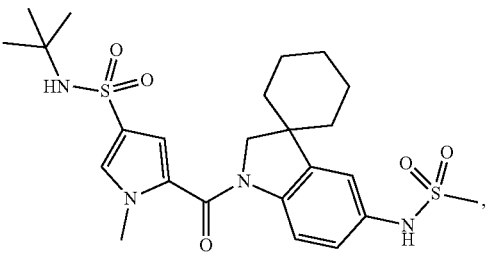
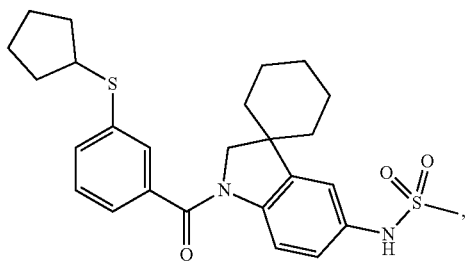
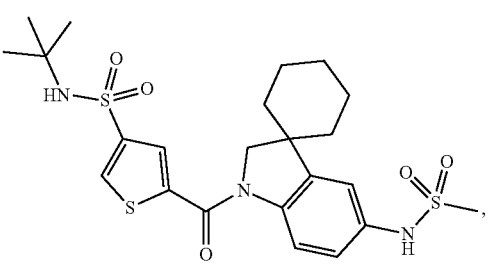
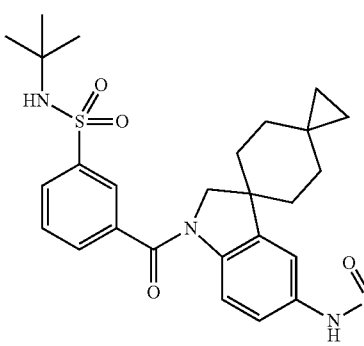
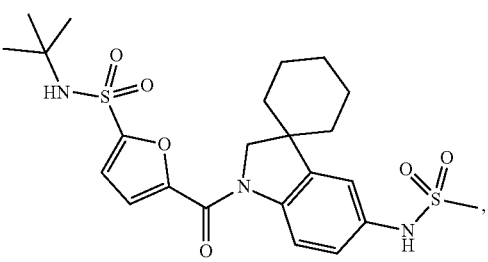

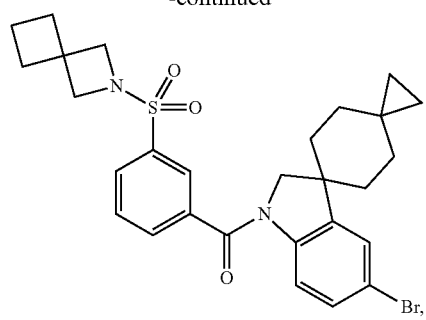
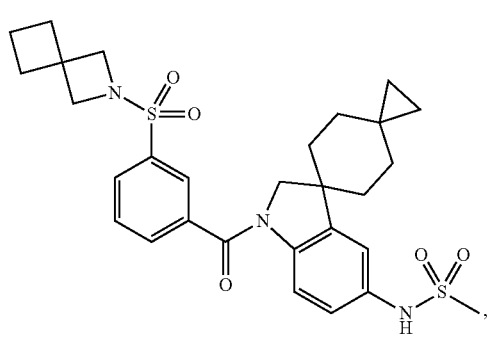
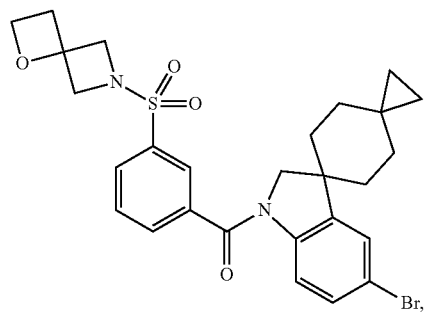
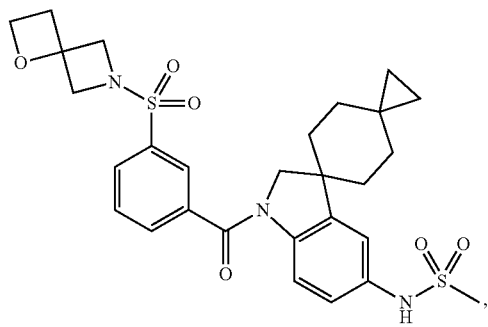
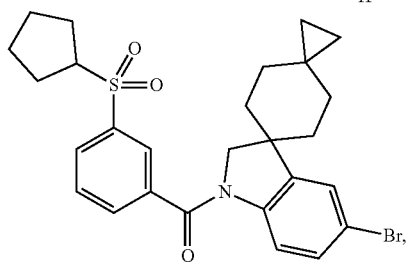
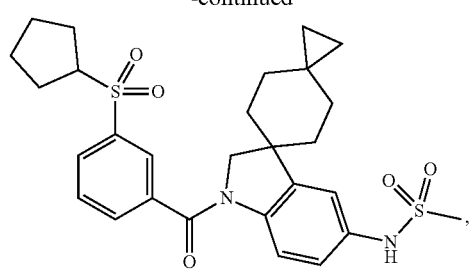
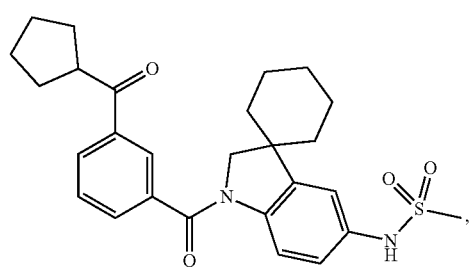
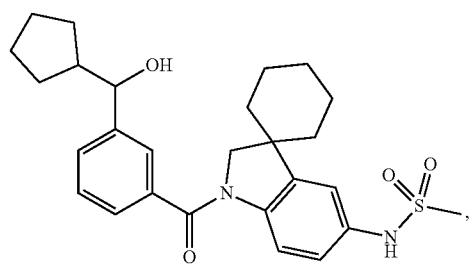
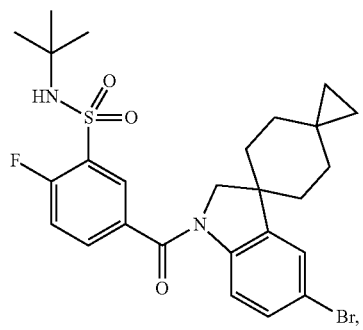
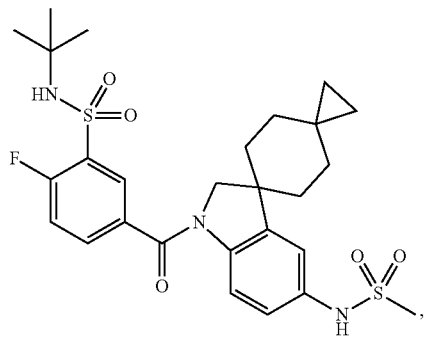

615
-continued
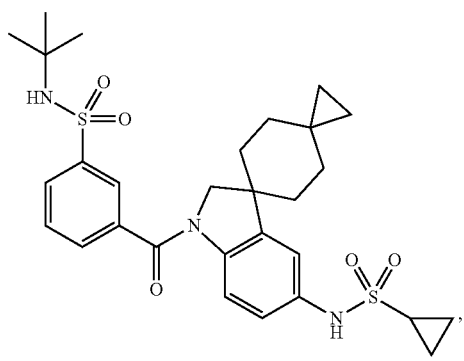
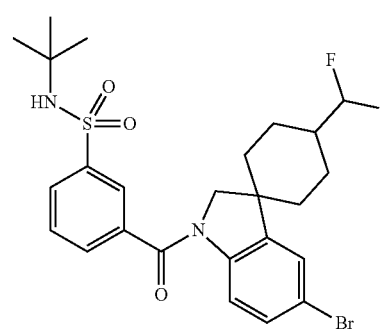
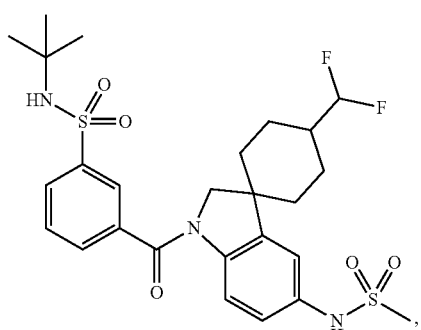
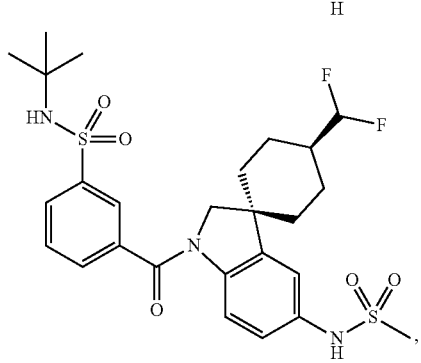
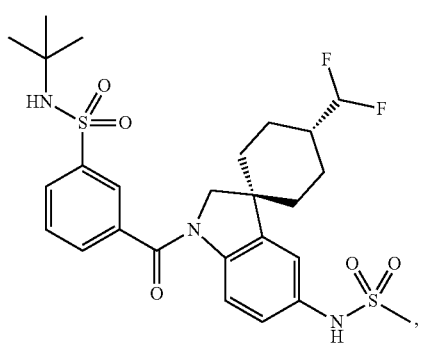
616
-continued
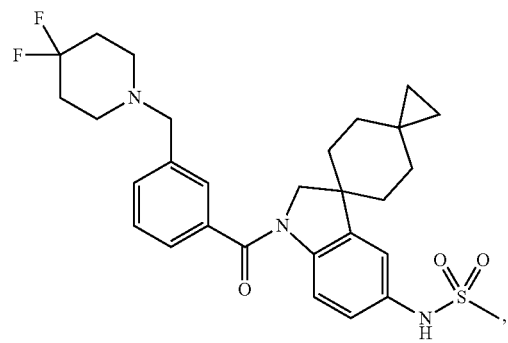
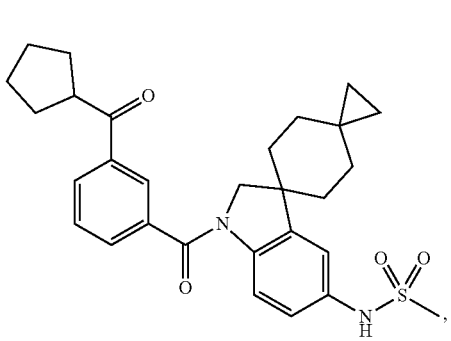
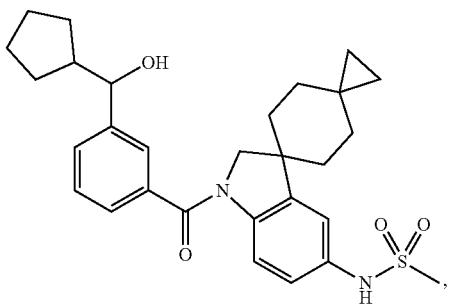
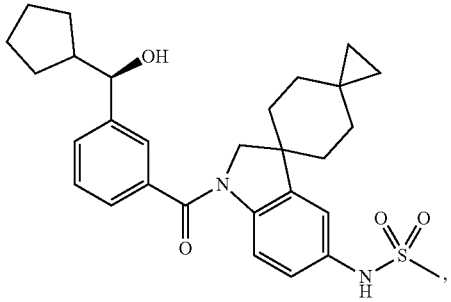
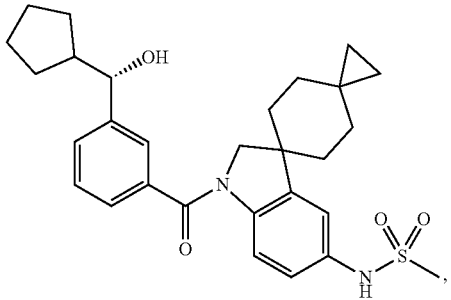

617
-continued
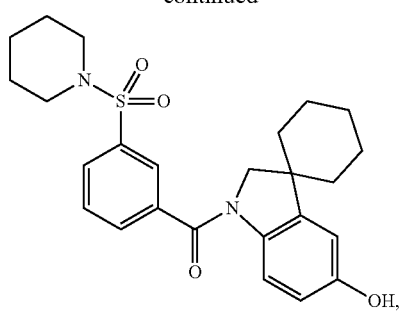
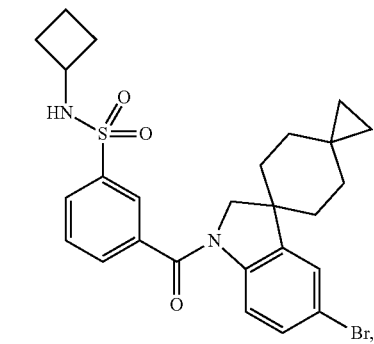
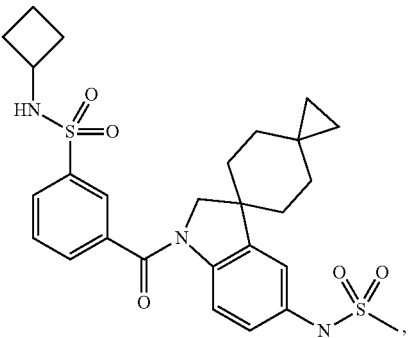
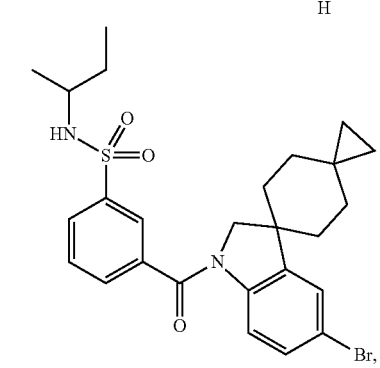
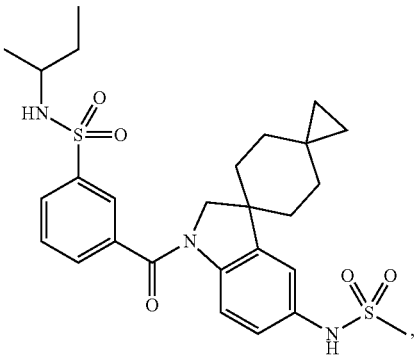
618
-continued
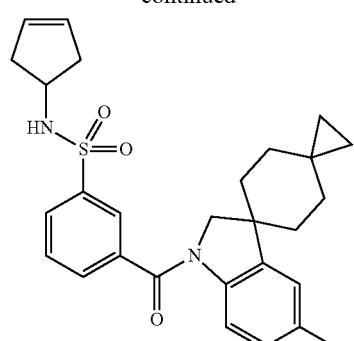
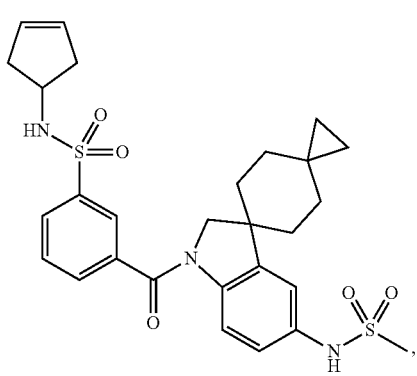
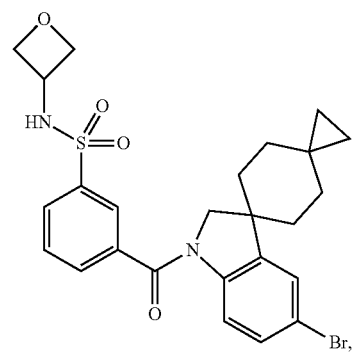
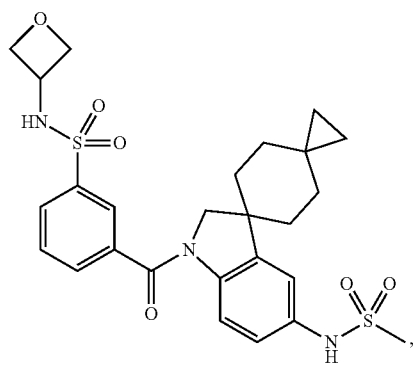

619
-continued
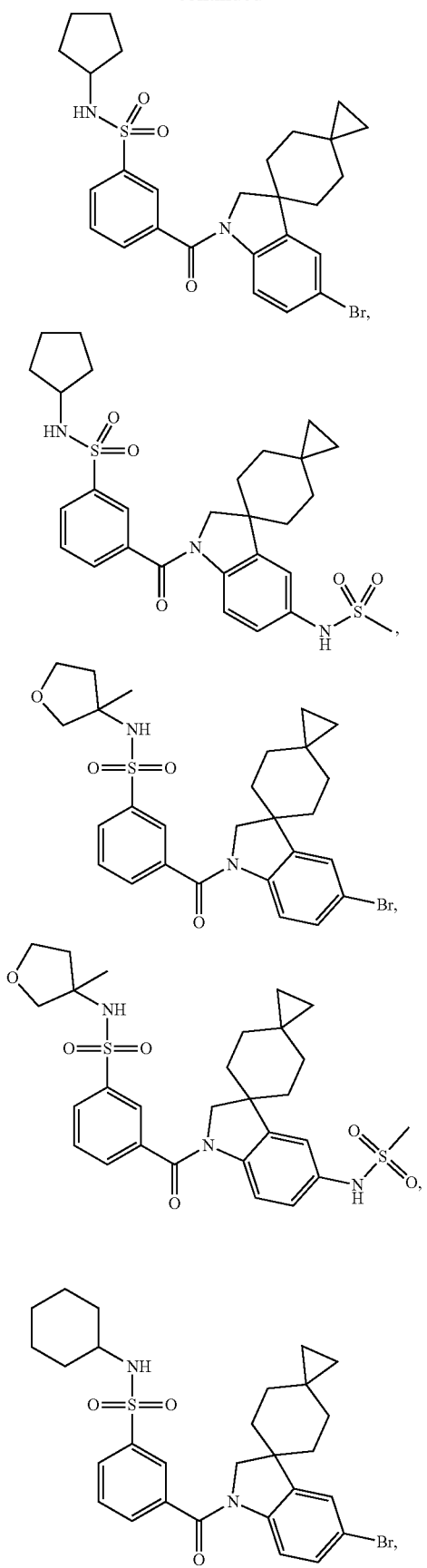
620
-continued
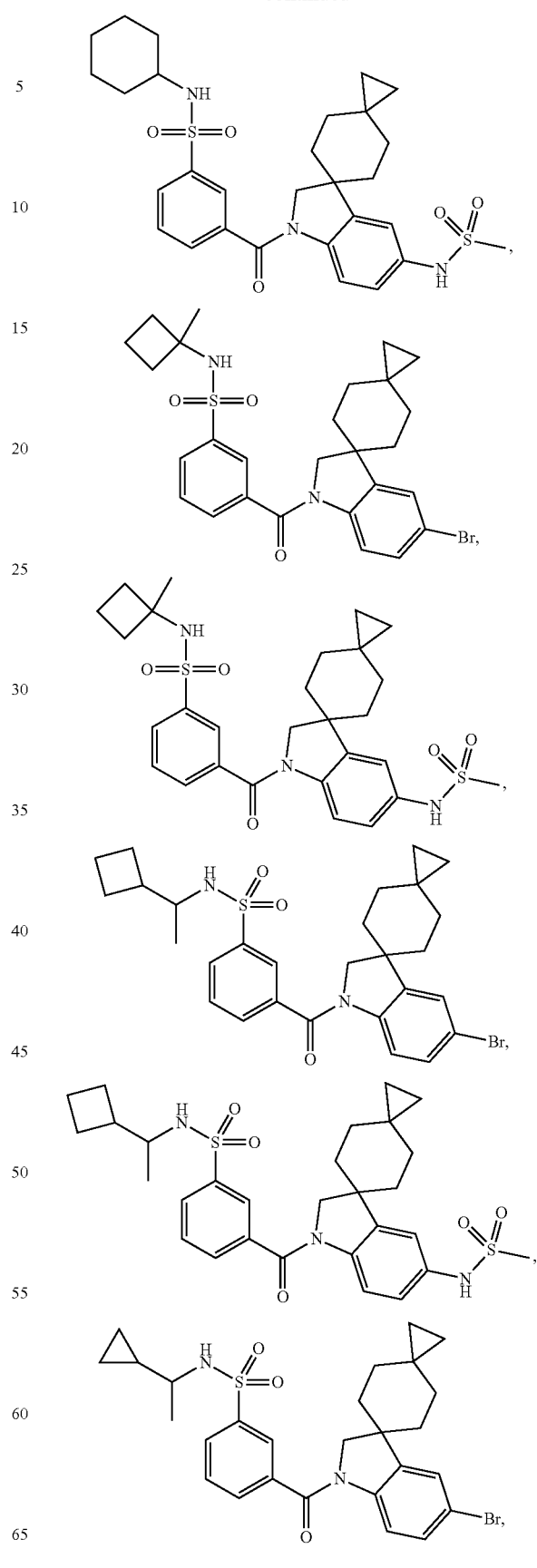

621
-continued
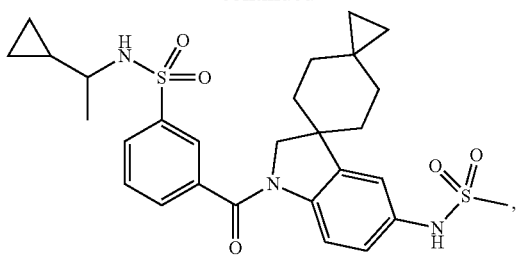
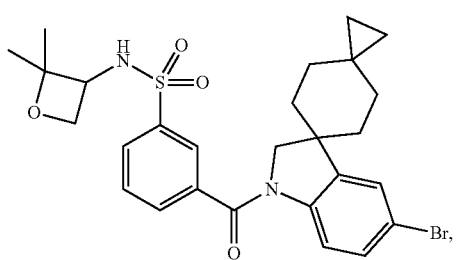
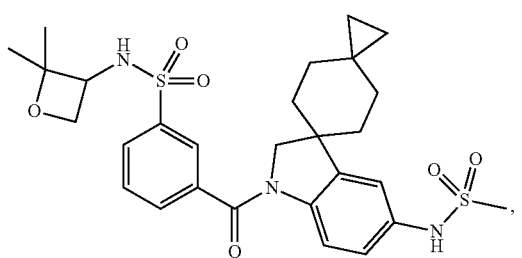
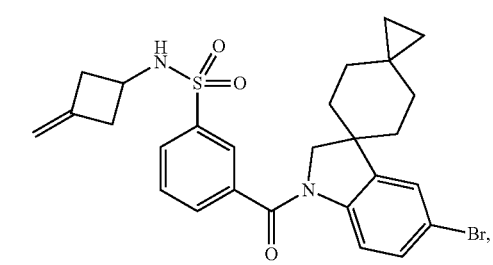
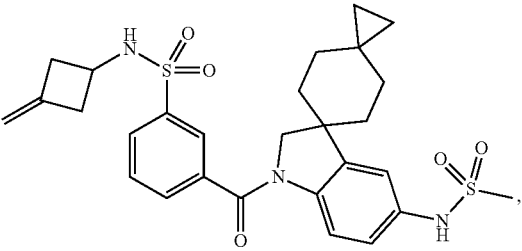
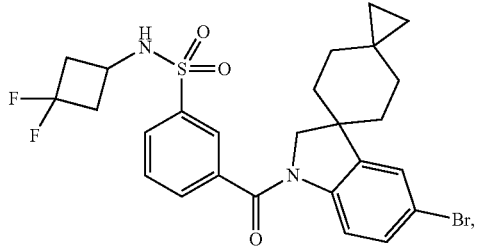
622
-continued
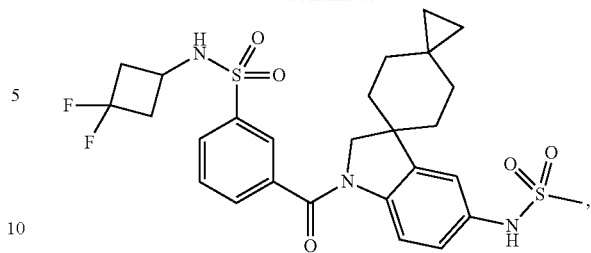
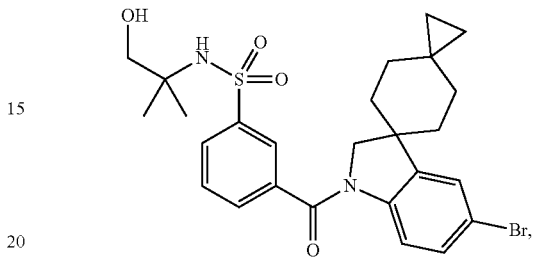
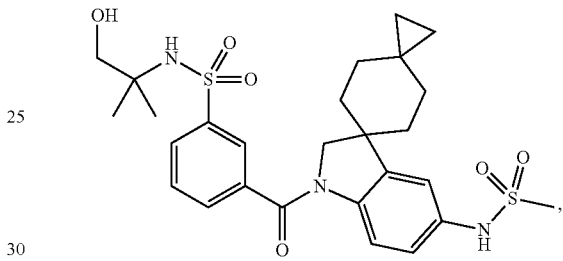
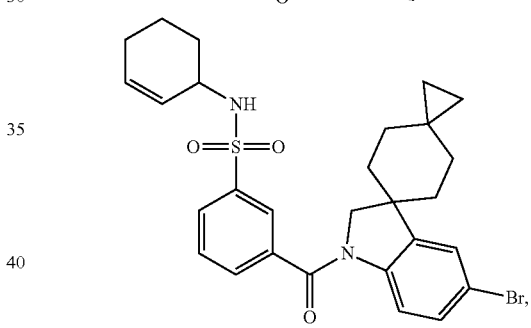
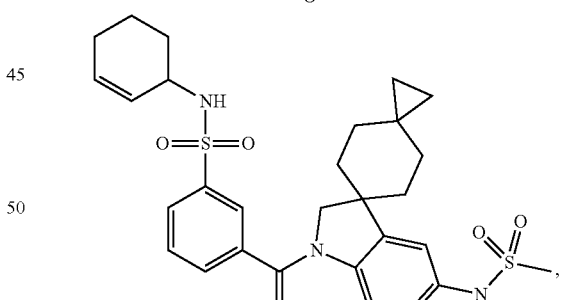
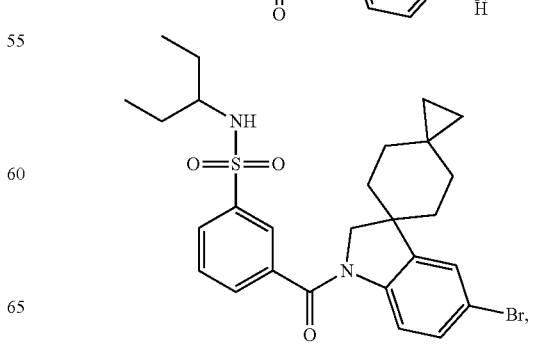

623
-continued
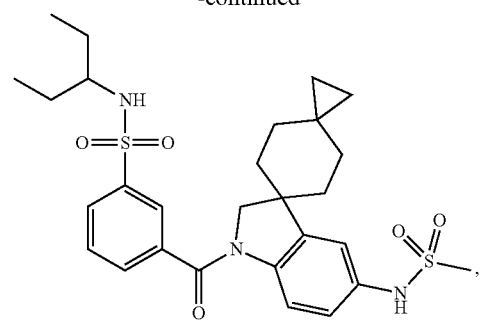
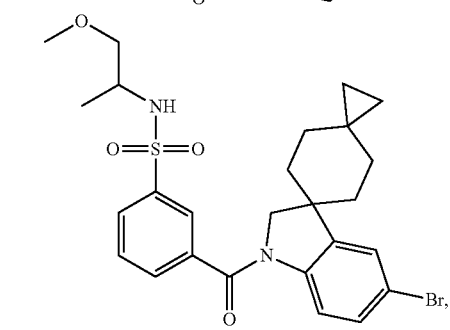
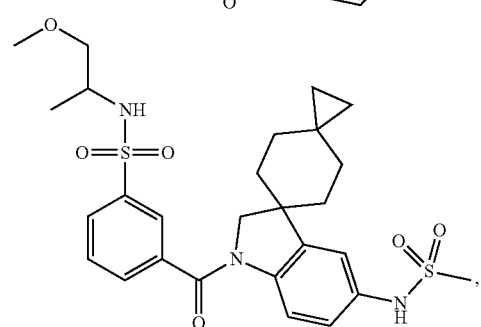
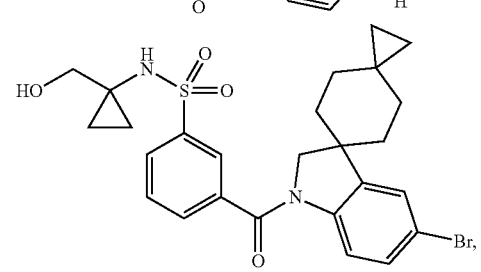
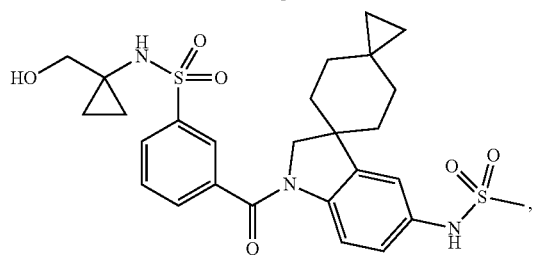
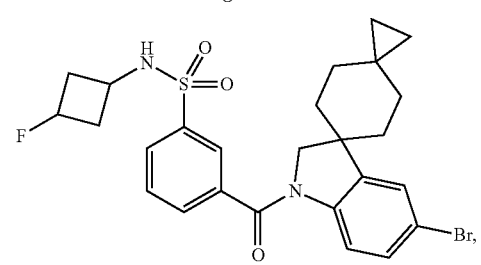
624
-continued
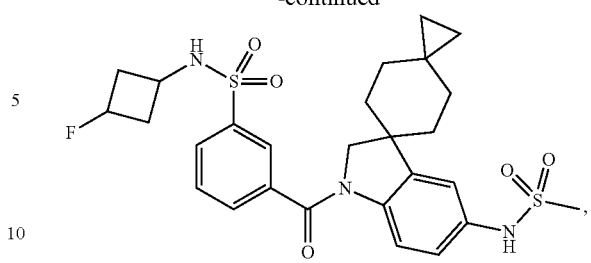
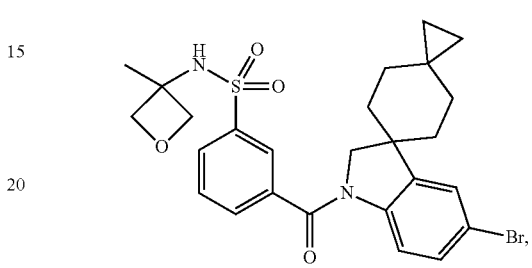
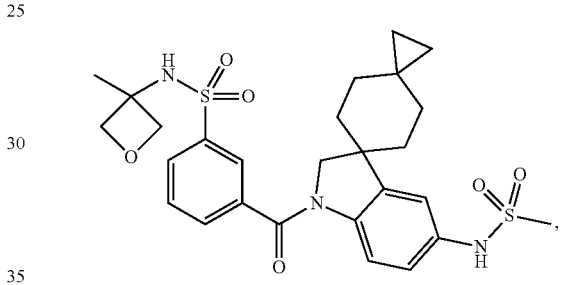
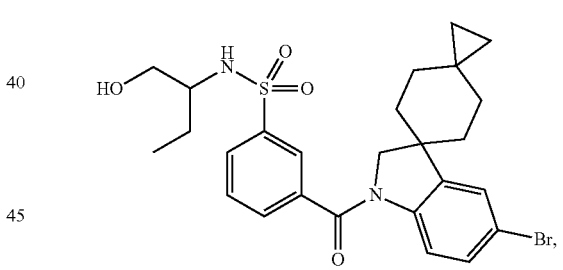
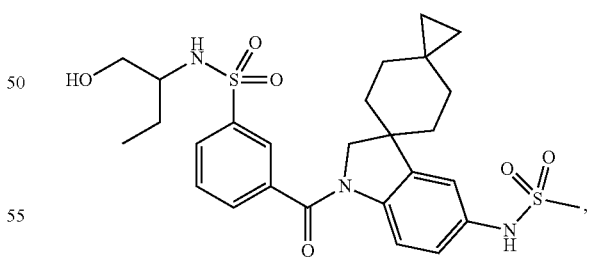
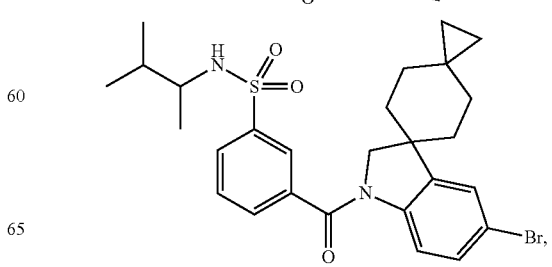

625
-continued
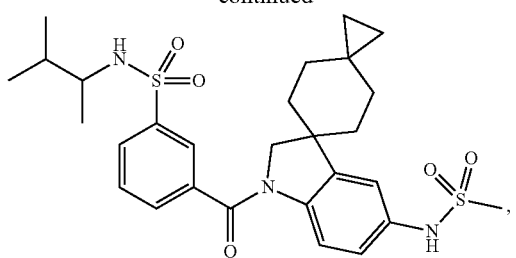
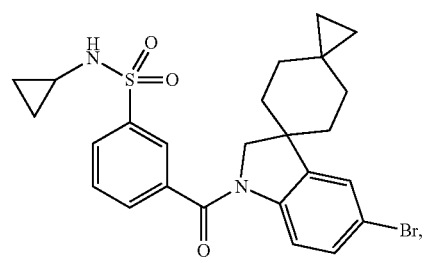
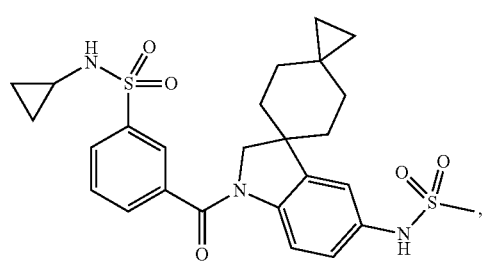
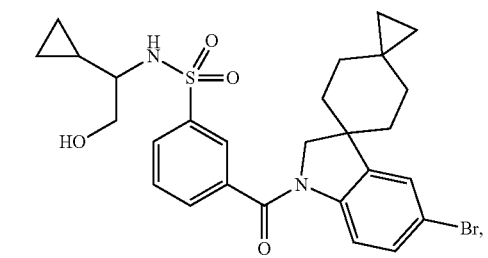
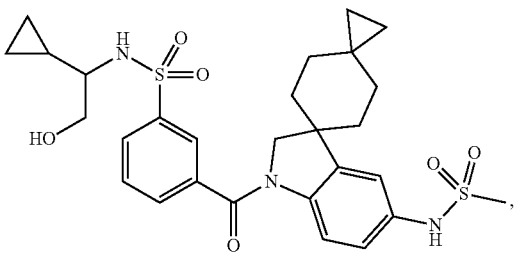
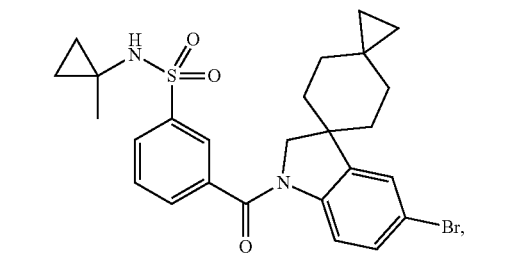
626
-continued
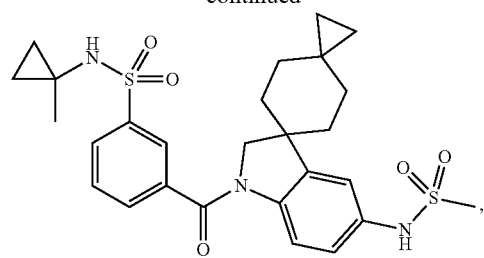
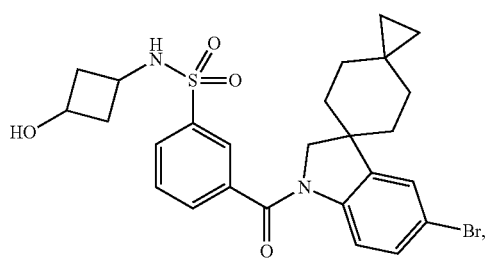
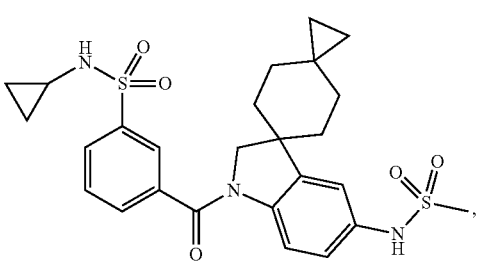
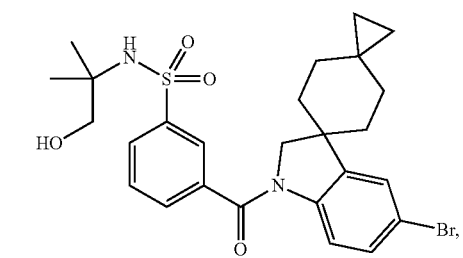
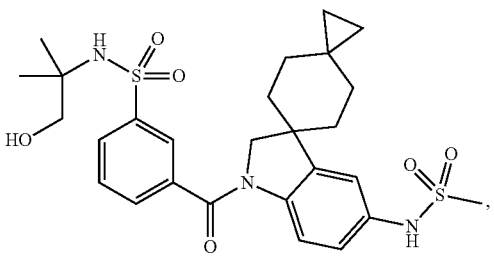
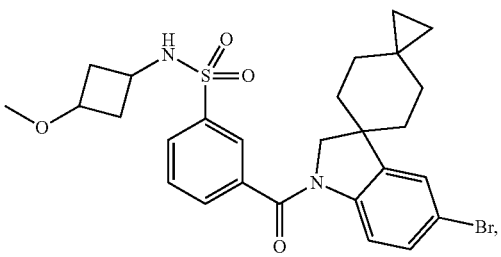

627
-continued
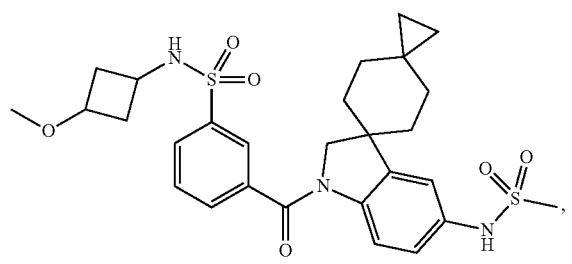
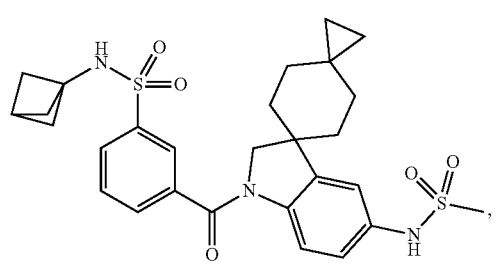
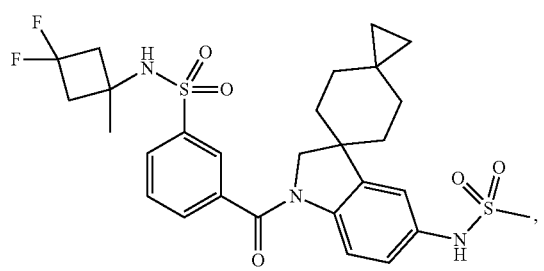
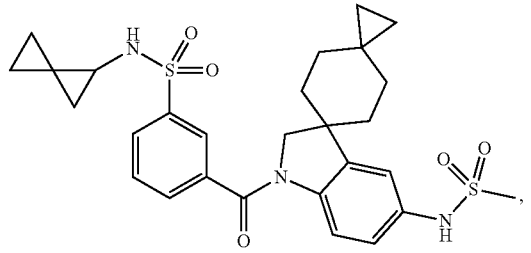
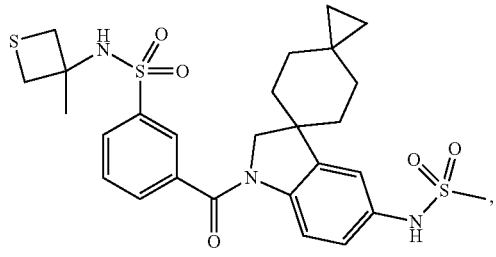
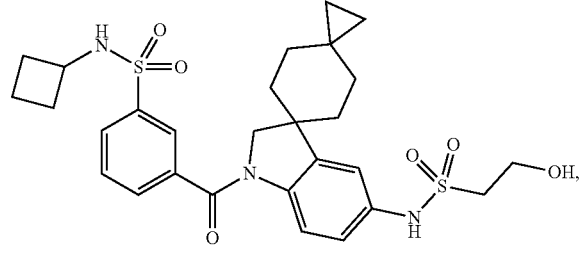
628
-continued
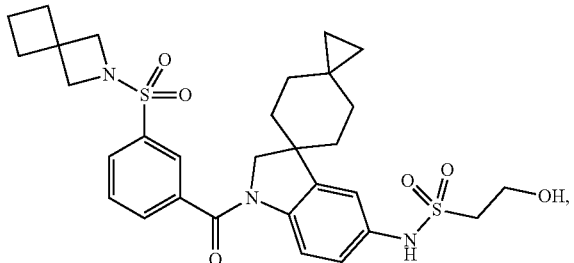
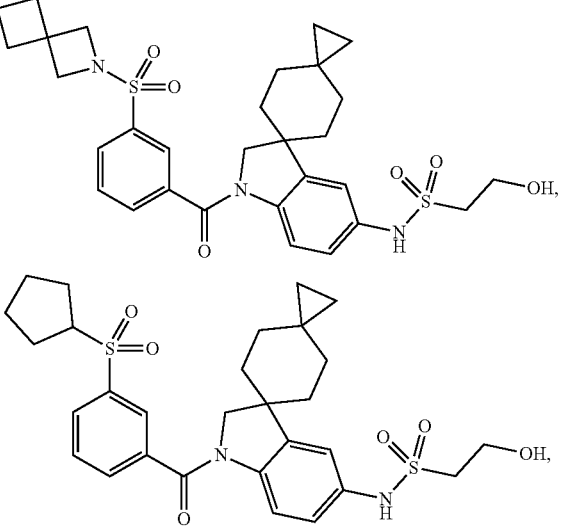
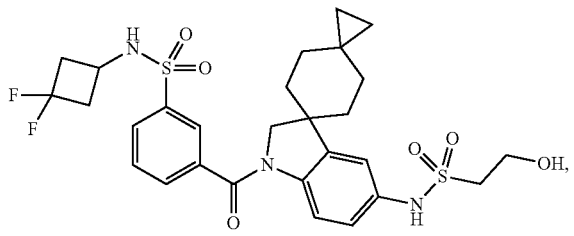
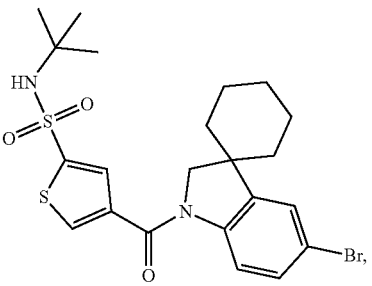
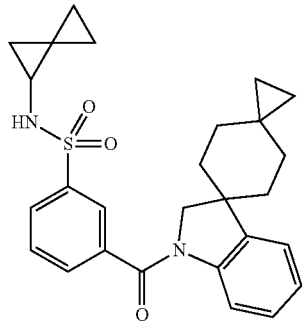
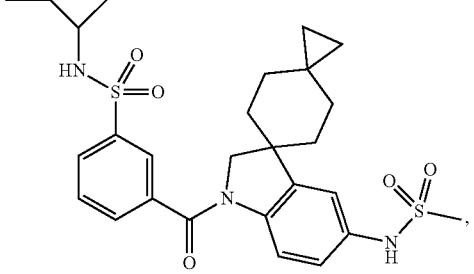

629
-continued
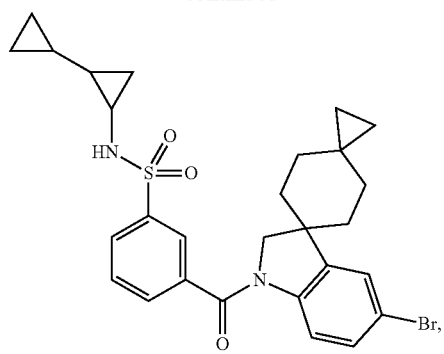
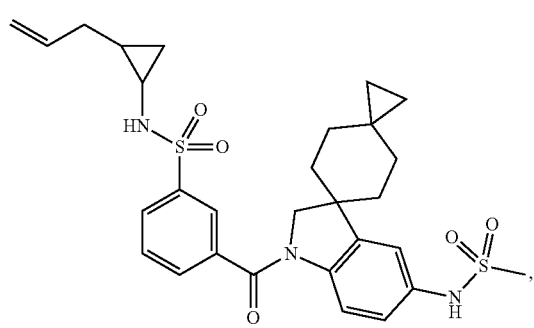
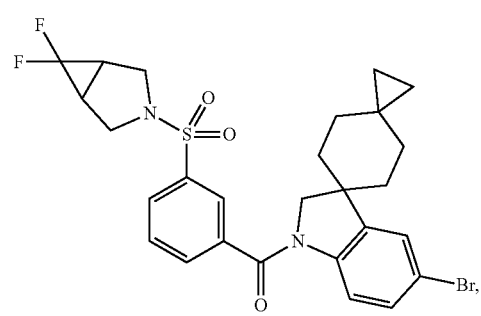
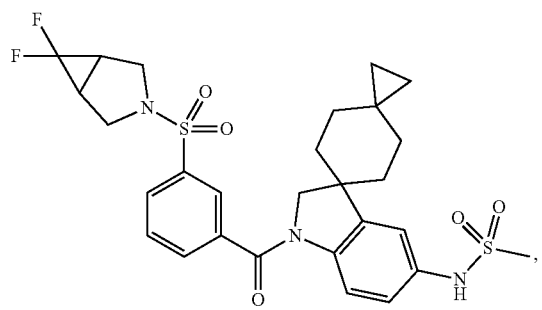
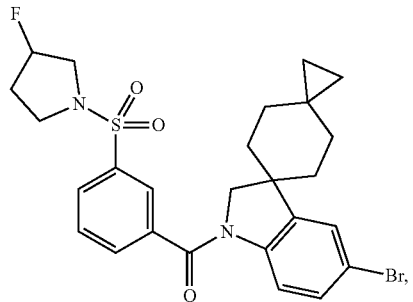
630
-continued
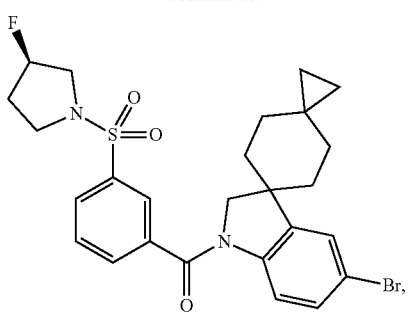
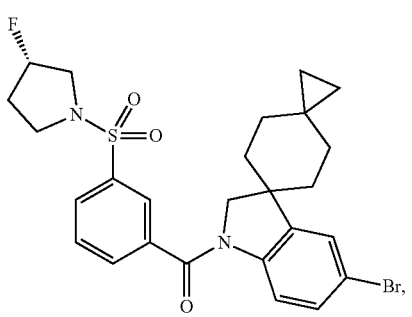
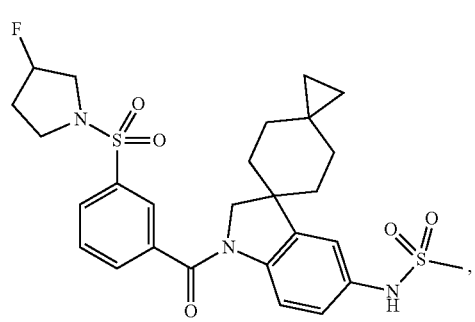
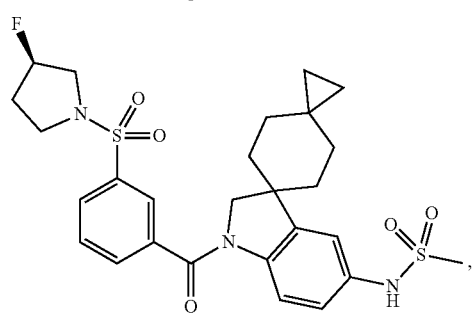
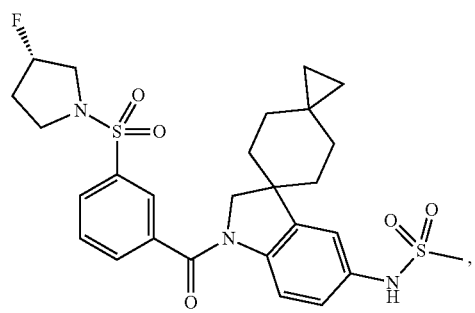

631
-continued
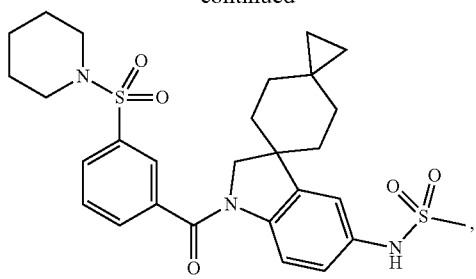
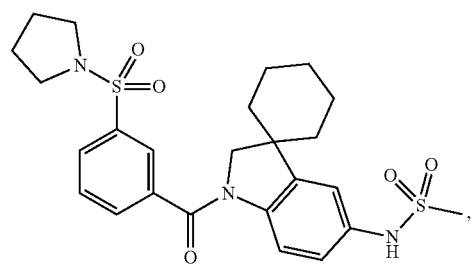
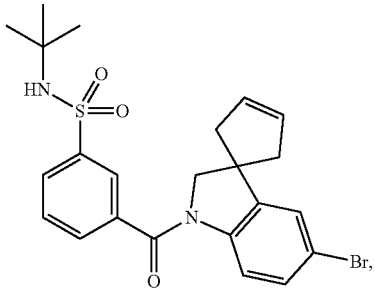
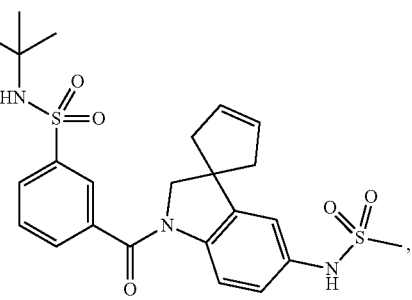
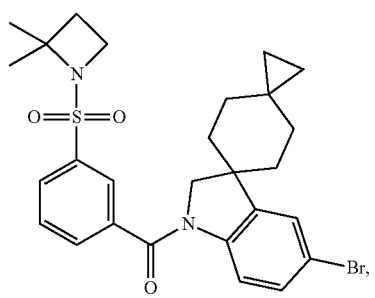
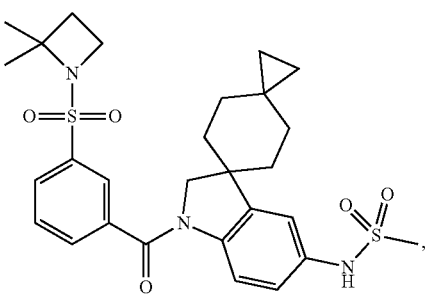
632
-continued
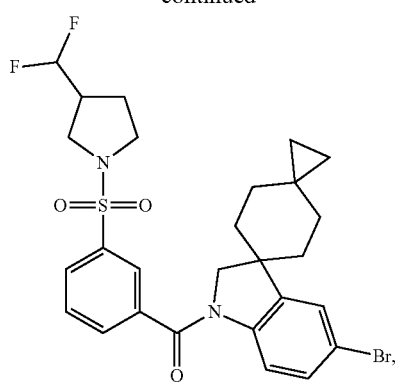
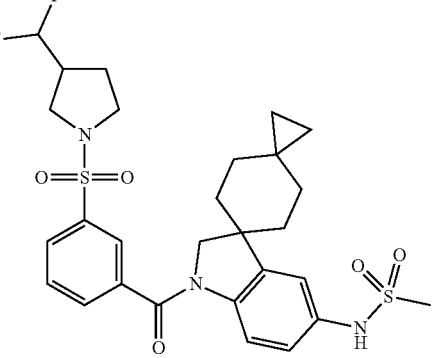
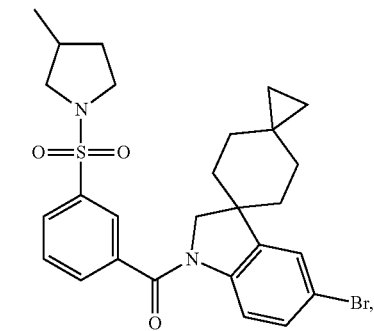
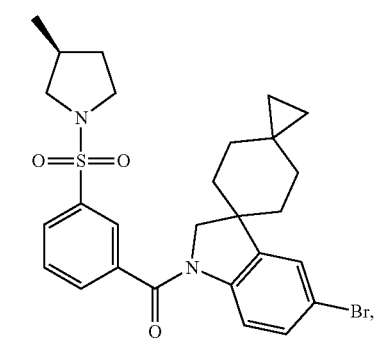

633
-continued
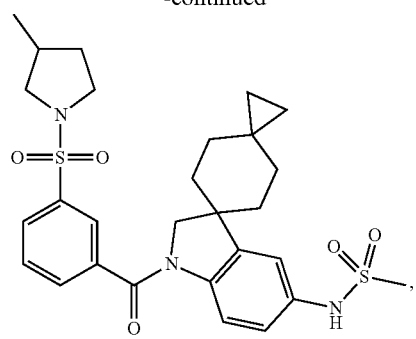
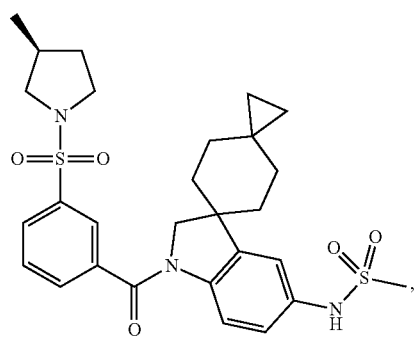
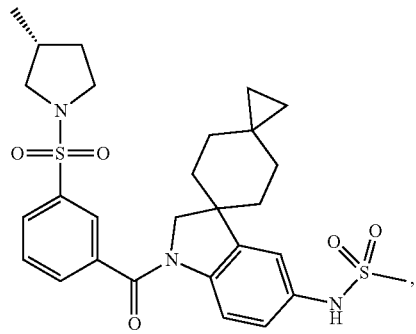
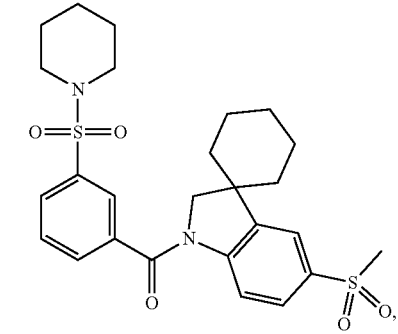
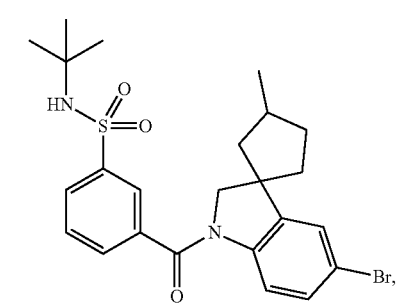
634
-continued
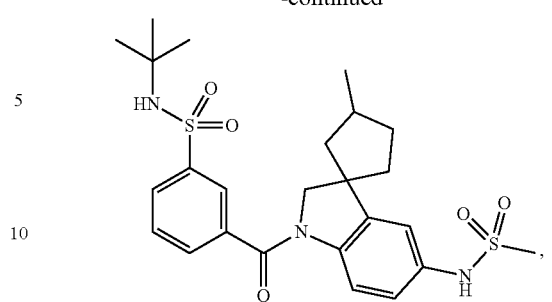
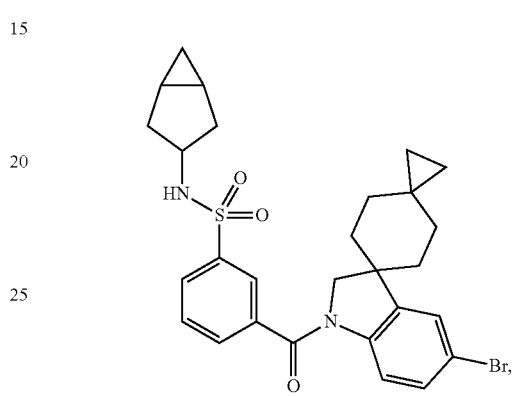
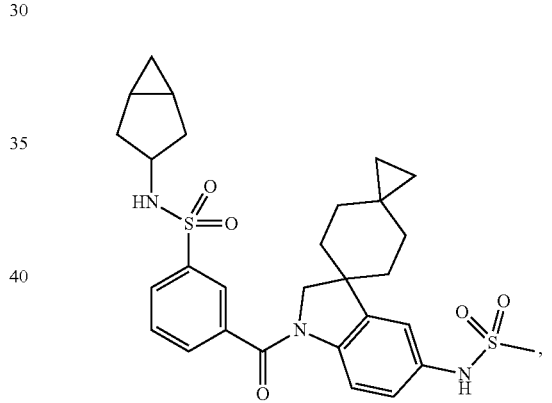
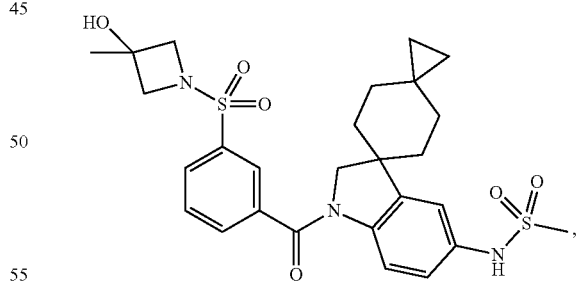
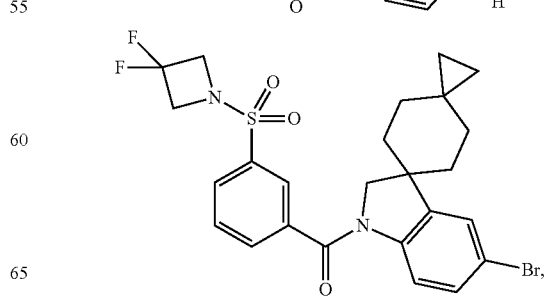

635
-continued
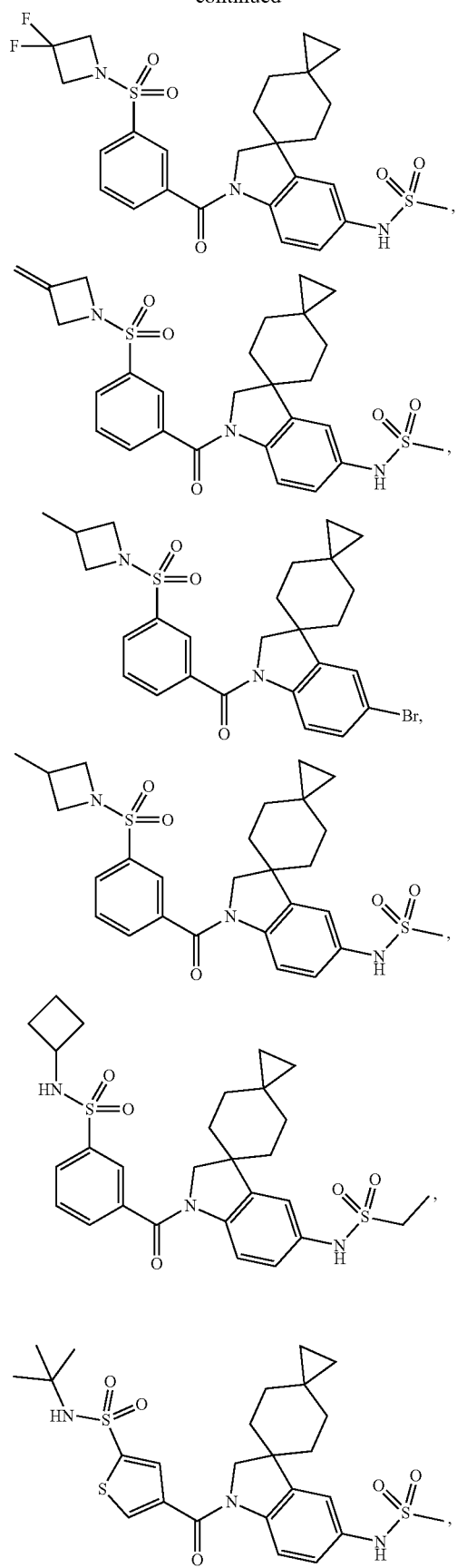
636
-continued
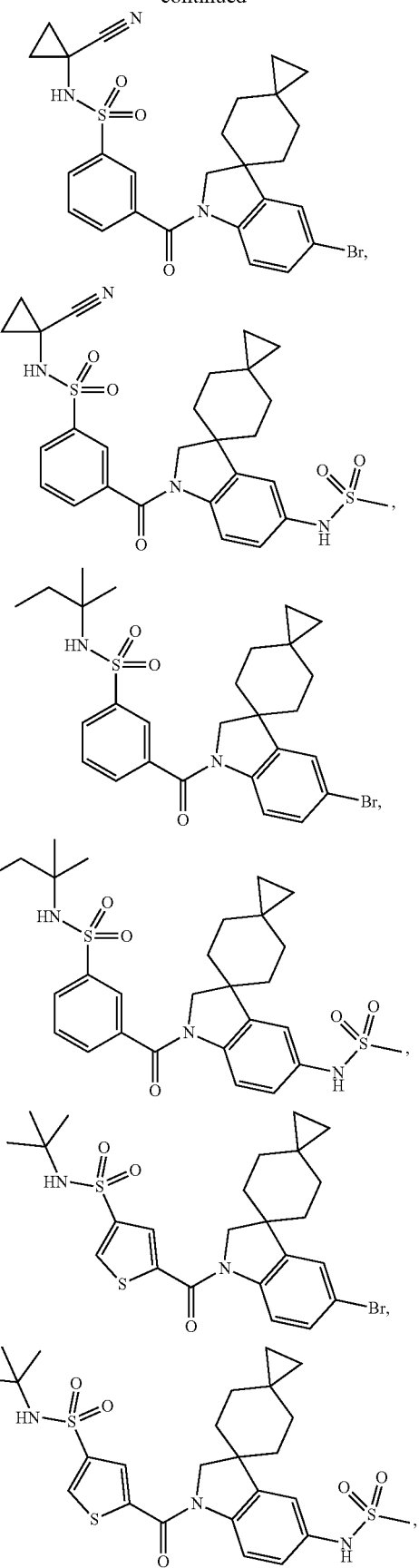

637
-continued
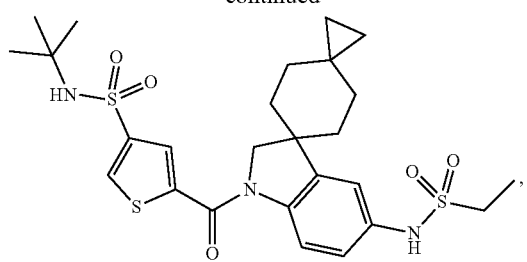
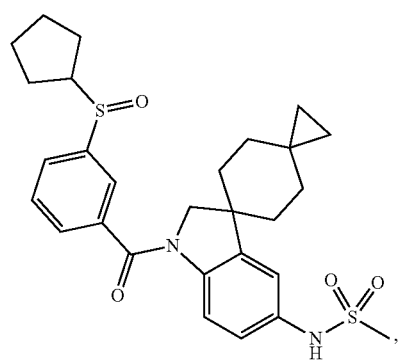
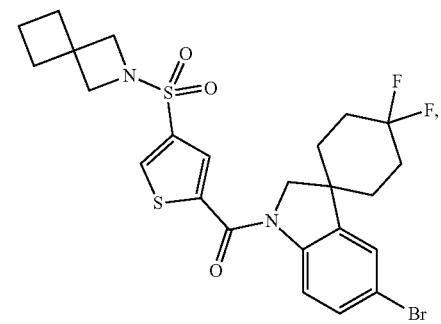
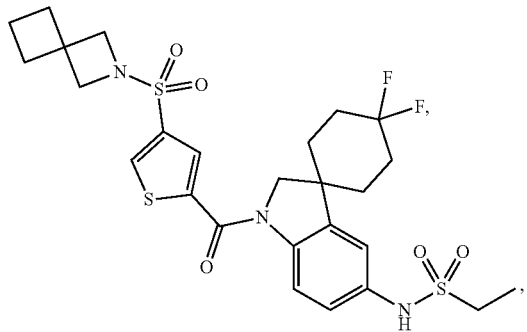
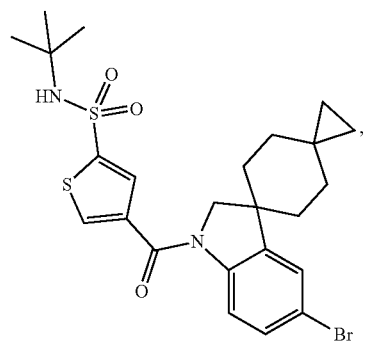
638
-continued
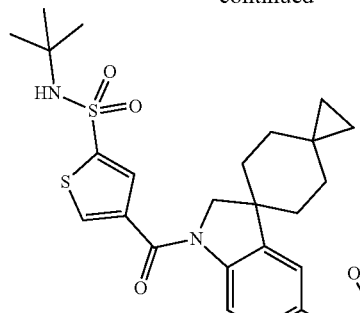
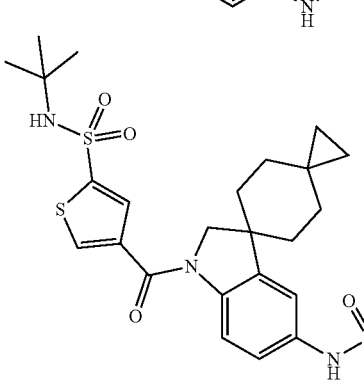
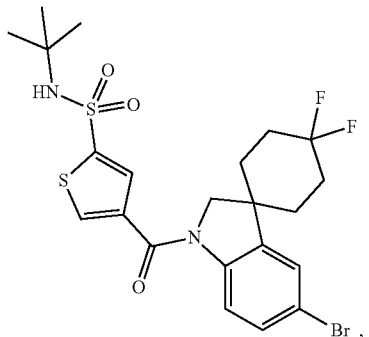
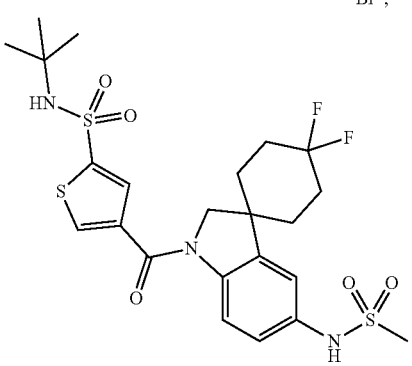
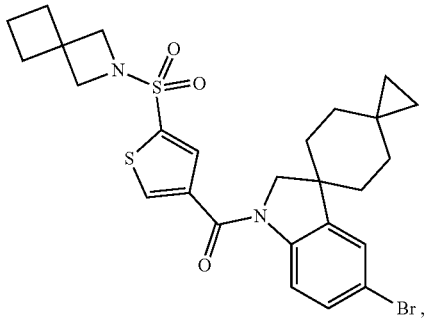

639
-continued
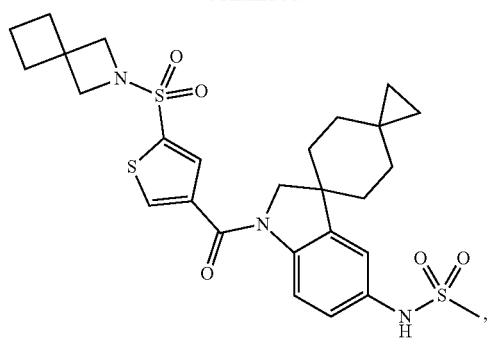
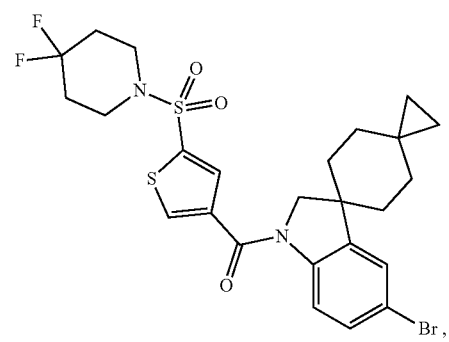
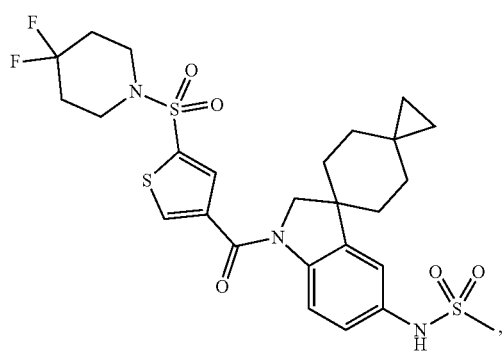
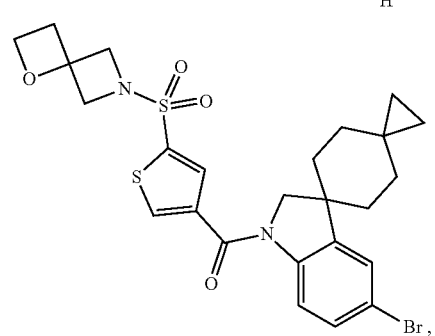
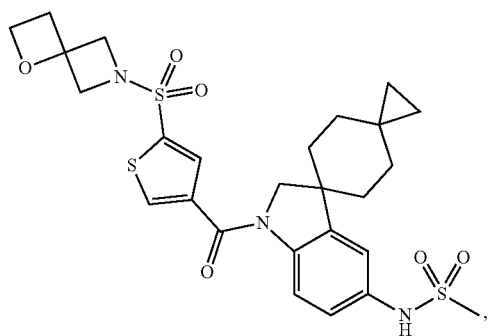
640
-continued
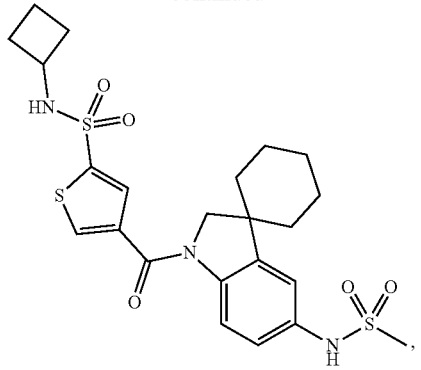
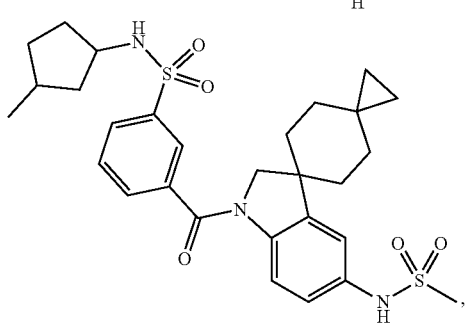
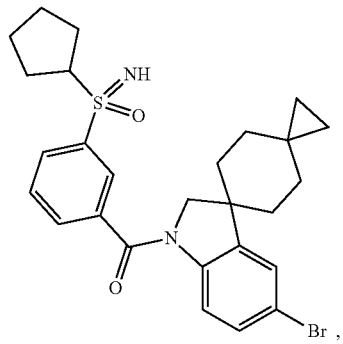
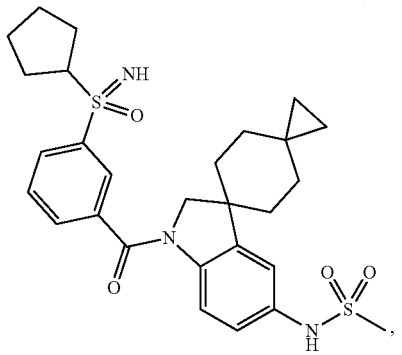
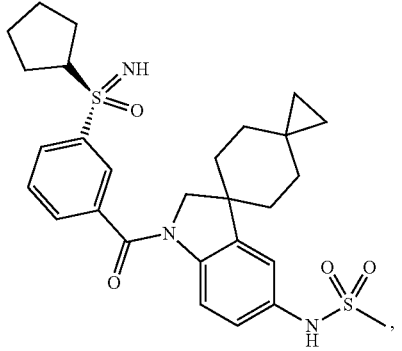

641
-continued
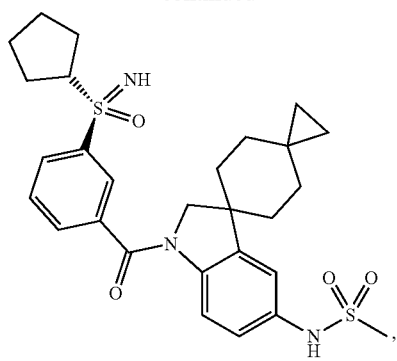
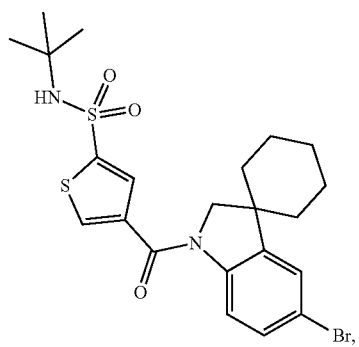
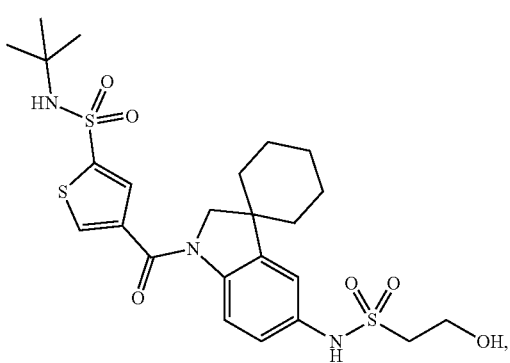
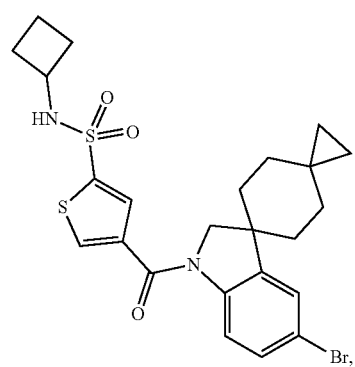
642
-continued
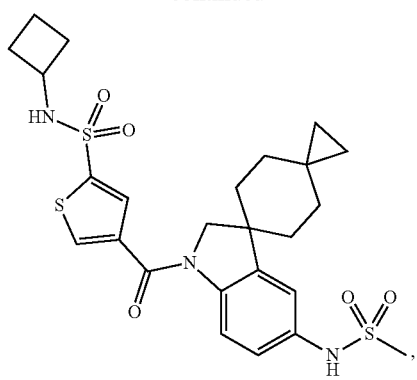
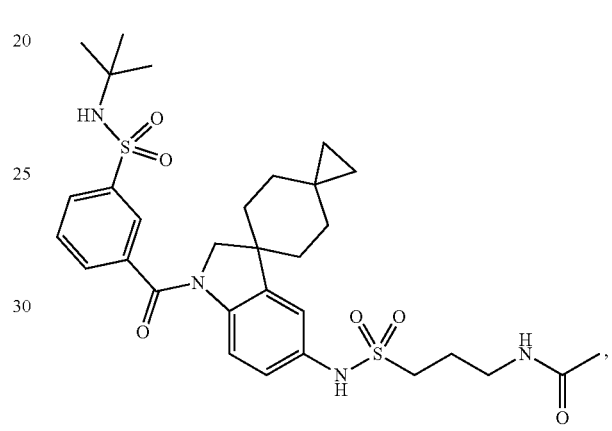
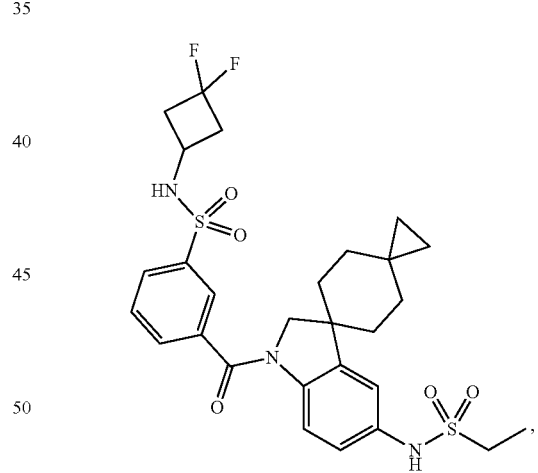

643
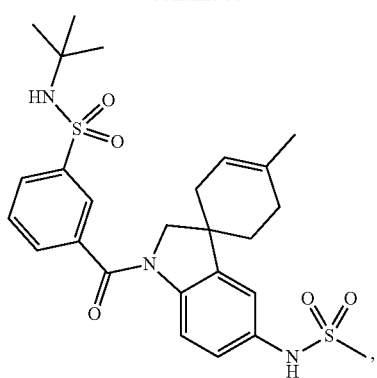
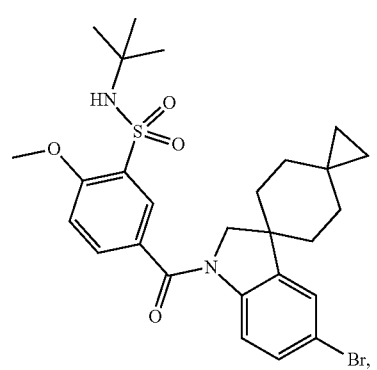
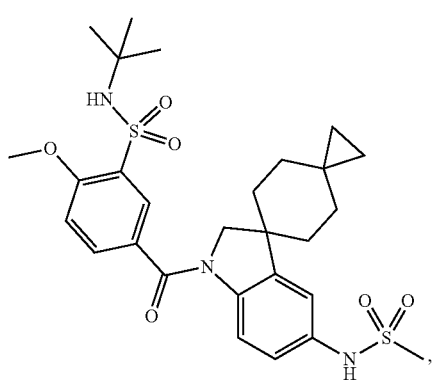
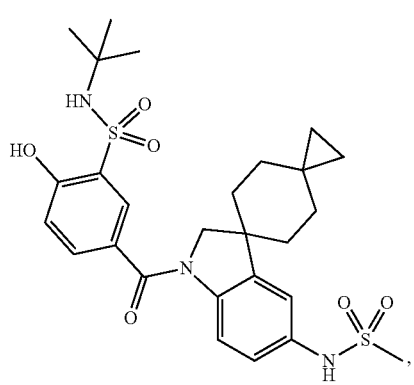
644
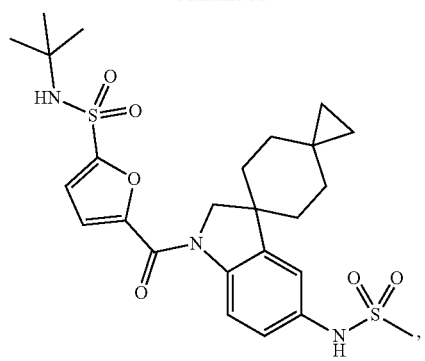
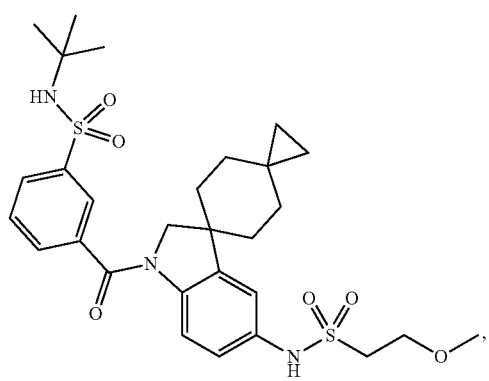
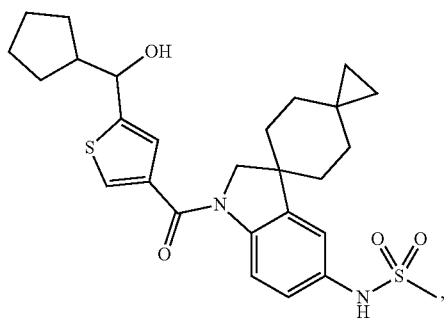
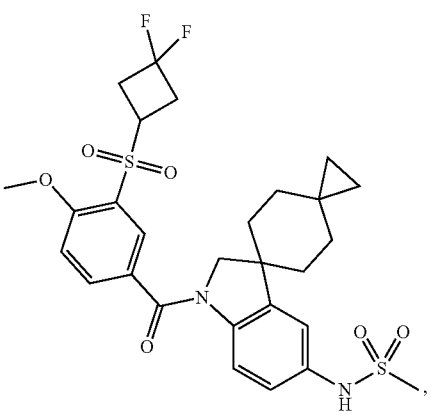

645
-continued
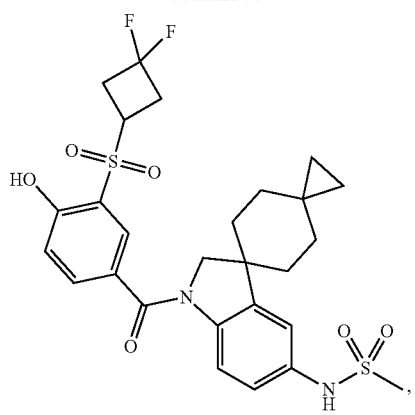
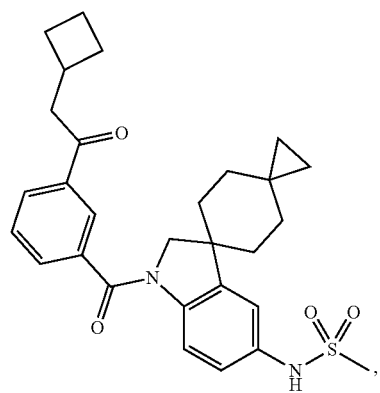
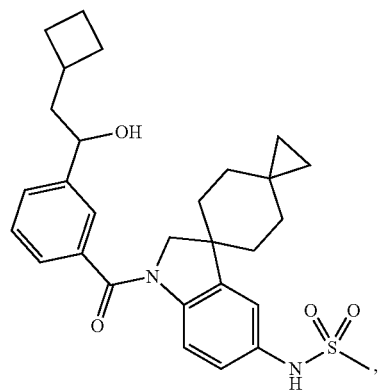
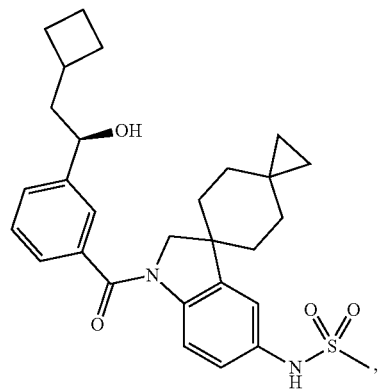
646
-continued
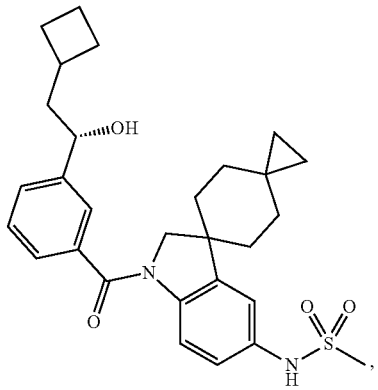
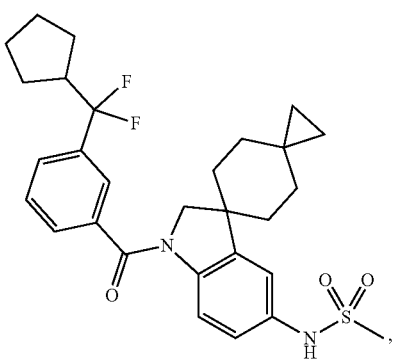
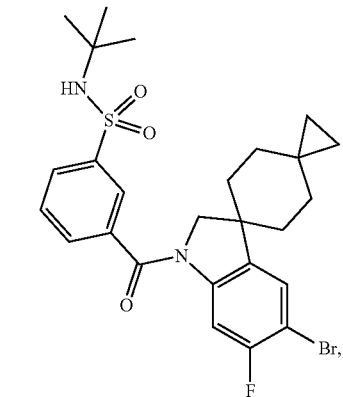
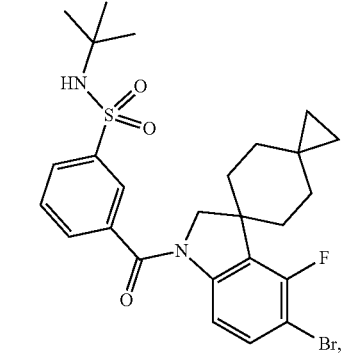

-continued
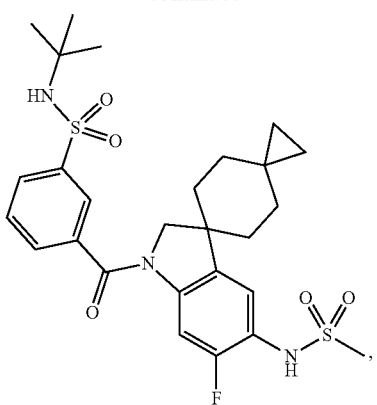
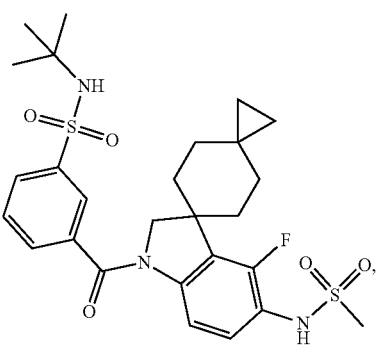
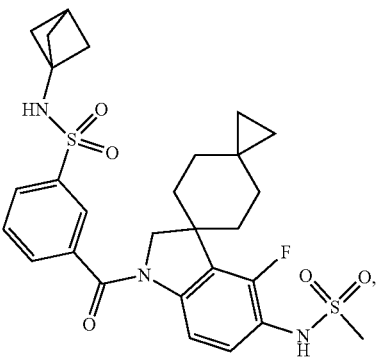
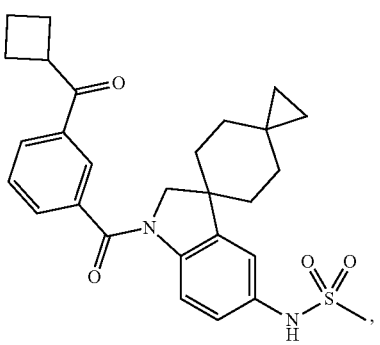
-continued
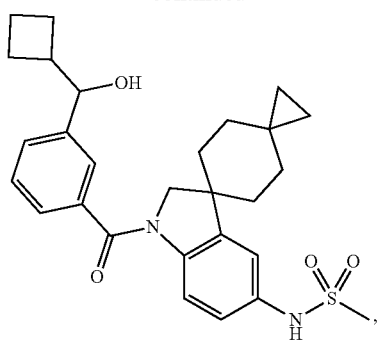
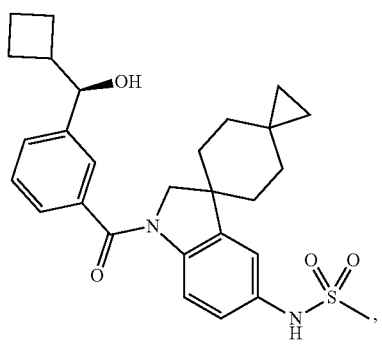
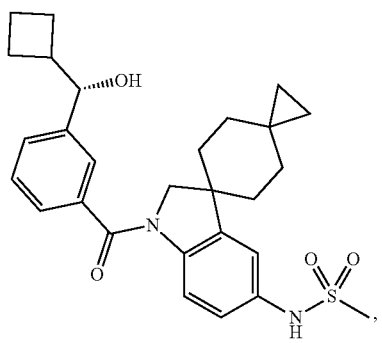
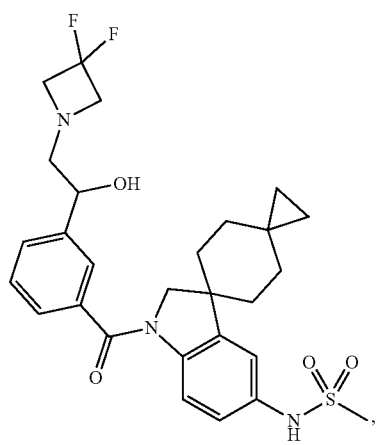

649
-continued
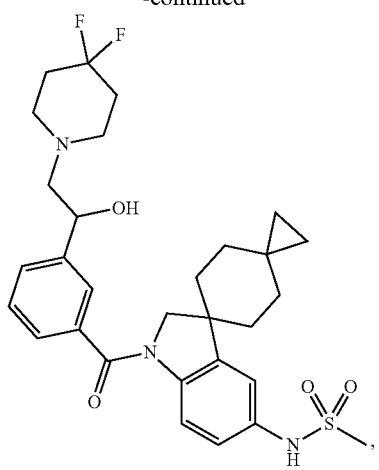
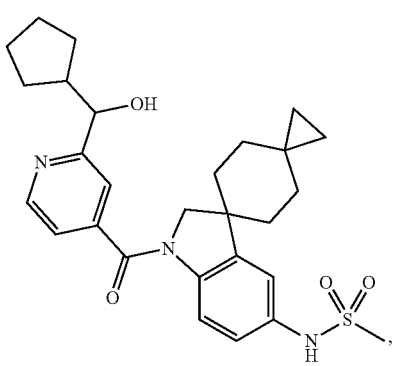
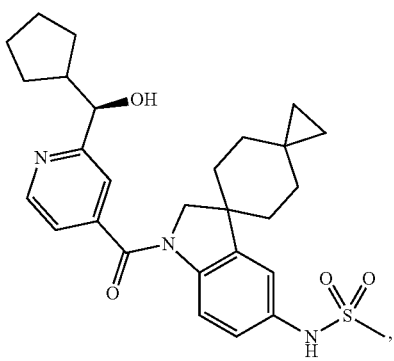
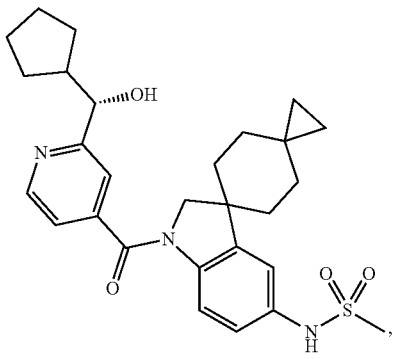
650
-continued
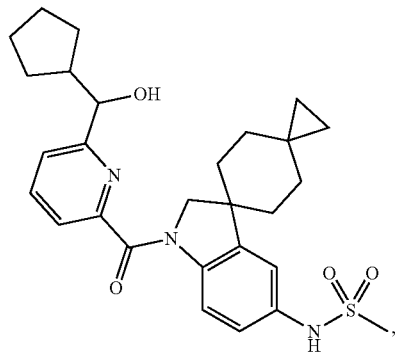
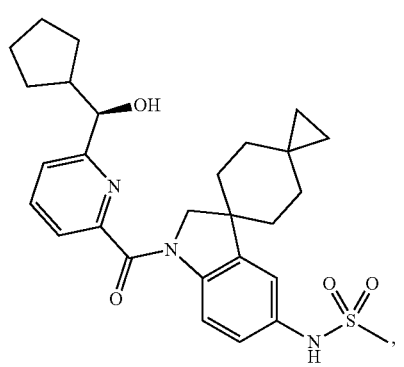
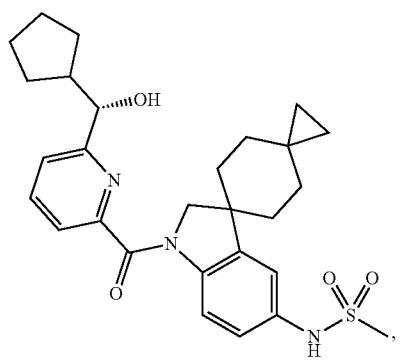
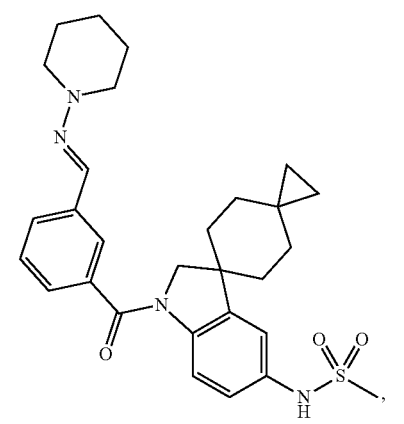

651
-continued
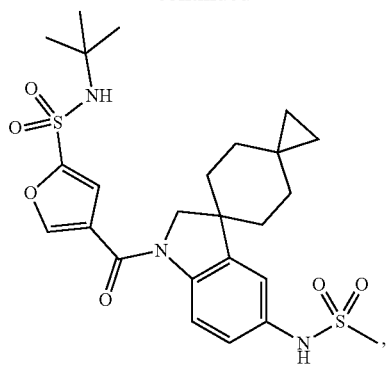
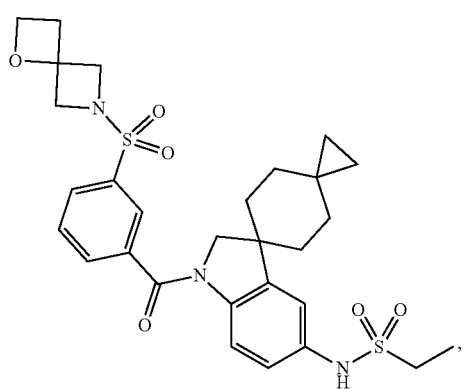
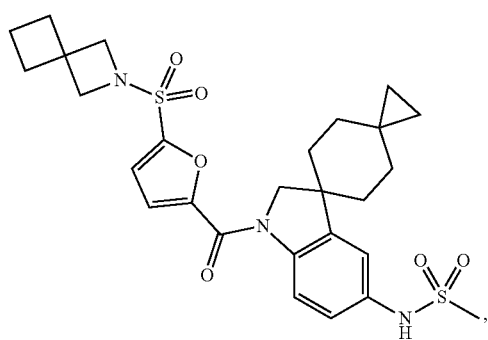
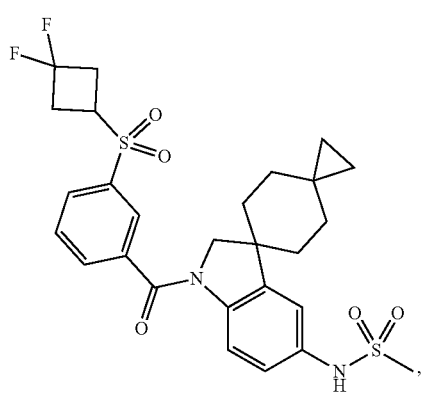
652
-continued
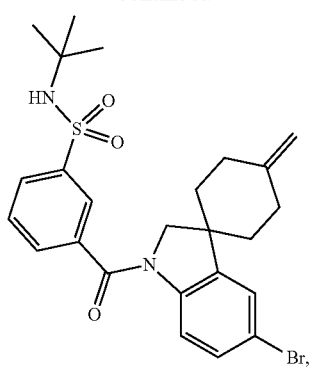
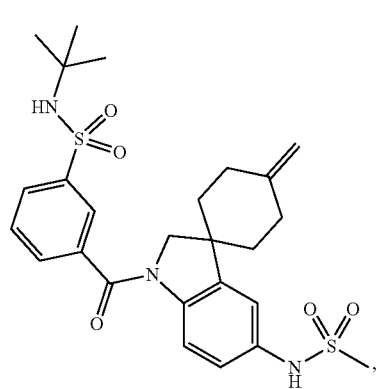
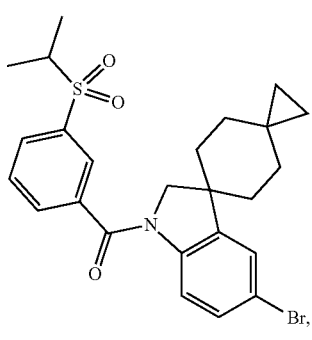
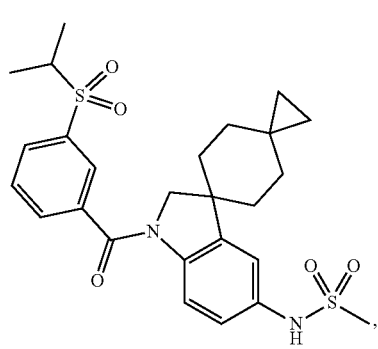

653
-continued
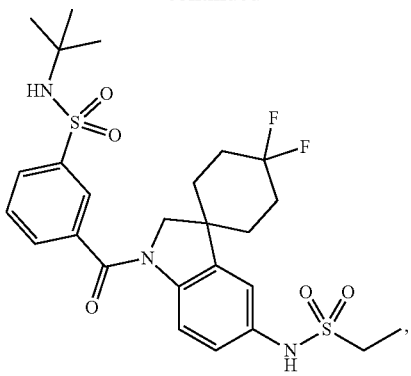
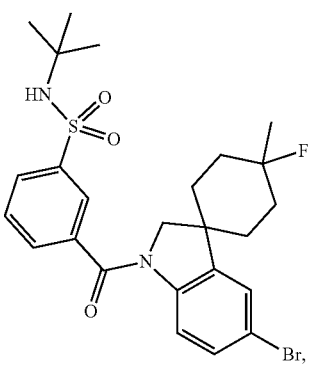
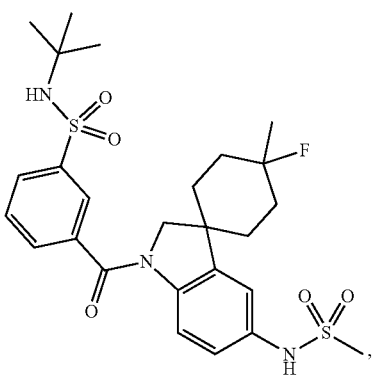
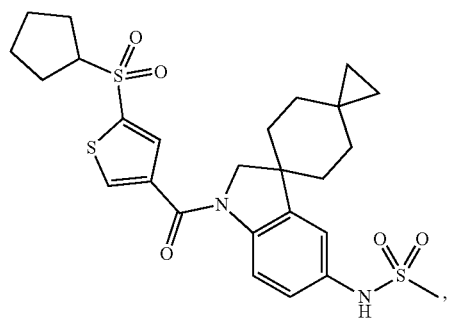
654
-continued
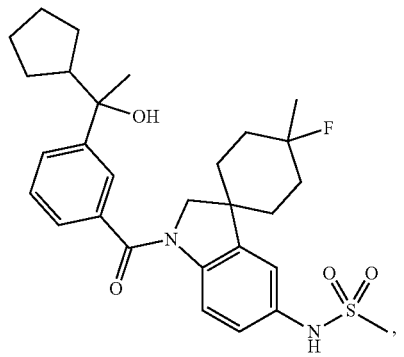
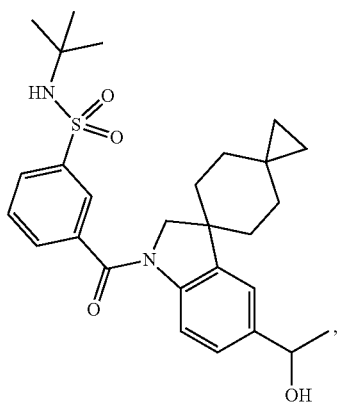
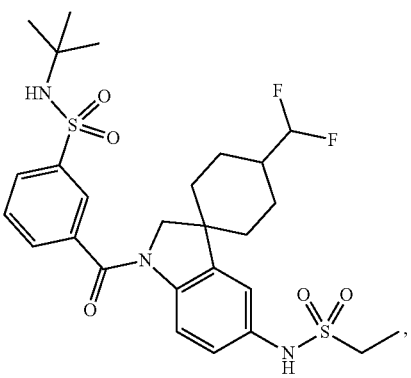
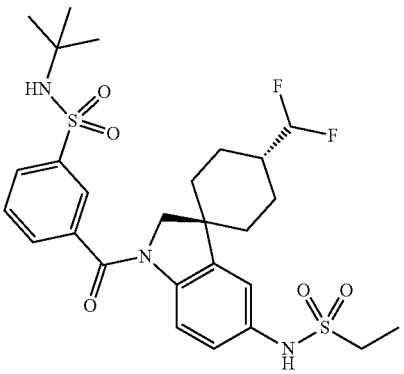

655
-continued
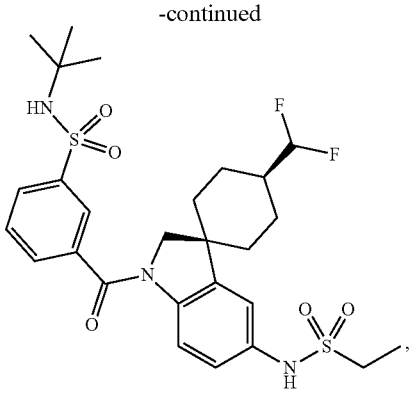
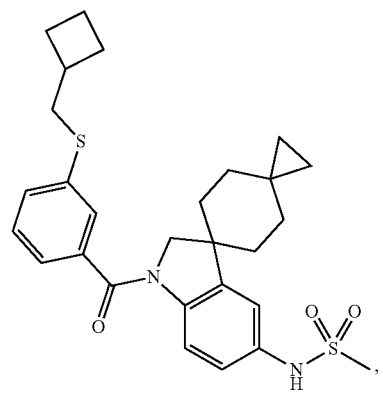
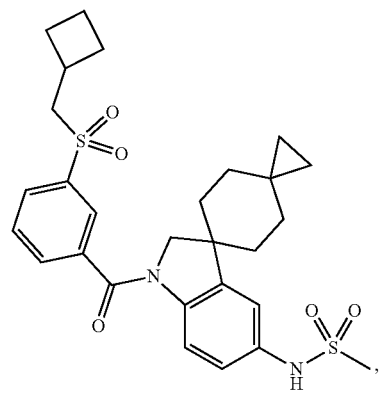
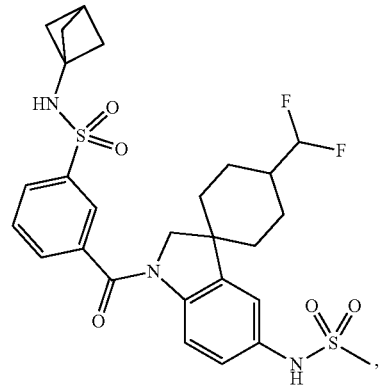
656
-continued
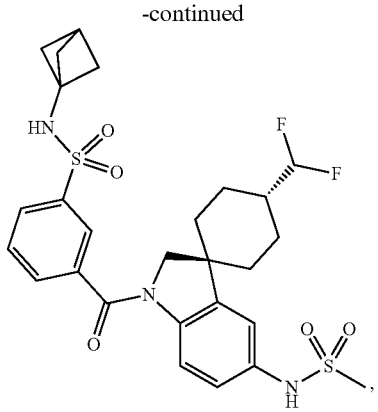
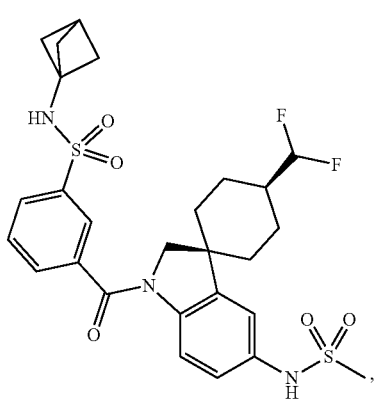
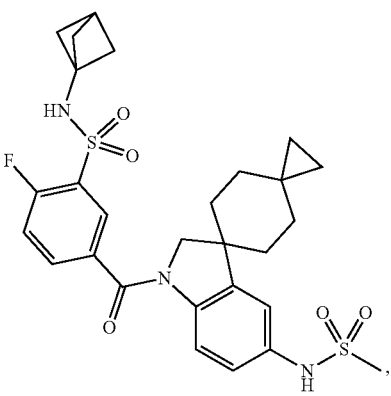
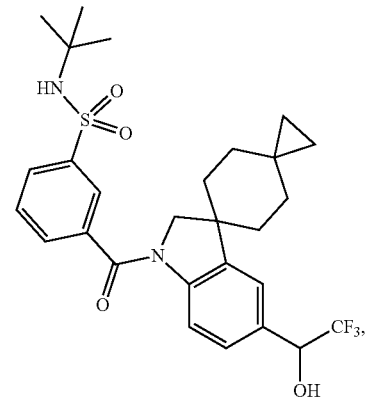

657
-continued
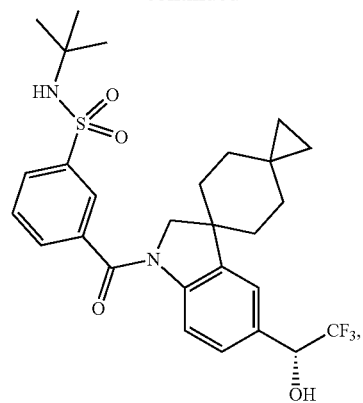
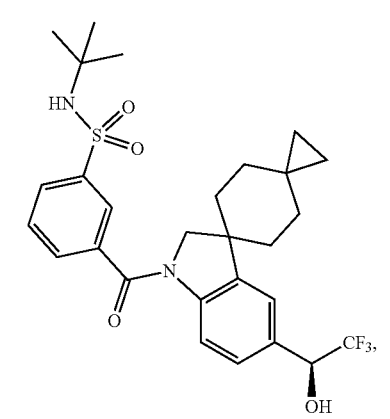
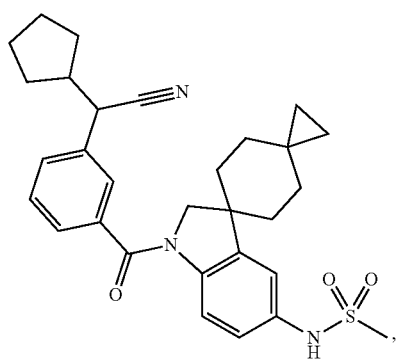
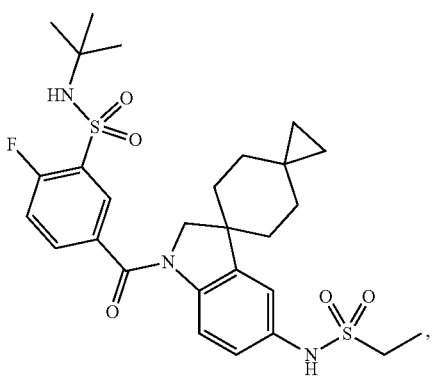
658
-continued
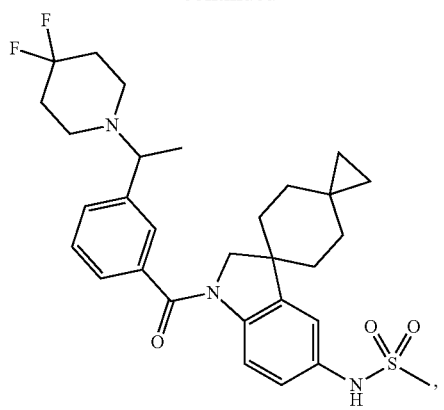
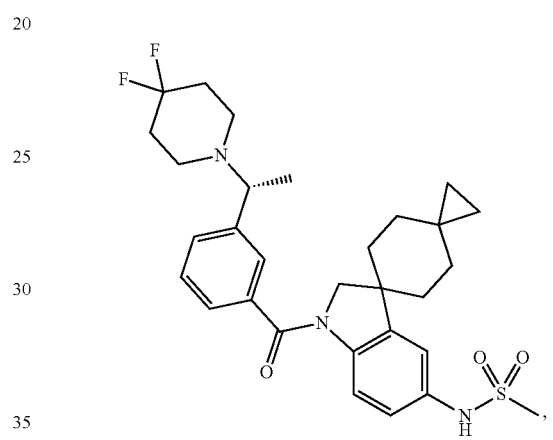
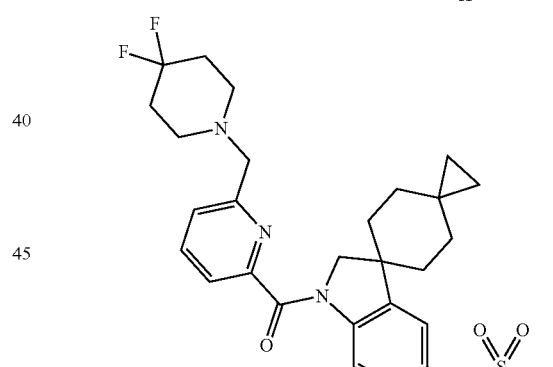
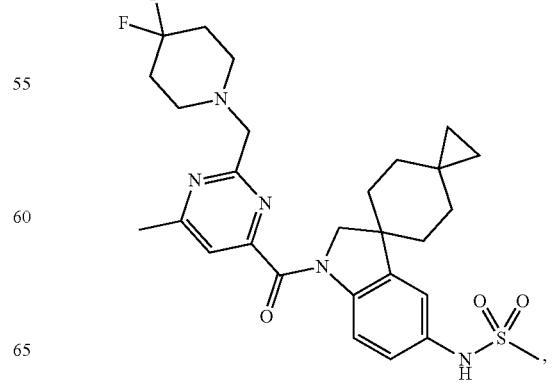

659
-continued
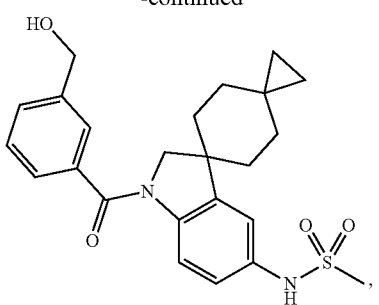
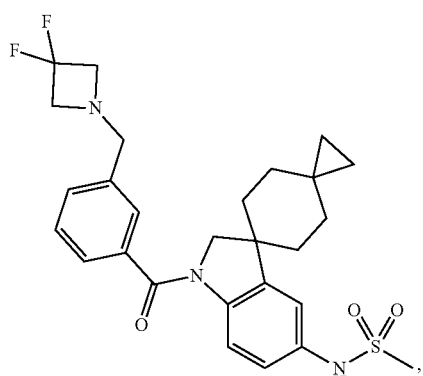
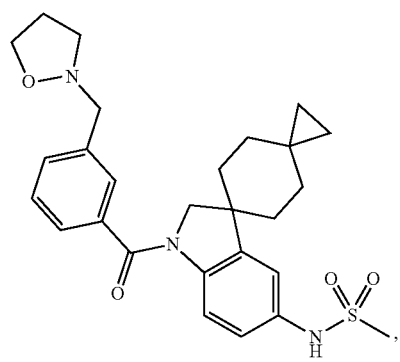
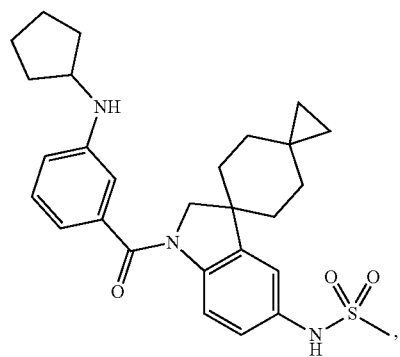
660
-continued
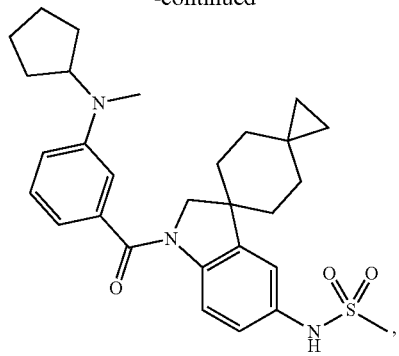
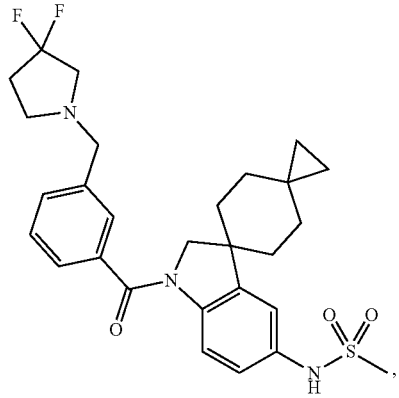
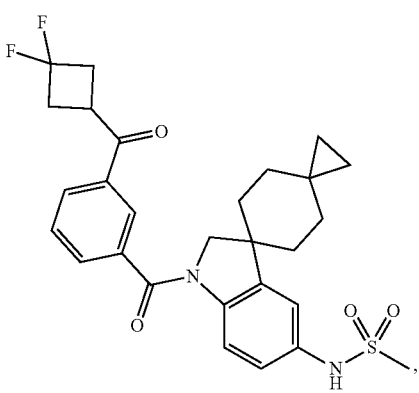
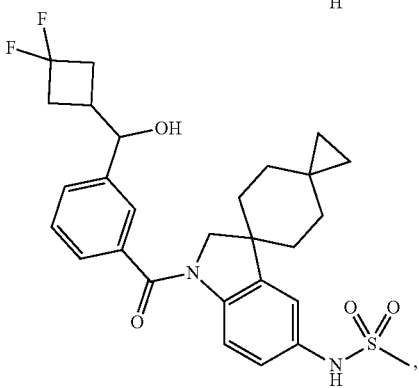

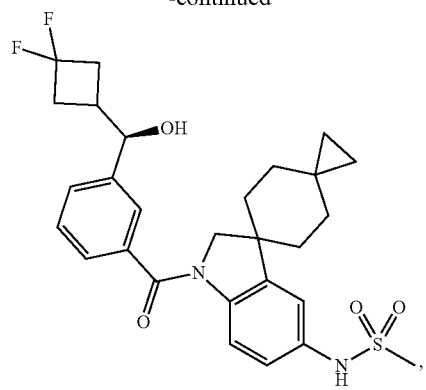
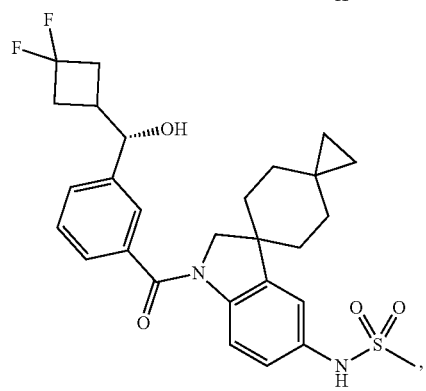
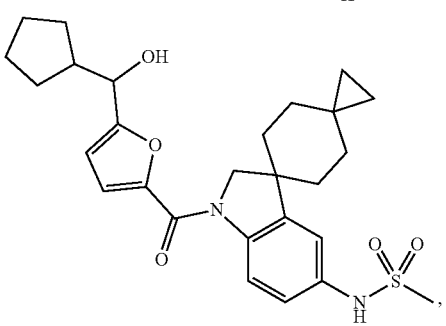
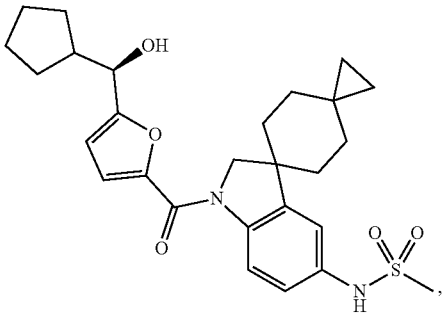
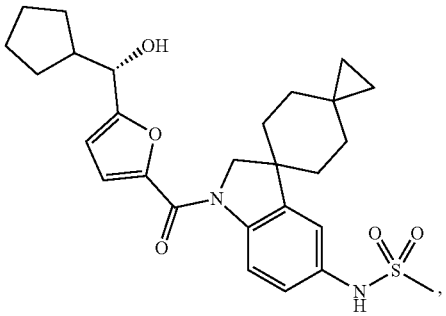
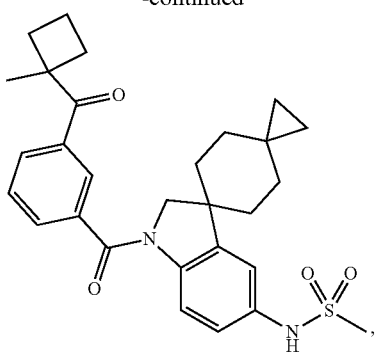
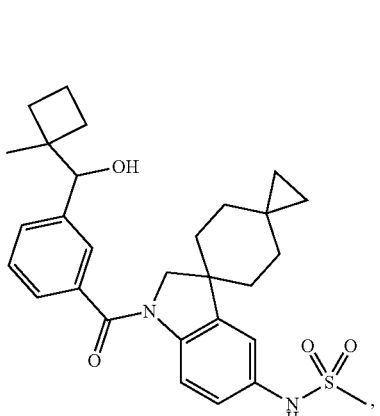
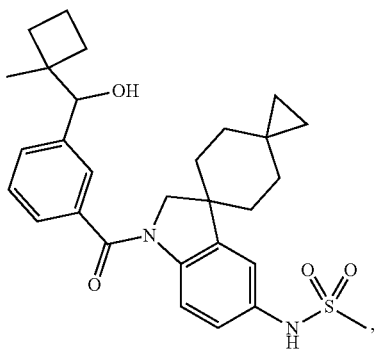
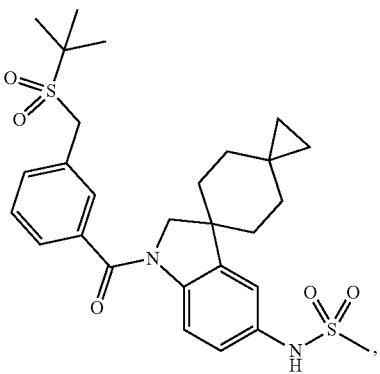
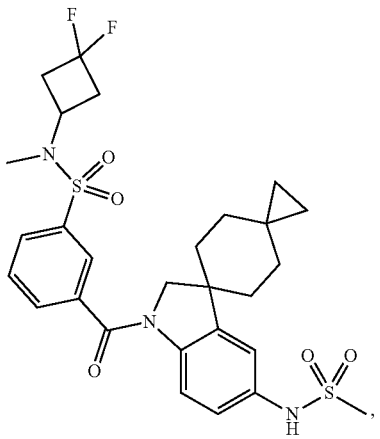

663
-continued
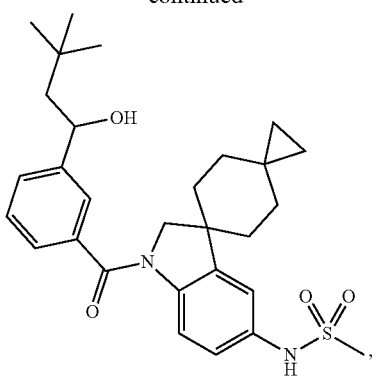
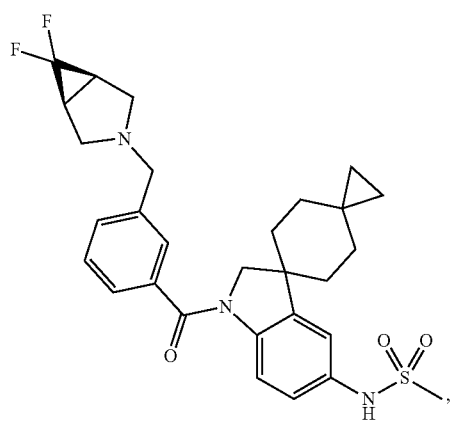
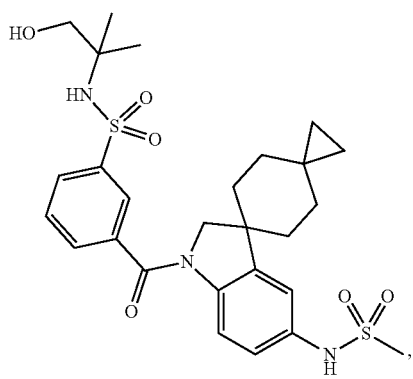
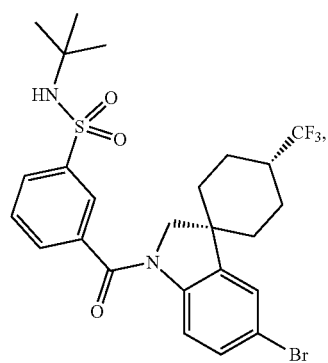
664
-continued
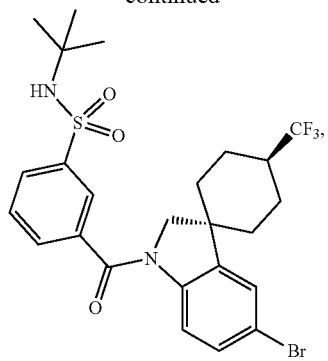
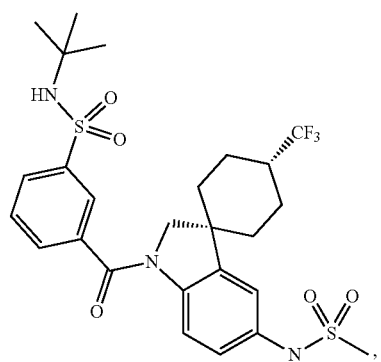
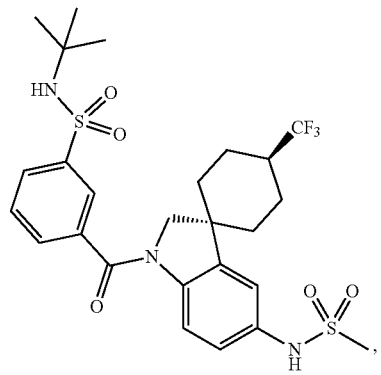
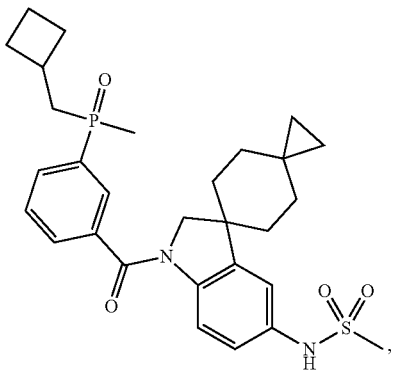

665
-continued
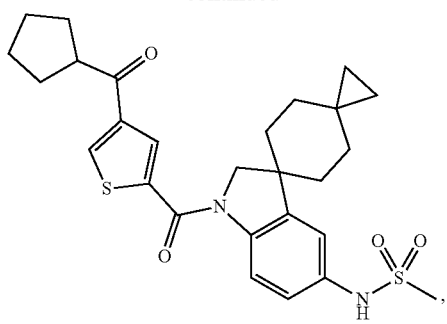
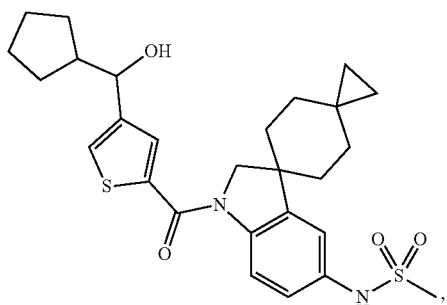
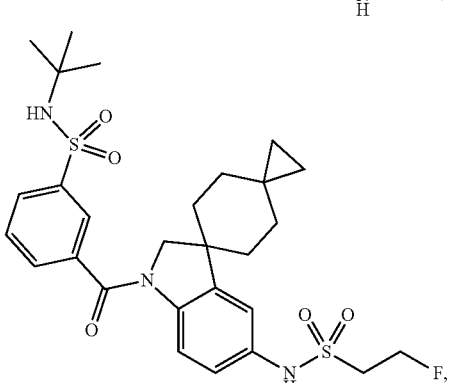
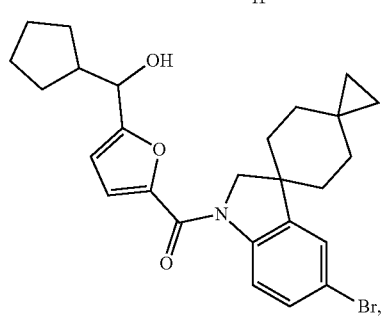
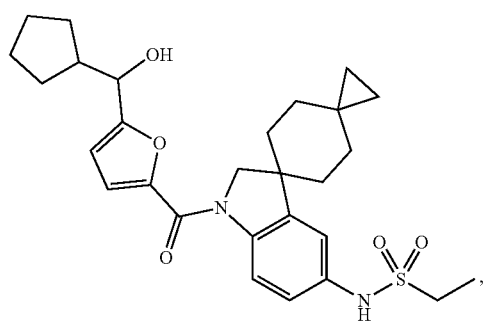
666
-continued
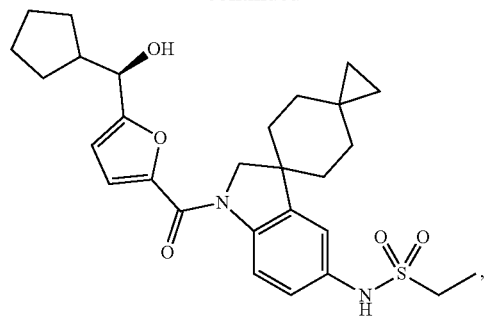
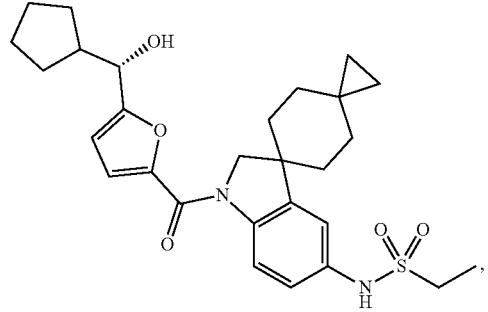
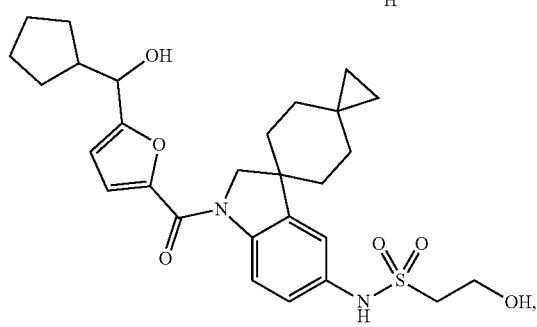
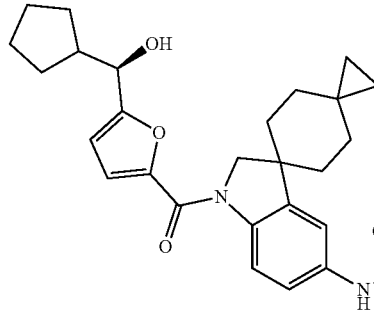
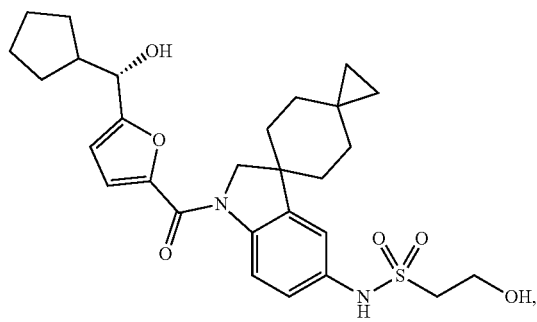

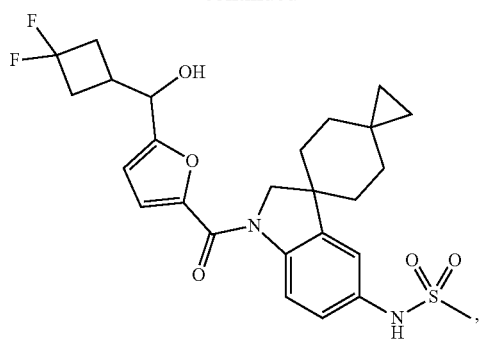
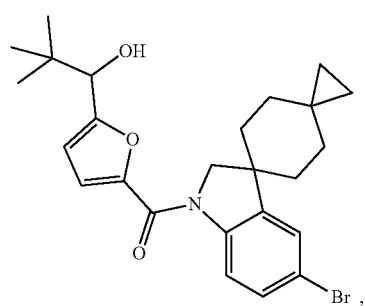
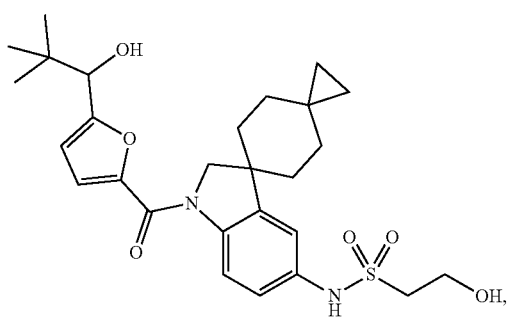
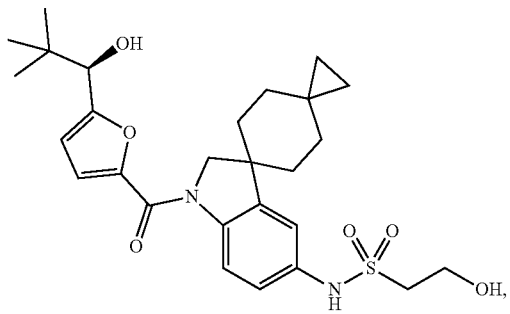
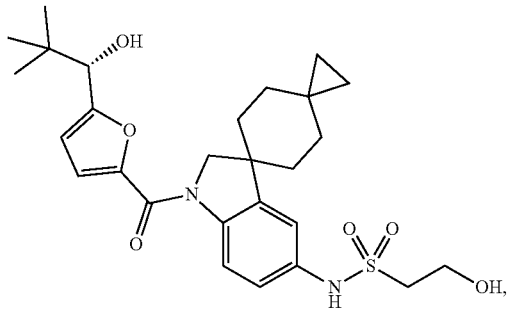
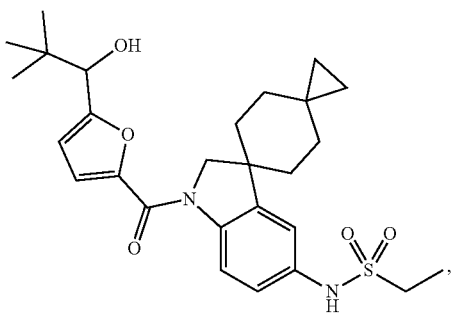
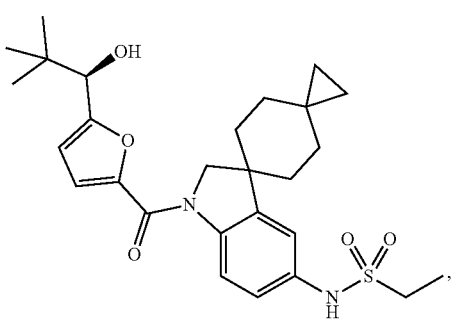
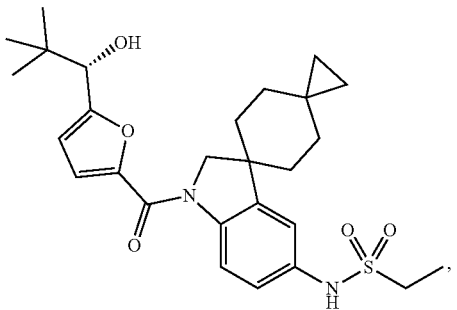
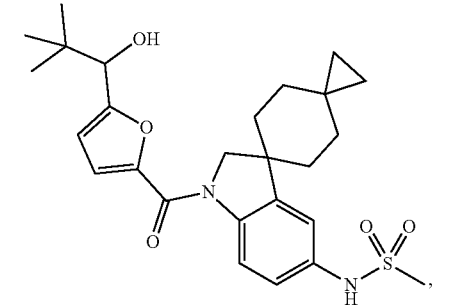
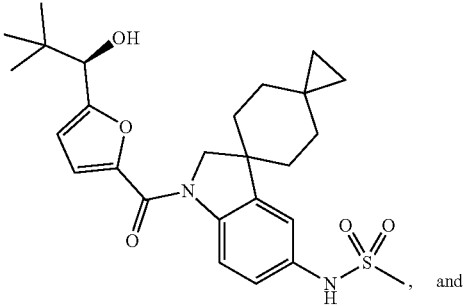
and -continued

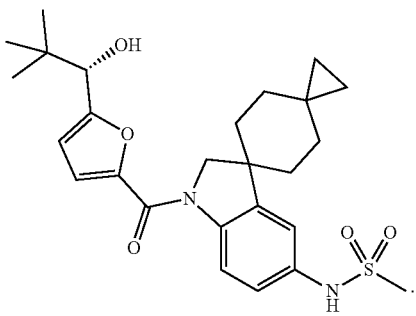

25. A pharmaceutical composition comprising a compound of claim 1, or a pharmaceutically acceptable salt thereof, and a pharmaceutically acceptable carrier or excipient.

26. The compound of claim 1, having the structure:

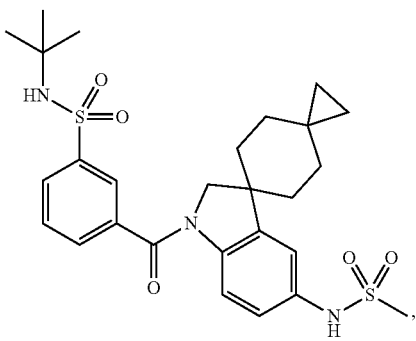 [SMILES: CC(C)(C)NS(=O)(=O)c1cccc(C(=O)N2CC3(CCC4(CC4)CC3)c3cc(NS(C)(=O)=O)ccc32)c1]

or a pharmaceutically acceptable salt thereof.

27. A pharmaceutical composition comprising the compound of claim 26, or a pharmaceutically acceptable salt thereof, and a pharmaceutically acceptable carrier or excipient.

28. The compound of claim 1, having the structure:

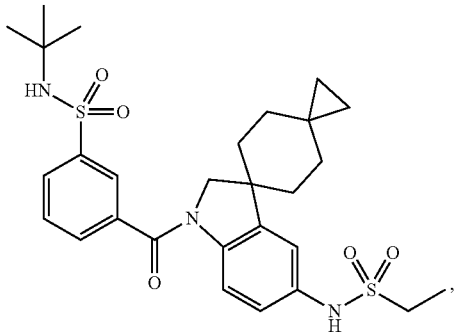 [SMILES: CCS(=O)(=O)Nc1ccc2c(c1)C1(CCC3(CC3)CC1)CN2C(=O)c1cccc(S(=O)(=O)NC(C)(C)C)c1]

or a pharmaceutically acceptable salt thereof.

29. A pharmaceutical composition comprising the compound of claim 28, or a pharmaceutically acceptable salt thereof, and a pharmaceutically acceptable carrier or excipient.

30. The compound of claim 1, having the structure:

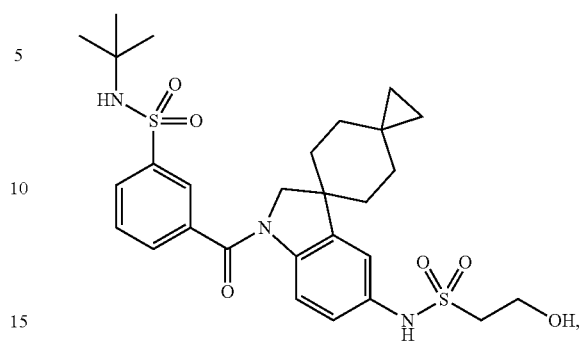

or a pharmaceutically acceptable salt thereof.

31. A pharmaceutical composition comprising the compound of claim 30, or a pharmaceutically acceptable salt thereof, and a pharmaceutically acceptable carrier or excipient.

32. The compound of claim 1, having the structure:

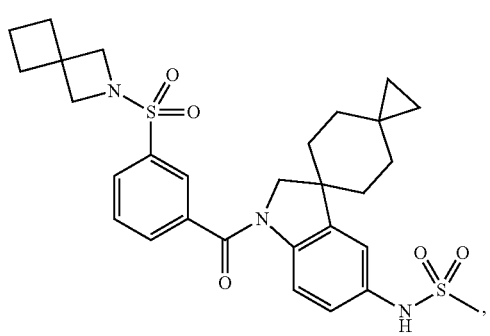 [SMILES: CS(=O)(=O)Nc1ccc2c(c1)C1(CCC3(CC3)CC1)CN2C(=O)c1cccc(S(=O)(=O)N2CC3(CCC3)C2)c1]

or a pharmaceutically acceptable salt thereof.

33. A pharmaceutical composition comprising the compound of claim 32, or a pharmaceutically acceptable salt thereof, and a pharmaceutically acceptable carrier or excipient.

34. The compound of claim 1, having the structure:

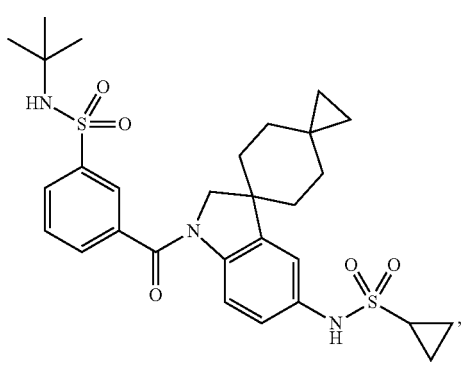 [SMILES: CC(C)(C)NS(=O)(=O)c1cccc(C(=O)N2CC3(CCC4(CC4)CC3)c3cc(NS(=O)(=O)C4CC4)ccc32)c1]

or a pharmaceutically acceptable salt thereof.

35. A pharmaceutical composition comprising the compound of claim 34, or a pharmaceutically acceptable salt thereof, and a pharmaceutically acceptable carrier or excipient.

* * * * *

UNITED STATES PATENT AND TRADEMARK OFFICE
CERTIFICATE OF CORRECTION

PATENT NO. : 12,084,420 B2
APPLICATION NO. : 17/896037
DATED : September 10, 2024
INVENTOR(S) : Derek A. Cogan It is certified that error appears in the above-identified patent and that said Letters Patent is hereby corrected as shown below:

On the Title Page

In the References Cited, item (56) U.S. PATENT DOCUMENTS: please replace:
"03/2021 Ehrlich et al."
With:
--05/2021 Cantley et al.--;

In the Claims

At Column 567, Claim number 2, Line number 16: please replace:
"—$CR^{1a1}R^{1a2}$,--;
With:
--=$CR^{1a1}R^{1a2}$,--;

At Column 568, Claim number 5, Line number 39: please replace:
"N=S(O)$R^{c9}R^{c10}$,"
With:
-- —N=S(O)$R^{c9}R^{c10}$,--;

At Column 569, Claim number 7, Line number 9: please replace:
"—$CR^{1a1}R^{1a2}$,"
With:
--=$CR^{1a1}R^{1a2}$,--;

At Column 575, Claim number 15, Line number 48: please replace:
"—$NR^{a26}C(O)NR\ a27\ R^{a28}$,"
With:
-- —$NR^{a26}C(O)NR^{a27}R^{a28}$,--;

Signed and Sealed this
First Day of July, 2025

Coke Morgan Stewart
*Acting Director of the United States Patent and Trademark Office*

At Column 576, Claim number 15, Line number 42: please replace:
"—NRCS(O)$_2$R$^{c6}$,"
With:
-- —NR$^{c5}$S(O)$_2$R$^{c6}$,--.